US006221865B1

(12) United States Patent
Sebti et al.

(10) Patent No.: US 6,221,865 B1
(45) Date of Patent: Apr. 24, 2001

(54) INHIBITORS OF PROTEIN ISOPRENYL TRANSFERASES

(75) Inventors: Said M. Sebti, Tampa, FL (US); Andrew D. Hamilton, Guilford, CT (US); Kenneth J. Barr, Chicago, IL (US); Stephen A. Fakhoury, Mundelein, IL (US); Stephen J. O'Connor, Wilmette, IL (US); Saul H. Rosenberg, Grayslake, IL (US); Wang Shen, Gurnee, IL (US); Bryan K. Sorensen, Waukegan, IL (US); Gerard M. Sullivan, Round Lake Beach, IL (US); James T. Wasicak, Waterford, IL (US); Kenneth J. Henry, Fishers, IN (US); Le Wang, Mundelein, IL (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/073,795

(22) Filed: May 7, 1998

Related U.S. Application Data

(63) Continuation-in-part of application No. 08/852,858, filed on May 7, 1997, now abandoned, which is a continuation-in-part of application No. 08/740,909, filed on Nov. 5, 1996, now abandoned.
(60) Provisional application No. 60/007,247, filed on Nov. 6, 1995.

(51) Int. Cl.$^7$ ................. A61K 31/5377; A61K 31/4025; C07D 401/06; C07D 413/06; C07D 207/06
(52) U.S. Cl. ................. 514/235.5; 514/326; 514/424; 514/428; 544/141; 546/208; 548/541; 548/567
(58) Field of Search ................. 514/408, 428, 514/235.5, 362, 424; 548/567, 569, 541; 544/141; 546/208

(56) References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,238,922 | 8/1993 | Graham et al. | 514/18 |
| 5,534,537 | 7/1996 | Ciccarone et al. | 514/397 |
| 5,578,629 | 11/1996 | Ciccarone et al. | 514/397 |
| 5,631,280 | 5/1997 | Ciccarone et al. | 514/416 |

FOREIGN PATENT DOCUMENTS

| | | | |
|---|---|---|---|
| 2072033 | 6/1992 | (CA) . | |
| 0203587 | 12/1986 | (EP) . | |
| 0456180 | 11/1991 | (EP) . | |
| 0461869 | 12/1991 | (EP) . | |
| 0512865 | 11/1992 | (EP) . | |
| 0520823 | 12/1992 | (EP) . | |
| 0523873 | 1/1993 | (EP) . | |
| 0528486 | 2/1993 | (EP) | C07K/5/10 |
| 0534546 | 3/1993 | (EP) | C07F/9/38 |
| 0535730 | 4/1993 | (EP) | C07K/5/08 |
| WO9116340 | 10/1991 | (WO) . | |
| WO9218465 | 10/1992 | (WO) . | |
| WO9409766 | 5/1994 | (WO) . | |
| WO9525086 | 9/1995 | (WO) . | |
| WO9630014 | 10/1996 | (WO) . | |
| WO9630015 | 10/1996 | (WO) . | |
| WO9706138 | 2/1997 | (WO) . | |
| WO9807692 | 2/1998 | (WO) . | |
| WO9838162 | 9/1998 | (WO) . | |

OTHER PUBLICATIONS

Omenn, Cancer Prevention, Cecil Textbook of Medicine, 20th Edition, vol. 1, pp. 1008–1010, 1996.*
Crispi et al., Chem. Abstract 98:72019, 1983.*
Hancock et al, "A polybasic Domain or Palmitoylation is Required in Addition to the CAAX Motif to Localize p21$^{ras}$ to the Plasma Membrane", Cell, vol. 63, Oct. 5, 1990, pp. 133–139.
Reiss et al, "Inhibition of Purified p21$^{ras}$ Farnesyl:Protein Transferase by Cys–AAX Tetrapeptides", Cell, vol. 62, Jul. 13, 1990, pp. 81–88.
Willumsen et al, "The p21 ras C–terminus is required for transformation and membrane association," Nature, vol. 310, Aug. 16, 1984, pp. 583–586.
Kohl et al., Selective Inhibition of ras–Dependent Transformation by a Farnesyltransferase Inhibitor, Science, 260:1934–1937 (1993).
Graham et al., Pseudopeptide Inhibitors of Ras Farnesyl–Protein Transferase, J. Med. Chem., 37:725–732 (1994).
Garcia et al., Peptidomimetic Inhibitors of Ras Farnesylation and Function in Whole Cells, J. Biol. Chem., 268:18415–18418 (1993).
Nigam et al., Potent Inhibition of Human Tumor p21$^{ras}$ Farnesyltransferase by A$_1$A$_2$–lacking p21$^{ras}$ CA$_1$A$_2$X Peptidomimetics, J. Biol. Chem., 268:20695–20698 (1993).
Qian et al., Design and Structural Requirements of Potent Peptidomimetic Inhibitors of p21$^{ras}$ Farnesyltransferase, J. Biol. Chem., 269:12410–12413 (1994).
Qian et al., Peptidomimetic Inhibitors of P21RAS Farnesyltransferase: Hydrophobic Functionalization Leads to Disruption of P21RAS Membrane Association in Whole Cells, Bioorg. Med. Chem. Lett., 4:2579–2584 (1994).
Goldstein et al., Benzodiazepine Peptidomimetics: Potent Inhibitors of Ras Farnesylation in Animal Cells, Science, 260:1937–1942 (1993).
Reiss et al., Inhibition of Purified p21$^{ras}$ Farnesyl:Protein Transferase by Cys–AAX Tetrapeptides, Cell, 62:81–88 (1990).
Vogt et al., A Non–peptide Mimetic of Ras–CAAX:Selective Inhibition of Farnesyltransferase and Ras Processing, (1995) J. Biol. Chem. 270:660–664.
Kohl et al., Protein farnesyltransferase inhibitors block the growth of ras–dependent tumors in nude mice, (1994) Proc. Natl. Acad. Sci. USA 91:9141–9145.
Cox et al., The CAAX Peptidomimetic Compound B581 Specifically Blocks Farnesylated, but Not Geranylgeranylated or Myristylated, Oncogenic Ras Signaling and Transformation, (1994) J. Biol. Chem. 269:19203–19206.
Lerner et al., Ras CAAX Peptidomimetic FTI–277 Selectively Blocks Oncogenic Ras Signaling by Inducing Cytoplasmic Accumulation of Inactive Ras–Raf Complexes (1995) J. Biol. Chem. 270:26802–26806.

Sun et al., Ras CAAX Peptidomimetic FTI 276 Selectively Blocks Tumor Growth in Nude Mice of a Human Lung Carcinoma with K–Ras Mutation and p53 Deletion, (1995) Cancer Research 55, 4243–4247.

Database HCAPLUS on STN, 1997:247953, Boyle, F.T. et al., 'Preparation of 2-aminomethyl-4-mercaptopyrrolidines and analogs as farnesyl transferase inhibitors', Feb. 20, 1997, PCT Int. Appl. 189 pp.

Database HCAPLUS on STN, 1996:567259, SEBTi et al., 'Peptidomimetic inhibitors of prenyl transferases, preparation and activity of the peptidomimetics, and use for treating tumors', Jul. 18, 1996, PCT Int. Appln. 186 pp.

Gibbs, J.B., Ras C–Terminal Processing Enzymes–New Drug Targets, Cell, 65:1–4 (1991).

Gibbs, et al., Farnesyltransferase Inhibitors: Ras Research Yields a Potential Cancer Terapeutic, Cell, 77:175–178 (1994).

Brown et al., Tetrapeptide inhibitors of protein farnesyl-transferase: Amino–terminal substitution in phenylalanine-containing tetrapeptides restores farnesylation, Proc. Natl. Acad. Sci. U.S.A., 89:8313–8316 (1992).

* cited by examiner

*Primary Examiner*—Mukund J. Shah
*Assistant Examiner*—Deepak R. Rao
(74) *Attorney, Agent, or Firm*—Pillsbury Madison & Sutro LLP

(57) ABSTRACT

Compounds having the formula

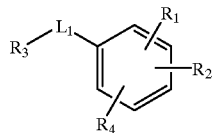

I or a pharmaceutically acceptable salt thereof wherein $R_1$ is (a) hydrogen, (b) loweralkyl, (c) alkenyl, (d) alkoxy, (e) thioalkoxy, (f) halo, (g) haloalkyl, (h) aryl-$L_2$—, and (i) heterocyclic-$L_2$—; $R_2$ is selected from (a)

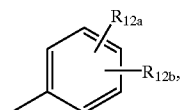

(b) —C(O)NH—CH($R_{14}$)—C(O)O$R_{15}$,

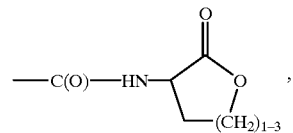

(d) —C(O)NH—CH($R_{14}$)—C(O)NHSO$_2R_{16}$,
(e) —C(O)NH—CH($R_{14}$)-tetrazolyl, (f) —C(O)NH-heterocyclic, and
(g) —C(O)NH—CH($R_{14}$)—C(O)N$R_{17}R_{18}$; $R_3$ is substituted or unsubstituted heterocyclic or aryl, substituted or unsubstituted cycloalkyl or cycloalkenyl,

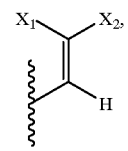

and —P(W)$R^{R3}R^{R3'}$; $R_4$ is hydrogen, lower alkyl, haloalkyl, halogen, aryl, arylakyl, heterocyclic, or (heterocyclic)alkyl; $L_1$ is absent or is selected from (a) —$L_4$—N($R_5$)—$L_5$—, (b) —$L_4$—O—$L_5$—, (c) —$L_4$—S(O)$_n$—$L_5$—(d) —$L_4$—$L_6$—C(W)—N($R_5$)—$L_5$—, (e) —$L_4$—$L_6$—S(O)$_m$—N($R_5$)—$L_5$—, (f) —$L_4$—N($R_5$)—C(W)—$L_7$—$L_5$—, (g) —$L_4$—N($R_5$)—S(O)$_p$—$L_7$—$L_5$—, (h) optionally substituted alkylene, (i) optionally substituted alkenylene, (j) optionally substituted alkynylene (k) a covalent bond, (l)

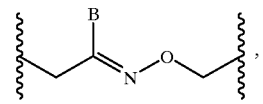

and (m)

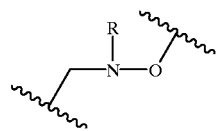

are inhibitors of protein isoprenyl transferases. Also disclosed are protein isoprenyl transferase inhibiting compositions and a method of inhibiting protein isoprenyl transferases.

15 Claims, No Drawings

INHIBITORS OF PROTEIN ISOPRENYL TRANSFERASES

CROSS REFERENCE TO RELATED APPLICATIONS

This application is a continuation-in-part of U.S. Ser. No. 08/852,858, filed May 7, 1997, now abandoned, which is a continuation-in-part of U.S. Ser. No. 08/740,909, filed Nov. 5, 1996, now abandoned, which claims the benefit of U.S. Provisional Application Ser. No. 60/007,247, filed Nov. 6, 1995.

TECHNICAL FIELD

The present invention relates to novel compounds which are useful in inhibiting protein isoprenyl transferases (for example, protein farnesyltransferase and protein geranylgeranyltransferase) and the farnesylation or geranylgeranylation of the oncogene protein Ras and other related small g-proteins, compositions containing such compounds and methods of using such compounds.

BACKGROUND OF THE INVENTION

Ras oncogenes are the most frequently identified activated oncogenes in human tumors. Transformed protein Ras is involved in the proliferation of cancer cells. The Ras must be farnesylated before this proliferation can occur. Farnesylation of Ras by farnesyl pyrophosphate (FPP) is effected by protein farnesyltransferase. Inhibition of protein farnesyltransferase, and thereby farnesylation of the Ras protein, blocks the ability of transformed cells to proliferate. Inhibition of protein geranylgeranyltransferase and, thereby, of geranylgeranylation of Ras proteins, also results in down regulation of Ras protein function.

Activation of Ras and other related small g-proteins that are farnesylated and/or geranylated also partially mediates smooth muscle cell proliferation (Circulation, I-3: 88 (1993), which is hereby incorporated herein by reference). Inhibition of protein isoprenyl transferases, and thereby farnesylation or geranylgeranylation of the Ras protein, also aids in the prevention of intimal hyperplasia associated with restenosis and atherosclerosis, a condition which compromises the success of angioplasty and surgical bypass for obstructive vascular lesions.

There is therefore a need for compounds which are inhibitors of protein farnesyltransferase and protein geranylgeranyltransferase.

SUMMARY OF THE INVENTION

In its principle embodiment, the invention provides a compound having the formula:

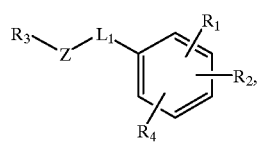

I or a pharmaceutically acceptable salt thereof, wherein
$R_1$ is selected from the group consisting of
(1) hydrogen,
(2) alkenyl,
(3) alkynyl,
(4) alkoxy,
(5) haloalkyl,
(6) halogen,
(7) loweralkyl,
(8) thioalkoxy,
(9) aryl-$L_2$— wherein aryl is selected from the group consisting of
(a) phenyl,
(b) naphthyl,
(c) dihydronaphthyl,
(d) tetrahydronaphthyl,
(e) indanyl, and
(f) indenyl
wherein (a)–(f) are unsubstituted or substituted with at least one of X, Y, or Z wherein X, Y, and Z are independently selected from the group consisting of
alkenyl,
alkynyl,
alkoxy,
aryl,
carboxy,
cyano,
halogen,
haloalkyl,
hydroxy,
hydroxyalkyl,
loweralkyl,
nitro,
N-protected amino, and
—NRR' wherein R and and R' are independently selected from the group consisting of
hydrogen and
loweralkyl,
oxo (=O), and
thioalkoxy and
$L_2$ is absent or is selected from the group consisting of
—CH$_2$—,
—CH$_2$CH$_2$—,
—CH(CH$_3$)—,
—O—,
—C(O)—,
—S(O)$_q$ wherein q is 0, 1 or 2, and
—N(R)—, and
(10) heterocycle-$L_2$— wherein $L_2$ is as defined above and the heterocycle is unsubstituted or substituted with 1, 2, 3 or 4 substituents independently selected from the group consisting of
(a) loweralkyl,
(b) hydroxy,
(c) hydroxyalkyl,
(d) halogen
(e) cyano,
(f) nitro,
(g) oxo (=O),
(h) —NRR',
(i) N-protected amino,
(j) alkoxy,
(k) thioalkoxy,
(l) haloalkyl,
(m) carboxy, and
(n) aryl;

3

R₂ is selected from the group consisting of
(1)

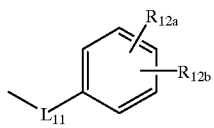

wherein L₁₁ is selected from the group consisting of
(a) a covalent bond,
(b) —C(W)N(R)— wherein R is defined previously and W is selected from the group consisting of and S,
(c) —C(O)—,
(d) —N(R)C(W)—,
(e) —CH₂O—,
(f) —C(O)O—, and
(g) —CH₂N(R)—,
R₁₂ₐ is selected from the group consisting of
(a) hydrogen,
(b) loweralkyl, and
(c) —C(O)OR₁₃ wherein R₁₃ is selected from the group consisting of
hydrogen and
a carboxy-protecting group, and
R₁₂ᵦ is selected from the group consisting of
(a) hydrogen and
(b) loweralkyl,
with the proviso that R₁₂ₐ and R₁₂ᵦ are not both hydrogen,
(2) —L₁₁—C(R₁₄)(Rᵥ)—C(O)OR₁₅ wherein L₁₁ is defined previously,
Rᵥ is selected from the group consisting of
(a) hydrogen and
(b) loweralkyl,
R₁₅ is selected from the group consisting of
(a) hydrogen,
(b) alkanoyloxyalkyl,
(c) loweralkyl, and
(b) a carboxy-protecting group, and
R₁₄ is selected from the group consisting of
(a) alkoxyalkyl,
(b) alkoxyarylalkyl,
(c) alkoxycarbonylalkyl,
(d) alkylsulfinylalkyl,
(e) alkylsulfonylalkyl,
(f) alkynyl,
(g) aminoalkyl,
(h) aminocarbonylalkyl,
(i) aminothiocarbonylalkyl,
(j) aryl,
(k) arylalkyl,
(l) carboxyalkyl,
(m) cyanoalkyl,
(n) cycloalkyl,
(o) cycloalkylalkoxyalkyl,
(p) cycloalkylalkyl,
(q) (heterocyclic)alkyl,
(r) hydroxyalkyl,
(s) hydroxyarylalkyl,
(t) loweralkyl,
(u) sulfhydrylalkyl,
(v) thioalkoxyalkyl wherein the thioalkoxyalkyl is unsubstituted or substituted with 1, 2, 3, or 4 substituents selected from the group consisting of halogen,

4

(w) thioalkoxyalkylamino, and
(x) thiocycloalkyloxyalkyl,
(3)

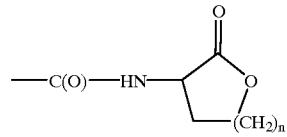

wherein is 1–3,
(4) —C(O)NH—CH(R₁₄)—C(O)NHSO₂R₁₆ wherein R₁₄ is defined previously and R₁₆ is selected from the group consisting of
(a) loweralkyl,
(b) haloalkyl,
(c) aryl wherein the aryl is unsubstituted or substituted with 1, 2, 3, 4, or 5 substituents independently selected from the group consisting of
loweralkyl,
hydroxy,
hydroxyalkyl,
halogen,
cyano,
nitro,
oxo (=O),
—NRR'
N-protected amino,
alkoxy,
thioalkoxy,
haloalkyl,
carboxy, and
aryl, and
(d) heterocycle wherein the heterocycle is unsubstituted or substituted with substituents independently selected from the group consisting of
loweralkyl,
hydroxy,
hydroxyalkyl,
halogen,
cyano,
nitro,
oxo (=O),
—NRR',
N-protected amino,
alkoxy,
thioalkoxy,
haloalkyl,
carboxy, and
aryl;
(5) —C(O)NH—CH(R₁₄)-tetrazolyl wherein the tetrazole ring is unsubstituted or substituted with loweralkyl or haloalkyl,
(6) —L₁₁-heterocycle,
(7) —C(O)NH—CH(R₁₄)—C(O)NR₁₇R₁₈ wherein R₁₄ is defined previously and R₁₇ and R₁₈ are independently selected from the group consisting of
(a) hydrogen,
(b) loweralkyl,
(c) arylalkyl,
(d) hydroxy, and
(e) dialkylaminoalkyl,
(8) —C(O)OR₁₅, and
(9) —C(O)NH—CH(R₁₄)-heterocycle wherein R₁₄ is as previously defined and the heterocycle is unsubstituted or substituted with loweralkyl or haloalkyl;

$L_1$ is absent or is selected from the group consisting of
(1) —$L_4$—N($R_5$)—$L_5$— wherein $L_4$ is absent or selected from the group consisting of
 (a) $C_1$-to-$C_{10}$-alkylene and
 (b) $C_2$-to-$C_{16}$-alkenylene,
 wherein the alkylene and alkenylene groups are unsubstituted or substituted with 1, 2, 3 or 4 substitutents independently selected from the group consisting of
  alkenyl,
  alkenyloxy,
  alkenyloxyalkyl,
  alkenyl[S(O)$_q$]alkyl,
  alkoxy,
  alkoxyalkyl wherein the alkoxyalkyl is unsubstituted or substituted with 1 or 2 hydroxyl substituents,
  with the proviso that no two hydroxyls are attached to the same carbon,
  alkoxycarbonyl wherein the alkoxycarbonyl is unsubstituted or substituted with 1, 2, or 3 substitutents independently selected from the group consisting of
   halogen and
   cycloalkyl,
  alkylsilyloxy,
  alkyl[S(O)$_q$],
  alkyl[S(O)$_q$]alkyl,
  aryl wherein the aryl is unsubstituted or substituted with 1, 2, 3, 4, or 5 substituents independently selected from the group consisting of
   alkoxy wherein the alkoxy is unsubstituted or substituted with substituents selected from the group consisting of cycloalkyl,
   aryl,
   arylalkyl,
   aryloxy wherein the aryloxy is unsubstituted or substituted with 1, 2, 3, 4, or 5 substituents independently selected from the group consisting of,
    halogen,
    nitro, and
    —NRR',
   cycloalkyl,
   halogen,
   loweralkyl,
   hydroxyl,
   nitro,
   —NRR', and
   —SO$_2$NRR',
  arylalkoxy wherein the arylalkoxy is unsubstituted or substituted with substituents selected from the group consisting of alkoxy,
  arylalkyl,
  arylalkyl[S(O)$_q$]alkyl,
  aryl[S(O)$_q$],
  aryl[S(O)$_q$]alkyl wherein the aryl[S(O)$_q$]alkyl is unsubstituted or substituted with 1, 2, 3, 4, or 5 substituents independently selected from
   alkoxy and
   loweralkyl,
  arylalkoxyalkyl wherein the arylalkoxyalkyl is unsubstituted or substituted with substituents selected from the group consisting of
   alkoxy, and
   halogen,
  aryloxy,
  aryloxyalkyl wherein the aryloxyalkyl is unsubstituted or substituted with substituents selected from the group consisting of halogen,
  carboxyl,
  —C(O)NR$_C$R$_D$ wherein R$_C$ and R$_D$ are independently selected from the group consisting of
   hydrogen,
   loweralkyl, and
   alkoxycarbonyl or
  R$_C$ and R$_D$ together with the nitrogen to which they are attached form a ring selected from the group consisting of
   morpholine,
   piperidine,
   pyrrolidine
   thiomorpholine,
   thiomorpholine sulfone, and
   thiomorpholine sulfoxide,
  wherein the ring formed by R$_C$ and R$_D$ together is unsubstituted or substituted with 1 or 2 substituents independently selected from the group consisting of alkoxy and alkoxyalkyl,
  cycloalkenyl wherein the cycloalkenyl is unsubstituted or substituted with 1 or 2 substituents selected from the group consisting of alkenyl,
  cyclolalkoxy,
  cycloalkoxycarbonyl,
  cyclolalkoxyalkyl,
  cyclolalkyl wherein the cycloalkyl is unsubstituted or substituted with 1, 2, 3, 4, or 5 substituents independently selected from the group consisting
   of aryl,
   loweralkyl, and
   alkanoyl,
  cycloalkylalkoxy,
  cycloalkylalkoxycarbonyl,
  cycloalkylalkoxyalkyl,
  cycloalkylalkyl,
  cyclolalkyl[S(O)$_q$]alkyl,
  cycloalkylalkyl[S(O)$_q$]alkyl,
  fluorenyl,
  heterocycle wherein the heterocycle is unsubstituted or substituted with 1, 2, 3, or 4 substituents independently selected from the group consisting of
  alkoxy wherein the alkoxy is unsubstituted or substituted with 1 or 2 substituents independently selected from the group consisting of aryl and cycloalkyl,
  alkoxyalkyl wherein the alkoxyalkyl is unsubstituted or substituted with 1 or 2 substituents independently selected from the group consisting of
   aryl and
   cycloalkyl,
  alkoxycarbonyl wherein the alkoxycarbonyl is unsubstituted or substituted with 1 or 2 substituents independently selected from the group consisting of
   aryl and
   cycloalkyl,
  aryl wherein the aryl is unsubstituted or substituted with 1, 2, 3, 4, or 5 substituents independently selected from the group consisting of
   alkanoyl,
   alkoxy,
   carboxaldehyde,
   haloalkyl,
   halogen, loweralkyl,
nitro,
—NRR', and
thioalkoxy,
arylalkyl,
aryloxy,
cycloalkoxyalkyl,
cycloalkyl,
cycloalkylalkyl,
halogen,
heterocycle,
hydroxyl,
loweralkyl wherein the loweralkyl is unsubstituted or substituted with 1, 2, or 3 substituents independently selected from the group consisting of
heterocycle,
hydroxyl,
with the proviso that no two hydroxyls are attached to the same carbon, and
—NR$^{R3R3'}$ wherein R$^{R3}$ and R$^{R3'}$ are independently selected from the group consisting of
hydrogen
aryl,
loweralkyl,
aryl,
arylalkyl,
heterocycle,
(heterocyclic)alkyl,
cycloalkyl, and
cycloalkylalkyl, and
sulfhydryl,
(heterocyclic)alkoxy,
(heterocyclic)alkyl,
(heterocyclic)alkyl[S(O)$_q$]alkyl,
(heterocyclic)oxy,
(heterocyclic)alkoxyalkyl,
(heterocyclic)oxyalkyl,
heterocycle[S(O)$_q$]alkyl,
hydroxyl,
hydroxyalkyl,
imino,
N-protected amino,
=N—O-aryl, and
=N—OH,
=N—O-heterocycle wherein the heterocycle is unsubstituted or substituted with 1, 2, 3, or 4 substituents independently selected from the group consisting of
loweralkyl,
hydroxy,
hydroxyalkyl,
halogen,
cyano,
nitro,
oxo (=O),
—NRR'
N-protected amino,
alkoxy,
thioalkoxy,
haloalkyl,
carboxy, and
aryl,
=N—O-loweralkyl,
—NR$^{R3}$R$^{R3'}$,
—NHNR$_C$R$_D$, —OG wherein G is a hydroxyl protecting group,
—O—NH—R,

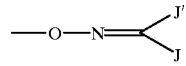

wherein J and J' are independently selected from the group consisting of
loweralkyl and
arylatkyl,
oxo,
oxyamino(alkyl)carbonylalkyl,
oxyamino(arylalkyl)carbonylalkyl,
oxyaminocarbonylalkyl,
—SO$_2$—A wherein A is selected from the group consisting of
loweralkyl,
aryl, and
heterocycle
wherein the loweralkyl, aryl, and heterocycle are unsubstituted or substituted with 1, 2, 3, 4, or 5 substituents independently selected from the group consisting of
alkoxy,
halogen,
haloalkyl,
loweralkyl, and
nitro,
sulfhydryl,
thioxo, and
thioalkoxy,
L$_5$ is absent or selected from the group consisting of
(a) C$_1$-to-C$_{10}$-alkylene and
(b) C$_2$-to-C$_{16}$-alkenylene
wherein (a) and (b) are unsubstituted or substituted as defined previously, and
R$_5$ is selected from the group consisting of
hydrogen,
alkanoyl wherein the alkanoyl is unsubstituted or substituted with substituents selected from the group consisting of aryl,
alkoxy,
alkoxyalkyl,
alkoxycarbonyl wherein the alkoxycarbonyl is unsubstituted or substituted with 1, 2 or 3 substituents independently selected from the group consisting of
aryl and
halogen,
alkylaminocarbonylalkyl wherein the alkylaminocarbonylalkyl is unsubstituted or substituted with 1 or 2 substituents independently selected from the group consisting of aryl,
(anthracenyl)alkyl,
aryl,
arylalkoxy,
arylalkyl wherein the arylalkyl is unsubstituted or substituted with 1, 2, 3, 4, or 5 substituents independently selected from the group consisting of
alkoxy,
aryl,
carboxyl,
cyano,
halogen,
haloalkoxy,
haloalkyl,
nitro, oxo, and
—$L_{11}$—$C(R_{14})(R_v)$—$C(O)OR_{15}$,
(aryl)oyl wherein the (aryl)oyl is unsubstituted or substituted with substituents selected from the group consisting of halogen,
aryloxycarbonyl,
carboxaldehyde,
—$C(O)NRR_{40}$,
cycloalkoxycarbonyl,
cycloalkylaminocarbonyl,
cycloalkcylaminothiocarbonyl,
cyanoalkyl,
cyclolalkyl,
cycloalkylalkyl wherein the cycloalkylalkyl is unsubstituted or substituted with 1 or 2 hydroxyl substituents,
with the proviso that no two hydroxyls are attached to the same carbon,
(cyclolalkyl)oyl,
(9,10-dihydroanthracenyl)alkyl wherein the (9,10-dihydroanthracenyl)alkyl is unsubstituted or substituted with 1 or 2 oxo substituents,
haloalkyl,
heterocycle,
(heterocyclic)alkyl wherein the (heterocyclic)alkyl is unsubstituted or substituted with 1, 2, 3, 4, or 5 substituents selected from the group consisting of loweralkyl,
(heterocyclic)oyl,
loweralkyl, wherein the loweralkyl is unsubstituted or substituted with substituents selected from the group consisting of —NRR',
—$SO_2$—A, and
thioalkoxyalkyl;
(3) —$L_4$—$S(O)_m$—$L_5$— wherein $L_4$ and $L_5$ are defined previously and m is 0, 1, or 2,
(4) —$L_4$—$L_6$—$C(W)$—$N(R_6)$—$L_5$— wherein $L_4$, W, and $L_5$ are defined previously,
$R_6$ is selected from the group consisting of
(a) hydrogen,
(b) loweralkyl,
(c) aryl,
(d) arylalkyl,
(e) heterocycle,
(f) (heterocyclic)alkyl,
(g) cyclolakyl, and
(h) cycloalkylalkyl, and
$L_6$ is absent or is selected from the group consisting of
(a) —O—,
(b) —S—, and
(c) —$N(R_{6'})$— wherein $R_{6'}$ is selected from the group consisting of
hydrogen,
loweralkyl,
aryl,
arylalkyl,
heterocycle,
(heterocyclic)alkyl,
cyclolakyl, and
cycloalkylalkyl,
(5) —$L_4$—$L_6$—$S(O)_m$—$N(R_5)$—$L_5$—,
(6) —$L_4$—$L_6$—$N(R_5)$—$S(O)_m$—$L_5$—,
(7) —$L_4$—$N(R_5)$—$C(W)$—$L_7$—$L_5$— wherein $L_4$, $R_5$, W, and and $L_5$ are defined previously and $L_7$ is absent or is selected from the group consisting of —O— and —S—,
(8) $C_1$–$C_{10}$-alkylene wherein the alkylene group is unsubstituted or substituted with 1 or 2 substituents independently selected from the group consisting of (a) aryl,
(b) arylalkyl,
(c) heterocycle,
(d) (heterocyclic)alkyl,
(e) cyclolakyl,
(f) cycloalkylalkyl,
(g) alkylthioalkyl, and
(h) hydroxy,
(9) $C_2$-to-$C_{10}$-alkenylene wherein the alkenylene group is unsubstituted or substituted with 1 or 2 substituents independently selected from the group consisting of
(a) aryl,
(b) arylalkyl,
(c) (aryl)oxyalkyl wherein the (aryl)oxyalkyl is unsubstituted or substituted with 1, 2, 3, 4, or 5 substituents selected from the group consisting of halogen,
(d) heterocycle,
(e) (hererocycle)alkyl,
(f) hydroxyalkyl,
(g) cyclolakyl,
(h) cycloalkylalkyl,
(i) alkylthioalkyl, and
(j) hydroxy,
(10) $C_2$-to-$C_{10}$-alkynylene wherein the alkynylene group is unsubstituted or substituted with 1 or 2 substituents independently selected from the group consisting of
(a) aryl,
(b) arylalkyl,
(c) heterocycle,
(d) (heterocyclic)alkyl,
(e) cyclolakyl,
(f) cycloalkylalkyl,
(g) alkylthioalkyl, and
(h) hydroxy,
(11) —$L_4$-heterocycle-$L_5$—,
(12) a covalent bond,
(13)

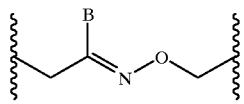

wherein B is selected from the group consisting of
loweralkyl and
arylalkyl, and
(14)

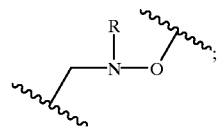

Z is selected from the group consisting of
(1) a covalent bond,
(2) —O—,
(3) —$S(O)_q$—, and
(4) —$NR_z$— wherein $R_z$ is selected from the group consisting of
(a) hydrogen
(b) loweralkyl,
(c) aryl, (d) arylatkyl,
(e) heterocycle,
(f) (heterocyclic)alkyl,
(g) cyclolakyl, and
(h) cycloalkylalkyl;

R$_3$ is selected from the group consisting of
(1) hydrogen,
(2) aryl,
(3) fluorenyl,
(4) heterocycle,
wherein (2)–(4) are unsubstituted or substituted with 1, 2, 3, 4, or 5 substituents independently selected from the group consisting of
  (a) alkanoyl,
  (b) alkoxy wherein the alkoxy is unsubstituted or substituted with 1, 2, 3, 4, or 5 substituents independently selected from the group consisting of
    halogen,
    aryl, and
    cycloalkyl,
  (c) alkoxyalkyl wherein the alkoxyalkyl is unsubstituted or substituted with 1 or 2, 3, 4 or 5 substituents independently selected from the group consisting of
    aryl and
    cycloalkyl,
  (d) alkoxycarbonyl wherein the alkoxycarbonyl is unsubstituted or substituted with 1, 2, 3, 4, or 5 substituents independently selected from the group consisting of
    aryl, and
    cycloalkyl,
  (e) alkylsilyloxyalkyl,
  (f) arylalkyl,
  (g) aryl wherein the aryl is unsubstituted or substituted with 1, 2, 3, 4, or 5 substituents independently selected from the group consisting of
    alkanoyl,
    alkoxy wherein the alkoxy is unsubstituted or substituted with 1 or 2 substituents selected from the group consisting of cycloalkyl,
    carboxaldehyde,
    haloalkyl,
    halogen,
    loweralkyl,
    nitro,
    —NRR', and
    thioalkoxy,
  (h) arylalkyl,
  (i) aryloxy wherein the aryloxy is unsubstituted or substituted with 1, 2, 3, 4, or 5 substituents independently selected from the group consisting of,
    halogen,
    nitro, and
    —NRR',
  (j) (aryl)oyl,
  (k) carboxaldehyde,
  (l) carboxy,
  (m) carboxyalkyl,
  (n) —C(O)NRR" wherein R is defined previously and R" is selected from the group consisting of
    hydrogen,
    loweralkyl, and
    carboxyalkyl,
  (o) cyano,
  (p) cyanoalkyl,
  (q) cycloalkyl,
  (r) cycloalkylalkyl,
  (s) cycloalkoxyalkyl,
  (t) halogen,
  (u) haloalkyl wherein the haloalkyl is unsubstituted or substituted with 1, 2, 3, 4, or 5 hydroxyl substituents,
    with the proviso that no two hydroxyls are attached to the same carbon,
  (v) heterocycle,
  (w) hydroxyl,
  (x) hydroxyalkyl wherein the hydroxyalkyl is unsubstituted or substituted with substitutients selected from the group consisting of aryl,
  (y) loweralkyl wherein the loweralkyl is unsubstituted or substituted with substituents selected from the group consisting of
    heterocycle,
    hydroxyl,
    with the proviso that no two hydroxyls are attached to the same carbon,
    —NR$^{R3}$R$^{R3'}$, and
    —P(O)(OR)(OR'),
  (z) nitro,
  (aa) —NRR',
  (bb) oxo,
  (cc) —SO$_2$NR$_{A'}$R$_{B'}$ wherein R$_{A'}$ and R$_{B'}$ are independently selected from the group consisting of
    hydrogen,
    (aryl)oyl,
    loweralkyl, and
    heterocycle wherein the heterocycle is unsubstituted or substituted with 1, 2, or 3 substituents independently selected from the group consisting of loweralkyl,
  (dd) sulfhydryl, and
  (ee) thioalkoxy,
(5) cycloalkyl wherein the cycloalkyl is unsubstituted or substituted with 1, 2, 3, 4 or 5 substituents selected from the group consisting of
  (a) alkoxy,
  (b) aryl,
  (c) arylalkoxy
  (d) aryloxy wherein the aryloxy is unsubstituted or substituted with 1, 2, 3, 4, or 5 substituents selected from the group consisting of halogen,
  (e) loweralkyl,
  (f) halogen,
  (g) NR$^{R3}$R$^{R3'}$,
  (h) oxo, and
  (i)

(6) cycloalkenyl wherein the cycloalkenyl is unsubstituted or substituted with 1, 2, 3 or 4 substituents independently selected from the group consisting of
  (a) loweralkyl,
  (b) alkoxy,
  (c) halogen,
  (d) aryl, (e) aryloxy,
(f) alkanoyl, and
(g) $NR^{R3}R^{R3'}$,
(7)

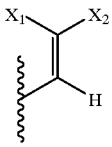

wherein $X_1$ and $X_2$ together are cycloalkyl wherein the cycloalkyl is unsubstituted or substituted with 1 or 2 substituents selected from the group consisting of aryl, and (8) —$P(W)R^{R3}R^{R3'}$; and $R_4$ is selected from the group consisting of
(1) hydrogen,
(2) loweralkyl,
(3) haloalkyl
(4) halogen,
(5) aryl,
(6) arylalkyl,
(7) heterocycle,
(8) (heterocyclic)alkyl
(9) alkoxy, and
(10) —NRR'; or $L_1$, Z, and $R_3$ together are selected from the group consisting of
(1) aminoalkyl,
(1) haloalkyl,
(2) halogen,
(3) carboxaldehyde, and
(4) (carboxaldehyde)alkyl, and
(5) hydroxyalkyl, with the proviso that when $L_1$, Z, and $R_3$ together are (1)–(5), $R_1$ is other than hydrogen.

In a further aspect of the present invention are disclosed pharmaceutical compositions which comprise a compound of formula I in combination with a pharmaceutically acceptable carrier.

In yet another aspect of the present invention are disclosed pharmaceutical compositions which comprise a compound of formula I in combination with another chemotherapeutic agent and a pharmaceutically acceptable carrier.

In yet another aspect of the present invention is disclosed a method for inhibiting protein isoprenyl transferases (i.e., protein farnesyltransferase and/or geranylgeranyltransferase) in a human or lower mammal, comprising administering to the patient a therapeutically effective amount of a compound compound of formula I.

In yet another aspect of the present invention is disclosed a method for inhibiting post-translational modification of the oncogenic Ras protein by protein farnesyltransferase, protein geranylgeranyltransferase or both.

In yet another aspect of the present invention is disclosed a method for treatment of conditions mediated by farnesylated or geranylgeranylated proteins, for example, treatment of Ras associated tumors in humans and other mammals.

In yet another aspect of the present invention is disclosed a method for inhibiting or treating cancer in a human or lower mammal comprising administering to the patient a therapeutically effective amount of a compound of the invention alone or in combination with another chemotherapeutic agent In yet another aspect of the present invention is disclosed a method for treating or preventing intimal hyperplasia associated with restenosis and atherosclerosis in a mammal comprising administering to the mammal a therapeutically effective amount of a compound of claim 1.

The compounds of the invention can comprise asymmetrically substituted carbon atoms. As a result, all stereoisomers of the compounds of the invention are meant to be included in the invention, including racemic mixtures, mixtures of diastereomers, as well as single diastereomers of the compounds of the invention. The terms "S" and "R" configuration, as used herein, are as defined by the IUPAC 1974 Recommendations for Section E, Fundamental Stereochemistry, Pure Appl. Chem. (1976) 45, 13–30, which is hereby incorporated herein by reference.

DETAILED DESCRIPTION

Definitions of Terms

As used herein the terms "Cys," "Glu," "Leu," "Lys," "Met," "nor-Leu," "nor-Val," "Phe," "Ser" and "Val" refer to cysteine, glutamine, leucine, lysine, methionine, norleucine, norvaline, phenylalanine, serine and valine in their L-, D- or DL forms. As used herein these amino acids are in their naturally occuring L- form.

As used herein, the term "carboxy protecting group" refers to a carboxylic acid protecting ester group employed to block or protect the carboxylic acid functionality while the reactions involving other functional sites of the compound are carried out. Carboxy protecting groups are disclosed in Greene, "Protective Groups in Organic Synthesis" pp. 152–186 (1981), which is hereby incorporated herein by reference. In addition, a carboxy protecting group can be used as a prodrug whereby the carboxy protecting group can be readily cleaved in vivo (for example by enzymatic hydrolysis) to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy protecting groups are well known to those skilled in the art, having been extensively used in the protection of carboxyl groups in the penicillin and cephalosporin fields (as described in U.S. Pat. Nos. 3,840,556 and 3,719,667, the disclosures of which are hereby incorporated herein by reference). Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy protecting groups are $C_1$ to $C_8$ loweralkyl (e.g., methyl, ethyl or tertiary butyl and the like); arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl or cycloalkyloxycarbonylalkyl, such as methoxycarbonylmethyl, cyclohexyloxycarbonylmethyl, 1-methoxycarbonyl-1-ethyl, and the like; alkoxycarbonyloxyalkyl or cycloalkyloxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl, such as 2-(phenoxycarbonyloxy)ethyl, 2-(5-indanyloxycarbonyloxy)ethyl and the like; alkoxyalkylcarbonyloxyalkyl, such as 2-(1-methoxy-2-methylpropan-2-oyloxy)ethyl and like; arylalkyloxycarbonyloxyalkyl, such as 2-(benzyloxycarbonyloxy)ethyl and the like; arylalkenyloxycarbonyloxyalkyl, such as 2-(3-phenylpropen-2-yloxycarbonyloxy)ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen4-yl)alkyl, such as (5-phenyl-2-oxo-1,3-dioxolen-4-yl)methyl and the like.

Preferred carboxy-protected compounds of the invention are compounds wherein the protected carboxy group is a loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated herein by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, a,a-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "alkanoyl" as used herein refers to $R_{29}C(O)$— wherein $R_{29}$ is a loweralkyl group. The alkanoyl groups of this invention can be optionally substituted.

The term "alkanoylaminoalkyl" as used herein refers to a loweralkyl radical to which is appended $R_{71}$—NH— wherein $R_{71}$ is an alkanoyl group. The alkanoylarninoalkyl groups of this invention can be optionally substituted.

The term "alkanoyloxy" as used herein refers to $R_{29}C(O)$—O— wherein $R_{29}$ is a loweralkyl group. The alkanoyloxy groups of this invention can be optionally substituted.

The term "alkanoyloxyalkyl" as used herein refers to a loweralkyl radical to which is appended an alkanoyloxy group. The alkanoyloxyalkyl groups of this invention can be optionally substituted.

The term "alkenyl" as used herein refers to a straight or branched chain hydrocarbon containing from 2 to 10 carbon atoms and also containing at least one carbon-carbon double bond. Examples of alkenyl include —CH=CH$_2$, —CH$_2$CH=CH$_2$, —C(CH$_3$)=CH$_2$, —CH$_2$CH=CHCH$_3$, and the like. The alkenyl groups of this invention can be optionally substituted.

The term "alkenylene" as used herein refers to a divalent group derived from a straight or branched chain hydrocarbon containing from 2 to 20 carbon atoms and also containing at least one carbon-carbon double bond. Examples of alkenylene include —CH=CH—, —CH$_2$CH=CH—, —C(CH$_3$)=CH—, —CH$_2$CH=CHCH$_2$—, and the like. The alkenylene groups of this invention can be optionally substituted.

The term "alkenyloxy" as used herein refers to an alkenyl group attached to the parent molecular group through an oxygen atom. The alkenyloxy groups of this invention can be optionally substituted.

The term "alkenyloxyalkyl" as used herein refers to a loweralkyl group to which is attached an alkenyloxy group. The alkenyloxyalkyl groups of this invention can be optionally substituted.

The term "alkoxy" as used herein refers to $R_{30}O$— wherein $R_{30}$ is loweralkyl as defined above. Representative examples of alkoxy groups include methoxy, ethoxy, t-butoxy and the like. The alkoxy groups of this invention can be optionally substituted.

The term "alkoxyalkyl" as used herein refers to a loweralkyl group to which is attached an alkoxy group. The alkoxyalkyl groups of this invention can be optionally substituted.

The term "alkoxyalkoxy" as used herein refers to $R_{31}O$—$R_{32}O$— wherein $R_{31}$ is loweralkyl as defined above and $R_{32}$ is an alkylene radical. Representative examples of alkoxyalkoxy groups include methoxymethoxy, ethoxymethoxy, t-butoxymethoxy and the like. The alkoxyalkoxy groups of this invention can be optionally substituted.

The term "alkoxyalkyl" as used herein refers to an alkoxy group as previously defined appended to an alkyl group as previously defined. Examples of alkoxyalkyl include, but are not limited to, methoxymethyl, methoxyethyl, isopropoxymethyl and the like. The alkoxyalkyl groups of this invention can be optionally substituted.

The term "alkoxyalkylcarbonyloxyalkyl" as used herein refers to a loweralkyl radical to which is appended $R_{66}$—C(O)—O— wherein $R_{66}$ is an alkoxyalkyl group.

The term "alkoxyarylalkyl" as used herein refers to a an arylalkyl group to which is attached an alkoxy group. The alkoxyarylalkyl groups of this invention can be optionally substituted.

The term "alkoxycarbonyl" as used herein refers to an alkoxy group as previously defined appended to the parent molecular moiety through a carbonyl group. Examples of alkoxycarbonyl include methoxycarbonyl, ethoxycarbonyl, isopropoxycarbonyl and the like. The alkoxycarbonyl groups of this invention can be optionally substituted. The alkoxycarbonyl groups of this invention can be optionally substituted.

The term "alkoxycarbonylalkyl" as used herein refers to an alkoxylcarbonyl group as previously defined appended to a loweralkyl radical. Examples of alkoxycarbonylaikyl include methoxycarbonylmethyl, 2-ethoxycarbonylethyl and the like. The alkoxycarbonylalkyl groups of this invention can be optionally substituted.

The term "alkoxycarbonylaminoalkyl" as used herein refers to a loweralkyl radical to which is appended $R_{69}$—NH— wherein $R_{69}$ is an alkoxycarbonyl group. The alkoxycarbonylaminoalkyl groups of this invention can be optionally substituted.

The term "alkoxycarbonyloxyalkyl" as used herein refers to a loweralkyl radical to which is appended $R_{63}$—O— wherein $R_{63}$ is an alkoxycarbonyl group. The alkoxycarbonyloxyalkyl groups of this invention can be optionally substituted.

The term "alkylamino" as used herein refers to $R_{35}$NH— wherein $R_{35}$ is a loweralkyl group, for example, methylamino, ethylamino, butylamino, and the like. The alkylamino groups of this invention can be optionally substituted.

The term "alkylaminoalkyl" as used herein refers a loweralkyl radical to which is appended an alkylamino group. The alkylaminoalkyl groups of this invention can be optionally substituted.

The term "alkylaminocarbonylaminoalkyl" as used herein refers to a loweralkyl radical to which is appended $R_{70}$—C(O)—NH— wherein $R_{70}$ is an alkylamino group. The alkylaminocarbonylaminoalkyl groups of this invention can be optionally substituted.

The term "alkylene" as used herein refers to a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like. The alkylene groups of this invention can be optionally substituted.

The term "alkylsilyloxy" as used herein refers to a loweralkyl group to which is attached —OSi$R_W R_X R_Y$ wherein $R_W$, $R_X$, and $R_Y$ are selected from the group consisting of loweralkyl.

The term "alkylsulfinyl" as used herein refers to $R_{33}$S(O)— wherein $R_{33}$ is a loweralkyl group. The alkylsulfinyl groups of this invention can be optionally substituted.

The term "alkylsulfinylalkyl" as used herein refers to an alkyl group to which is attached a alkylsulfinyl group. The alkylsulfinylalkyl groups of this invention can be optionally substituted.

The term "alkylsulfonyl" as used herein refers to $R_{34}$S(O)$_2$— wherein $R_{34}$ is a loweralkyl group. The alkylsulfonyl groups of this invention can be optionally substituted.

The term "alkylsulfonylalkyl" as used herein refers to a loweralkyl radical to which is appended an alkylsulfonyl group. The alkylsulfonylalkyl groups of this invention can be optionally substituted.

The term alkylthioalkyl as used herein refers to a lower alkyl group as defined herein attached to the parent molecular moiety through a sulfur atom and an alkylene group. The alkylthioalkyl groups of this invention can be optionally substituted.

The term "alkynyl" as used herein refers to a straight or branched chain hydrocarbon containing from 2 to 10 carbon atoms and also containing at least one carbon-carbon triple bond. Examples of alkynyl include —C≡CH, —CH$_2$C≡CH, —CH$_2$C≡CCH$_3$, and the like. The alkynyl groups of this invention can be optionally substituted.

The term "alkynylene" as used herein refers to a divalent group derived from a straight or branched chain hydrocarbon containing from 2 to 10 carbon atoms and also containing at least one carbon-carbon triple bond. Examples of alkynylene include —C≡C—, —CH$_2$C≡C—, —CH$_2$C≡CCH$_2$—, and the like. The alkynylene groups of this invention can be optionally substituted.

The term "amino" as used herein refers to —NH$_2$.

The term "aminocarbonyl" as used herein refers to an amino group attached to the parent molecular group through a carbonyl group. The aminocarbonyl groups of this invention can be optionally substituted.

The term "aminocarbonylalkyl" as used herein refers to an alkyl group to which is attached an aminocarbonyl group. The aminocarbonylalkyl groups of this invention can be optionally substituted.

The term "aminoalkyl" as used herein refers to a loweralkyl radical to which is appended an amino group. The aminoalkyl groups of this invention can be optionally substituted.

The term "aminothiocarbonyl" as used herein refers to an amino group attached to the parent molecular group through a thiocarbonylcarbonyl (C=S) group. The aminothiocarbonyl groups of this invention can be optionally substituted.

The term "aroyloxyalkyl" as used herein refers to a loweralkyl radical to which is appended an aroyloxy group (i.e., $R_{61}$—C(O)O— wherein $R_{61}$ is an aryl group). The aroyloxyalkyl groups of this invention can be optionally substituted.

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups (including bicyclic aryl groups) can be unsubstituted or substituted with one, two or three substituents independently selected from loweralkyl, haloalkyl, alkoxy, thioalkoxy, amino, alkylamino, dialkylamino, hydroxy, halo, mercapto, sulfhydryl, nitro, cyano, carboxaldehyde, carboxy, alkoxycarbonyl, haloalkyl-C(O)—NH—, haloalkenyl-C(O)—NH— and carboxanide. In addition, substituted aryl groups include tetrafluorophenyl and pentafluorophenyl.

The term "arylalkenyl" as used herein refers to an alkenyl radical to which is appended an aryl group. The arylalkenyl groups of this invention can be optionally substituted.

The term "arylalkenyloxycarbonyloxyalkyl" as used herein refers to a loweralkyl radical to which is appended $R_{68}$—O—C(Q)—O— wherein $R_{68}$ is an arylalkenyl group. The arylalkenyloxycarbonyloxyalkyl groups of this invention can be optionally substituted.

The term "arylalkoxy" as used herein refers to an alkoxy group to which is attached an aryl group. The arylalkoxy groups of this invention can be optionally substituted.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like. The arylalkyl groups of this invention can be optionally substituted.

The term "arylalkylcarbonyloxyalkyl" as used herein refers to a loweralkyl radical to which is appended an arylalkylcarbonyloxy group (i.e., $R_{62}$C(O)O— wherein $R_{62}$ is an arylalkyl group). The arylalkylcarbonyloxyalkyl groups of this invention can be optionally substituted.

The term "aryloxy" as used herein refers to an aryl group attached to the parent molecular group through an oxygen atom. The aryloxy groups of this invention can be optionally substituted.

The term "aryloxycarbonyl" as used herein refers to an aryloxy group attached to the parent molecular group through a carbonyl group. The aryloxycarbonyl groups of this invention can be optionally substituted.

The term "aryloyl" as used herein refers to an aryl group attached to the parent molecular group through a carbonyl group. The aryloyl groups of this invention can be optionally substituted.

The term "arylalkyloxycarbonyloxyalkyl" as used herein refers to a loweralkyl radical to which is appended $R_{67}$—O—C(O)—O— wherein $R_{67}$ is an arylalkyl group. The arylalkyloxycarbonyloxyalkyl groups of this invention can be optionally substituted.

The term "aryloxyalkyl" as used herein refers to a loweralkyl radical to which is appended $R_{65}$—O— wherein $R_{65}$ is an aryl group. The aryloxyalkyl groups of this invention can be optionally substituted.

The term "arylalkoxy" as used herein refers to an alkoxy radical to which is appended $R_{65}$—O— wherein $R_{65}$ is an aryl group. The arylalkoxy groups of this invention can be optionally substituted.

The term "arylalkyloxyalkyl" as used herein refers to a loweralkyl radical to which is appended an arylalkoxy group. The arylalkyloxyalkyl groups of this invention can be optionally substituted.

The term "aryloxy" as used herein refers to $R_{65}$—O— wherein $R_{65}$ is an aryl group. The aryloxy groups of this invention can be optionally substituted. The aryloxy groups of this invention can be optionally substituted.

The term "(aryl)oyl" as used herein refers to an aryl group attached to the parent molecular group through a carbonyl group. The (aryl)oyl groups of this invention can be optionally substituted.

The term "aryloxythioalkoxyalkyl" as used herein refers to a loweralkyl radical to which is appended $R_{75}$—S— wherein $R_{75}$ is an aryloxyalkyl group. The aryloxythioalkoxyalkyl groups of this invention can be optionally substituted.

The term "aryloxycarbonyloxyalkyl" as used herein refers to a loweralkyl radical to which is appended $R_{65}$—O—C(O)—O— wherein $R_{65}$ is an aryl group. The aryloxycarbonyloxyalkyl groups of this invention can be optionally substituted.

The term "arylsulfonyl" as used herein refers to $R_{36}$S(O)$_2$— wherein $R_{36}$ is an aryl 1065 group. The arylsulfonyl groups of this invention can be optionally substituted.

The term "arylsulfonyloxy" as used herein refers to $R_{37}$S(O)$_2$O— wherein $R_{37}$ is an aryl group. The arylsulfonyloxy groups of this invention can be optionally substituted.

The term "carboxy" as used herein refers to —COOH.

The term "carboxyalkyl" as used herein refers to a loweralkyl radical to which is appended a carboxy (—COOH) group. The carboxyalkyl groups of this invention can be optionally substituted.

The term "cyanoalkyl" as used herein used herein refers to a loweralkyl radical to which is appended a cyano (—CN) group. The cyanoalkyl groups of this invention can be optionally substituted.

The term "carboxaldehyde" as used herein used herein refers to —CHO.

The term "(carboxaldehyde)alkyl" as used herein refers to a carboxaldehyde group attached to a loweralkyl group. The (carboxaldehyde)alkyl groups of this invention can be optionally substituted.

The terms "cycloalkanoyl" and "(cycloalkyl)oyl" refer to a cycloalkyl group attached to the parent molecular group through a carbonyl group. The cycloalkanoyl and (cycloalkyl)oyl groups of this invention can be optionally substituted.

The term "cycloalkanoylalkyl" as used herein refers to a loweralkyl radical to which is appended a cycloalkanoyl group (i.e., $R_{60}$—C(O)— wherein $R_{60}$ is a cycloalkyl group). The cycloalkanoylalkyl groups of this invention can be optionally substituted.

The term "cycloalkylalkoxyalkyl" as used herein refers to an alkoxyalkyl group to which is attached a cycloalkyl group. The cycloalkylalkoxyalkyl groups of this invention can be optionally substituted.

The term "cycloalkenyl" as used herein refers to an alicyclic group comprising from 3 to 10 carbon atoms and containing a carbon-carbon double bond including, but not limited to, cyclopentenyl, cyclohexenyl and the like. The cycloalkenyl groups of this invention can be optionally substituted.

The term "cycloalkoxy" as used herein refers to a cycloalkyl group attached to the parent molecular group through an oxygen atom. The cycloalkoxy groups of this invention can be optionally substituted.

The term "cycloalkoxyalkyl" as used herein refers to a loweralkyl group to which is attached a cycloalkoxy group. The cycloalkoxyalkyl groups of this invention can be optionally substituted.

The term "cycloalkoxycarbonyl" as used herein refers to a cycloalkoxy group attached to the parent molecular group through a carbonyl group. The cycloalkoxycarbonyl groups of this invention can be optionally substituted.

The term "cycloalkyl" as used herein refers to an alicyclic group comprising from 3 to 10 carbon atoms including, but not limited to, cyclopropyl, cyclobutyl, cyclopentyl, cyclohexyl, norbornyl, adamantyl and the like. The cycloalkyl groups of this invention can be optionally substituted. The cycloalkyl groups of this invention can be optionally substituted.

The term "cycloalkylaminocarbonyl" as used herein refers to NHR$_{60'}$C(O)— wherein $R_{60'}$ is a cycloalkyl group. The cycloalkylaminocarbonyl groups of this invention can be optionally substituted.

The term "cycloalkylaminothiocarbonyl" as used herein refers to NHR$_{60'}$C(S)— wherein $R_{60'}$ is defined above. The cycloalkylarinothiocarbonyl groups of this invention can be optionally substituted.

The term "cycloalkylalkoxy" as used herein refers to an alkoxy radical to which is appended a cycloalkyl group. The cycloalkylalkoxy groups of this invention can be optionally substituted.

The term "cycloalkylalkoxyalkyl" as used herein refers to an alkyl radical to which is appended a cycloalkylalkoxy group. The cycloalkylalkoxyalkyl groups of this invention can be optionally substituted.

The term "cycloalkylalkoxycarbonyl" as used herein refers to a cycloalkylalkoxy radical attached to the parent molecular group through a carbonyl group. The cycloalkylalkoxycarbonyl groups of this invention can be optionally substituted.

The term "cycloalkylalkyl" as used herein refers to a loweralkyl radical to which is appended a cycloalkyl group. Representative examples of cycloalkylalkyl include cyclopropylmethyl, cyclohexylmethyl, 2-(cyclopropyl)ethyl, adamantylmethyl and the like. The cycloalkylalkyl groups of this invention can be optionally substituted.

The term "cycloalkyloxycarbonyloxyalkyl" as used herein refers to a loweralkyl radical to which is appended $R_{64}$—O—C(O)—O— wherein $R_{64}$ is a cycloalkyl group. The cycloalkyloxycarbonyloxyalkyl groups of this invention can be optionally substituted.

The term "dialkoxyalkyl" as used herein refers to a loweralkyl radical to which is appended two alkoxy groups. The dialkoxyalkyl groups of this invention can be optionally substituted.

The term "dialkylamino" as used herein refers to $R_{38}R_{39}N$— wherein $R_{38}$ and $R_{39}$ are independently selected from loweralkyl, for example dimethylamino, diethylamino, methyl propylamino, and the like. The dialkylamino groups of this invention can be optionally substituted.

The term "dialkylaminoalkyl" as used herein refers to a loweralkyl radical to which is appended a dialkylamino group. The dialkylaminoalkyl groups of this invention can be optionally substituted.

The term "dialkyaminocarbonylalkyl" as used herein refers to a loweralkyl radical to which is appended $R_{73}$—C(O)— wherein $R_{73}$ is a dialkylamino group. The dialkyaminocarbonylalkyl groups of this invention can be optionally substituted.

The term "dioxoalkyl" as used herein refers to a loweralkyl radical which is substituted with two oxo (=O) groups. The dioxoalkyl groups of this invention can be optionally substituted.

The term "dithioalkoxyalkyl" as used herein refers to a loweralkyl radical to which is appended two thioalkoxy groups. The dithioalkoxyalkyl groups of this invention can be optionally substituted.

The term "halogen" or "halo" as used herein refers to I, Br, Cl or F.

The term "haloalkenyl" as used herein refers to an alkenyl radical, as defined above, bearing at least one halogen substituent. The haloalkenyl groups of this invention can be optionally substituted.

The term "haloalkyl" as used herein refers to a lower alkyl radical, as defined above, bearing at least one halogen substituent, for example, chloromethyl, fluoroethyl or trifluoromethyl and the like. Haloalkyl can also include perfluoroalkyl wherein all hydrogens of a loweralkyl group are replaced with fluorides.

The term "heterocyclic ring" or "heterocyclic" or "heterocycle" as used herein refers to a 5-, 6- or 7-membered ring containing one, two or three heteroatoms independently selected from the group consisting of nitrogen, oxygen and sulfur or a 5-membered ring containing 4 nitrogen atoms; and includes a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; two sulfur atoms in non-adjacent positions; two sulfur atoms in adjacent positions and one nitrogen atom; two adjacent nitrogen atoms and one sulfur atom; two non-adjacent nitrogen atoms and one sulfur atom; two non-adjacent nitrogen atoms and one oxygen atom. The 5-membered ring has 0–2 double bonds and the 6- and 7-membered rings have 0–3 double bonds. The term "heterocyclic" also includes bicyclic, tricyclic and tetracyclic groups in which any of the above heterocyclic rings is fused to one or two rings independently selected from the group consisting of an aryl ring, a cyclohexane ring, a cyclohexene ring, a cyclopentane ring, a cyclopentene ring and another monocyclic heterocyclic ring (for example, indolyl, quinolyl, isoquinolyl, tetrahydroquinolyl, benzofuryl or benzothienyl and the like). Heterocyclics include: pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, oxadiazolyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl and benzothienyl. Heterocyclics also include bridged bicyclic groups wherein a monocyclic heterocyclic group is bridged by an alkylene group, for example,

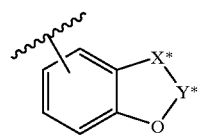

and the like.

Heterocyclics also include compounds of the formula

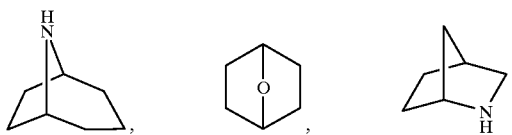

wherein X* is —CH$_2$—, —CH$_2$O— or —O— and Y* is —C(O)— or —(C(R")$_2$)$_v$— wherein R" is hydrogen or C$_1$–C$_4$-alkyl and v is 1, 2 or 3 such as 1,3-benzodioxolyl, 1,4-benzodioxanyl and the like.

Heterocyclics can be unsubstituted or substituted with one, two, three, four or five substituents independently selected from the group consisting of
a) hydroxy, b) —SH, c) halo, d) oxo (=O), e) thioxo (=S), f) amino, g) —NHOH, h) alkylamino, i) dialkylamino, j) alkoxy, k) alkoxyalkoxy, l) haloalkyl, m) hydroxyalkyl, n) alkoxyalkyl, o) cycloalkyl which is unsubstituted or substituted with one, two, three or four loweralkyl groups, p) cycloalkenyl which is unsubstituted or substituted with one, two, three or four loweralkyl groups, q) alkenyl, r) alkynyl, s) aryl, t) arylalkyl, u) —COOH, v) —SO$_3$H, w) loweralkyl, x) alkoxycarbonyl, y) —C(O)NH$_2$, z) —C(S)NH$_2$, aa) —C(=N—OH)NH$_2$, bb) aryl-L$_{16}$—C(O)— wherein L$_{16}$ is an alkenylene radical, cc) —S—L$_{17}$—C(O)OR$_{40}$ wherein L$_{17}$ is an alkylene radical which is unsubstituted or substituted with one or two substituents independently selected from the group consisting of alkanoyl, oxo (=O) or methinylamino (=CHNR$_{41}$R$_{42}$ wherein R$_{41}$ is hydrogen or loweralkyl and R$_{42}$ is loweralkyl) and R$_{40}$ is hydrogen or a carboxy-protecting group, dd) —S—L$_{18}$—C(O)NR$_{43}$R$_{44}$ wherein L$_{18}$ is an alkylene radical which is unsubstituted or substituted with one or two substituents independently selected from the group consisting of alkanoyl, oxo (=O) or methinylamino (=CHNR$_{41}$R$_{42}$ wherein R$_{41}$ is hydrogen or loweralkyl and R$_{43}$ and R$_{44}$ are independently selected from the group consisting of hydrogen, loweralkyl and aryl, ee) —S—L$_{19}$—CN wherein L$_{19}$ is an alkylene radical, ff) —S—L$_{20}$—R$_{45}$ wherein L$_{20}$ is absent or is an alkylene radical or an alkenylene radical or an alkynylene radical wherein the alkylene, alkenylene or alkynylene radical is unsubstituted or substituted with oxo (=O) and R$_{45}$ is hydrogen, aryl, arylalkyl or heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, gg) —O—L$_{21}$—R$_{46}$ wherein L$_{21}$ is absent or is an alkylene radical or an alkenylene radical or an alkenylene radical wherein the alkylene, alkenylene or alkynylene radical is unsubstituted or substituted with one or two substituents independently selected from the group consisting of alkanoyl, oxo (=O) or methinylamino (=CHNR$_{41}$R$_{42}$ wherein R$_{41}$ is hydrogen or loweralkyl and R$_{46}$ is hydrogen, aryl, arylalkyl or heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, hh) —O—S(O)$_2$—R$_{47}$ wherein R$_{47}$ is aryl, arylalkyl, heterocyclic or heterocyclicalkyl wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, ii) —S(O)$_2$—NH—R$_{48}$ wherein R$_{48}$ is aryl, arylalkyl, heterocyclic or heterocyclicalkyl wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, jj) alkylsulfinyl, kk) alkylsulfonyl, ll) arylsulfonyl, mm) arylsulfonyloxy, nn) —C(=NOR$_{49}$)C(O)OR$_{50}$ wherein R$_{49}$ is hydrogen or loweralkyl and R$_{50}$ is hydrogen or a carboxy-protecting group, oo) alkoxycarbonylalkyl, pp) carboxyalkyl, qq) cyanoalkyl, rr) alkylaminoalkyl, ss) N-protected alkylaminoalkyl, tt) dialkylaminoalkyl, uu) dioxoalkyl, vv) loweralkyl-C(O)—, ww) loweralkyl-C(S)—, xx) aryl-C(O)—, yy) aryl-C(S)—, zz) loweralkyl-C(O)—O—, aaa) loweralkyl-S—C(S)— bbb) N-protected amino, ccc) aminoalkyl-C(O)—, dddd) N-protected aminoalkyl-C(O)— eee) aminoalkyl-C(S)—, fff) N-protected aminoalkyl-C(S)—, ggg) aminoalkyl, hhh) N-protected aminoalkyl, iii) formyl, jjj) cyano, kkk) nitro, lll) spiroalkyl, mmm) oxoalkyloxy, nnn) R$_{53}$—L$_{22}$—, wherein L$_{22}$ is alkenylene or alkynylene and R$_{53}$ is aryl or heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, ooo) aryl-NH—C(O)—, ppp) R$_{54}$—N=N— wherein R$_{54}$ is aryl or heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, qqq) =N—R$_{55}$ wherein R$_{55}$ is hydrogen, aryl, heterocyclic, —S(O)$_2$-aryl or —S(O)$_2$-heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, rrr) diarylalkyl-N=N—, sss) aryl-N(R$_{56}$)— or arylalkyl-N(R$_{56}$)— wherein R$_{56}$ is hydrogen or an N-protecting group, ttt) aryl-sulfonylalkyl, uuu) heterocyclicsulfonylalkyl wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, vvv) =C(CN)(C(O)NH$_2$), www) =C(CN)(C(O)O-loweralkyl), xxx) heterocyclic or heterocyclicalkyl wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, yyy) hydroxythioalkoxy, zzz) aryloxyalkyl, aaaa) aryloxyalkylthioalkoxy, bbbb) dialkoxyalkyl, cccc) dithioalkoxyalkyl, dddd) arylalkyl-NH—L$_{23}$— wherein L$_{23}$ is an alkylene group, eeee) heterocyclicalkyl-NH—L$_{24}$— wherein L$_{24}$ is an alkylene group, ffff) aryl-S(O)$_2$—NH—L$_{25}$— wherein L$_{25}$ is an alkylene group, gggg) heterocyclic-S(O)$_2$—NH—L$_{26}$— wherein L$_{26}$ is an alkylene group, hhhh) aryl-C(O)—NH—L$_{27}$— wherein L$_{27}$ is an alkylene group and iiii) heterocyclic-C(O)—NH—L$_{28}$— wherein L$_{28}$ is an alkylene group, jjjj) R$_{yy}$(CH$_2$)$_n$—X—Y—Z—(CH$_2$)$_m$ wherein R$_{yy}$ is cycloalkyl, aryl and loweralkyl, n amd m are independently 0–2, Z is O or absent, Y is absent, CH$_2$, CHOH or C(O), with the proviso that when X is O, Z is absent and with the proviso that when Z is O, X is absent and with the proviso that when Y is CHOH, X and Z are absent.

The term "(heterocyclic)alkoxy" as used herein refers to an alkoxy group to which is attached a heterocycle. The (heterocyclic)alkoxy groups of this invention can be optionally substituted.

The term "(heterocyclic)alkyl" as used herein refers to a heterocyclic group as defined above appended to a loweralkyl radical as defined above. Examples of heterocyclic alkyl include 2-pyridylmethyl, 4-pyridylmethyl, 4-quinolinylmethyl and the like. The (heterocyclic)alkyl groups of this invention can be optionally substituted.

The term "(heterocyclic)oxy" as used herein refers to a heterocycle connected to the parent molecular group through an oxygen atom. The (heterocyclic)oxy groups of this invention can be optionally substituted. The term "(heterocyclic) oxyalkyl" as used herein refers to a loweralkyl group to which is attached a (heterocyclic)oxy group. The (heterocyclic)oxyalkyl groups of this invention can be optionally substituted.

The term "(heterocyclic)alkoxyalkyl" as used herein refers to an alkoxyalkyl group to which is attached a heterocycle. The (heterocyclic)alkoxyalkyl groups of this invention can be optionally substituted.

The term "heterocycliccarbonyloxyalkyl" as used herein refers to a loweralkyl radical to which is appended $R_{72}$—C(O)—O— wherein $R_{72}$ is a heterocyclic group. The heterocycliccarbonyloxyalkyl groups of this invention can be optionally substituted.

The term "hydroxy" as used herein refers to —OH.

The term "hydroxyalkyl" as used herein refers to a loweralkyl radical to which is appended an hydroxy group. The hydroxyalkyl groups of this invention can be optionally substituted.

The term "hydroxyarylalkyl" as used herein refers to a arylalkyl group to which is appended a hydroxy group. The hydroxyarylalkyl groups of this invention can be optionally substituted.

The term "hydroxythioalkoxy" as used herein refers to $R_{51}S_{13}$ wherein $R_{51}$ is a hydroxyalkyl group. The hydroxythioalkoxy groups of this invention can be optionally substituted.

The term "loweralkyl" as used herein refers to branched or straight chain alkyl groups comprising one to ten carbon atoms, including methyl, ethyl, propyl, isopropyl, n-butyl, t-butyl, neopentyl and the like. The loweralkyl groups of this invention can be optionally substituted.

The term "N-protected alkylarninoalkyl" as used herein refers to an alkylaminoalkyl group wherein the nitrogen is N-protected. The N-protected alkylaminoalkyl groups of this invention can be optionally substituted.

The term "nitro" as used herein refers to —NO$_2$.

The term "oxo" as used herein refers to (=O).

The term "oxoalkyloxyl" as used herein refers to an alkoxy radical wherein the loweralkyl moiety is substituted with an oxo (=O) group. The oxoalkyloxy groups of this invention can be optionally substituted.

The term "oxyamino(alkyl)carbonylalkyl" as used herein refers to a —O—NR—C(O)—R' group wherein R and R' are loweralkyl.

The term "oxyarnino(arylalkyl)carbonylalkyl" as used herein refers to a —O—NR$^R$3—C(O)—R group wherein R$^R$3 is arylalkyl and R is loweralkyl.

The term "oxyaminocarbonylalkyl" as used herein refers to —O—NH—C(O)—R group wherein R is loweralkyl.

The term "spiroalkyl" as used herein refers to an alkylene diradical, both ends of which are bonded to the same carbon atom of the parent group to form a spirocyclic group. The spiroalkyl groups of this invention can be optionally substituted.

The term "sulfhydryl" as used herein refers to —SH.

The term "sulfhydrylalkyl" as used herein refers to a loweralkyl group to which is attached a sulfhydryl group. The sulfhydrylalkyl groups of this invention can be optionally substituted.

The term "thioalkoxy" as used herein refers to $R_{52}S$— wherein $R_{52}$ is loweralkyl. Examples of thioalkoxy include, but are not limited to, methylthio, ethylthio and the like. The thioalkoxy groups of this invention can be optionally substituted.

The term "thioalkoxyalkyl" as used herein refers to a thioalkoxy group as previously defined appended to a loweralkyl group as previously defined. Examples of thioalkoxyalkyl include thiomethoxymethyl, 2-thiomethoxyethyl and the like. The thioalkoxyalkyl groups of this invention can be optionally substituted.

The term "thiocycloalkoxy" as used herein refers to a cycloalkyl group attached to the parent molecular group through a sulfur atom. The thiocycloalkoxy groups of this invention can be optionally substituted.

The term "thiocycloalkoxyalkyl" as used herein refers to a loweralkyl group to which is attached a thiocycloalkoxy group. The thiocycloalkoxyalkyl groups of this invention can be optionally substituted.

Preferred Embodiments

Preferred compounds of the invention are compounds of formula I wherein $R_1$ is unsubstituted or substituted phenyl and $R_2$ is —C(O)NH—CH($R_{14}$)—C(O)OR$_{15}$ or —C(O)NH—CH($R_{14}$)—C(O)NHSO$_2$R$_{16}$ wherein $L_2$, $R_{14}$ $R_{15}$ and $R_{16}$ are defined above.

More preferred compounds of the invention are compounds of formula I wherein $R_1$ is unsubstituted or substituted phenyl and $R_2$ is

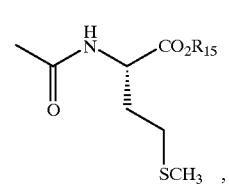

(a)

(b)

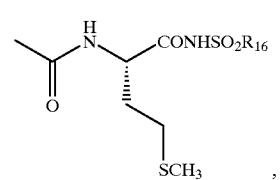

(c)

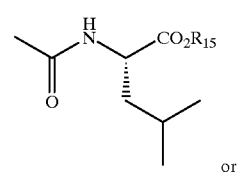

or (d)

(e)

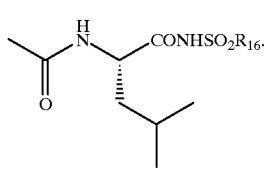

Still more preferred compounds have formula I wherein $R_3$ is selected from the group consisting of (a) pyridyl, (b) imidazolyl, and (c) furyl wherein the pyridyl, imidazolyl, or furyl group may be substituted with 1, 2 or 3 substituents selected from the group consisting of aryl, loweralkyl, halo, nitro, haloalkyl, hydroxy, hydroxyalkyl, amino, N-protected amino, alkoxy, and thioalkoxy.

Still more preferred compounds of the invention have the structure defined immediately above wherein $R_1$ is unsubstituted or substituted phenyl and $R_2$ is (a)

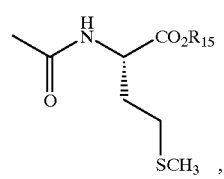

(b)

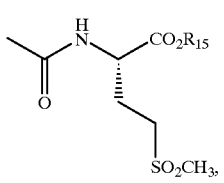

(c)

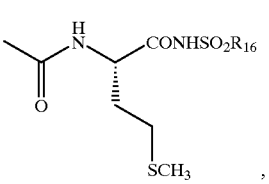

(d)

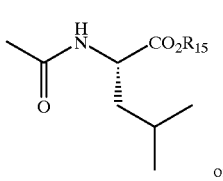

or (e)

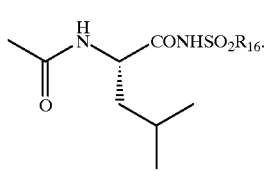

The most preferred compounds have the structure defined immediately above wherein $R_3$ is unsubstituted or substituted pyridyl or imidazolyl.

Protein Farnesyltransferase Inhibition

The ability of the compounds of the invention to inhibit protein farnesyltransferase or protein geranylgeranyltransferase can be measured according to the method of Moores, et al., J. Biol. Chem. 266: 14603 (1991) or the method of Vogt, et al., J. Biol. Chem. 270:660–664 (1995). In addition, procedures for determination of the inhibition of farnesylation of the oncogene protein Ras are described by Goldstein, et al., J. Biol. Chem., 266:15575–15578 (1991) and by Singh in U.S. Pat. No. 5,245,061.

In addition, in vitro inhibition of protein farnesyltransferase may be measured by the following procedure. Rat brain protein farnesyltransferase activity is measured using an Amersham Life Science commercial scintillation proximity assay kit and substituting a biotin-K Ras B fragment (biotin-Lys-Lys-Ser-Lys-Thr-Lys-Cys-Val-Ble-Met-$CO_2H$), 0.1 m$\underline{M}$ final concentration, for the biotin-lamin substrate provided by Amersham. The enzyme is purified according to Reiss, Y., et al., Cell, 62: 81–88 (1990), utilizing steps one through three. The specific activity of the enzyme is approximately 10 nmol substrate farnesylated/mg enzyme/hour. The percent inhibition of the farnesylation caused by the compounds of the invention (at $10 \times 10^{-6}$ $\underline{M}$) compared to an uninhibited control sample is evaluated in the same Amersham test system.

The % inhibition of protein farnesyltransferase was determined for representative compounds of the invention. The results are summarized in Table 1.

Tables 1–5
In Vitro Potencies of Representative Compounds

TABLE 1

| Inhibition of farnesyltransferase | |
|---|---|
| Example | % inhibition at $1 \times 10^{-5}$ $\underline{M}$ |
| 200 | 93 |
| 350 | 53 |
| 351 | 82 |
| 352 | 52 |
| 353 | 62 |
| 354 | 47 |
| 355 | 43 |
| 356 | 58 |
| 357 | 56 |
| 358 | 45 |
| 359 | 36 |
| 360 | 88 |
| 361 | 97 |
| 362 | 83 |
| 363 | 96 |
| 364 | 69 |
| 365 | 97 |
| 366 | 83 |
| 367 | 81 |
| 368 | 71 |
| 369 | 87 |
| 370 | 86 |
| 371 | 66 |
| 372 | 69 |
| 373 | 76 |
| 374 | 61 |
| 375 | 68 |
| 376 | 80 |
| 377 | 71 |
| 378 | 54 |
| 380 | 45 |
| 381 | 79 |
| 382 | >50 |
| 383 | >50 |
| 387 | >50 |
| 388 | >50 |
| 390 | >50 |
| 639 | 44 |

TABLE 1-continued

Inhibition of farnesyltransferase

| Example | % inhibition at $1 \times 10^{-5}$ M |
|---|---|
| 659 | 55 |
| 663 | 43 |
| 664 | 75 |
| 669 | 52 |
| 670 | 78 |
| 672 | 48 |
| 674 | 40 |
| 676 | 76 |
| 678 | 73 |
| 680 | 58 |
| 683 | 57 |
| 684 | 48 |
| 685 | 55 |
| 686 | 48 |
| 687 | 78 |
| 688 | 71 |
| 689 | 73 |
| 690 | 61 |
| 692 | 74 |
| 699 | 74 |
| 700 | 68 |
| 701 | 64 |
| 702 | 79 |
| 704 | 67 |
| 705 | 72 |
| 706 | 53 |
| 707 | 66 |
| 708 | 76 |
| 709 | 55 |
| 710 | 45 |
| 711 | 46 |
| 712 | 69 |
| 713 | 40 |
| 714 | 56 |
| 715 | 67 |
| 717 | 75 |
| 718 | 40 |
| 750 | 44 |
| 752 | 58 |
| 753 | 55 |
| 754 | 40 |
| 755 | 44 |
| 756 | 47 |
| 757 | 58 |
| 758 | 46 |
| 759 | 49 |
| 952 | >50 |
| 955 | 50 |
| 974 | >50 |

TABLE 2

Inhibition of farnesyltransferase

| Example | % inhibition at $1 \times 10^{-6}$ M |
|---|---|
| 157 | 92 |
| 158 | 2 |
| 159 | 84 |
| 160 | 30 |
| 161 | 54 |
| 162 | 12 |
| 163 | 18 |
| 164 | 92 |
| 165 | 74 |
| 166 | 97 |
| 167 | 98 |
| 168 | 92 |
| 183 | 98 |
| 184 | 36 |

TABLE 2-continued

Inhibition of farnesyltransferase

| Example | % inhibition at $1 \times 10^{-6}$ M |
|---|---|
| 185 | 93 |
| 186 | 86 |
| 187 | 68 |
| 188 | 40 |
| 189 | 88 |
| 190 | 4 |
| 191 | 28 |
| 192 | 95 |
| 193 | 4 |
| 196 | 43 |
| 197 | 1 |
| 201 | 63 |
| 202 | 31 |
| 203 | 76 |
| 204 | 98 |
| 205 | 98 |
| 206 | 67 |
| 207 | 98 |
| 208 | 98 |
| 209 | 74 |
| 210 | 5 |
| 211 | 98 |
| 212 | 12 |
| 213 | 98 |
| 214 | 97 |
| 215 | 82 |
| 216 | 67 |
| 217 | 99 |
| 218 | 89 |
| 219 | 56 |
| 220 | 92 |
| 221 | 55 |
| 222 | 41 |
| 223 | 63 |
| 224 | 41 |
| 225 | 93 |
| 226 | 23 |
| 227 | 94 |
| 228 | 39 |
| 231 | 50 |
| 233 | 65 |
| 234 | 4 |
| 235 | 95 |
| 237 | 98 |
| 238 | 22 |
| 239 | 97 |
| 240 | 98 |
| 241 | 41 |
| 242 | 99 |
| 243 | 23 |
| 244 | 21 |
| 245 | 50 |
| 248 | 79 |
| 249 | 77 |
| 250 | 96 |
| 252 | 98 |
| 253 | 99 |
| 254 | 96 |
| 255 | 98 |
| 256 | 98 |
| 257 | 98 |
| 258 | 98 |
| 259 | 98 |
| 260 | 98 |
| 261 | 98 |
| 262 | 98 |
| 263 | 99 |
| 264 | 98 |
| 265 | 98 |
| 266 | 97 |
| 267 | 96 |
| 268 | 98 |
| 269 | 98 |
| 270 | 98 |

TABLE 2-continued

Inhibition of farnesyltransferase

| Example | % inhibition at $1 \times 10^{-6}$ M |
|---|---|
| 271 | 84 |
| 272 | 96 |
| 273 | 96 |
| 274 | 94 |
| 276 | 98 |
| 277 | 98 |
| 278 | 99 |
| 279 | 99 |
| 280 | 98 |
| 281 | 98 |
| 282 | 76 |
| 283 | 98 |
| 284 | 83 |
| 286 | 84 |
| 287 | 24 |
| 288 | 22 |
| 289 | 23 |
| 290 | 74 |
| 291 | 23 |
| 292 | 36 |
| 294 | 98 |
| 295 | 94 |
| 296 | 89 |
| 297 | 65 |
| 298 | 43 |
| 299 | 94 |
| 300 | 22 |
| 301 | 98 |
| 302 | 31 |
| 304 | 99 |
| 305 | 99 |
| 306 | 99 |
| 307 | 82 |
| 308 | 62 |
| 309 | 98 |
| 310 | 98 |
| 311 | 97 |
| 313 | 94 |
| 314 | 97 |
| 315 | 93 |
| 316 | 63 |
| 317 | 54 |
| 318 | 98 |
| 319 | 98 |
| 320 | 93 |
| 321 | 90 |
| 322 | 98 |
| 323 | 98 |
| 324 | 98 |
| 325 | 99 |
| 326 | 91 |
| 327 | 97 |
| 328 | 96 |
| 329 | 98 |
| 330 | 98 |
| 331 | 98 |
| 332 | 26 |
| 333 | 99 |
| 334 | 93 |
| 343 | 72 |
| 344 | 95 |
| 345 | 91 |
| 346 | 98 |
| 347 | 95 |
| 348 | 66 |
| 349 | 99 |
| 379 | 21 |
| 541 | 37 |
| 542 | 67 |
| 544 | 35 |
| 545 | 88 |
| 546 | 97 |
| 547 | 91 |
| 550 | 96 |
| 552 | 88 |
| 553 | 92 |
| 554 | 96 |
| 555 | 85 |
| 556 | 99 |
| 557 | 93 |
| 560 | 91 |
| 561 | 91 |
| 564 | 98 |
| 565 | 94 |
| 566 | 98 |
| 568 | 93 |
| 569 | 91 |
| 572 | 91 |
| 575 | 70 |
| 576 | 88 |
| 577 | 94 |
| 582 | 99 |
| 583 | 98 |
| 587 | 97 |
| 595 | 97 |
| 607 | 96 |
| 610 | 94 |
| 613 | 97 |
| 617 | 99 |
| 620 | 98 |
| 626 | 61 |
| 627 | 85 |
| 632 | 43 |
| 633 | 32 |
| 636 | 72 |
| 641 | 34 |
| 642 | 48 |
| 644 | 54 |
| 386 | >50 |
| 399 | >50 |
| 403 | 99 |
| 404 | 98 |
| 405 | 98 |
| 406 | 95 |
| 407 | 98 |
| 435 | 96 |
| 451 | 85 |
| 452 | 96 |
| 453 | 90 |
| 456 | 81 |
| 457 | 92 |
| 460 | 88 |
| 463 | 91 |
| 465 | 92 |
| 466 | 93 |
| 467 | 97 |
| 468 | 96 |
| 469 | 92 |
| 470 | 95 |
| 471 | 94 |
| 472 | 97 |
| 473 | 96 |
| 474 | 92 |
| 475 | 21 |
| 476 | 91 |
| 477 | 98 |
| 478 | 98 |
| 479 | 95 |
| 480 | 87 |
| 481 | 95 |
| 488 | 41 |
| 494 | 96 |
| 495 | 95 |
| 496 | 93 |
| 497 | 94 |
| 498 | 98 |
| 728 | 78 |

TABLE 2-continued

Inhibition of farnesyltransferase

| Example | % inhibition at $1 \times 10^{-6}$ M |
|---|---|
| 499 | 98 |
| 500 | 98 |
| 501 | 84 |
| 502 | 24 |
| 503 | 57 |
| 504 | 90 |
| 505 | 72 |
| 507 | 95 |
| 507 | 96 |
| 508 | 95 |
| 509 | 77 |
| 510 | 84 |
| 512 | 94 |
| 513 | 96 |
| 514 | 94 |
| 515 | 72 |
| 516 | 95 |
| 525 | 99 |
| 528 | 99 |
| 529 | 99 |
| 530 | 94 |
| 537 | 97 |
| 540 | 40 |
| 645 | 37 |
| 646 | 58 |
| 649 | 86 |
| 650 | 68 |
| 651 | 33 |
| 652 | 41 |
| 653 | 62 |
| 655 | 35 |
| 657 | 32 |
| 658 | 73 |
| 661 | 45 |
| 662 | 68 |
| 665 | 55 |
| 666 | 82 |
| 667 | 83 |
| 671 | 36 |
| 673 | 59 |
| 677 | 37 |
| 682 | 31 |
| 691 | 34 |
| 693 | 53 |
| 694 | 45 |
| 696 | 57 |
| 697 | 39 |
| 703 | 40 |
| 716 | 69 |
| 719 | 90 |
| 720 | 70 |
| 721 | 83 |
| 722 | 96 |
| 723 | 87 |
| 724 | 87 |
| 725 | 78 |
| 726 | 81 |
| 727 | 95 |
| 744 | 84 |
| 749 | 84 |
| 751 | 32 |
| 764 | 88 |
| 765 | 76 |
| 768 | 67 |
| 771 | 72 |
| 772 | 79 |
| 773 | 41 |
| 774 | 48 |
| 775 | 32 |
| 776 | 36 |
| 777 | 83 |
| 782 | 96 |
| 786 | 34 |
| 787 | 70 |

TABLE 2-continued

Inhibition of farnesyltransferase

| Example | % inhibition at $1 \times 10^{-6}$ M |
|---|---|
| 788 | 44 |
| 789 | 86 |
| 790 | 88 |
| 791 | 53 |
| 792 | 88 |
| 793 | 94 |
| 794 | 92 |
| 796 | 35 |
| 797 | 35 |
| 806 | 72 |
| 807 | 90 |
| 808 | 88 |
| 809 | 78 |
| 810 | 89 |
| 812 | 94 |
| 813 | 95 |
| 816 | 87 |
| 824 | 90 |
| 831 | 92 |
| 832 | 80 |
| 834 | 55 |
| 835 | 96 |
| 844 | 92 |
| 846 | 85 |
| 850 | 90 |
| 862 | 95 |
| 866 | 62 |
| 867 | 71 |
| 868 | 89 |
| 872 | 74 |
| 878 | 95 |
| 879 | 95 |
| 886 | 35 |
| 889 | 95 |
| 902 | 85 |
| 903 | 78 |
| 908 | 88 |
| 910 | 42 |
| 911 | 65 |
| 918 | 97 |
| 923 | 78 |
| 924 | 77 |
| 925 | 87 |
| 926 | 69 |
| 936 | 69 |
| 937 | 95 |
| 962 | >50 |
| 964 | >50 |
| 979 | 26 |
| 982 | 64 |
| 987 | 93 |
| 988 | 92 |
| 989 | 88 |

TABLE 3

Inhibition of farnesyltransferase

| Example | % inhibition at $1 \times 10^{-7}$ M |
|---|---|
| 434 | 93 |
| 436 | 89 |
| 437 | 89 |
| 438 | 90 |
| 439 | 80 |
| 440 | 92 |
| 441 | 91 |
| 442 | 88 |
| 443 | 97 |

TABLE 3-continued

Inhibition of farnesyltransferase

| Example | % inhibition at $1 \times 10^{-7}$ M |
|---|---|
| 444 | 95 |
| 445 | 94 |
| 446 | 91 |
| 447 | 91 |
| 448 | 92 |
| 449 | 91 |
| 450 | 96 |
| 455 | 83 |
| 458 | 87 |
| 459 | 92 |
| 461 | 93 |
| 462 | 91 |
| 464 | 86 |
| 482 | 96 |
| 483 | 95 |
| 484 | 97 |
| 485 | 96 |
| 486 | 97 |
| 487 | 81 |
| 489 | 86 |
| 490 | 70 |
| 491 | 94 |
| 492 | 95 |
| 493 | 51 |
| 511 | 82 |
| 519 | 89 |
| 520 | 97 |
| 521 | 94 |
| 522 | 93 |
| 523 | 97 |
| 524 | 99 |
| 526 | 96 |
| 527 | 97 |
| 531 | 74 |
| 532 | 88 |
| 533 | 91 |
| 534 | 84 |
| 535 | 89 |
| 536 | 79 |
| 539 | 89 |
| 548 | 86 |
| 549 | 98 |
| 551 | 93 |
| 558 | 87 |
| 559 | 96 |
| 562 | 95 |
| 563 | 95 |
| 570 | 92 |
| 571 | 88 |
| 573 | 72 |
| 574 | 81 |
| 578 | 90 |
| 579 | 92 |
| 580 | 90 |
| 581 | 96 |
| 584 | 96 |
| 585 | 96 |
| 589 | 91 |
| 590 | 95 |
| 592 | 93 |
| 593 | 86 |
| 594 | 95 |
| 597 | 75 |
| 600 | 93 |
| 601 | 92 |
| 602 | 97 |
| 604 | 86 |
| 609 | 95 |
| 611 | 95 |
| 615 | 94 |
| 616 | 95 |
| 618 | 89 |
| 621 | 98 |
| 622 | 95 |
| 623 | 96 |
| 729 | 73 |
| 730 | 96 |
| 731 | 65 |
| 732 | 84 |
| 733 | 60 |
| 734 | 49 |
| 735 | 96 |
| 736 | 96 |
| 737 | 95 |
| 738 | 54 |
| 739 | 83 |
| 740 | 94 |
| 741 | 89 |
| 742 | 87 |
| 743 | 51 |
| 745 | 93 |
| 746 | 84 |
| 747 | 68 |
| 748 | 56 |
| 769 | 90 |
| 770 | 91 |
| 781 | 91 |
| 785 | 96 |
| 795 | 87 |
| 798 | 95 |
| 799 | 96 |
| 800 | 74 |
| 801 | 87 |
| 802 | 88 |
| 811 | 85 |
| 814 | 81 |
| 815 | 71 |
| 817 | 60 |
| 818 | 78 |
| 822 | 93 |
| 823 | 75 |
| 825 | 79 |
| 839 | 63 |
| 849 | 66 |
| 854 | 78 |
| 855 | 92 |
| 856 | 97 |
| 857 | 92 |
| 859 | 86 |
| 861 | 65 |
| 863 | 72 |
| 864 | 84 |
| 865 | 95 |
| 869 | 92 |
| 874 | 90 |
| 875 | 92 |
| 876 | 92 |
| 891 | 94 |
| 893 | 87 |
| 894 | 89 |
| 895 | 92 |
| 896 | 96 |
| 900 | 95 |
| 906 | 88 |
| 912 | 85 |
| 913 | 89 |
| 914 | 91 |
| 917 | 78 |
| 919 | 91 |
| 921 | 82 |
| 929 | 81 |
| 931 | 98 |
| 933 | 91 |
| 935 | 72 |
| 940 | 92 |
| 941 | 90 |
| 945 | 80 |
| 947 | 79 |

TABLE 3-continued

Inhibition of farnesyltransferase

| Example | % inhibition at $1 \times 10^{-7}$ M |
|---|---|
| 948 | 75 |
| 949 | 57 |
| 950 | 71 |
| 951 | 71 |
| 959 | >50 |
| 983 | 66 |
| 984 | 86 |
| 990 | 84 |
| 993 | 90 |

TABLE 4

Inhibition of farnesyltransferase

| Example | % inhibition at $1 \times 10^{-8}$ M |
|---|---|
| 384 | 91 |
| 397 | 50 |
| 398 | >50 |
| 400 | 98 |
| 401 | 66 |
| 408 | >95 |
| 409 | 84 |
| 410 | 94 |
| 517 | 92 |
| 518 | 90 |
| 567 | 69 |
| 586 | 90 |
| 588 | 68 |
| 591 | 82 |
| 599 | 86 |
| 603 | 94 |
| 605 | 68 |
| 606 | 93 |
| 608 | 91 |
| 612 | 96 |
| 614 | 92 |
| 619 | 95 |
| 760 | 95 |
| 762 | 84 |
| 763 | 92 |
| 766 | 95 |
| 767 | 97 |
| 779 | 70 |
| 780 | 71 |
| 803 | 95 |
| 804 | 95 |
| 805 | 96 |
| 819 | 76 |
| 820 | 66 |
| 821 | 75 |
| 826 | 92 |
| 827 | 77 |
| 828 | 87 |
| 829 | 92 |
| 833 | 78 |
| 836 | 95 |
| 837 | 91 |
| 838 | 92 |
| 840 | 73 |
| 841 | 93 |
| 842 | 88 |
| 843 | 96 |
| 845 | 85 |
| 847 | 85 |
| 848 | 87 |
| 851 | 82 |
| 852 | 79 |
| 853 | 85 |
| 858 | 60 |
| 860 | 85 |
| 870 | 91 |
| 871 | 94 |
| 873 | 97 |
| 877 | 68 |
| 880 | 95 |
| 881 | 69 |
| 882 | 79 |
| 883 | 91 |
| 884 | 94 |
| 885 | 95 |
| 887 | 92 |
| 888 | 86 |
| 892 | 59 |
| 897 | 76 |
| 898 | 82 |
| 899 | 88 |
| 901 | 84 |
| 904 | 85 |
| 905 | 86 |
| 907 | 79 |
| 909 | 79 |
| 916 | 96 |
| 920 | 96 |
| 922 | 96 |
| 927 | 74 |
| 928 | 84 |
| 930 | 66 |
| 932 | 60 |
| 934 | 71 |
| 938 | 61 |
| 939 | 72 |
| 942 | 58 |
| 943 | 79 |
| 944 | 88 |
| 946 | 52 |
| 954 | >50 |
| 958 | >50 |
| 960 | >50 |
| 985 | 89 |
| 986 | 95 |
| 991 | 69 |
| 992 | 93 |
| 994 | 83 |
| 995 | 92 |
| 996 | 80 |

TABLE 5

Inhibition of geranylgeranyltransferase I.

| Example | Activity |
|---|---|
| 387 | >50% inhibition at $1 \times 10^{-6}$ M |
| 388 | >50% inhibition at $1 \times 10^{-7}$ M |
| 389 | >50% inhibition at $1 \times 10^{-6}$ M |
| 390 | >50% inhibition at $1 \times 10^{-5}$ M |
| 392 | >50% inhibition at $1 \times 10^{-5}$ M |
| 399 | >50% inhibition at $1 \times 10^{-6}$ M |
| 953 | >50% inhibition at $1 \times 10^{-6}$ M |
| 955 | >50% inhibition at $1 \times 10^{-7}$ M |
| 962 | >50% inhibition at $1 \times 10^{-7}$ M |
| 964 | >50% inhibition at $1 \times 10^{-6}$ M |
| 966 | >50% inhibition at $1 \times 10^{-6}$ M |
| 967 | >50% inhibition at $1 \times 10^{-6}$ M |
| 969 | >50% inhibition at $1 \times 10^{-5}$ M |
| 974 | >50% inhibition at $1 \times 10^{-5}$ M |

TABLE 6

Inhibition of farnesyltransferase at concentrations of 10 mM and 1 mM unless specified as *(0.1 mM) or **(0.01 mM)

| Example | % inhibition 10 mM | % inhibition 1 mM |
|---|---|---|
| 997 | | 91** |
| 998 | | 79** |
| 999 | | 90 |
| 1000 | | 82* |
| 1001 | | 92** |
| 1002 | | 82** |
| 1003 | | 92* |
| 1004 | | 92** |
| 1005 | | 95** |
| 1006 | | 95** |
| 1007 | | 85** |
| 1008 | | 95** |
| 1009 | | 86** |
| 1010 | | 90* |
| 1011 | | 92** |
| 1012 | | 88* |
| 1013 | | 80* |
| 1014 | | 91 |
| 1015 | | 59* |
| 1016 | | 92* |
| 1017 | | 51* |
| 1018 | | 97 |
| 1019 | | 70 |
| 1020 | | 39 |
| 1021 | | 93* |
| 1022 | | 91** |
| 1023 | | 89** |
| 1024 | | 89** |
| 1025 | | 91** |
| 1026 | | 74** |
| 1027 | | 81** |
| 1028 | | 92** |
| 1629 | | 82** |
| 1030 | | 92** |
| 1031 | | 90** |
| 1032 | | 93** |
| 1033 | | 76** |
| 1034 | | 77 |
| 1035 | | 76 |
| 1036 | | 79 |
| 1037 | | 88 |
| 1038 | | 57 |
| 1039 | | 89** |
| 1040 | | 90** |
| 1041 | | 48 |
| 1042 | | 88 |
| 1043 | | 90* |
| 1044 | | 76* |
| 1045 | | 86* |
| 1046 | | 93 |
| 1047 | | 95 |
| 1048 | | 78** |
| 1049 | | 93** |
| 1050 | | 62** |
| 1051 | | 79** |
| 1052 | | 91** |
| 1053 | | 60** |
| 1054 | | 89** |
| 1055 | | 85** |
| 1056 | | 75** |
| 1057 | | 82* |
| 1058 | | 89 |
| 1059 | | 92* |
| 1060 | | 42 |
| 1061 | | 88* |
| 1062 | | 93 |
| 1063 | | 92** |
| 1064 | | 95** |
| 1065 | | 78* |
| 1066 | | 73** |
| 1067 | | 93* |
| 1068 | | 79** |
| 1069 | | 74* |
| 1070 | | 93** |
| 1071 | | 95* |
| 1072 | | 82* |
| 1073 | | 93** |
| 1074 | | 82 |
| 1075 | | 90** |
| 1076 | | 69** |
| 1077 | | 93** |
| 1078 | | 86* |
| 1079 | | 90 |
| 1080 | | 87 |
| 1081 | | 61 |
| 1082 | | 84* |
| 1083 | | 88 |
| 1084 | | 76** |
| 1085 | | 93* |
| 1086 | | 87* |
| 1087 | | 76* |
| 1088 | | 73* |
| 1089 | | 86* |
| 1090 | | 81** |
| 1091 | | 87* |
| 1092 | | 74** |
| 1093 | | 95** |
| 1094 | | 96** |
| 1095 | | 76* |
| 1096 | | 86* |
| 1097 | | 80** |
| 1098 | | 60* |
| 1099 | | 87** |
| 1100 | | 82** |
| 1101 | | 86* |
| 1102 | | 84** |
| 1103 | | 92* |
| 1104 | | 89** |
| 1105 | | 91** |
| 1106 | | 67** |
| 1107 | | 88** |
| 1108 | | 95** |
| 1109 | | 74** |
| 1110 | | |
| 1111 | | 63** |
| 1112 | | 62 |
| 1113 | | 55 |
| 1114 | | 83** |
| 1115 | | 94* |
| 1116 | | 91** |
| 1117 | | 92* |
| 1118 | | 86* |
| 1119 | | 84** |
| 1120 | | 93 |
| 1121 | | 72* |
| 1122 | | 92** |
| 1123 | | 90* |
| 1124 | | 90* |
| 1125 | | 92* |
| 1126 | | 87 |
| 1127 | | 90* |
| 1128 | | 86* |
| 1129 | | 92** |
| 1130 | | 88** |
| 1131 | | 96** |
| 1132 | | 97* |
| 1133 | | 75* |
| 1134 | | 95** |
| 1135 | | 88* |
| 1136 | | 91 |
| 1137 | | 83** |
| 1138 | | 65* |
| 1139 | | 92* |
| 1140 | | 77** |
| 1141 | | 80* |
| 1142 | | 84** |

TABLE 6-continued

Inhibition of farnesyltransferase at concentrations of 10 mM and 1 mM unless specified as *(0.1 mM) or **(0.01 mM)

| Example | % inhibition 10 mM | % inhibition 1 mM |
|---|---|---|
| 1143 | | 92* |
| 1144 | | 76* |
| 1145 | | 83* |
| 1146 | | 61** |
| 1147 | | 93* |
| 1148 | | 79** |
| 1149 | | 94* |
| 1150 | | 92* |
| 1151 | | 91* |
| 1152 | | 96* |
| 1153 | | 89* |
| 1154 | | 93* |
| 1155 | | 91* |
| 1156 | | 87 |
| 1157 | | 66** |
| 1158 | 75 | |
| 1159 | | 72* |
| 1160 | | 83* |
| 1161 | | 87* |
| 1162 | | 84* |
| 1163 | | 73** |
| 1164 | | 94 |
| 1165 | | 84* |
| 1166 | | 74** |
| 1167 | | 91* |
| 1168 | | 88* |
| 1169 | | 77 |
| 1170 | | 74* |
| 1171 | | 74** |
| 1172 | | 38* |
| 1173 | | 89** |
| 1174 | | 79** |
| 1175 | | 96 |
| 1176 | | 97* |
| 1177 | | 19 |
| 1178 | | 88** |
| 1179 | | 85* |
| 1180 | | 93* |
| 1181 | | 82* |
| 1182 | | 92** |
| 1183 | | 79** |
| 1184 | | 84** |
| 1185 | | 85** |
| 1186 | | 93** |
| 1187 | | 93** |
| 1188 | | 93** |
| 1189 | | 74** |
| 1190 | | 95** |
| 1191 | | 85** |
| 1192 | | 91* |
| 1193 | | 95** |
| 1194 | | 78** |
| 1195 | | 94* |
| 1196 | | 87* |
| 1197 | | 85* |
| 1198 | | 86* |
| 1199 | | 71 |
| 1200 | | 97* |
| 1201 | | 73* |
| 1202 | | 96** |
| 1203 | | 84* |
| 1204 | | 93* |
| 1205 | | 55** |
| 1206 | | 63** |
| 1207 | | 91* |
| 1208 | | 89* |
| 1209 | | 87* |
| 1210 | | 64** |
| 1211 | | 94 |
| 1212 | | 86* |
| 1213 | | 79** |
| 1214 | | 92** |
| 1215 | | 17 |
| 1216 | | 88** |
| 1217 | | 87* |
| 1218 | | 54** |
| 1219 | | 85** |
| 1220 | | |
| 1221 | | 82** |
| 1222 | | 89* |
| 1223 | | 91** |
| 1224 | | 88* |
| 1225 | | 92** |
| 1226 | | 69** |
| 1227 | | 91 |
| 1228 | | 88* |
| 1229 | | 66** |
| 1230 | | 77** |
| 1231 | | 93* |
| 1232 | | 68** |
| 1233 | | 77** |
| 1234 | | 71** |
| 1235 | | 86** |
| 1236 | | 83** |
| 1237 | | 89** |
| 1238 | | 91** |
| 1239 | | 85* |
| 1240 | | 64** |
| 1241 | | 74* |
| 1242 | | 75* |
| 1243 | | 95* |
| 1244 | | 84 |
| 1245 | | 92 |
| 1246 | | 82 |
| 1247 | | 95* |
| 1248 | | 88 |
| 1249 | | 89 |
| 1250 | | 79** |
| 1251 | | 91** |
| 1252 | | 84* |
| 1253 | | 76* |
| 1254 | | 67 |
| 1255 | | 82* |
| 1256 | | 95* |
| 1257 | | 93** |
| 1258 | | 97** |
| 1259 | | 89** |
| 1260 | | 90** |
| 1261 | | 94 |
| 1262 | | 95 |
| 1263 | | 85* |
| 1264 | | 83** |
| 1265 | | 90 |
| 1266 | | 85* |
| 1267 | | 96 |
| 1268 | | 95* |
| 1269 | | 84** |
| 1270 | | 91** |
| 1271 | | 78** |
| 1272 | | 73** |
| 1273 | | 94* |
| 1274 | | 89* |
| 1275 | | 86** |
| 1276 | | 88** |
| 1277 | | 90** |
| 1278 | | 68 |
| 1279 | | 87** |
| 1280 | | 78** |
| 1281 | | 81* |
| 1282 | | 69* |
| 1283 | | 74* |
| 1284 | | 86 |
| 1285 | | 94 |
| 1286 | | 85** |
| 1287 | | 95** |
| 1288 | | 69* |

TABLE 6-continued

Inhibition of farnesyltransferase at concentrations of 10 mM and 1 mM unless specified as *(0.1 mM) or **(0.01 mM)

| Example | % inhibition 10 mM | % inhibition 1 mM |
|---|---|---|
| 1289 | | 93 |
| 1290 | | 80 |
| 1291 | | |
| 1292 | | |
| 1293 | | |
| 1294 | | |
| 1295 | | |
| 1296 | | |
| 1297 | | |
| 1298 | | 97** |
| 1299 | | 96** |
| 1300 | | 97* |
| 1301 | | 97* |
| 1302 | | 93** |
| 1303 | | 91** |
| 1304 | | 90** |
| 1305 | | 91** |
| 1306 | | 85** |
| 1307 | | 85** |
| 1308 | | 91** |
| 1309 | | 96* |
| 1310 | | 90** |
| 1311 | | 95** |
| 1312 | | 91** |
| 1313 | | 91** |
| 1314 | | 96* |
| 1315 | | 86* |
| 1316 | | 78* |
| 1317 | 99 | 96 |
| 1318 | | |
| 1319 | | 79** |
| 1320 | | 79 |
| 1321 | | |
| 1322 | | |
| 1323 | | |
| 1324 | | |
| 1325 | | |
| 1326 | | |
| 1327 | | |
| 1328 | | |
| 1329 | | |
| 1330 | | |
| 1331 | | |
| 1332 | | 92** |
| 1333 | | 95* |
| 1334 | | 72** |
| 1335 | | 90* |
| 1336 | | 74 |
| 1337 | | 83** |
| 1338 | | 65* |
| 1339 | | |
| 1340 | | 77* |
| 1341 | | 89 |
| 1342 | | |
| 1343 | | 88 |
| 1344 | | 93** |
| 1345 | | 94** |
| 1346 | | 94* |
| 1347 | | 81** |
| 1348 | | 78** |
| 1349 | | 92** |
| 1350 | | |
| 1351 | | |
| 1352 | | |
| 1353 | | |
| 1354 | | 38 |
| 1355 | | 46 |
| 1356 | | 80 |
| 1357 | | 78 |
| 1358 | | |
| 1359 | | |
| 1360 | | 98** |
| 1361 | | 96* |
| 1362 | | 83** |
| 1363 | | 88** |
| 1364 | | |
| 1365 | | |
| 1366 | | 79* |
| 1367 | | 93* |
| 1368 | | 92** |
| 1369 | | 94* |
| 1370 | | 86** |
| 1371 | | 94* |
| 1372 | | 95** |
| 1373 | | 95** |
| 1374 | | 93** |
| 1375 | | 80** |
| 1376 | | 86** |
| 1377 | | 95* |
| 1378 | | 68 |
| 1379 | | 41 |
| 1380 | | 87** |
| 1381 | | 65** |
| 1382 | | 86** |
| 1383 | | 88* |
| 1384 | | 69** |
| 1385 | | 93* |
| 1386 | | 88* |
| 1387 | | 82** |
| 1392 | | 93* |
| 1397 | | 87** |
| 1398 | | 81* |
| 1399 | | 94 |
| 1400 | | 95 |

*% inhibition at 0.1 µM
**% inhibition at 0.01 µM

Additional methods for the measurement of in vitro inhibition of protein prenylation (i.e., inhibition of farnesyltransferase or geranygeranyltransferase) are described below.

Assays are performed using the glass fiber filter binding assay procedure with either rabbit reticulocyte lysate or Frase or GGTase I fractions isolated from bovine brains using a combination of hydrophobic and DEAE column chromatography procedures. Protein substrates are purchased from Panvera Corporation (H-ras for Frase, H-ras-CVLL for GGTase I). Tritium labeled prenyl lipid substrates (FPP or GGPP) are obtained from Amersham Life Science.

FTase $^3$H-Farnesyldiphosphate (final concentration 0.6 µM), H-Ras (final concentration 5.0 µM) and the test compound (various final concentrations from a stock solution in 50% DMSO/water; final concentration DMSO<2%) were mixed in buffer (50 mM HEPES (pH 7.5), 30 mM MgCl$_2$, 20 mM KCl, 10 µM ZnCl$_2$, 5 mM DTT, 0.01% Triton X-100) to give a final volume of 50 µL. The mixture was brought to 37° C., enzyme was added, and the reaction is incubated for 30 minutes. 1 mL of 1 M HCl/ethanol was added to stop the reaction, and the mixture was allowed to stand for 15 minutes at room temperature then diluted with 2 mL of ethanol. The reaction mixture was filtered through a 2.5 cm glass microfiber filter from Whatman and washed with four 2 mL portions of ethanol. The glass filter was transferred to a scintillation vial and 5 mL of scintillation fluid was added. The radioisotope retained on the glass fiber filter was counted to reflect the activity of the enzymes. The IC$_{50}$ value was calculated by measuring the activity of the enzyme over a suitable range of inhibitor concentrations.

GGTase I

³H-geranylgeranyldiphosphate (final concentration 0.5 $\mu$M), H-Ras-CVLL (final concentration 5.0 $\mu$M) and the test compound (various final concentrations from a stock solution in 1:1 DMSO/water; final concentration DMSO<2%) were mixed in buffer (50 mM Tris-HCl (pH 7.2), 30 mM MgCl$_2$, 20 mM KCl, 10 $\mu$M ZnCl$_2$, 5 mM DTT, 0.01% Triton X-100) to give a final volume of 50 $\mu$L. The mixture was brought to 37° C., treated with enzyme, andincubated for 30 minutes. 1 mL of 1 M HCl/ethanol was added to stop the reaction, and the mixture was allowed to stand for 15 minutes at room temperature then diluted with 2 mL of ethanol. The reaction mixture was filtered through a 2.5 cm glass microfiber filter from Whatman and washed with four 2 mL portions of ethanol. The glass filter was transferred to a scintillation vial, and 5 mL scintillation fluid was added. The radioisotope retained on the glass fiber filter was counted to reflect the activity of the enzymes. The IC$_{50}$ value was calculated by measuring the activity of the enzyme over a suitable range of inhibitor concentrations.

Additionally, the ability of the compounds of the invention to inhibit prenylation in whole cells, inhibit anchorage-independent tumor cell growth and inhibit human tumor xenograft in mice could be demonstrated according to the methods described in PCT Patent Application No. WO95/25086, published Sep. 21, 1995, which is hereby incorporated herein by reference.

Pharmaceutical Compositions

The compounds of the present invention can be used in the form of pharmaceutically acceptable salts derived from inorganic or organic acids. These salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quatemized with such agents as loweralkyl halides (such as methyl, ethyl, propyl, and butyl chloride, bromides, and iodides), dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid.

Basic addition salts can be prepared in situ during the final isolation and purification of the compounds of formula (I)–(XII) or separately by reacting the carboxylic acid function with a suitable base such as the hydroxide, carbonate or bicarbonate of a pharmaceutically acceptable metal cation or with ammonia or an organic primary, secondary or tertiary amine. Such pharmaceutically acceptable salts include, but are not limited to, cations based on the alkali and alkaline earth metals such as sodium, lithium, potassium, calcium, magnesium, aluminum salts and the like as well as nontoxic ammonium, quaternary ammonium, and amine cations including, but not limited to, ammonium, tetramethylammonium, tetraethylammonium, methylamine, dimethylamine, trimethylamine, triethylamine, ethylamine and the like. Other representative organic amines useful for the formation of base addition salts include diethylamine, ethylenediamine, ethanolamine, diethanolamine, piperazine and the like.

The compounds of the invention are useful (in humans and other mammals) for inhibiting protein isoprenyltransferases (i.e, protein farnesyltransferase and/or protein geranylgeranyltransferase) and the isoprenylation (i.e., farnesylation and/or geranylgeranylation) of Ras. These inhibitors of protein isoprenyltransferases are also useful for inhibiting or treating cancer in humans and other mammals. Examples of cancers which may be treated with the compounds of the invention include, but are not limited to, carcinomas such as lung, colorectal, bladder, breast, kidney, ovarian, liver, exocrine pancreatic, cervical, esophageal, stomach and small intestinal; sarcomas such as oesteroma, osteosarcoma, lepoma, liposarcoma, hemanioma and hemangiosarcoma; melanomas such as amelanotic and melanotic; mixed types of cancers such as carcinosarcoma, lymphoid tissue type, follicular reticulum, cell sarcoma and Hodgkins disease and leukemias, such as myeloid, acute lymphoblastic, chronic lymphocytic, acute myloblastic and chronic mylocytic.

The ability of the compounds of the invention to inhibit or treat cancer can be demonstrated according to the methods of Mazerska Z., Woynarowska B., Stefanska B., Borowski S., Drugs Exptl. Clin. Res. 13(6), 345–351 (1987) Bissery, M. C., Guenard F., Guerritte-Voegelein F., Lavelle F., Cancer Res. 51, 4845–4852 (1991) and Rygaard J., and Povlsen C., Acta Pathol. Microbiol. Scand. 77, 758 (1969), which are hereby incorporated herein by reference.

These inhibitors of protein isoprenyltransferases are also useful for treating or preventing restenosis in humans and other mammals. The ability of the compounds of the invention to treat or prevent restenosis can be demonstrated according to the methods described by Kranzhofer, R. et al. Circ. Res. 73: 264–268 (1993), Mitsuka, M. et al. Circ. Res. 73: 269–275 (1993) and Santoian, E. C. et al. Circulation 88: 11–14 (1993), which are hereby incorporated herein by reference.

For use as a chemotherapeutic agent, the total daily dose administered to a host in single or divided doses may be in amounts, for example, from 0.01 to 500 mg/kg body weight daily, preferably in amounts from 0.1 to 20 mg/kg body weight daily and more preferably in amounts from 0.5 to 10 mg/kg body weight daily. Dosage unit compositions may contain such amounts of submultiples thereof to make up the daily dose.

For treatment or prevention of restenosis, the total daily dose administered to a host in single or divided doses may be in amounts, for example, from 0.001 to 1000 mg/kg body weight daily and more preferred from 1.0 to 50 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of the present invention may be administered orally, parenterally, sublingually, by inhalation spray, rectally or topically in dosage unit formulations containing conventional nontoxic pharmaceutically acceptable carriers, adjuvants, and vehicles. Topical administration may also involve the use of transdermal administration such as transdermal patches or iontophoresis devices. The term parenteral as used herein includes subcutaneous injections, intravenous, intramuscular, intrastemal injection or infusion techniques.

Injectable preparations, for example sterile injectable aqueous or oleagenous suspensions, may be formulated according to the known art using suitable dispersing or wetting and suspending agents. The sterile injectable preparation may also be a sterile injectable solution or suspension in a nontoxic parenterally acceptable diluent or solvent (as in a solution in 1,3-propanediol, for example). Among the acceptable vehicles and solvents that may be employed are water, Ringer's solution and isotonic sodium chloride solution. Additionally, sterile, fixed oils are conventionally employed as a solvent or suspending medium. For this purpose, any bland fixed oil may be employed including synthetic mono- or diglycerides. Fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at rectal temperature and will therefore melt in the rectum and release the drug.

Solid dosage forms for oral administration may include capsules, tablets, pills, powders and granules. In such solid dosage forms, the active compound may be admixed with at least one inert diluent such as sucrose, lactose or starch. These dosage forms may also comprise additional substances other than inert diluents such as lubricating agents like magnesium stearate. With capsules, tablets and pills, the dosage forms may also comprise buffering agents. Tablets and pills mayalso be prepared with enteric coatings.

Liquid dosage forms for oral administration may include pharmaceutically acceptable emulsions, solutions, suspensions, syrups and elixirs containing inert diluents commonly used in the art such as water. Such compositions may also comprise adjuvants such as wetting agents, emulsifying and suspending agents and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals dispersed in an aqueous medium. Any non-toxic, physiologically aceptable and metabolizable lipid capable of forming liposomes can be used. The present compositions in liposome form can contain, in addition to a compound of the present invention, stabilizers, preservatives, excipients and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq., which is hereby incorporated herein by reference.

While the compounds of the invention can be administered as the sole active pharmaceutical agent for the treatment of cancer, they can also be used in combination with one or more other chemotherapeutic agents.

Representative examples of chemotherapeutic agents are described in Holleb, et al., *Clinical Oncology*, American Cancer Society, United States (1991) p 56 et seq., which is hereby incorporated herein by reference These agents include alkylating agents such as the nitrogen mustards (mechloethamine, melphalan, chlorambucil, cyclophosphamide and ifosfamide), nitrosoureas (carmustine, lomustine, semustine, streptozocin), alkyl sulfonates (busulfan), triazines (dacarbazine) and ethyenimines (thiotepa, hexamethylmelamine); folic acid analogues (methotrexate); pyrimidine analogues (5-fluorouracil, cytosine arabinoside); purine analogues (6-mercaptopurine, 6-thioguanine); antitumor antibiotics (actinomycin D, the anthracyclines (doxorubicin), bleomycin, mitomycin C, methramycin); plant alkaloids such as vinca alkaloids (vincristine and vinblastine) and etoposide (VP-16); hormones and hormone antagonists (tamoxifen and corticosteroids); and miscellaneous agents (cisplatin, taxol and brequinar).

The above compounds to be employed in combination with the isoprenyl protein transferase inhibitor of the invention will be used in therapeutic amounts as indicated in the Physicians' Desk Reference (PDR) 47th Edition (1993), which is incorporated herein by reference or by such therapeutically useful amounts as would be known to one of ordinary skill in the art.

The compounds of the invention and the other chemotherapeutic agent can be administered at the recommended maximum clinical dosage or at lower doses. Dosage levels of the active compounds in the compositions of the invention may be varied to obtain a desired therapeutic response depending on the route of administration, severity of the disease and the response of the patient.

When administered as a combination, the therapeutic agents can be formulated as separate compositions which are given at the same time or different times, or the therapeutic agents can be given as a single composition.

Preparation of the Compounds of the Invention

In general, the compounds of the invention can be prepared by the processes illustrated in the following Schemes 1–16. In these general schemes compounds of the formula I are used to exemplify the methods, but the methods are intended to be applicable to all of the compounds of the invention.

SCHEME 1

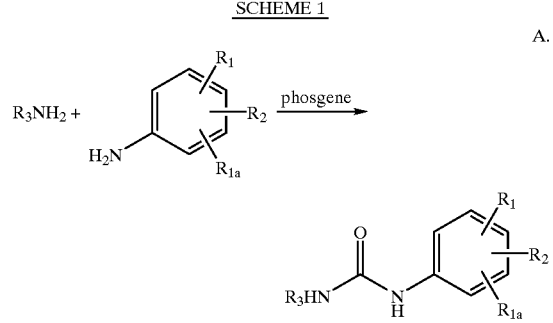

B. 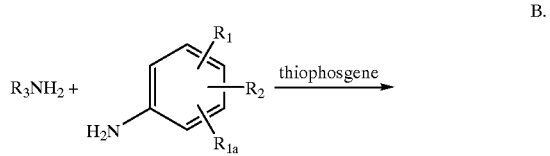
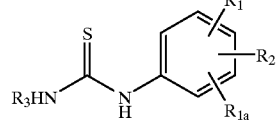
C. 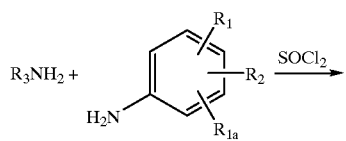
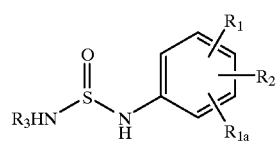
D. 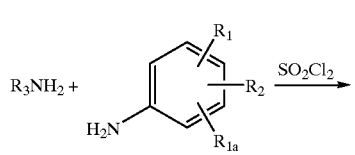
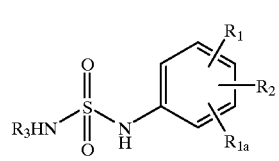
SCHEME 2
A. 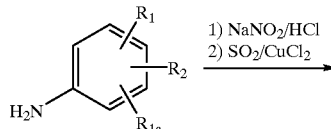
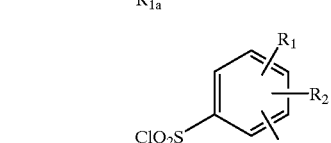
B. 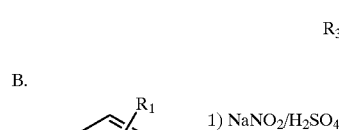
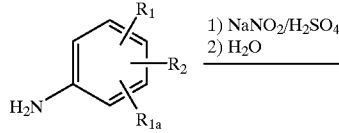
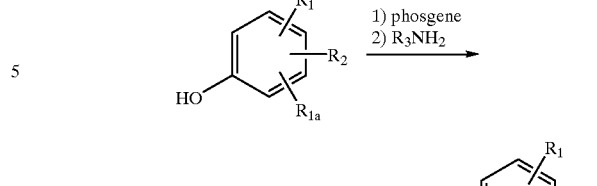
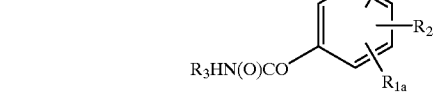
C. 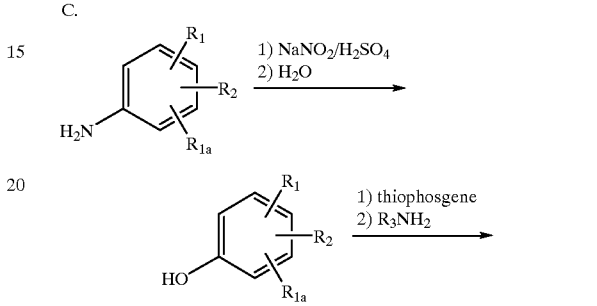
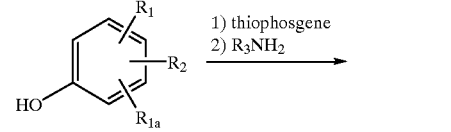
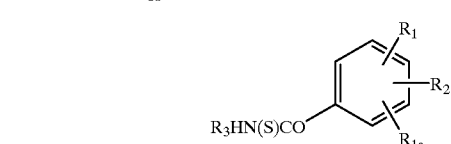
D. 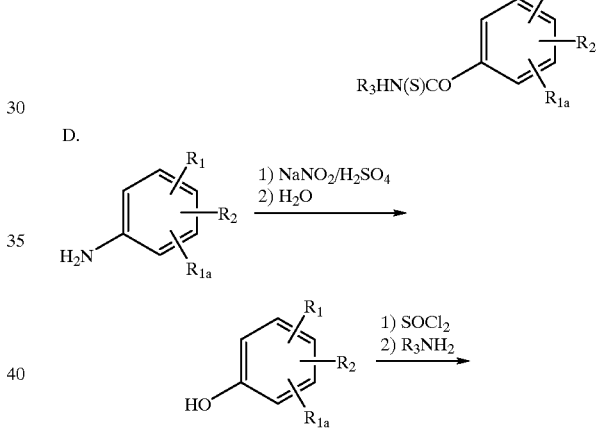
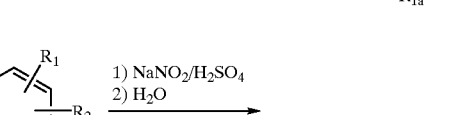
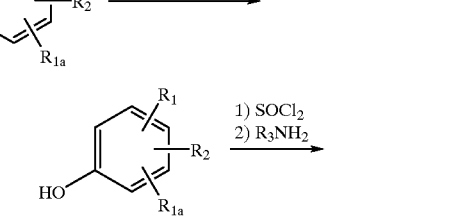
E. 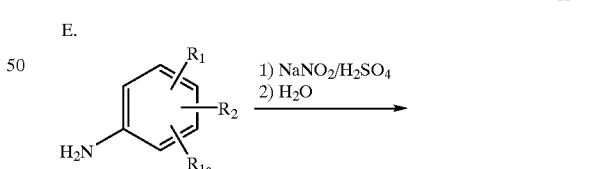
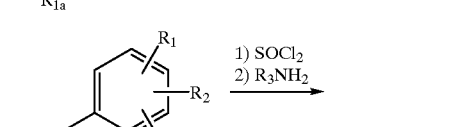
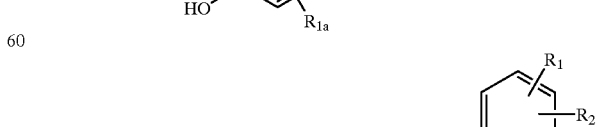

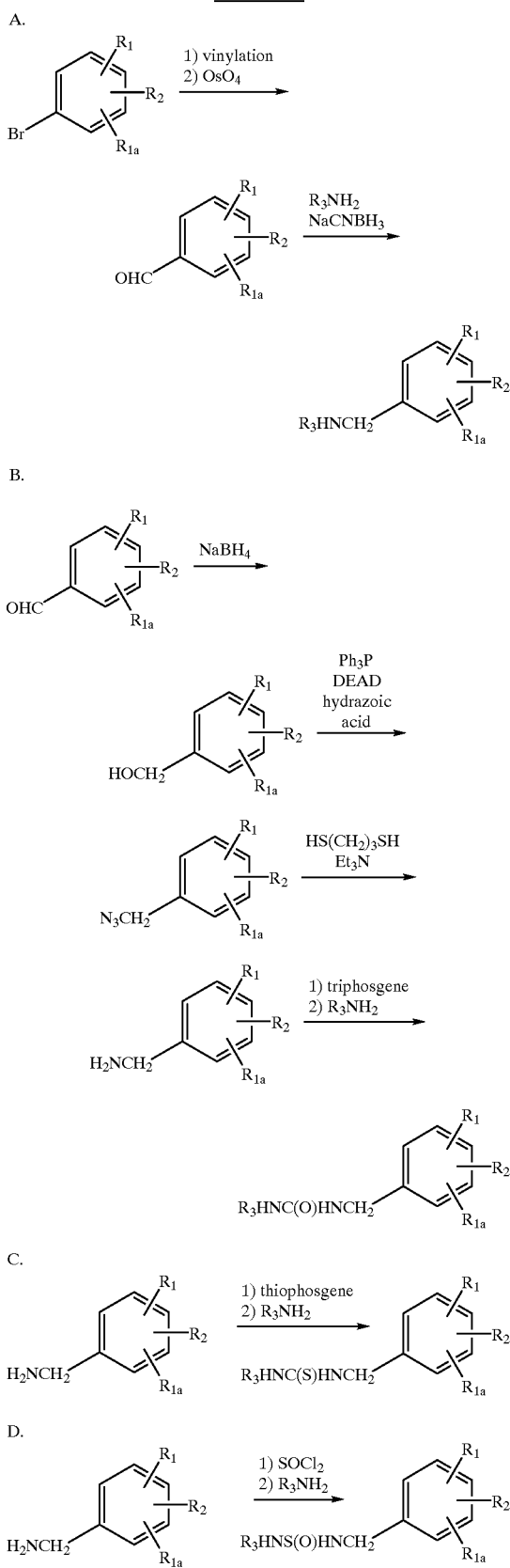
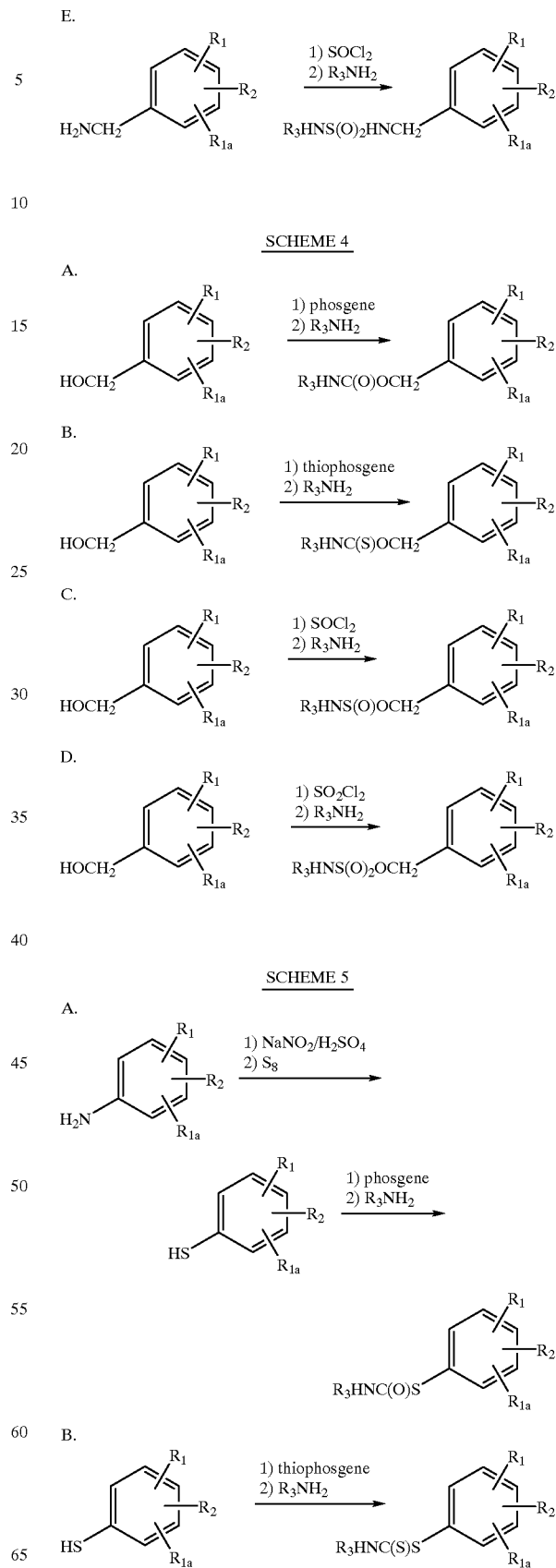

C.
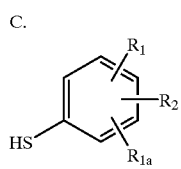
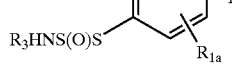
B.
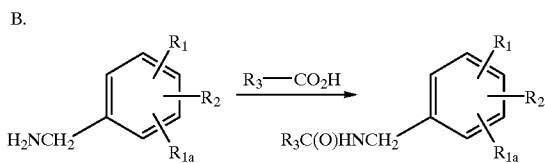
D.
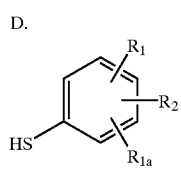
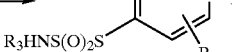
C.
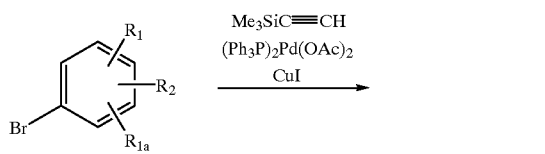
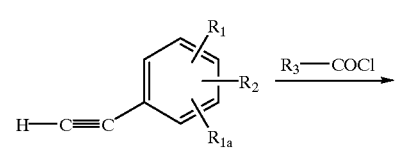
SCHEME 6
A.
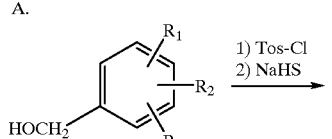
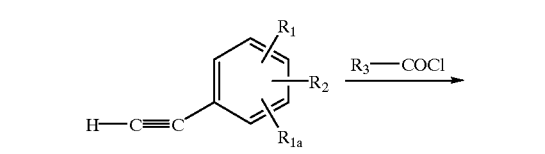
D.
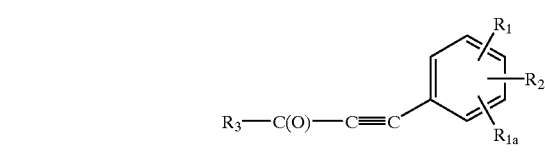
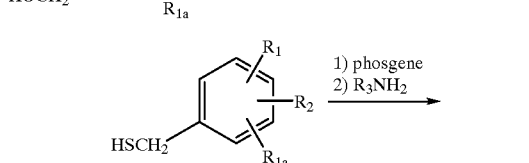
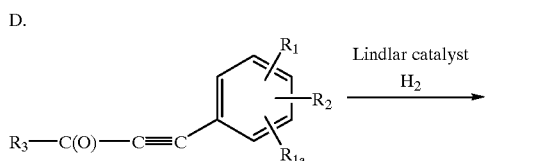
E.
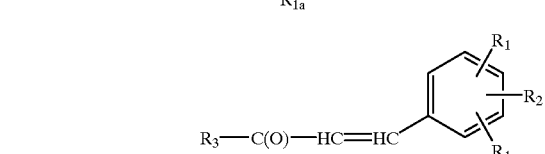
B.
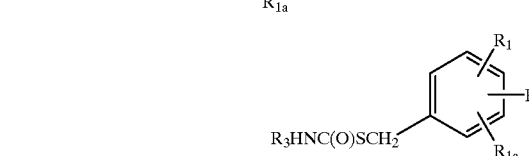
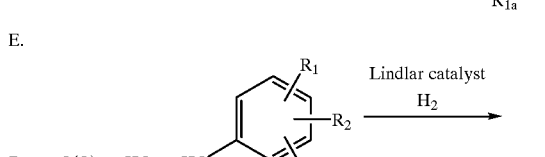
C.
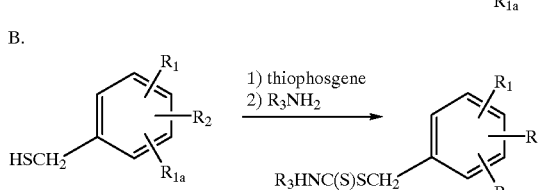
SCHEME 8
A.
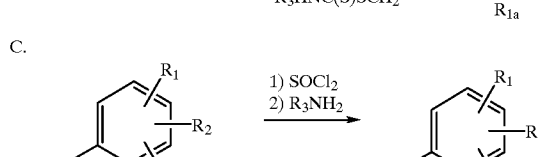
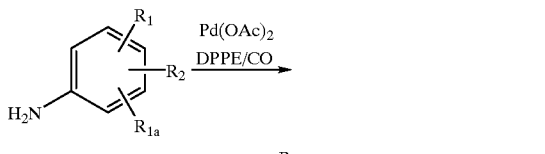
D.
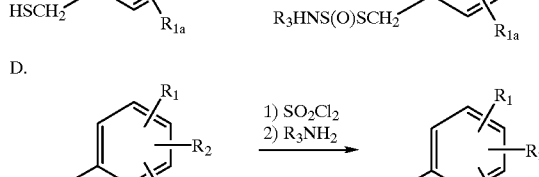
SCHEME 7
A.
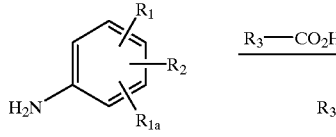
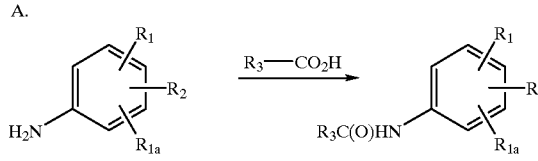
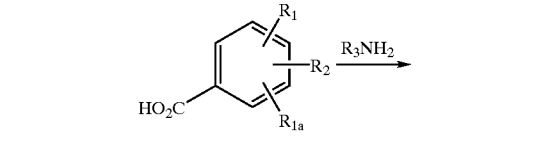

-continued
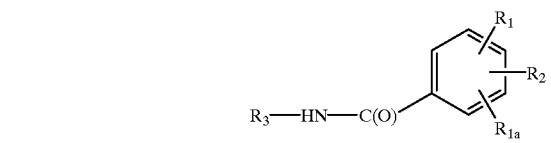
B.
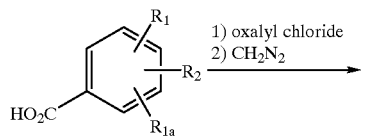
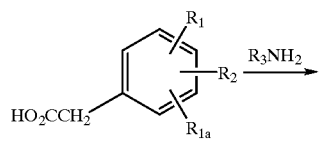
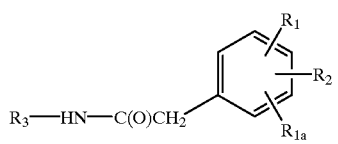
C.
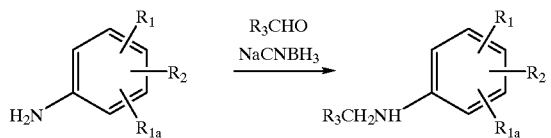
D.
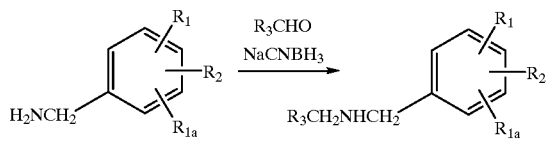
SCHEME 9
A.
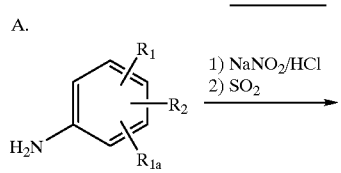
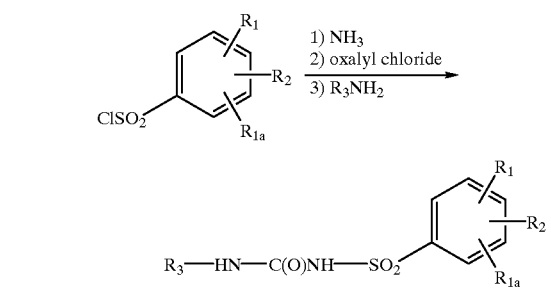
B.
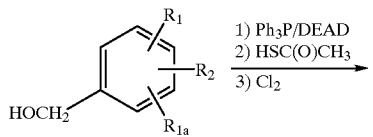
-continued
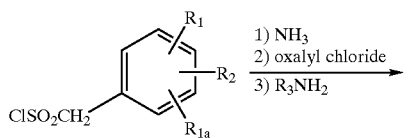
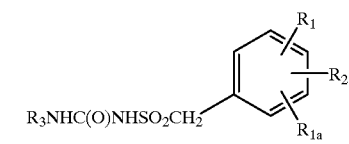
C.
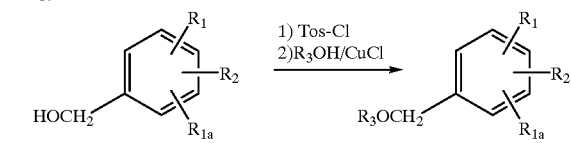
D.
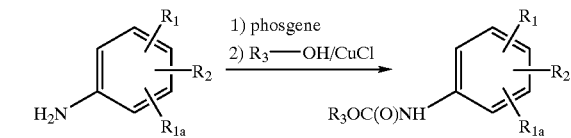
E.
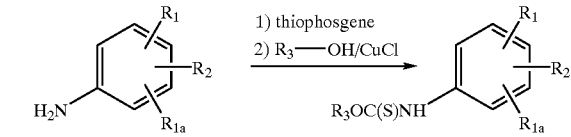
F.
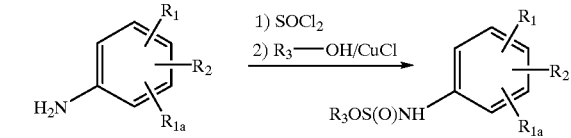
G.
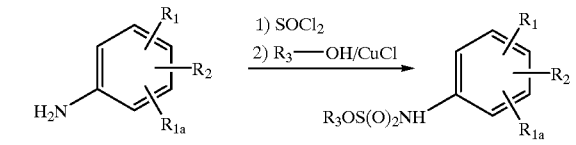
SCHEME 10
A.
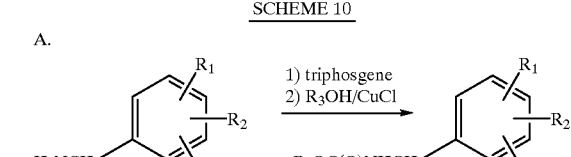
B.
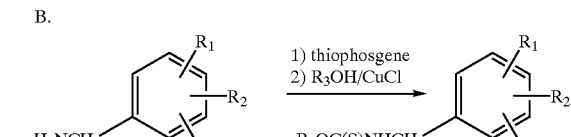

C. 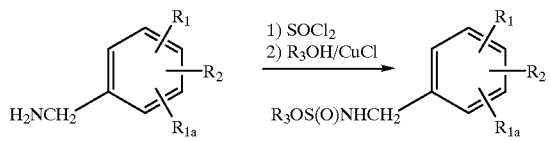
D. 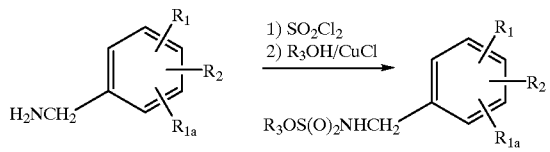
SCHEME 11
A. 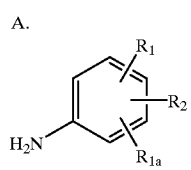 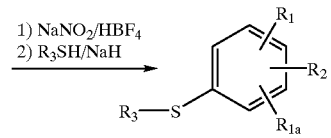
B.  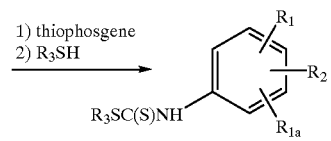
C.  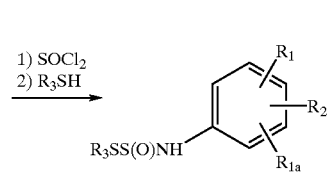
D. 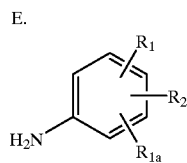 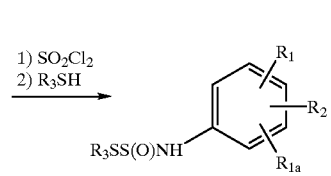
E. 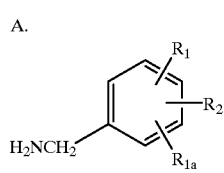
SCHEME 12
A. 
B. 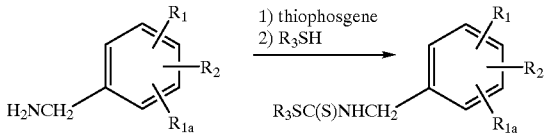
C. 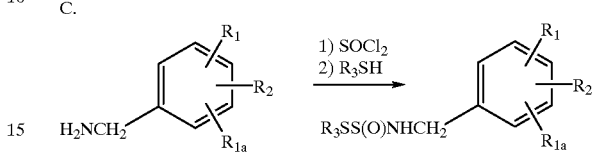
D. 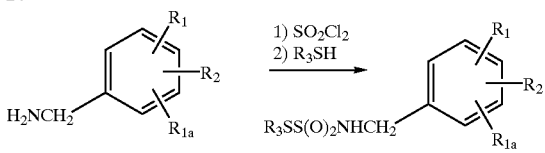
SCHEME 13
A. 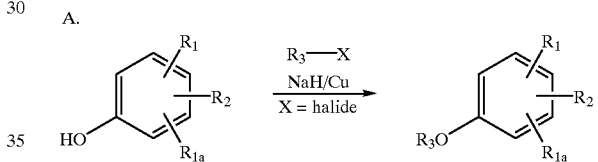
B. 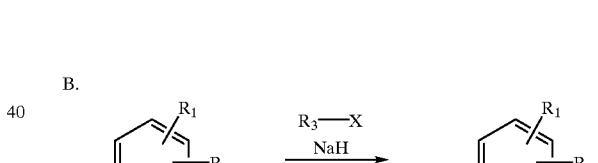
C. 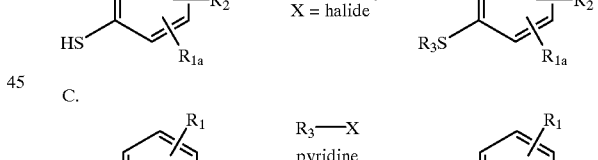
D. 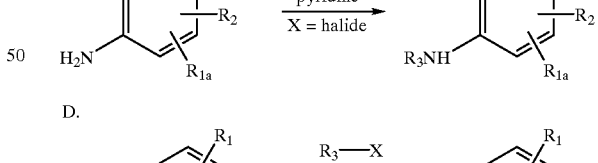
E. 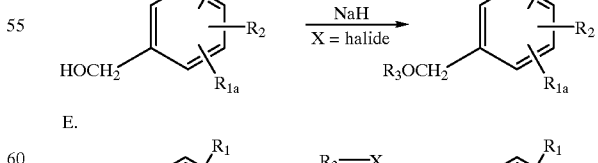
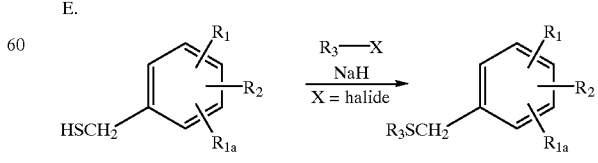

SCHEME 14
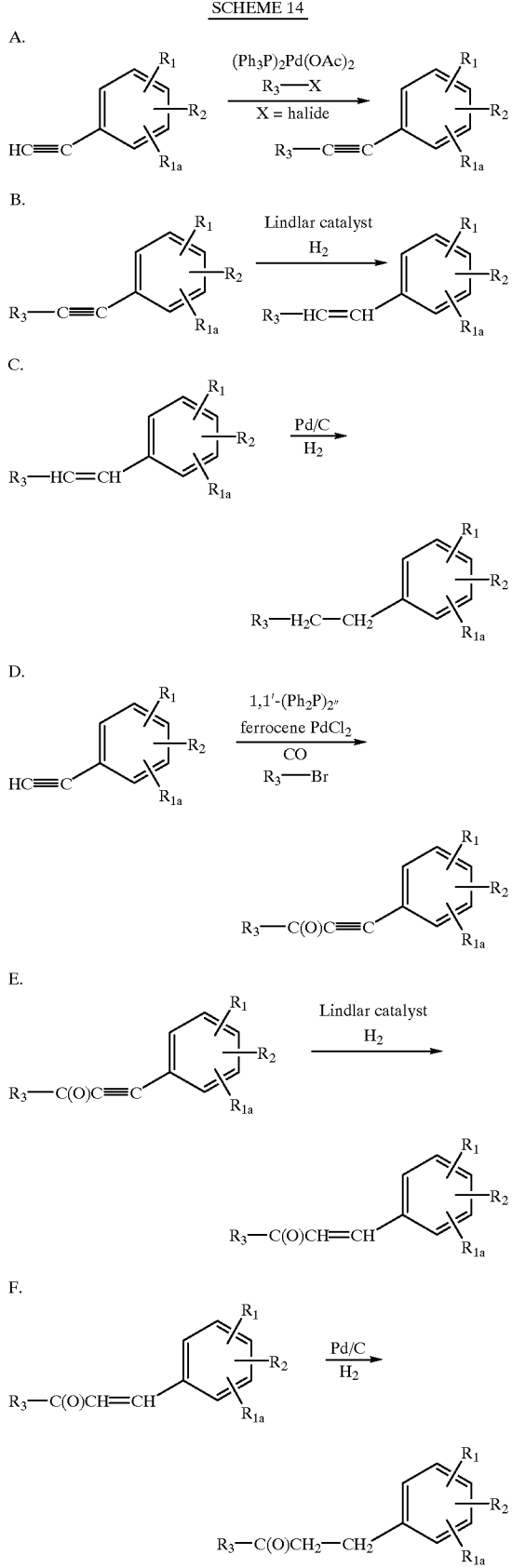
SCHEME 15
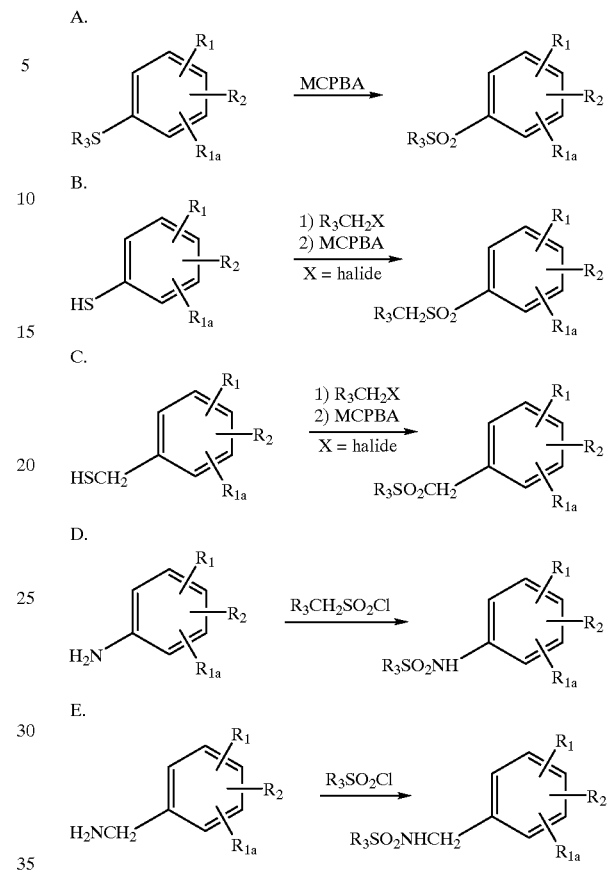
Scheme 16 illustrates an alternative method for preparing compounds wherein $R_2$ is $-C(O)NH-CH(R_{14})-C(O)OR_{15}$ or
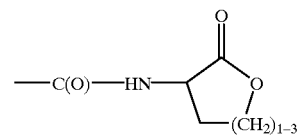
as defined above.
SCHEME 16
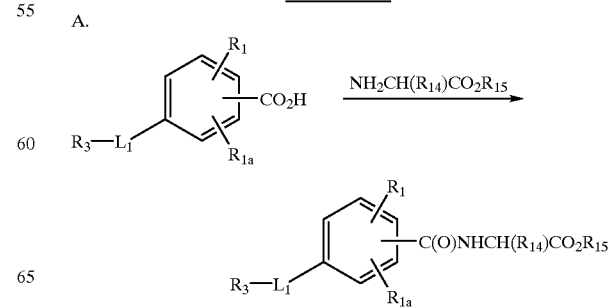

B.
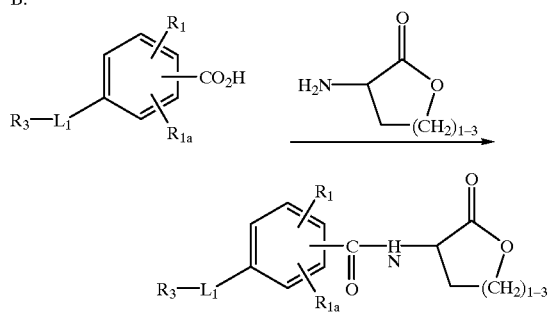
TABLE 6
Amines of the Type A(B)N-L₁
1
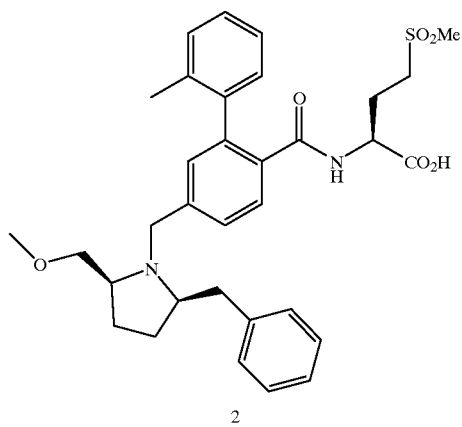
2
TABLE 6-continued
Amines of the Type A(B)N-L₁
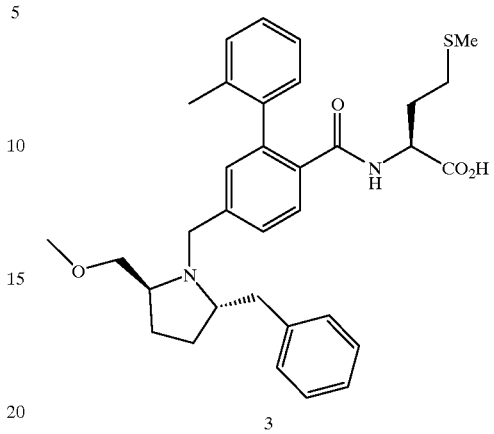
3
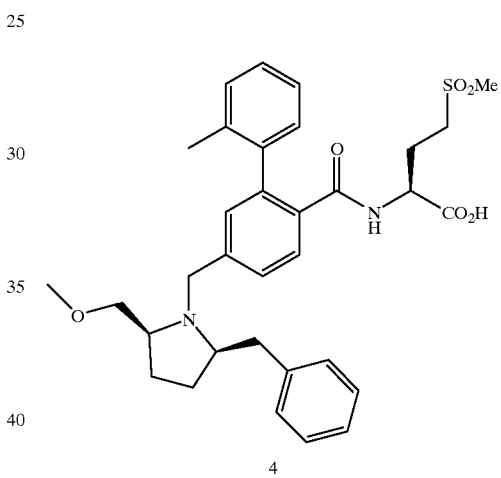
4
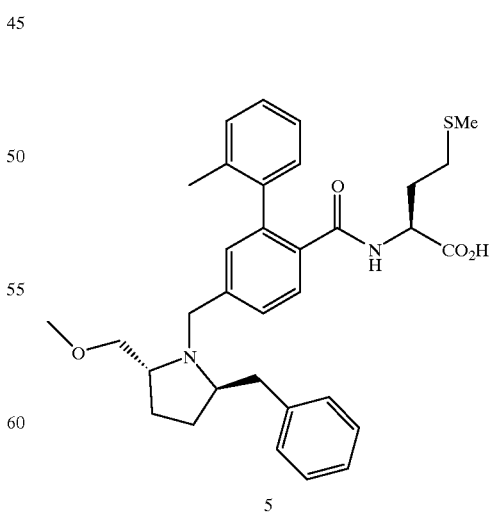
5

TABLE 6-continued
Amines of the Type A(B)N-L$_1$
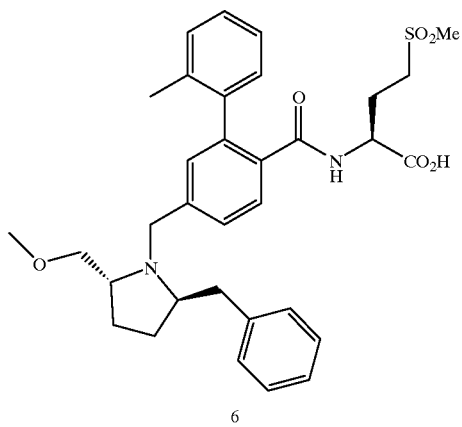
6
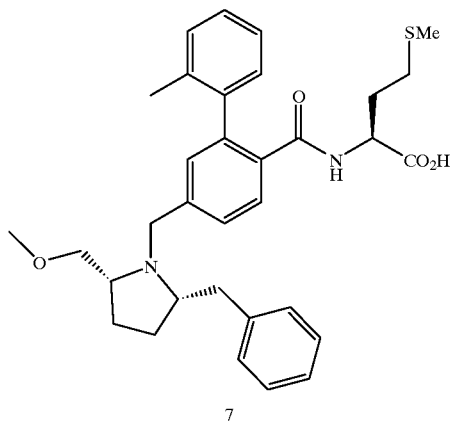
7
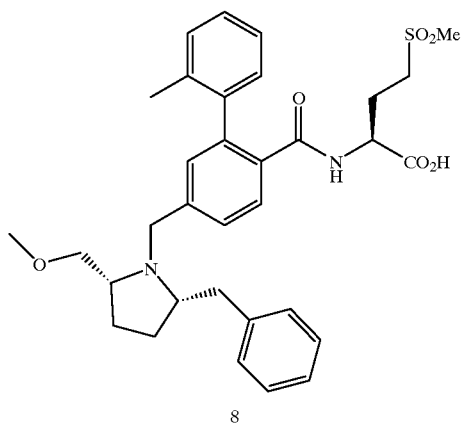
8
TABLE 6-continued
Amines of the Type A(B)N-L$_1$
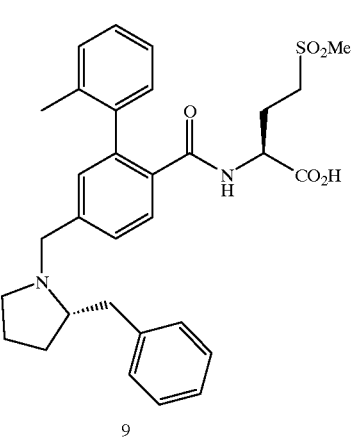
9
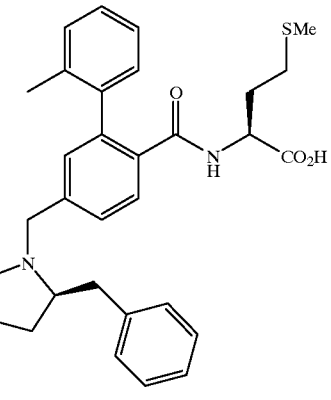
10
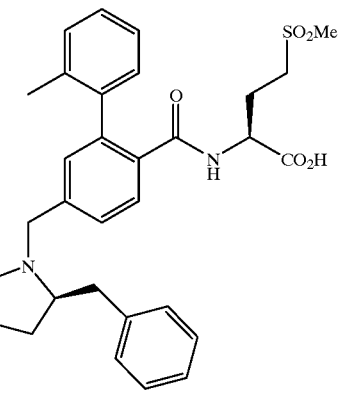
11

TABLE 6-continued
Amines of the Type A(B)N-L₁
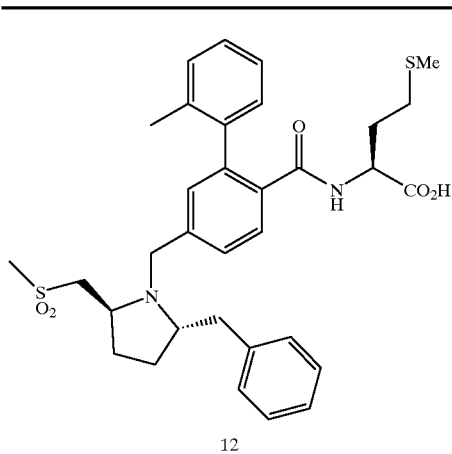
12
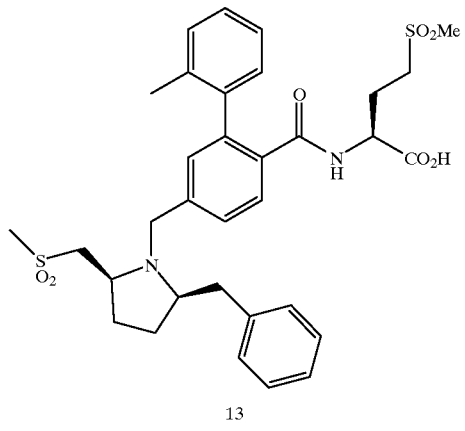
13
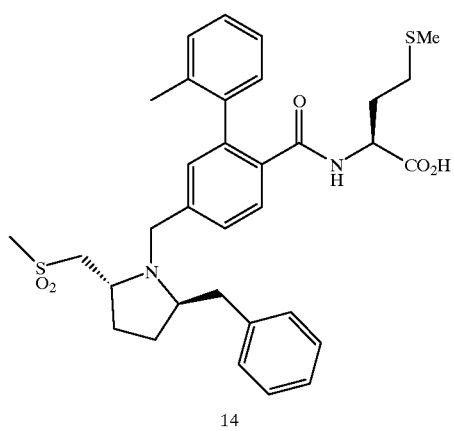
14
TABLE 6-continued
Amines of the Type A(B)N-L₁
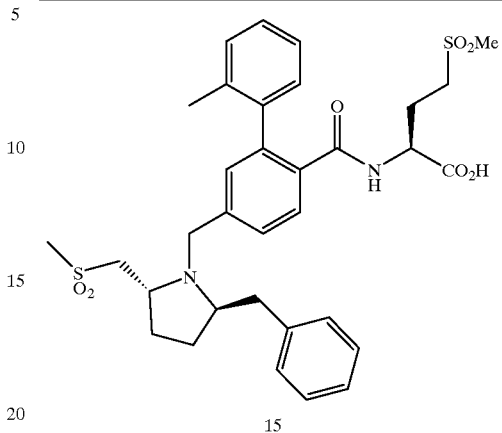
15
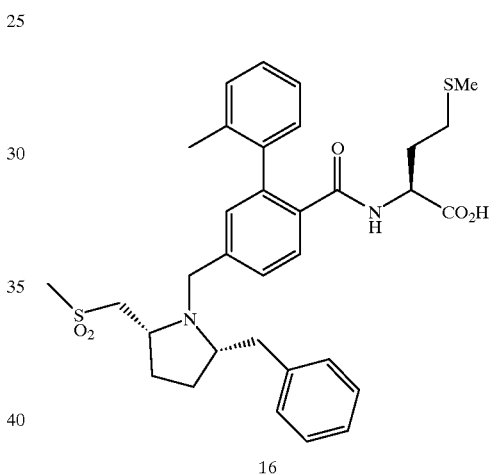
16
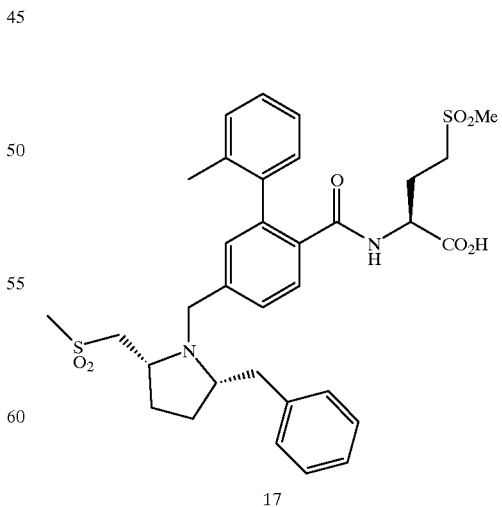
17

TABLE 6-continued
Amines of the Type A(B)N-L₁
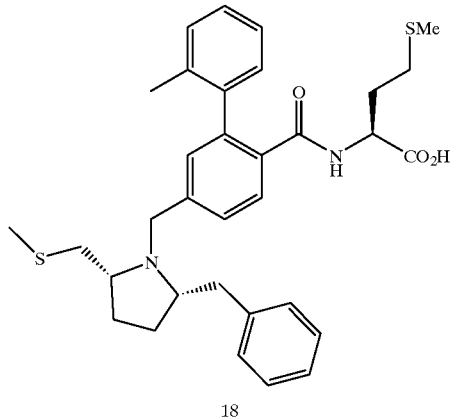
18
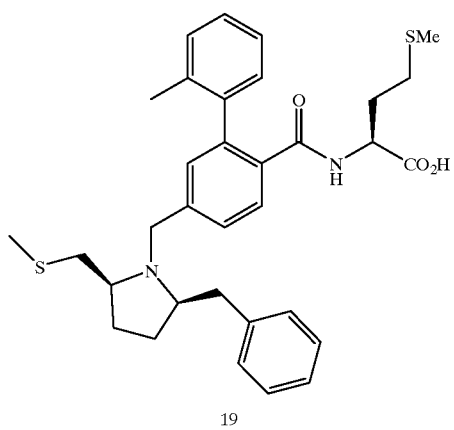
19
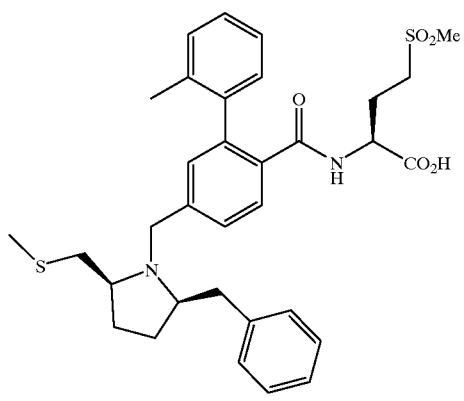
20
TABLE 6-continued
Amines of the Type A(B)N-L₁
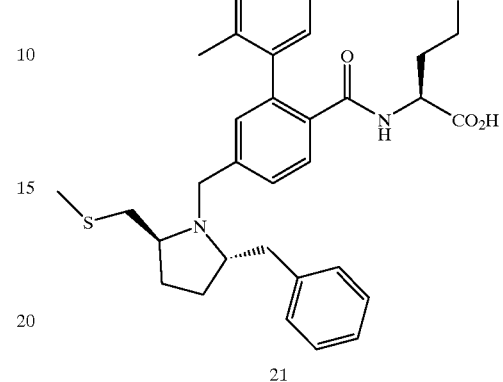
21
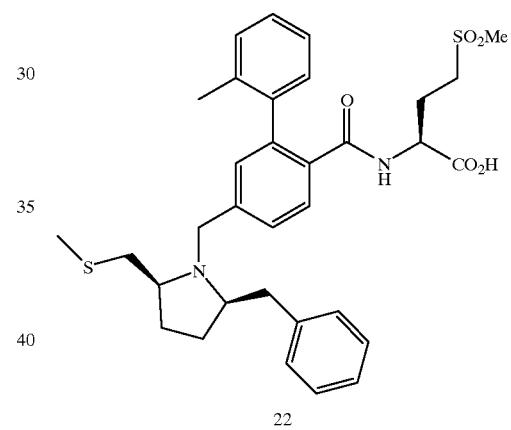
22
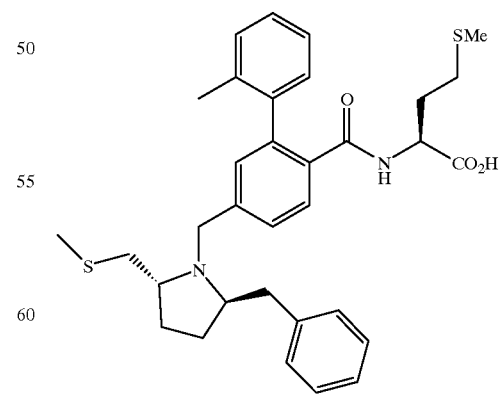
23

TABLE 6-continued
Amines of the Type A(B)N-L₁
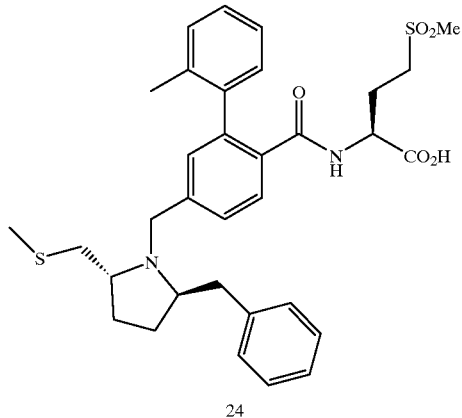
24
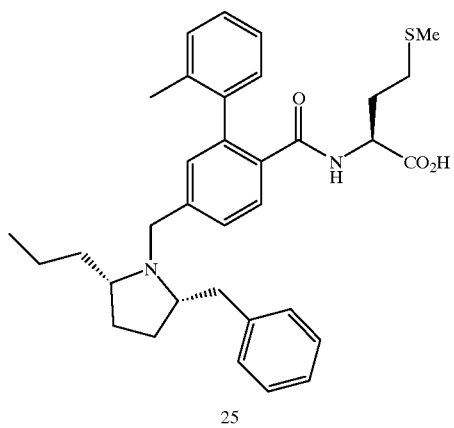
25
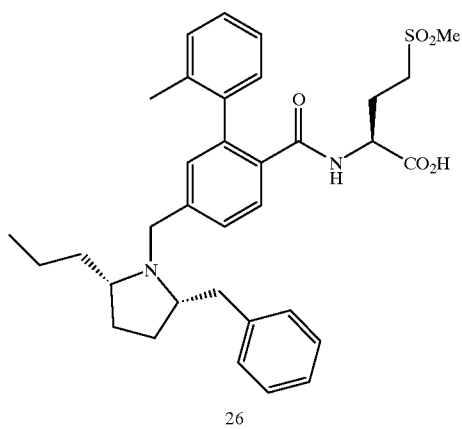
26
TABLE 6-continued
Amines of the Type A(B)N-L₁
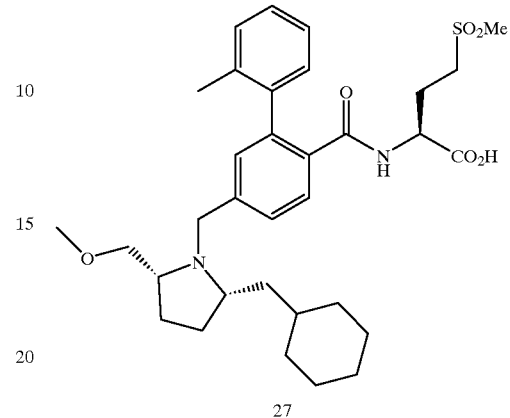
27
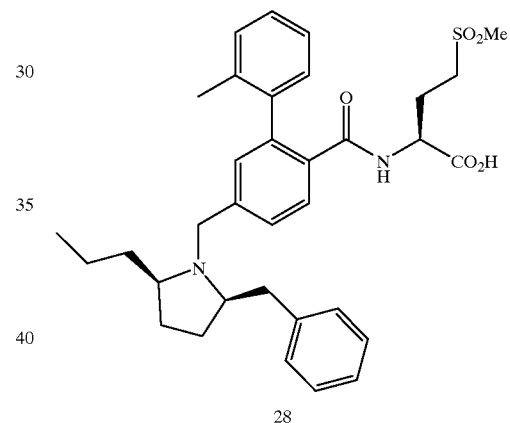
28
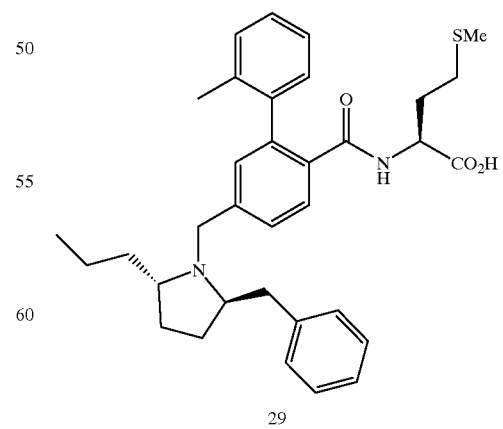
29

TABLE 6-continued
Amines of the Type A(B)N-L₁
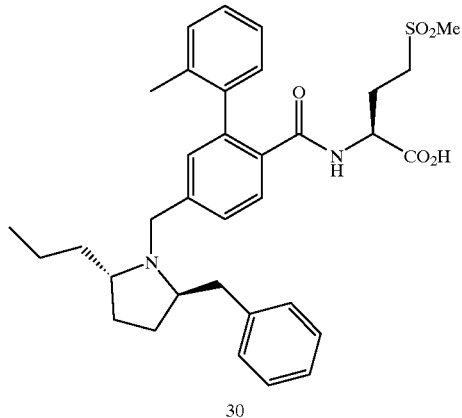
30
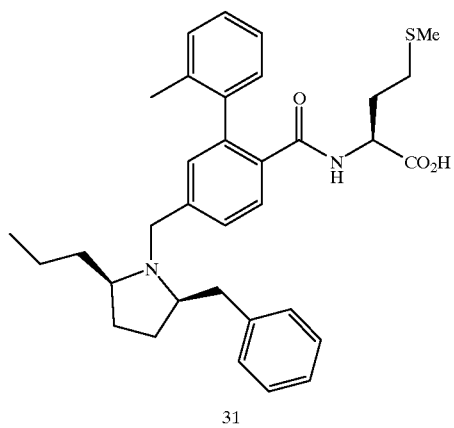
31
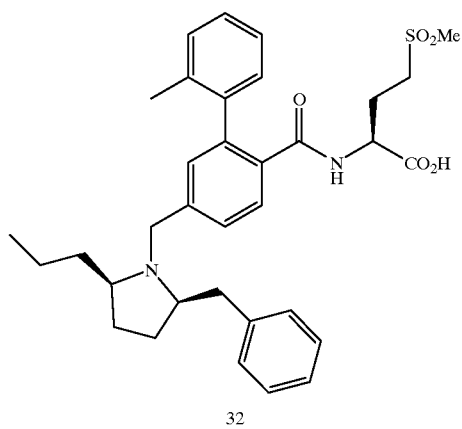
32
TABLE 6-continued
Amines of the Type A(B)N-L₁
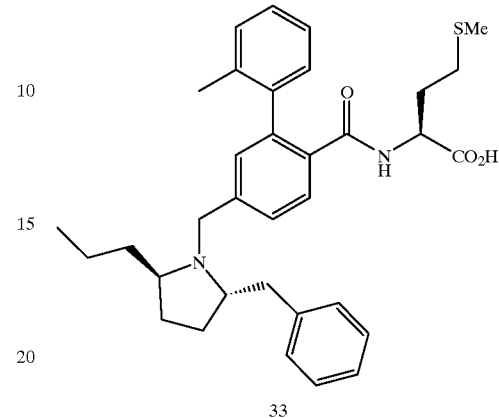
33
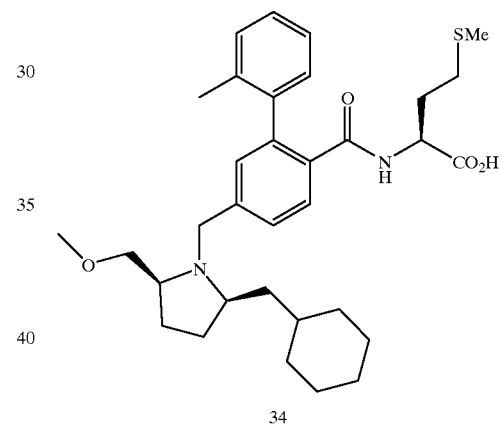
34
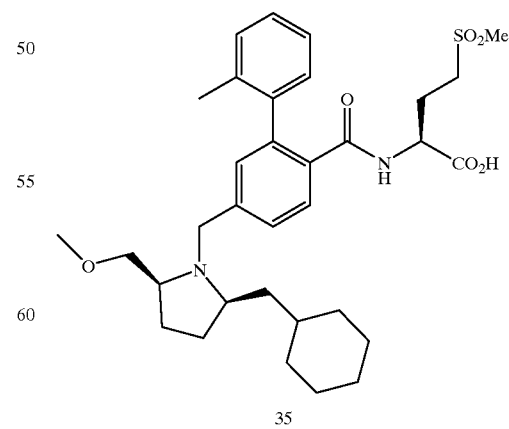
35

TABLE 6-continued
Amines of the Type A(B)N-L$_1$
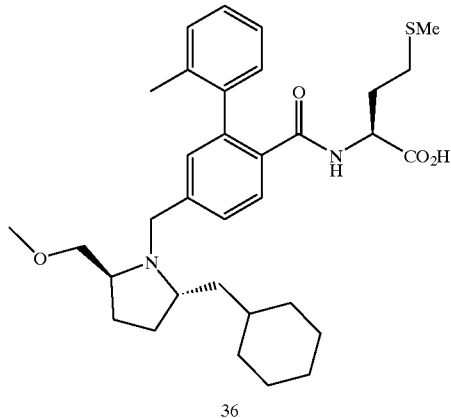
36
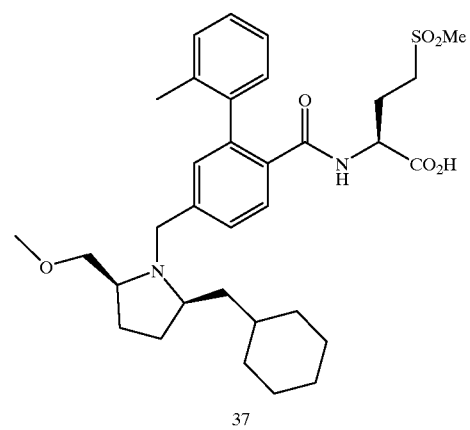
37
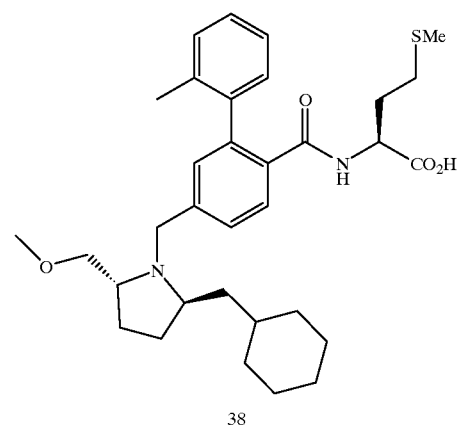
38
TABLE 6-continued
Amines of the Type A(B)N-L$_1$
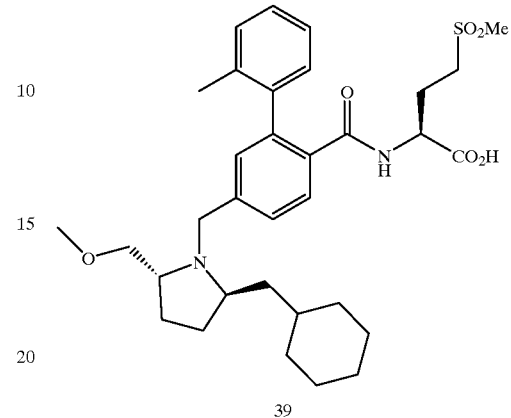
39
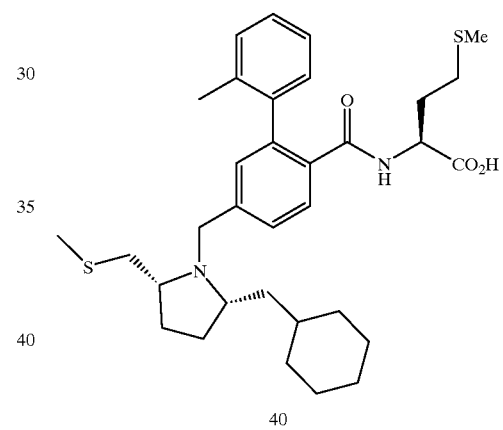
40
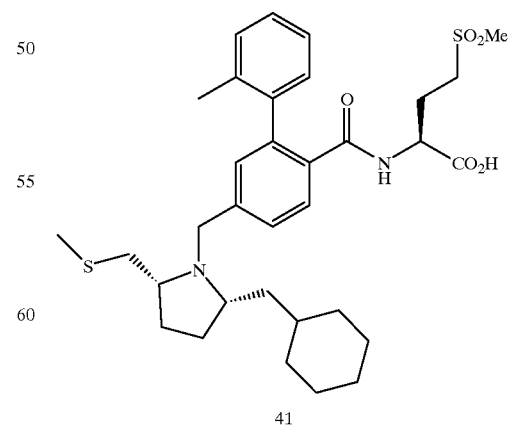
41

TABLE 6-continued
Amines of the Type A(B)N-L₁
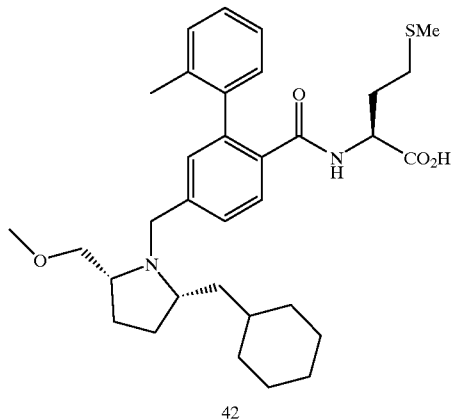
42
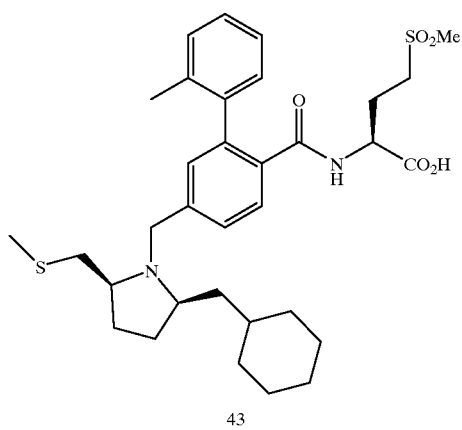
43
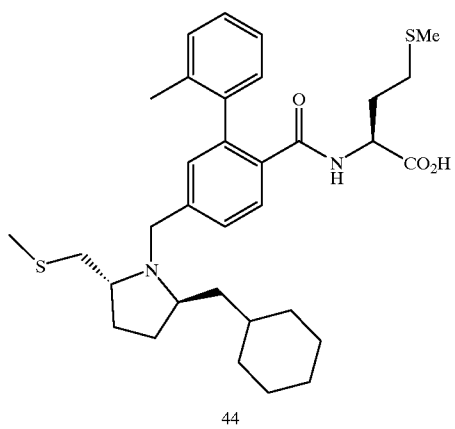
44
TABLE 6-continued
Amines of the Type A(B)N-L₁
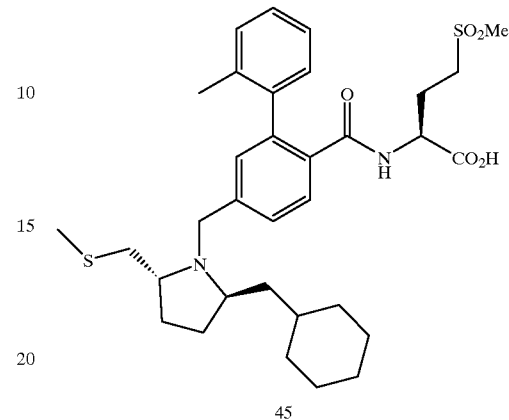
45
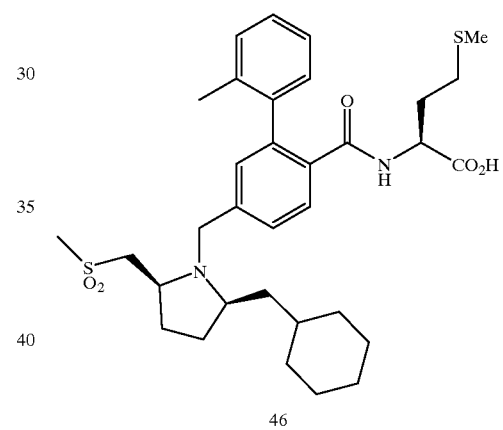
46
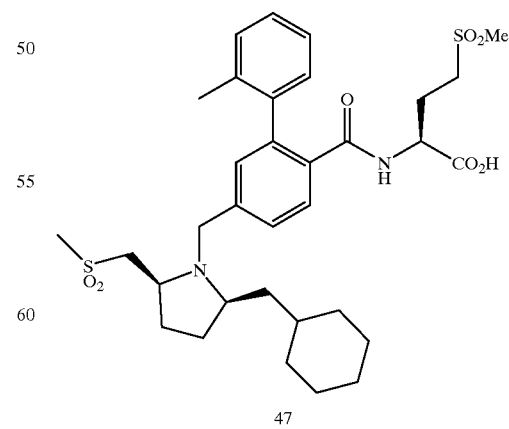
47

TABLE 6-continued
Amines of the Type A(B)N-L₁
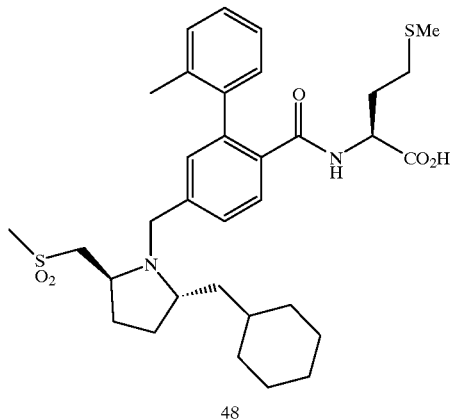
48
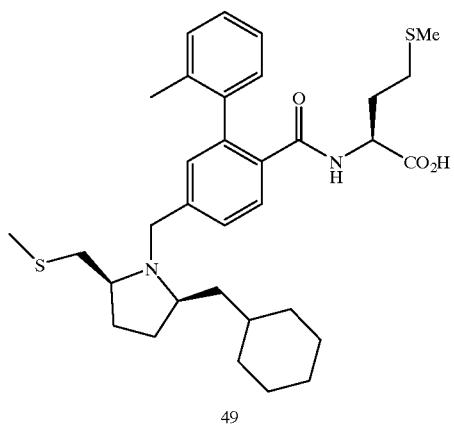
49
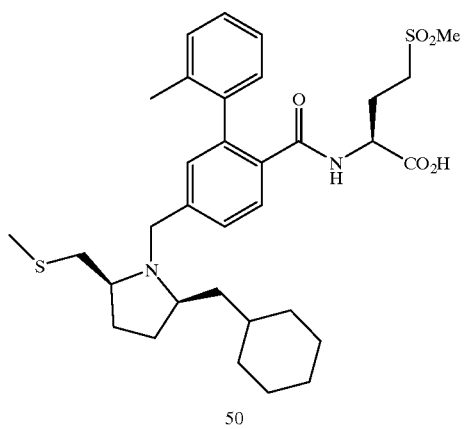
50
TABLE 6-continued
Amines of the Type A(B)N-L₁
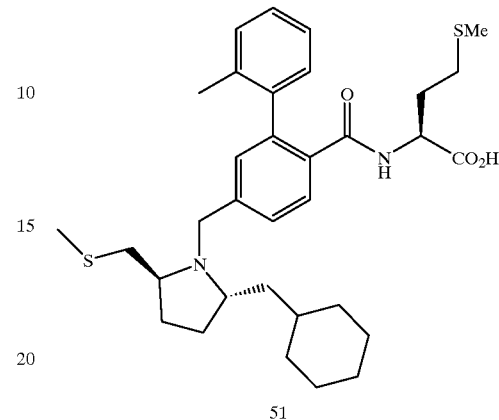
51
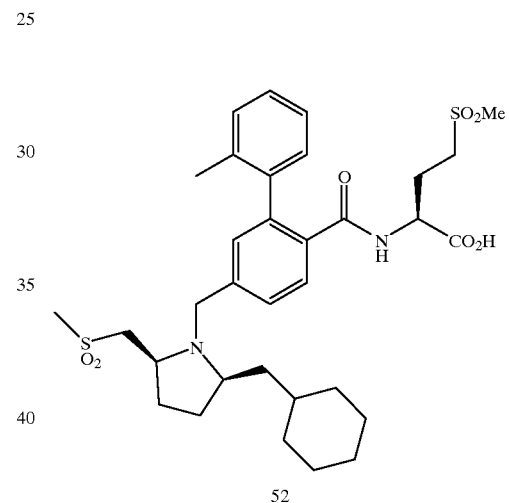
52
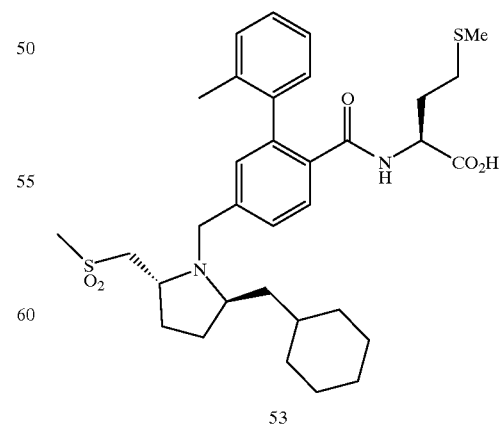
53

TABLE 6-continued
Amines of the Type A(B)N-L₁
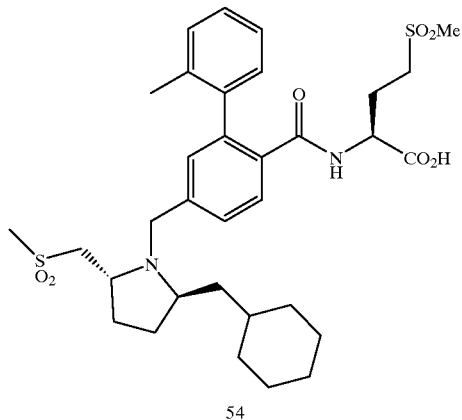
54
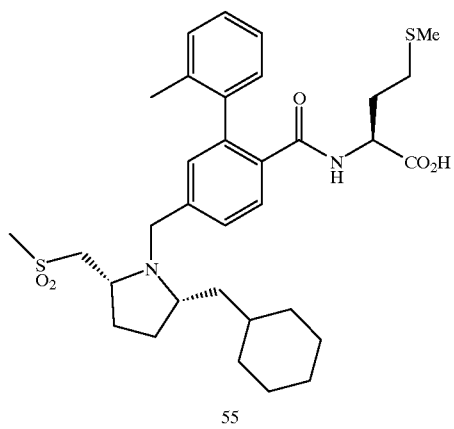
55
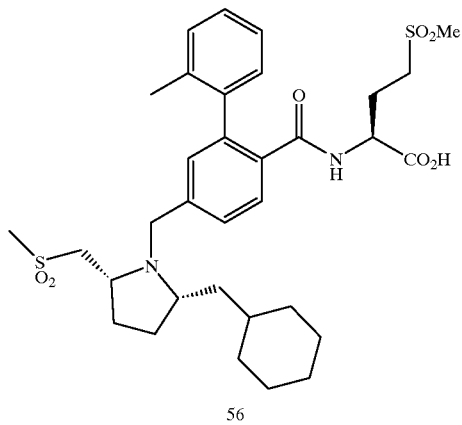
56
TABLE 6-continued
Amines of the Type A(B)N-L₁
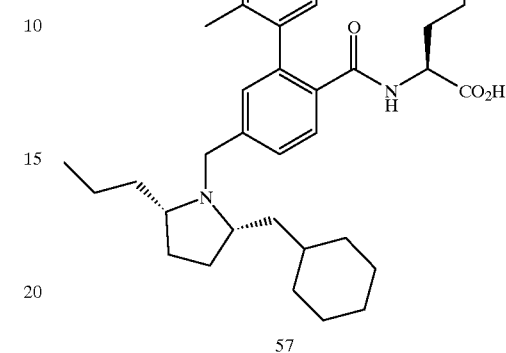
57
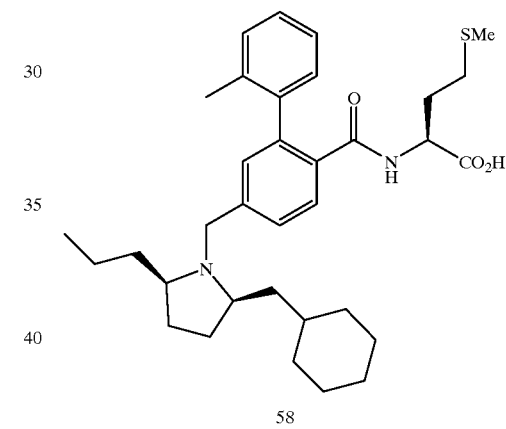
58
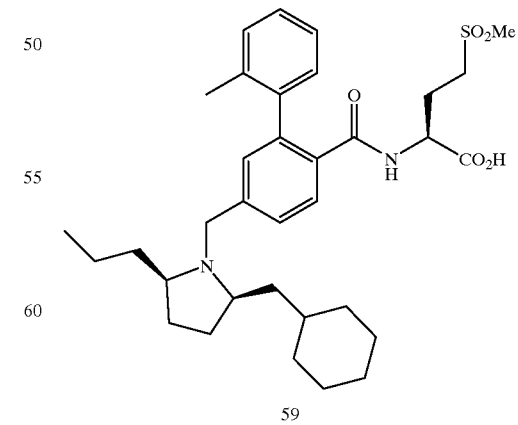
59

TABLE 6-continued
Amines of the Type A(B)N-L₁
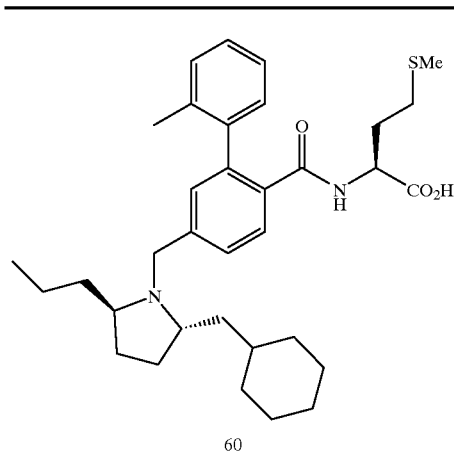
60
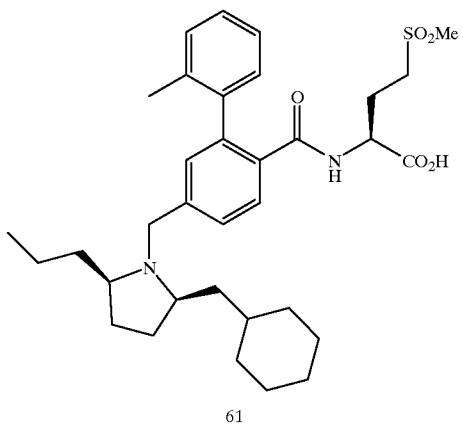
61
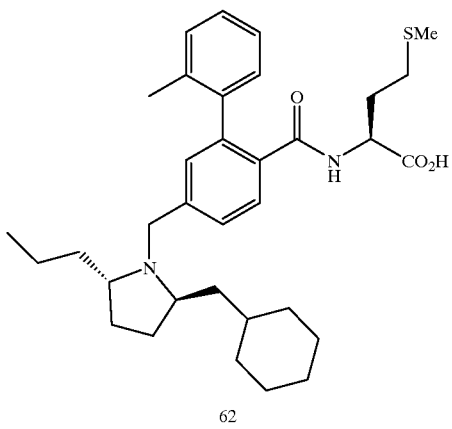
62
TABLE 6-continued
Amines of the Type A(B)N-L₁
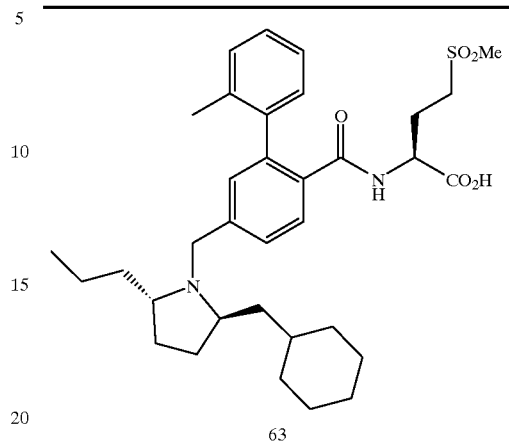
63
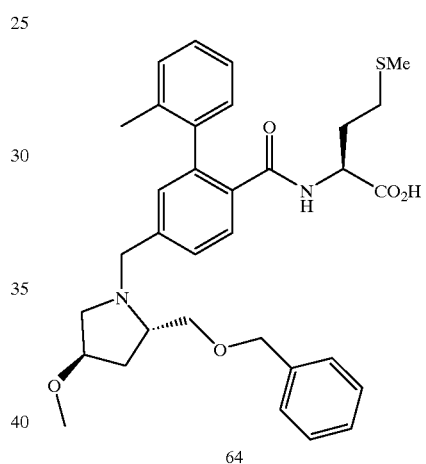
64
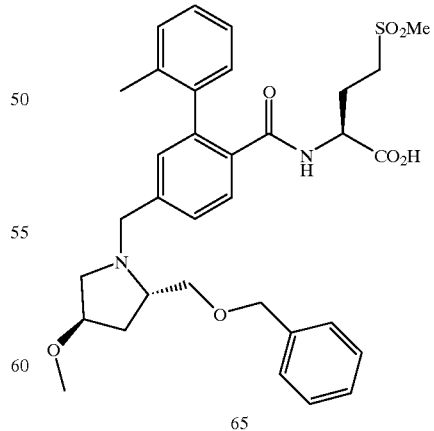
65

TABLE 6-continued
Amines of the Type A(B)N-L₁
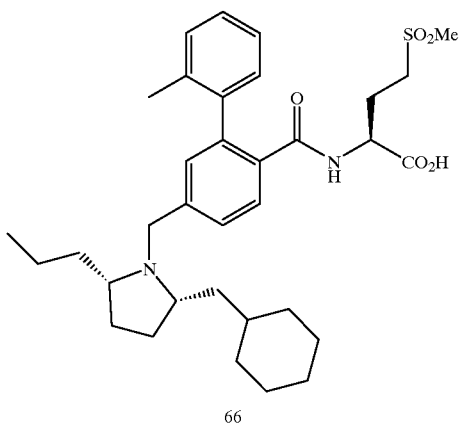
66
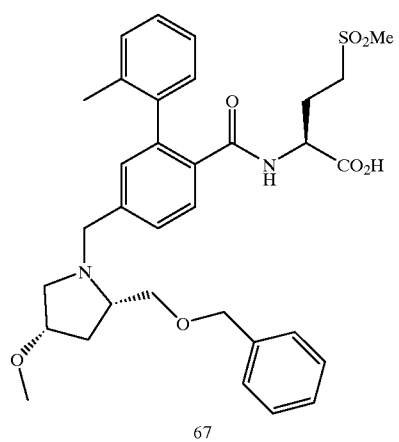
67
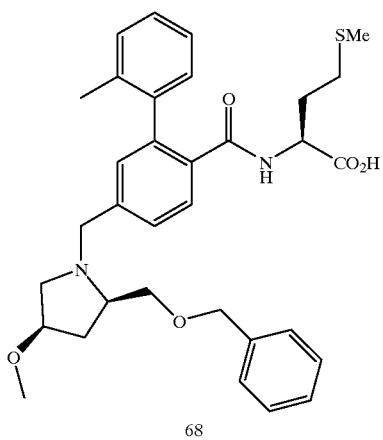
68
TABLE 6-continued
Amines of the Type A(B)N-L₁
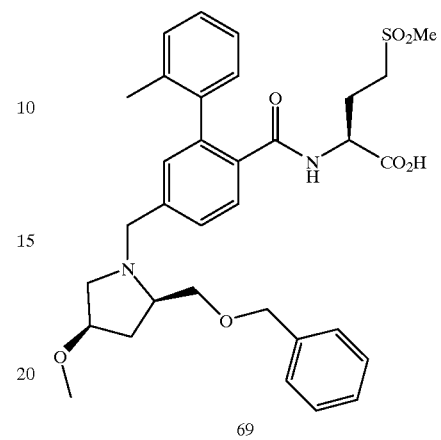
69
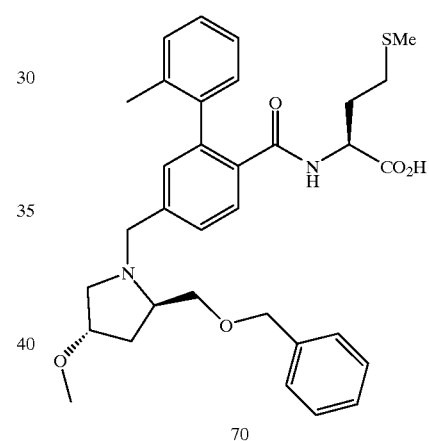
70
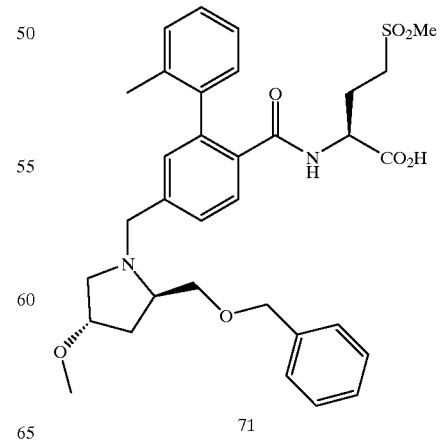
71

TABLE 6-continued
Amines of the Type A(B)N-L₁
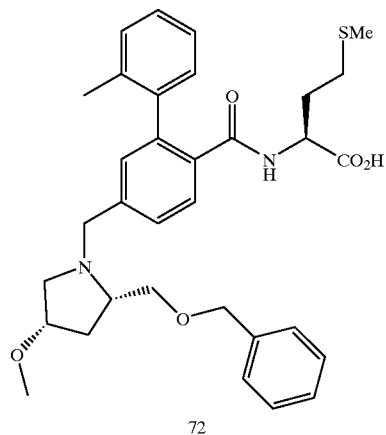
72
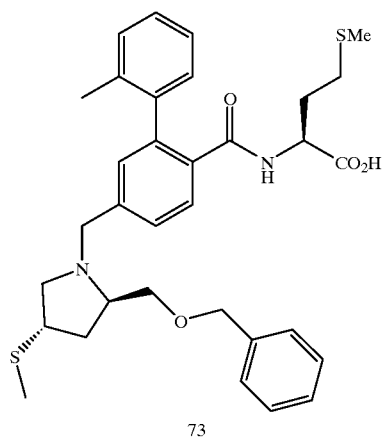
73
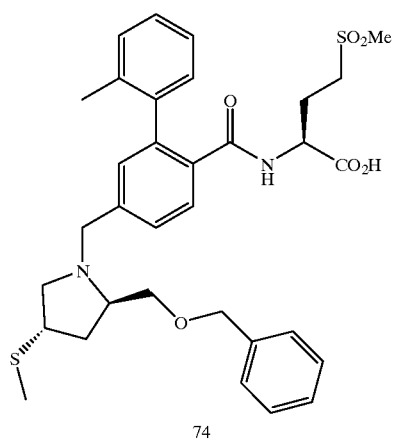
74
TABLE 6-continued
Amines of the Type A(B)N-L₁
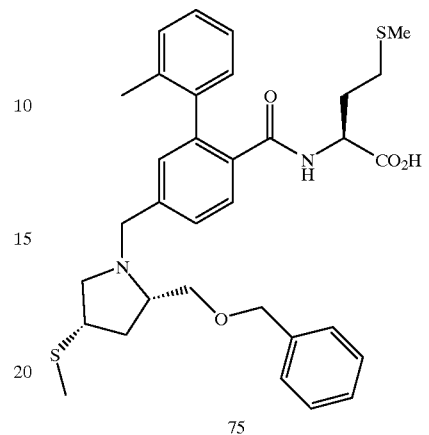
75
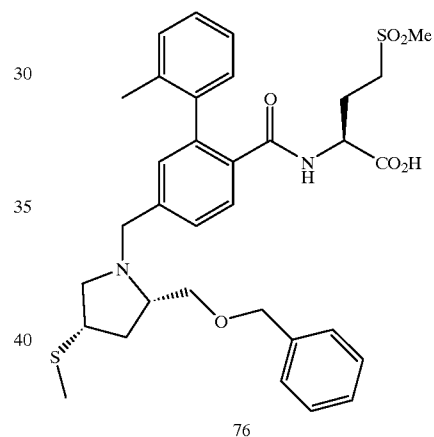
76
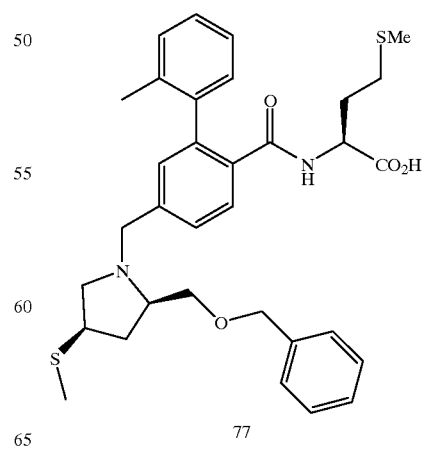
77

TABLE 6-continued
Amines of the Type A(B)N-L₁
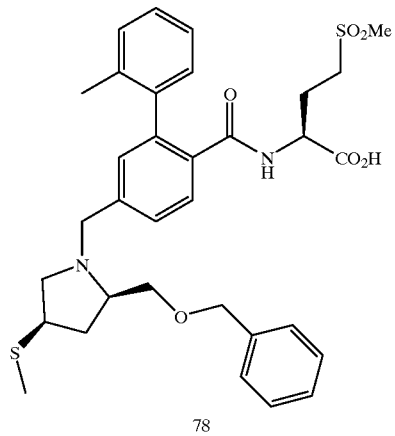
78
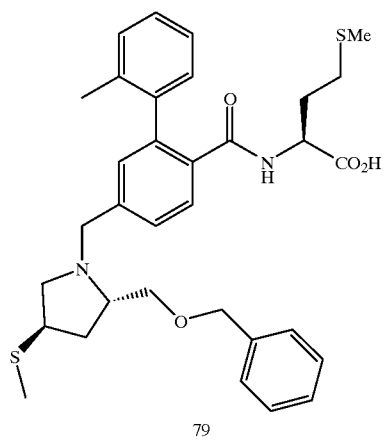
79
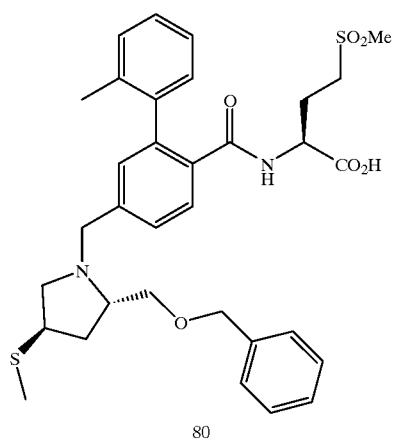
80
TABLE 6-continued
Amines of the Type A(B)N-L₁
81
82
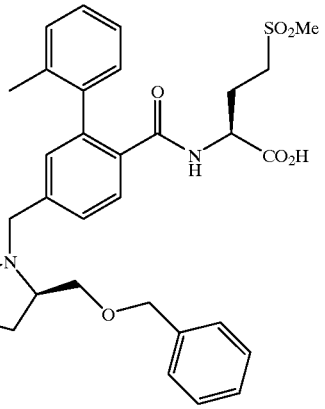
83

TABLE 6-continued
Amines of the Type A(B)N-L₁
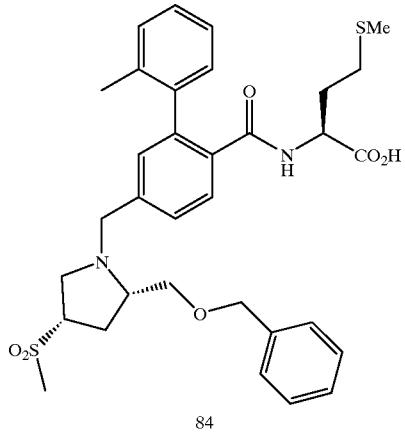
84
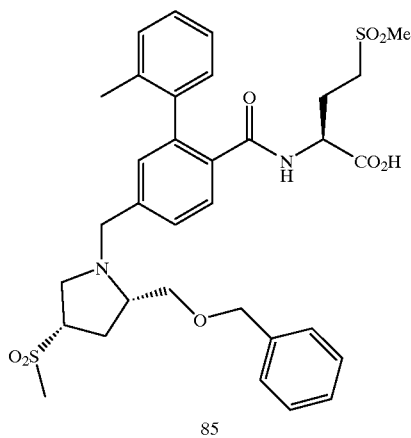
85
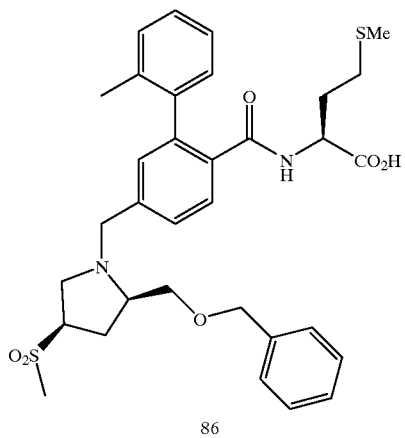
86
TABLE 6-continued
Amines of the Type A(B)N-L₁
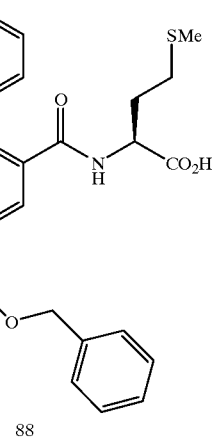
87
88
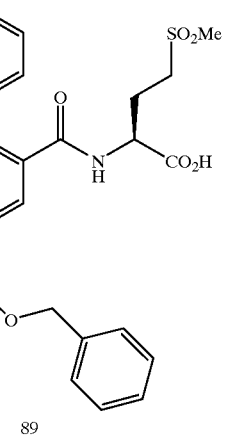
89

TABLE 6-continued
Amines of the Type A(B)N-L$_1$
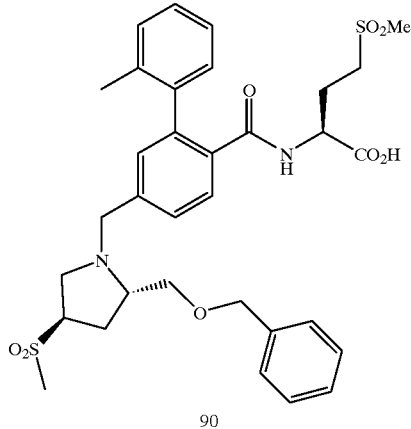
90
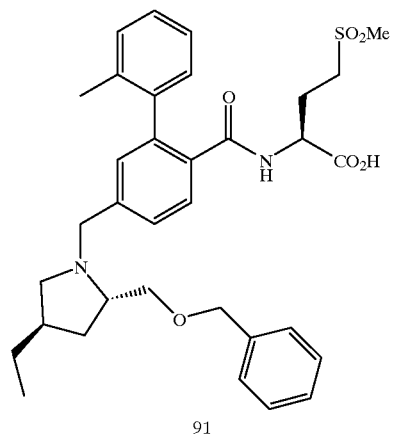
91
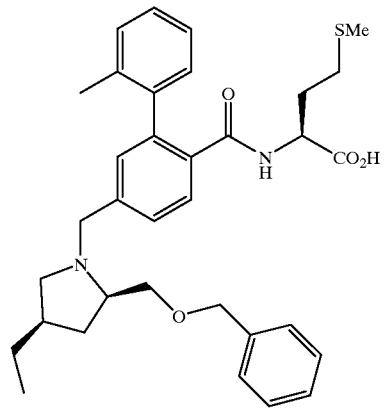
92
TABLE 6-continued
Amines of the Type A(B)N-L$_1$
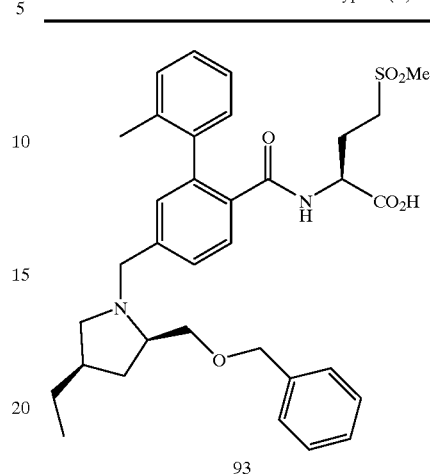
93
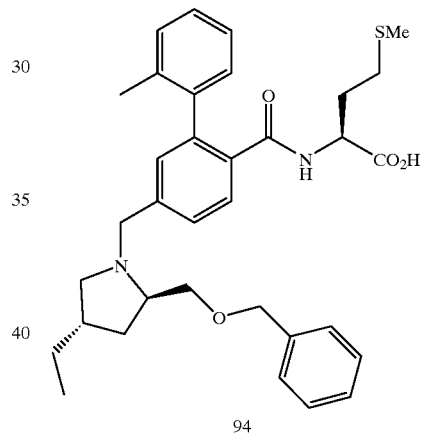
94
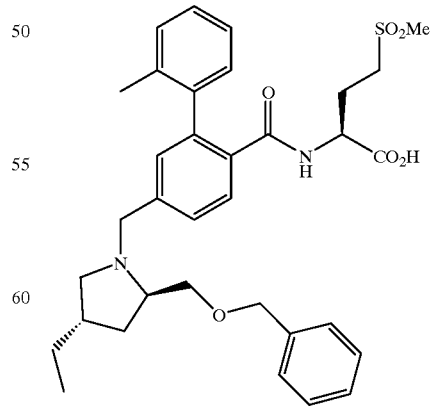
95

TABLE 6-continued
Amines of the Type A(B)N-L₁
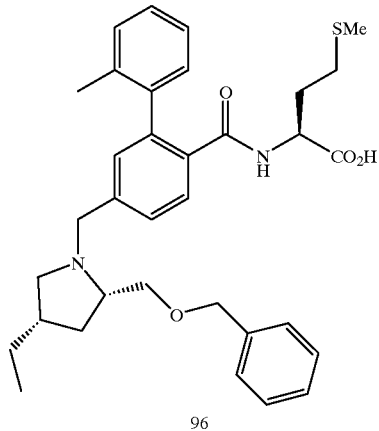
96
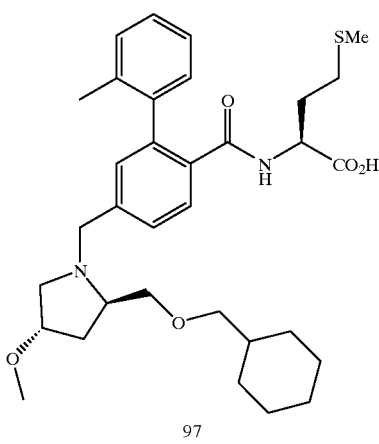
97
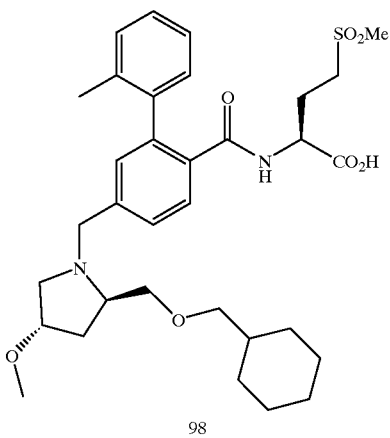
98
TABLE 6-continued
Amines of the Type A(B)N-L₁
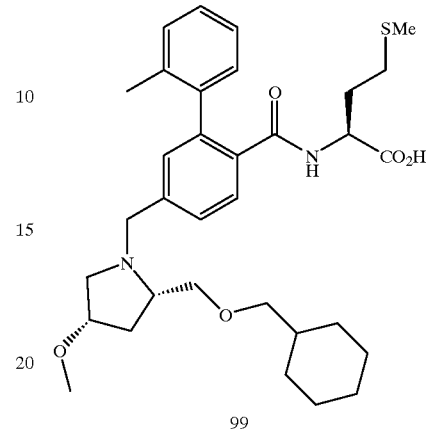
99
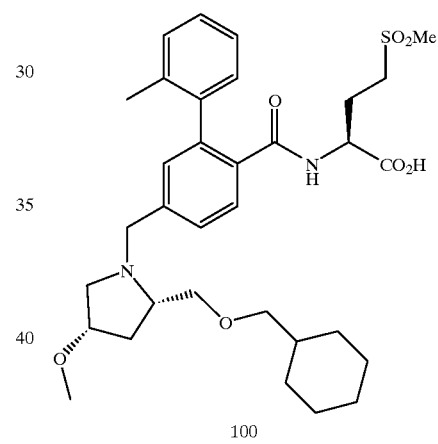
100
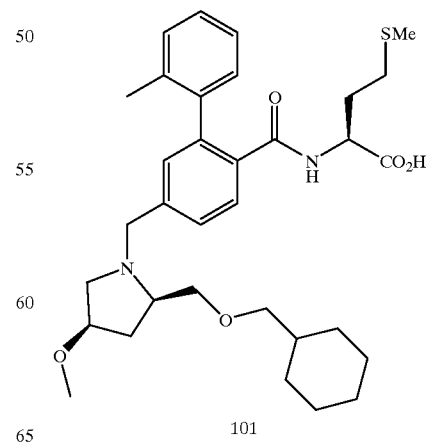
101

TABLE 6-continued
Amines of the Type A(B)N-L$_1$
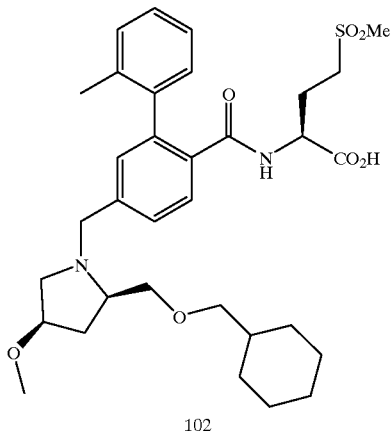
102
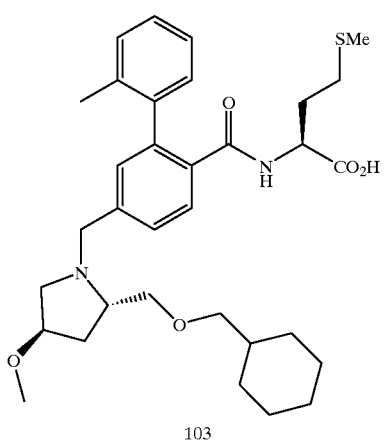
103
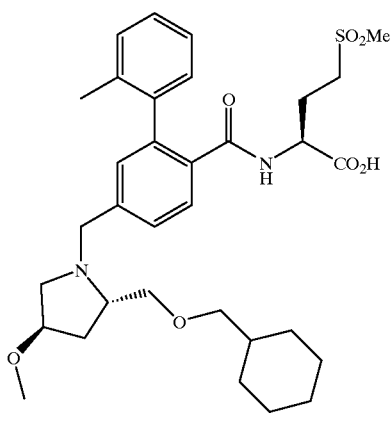
104
TABLE 6-continued
Amines of the Type A(B)N-L$_1$
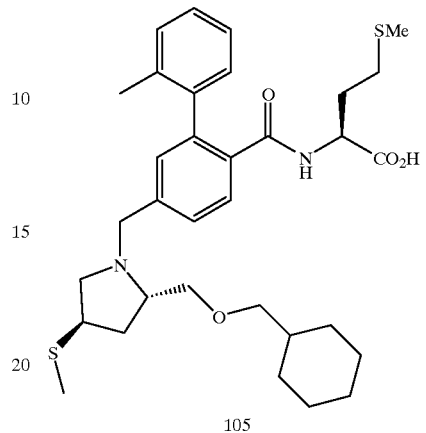
105
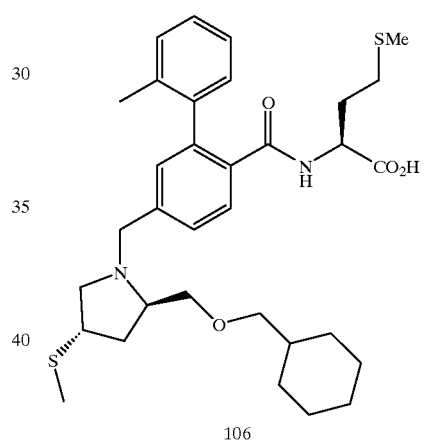
106
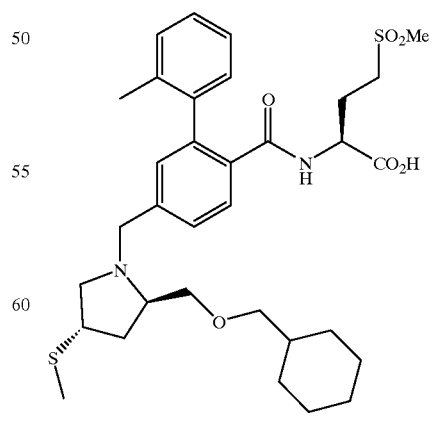
107

TABLE 6-continued
Amines of the Type A(B)N-L₁
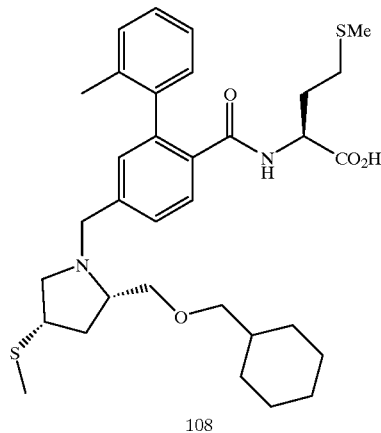
108
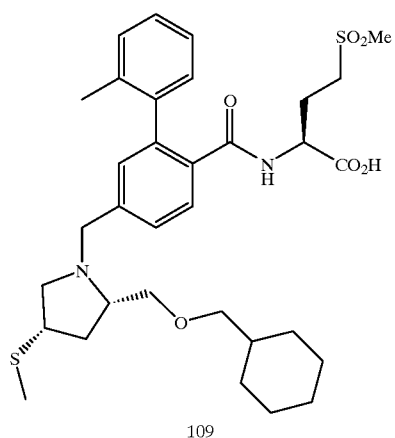
109
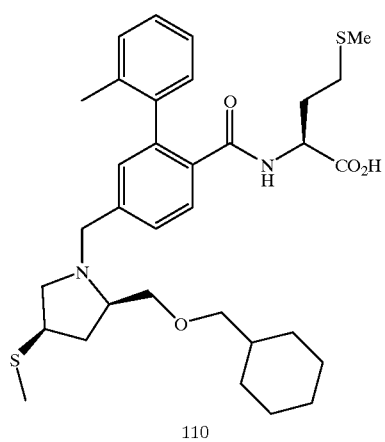
110
TABLE 6-continued
Amines of the Type A(B)N-L₁
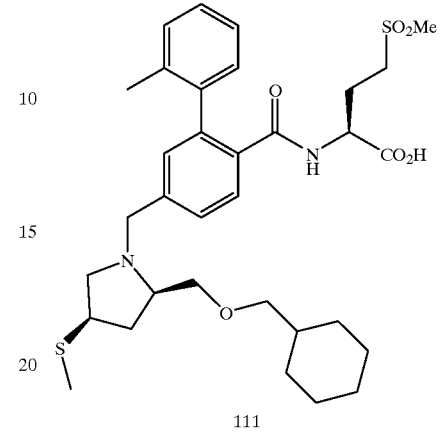
111
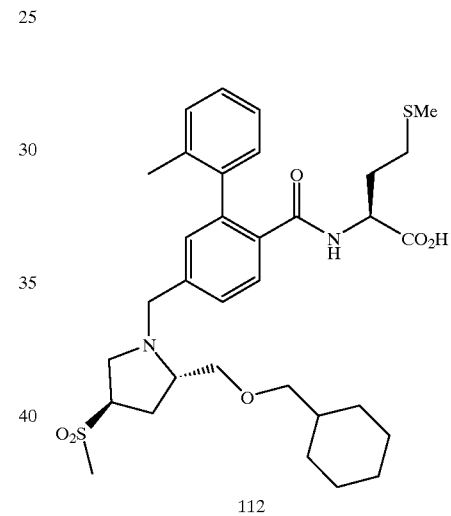
112
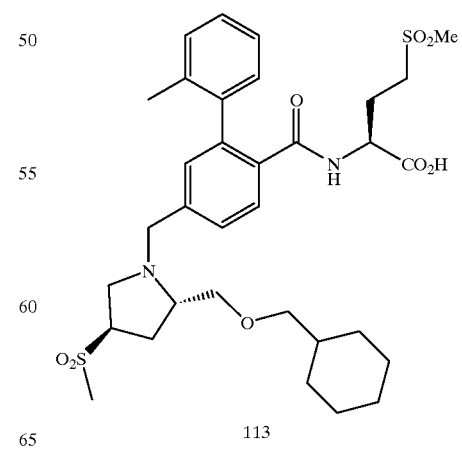
113

TABLE 6-continued
Amines of the Type A(B)N-L₁
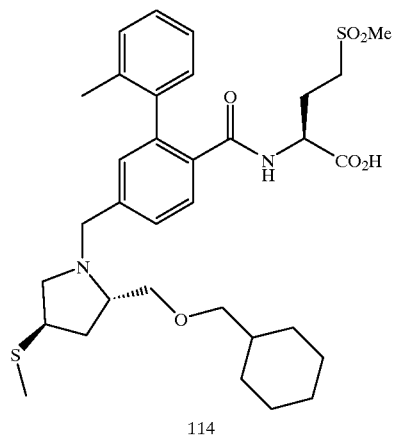
114
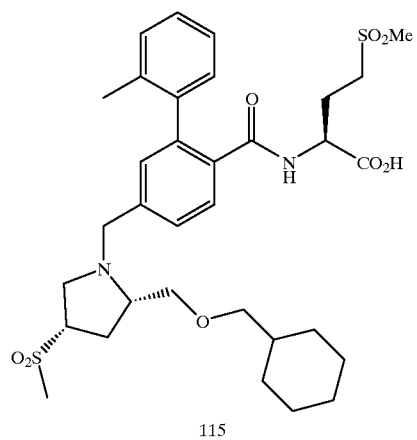
115
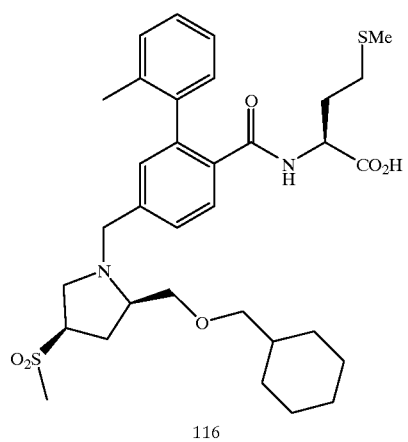
116
TABLE 6-continued
Amines of the Type A(B)N-L₁
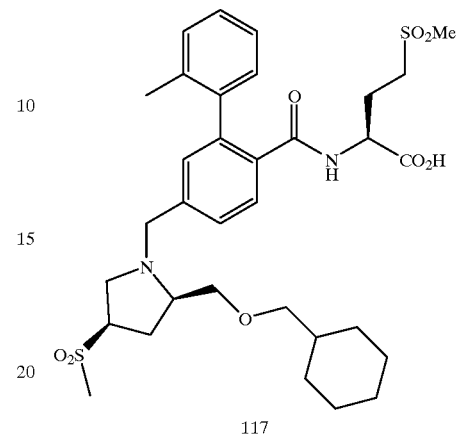
117
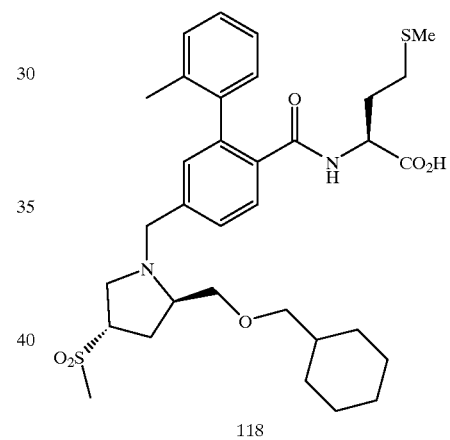
118
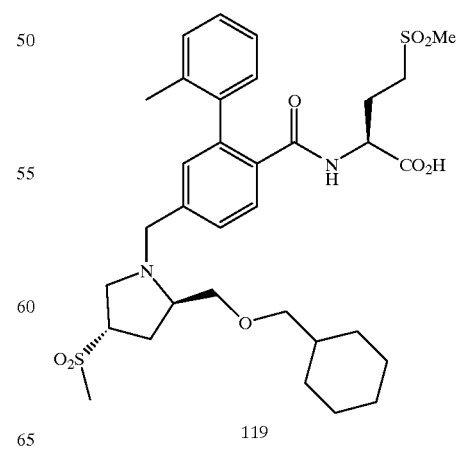
119

TABLE 6-continued
Amines of the Type A(B)N-L₁
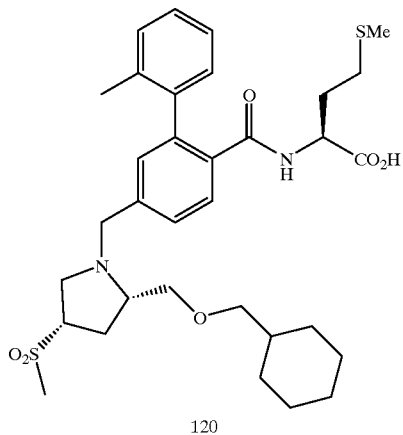
120
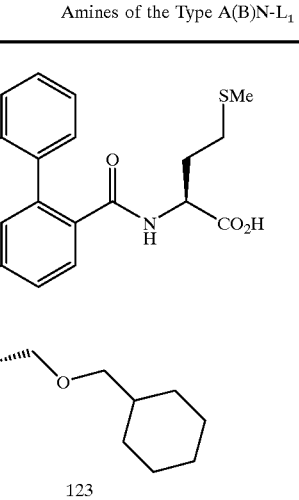
123
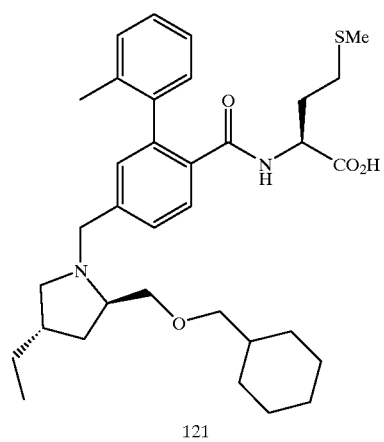
121
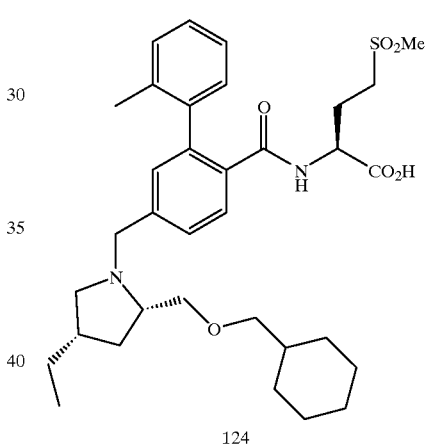
124
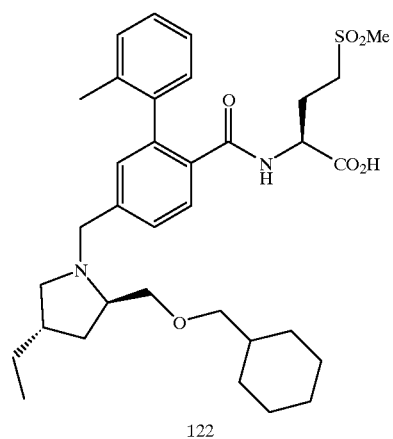
122
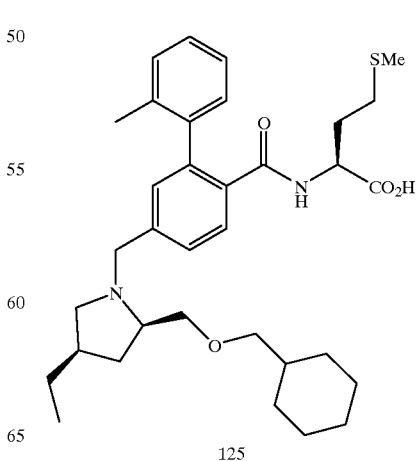
125

TABLE 6-continued
Amines of the Type A(B)N-L₁
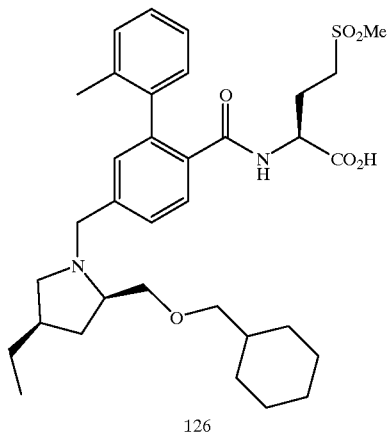
126
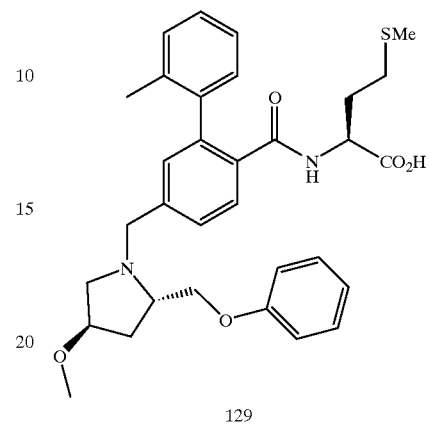
129
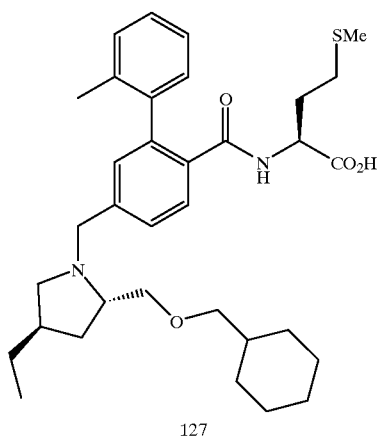
127
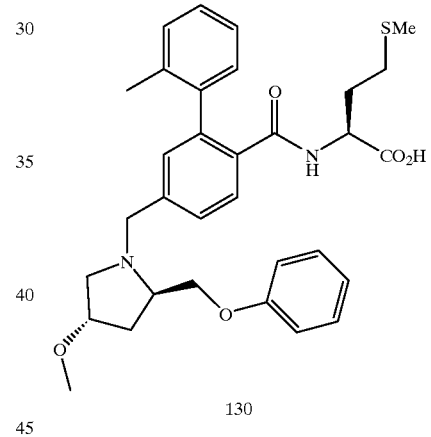
130
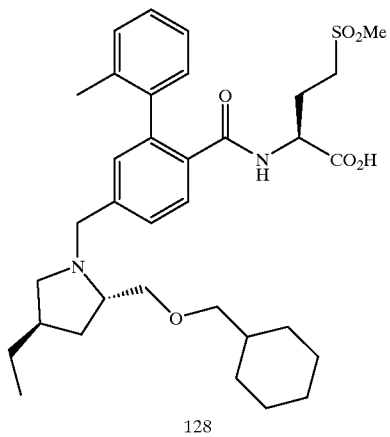
128
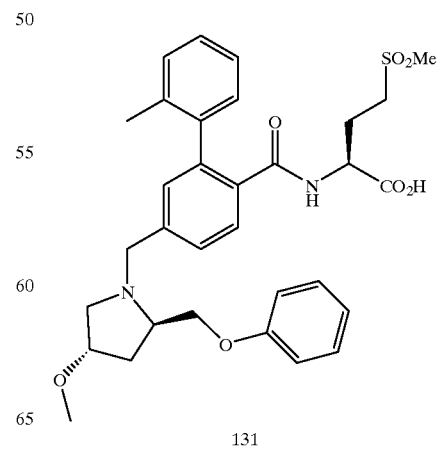
131

TABLE 6-continued
Amines of the Type A(B)N-L₁
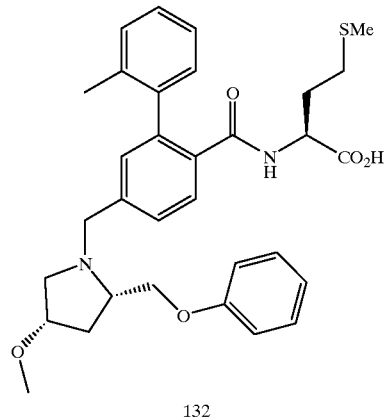
132
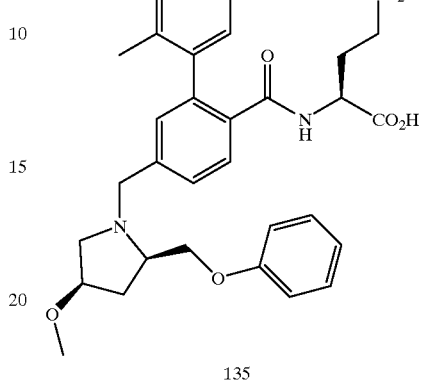
135
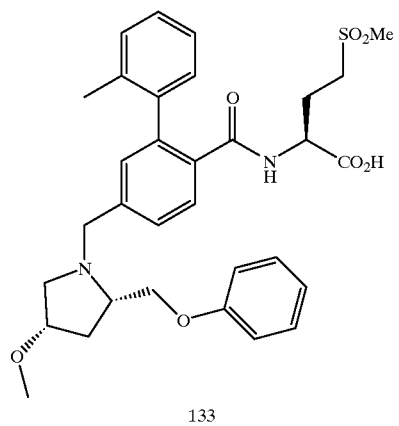
133
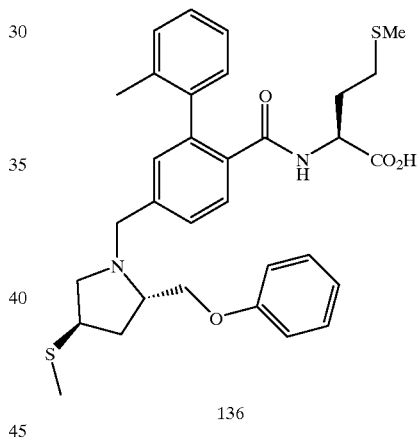
136
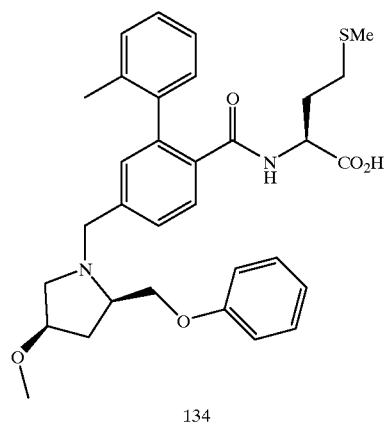
134
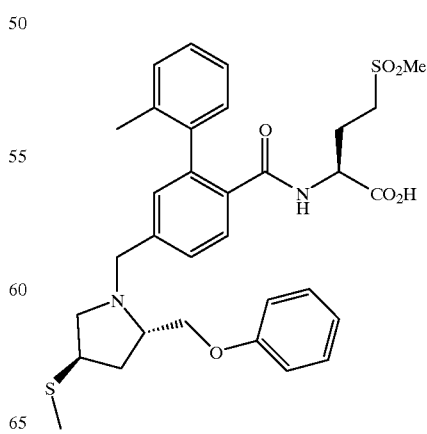
137

TABLE 6-continued
Amines of the Type A(B)N-L₁
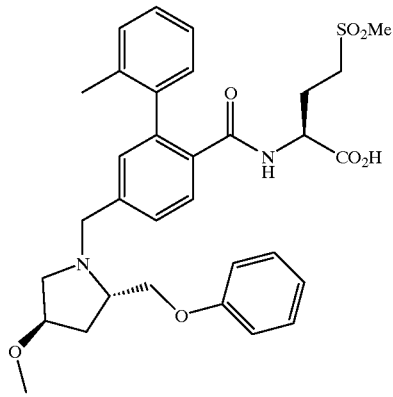
138
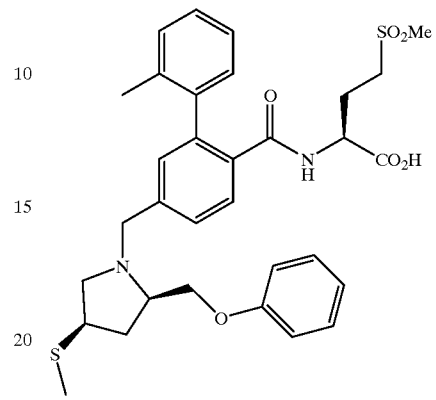
141
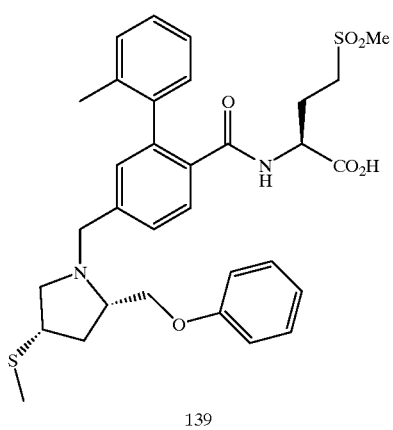
139
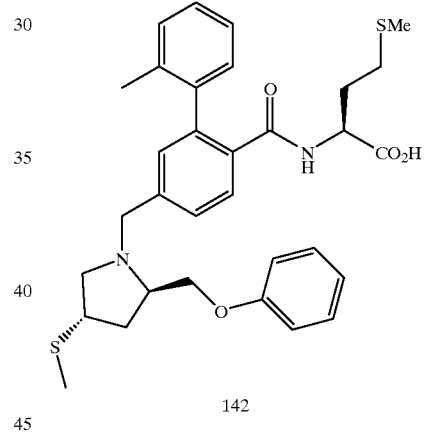
142
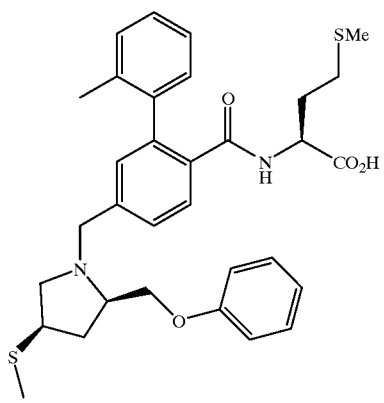
140
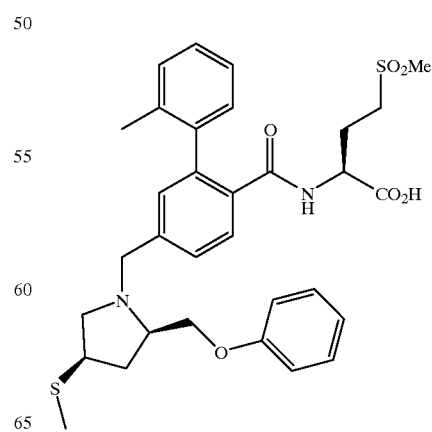
143

TABLE 6-continued
Amines of the Type A(B)N-L₁
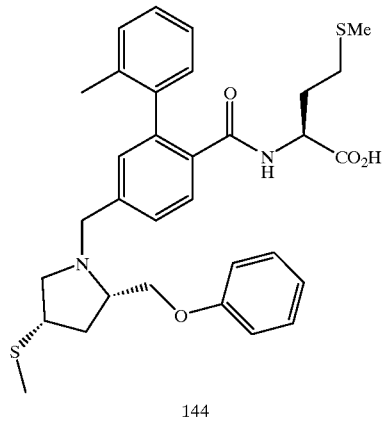
144
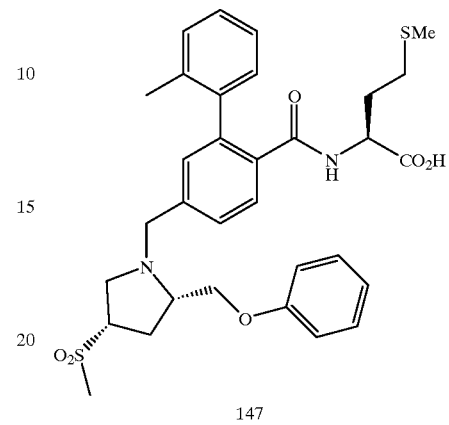
147
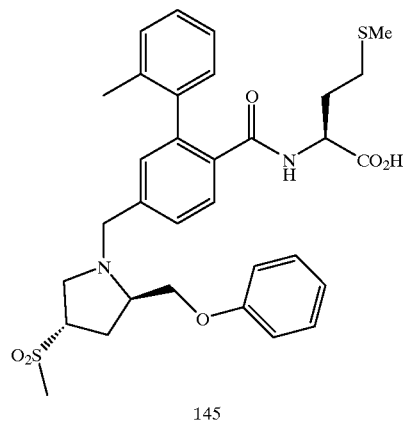
145
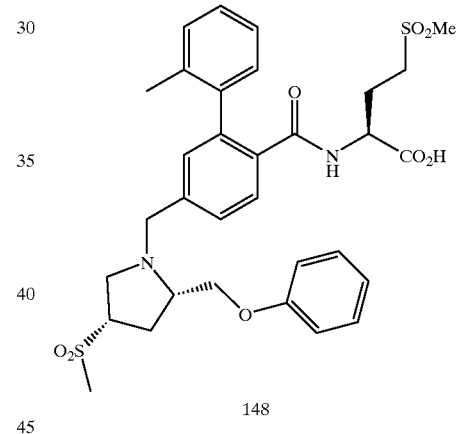
148
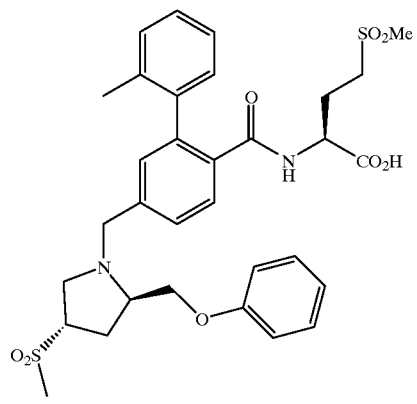
146
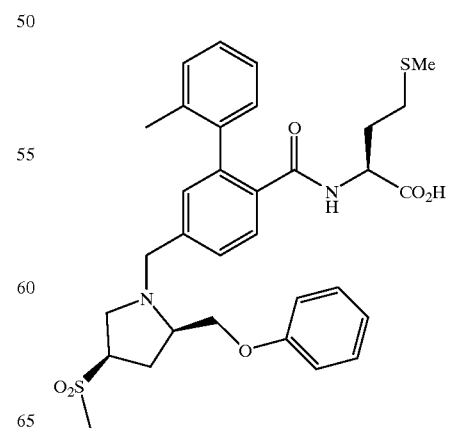
149

TABLE 6-continued
Amines of the Type A(B)N-L₁
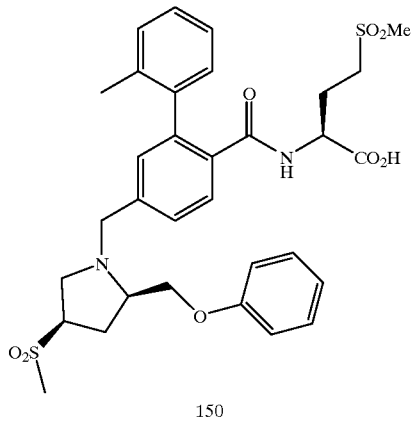
150
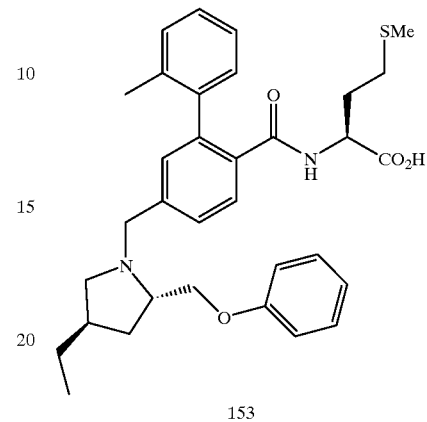
153
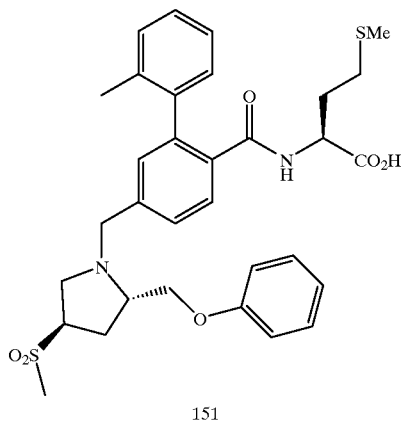
151
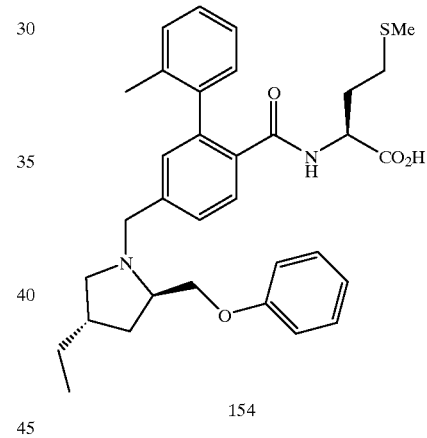
154
152
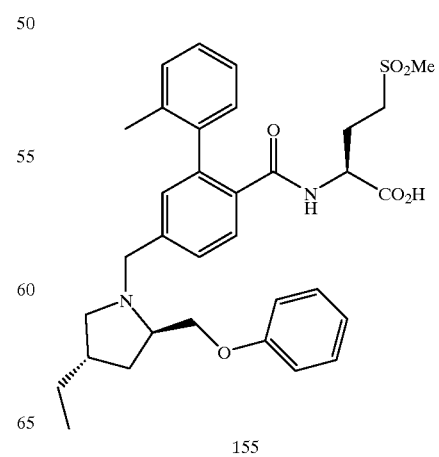
155

TABLE 6-continued
Amines of the Type A(B)N-L₁
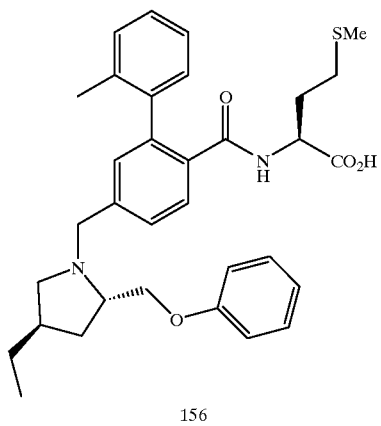
156
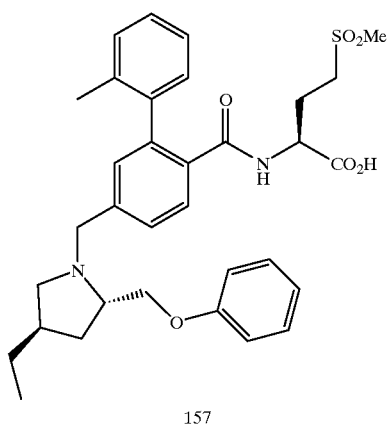
157
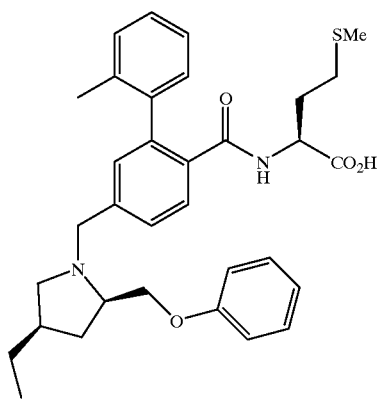
158
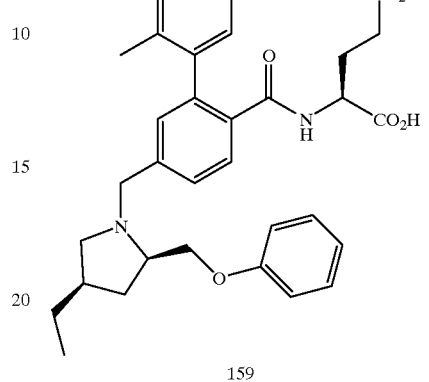
159
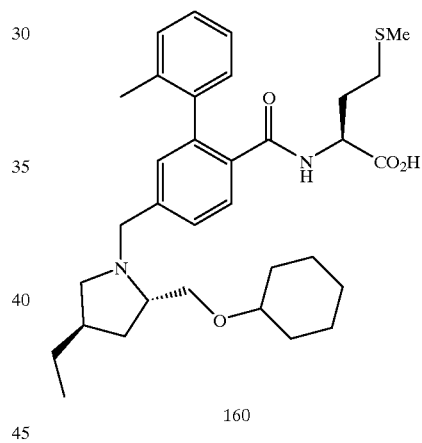
160
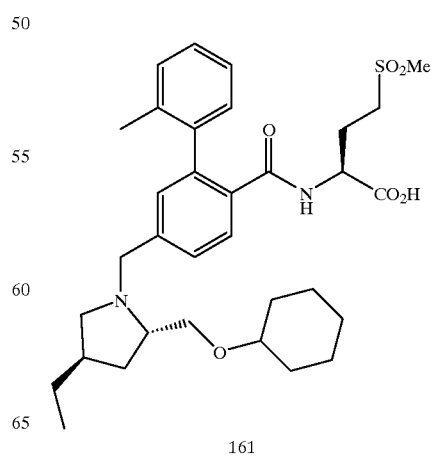
161

TABLE 6-continued
Amines of the Type A(B)N-L₁
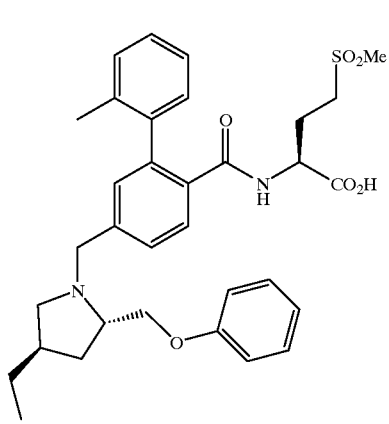
162
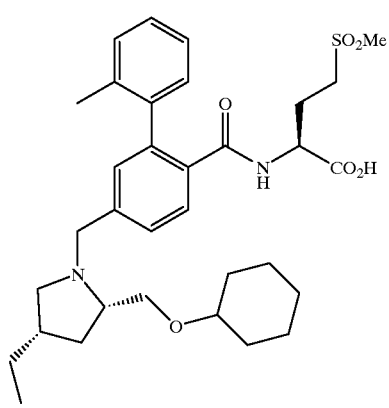
163
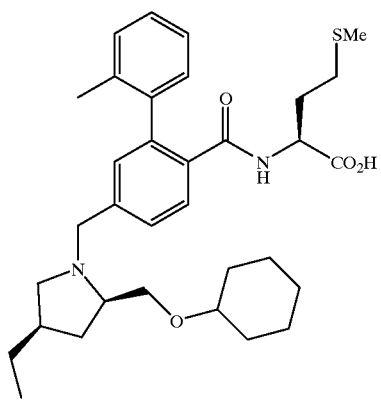
164
TABLE 6-continued
Amines of the Type A(B)N-L₁
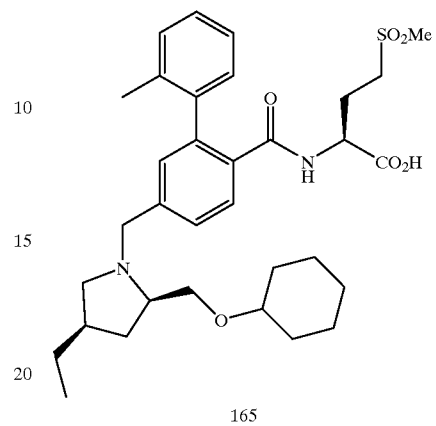
165
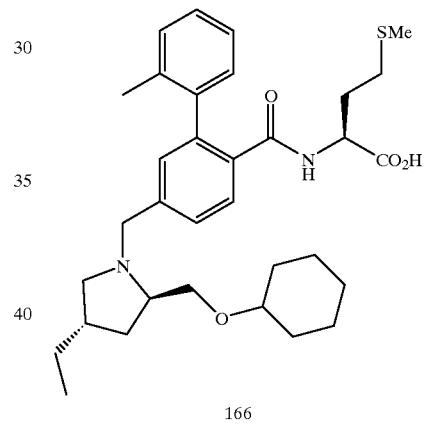
166
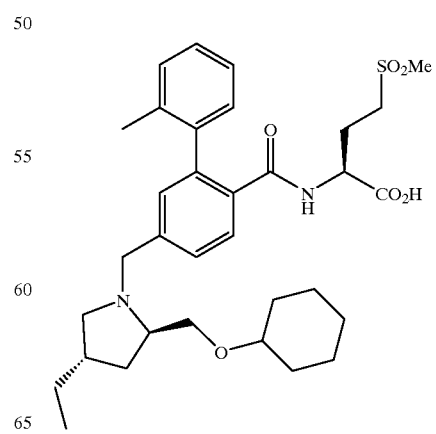
167

TABLE 6-continued
Amines of the Type A(B)N-L$_1$
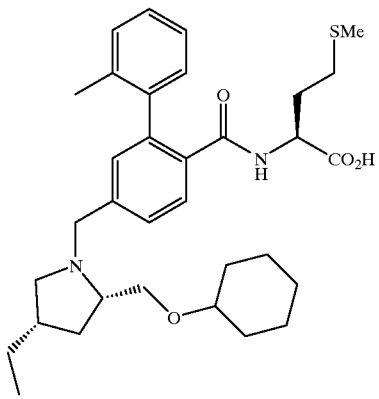
168
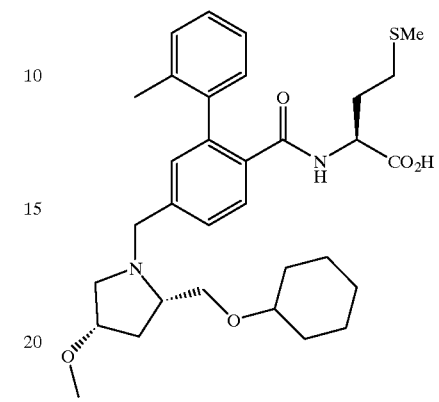
171
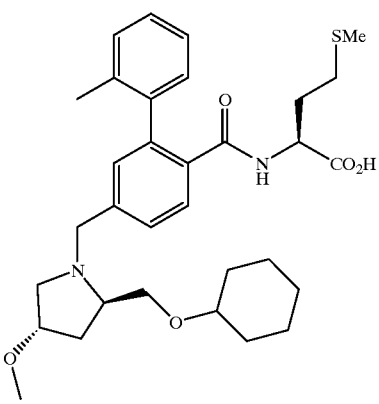
169
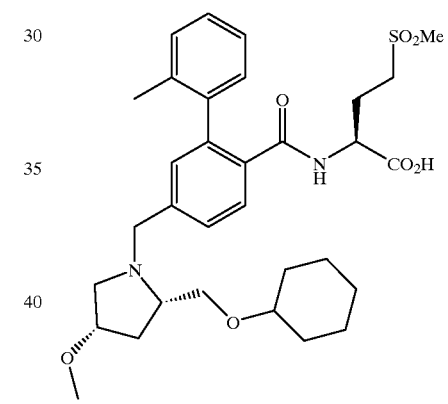
172
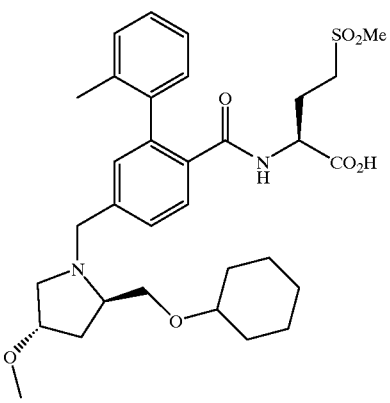
170
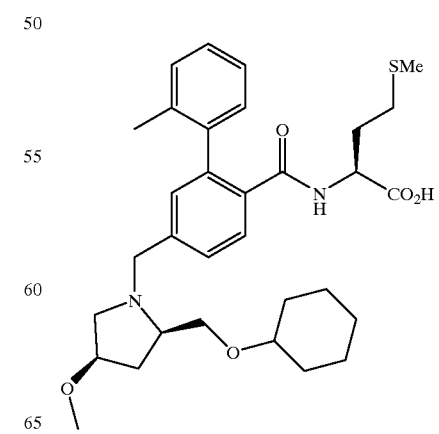
173

TABLE 6-continued
Amines of the Type A(B)N-L₁
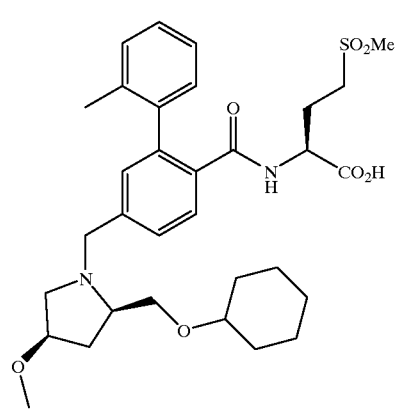
174
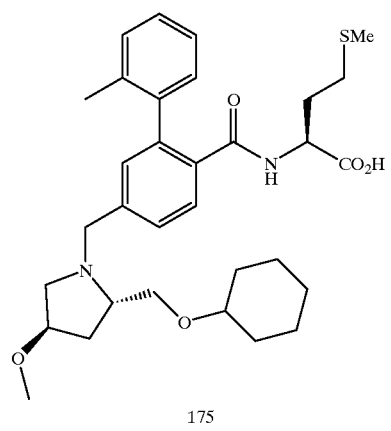
175
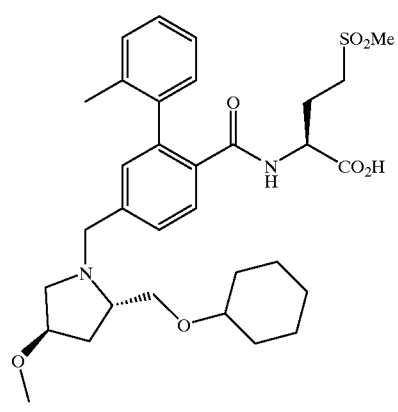
176
TABLE 6-continued
Amines of the Type A(B)N-L₁
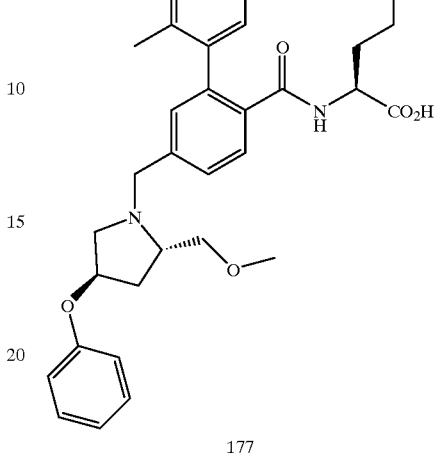
177
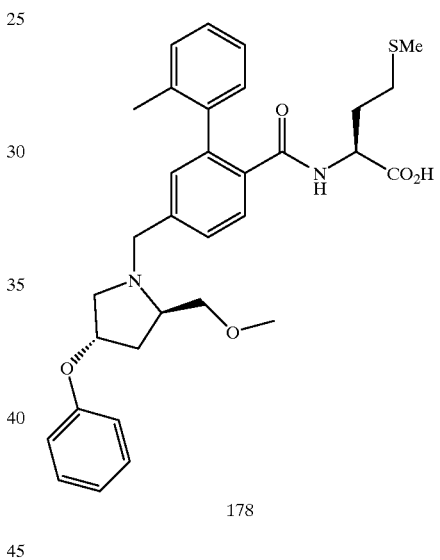
178
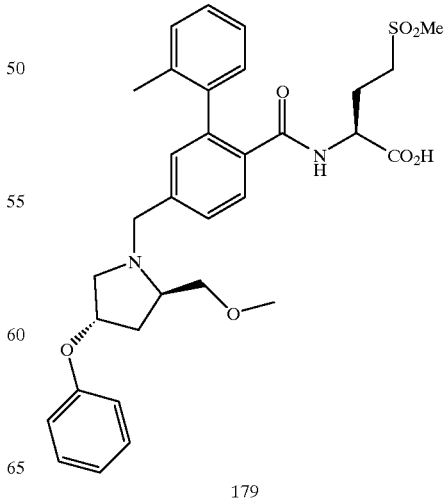
179

TABLE 6-continued
Amines of the Type A(B)N-L₁
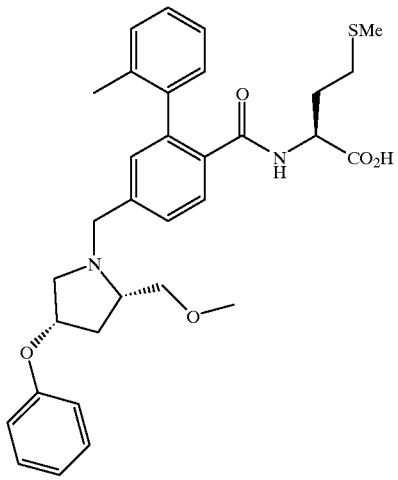
180
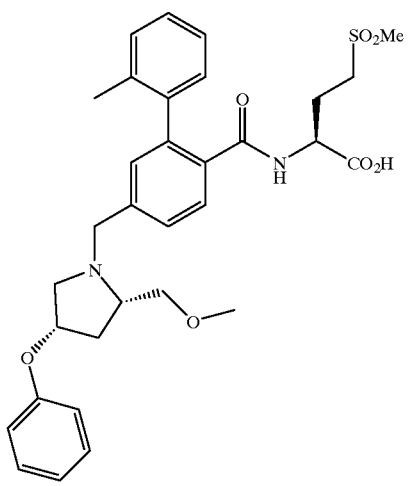
181
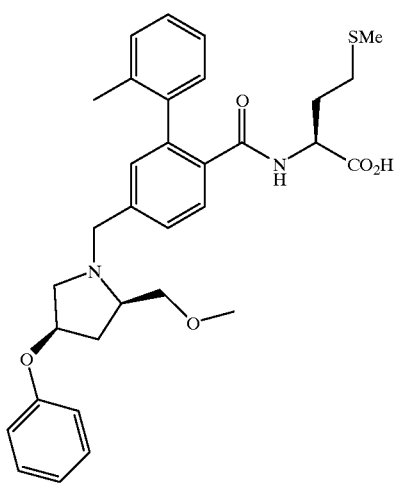
182
TABLE 6-continued
Amines of the Type A(B)N-L₁
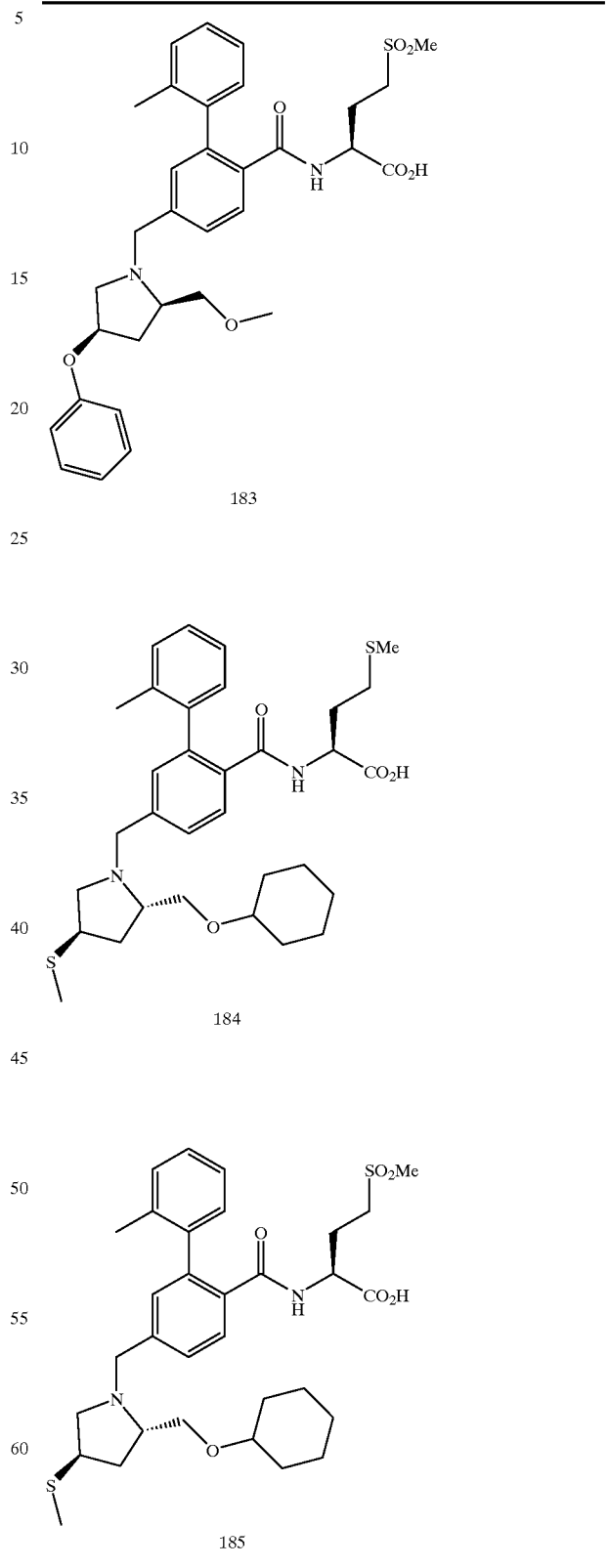

TABLE 6-continued
Amines of the Type A(B)N-L₁
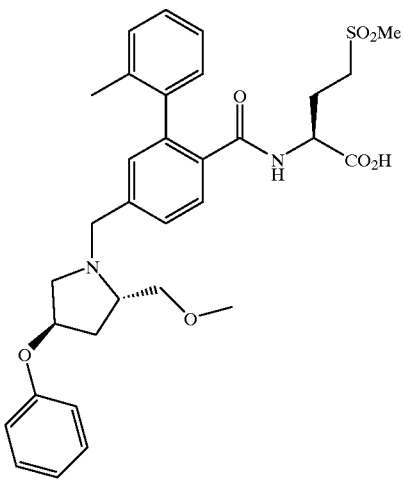
186
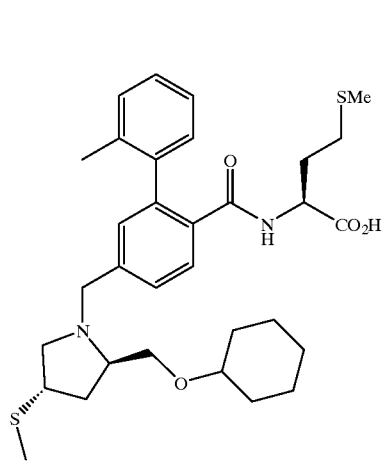
187
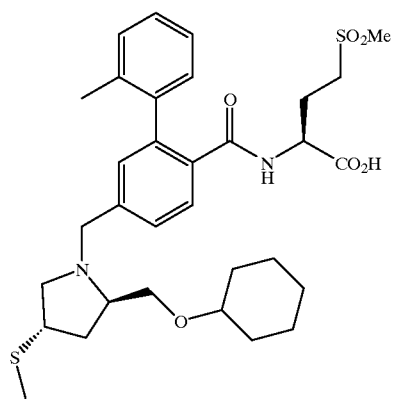
188
TABLE 6-continued
Amines of the Type A(B)N-L₁
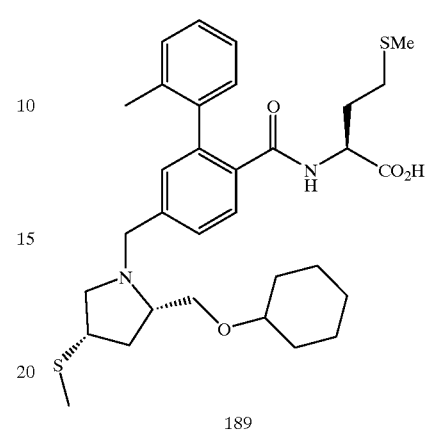
189
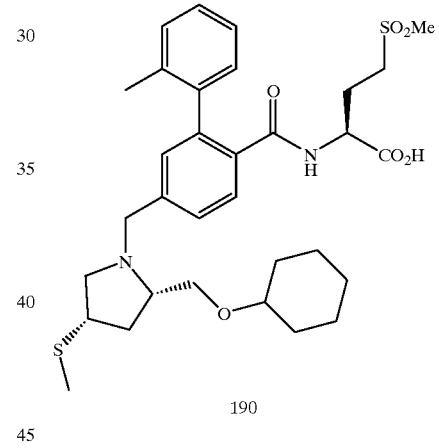
190
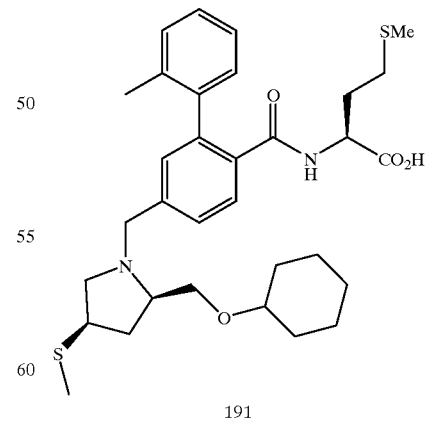
191

TABLE 6-continued
Amines of the Type A(B)N-L₁
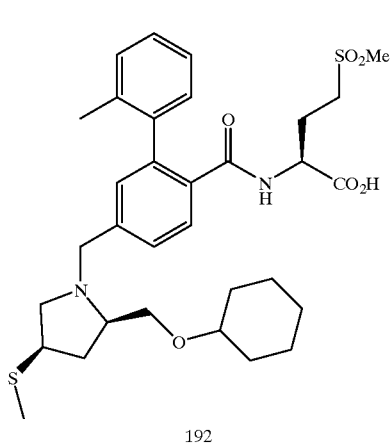
192
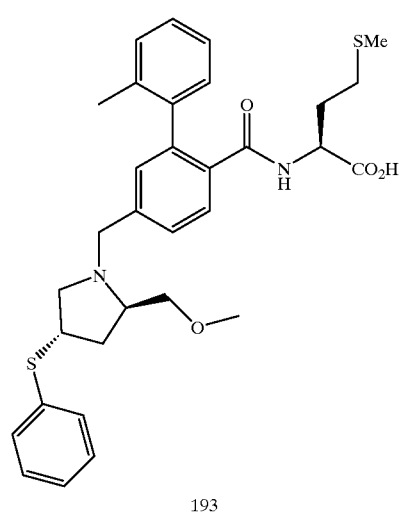
193
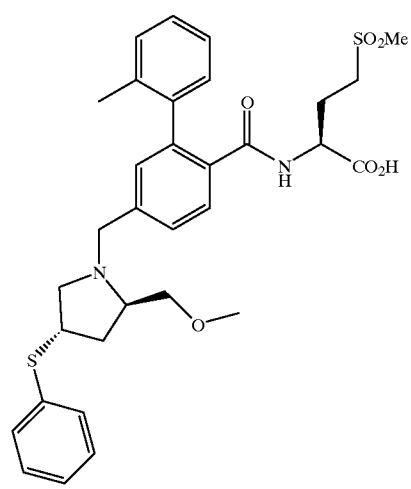
194
TABLE 6-continued
Amines of the Type A(B)N-L₁
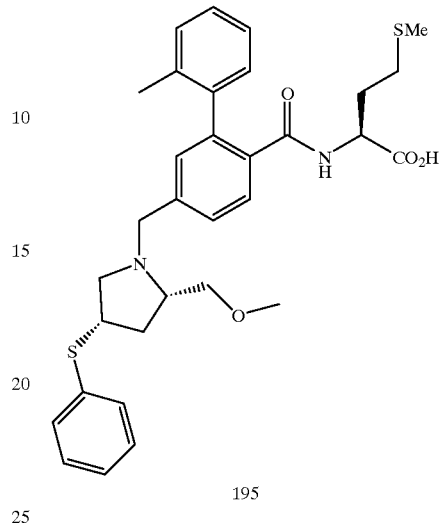
195
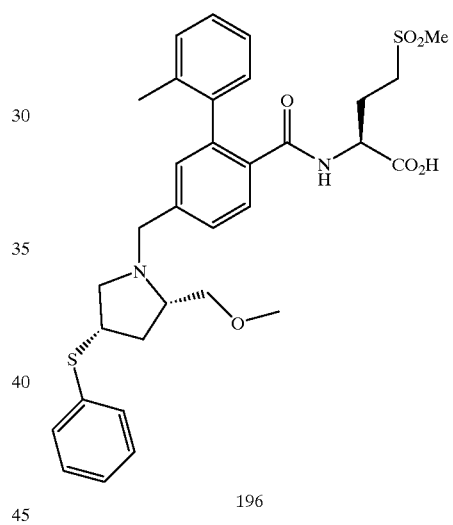
196
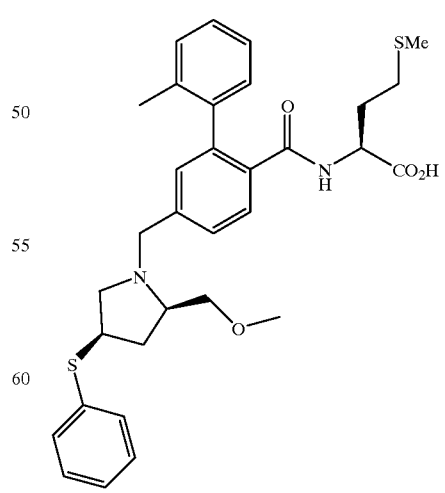
197

TABLE 6-continued
Amines of the Type A(B)N-L₁
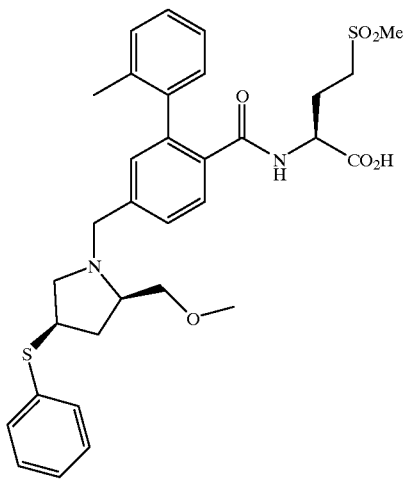
198
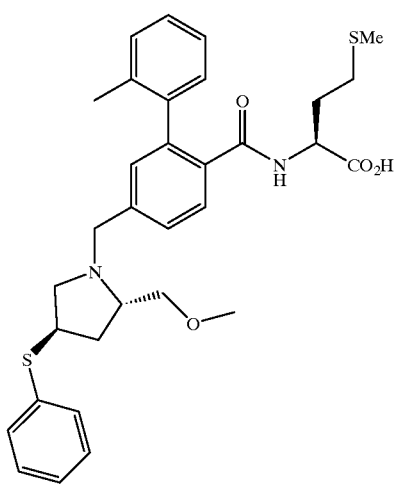
199
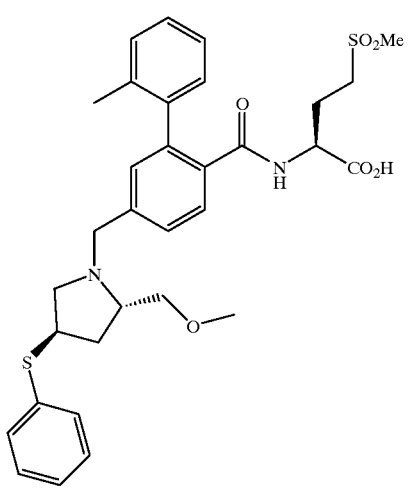
200
TABLE 6-continued
Amines of the Type A(B)N-L₁
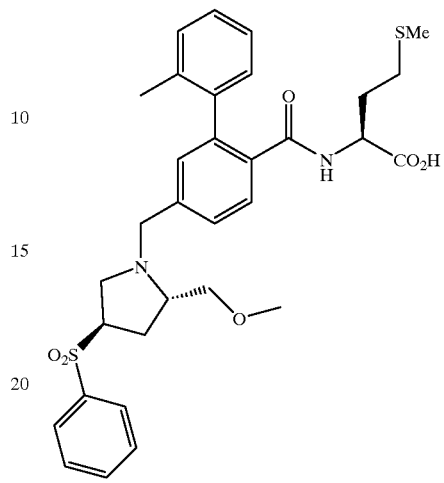
201

202
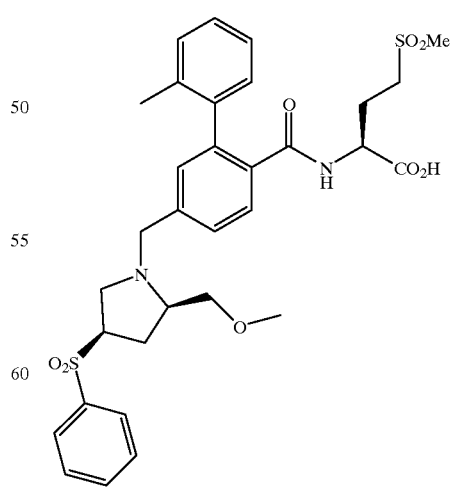
203

TABLE 6-continued
Amines of the Type A(B)N-L₁
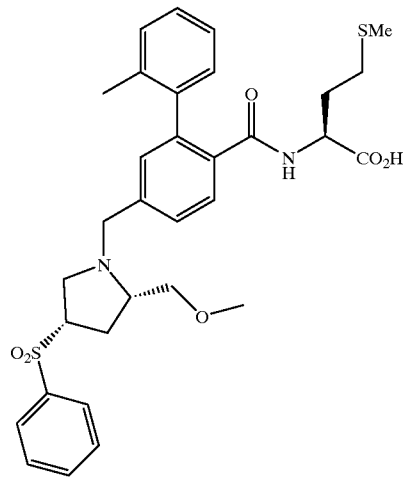
204
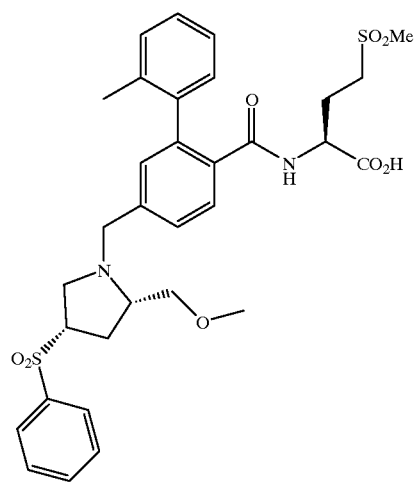
205
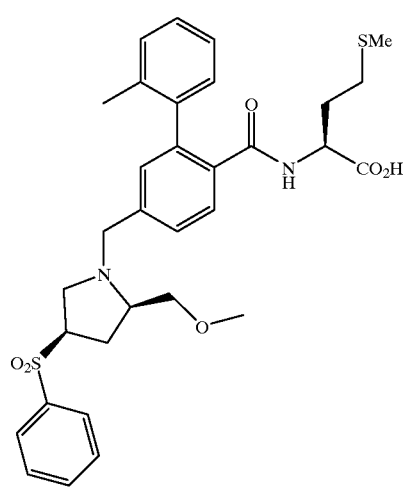
206
TABLE 6-continued
Amines of the Type A(B)N-L₁
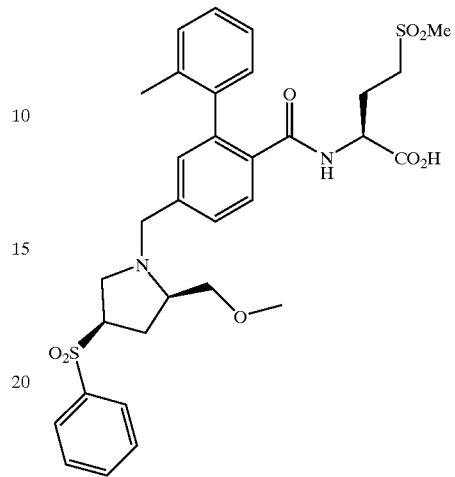
207
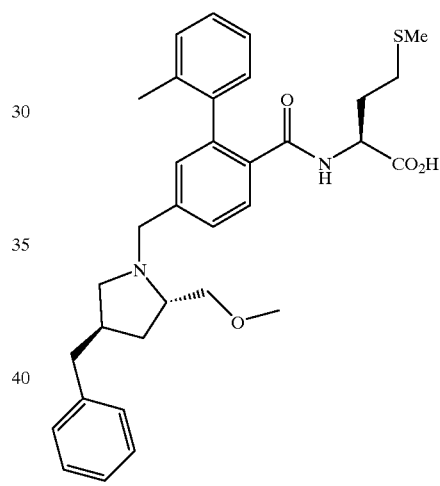
208
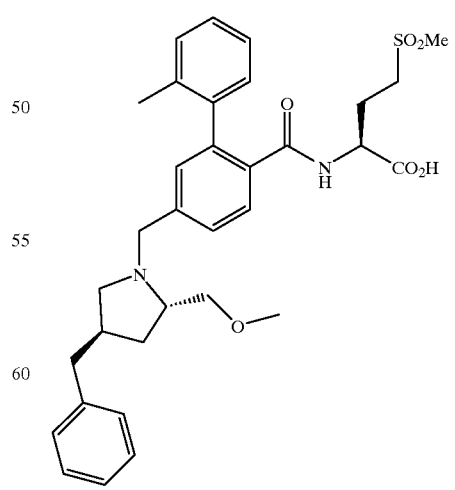
209

TABLE 6-continued
Amines of the Type A(B)N-L₁
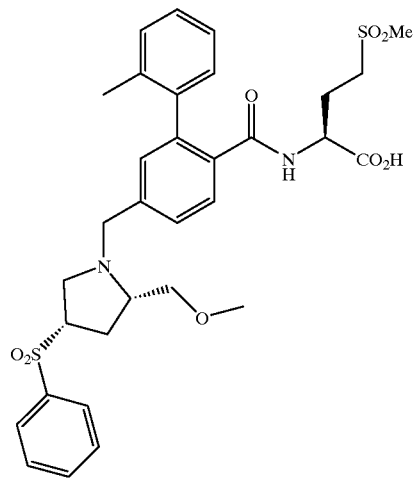
210
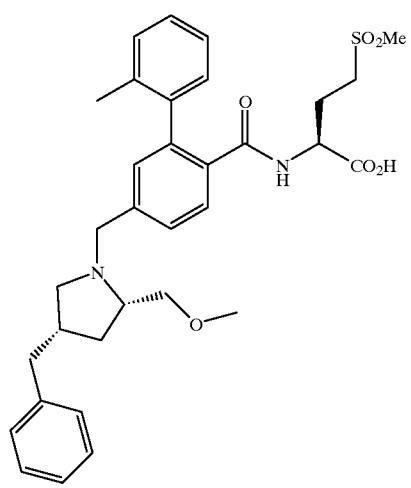
211
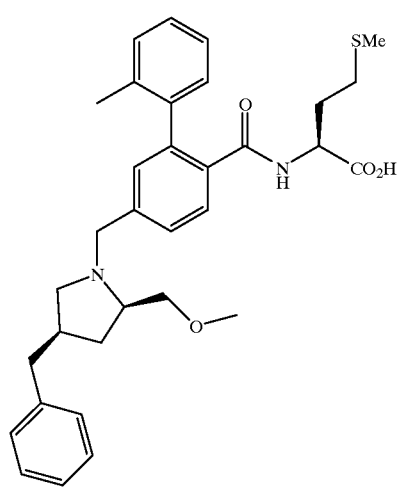
212
TABLE 6-continued
Amines of the Type A(B)N-L₁
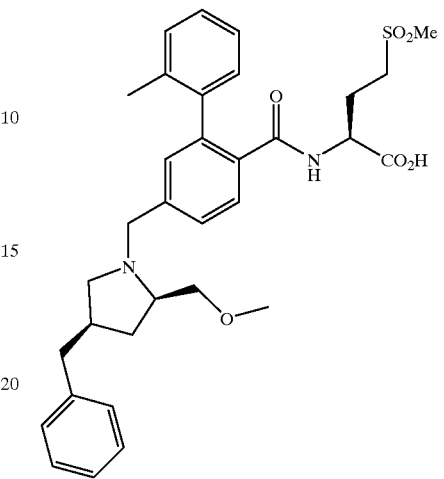
213
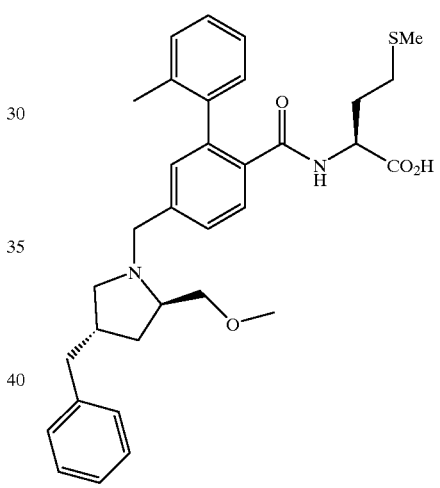
214
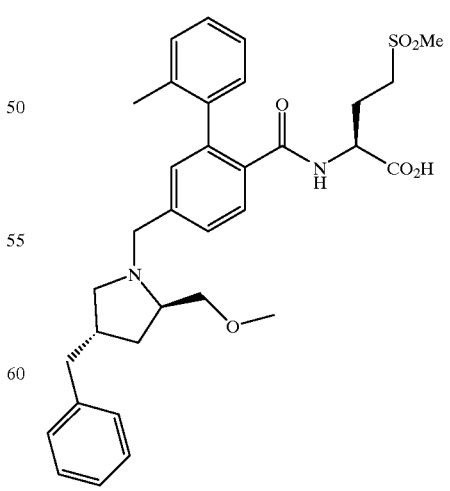
215

TABLE 6-continued
Amines of the Type A(B)N-L₁
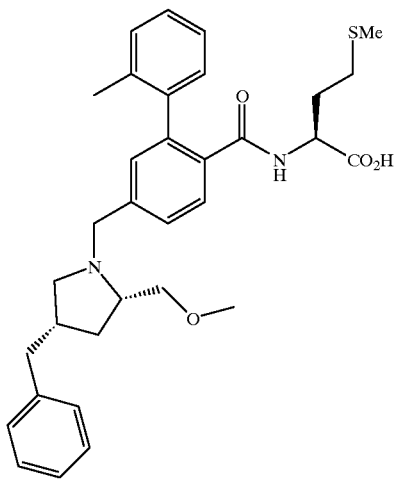
216
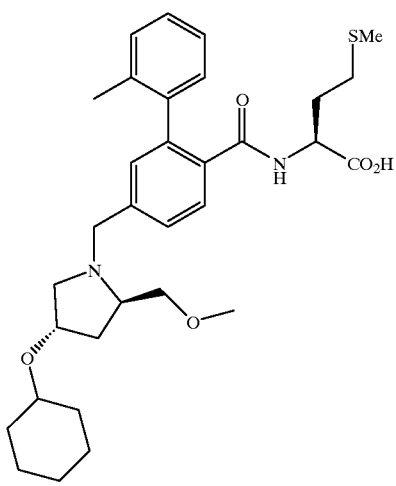
217
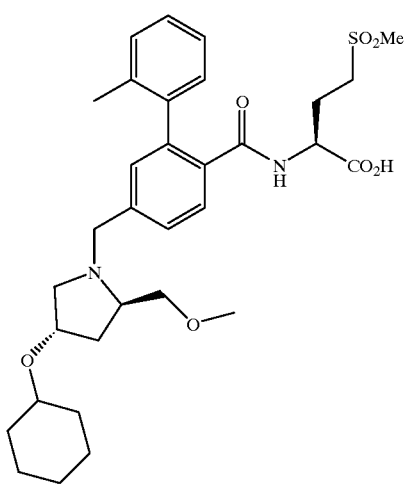
218
TABLE 6-continued
Amines of the Type A(B)N-L₁
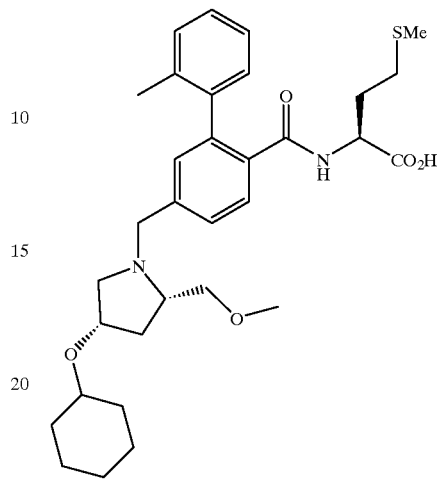
219
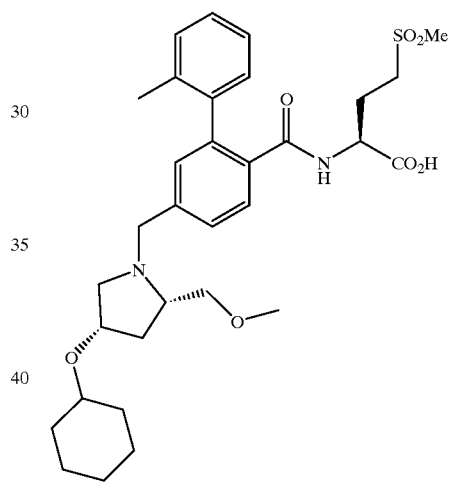
220
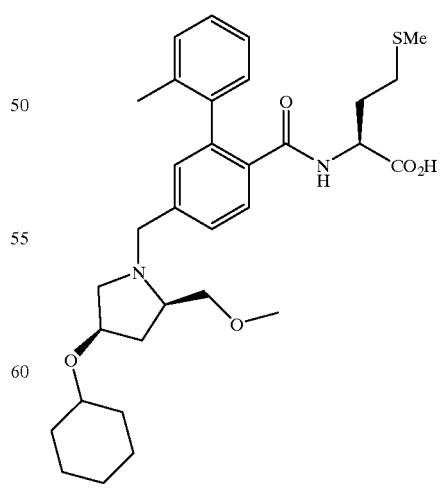
221

TABLE 6-continued
Amines of the Type A(B)N-L₁
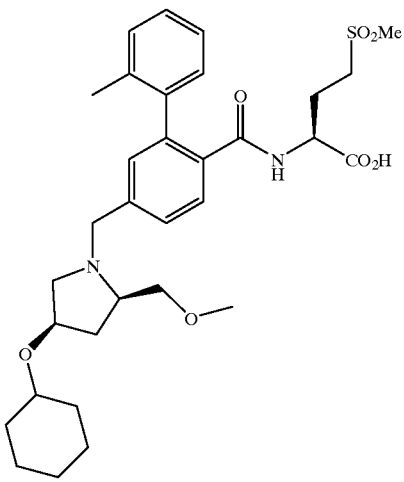
222
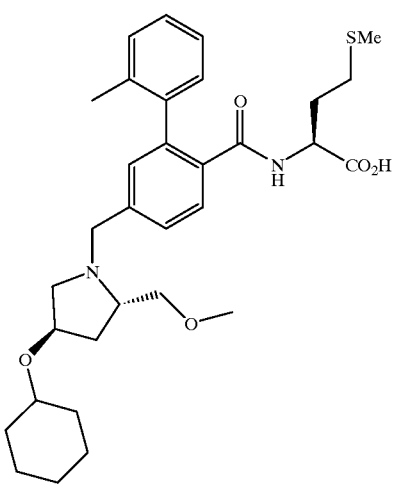
223
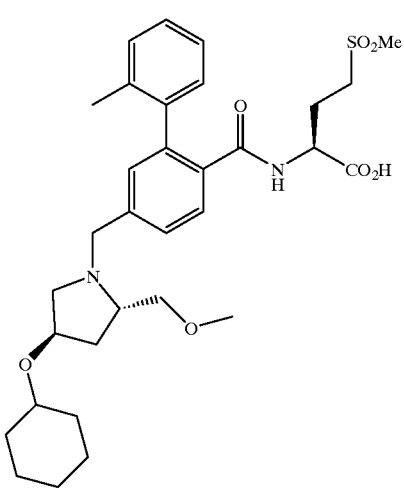
224
TABLE 6-continued
Amines of the Type A(B)N-L₁
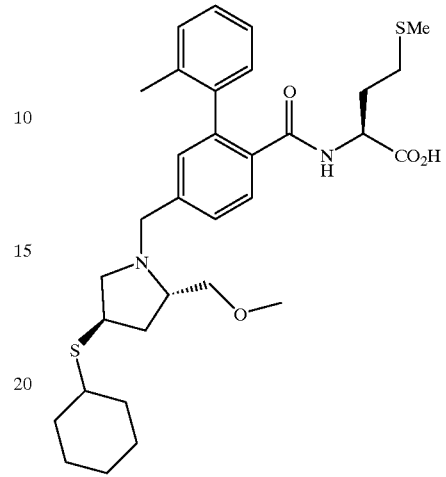
225

226
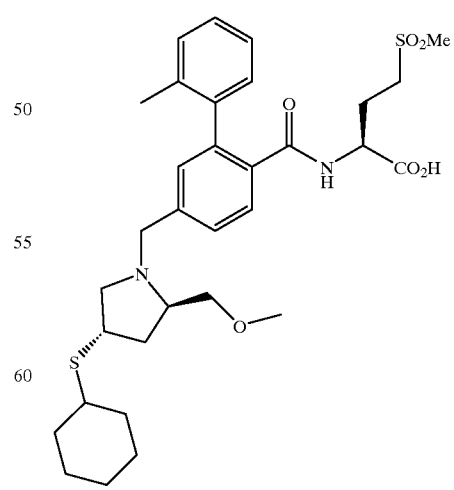
227

TABLE 6-continued
Amines of the Type A(B)N-L₁
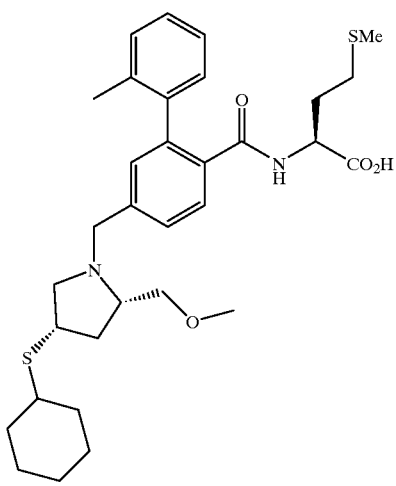
228
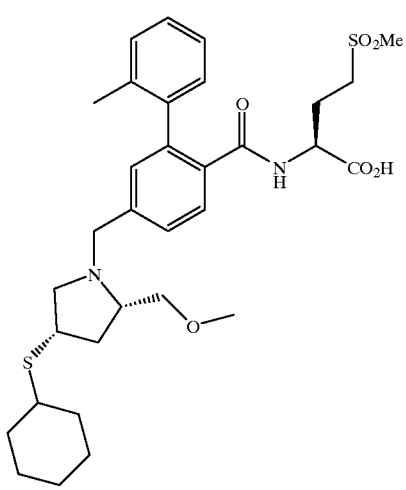
229
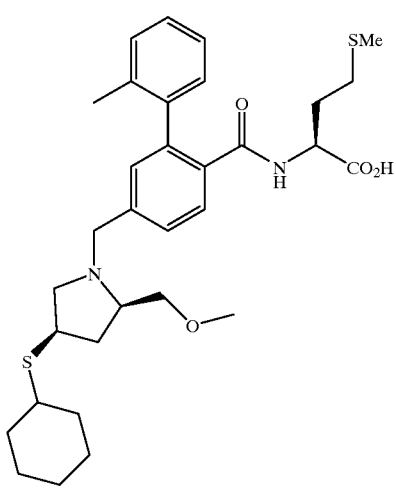
230
TABLE 6-continued
Amines of the Type A(B)N-L₁
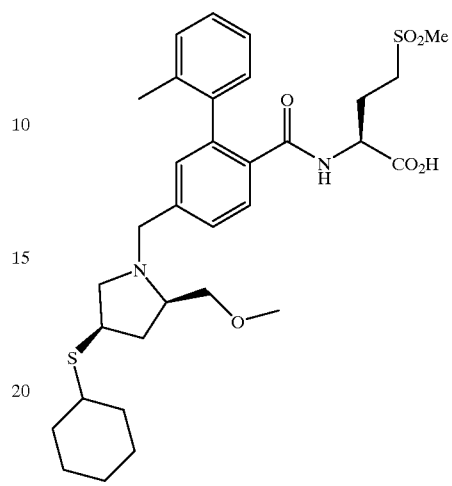
231
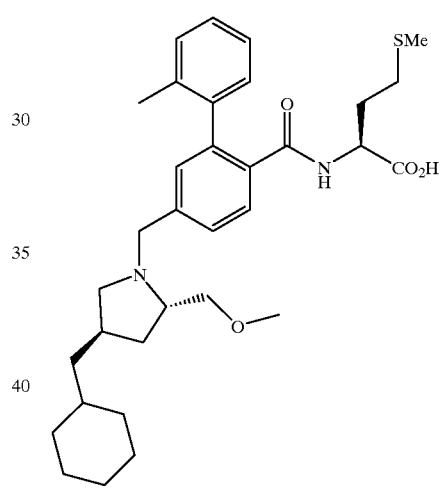
232
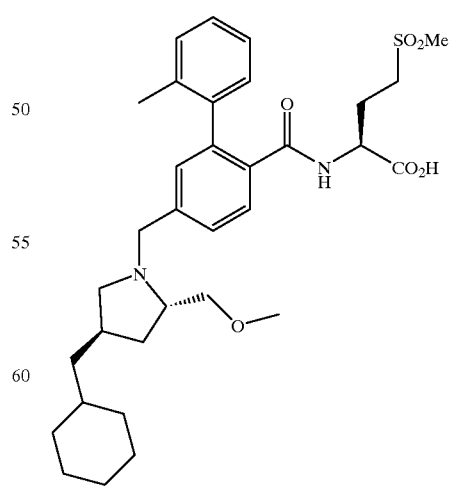
233

TABLE 6-continued
Amines of the Type A(B)N-L₁
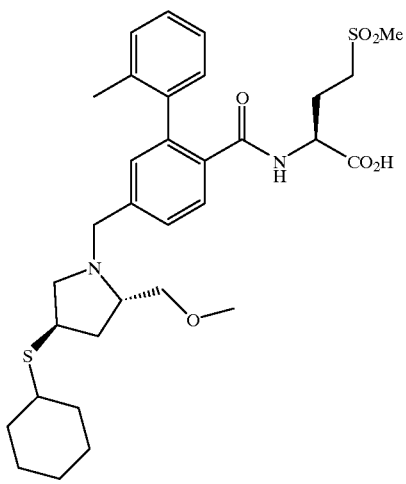
234
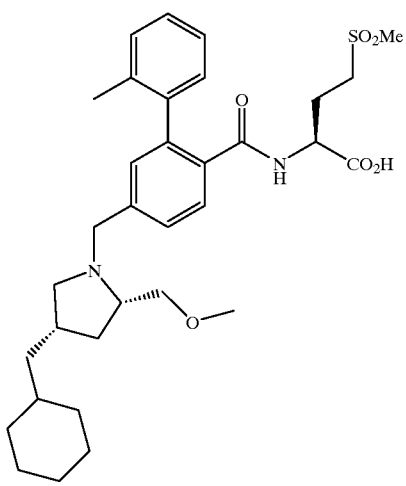
235
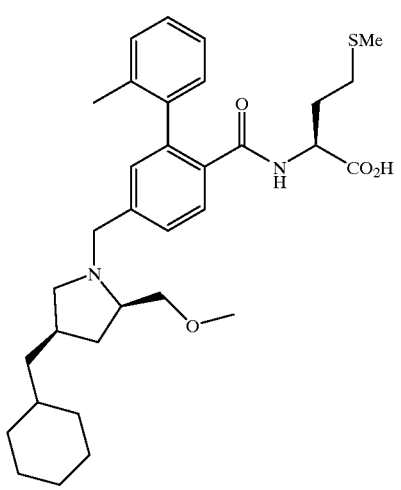
236
TABLE 6-continued
Amines of the Type A(B)N-L₁
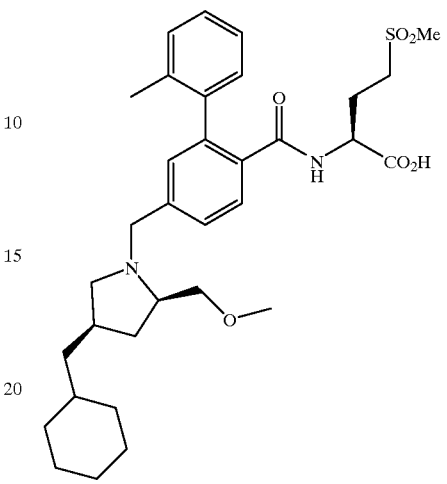
237
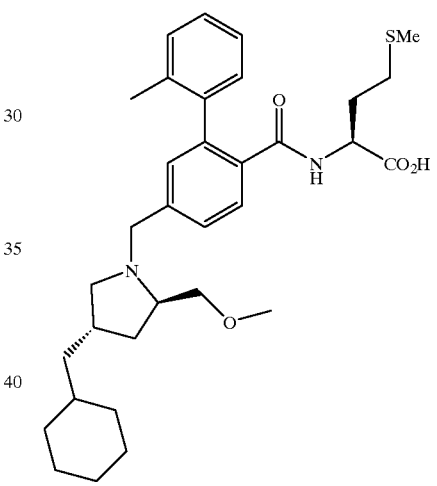
238
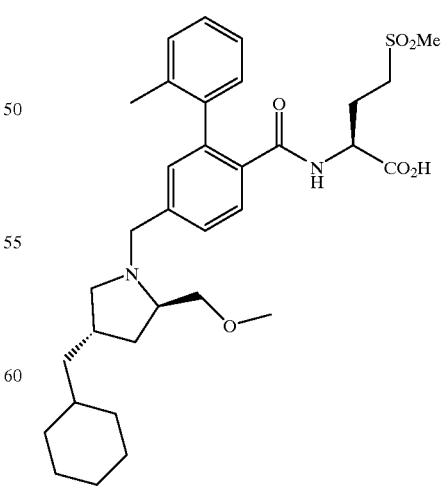
239

TABLE 6-continued
Amines of the Type A(B)N-L₁
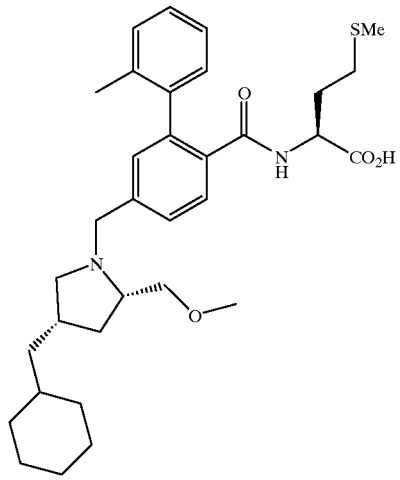
240
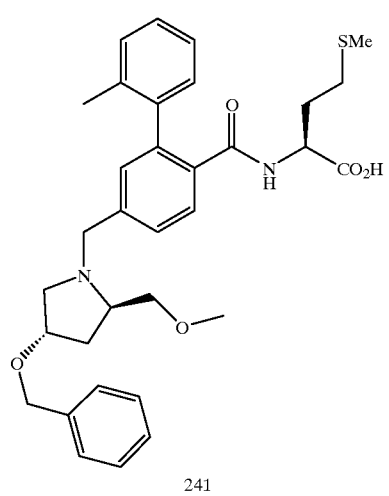
241
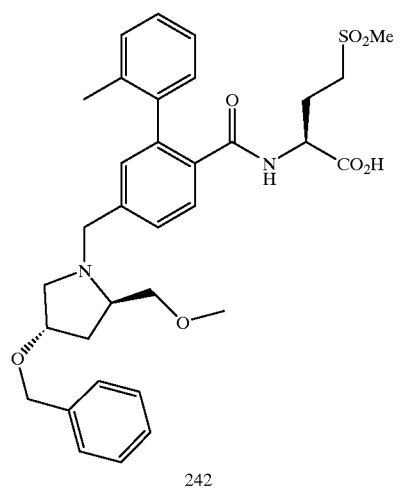
242
TABLE 6-continued
Amines of the Type A(B)N-L₁
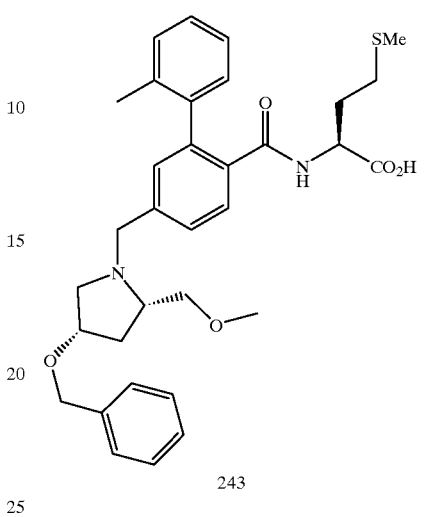
243
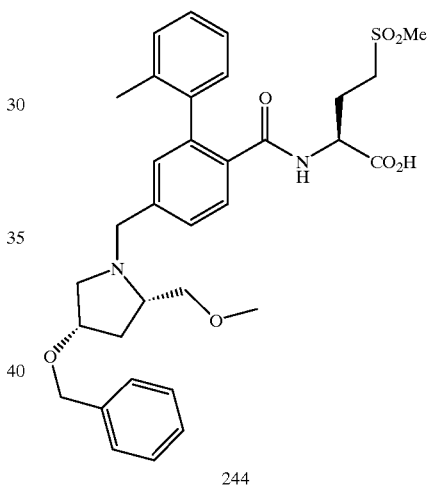
244
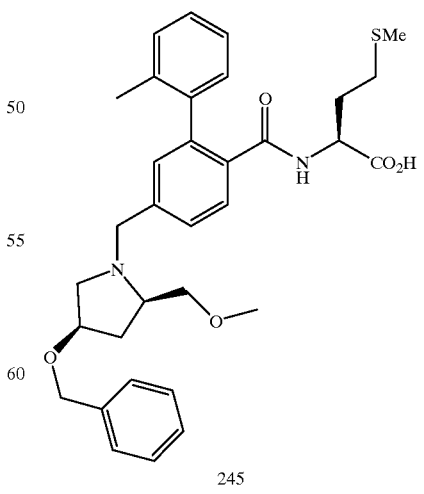
245

TABLE 6-continued
Amines of the Type A(B)N-L₁
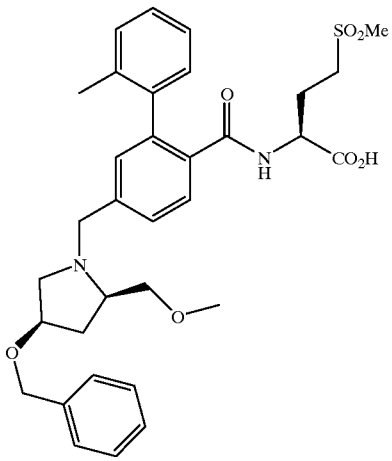
246
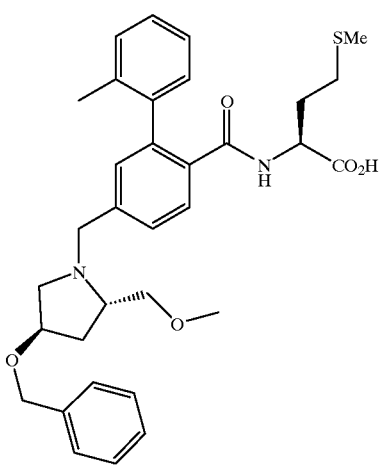
247
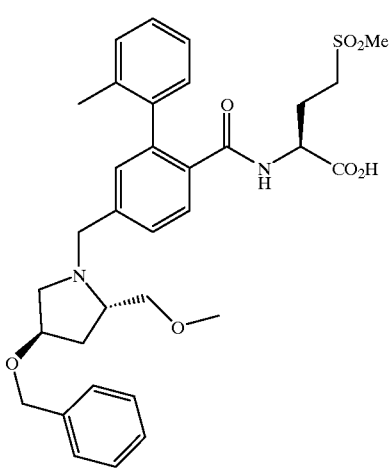
248
TABLE 6-continued
Amines of the Type A(B)N-L₁
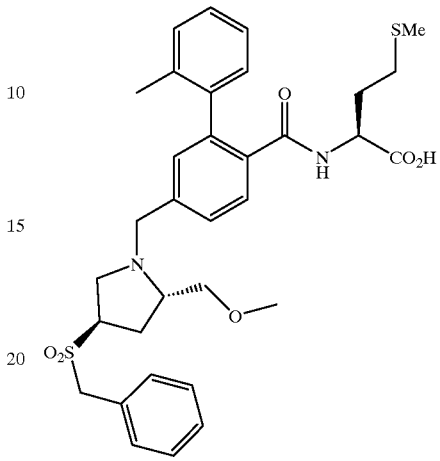
249
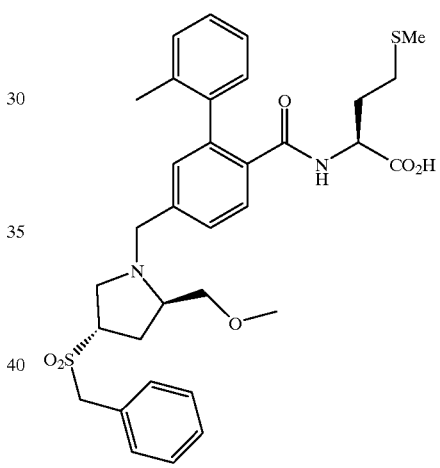
250
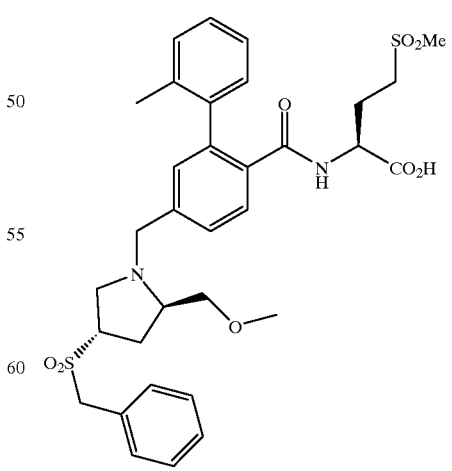
251

TABLE 6-continued
Amines of the Type A(B)N-L₁
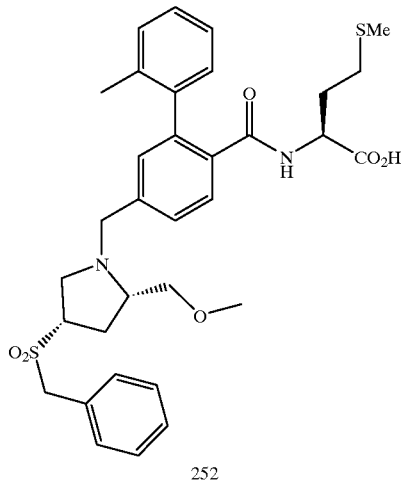
252
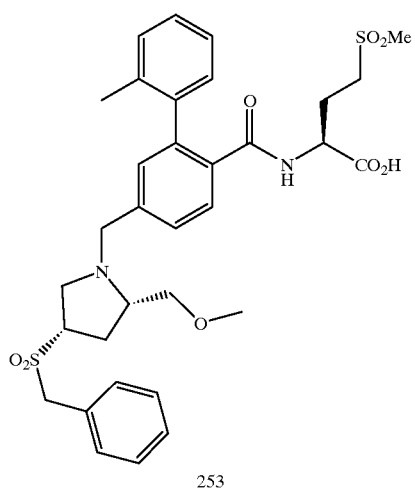
253
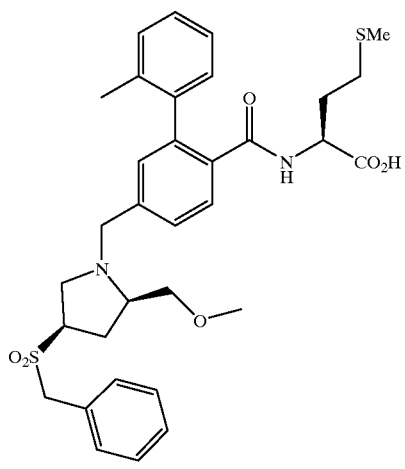
254
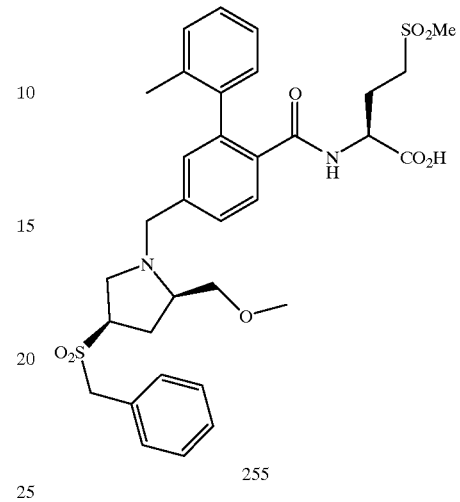
255
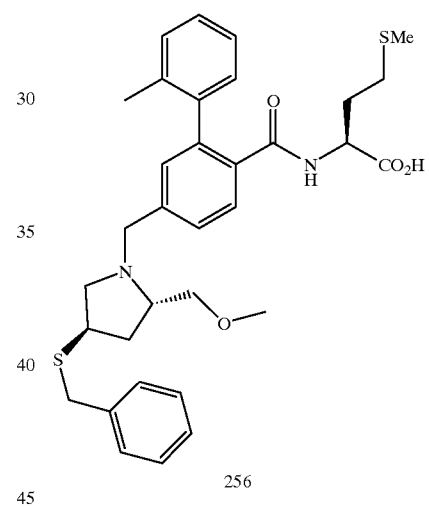
256
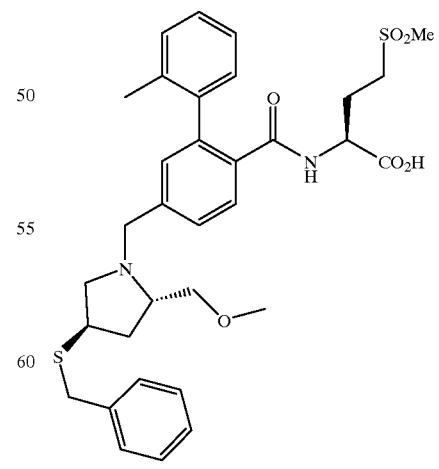
257

TABLE 6-continued
Amines of the Type A(B)N-L$_1$
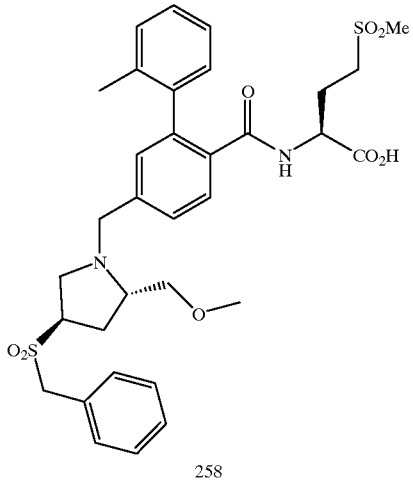
258
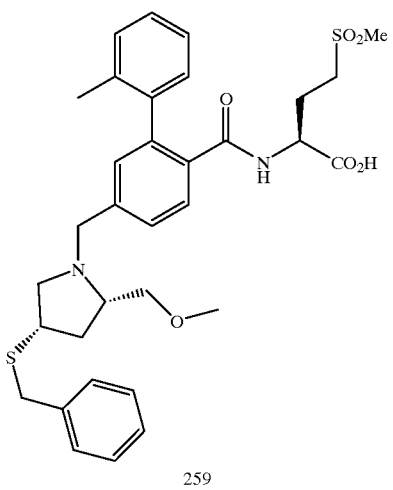
259
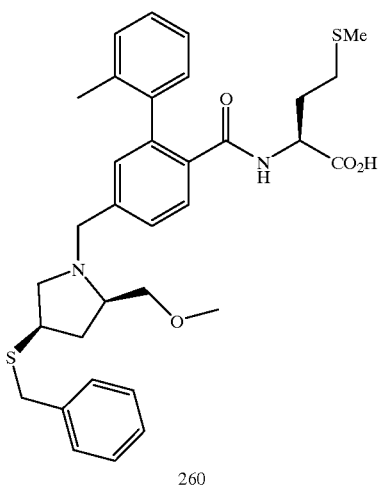
260
TABLE 6-continued
Amines of the Type A(B)N-L$_1$
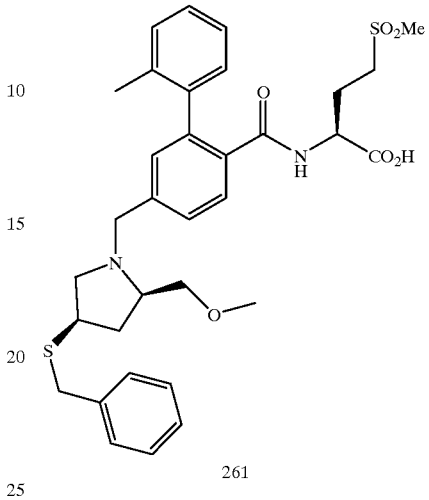
261
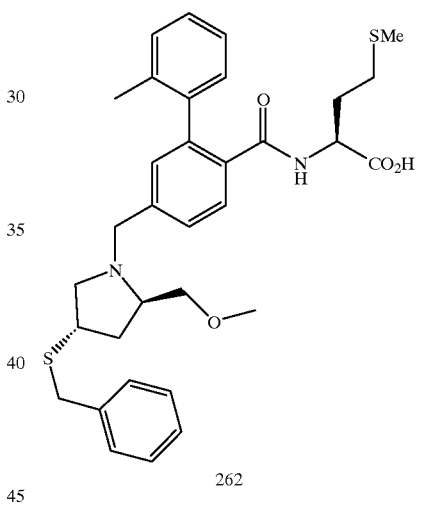
262
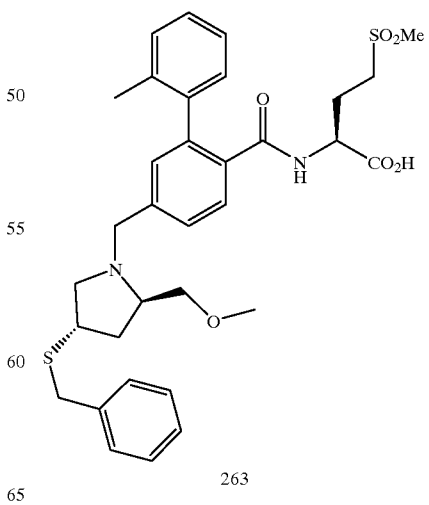
263

TABLE 6-continued
Amines of the Type A(B)N-L₁
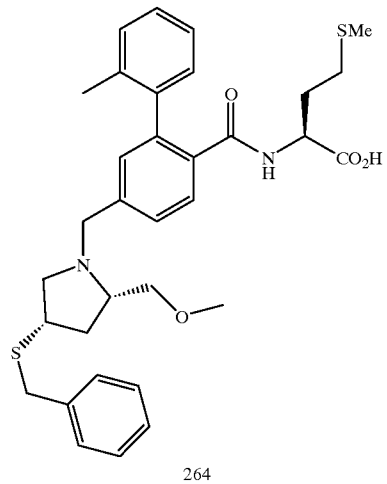
264
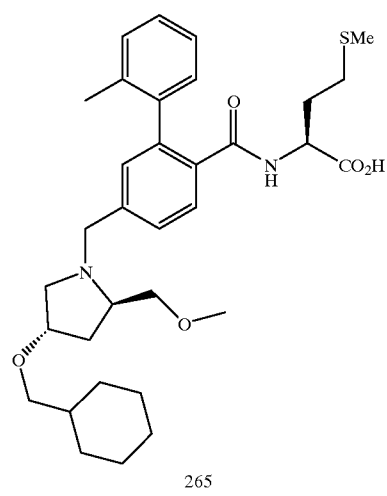
265
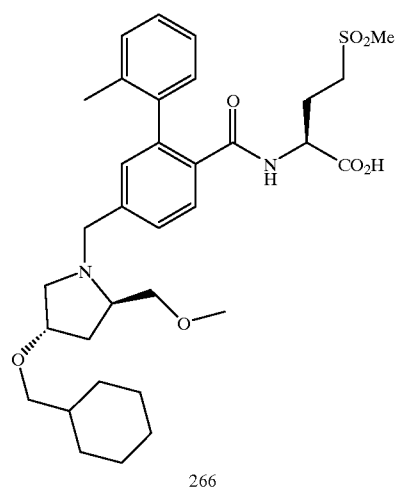
266
TABLE 6-continued
Amines of the Type A(B)N-L₁
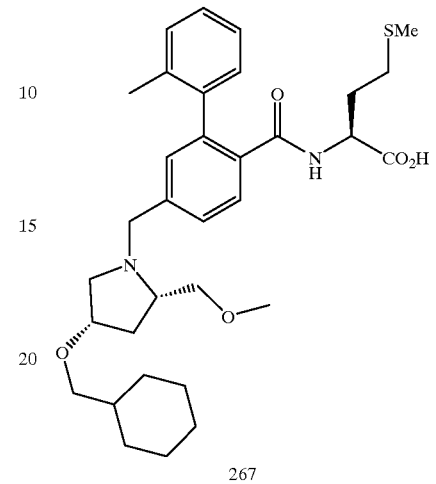
267
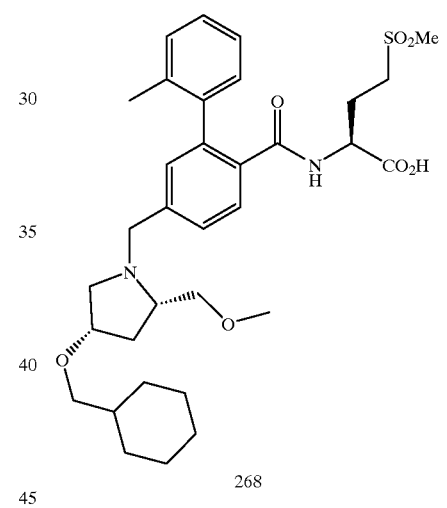
268
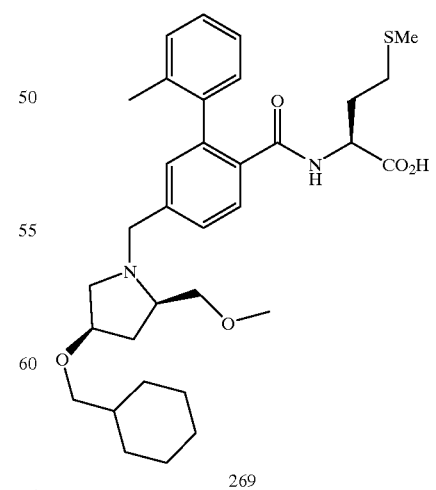
269

TABLE 6-continued
Amines of the Type A(B)N-L₁
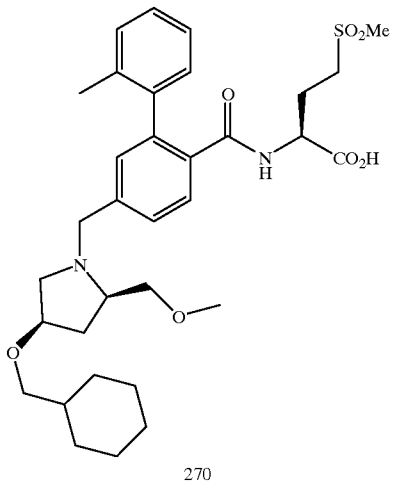
270
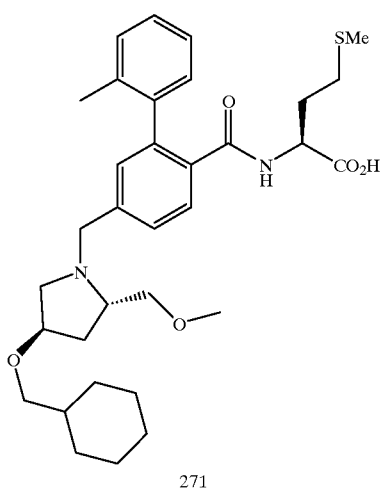
271
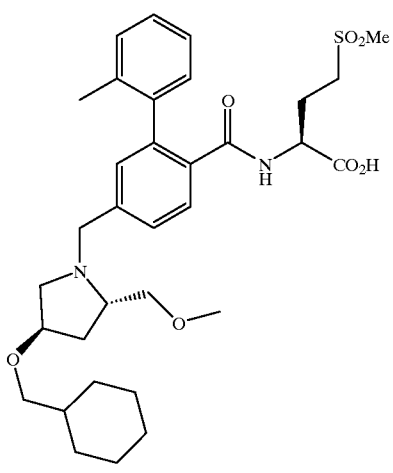
272
TABLE 6-continued
Amines of the Type A(B)N-L₁
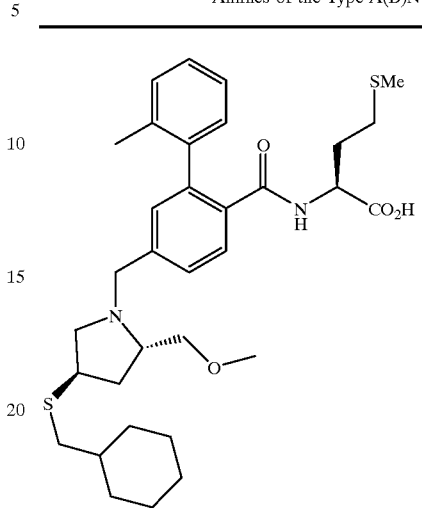
273
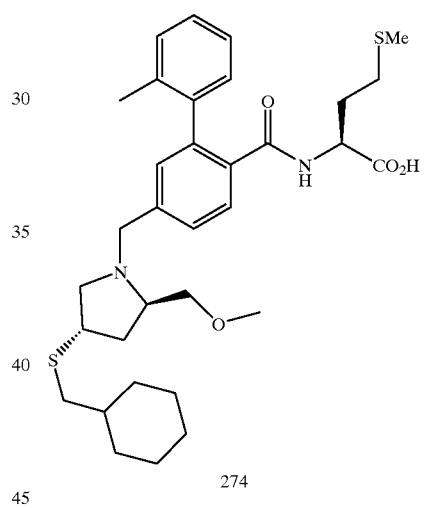
274
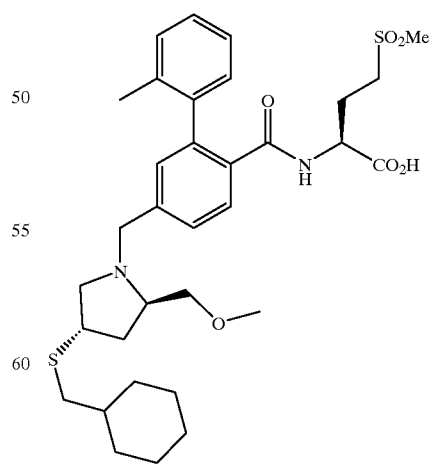
275

TABLE 6-continued
Amines of the Type A(B)N-L₁
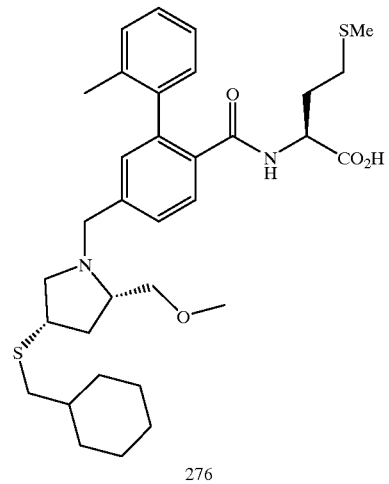
276
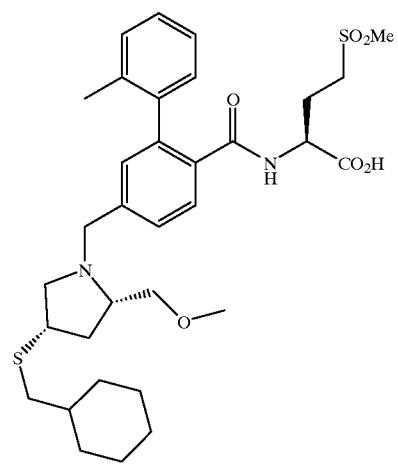
277
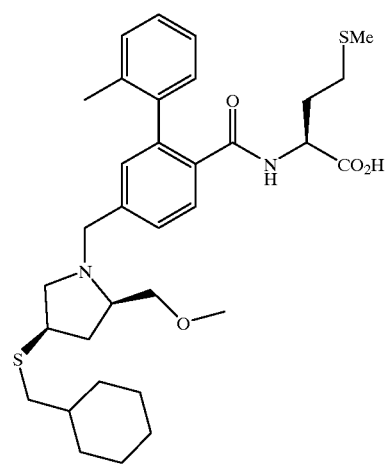
278
TABLE 6-continued
Amines of the Type A(B)N-L₁
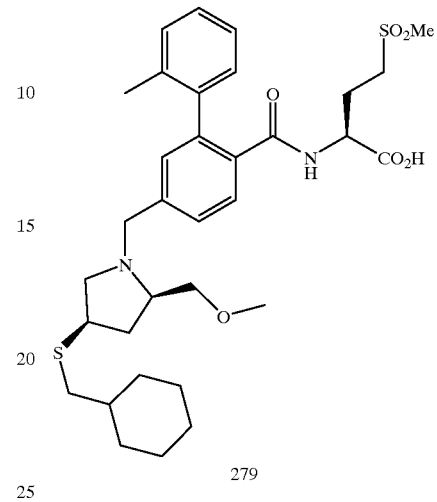
279
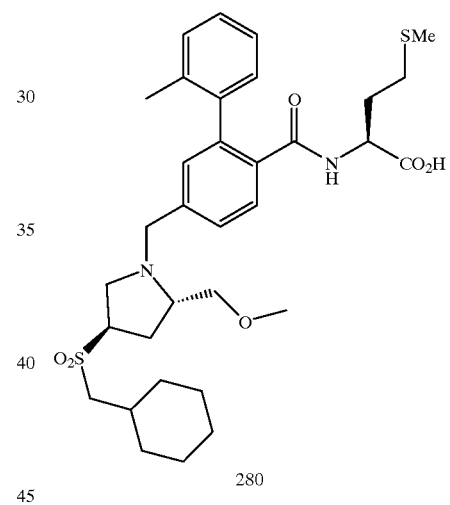
280
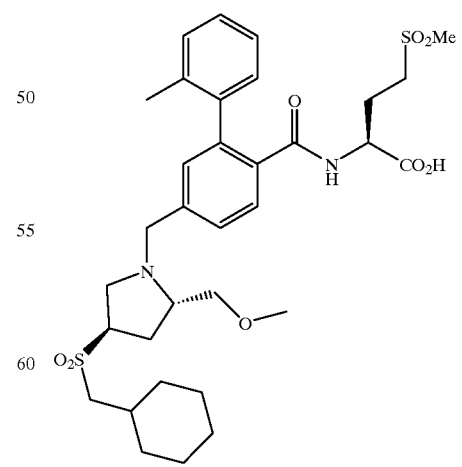
281

TABLE 6-continued
Amines of the Type A(B)N-L₁
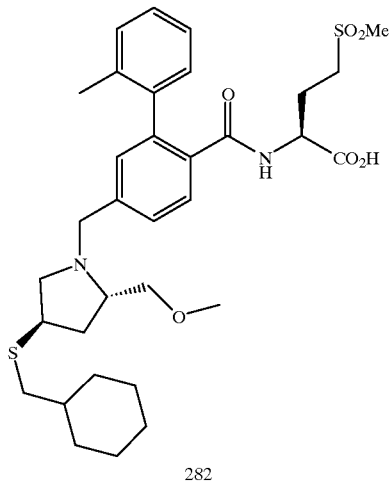
282
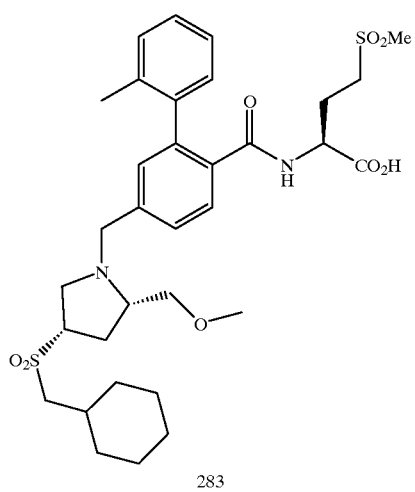
283
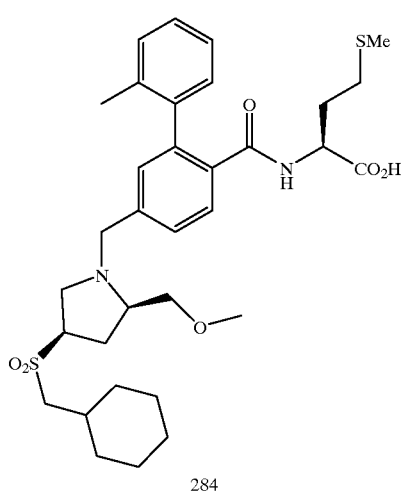
284
TABLE 6-continued
Amines of the Type A(B)N-L₁
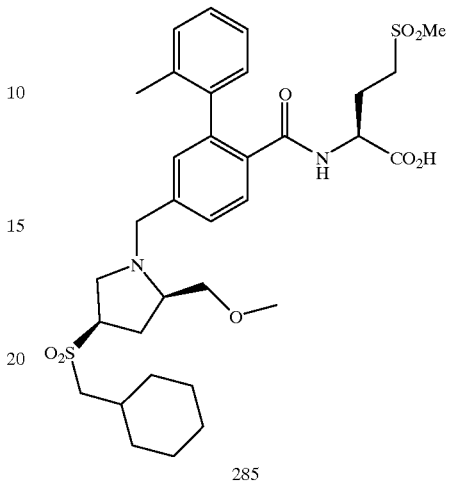
285
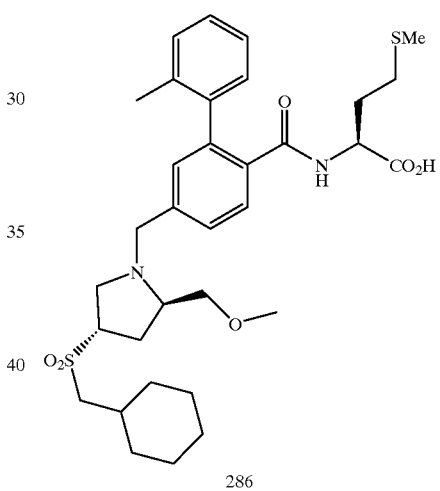
286
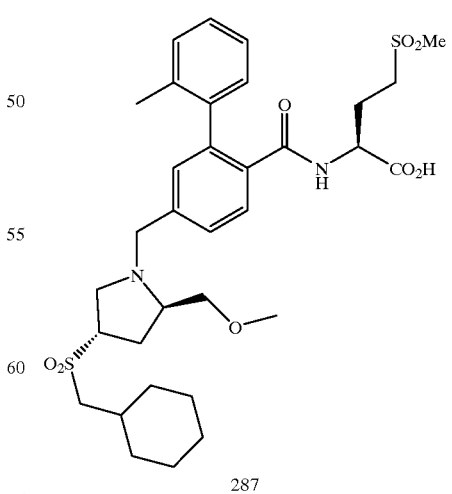
287

TABLE 6-continued
Amines of the Type A(B)N-L₁
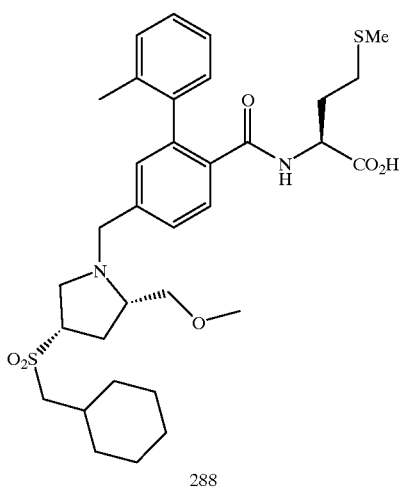
288
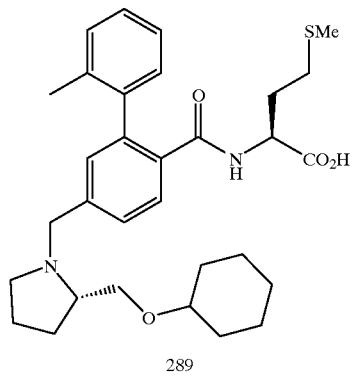
289
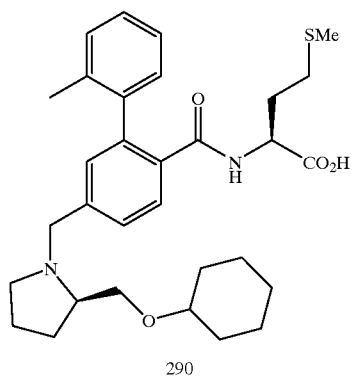
290
TABLE 6-continued
Amines of the Type A(B)N-L₁
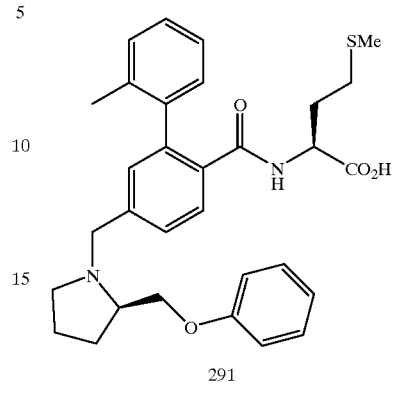
291
292
293
294

TABLE 6-continued
Amines of the Type A(B)N-L₁
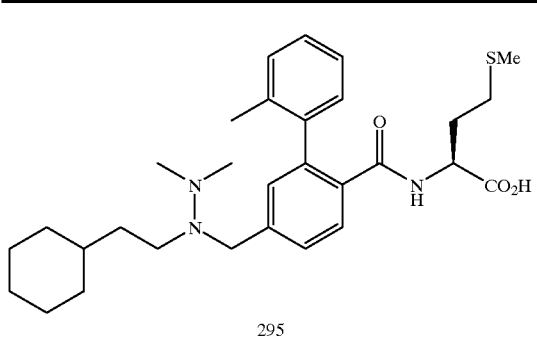
295
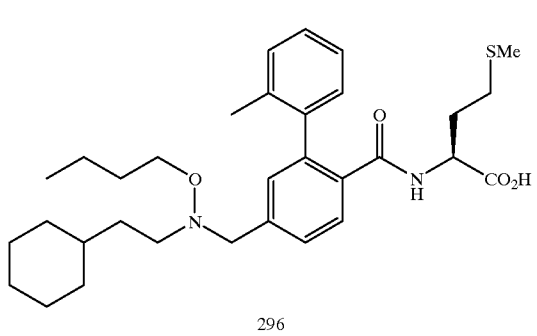
296
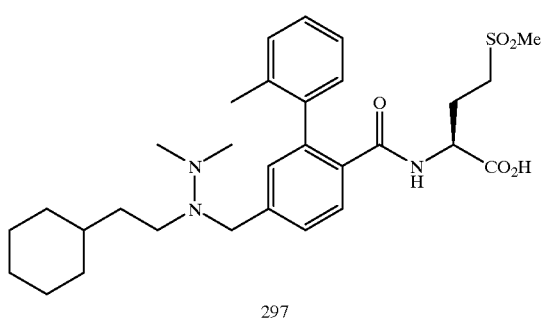
297
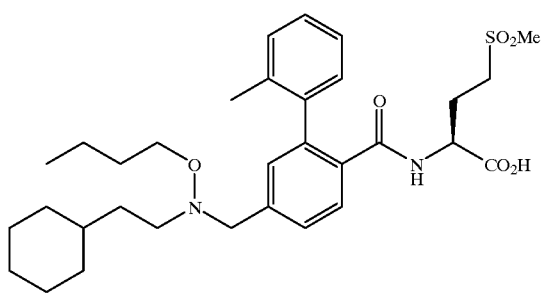
298
TABLE 6-continued
Amines of the Type A(B)N-L₁
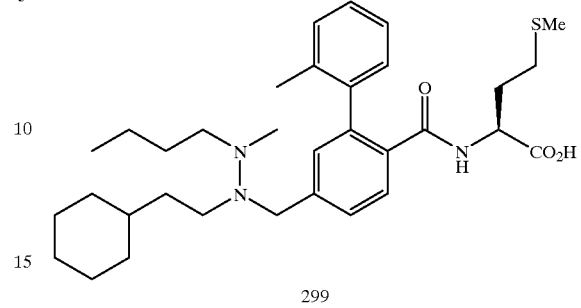
299
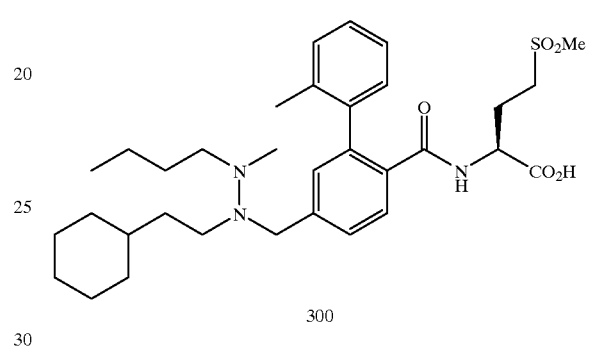
300
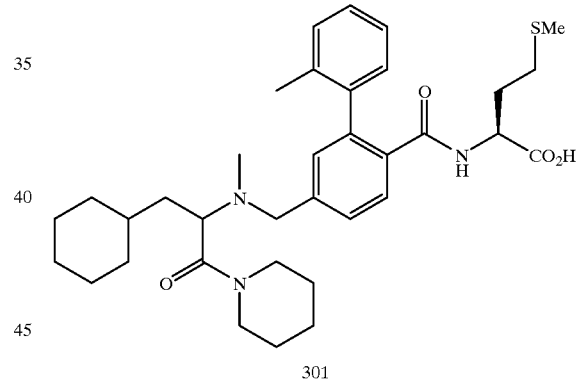
301
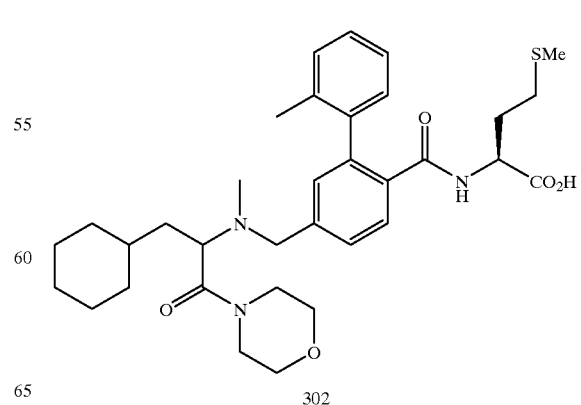
302

TABLE 6-continued
Amines of the Type A(B)N-L$_1$
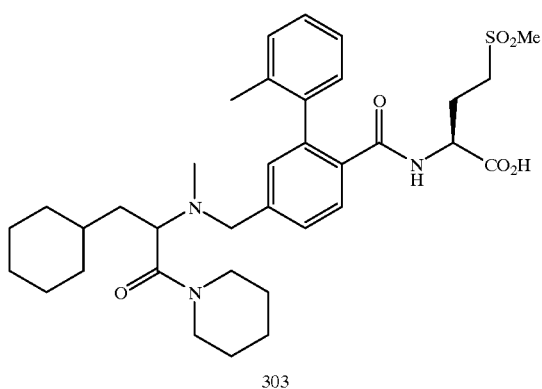
303
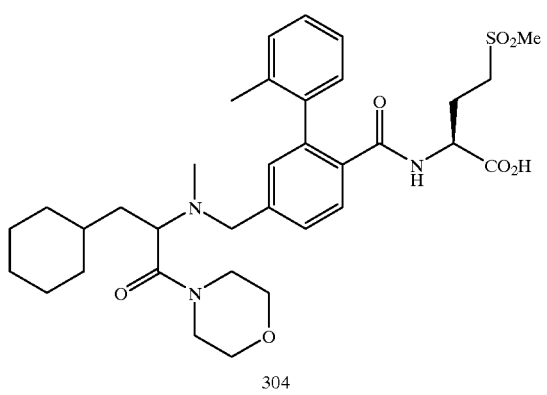
304
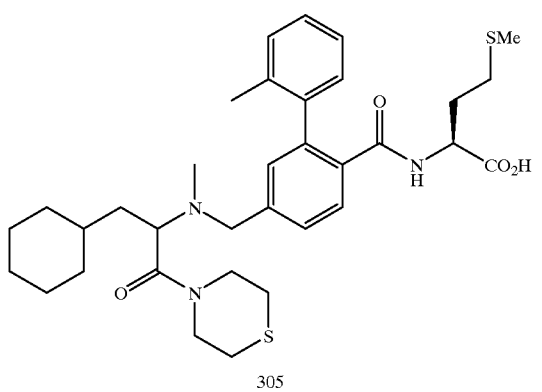
305
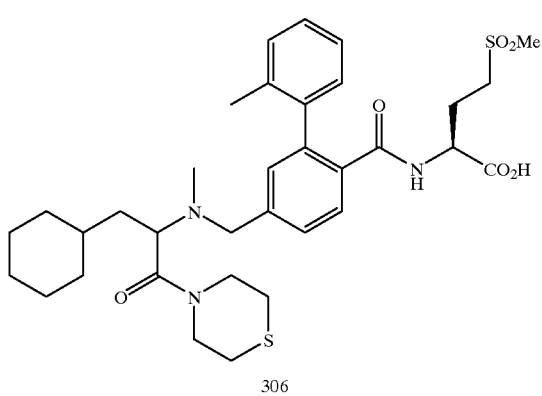
306
TABLE 6-continued
Amines of the Type A(B)N-L$_1$
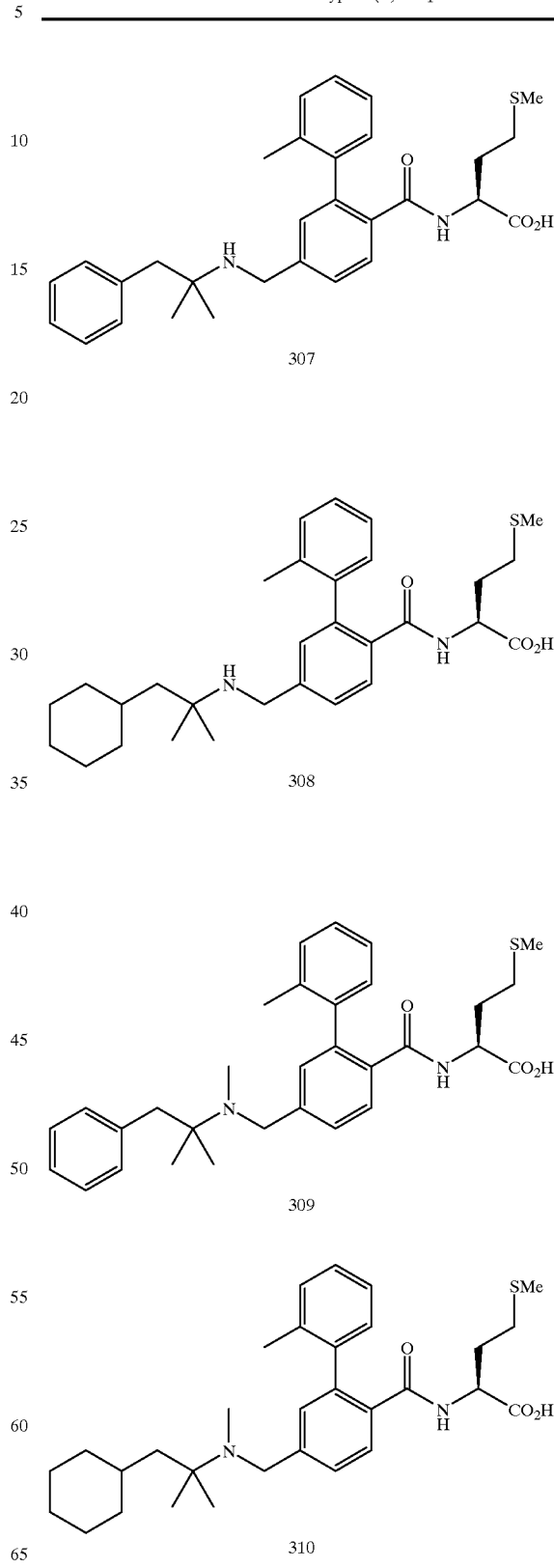
307
308
309
310

TABLE 6-continued
Amines of the Type A(B)N-L₁
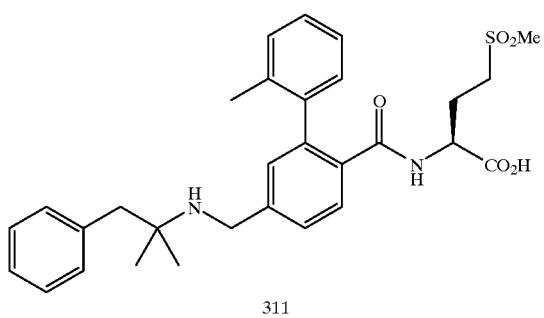
311
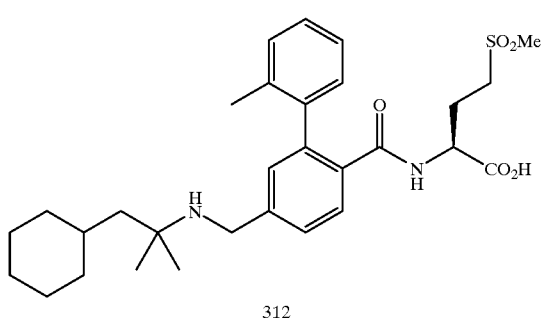
312
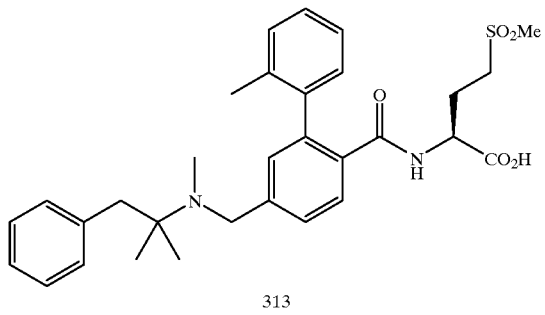
313
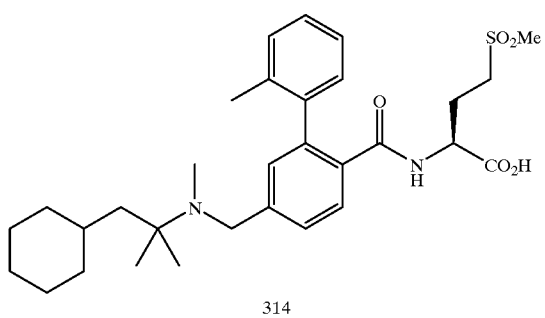
314
TABLE 6-continued
Amines of the Type A(B)N-L₁
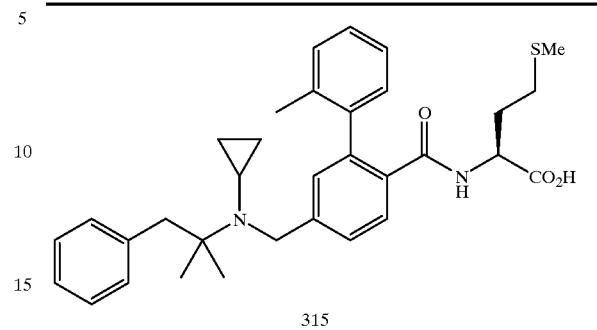
315
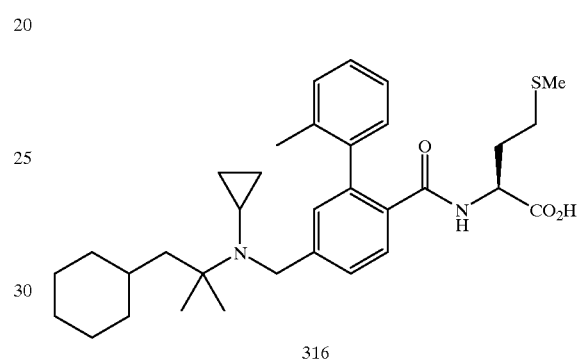
316
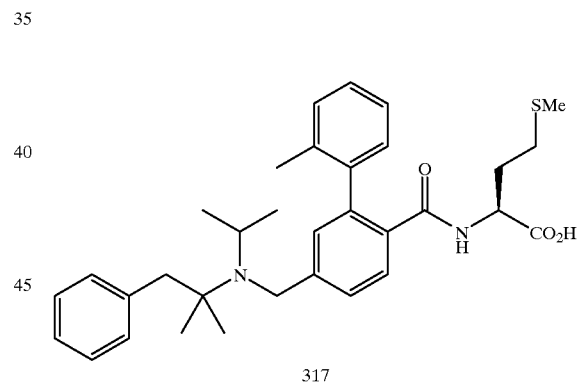
317
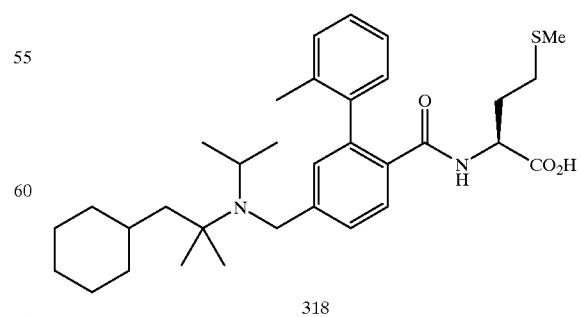
318

TABLE 6-continued
Amines of the Type A(B)N-L₁
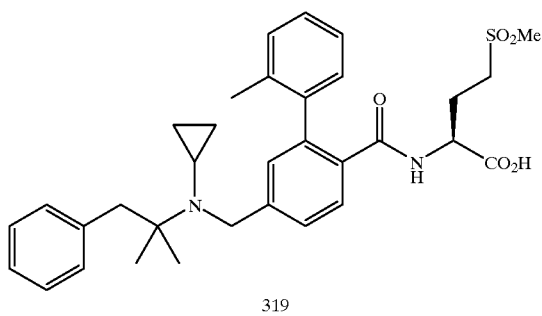
319
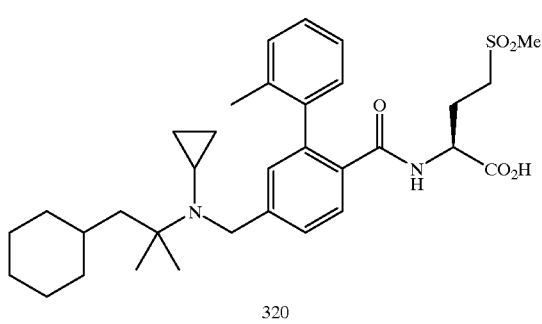
320
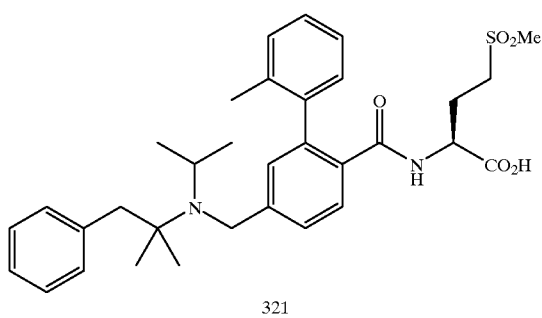
321
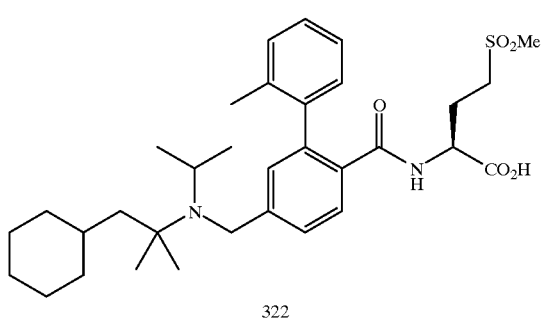
322
TABLE 6-continued
Amines of the Type A(B)N-L₁
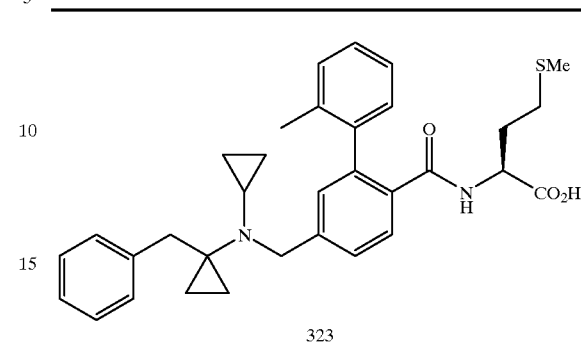
323
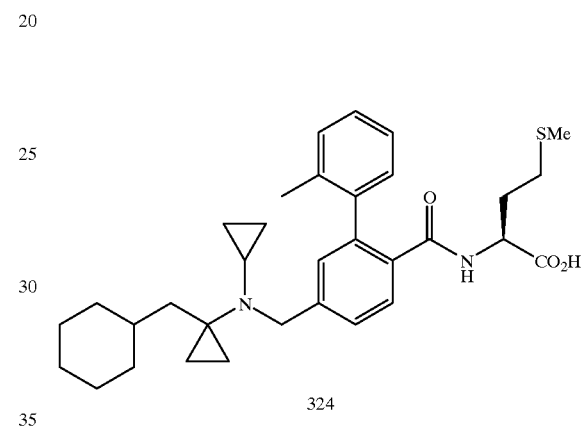
324
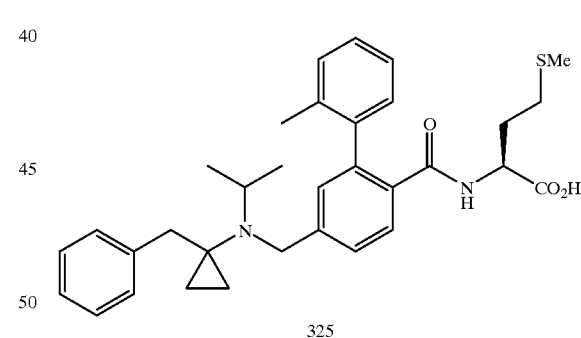
325
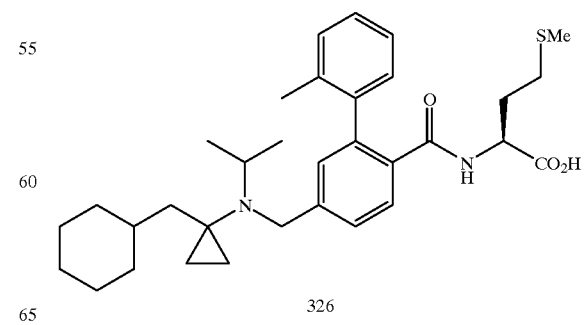
326

TABLE 6-continued
Amines of the Type A(B)N-L₁
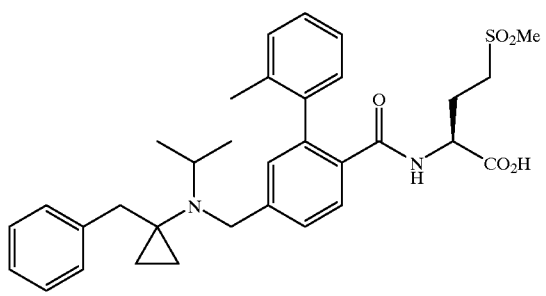
327
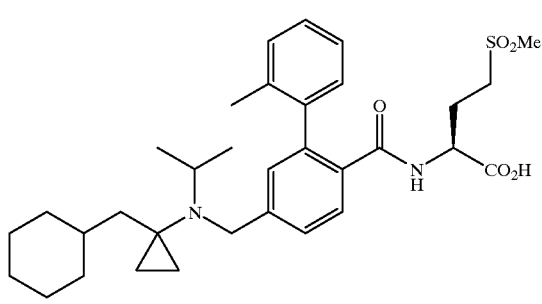
328
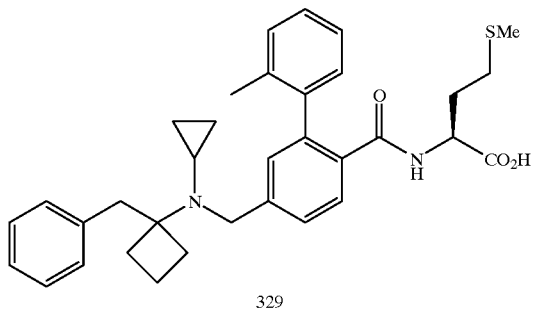
329
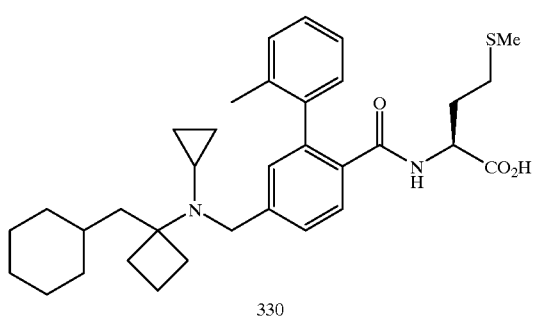
330
TABLE 6-continued
Amines of the Type A(B)N-L₁
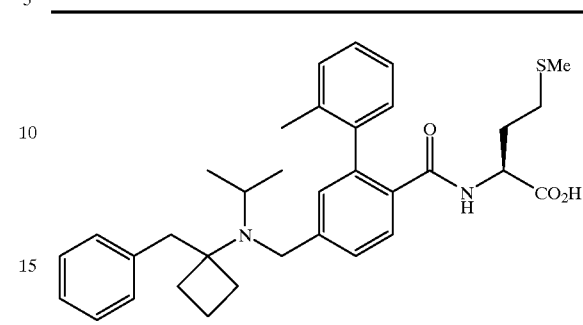
331
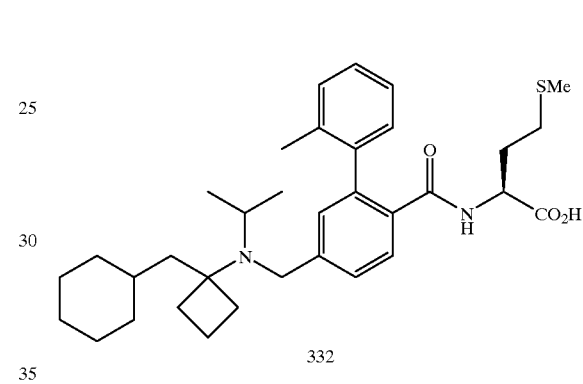
332
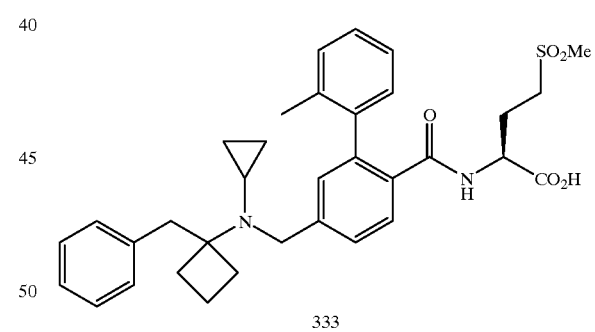
333
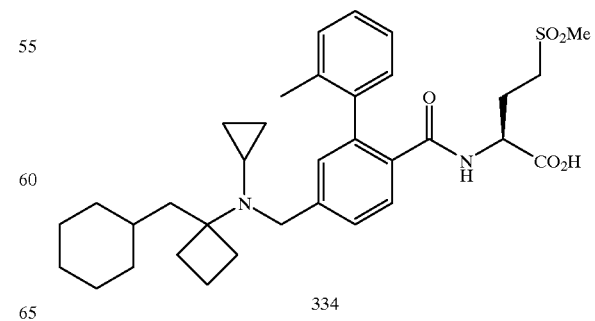
334

TABLE 6-continued

Amines of the Type A(B)N-L$_1$

335

336

337

338

339

340

341

342

TABLE 6-continued
Amines of the Type A(B)N-L₁
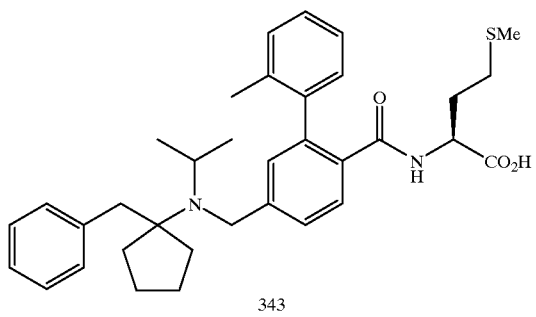
343
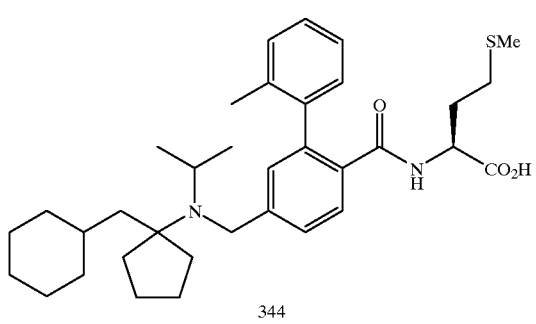
344
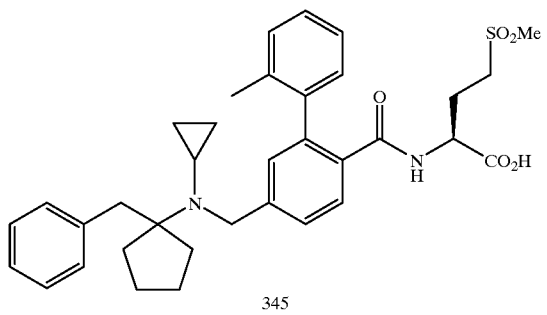
345
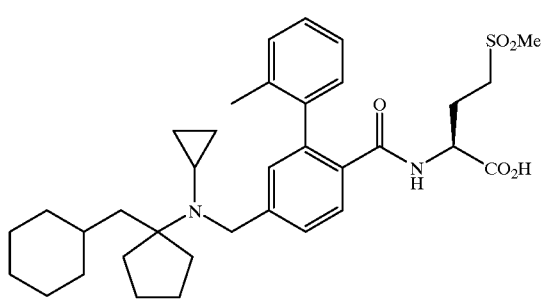
346
TABLE 6-continued
Amines of the Type A(B)N-L₁
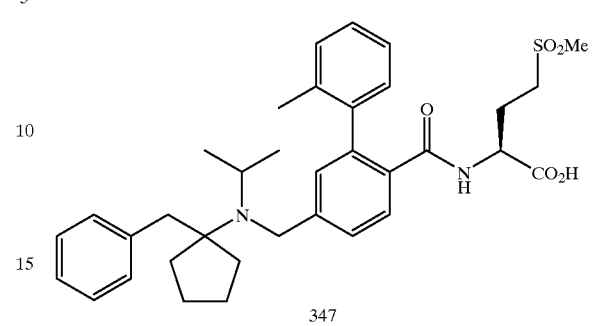
347
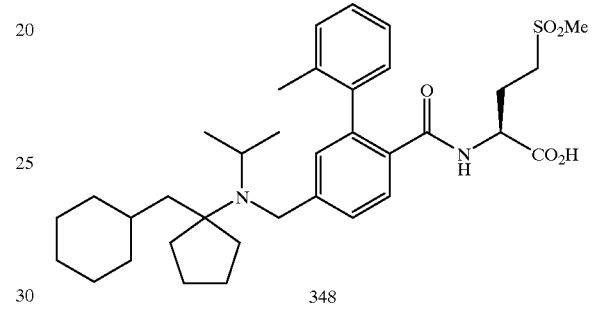
348
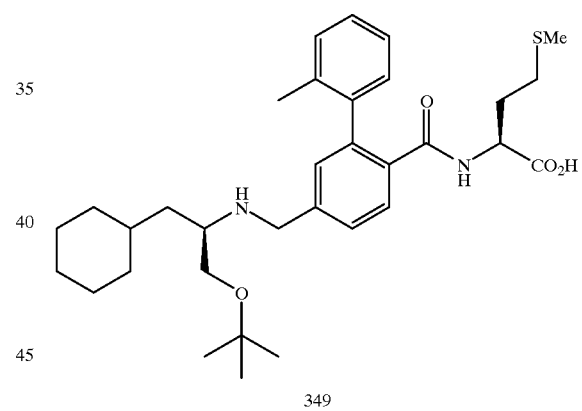
349
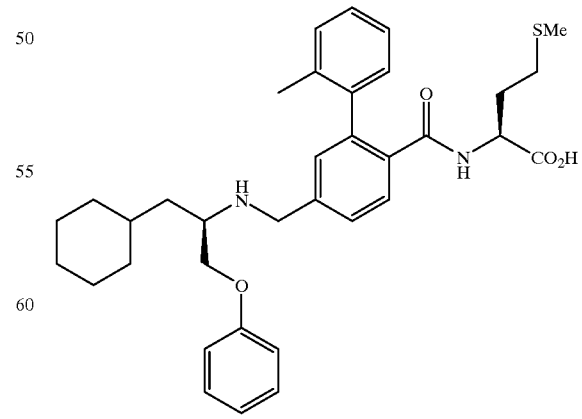
350

TABLE 6-continued
Amines of the Type A(B)N-L₁
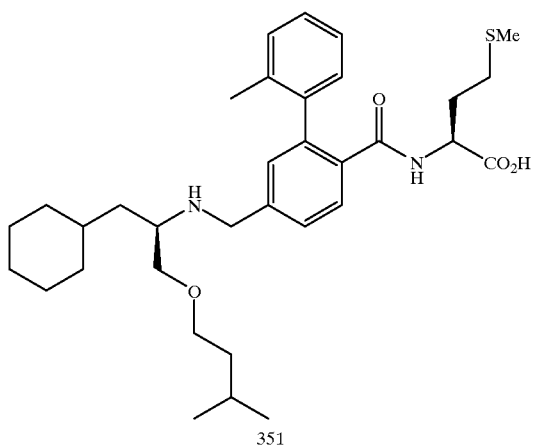
351
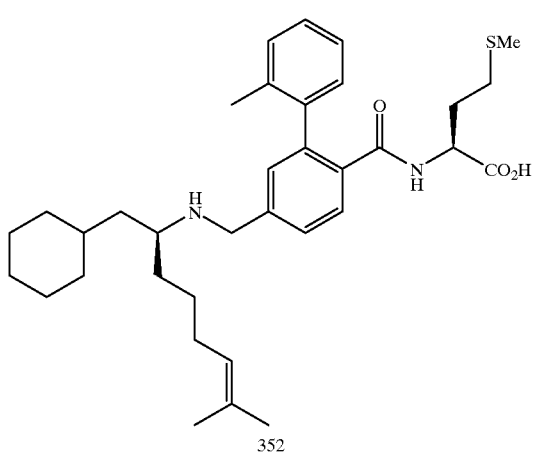
352
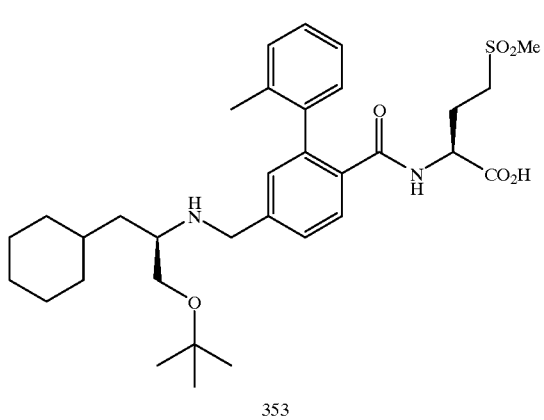
353
TABLE 6-continued
Amines of the Type A(B)N-L₁
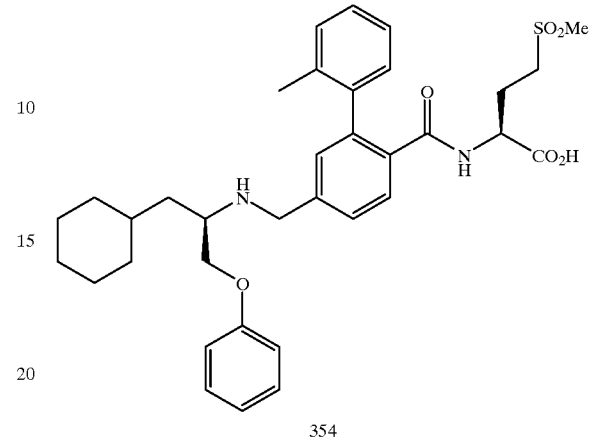
354
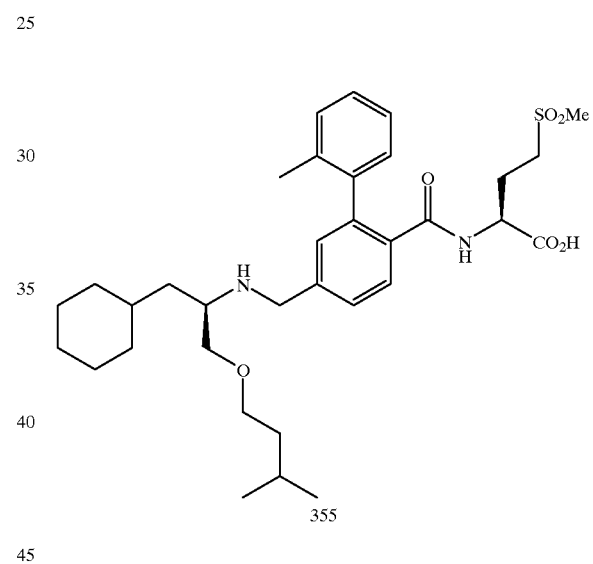
355
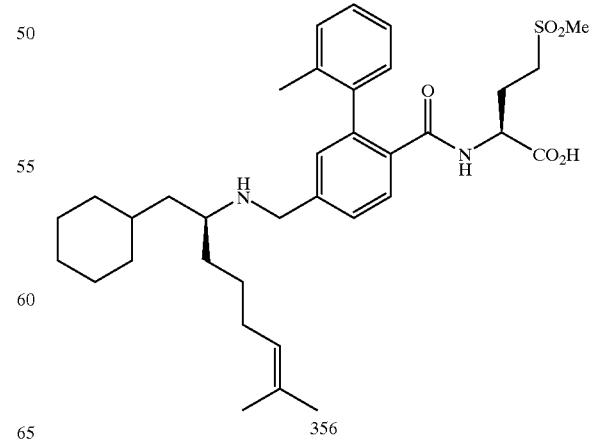
356

TABLE 6-continued
Amines of the Type A(B)N-L₁
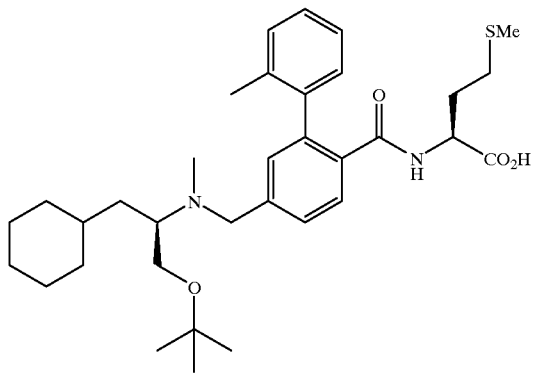
357
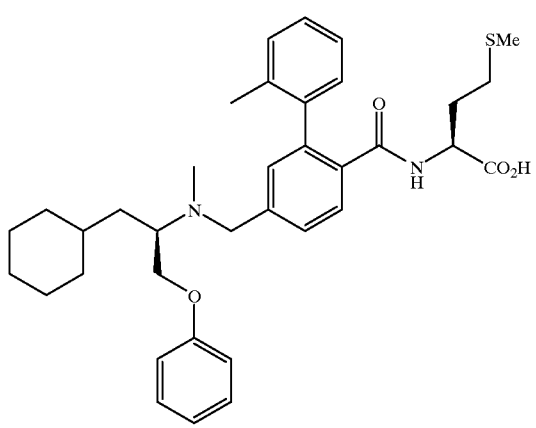
358
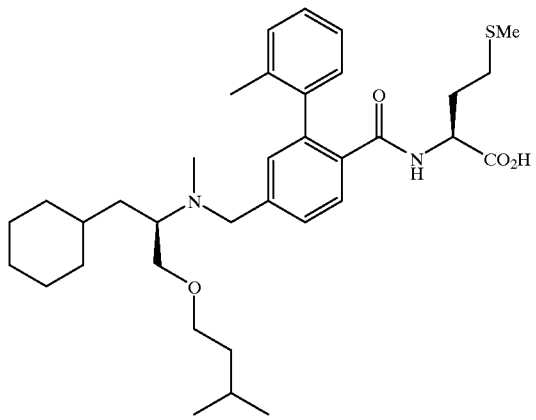
359
TABLE 6-continued
Amines of the Type A(B)N-L₁
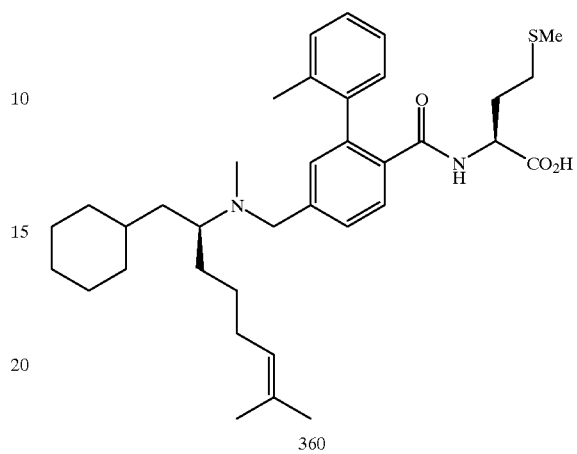
360
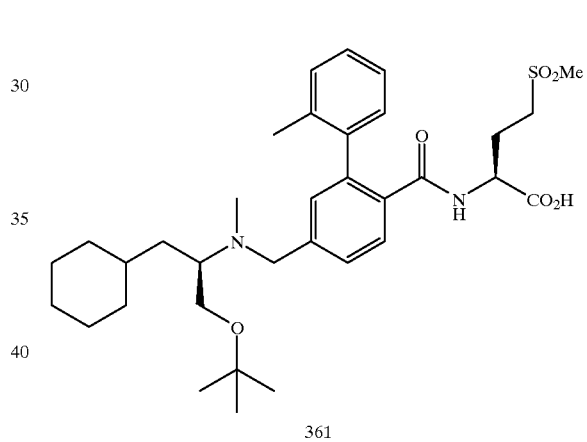
361
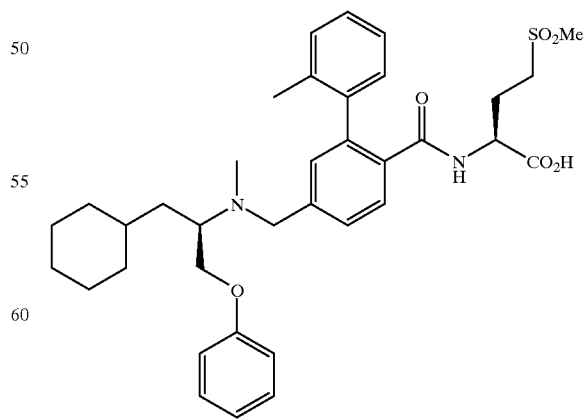
362

TABLE 6-continued
Amines of the Type A(B)N-L₁
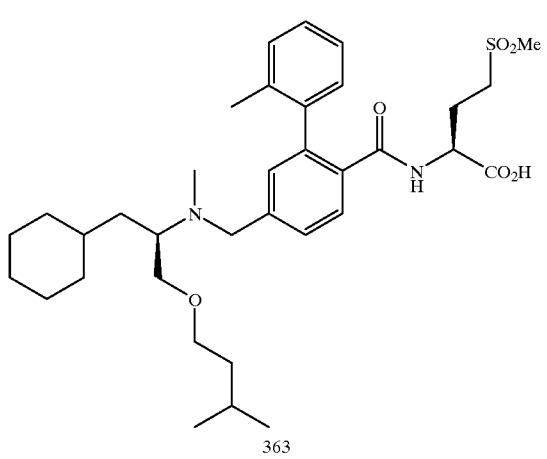
363
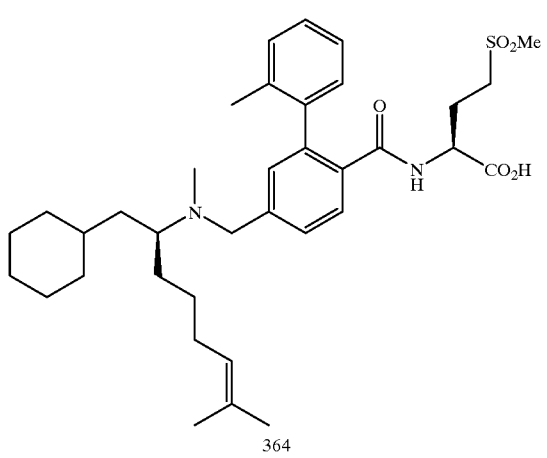
364
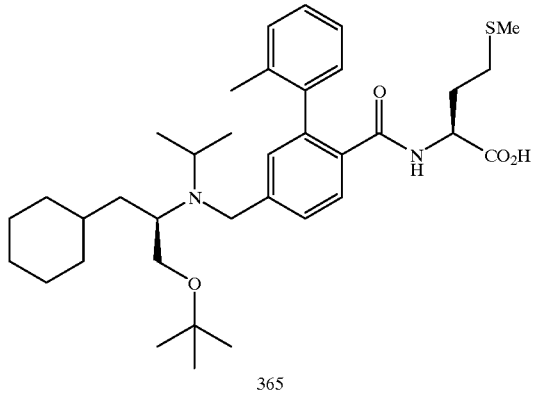
365
TABLE 6-continued
Amines of the Type A(B)N-L₁
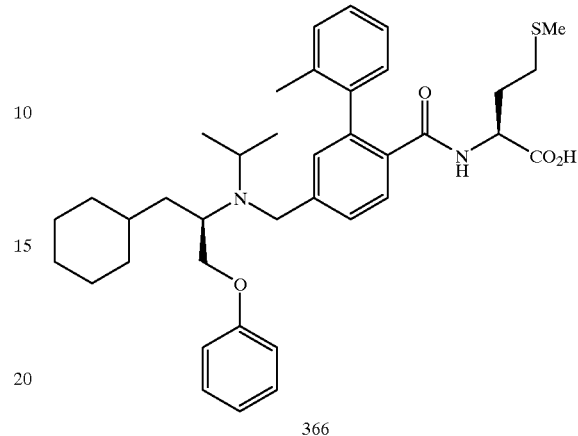
366
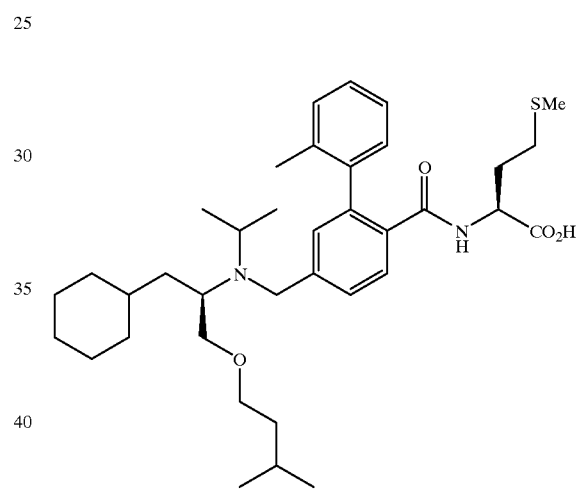
367
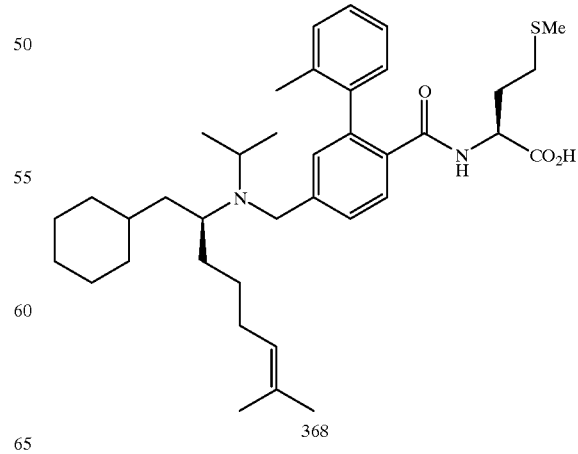
368

TABLE 6-continued
Amines of the Type A(B)N-L₁
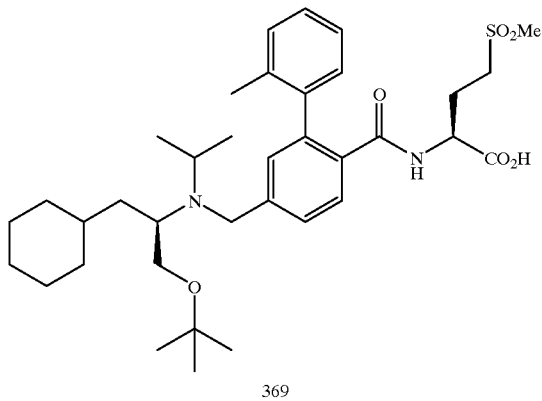
369
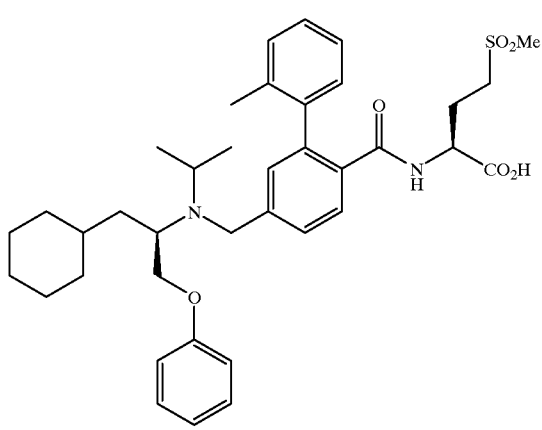
370
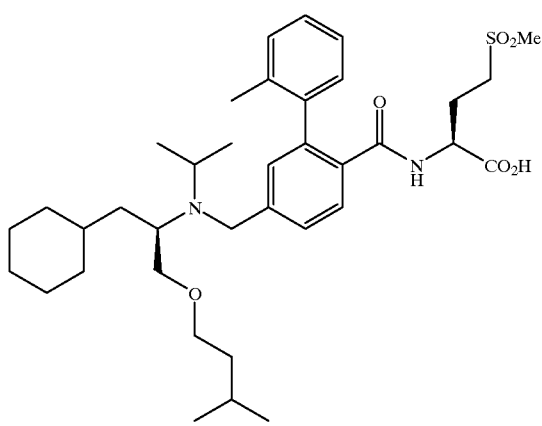
371
TABLE 6-continued
Amines of the Type A(B)N-L₁
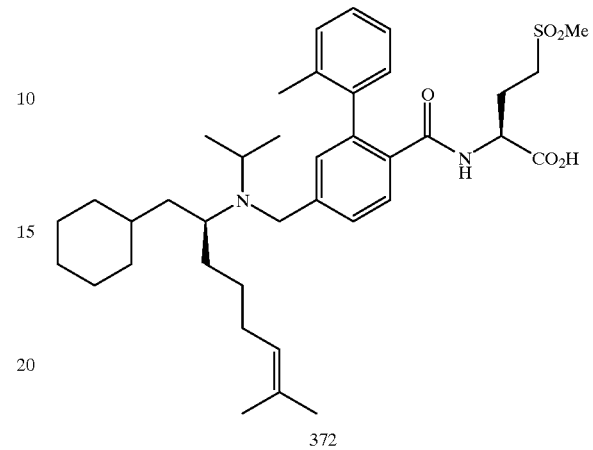
372
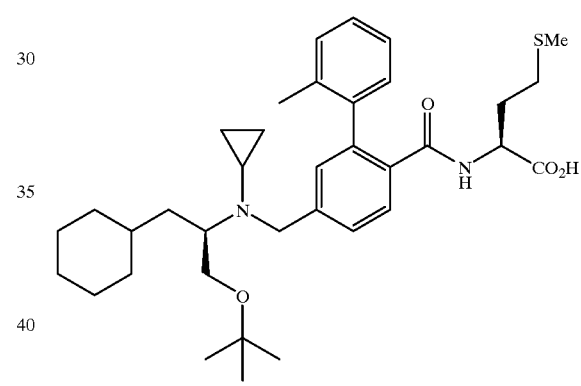
373
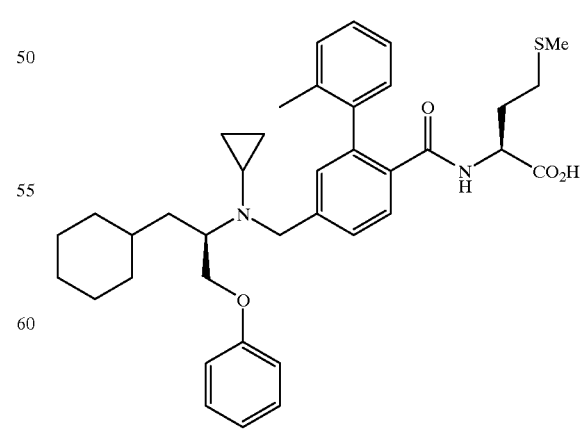
374

TABLE 6-continued
Amines of the Type A(B)N-L$_1$
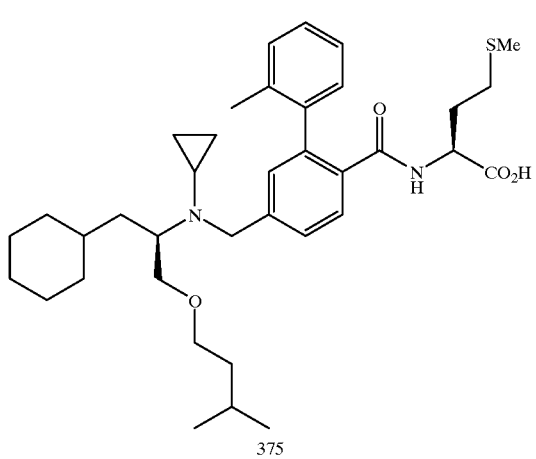
375
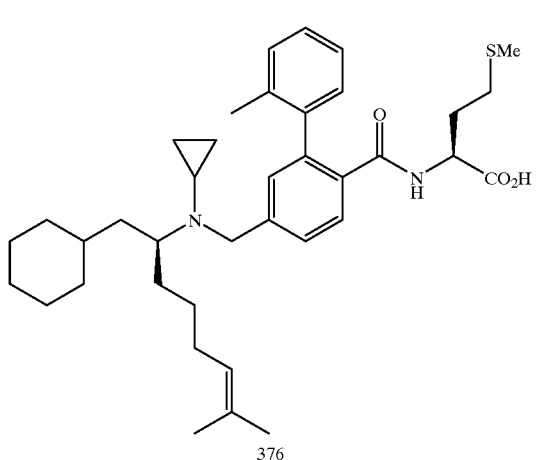
376
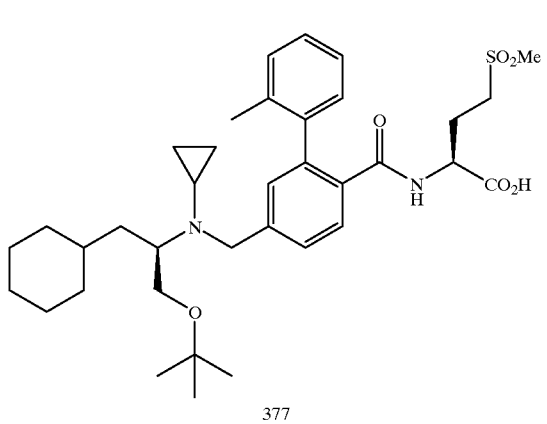
377
TABLE 6-continued
Amines of the Type A(B)N-L$_1$
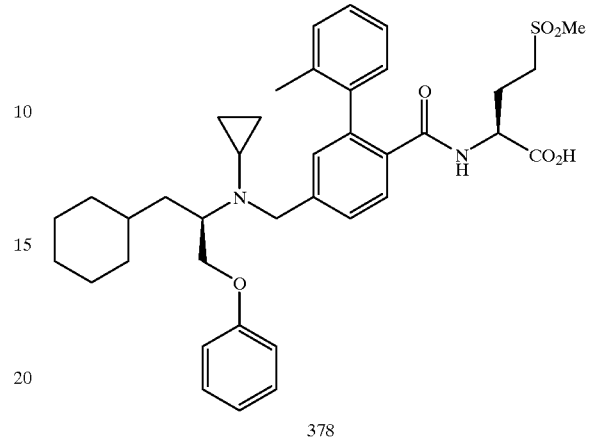
378
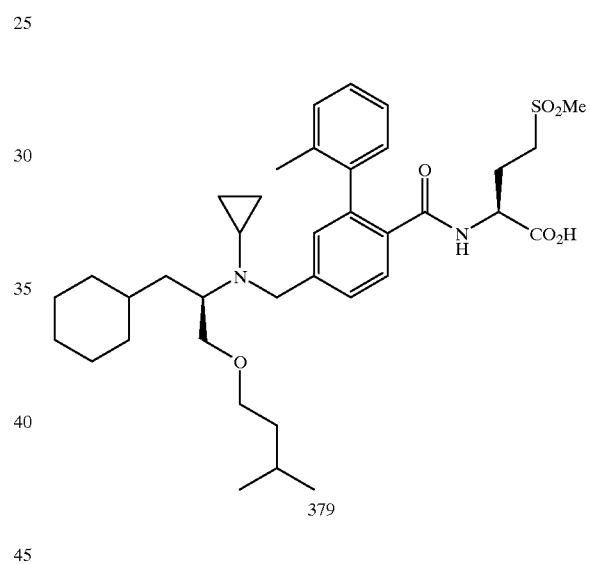
379
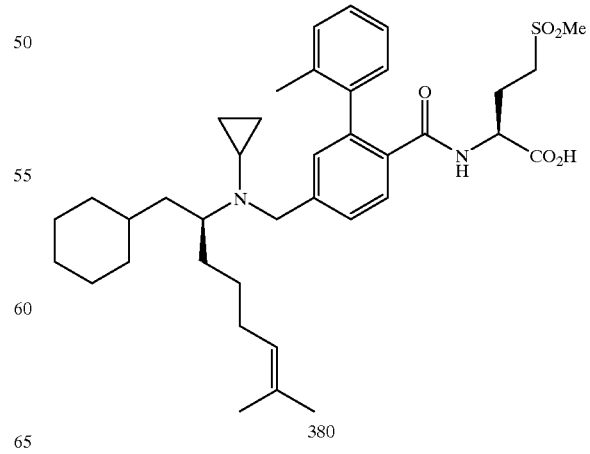
380

TABLE 7
Ethers of the Type A-OL₁

1

2
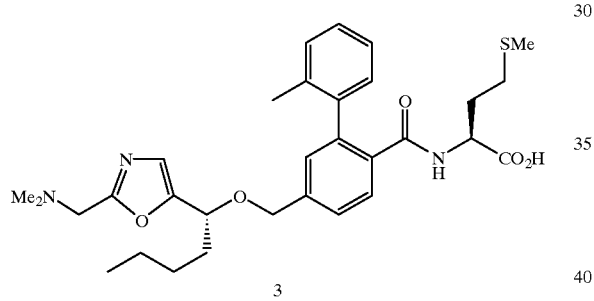
3
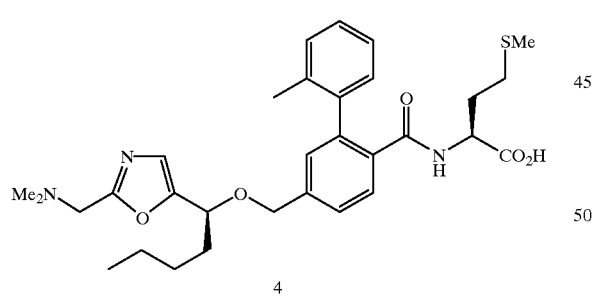
4
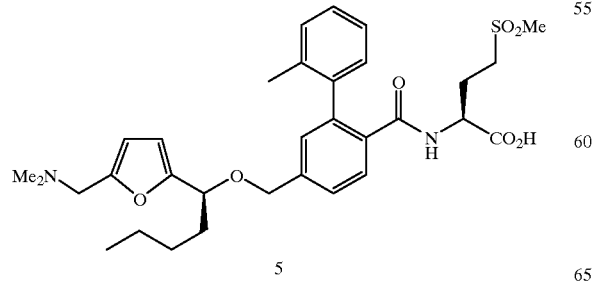
5
TABLE 7-continued
Ethers of the Type A-OL₁
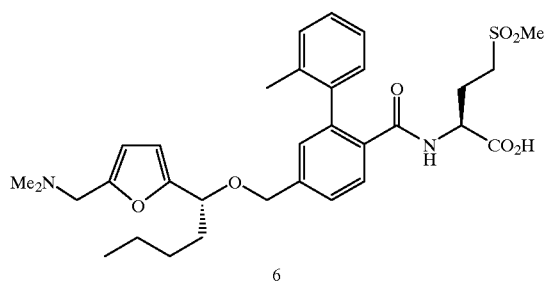
6
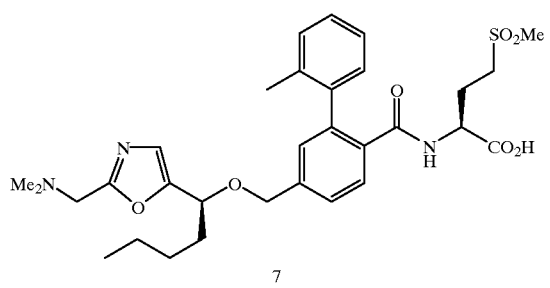
7
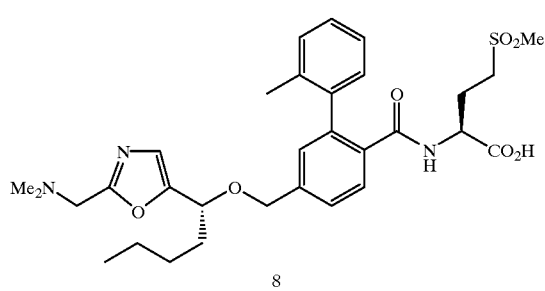
8
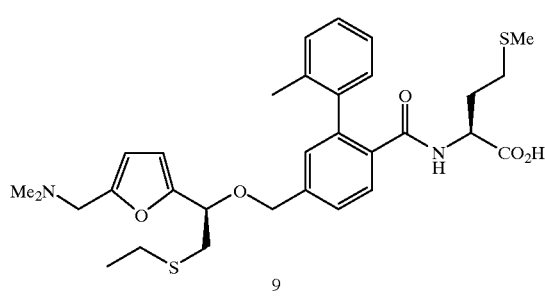
9
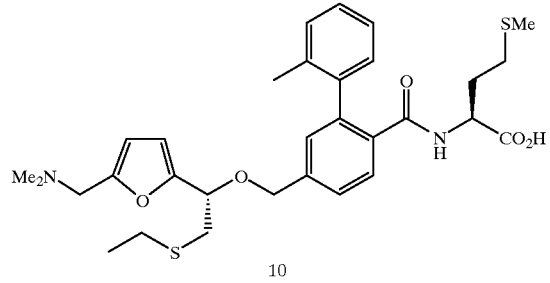
10

TABLE 7-continued

Ethers of the Type A-OL₁

TABLE 7-continued

Ethers of the Type A-OL₁

TABLE 7-continued
Ethers of the Type A-OL₁
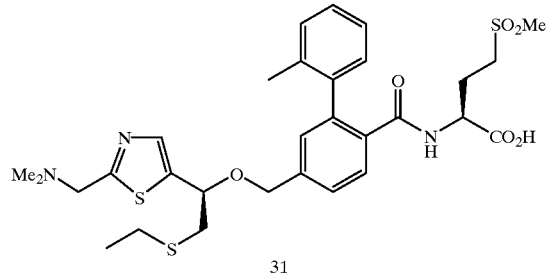
31
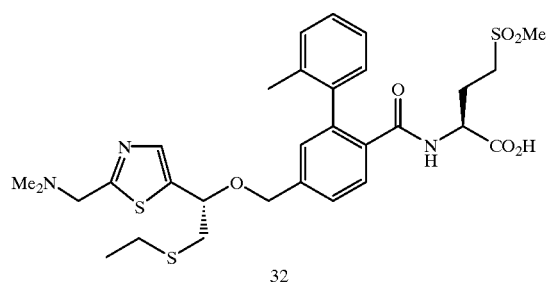
32
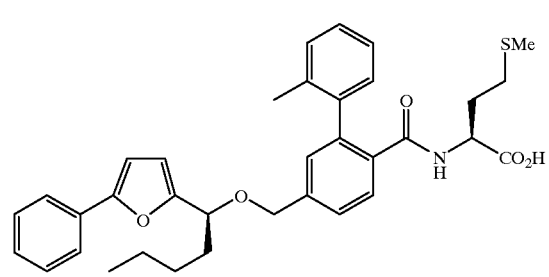
33
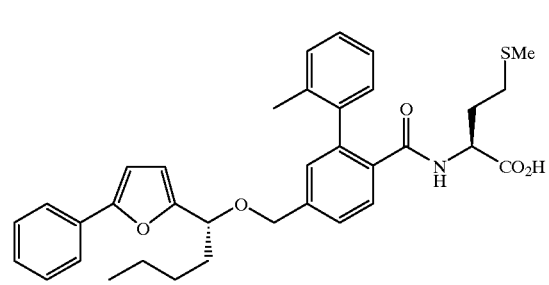
34
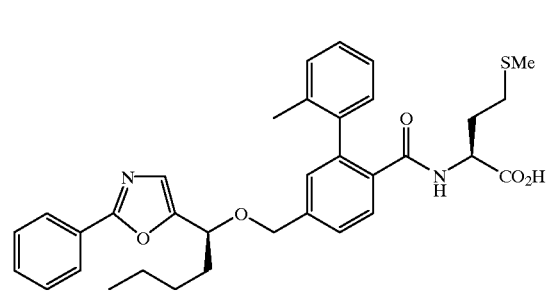
35
TABLE 7-continued
Ethers of the Type A-OL₁
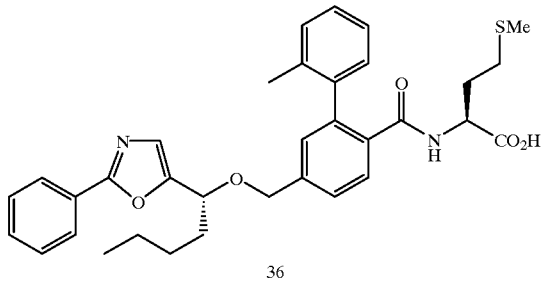
36
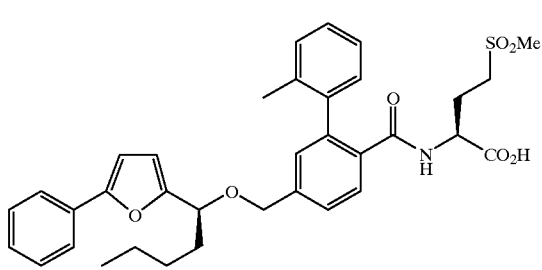
37
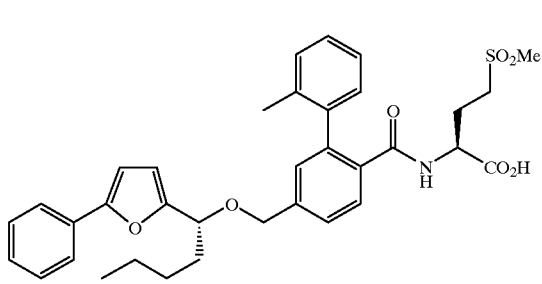
38
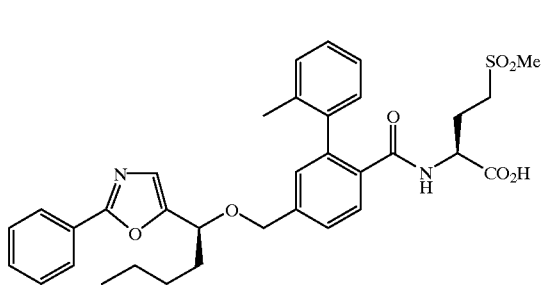
39
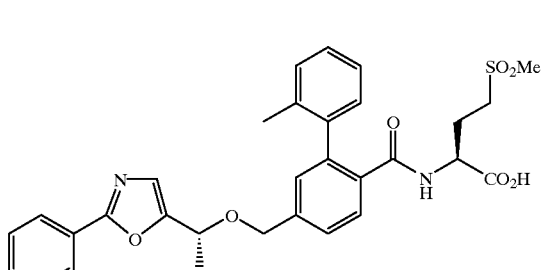
40

TABLE 7-continued
Ethers of the Type A-OL₁
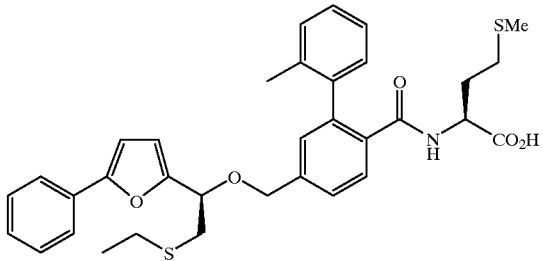
41
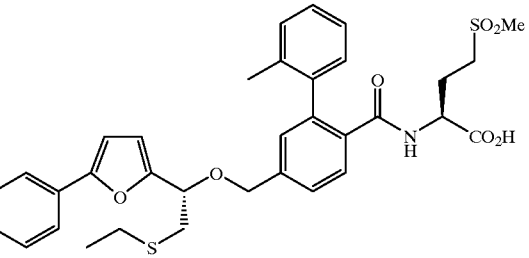
42
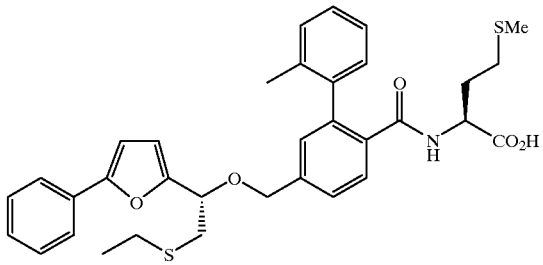
43
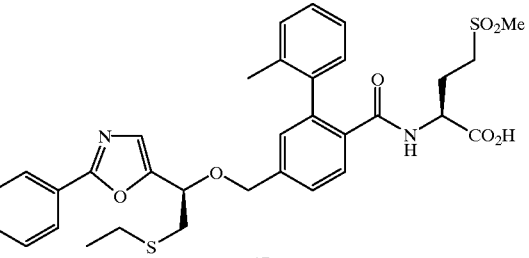
44
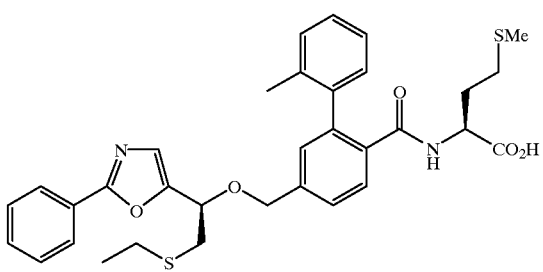
45
TABLE 7-continued
Ethers of the Type A-OL₁
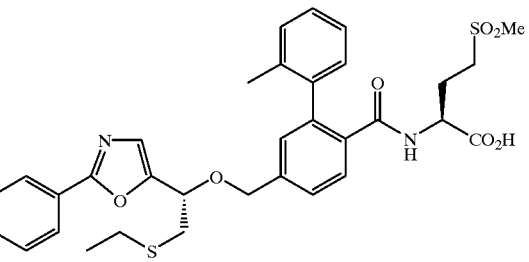
46
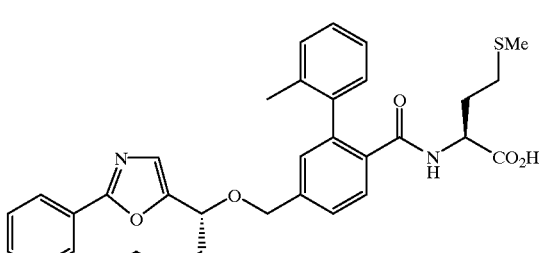
47
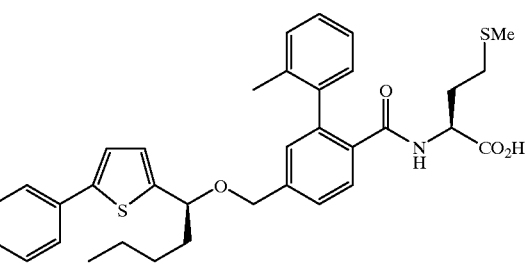
48
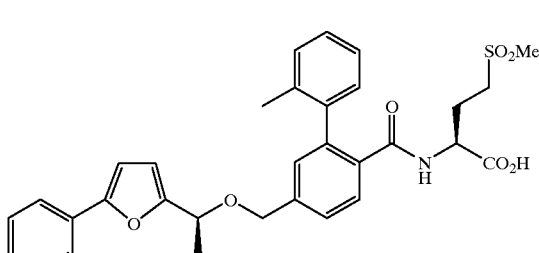
49
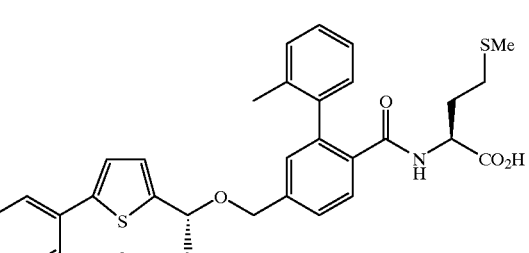
50

TABLE 7-continued
Ethers of the Type A-OL₁
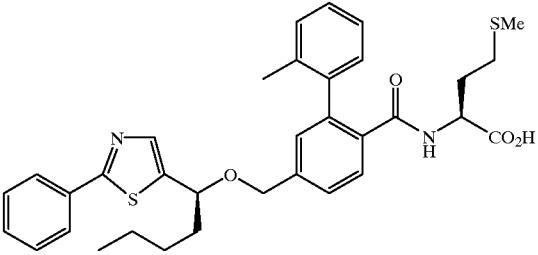
51
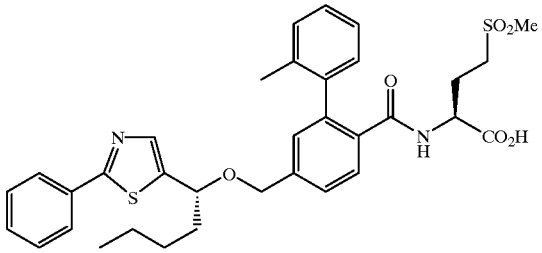
52
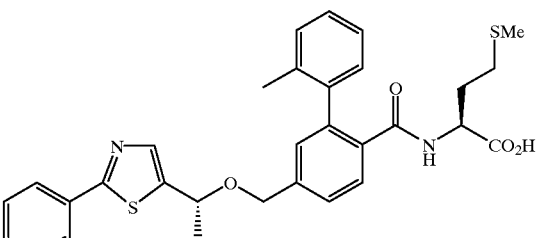
53
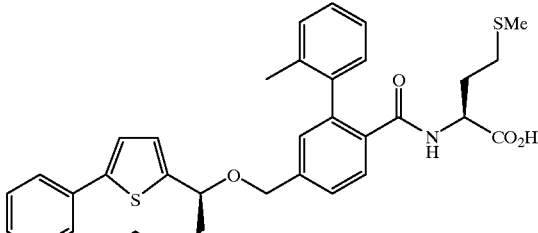
54
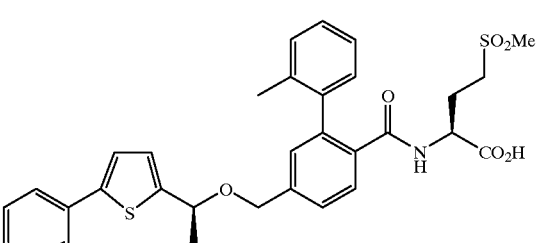
55
TABLE 7-continued
Ethers of the Type A-OL₁
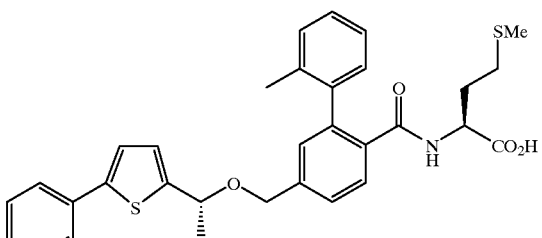
56
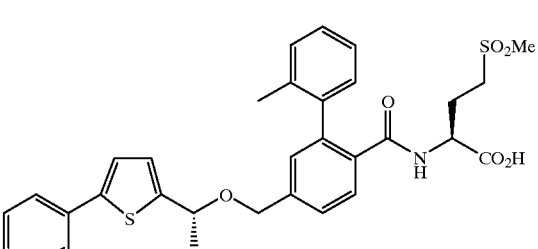
57
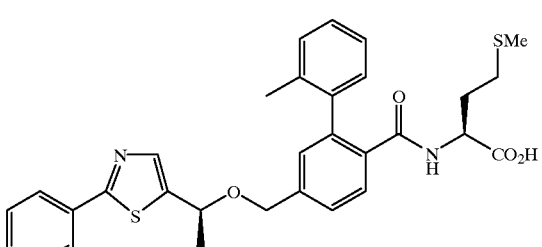
58
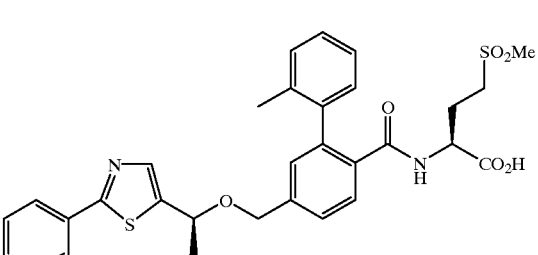
59
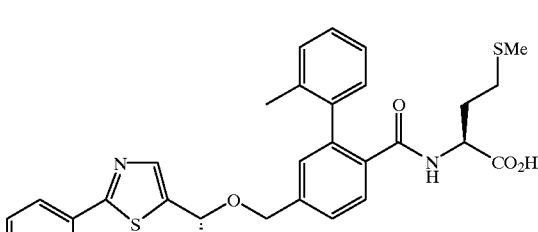
60

TABLE 7-continued
Ethers of the Type A-OL₁
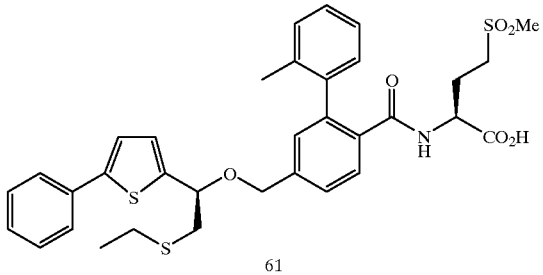
61
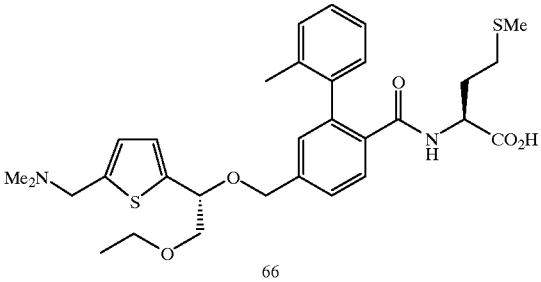
62
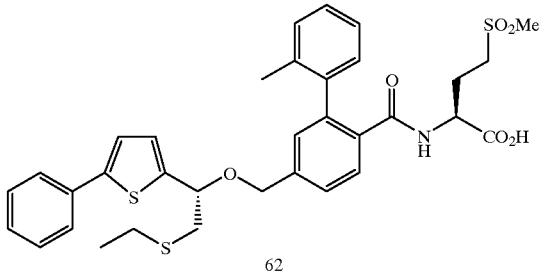
63
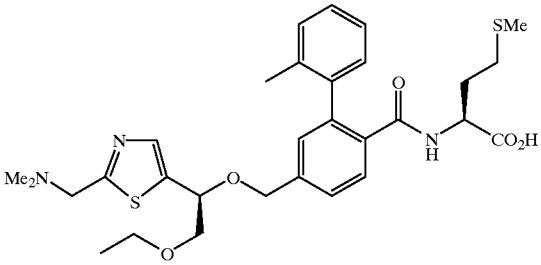
64
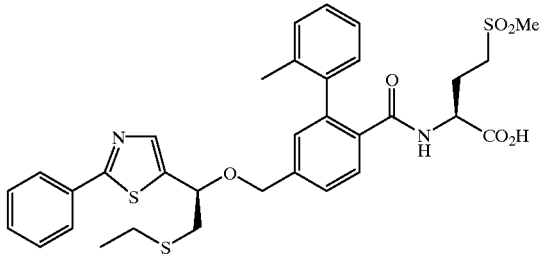
65
TABLE 7-continued
Ethers of the Type A-OL₁
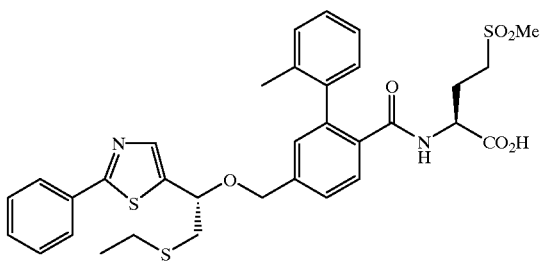
66
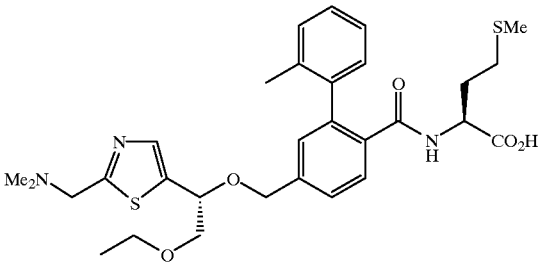
67
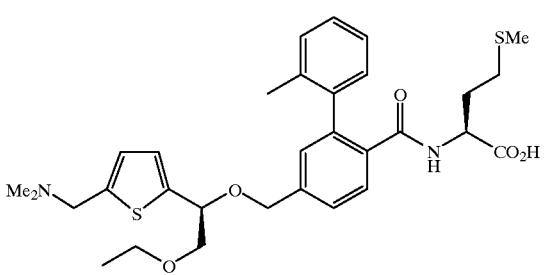
68
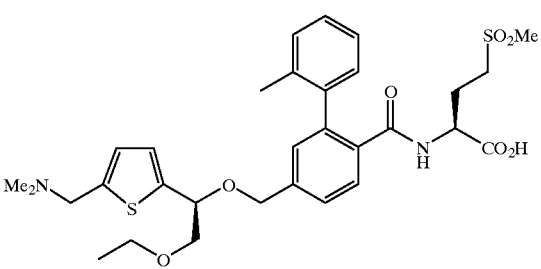
69
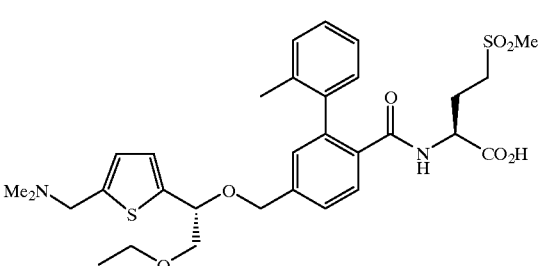
70

TABLE 7-continued
Ethers of the Type A-OL₁
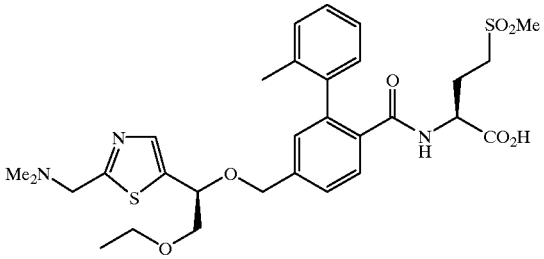
71
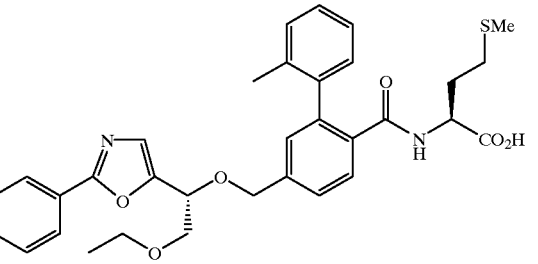
72
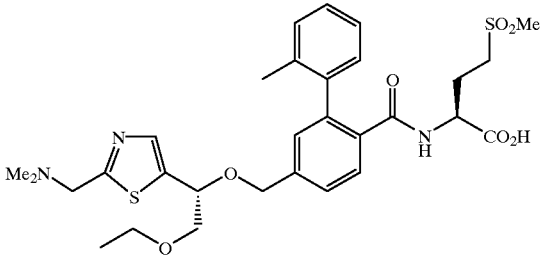
73
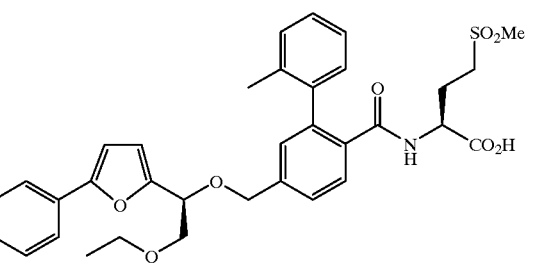
74
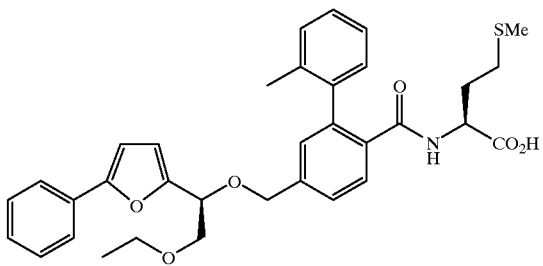
75
TABLE 7-continued
Ethers of the Type A-OL₁
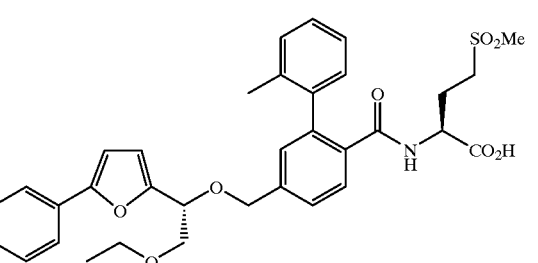
76
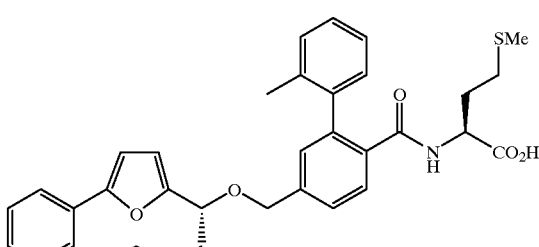
77
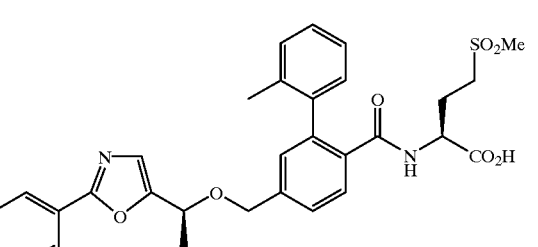
78
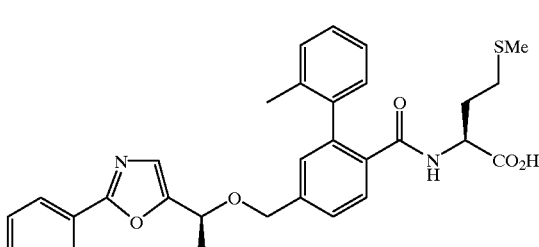
79
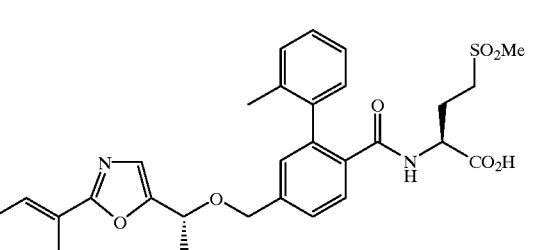
80

TABLE 7-continued
Ethers of the Type A-OL₁
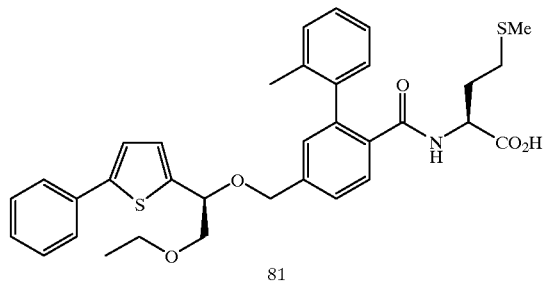
81
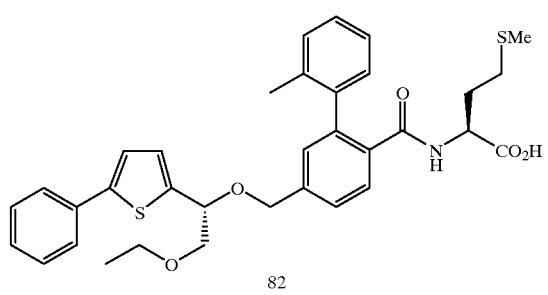
82
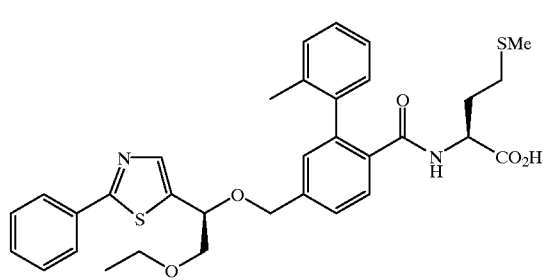
83
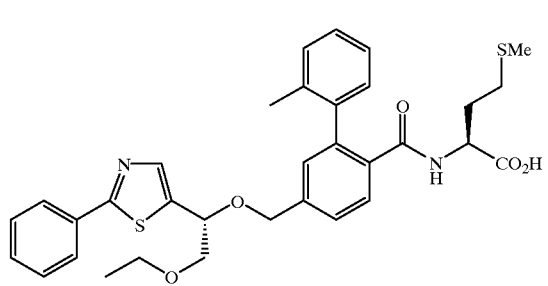
84
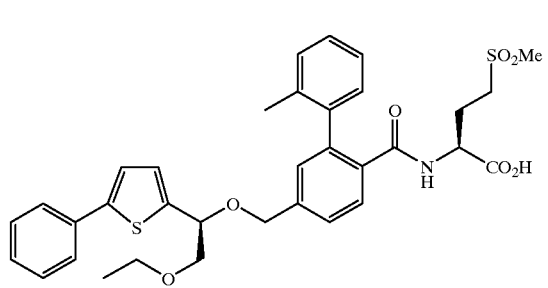
85
TABLE 7-continued
Ethers of the Type A-OL₁
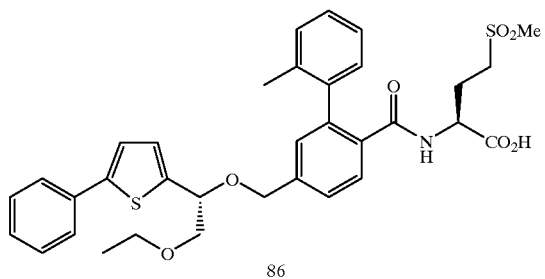
86
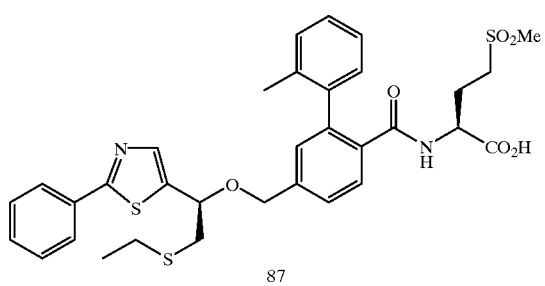
87
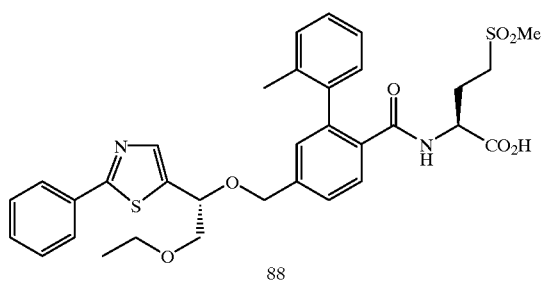
88
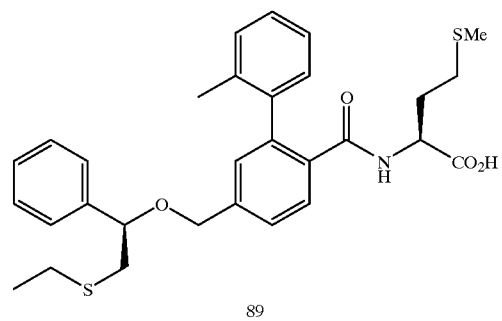
89
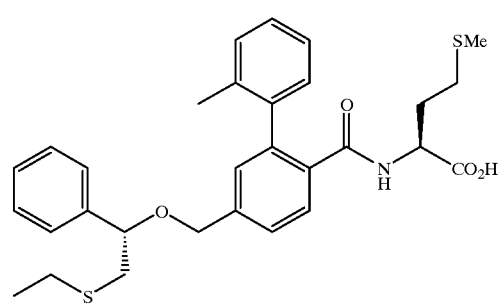
90

TABLE 7-continued
Ethers of the Type A-OL₁
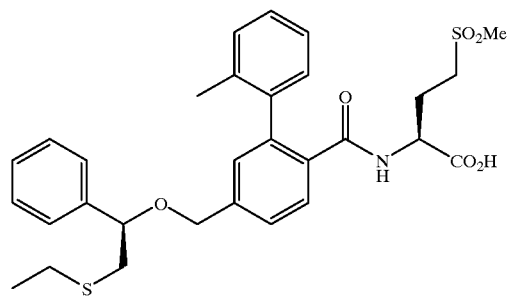
91
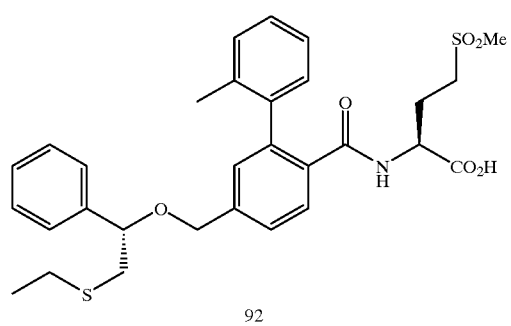
92
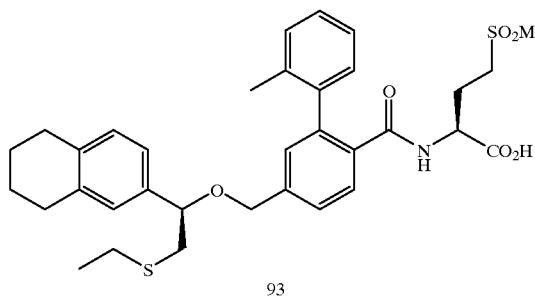
93
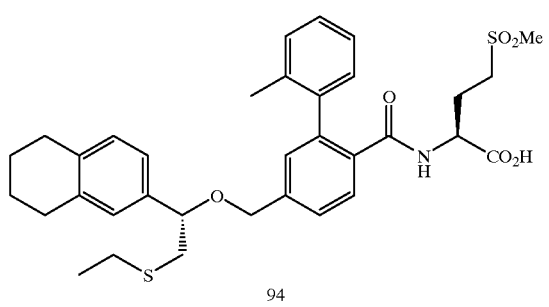
94
TABLE 7-continued
Ethers of the Type A-OL₁
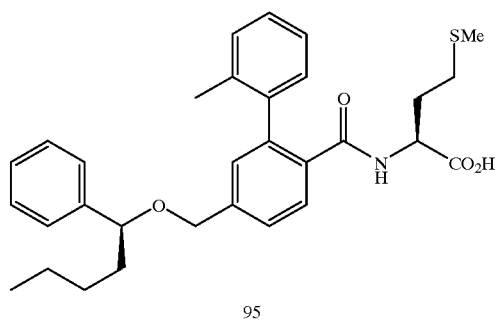
95
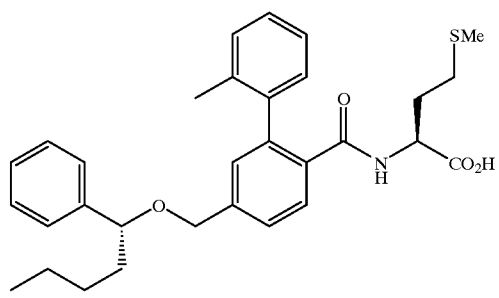
96
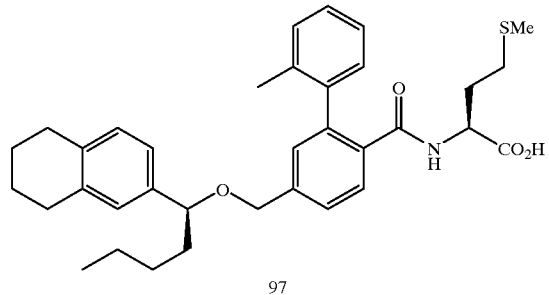
97
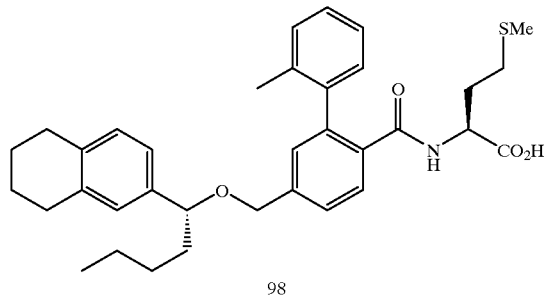
98

TABLE 7-continued
Ethers of the Type A-OL₁
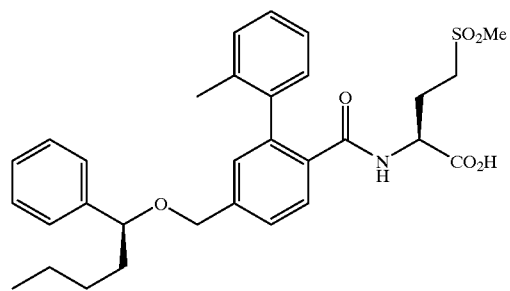
99
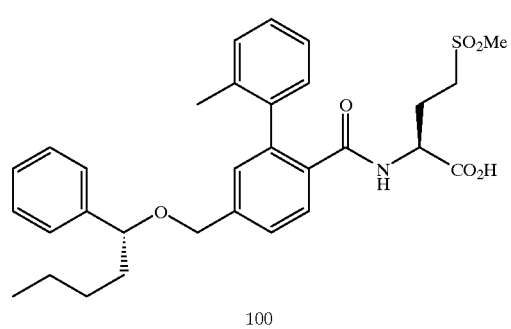
100
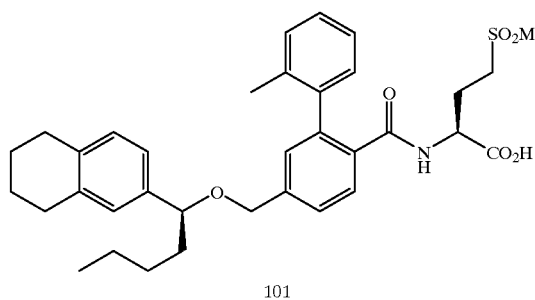
101
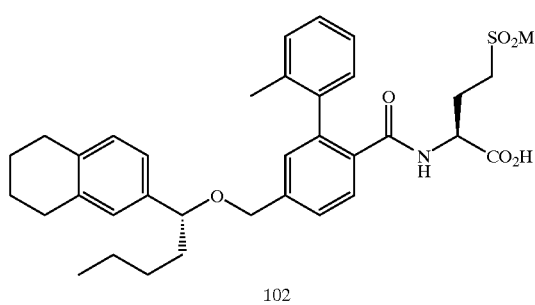
102
TABLE 7-continued
Ethers of the Type A-OL₁
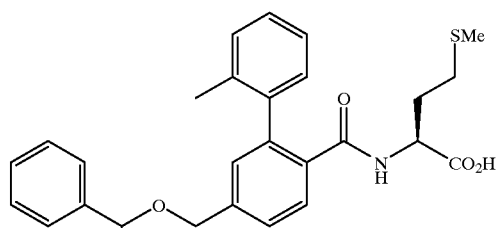
103
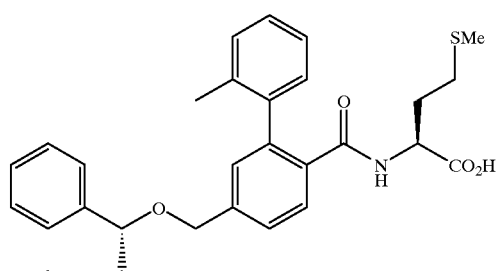
104
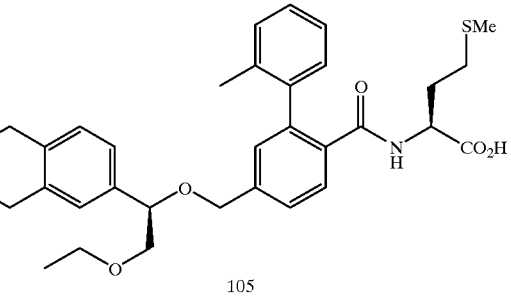
105
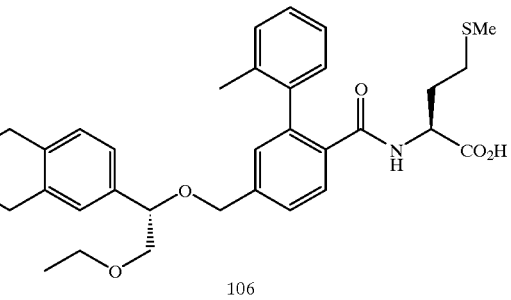
106

TABLE 7-continued
Ethers of the Type A-OL$_1$
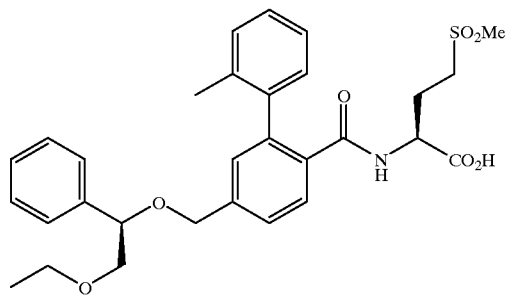
107
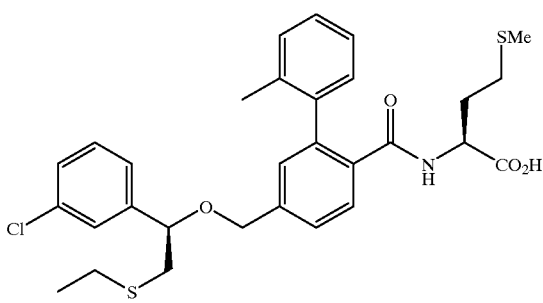
111
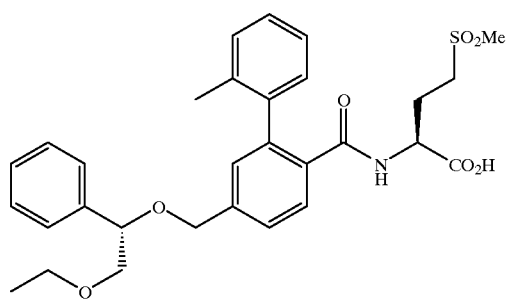
108
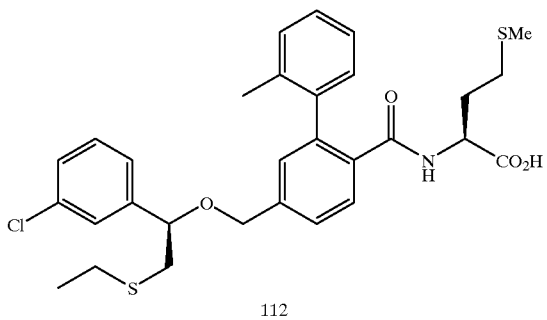
112
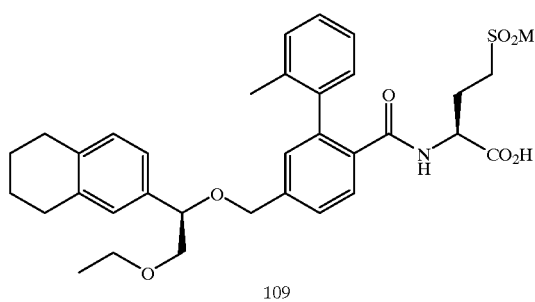
109
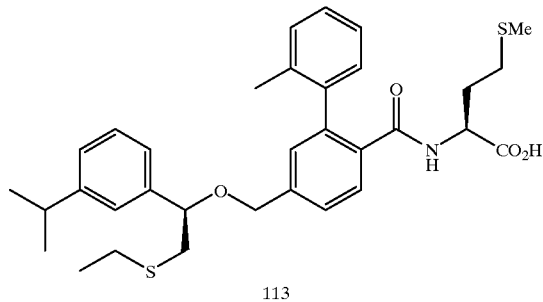
113
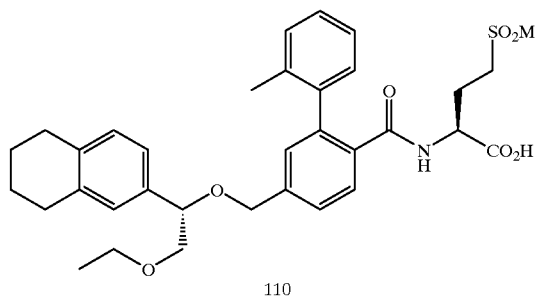
110
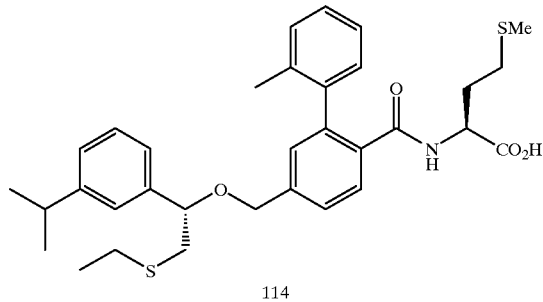
114

TABLE 7-continued
Ethers of the Type A-OL₁
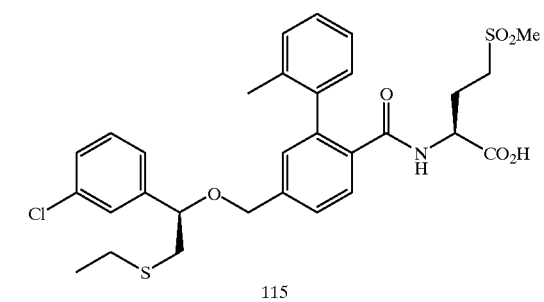
115
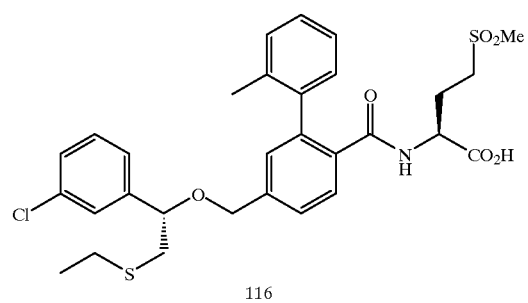
116
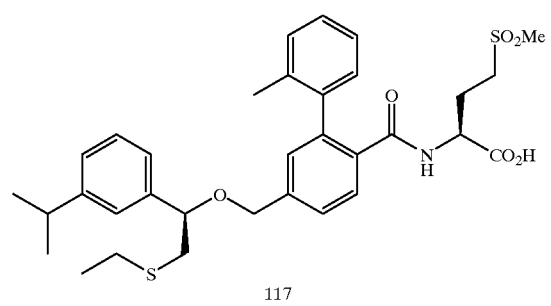
117
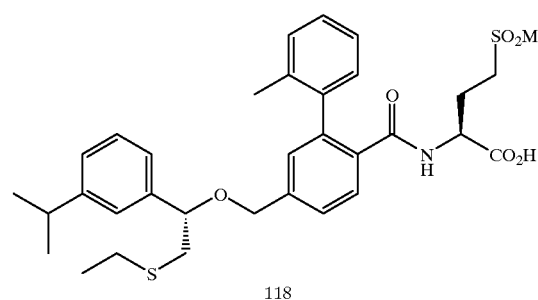
118
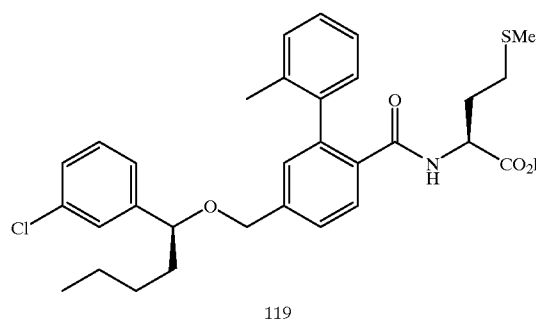
119
TABLE 7-continued
Ethers of the Type A-OL₁
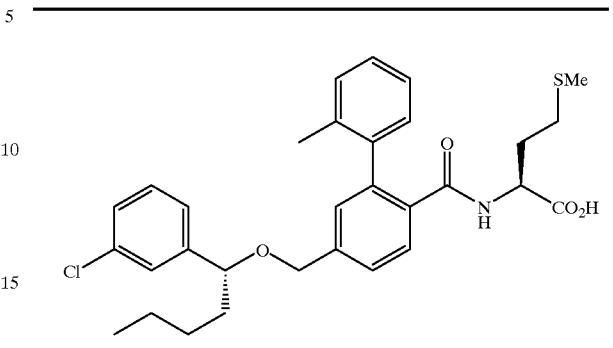
120
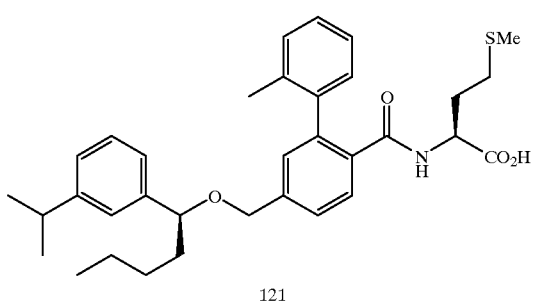
121
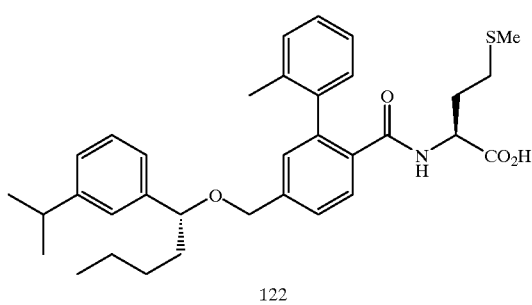
122
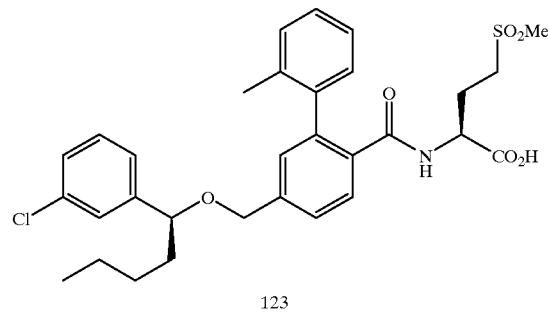
123

TABLE 7-continued
Ethers of the Type A-OL₁
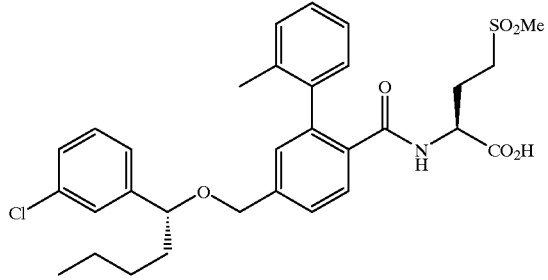
124
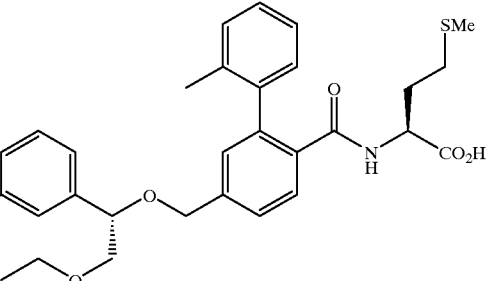
125
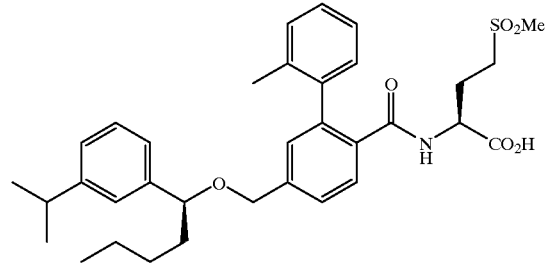
126
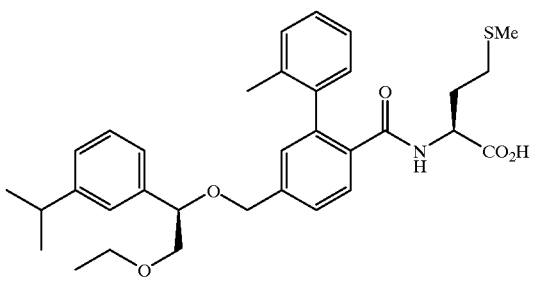
127
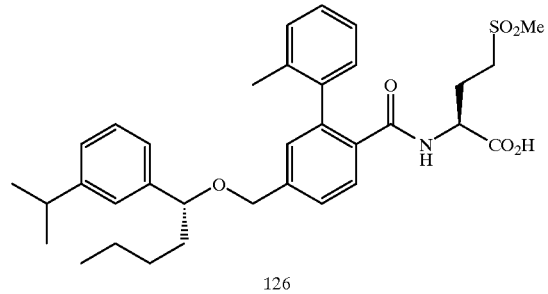
128
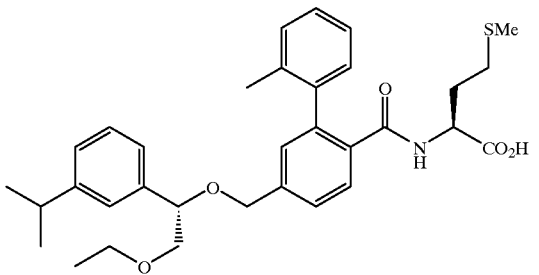
129
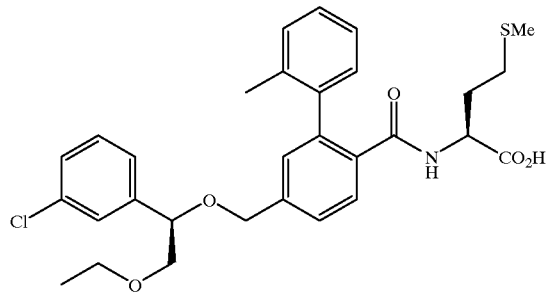
130
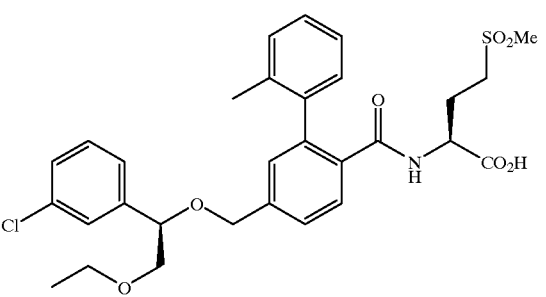
131

TABLE 7-continued

Ethers of the Type A-OL₁

132

133

134

135

136

137

138

139

TABLE 7-continued
Ethers of the Type A-OL₁
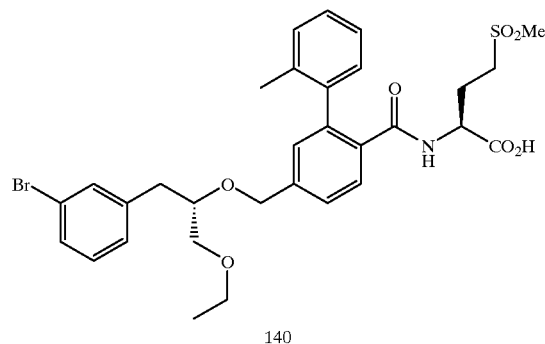
140
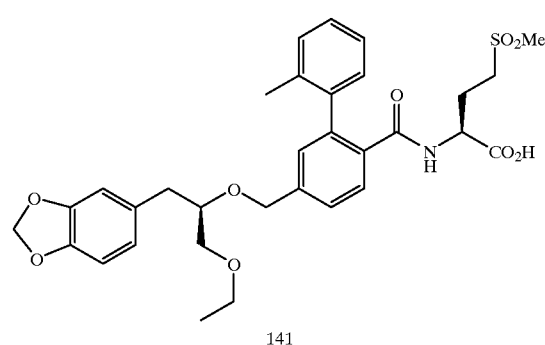
141
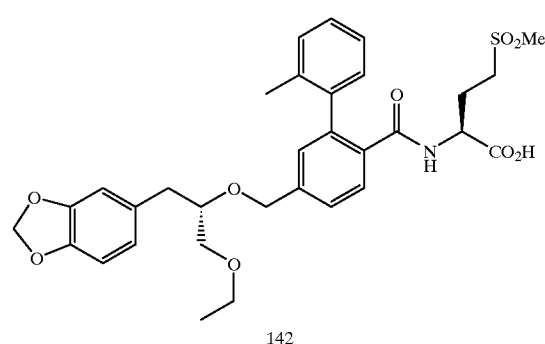
142
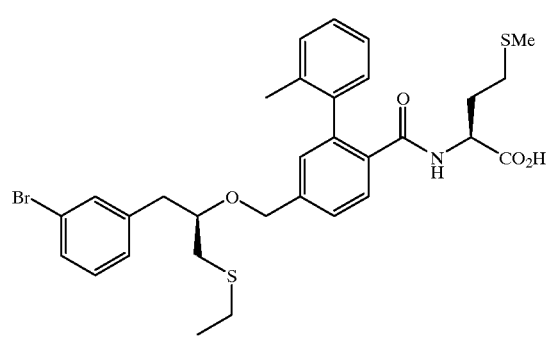
143
TABLE 7-continued
Ethers of the Type A-OL₁
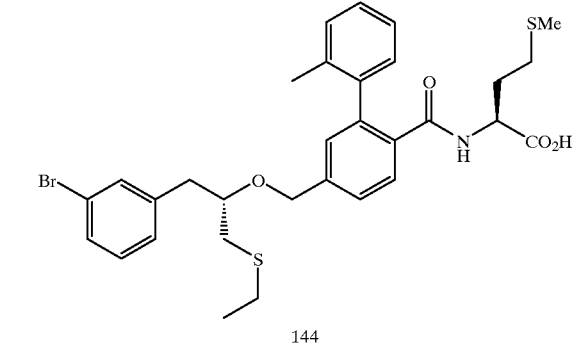
144
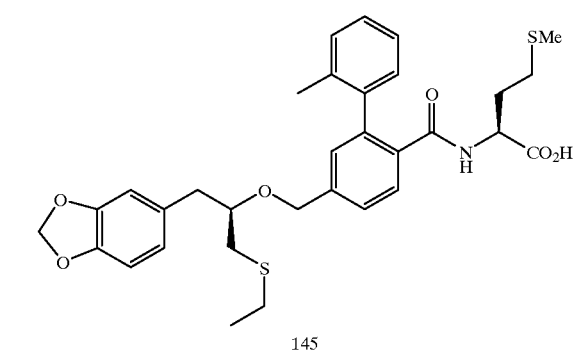
145
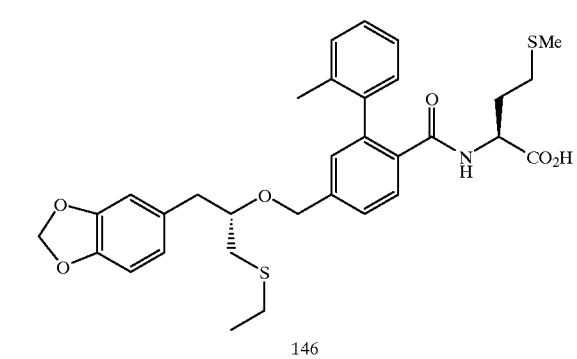
146
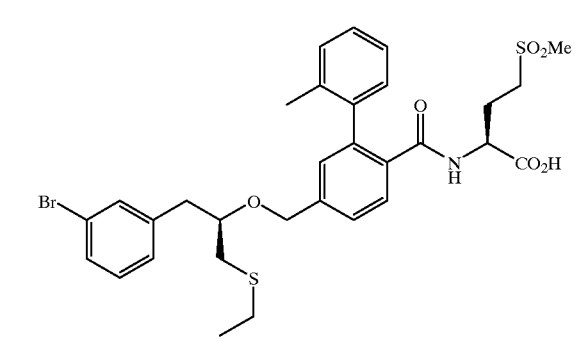
147

TABLE 7-continued
Ethers of the Type A-OL₁
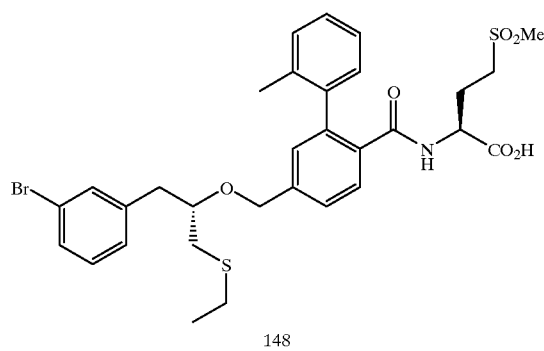
148
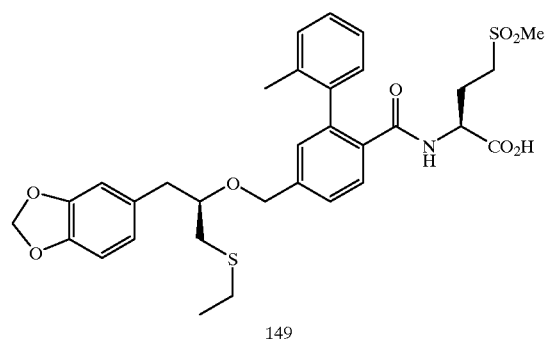
149
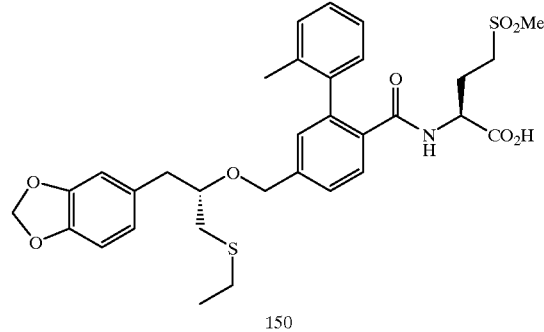
150
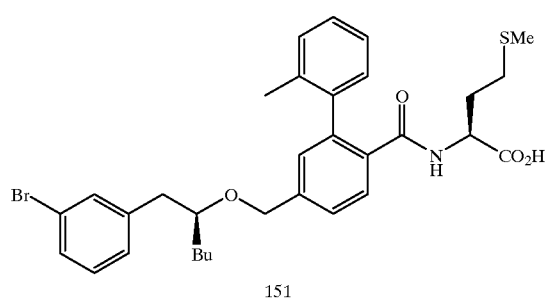
151
TABLE 7-continued
Ethers of the Type A-OL₁
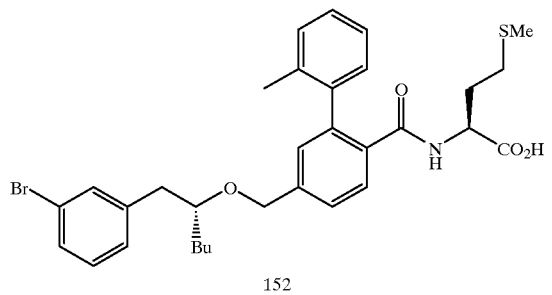
152
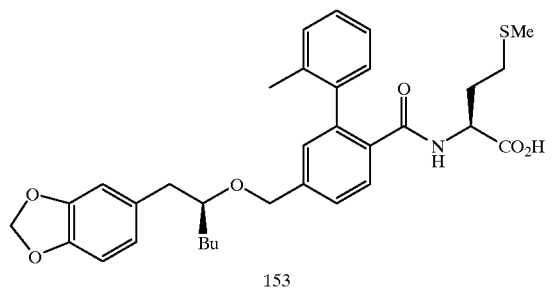
153
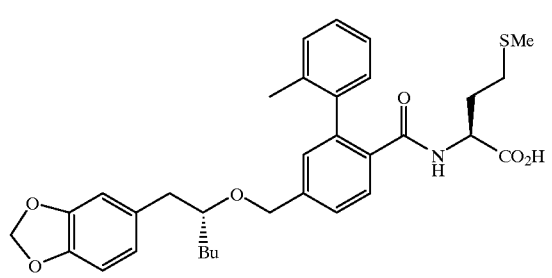
154
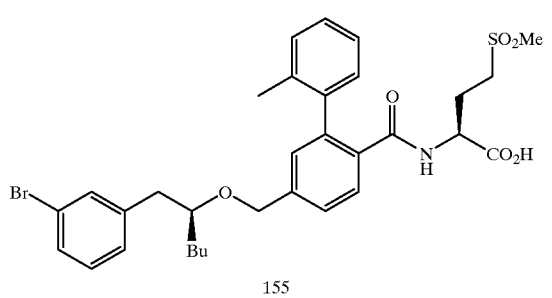
155
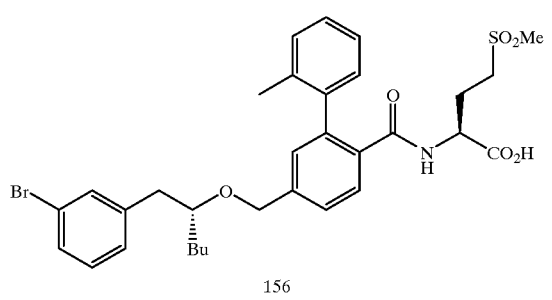
156

TABLE 7-continued
Ethers of the Type A-OL₁
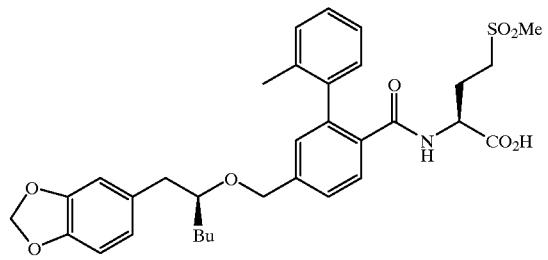
157
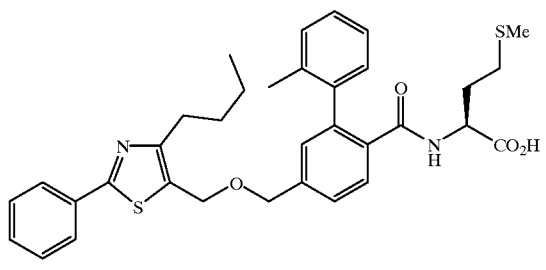
162
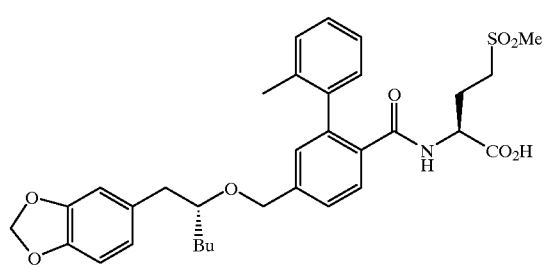
158
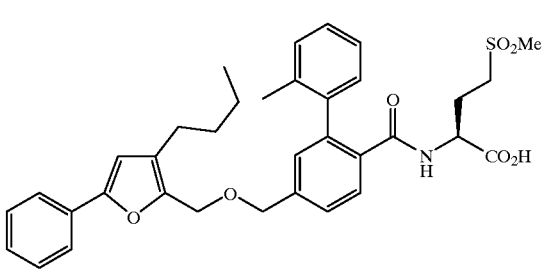
163
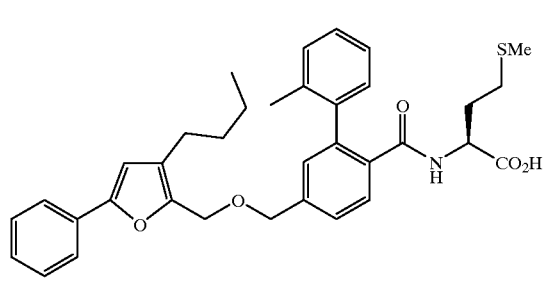
159
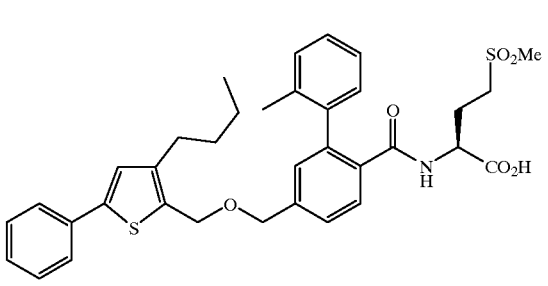
164
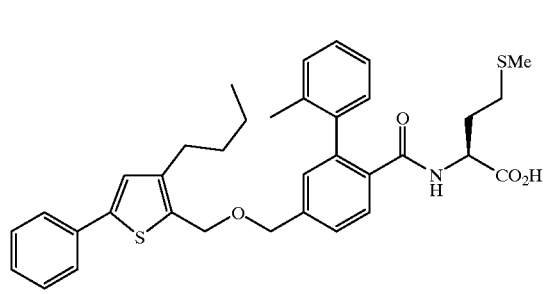
160
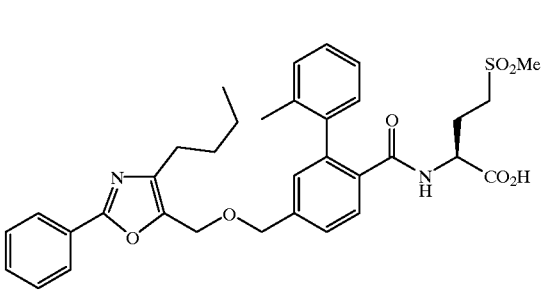
165
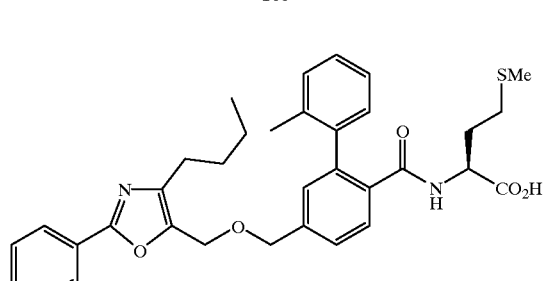
161
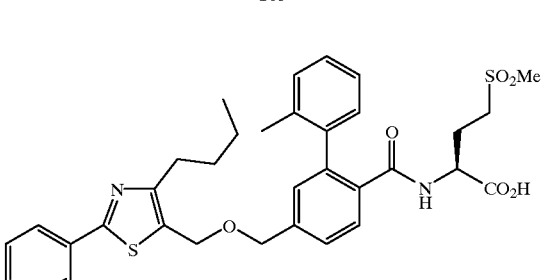
166

TABLE 7-continued
Ethers of the Type A-OL₁
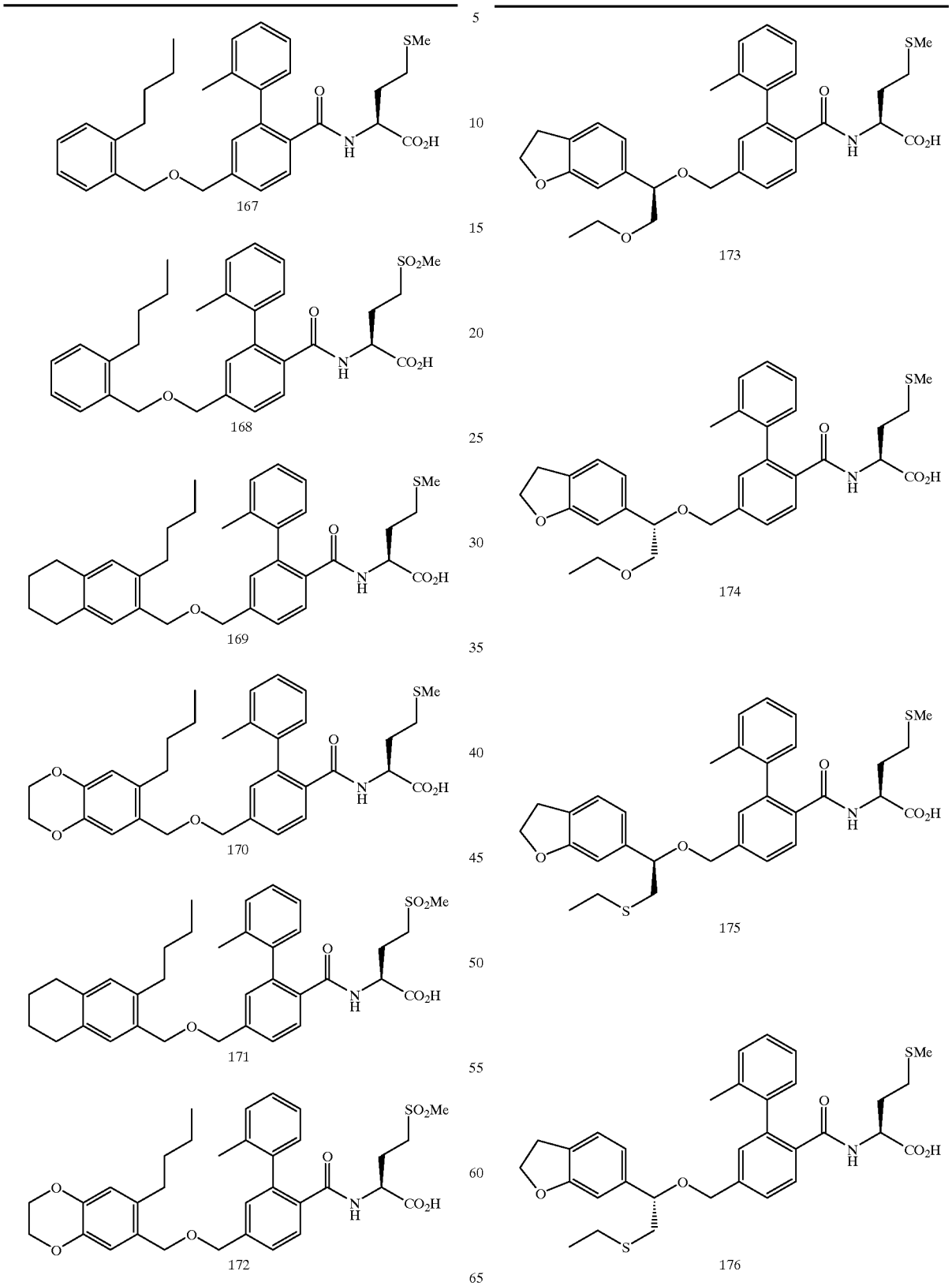

TABLE 7-continued
Ethers of the Type A-OL₁
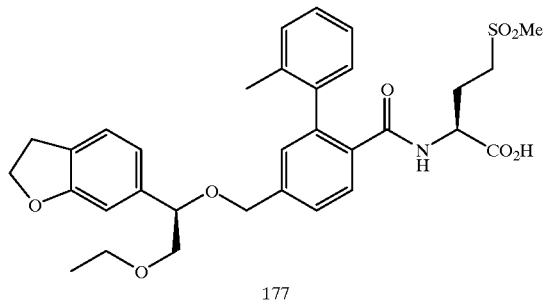
177
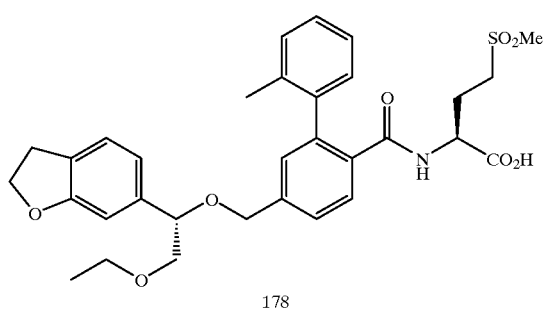
178
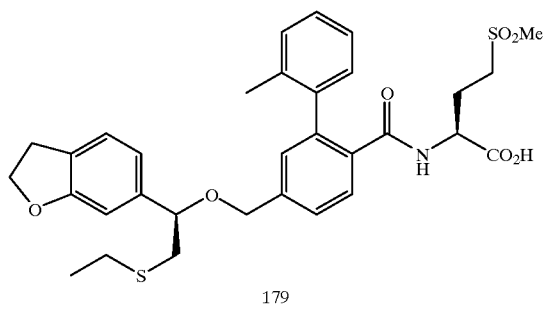
179
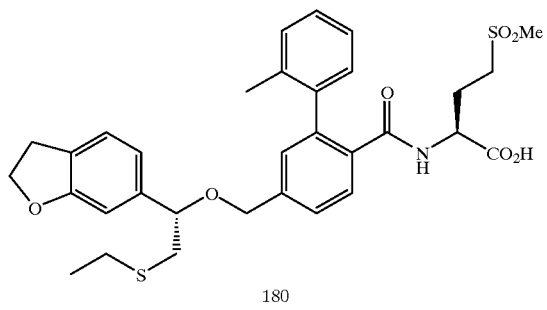
180
TABLE 7-continued
Ethers of the Type A-OL₁
181
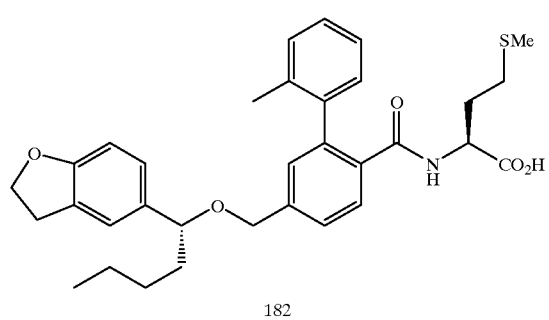
182
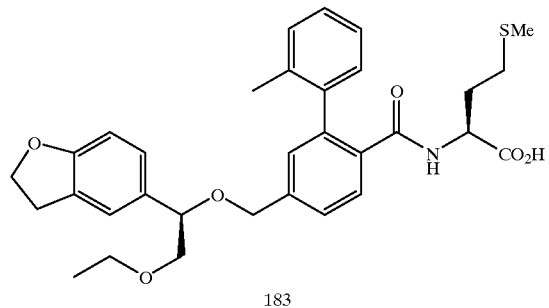
183
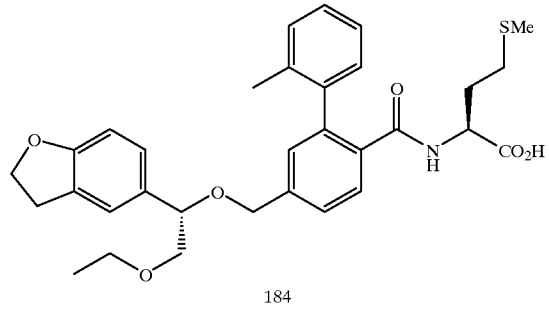
184

TABLE 7-continued
Ethers of the Type A-OL₁
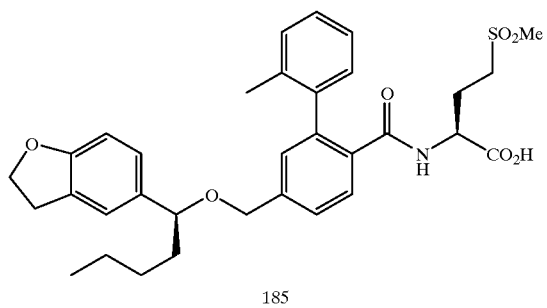
185
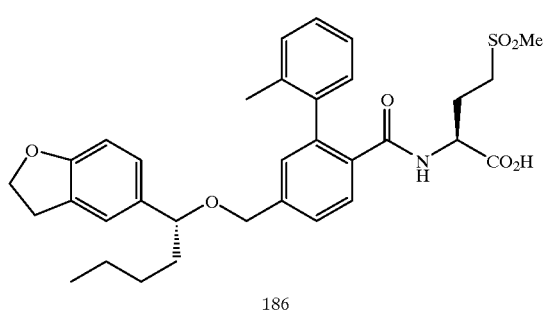
186
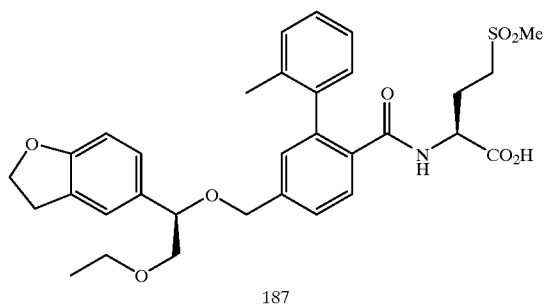
187
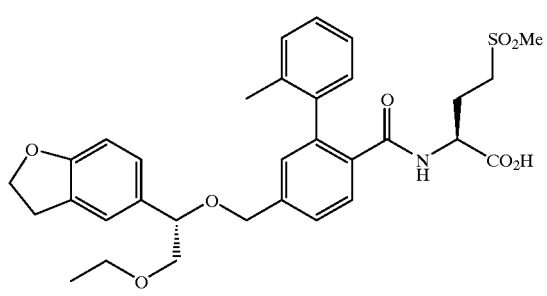
188
TABLE 7-continued
Ethers of the Type A-OL₁
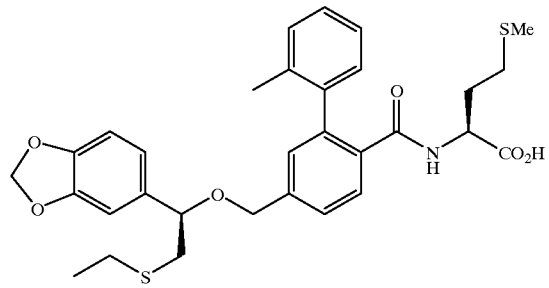
189
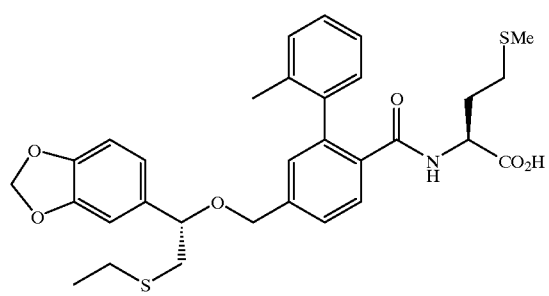
190
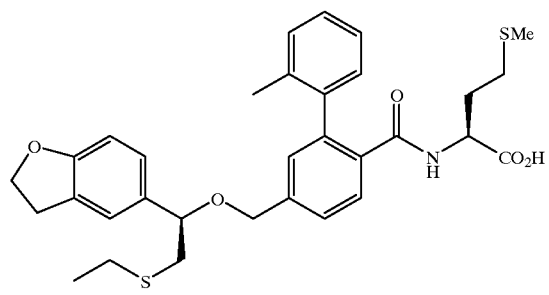
191
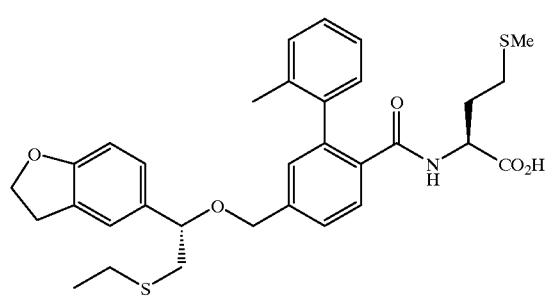
192

TABLE 7-continued
Ethers of the Type A-OL₁
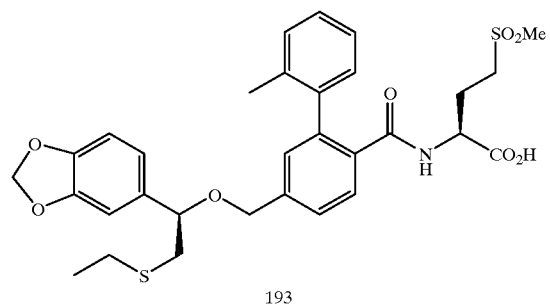
193
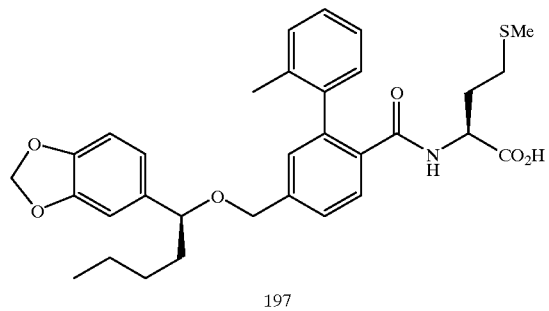
197
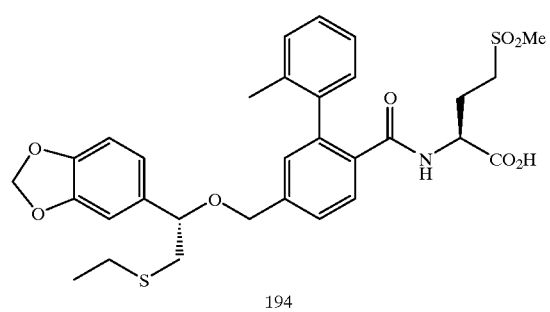
194
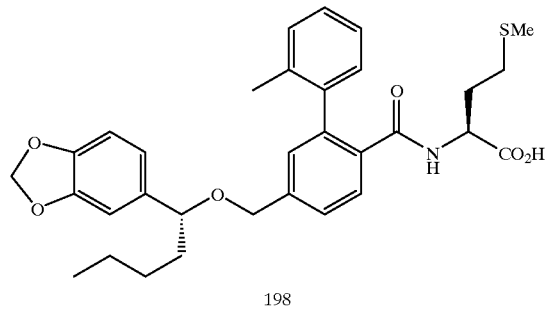
198
195
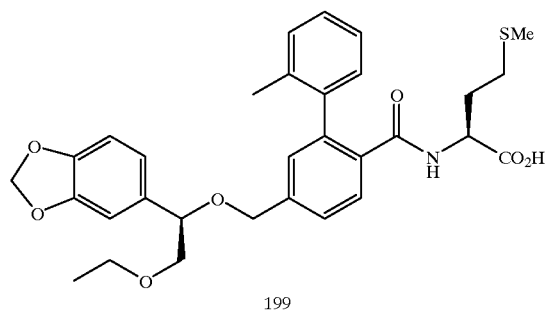
199
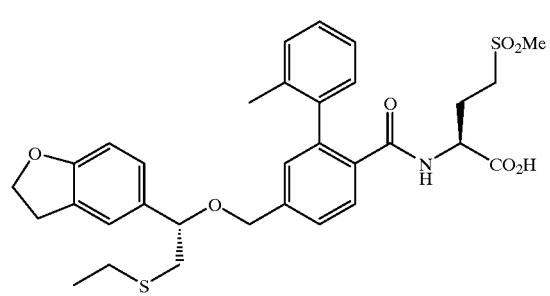
196
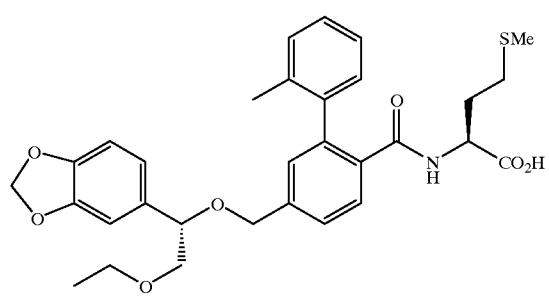
200

TABLE 7-continued
Ethers of the Type A-OL₁
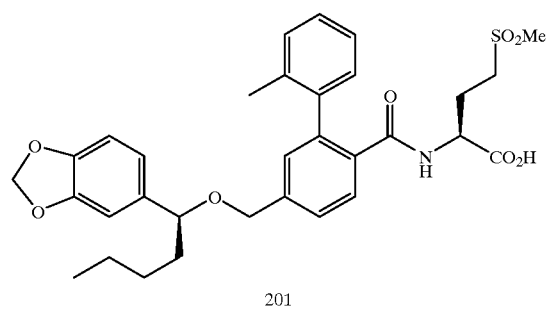
201
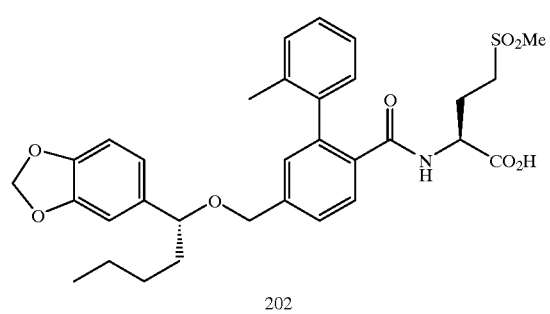
202
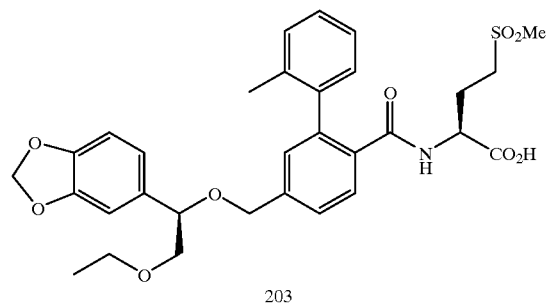
203
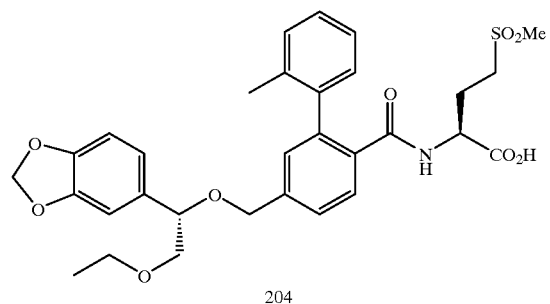
204
TABLE 7-continued
Ethers of the Type A-OL₁
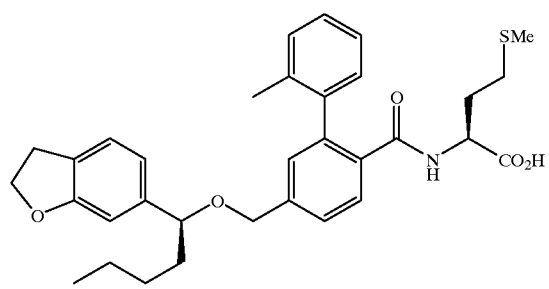
205
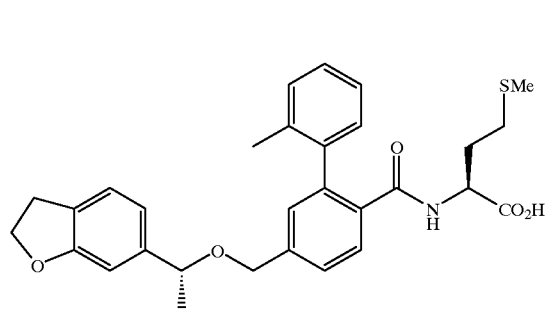
206
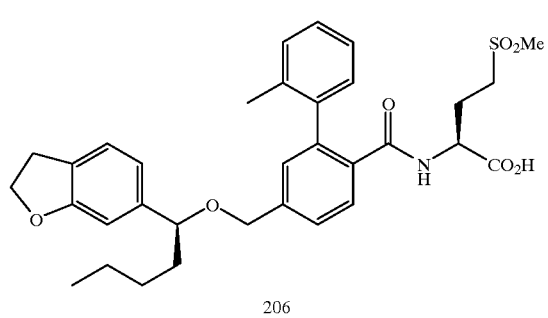
206
208

TABLE 7-continued
Ethers of the Type A-OL₁
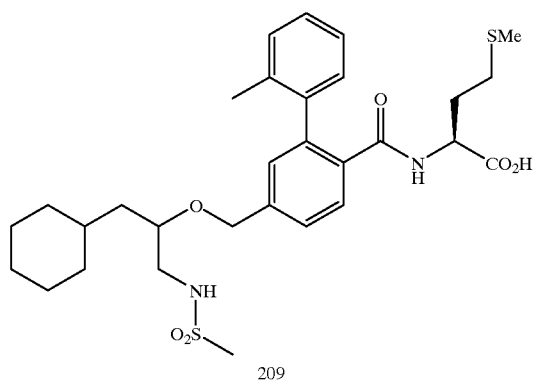
209
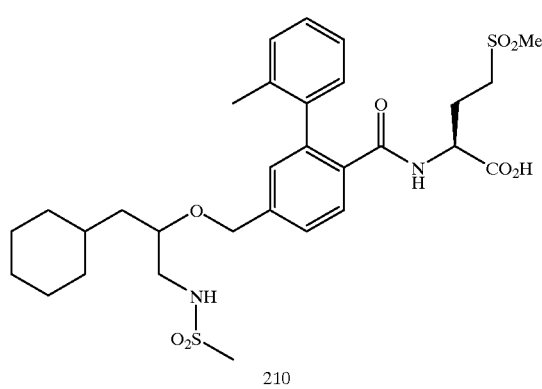
210
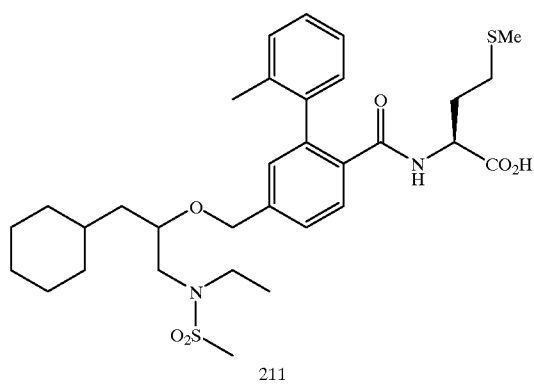
211
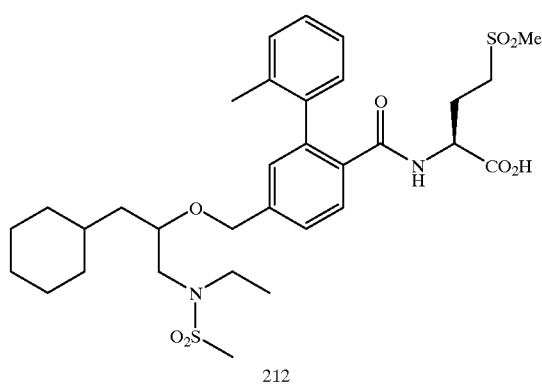
212
TABLE 7-continued
Ethers of the Type A-OL₁
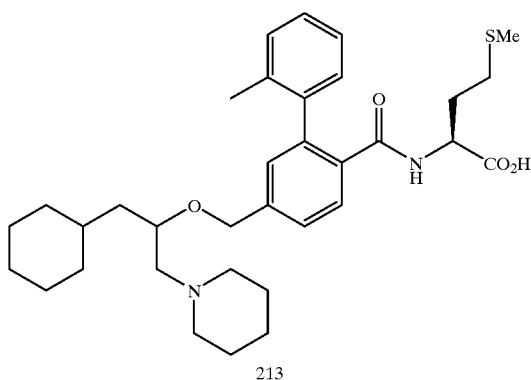
213
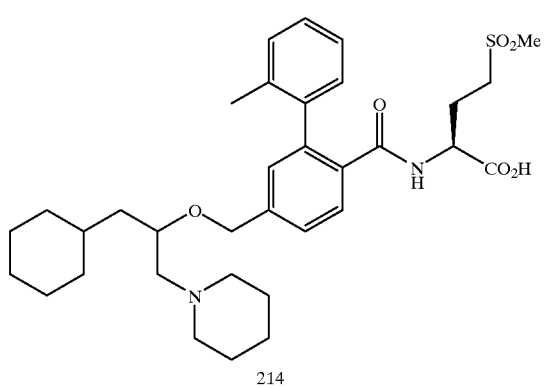
214
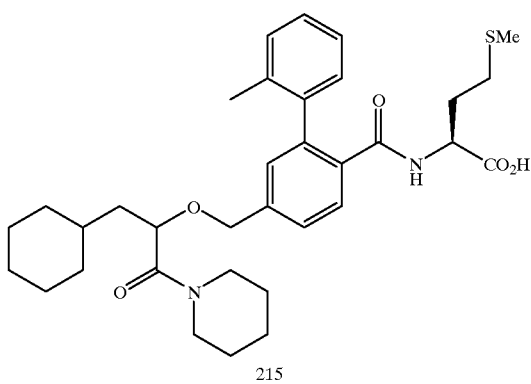
215
216

TABLE 7-continued
Ethers of the Type A-OL₁
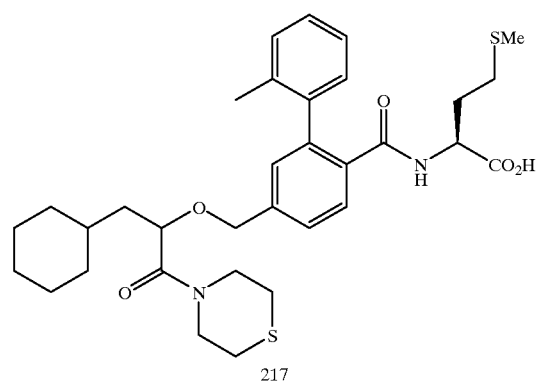
217
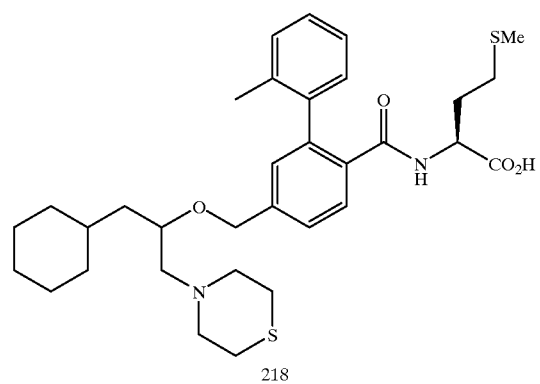
218
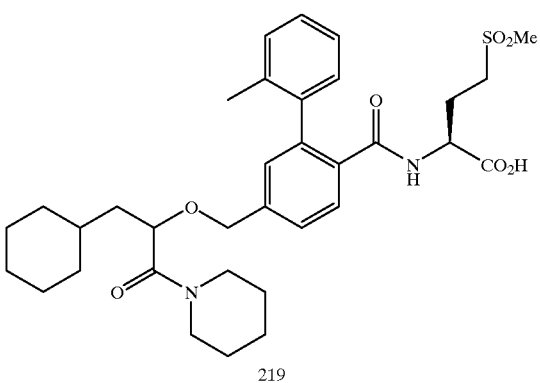
219
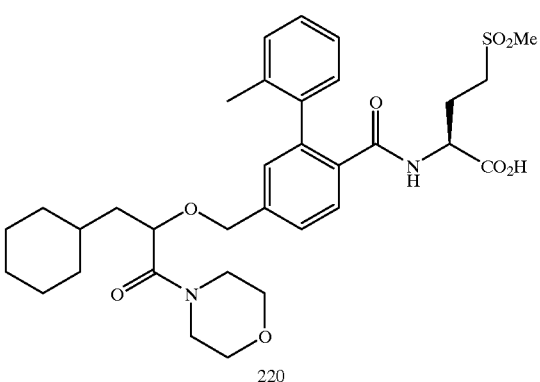
220
TABLE 7-continued
Ethers of the Type A-OL₁
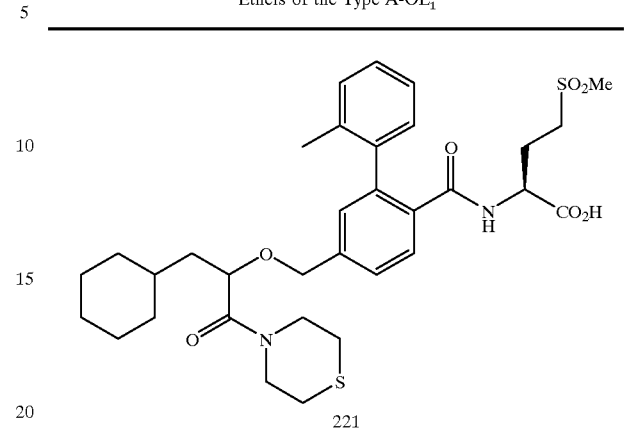
221
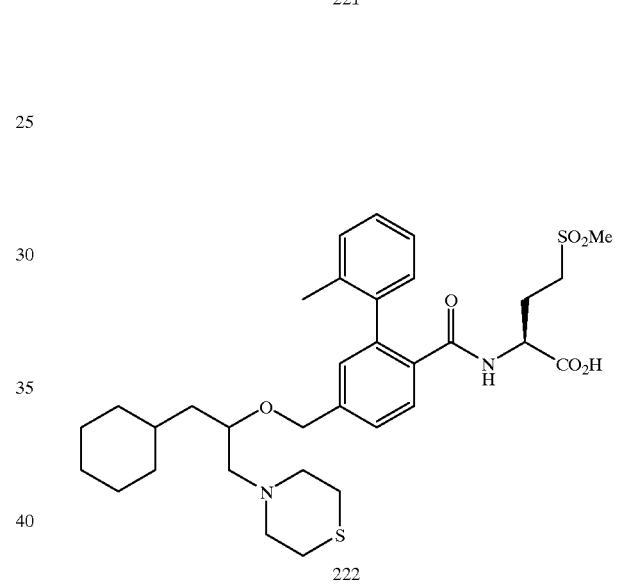
222
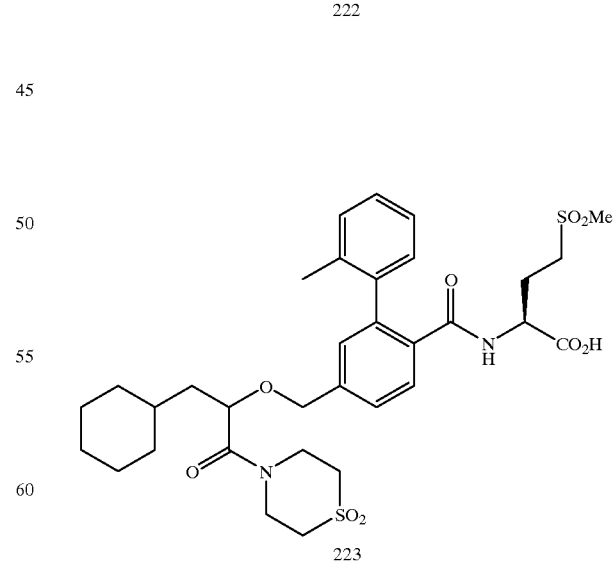
223

TABLE 7-continued
Ethers of the Type A-OL₁
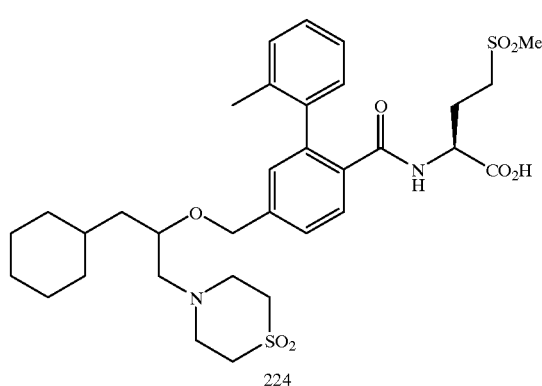
224
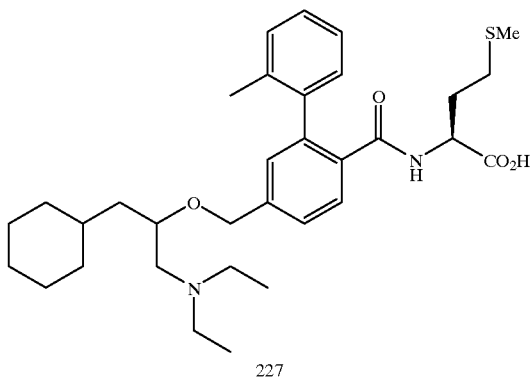
227
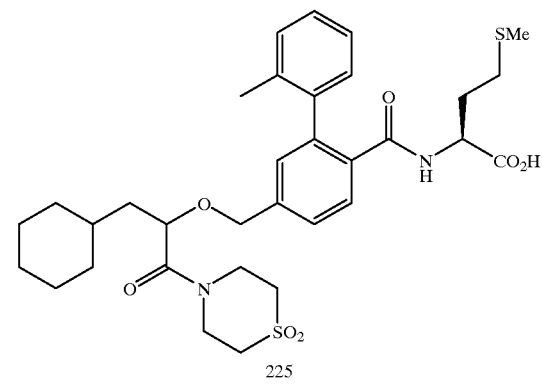
225
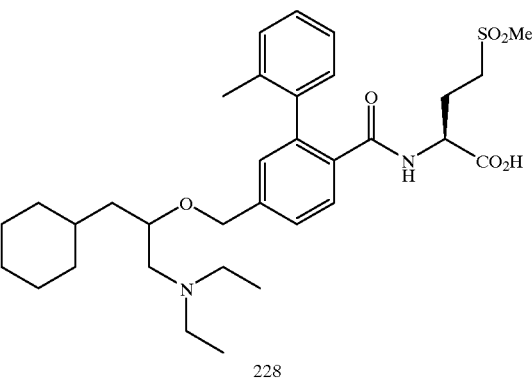
228
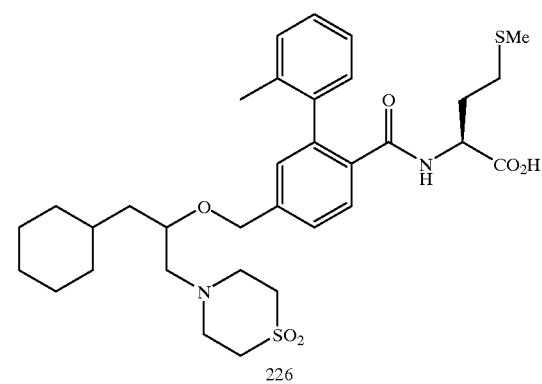
226

TABLE 8
Sulfonamides of the Type ASO₂(B)N-L₁
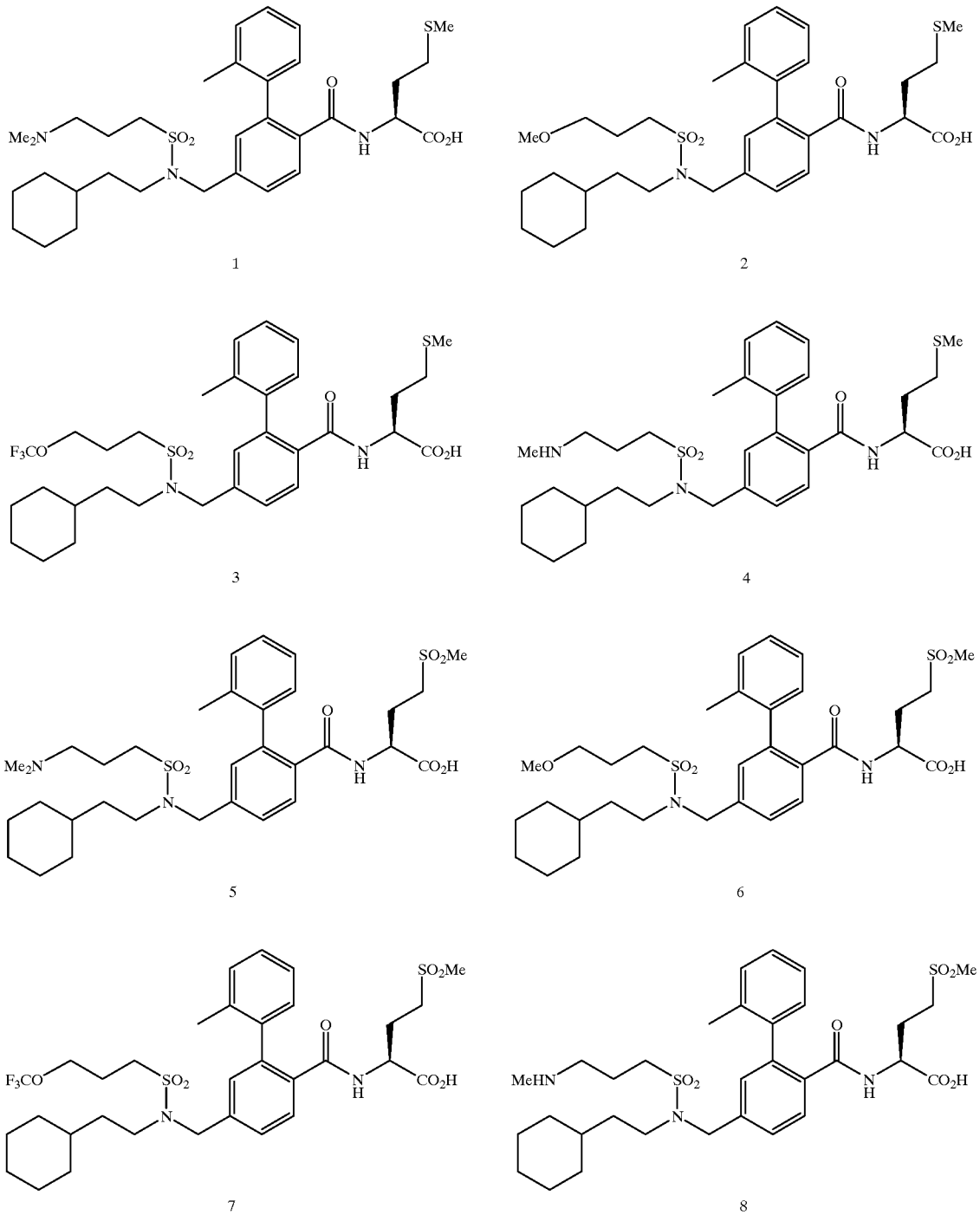

TABLE 8-continued
Sulfonamides of the Type $ASO_2(B)N-L_1$
9
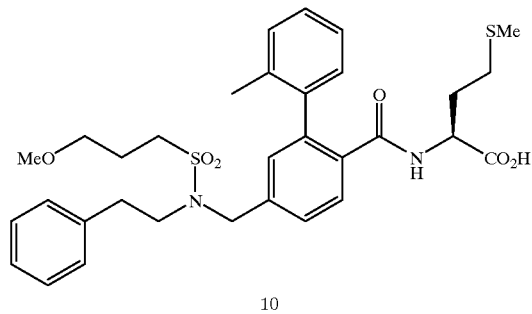
10
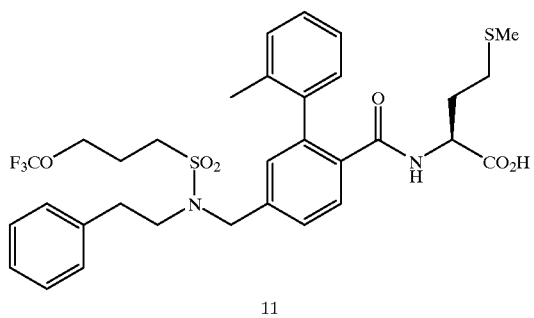
11
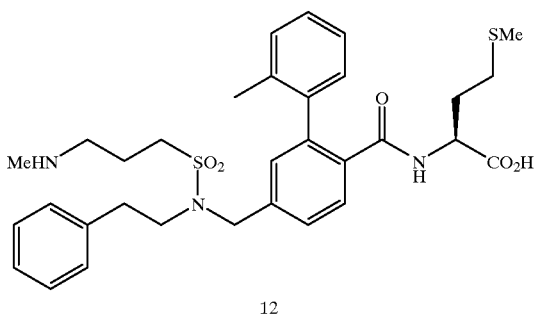
12
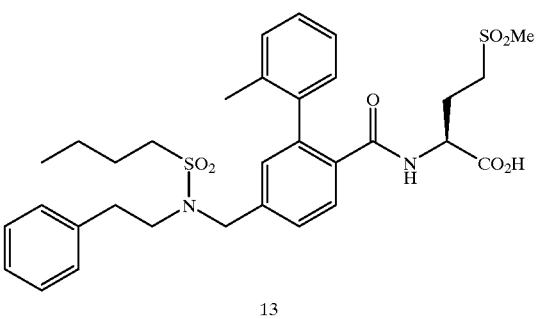
13
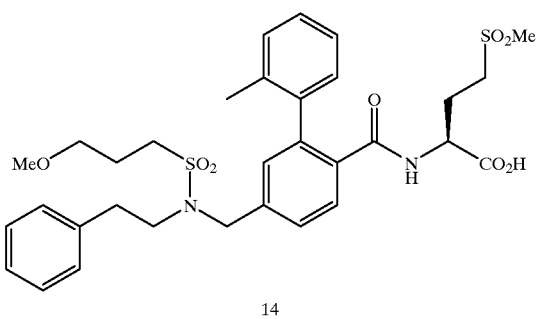
14
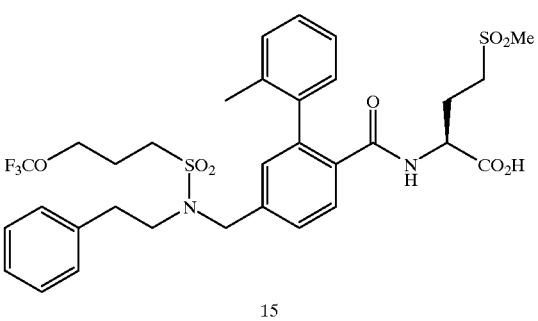
15
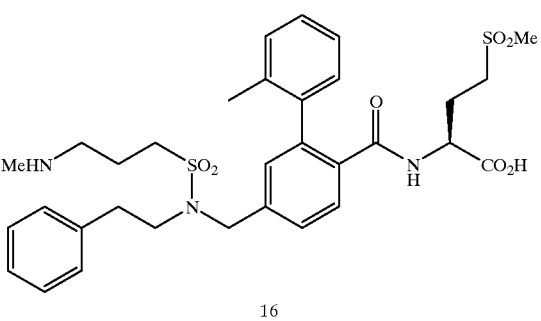
16

TABLE 8-continued
Sulfonamides of the Type $ASO_2(B)N-L_1$
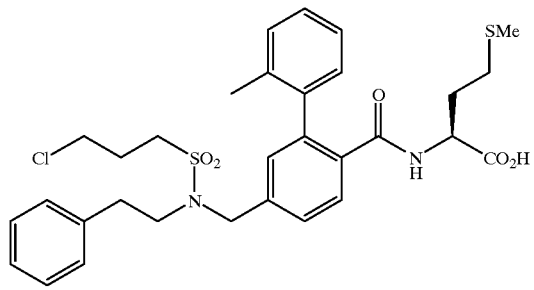
17
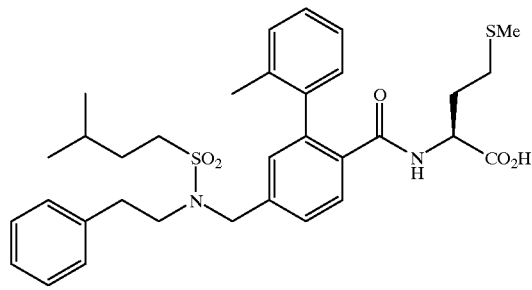
18
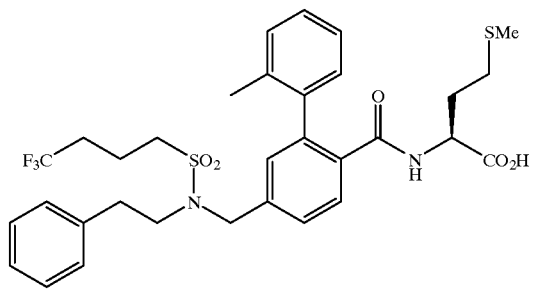
19
20
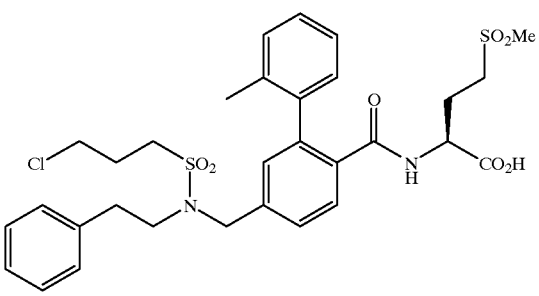
21
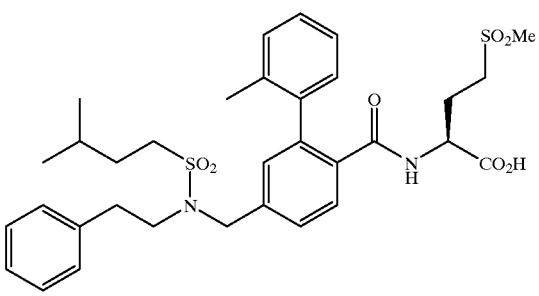
22
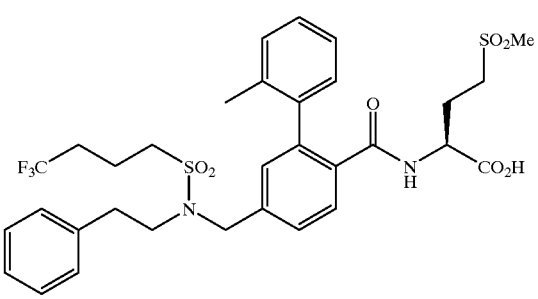
23
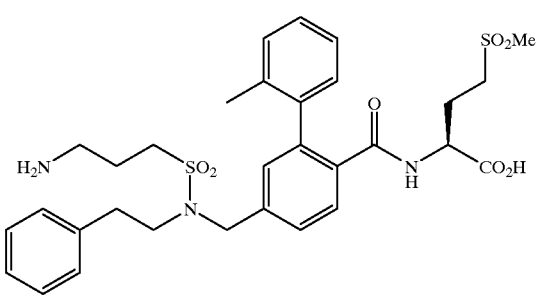
24

TABLE 8-continued
Sulfonamides of the Type ASO$_2$(B)N-L$_1$
25
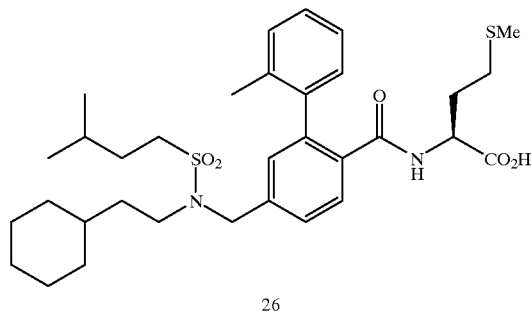
26
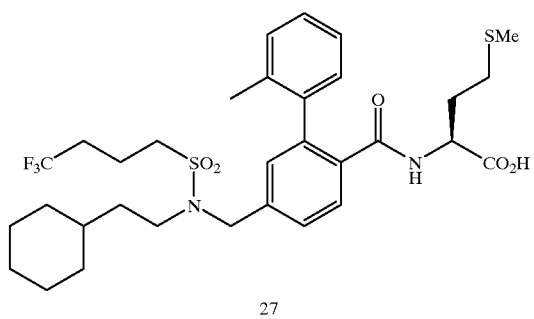
27
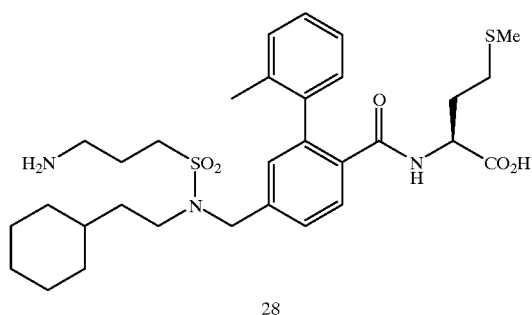
28
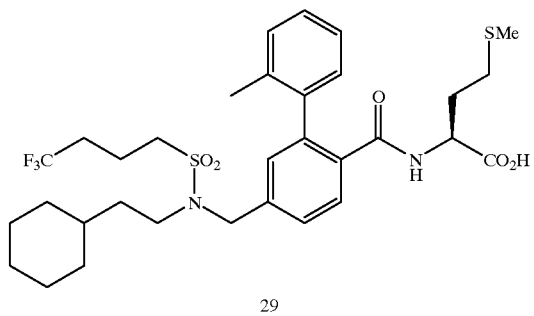
29
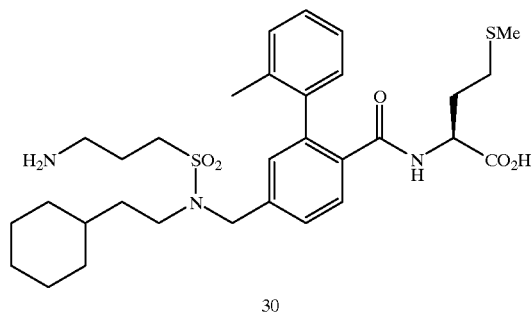
30
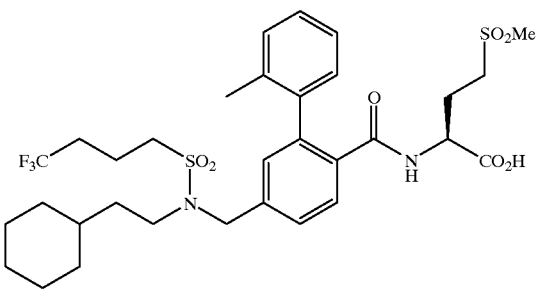
31
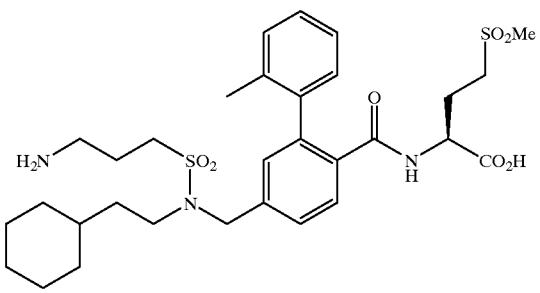
32

TABLE 9
Hydrocarbons of the Type $A(B)CH_2-L_1$
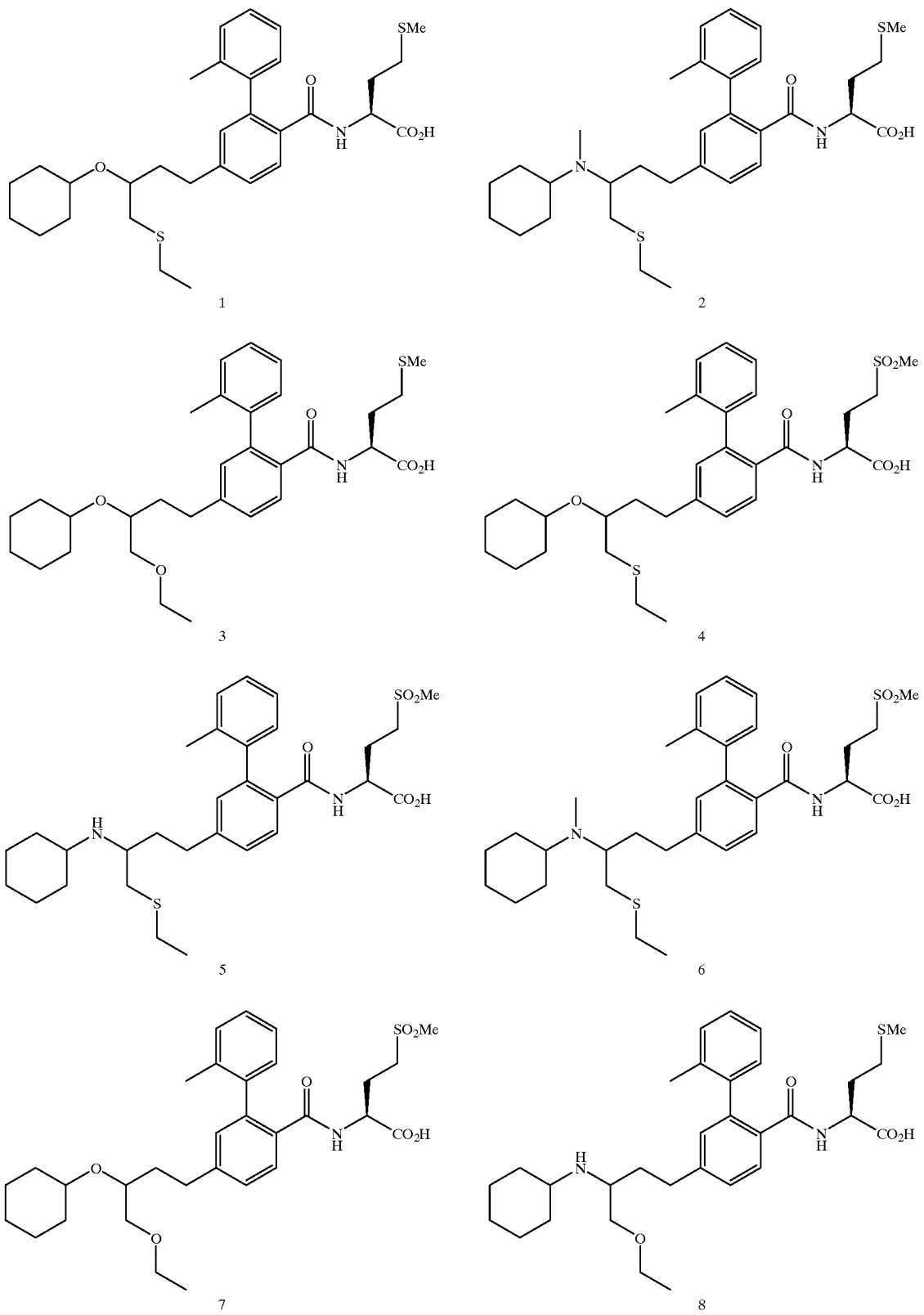

TABLE 9-continued
Hydrocarbons of the Type A(B)CH$_2$-L$_1$
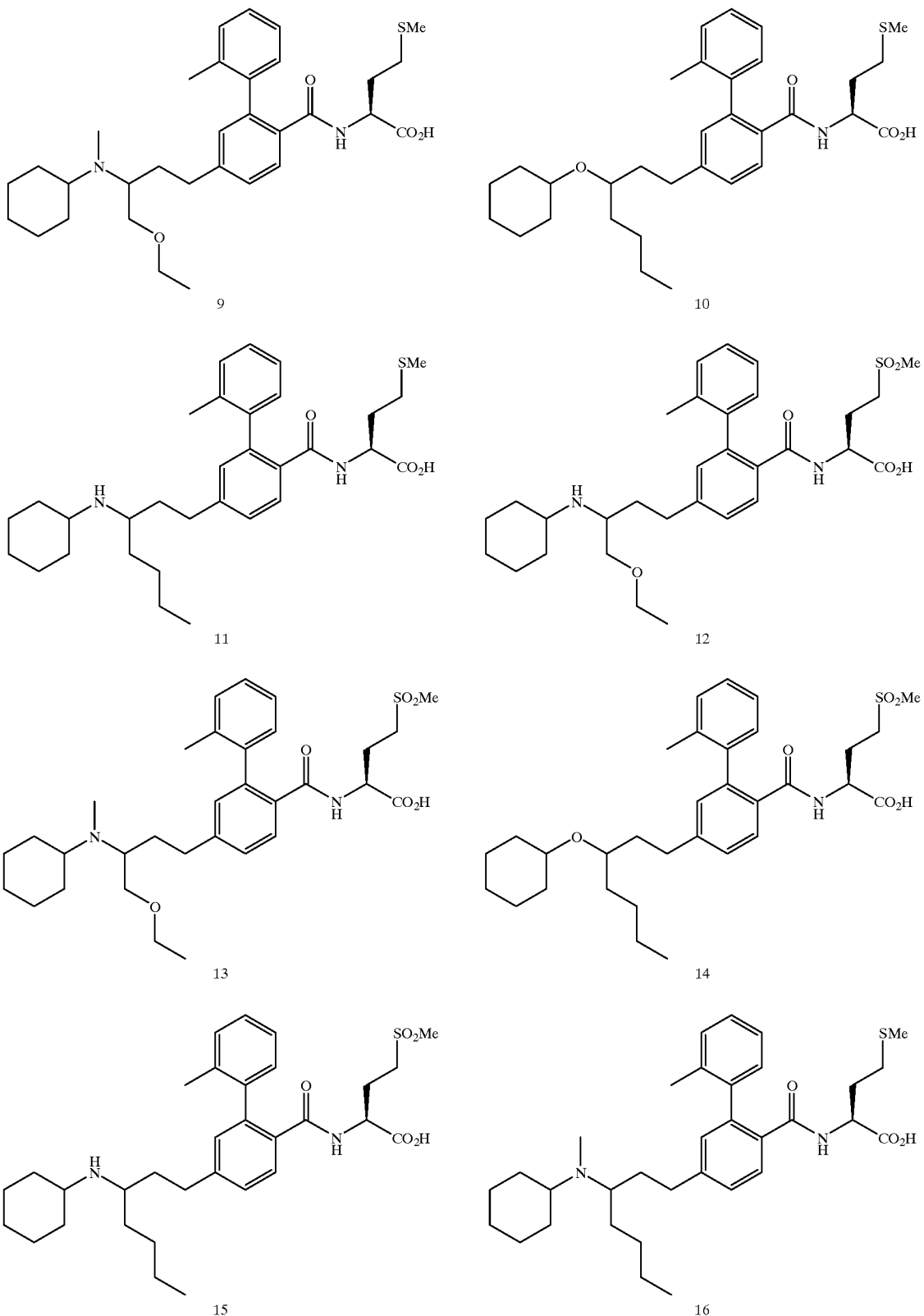

TABLE 9-continued
Hydrocarbons of the Type A(B)CH$_2$-L$_1$
17
TABLE 10
Amines of the type B—NH$_2$
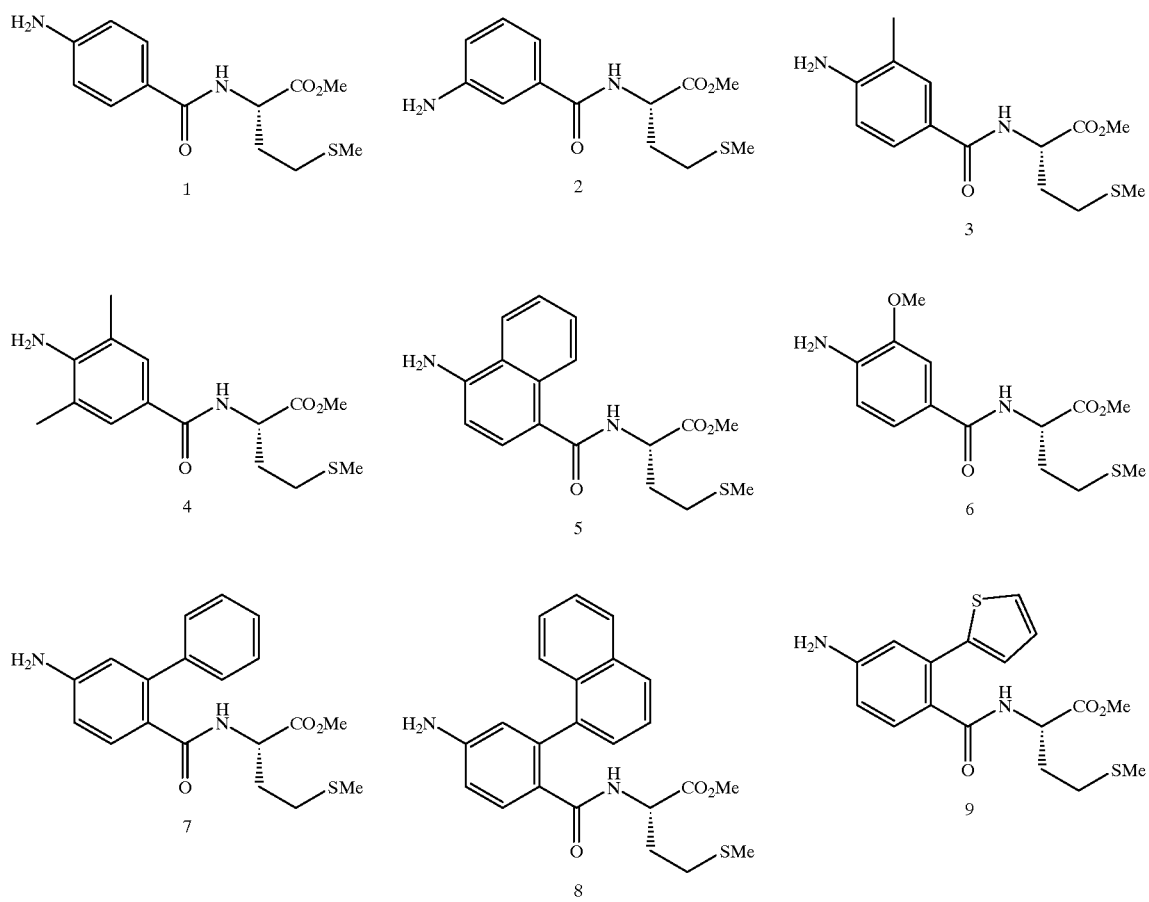

TABLE 10-continued
Amines of the type B—NH$_2$
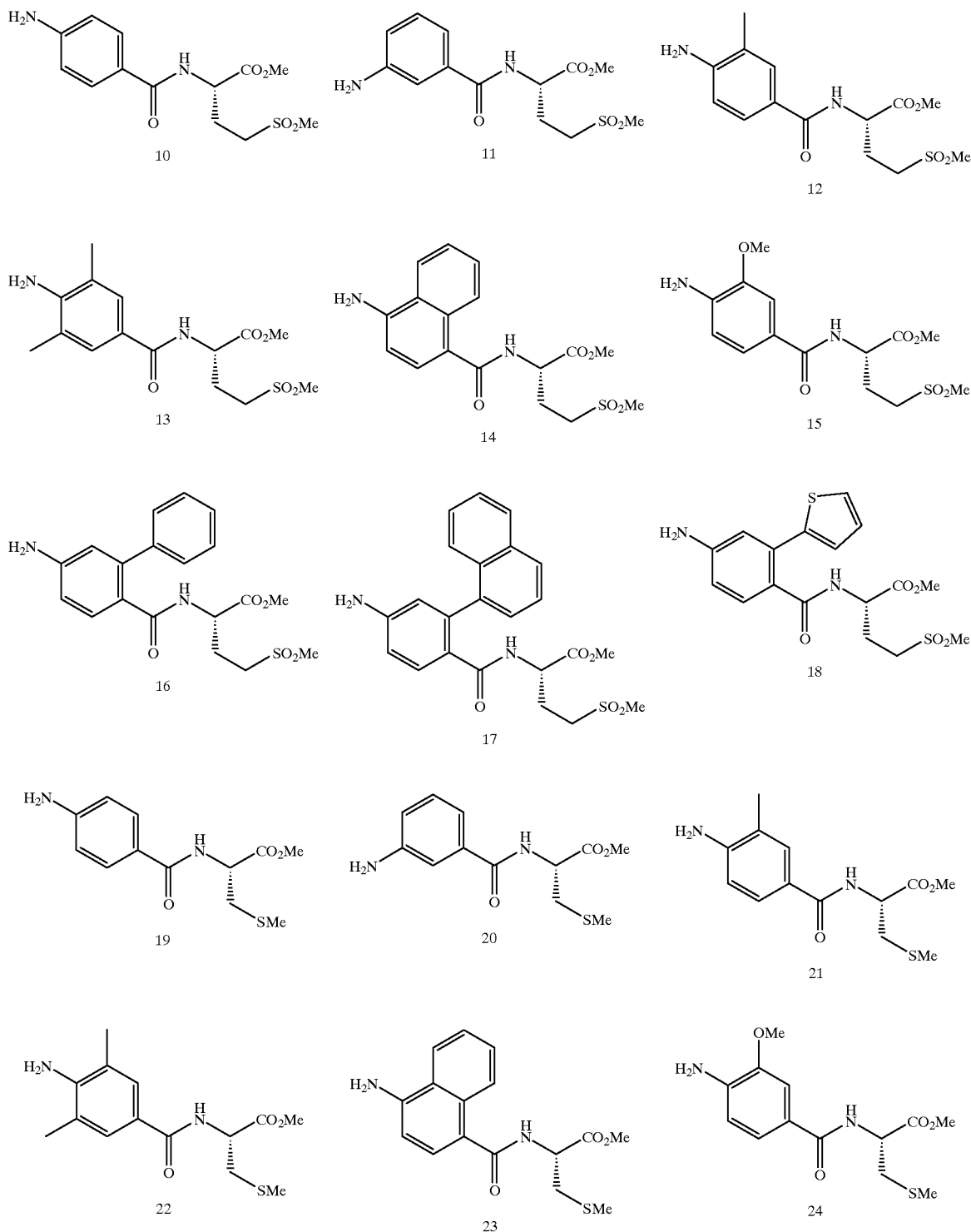

TABLE 10-continued
Amines of the type B—NH₂
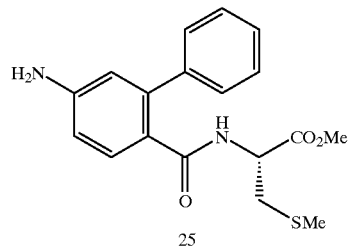
25
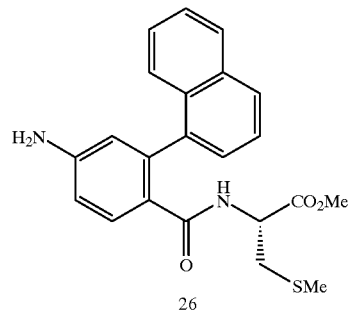
26
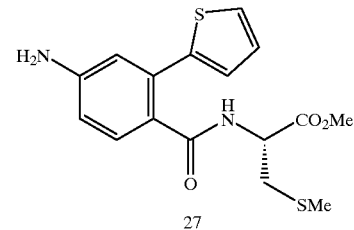
27
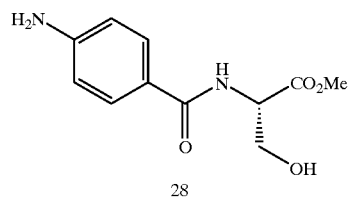
28
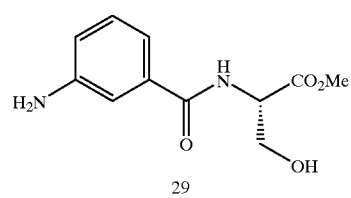
29
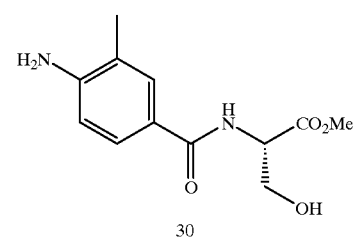
30
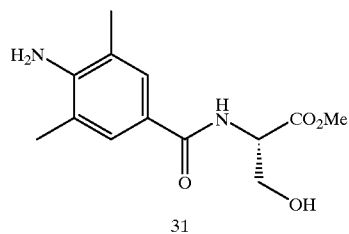
31
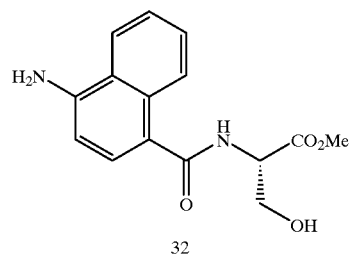
32
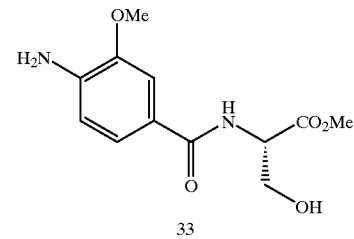
33
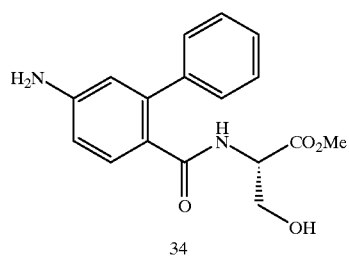
34
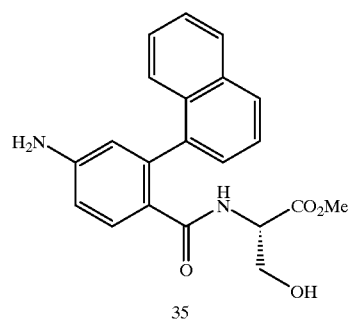
35
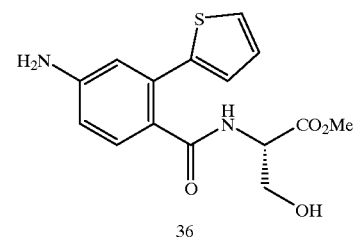
36
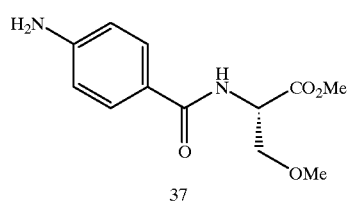
37
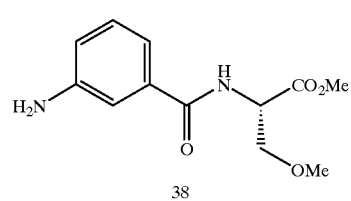
38
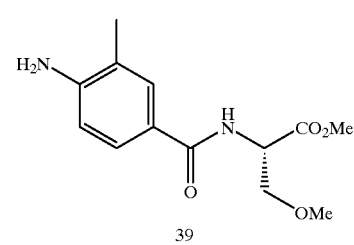
39

TABLE 10-continued
Amines of the type B—NH$_2$
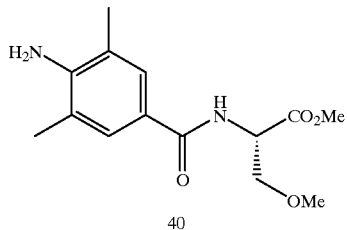
40
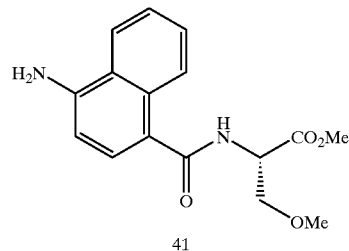
41
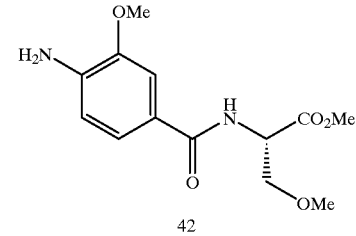
42
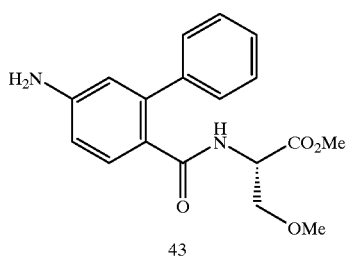
43
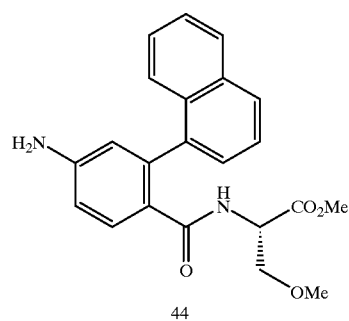
44
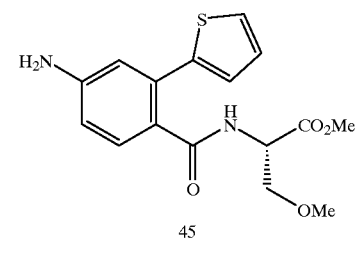
45
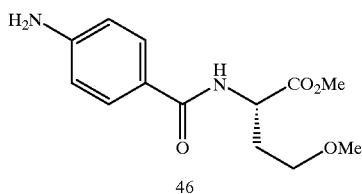
46
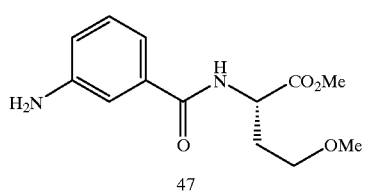
47
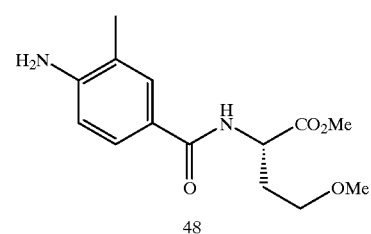
48
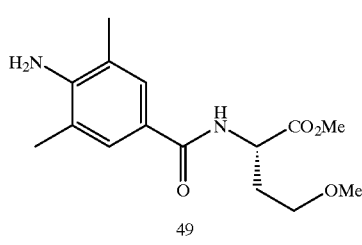
49
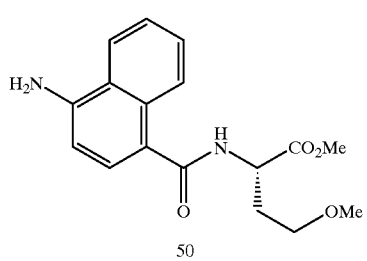
50
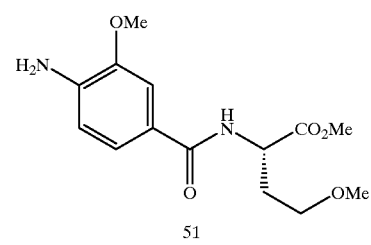
51
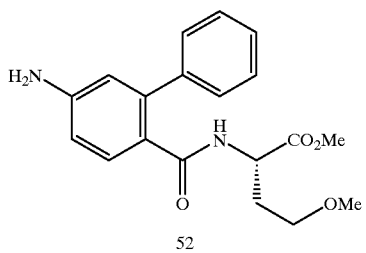
52
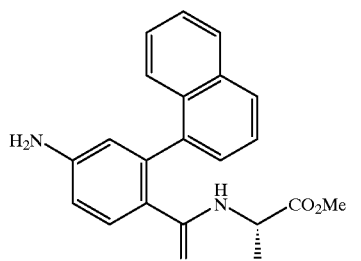
53
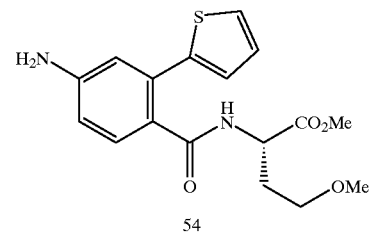
54

TABLE 10-continued
Amines of the type B—NH$_2$
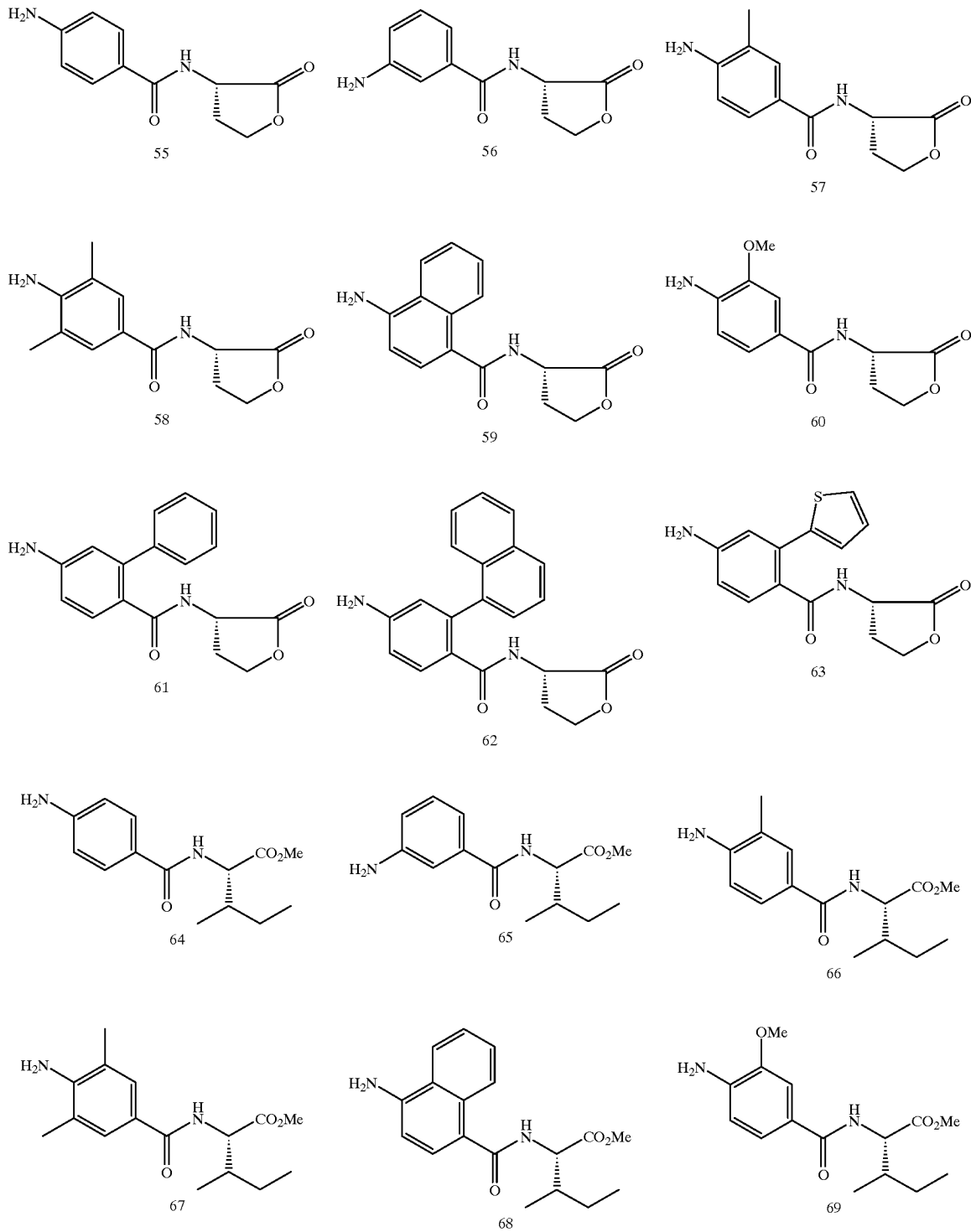

TABLE 10-continued
Amines of the type B—NH₂
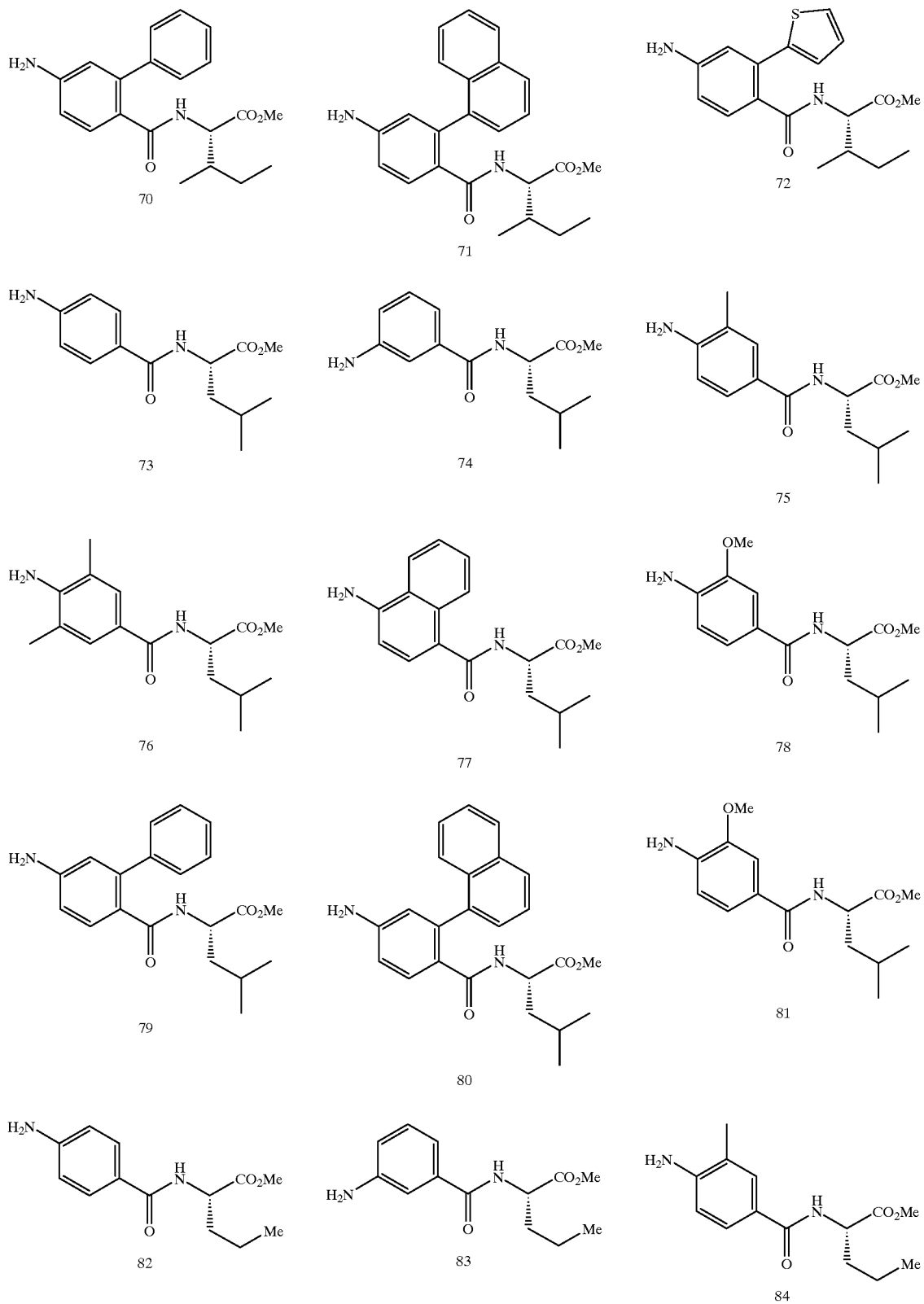

TABLE 10-continued
Amines of the type B—NH$_2$
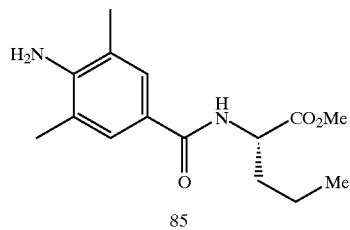
85
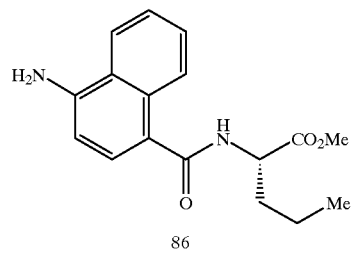
86
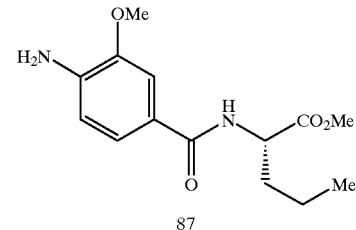
87
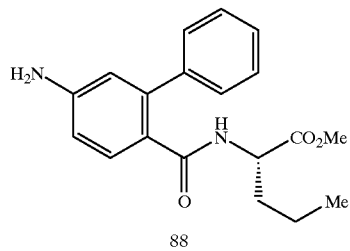
88
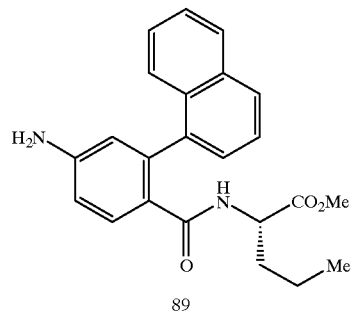
89
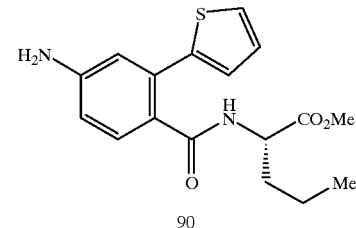
90
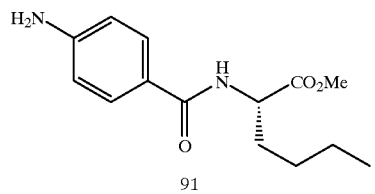
91
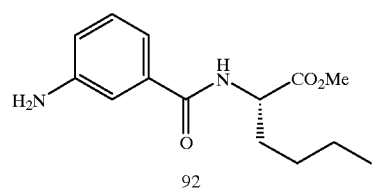
92
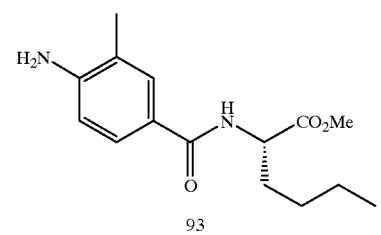
93
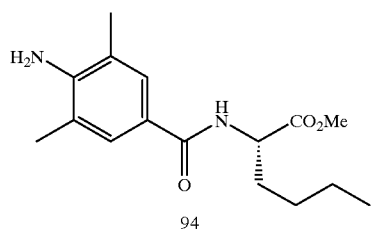
94
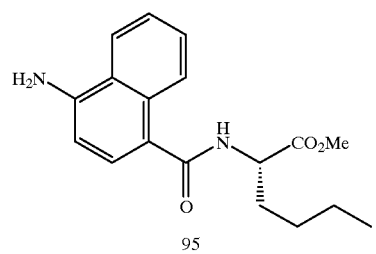
95
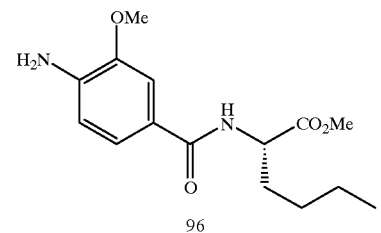
96
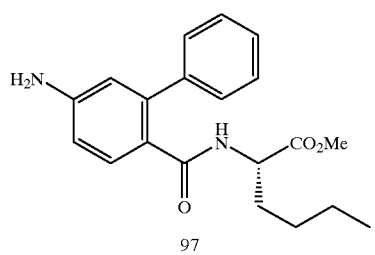
97
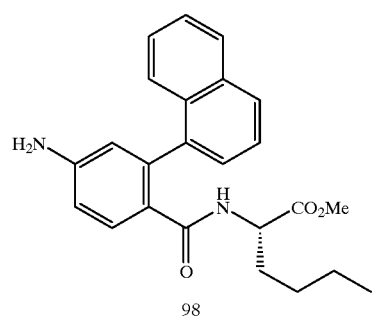
98
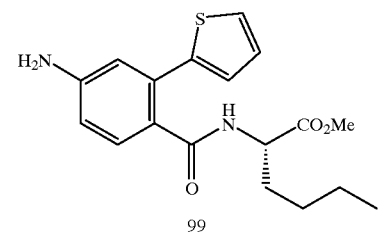
99

TABLE 10-continued
Amines of the type B—NH₂
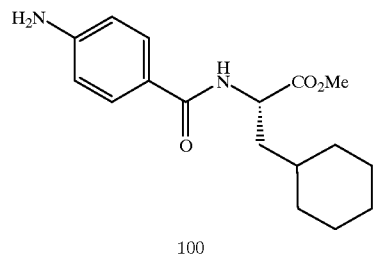
100
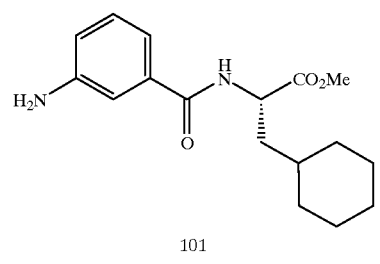
101
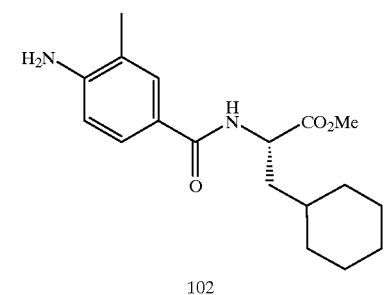
102
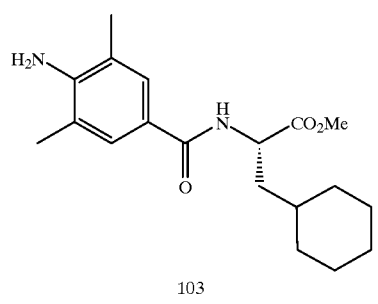
103
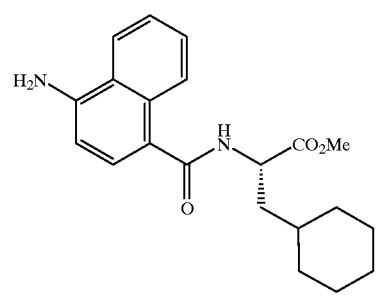
104
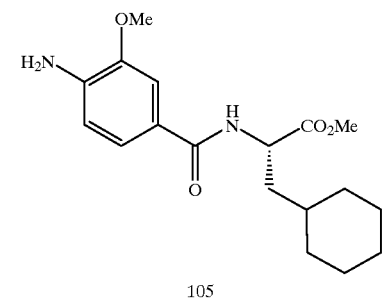
105
106
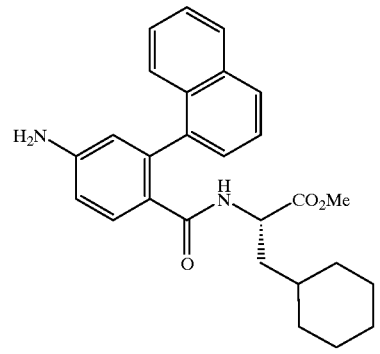
107
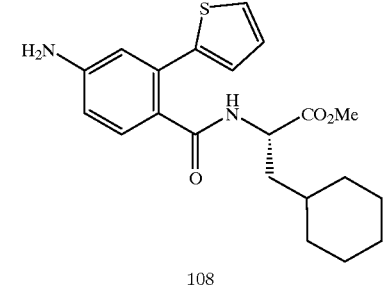
108
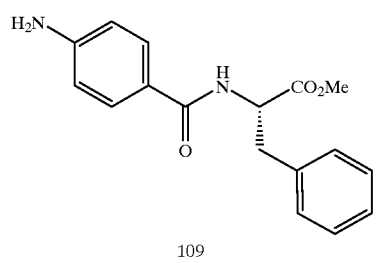
109
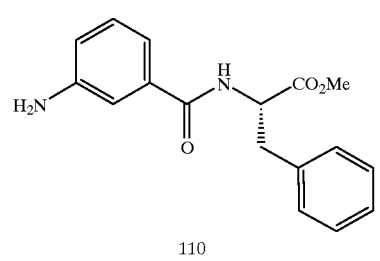
110
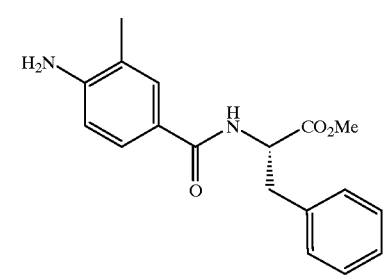
111

TABLE 10-continued
Amines of the type B—NH$_2$
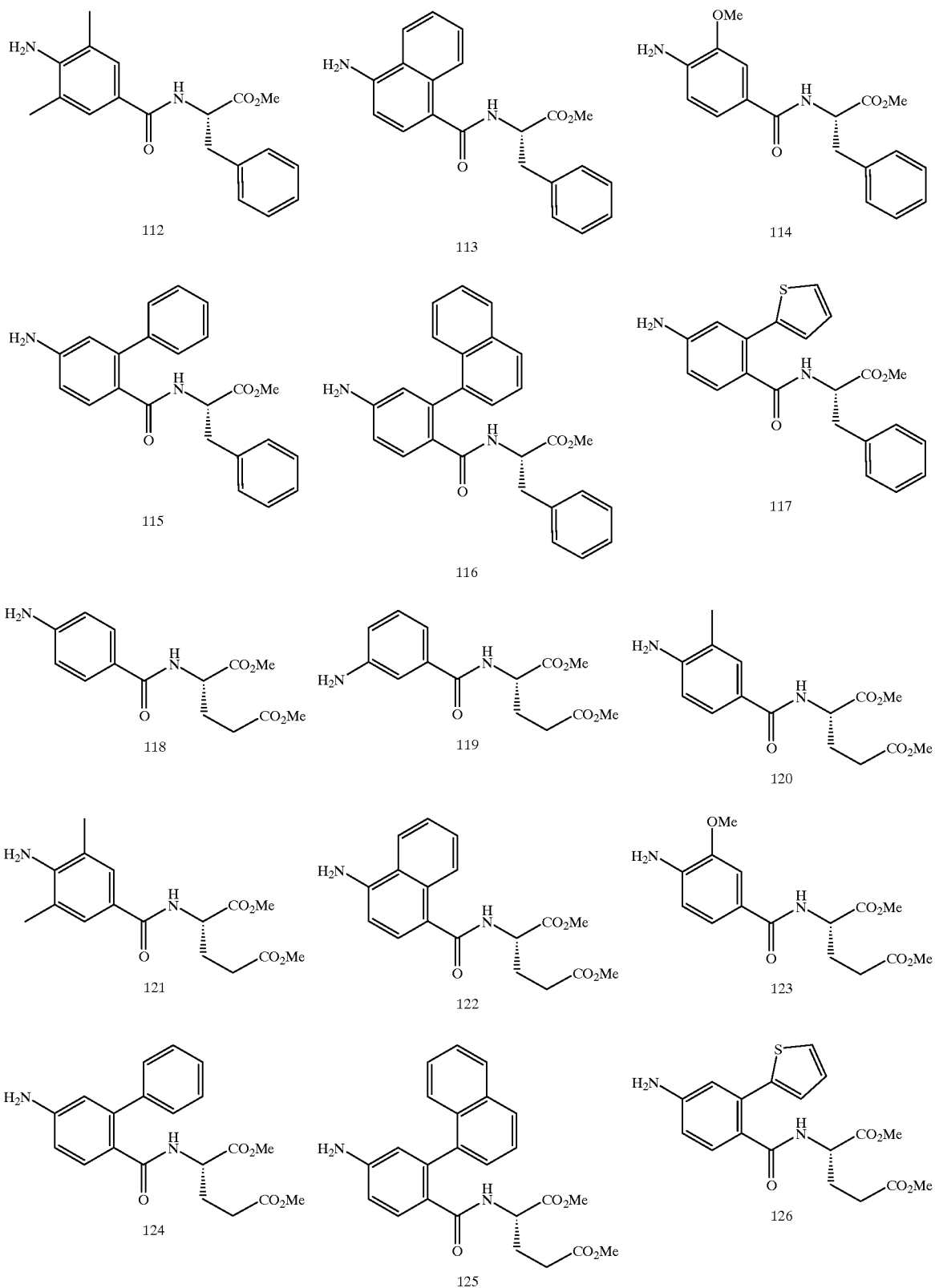

TABLE 10-continued
Amines of the type B—NH$_2$
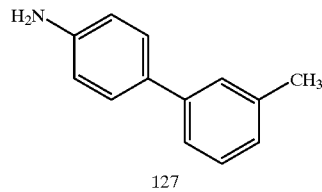
127
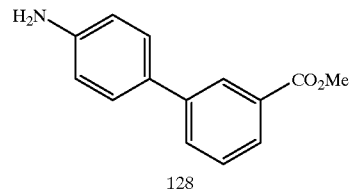
128
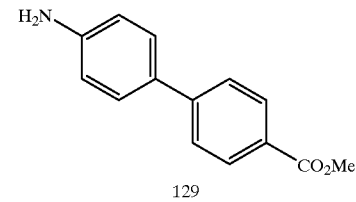
129
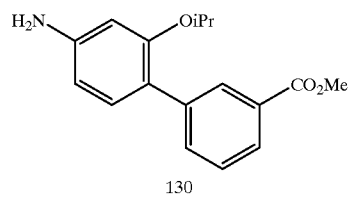
130
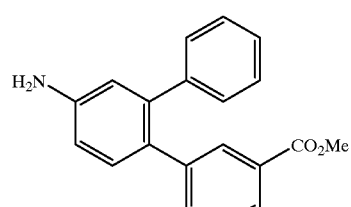
131
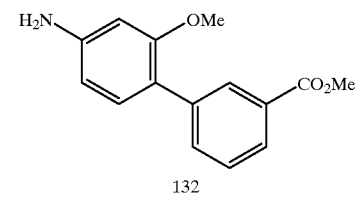
132
TABLE 11
Bromides of the type B—Br
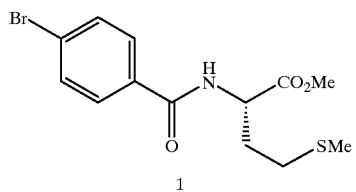
1
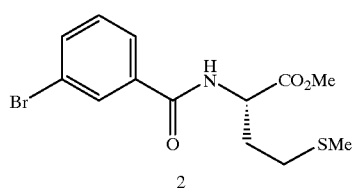
2
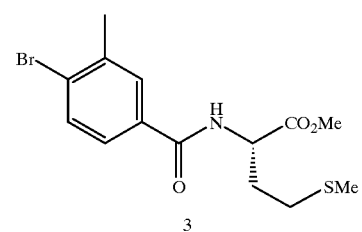
3
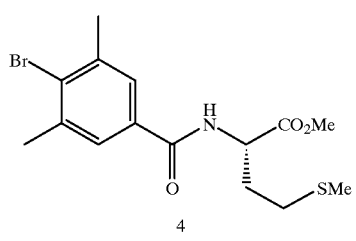
4
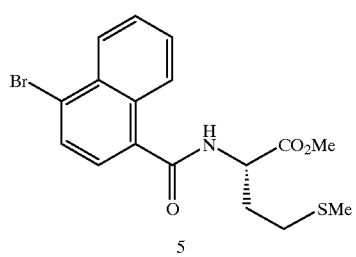
5
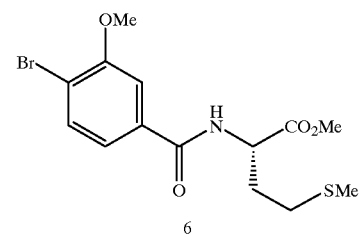
6
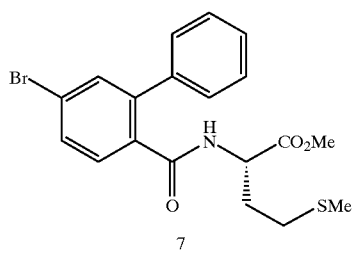
7
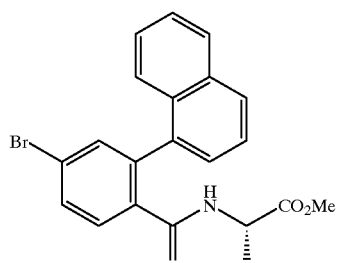
8
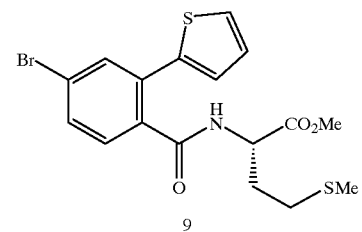
9

TABLE 11-continued
Bromides of the type B—Br
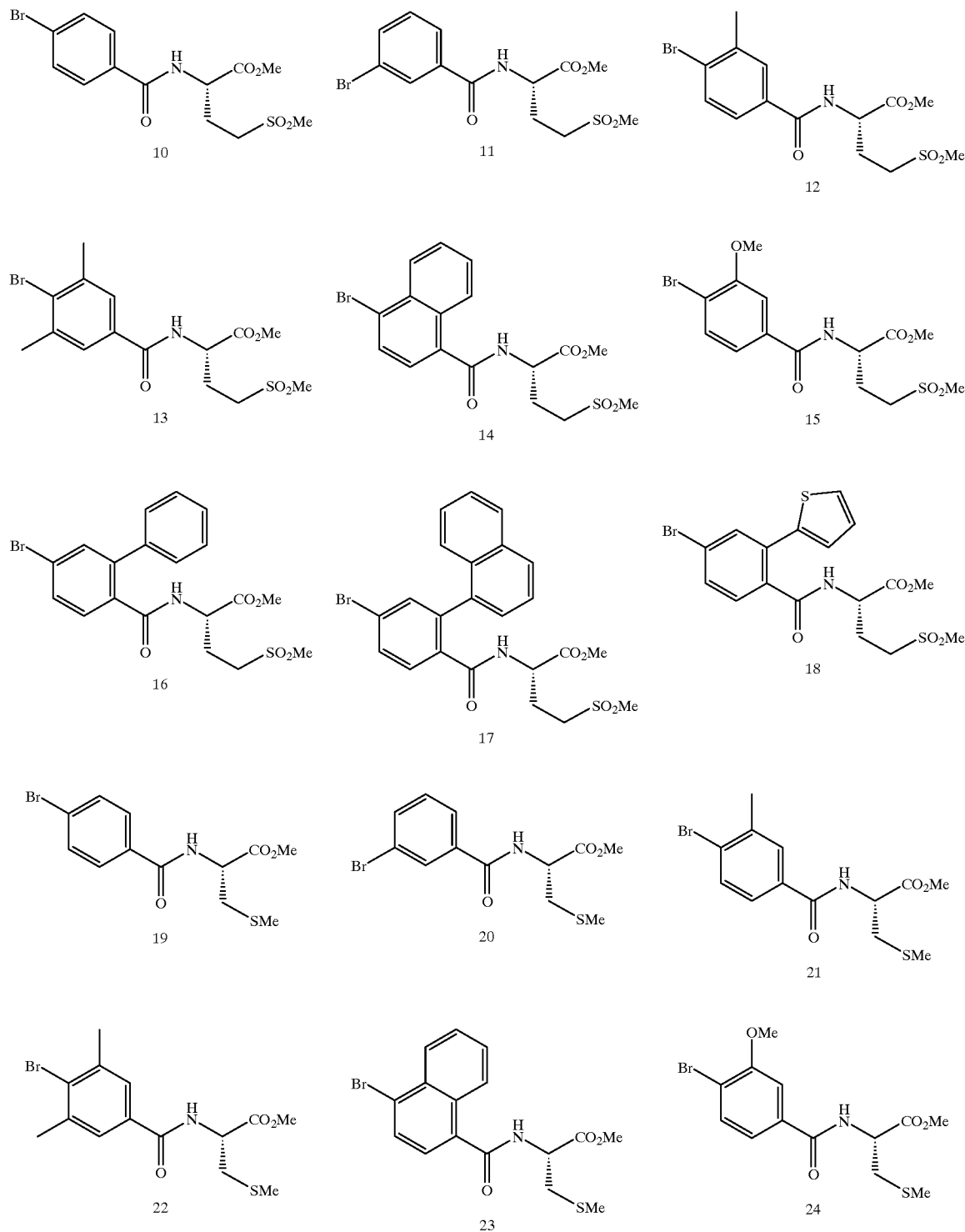

TABLE 11-continued
Bromides of the type B—Br
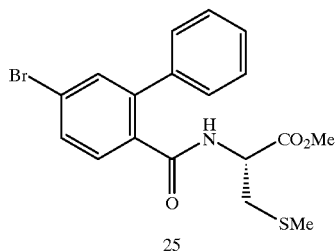
25
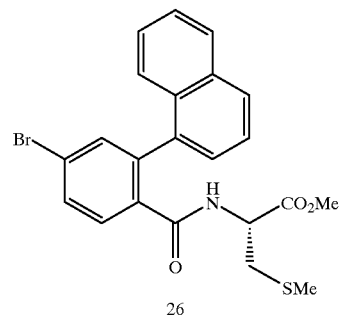
26
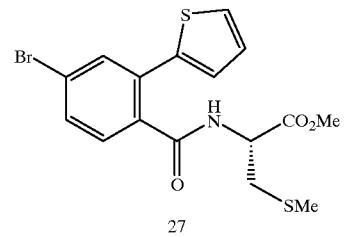
27
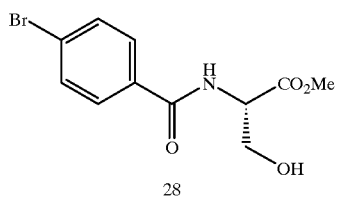
28
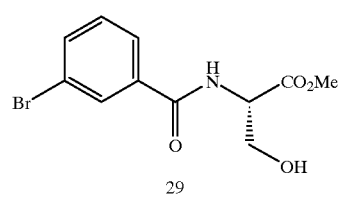
29
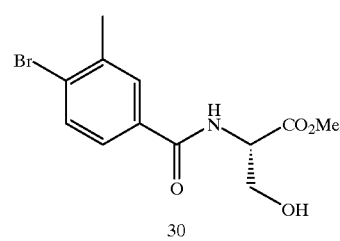
30
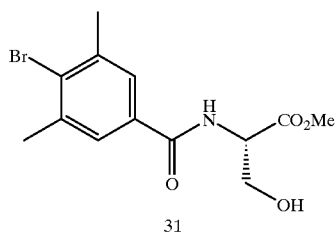
31
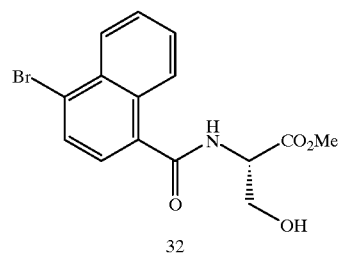
32
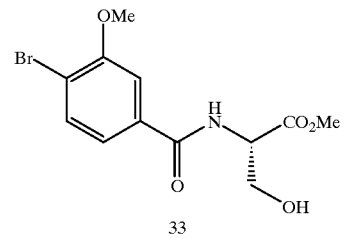
33
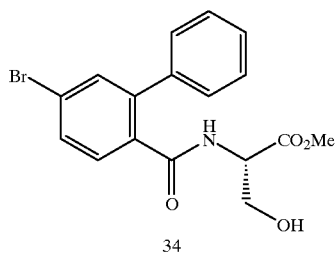
34
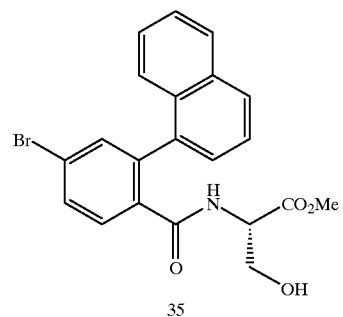
35
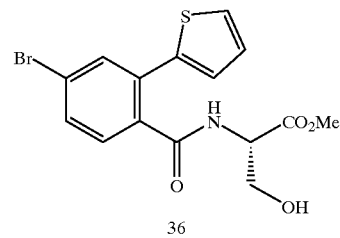
36
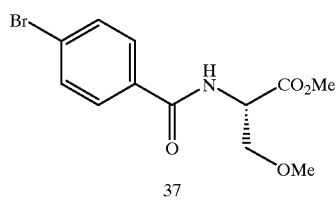
37
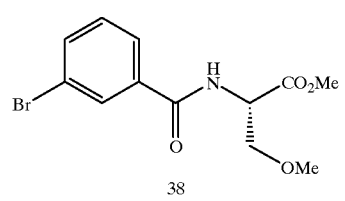
38
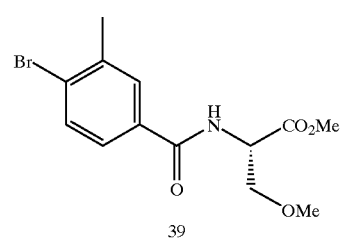
39

TABLE 11-continued
Bromides of the type B—Br
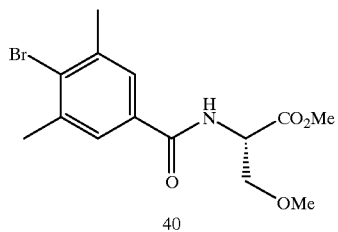
40
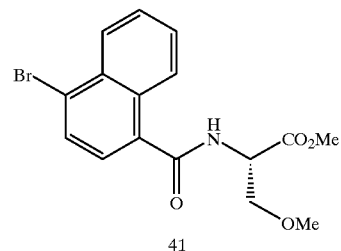
41
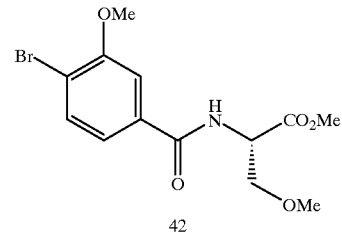
42
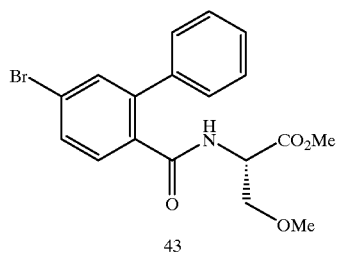
43
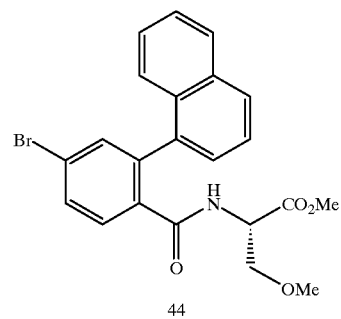
44
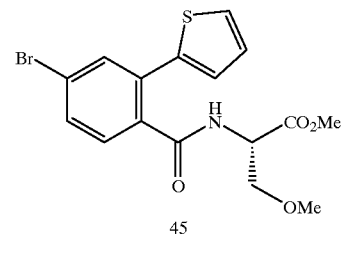
45
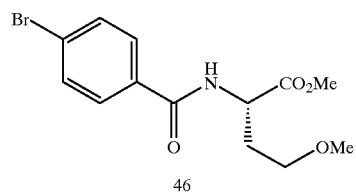
46
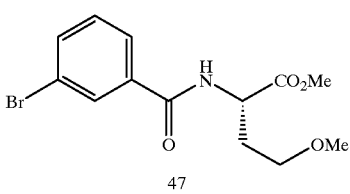
47
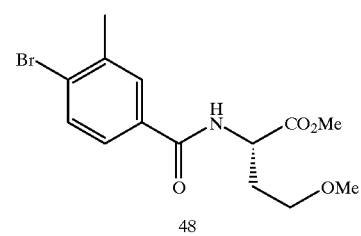
48
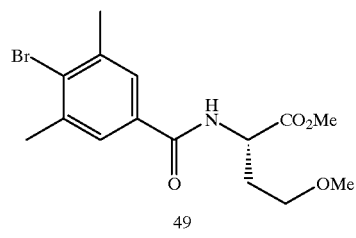
49
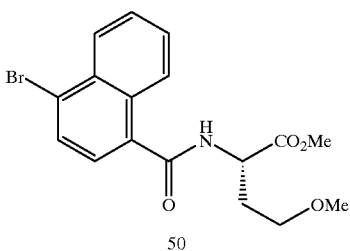
50
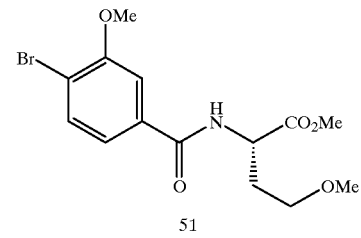
51
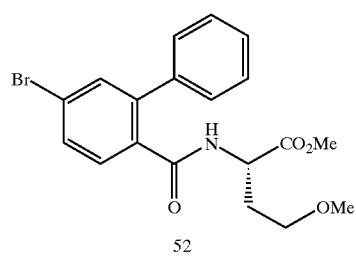
52
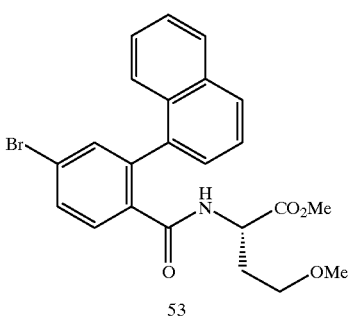
53
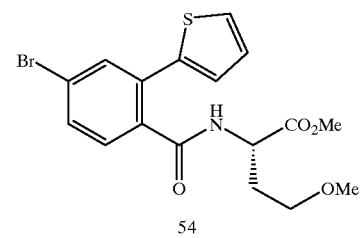
54

TABLE 11-continued
Bromides of the type B—Br
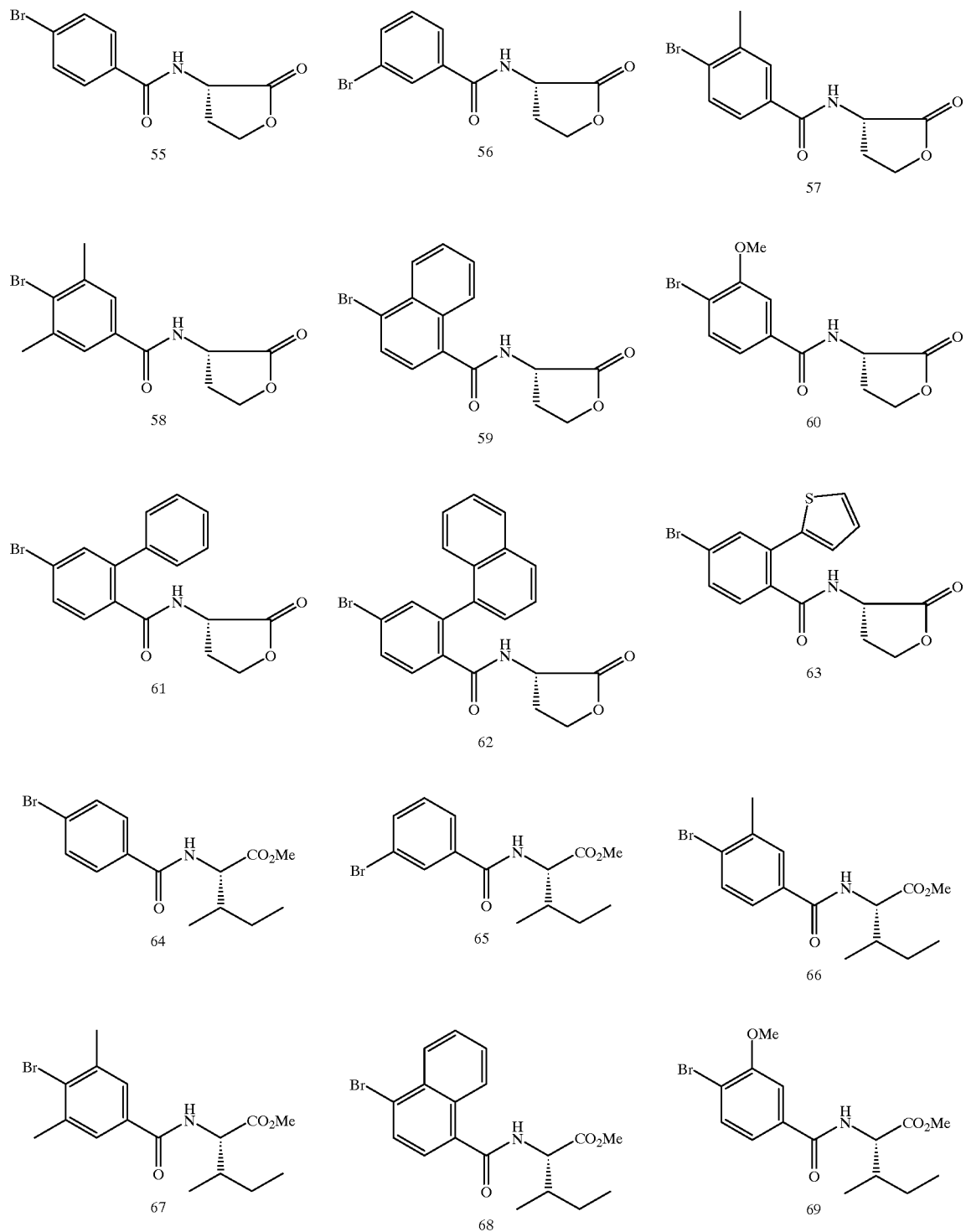

TABLE 11-continued
Bromides of the type B—Br
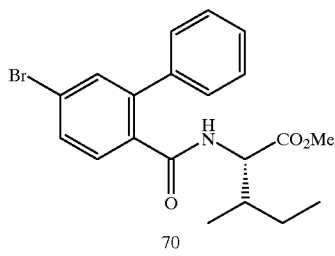
70
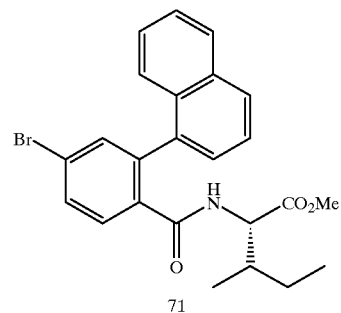
71
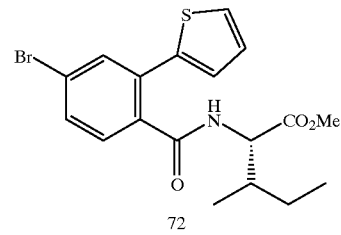
72
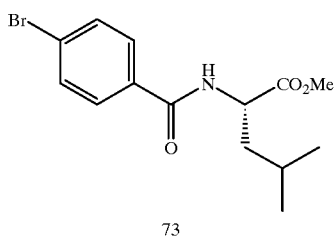
73
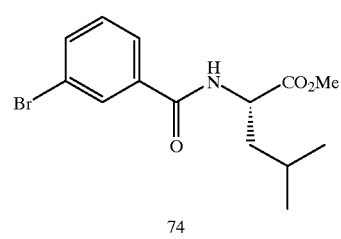
74
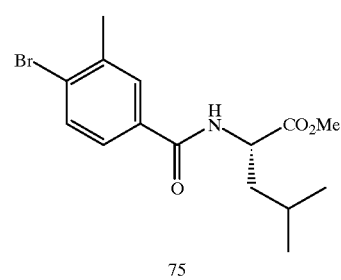
75
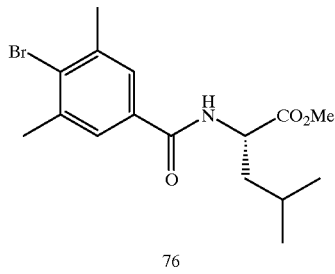
76
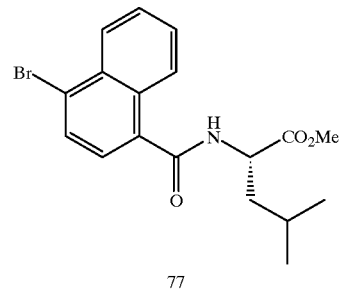
77
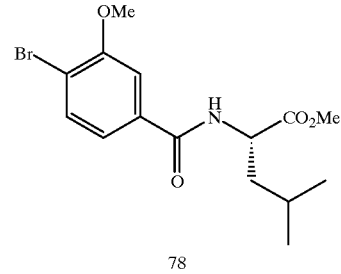
78
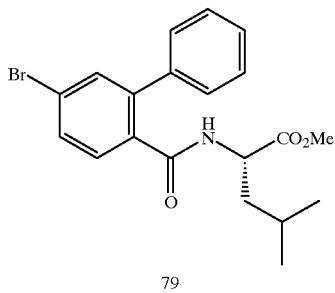
79
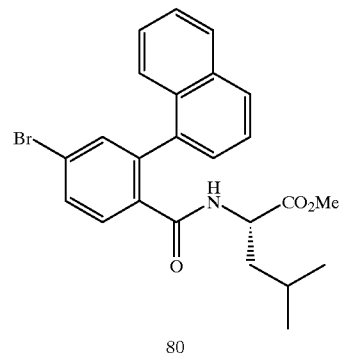
80
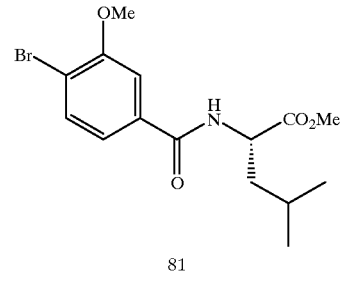
81
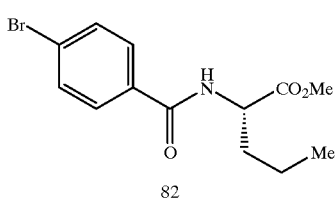
82
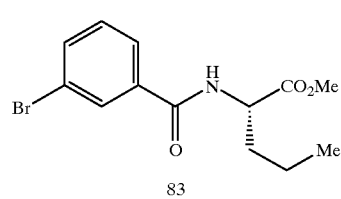
83
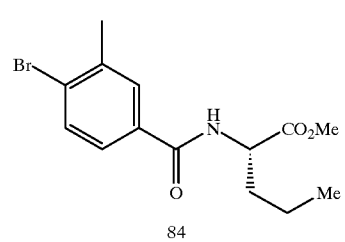
84

TABLE 11-continued
Bromides of the type B—Br
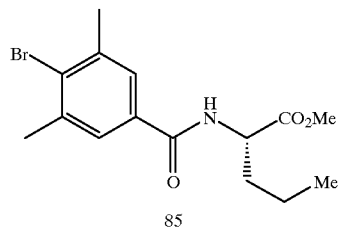
85
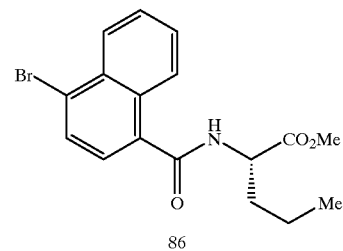
86
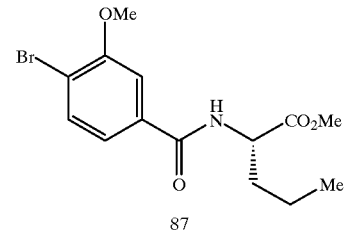
87
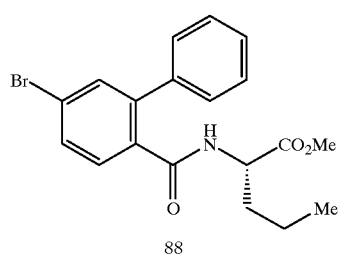
88
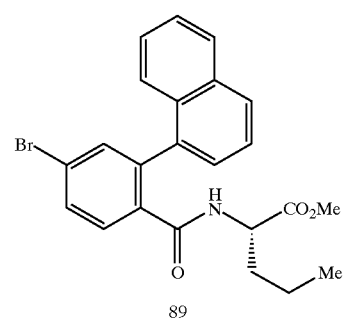
89
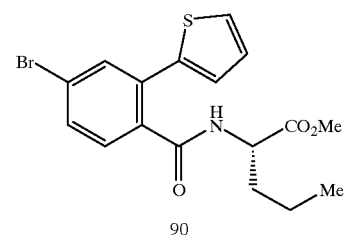
90
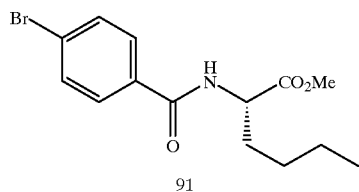
91
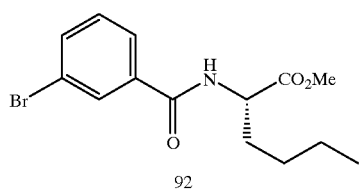
92
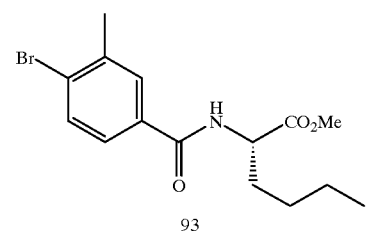
93
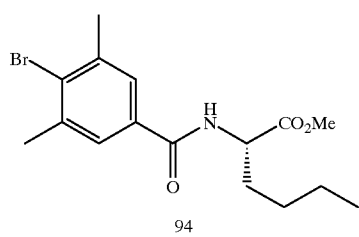
94
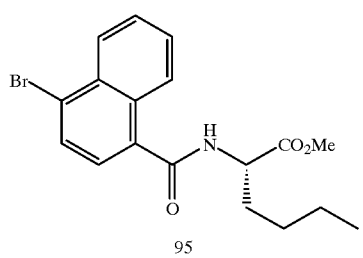
95
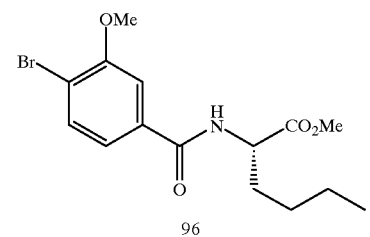
96
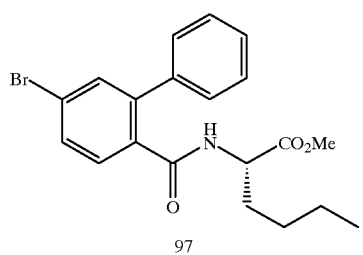
97
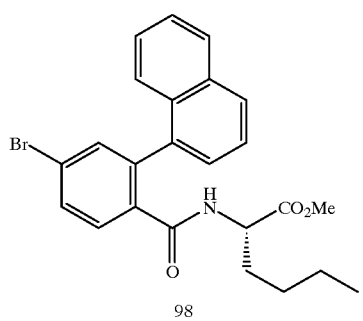
98
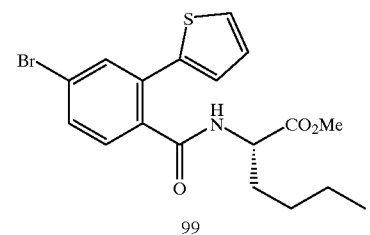
99

TABLE 11-continued
Bromides of the type B—Br
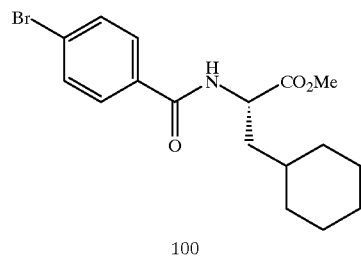
100
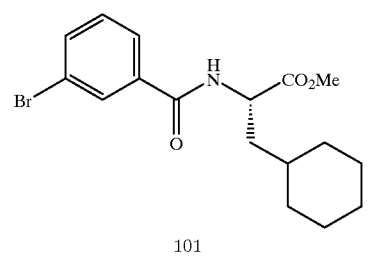
101
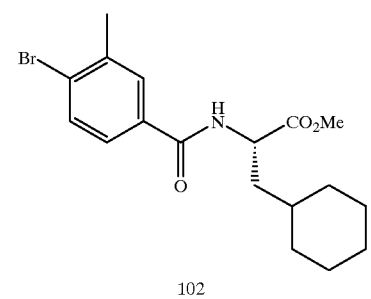
102
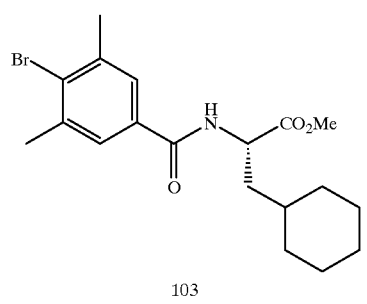
103
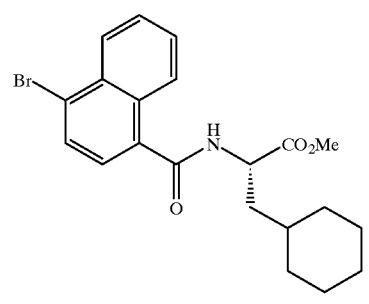
104
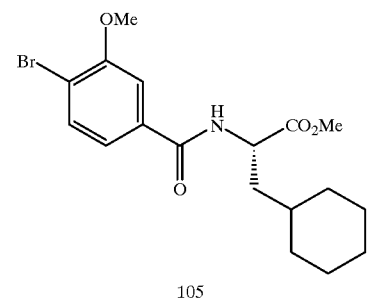
105
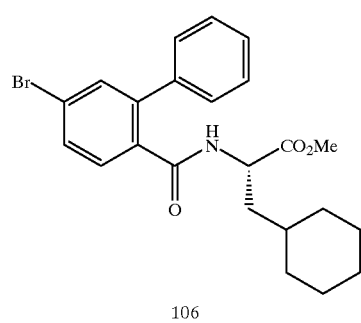
106
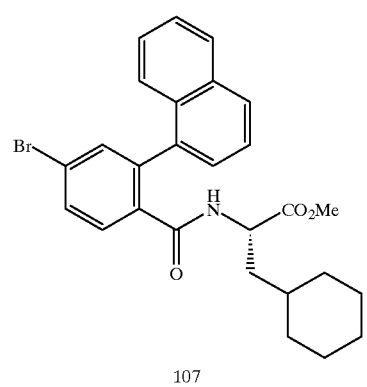
107
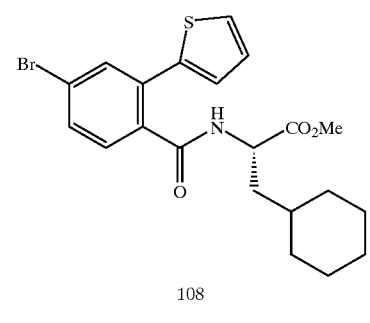
108
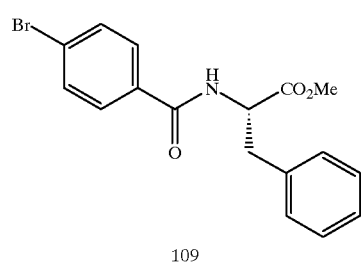
109
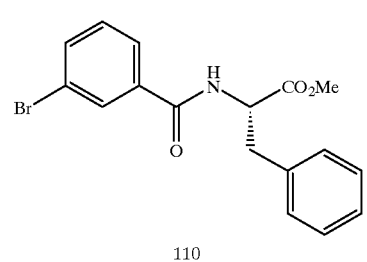
110
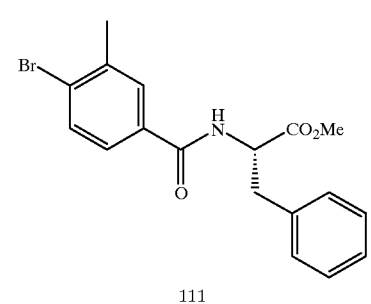
111

TABLE 11-continued
Bromides of the type B—Br
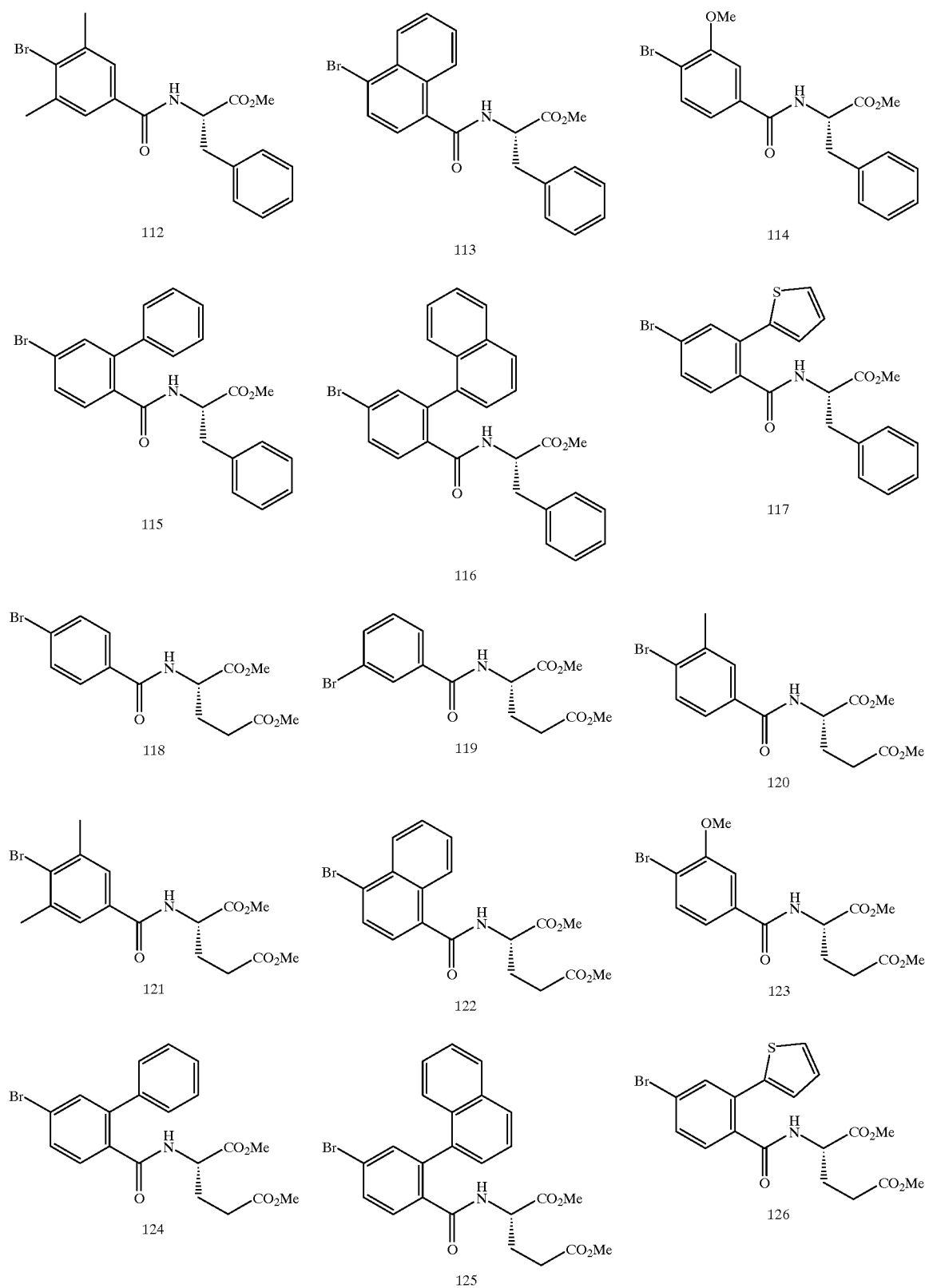

TABLE 11-continued
Bromides of the type B—Br
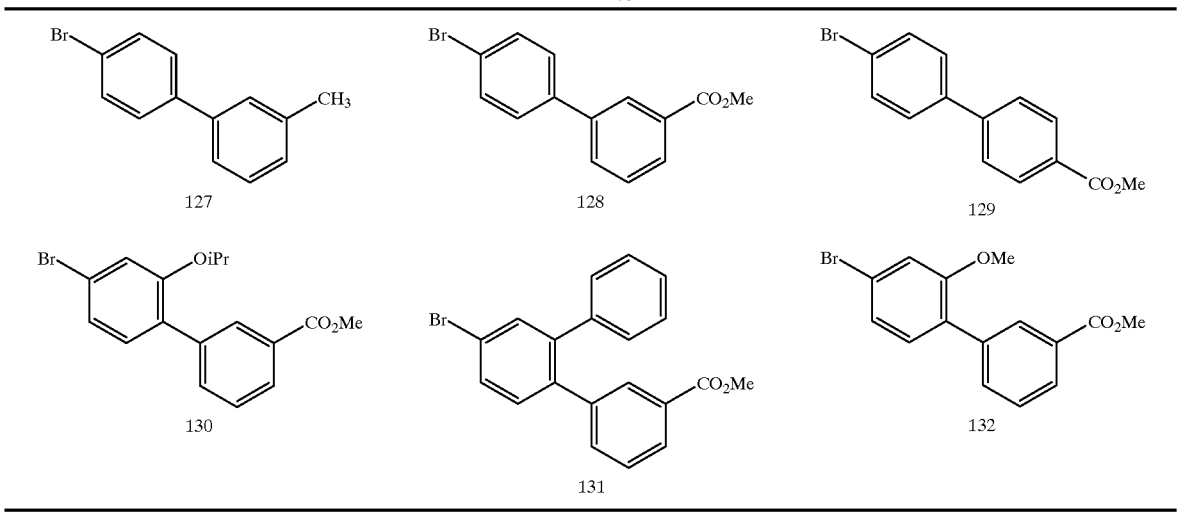
TABLE 12
Amines of the type A—NH$_2$
TABLE 12-continued
Amines of the type A—NH$_2$
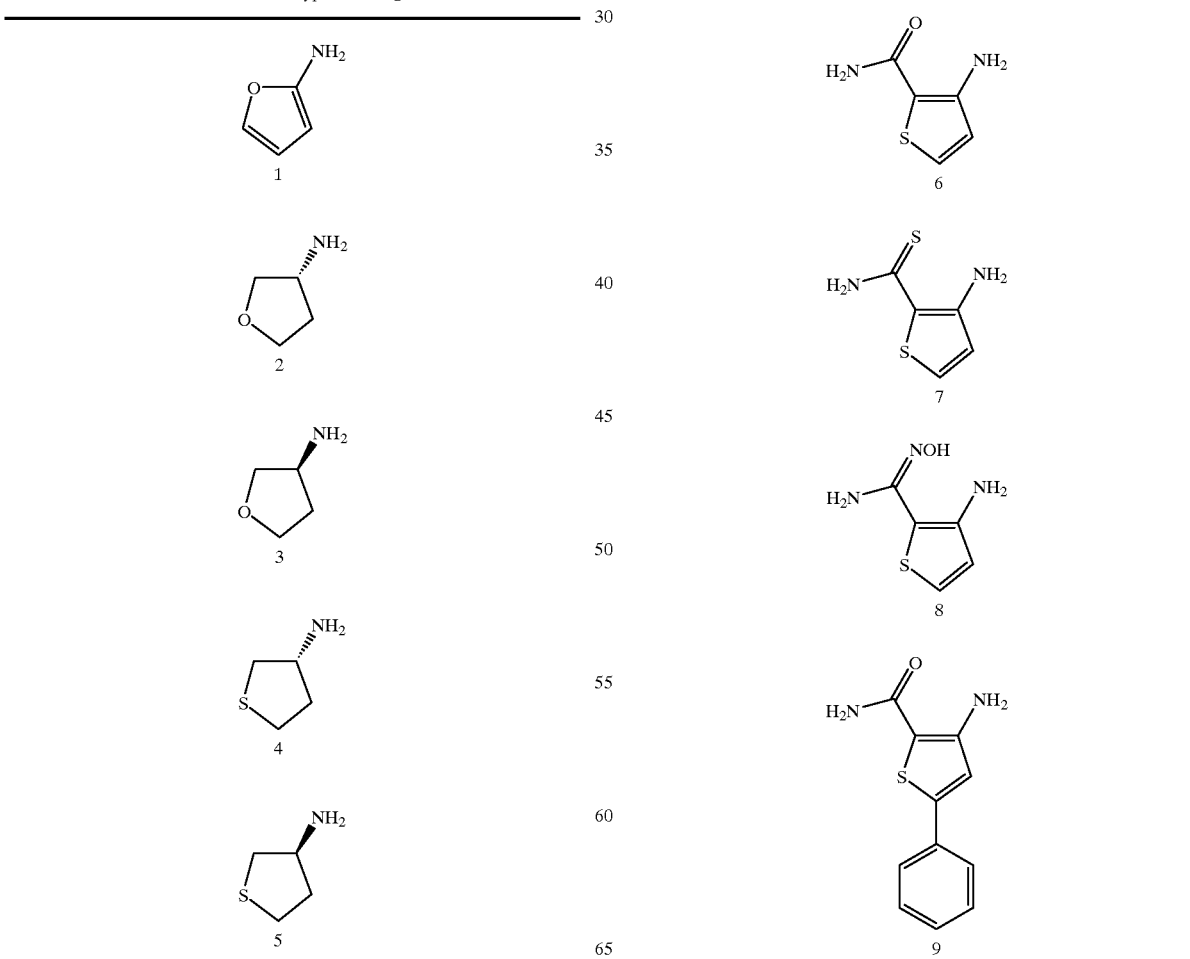

TABLE 12-continued
Amines of the type A—NH$_2$
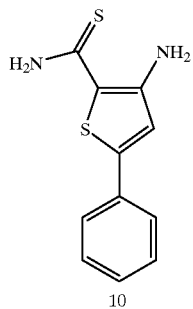
10
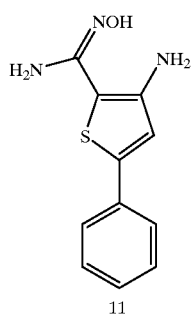
11
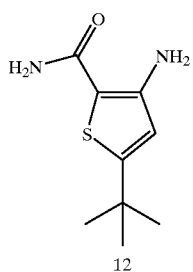
12
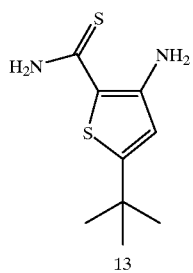
13
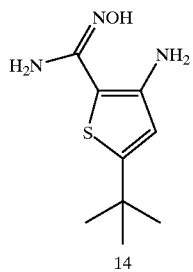
14
TABLE 12-continued
Amines of the type A—NH$_2$
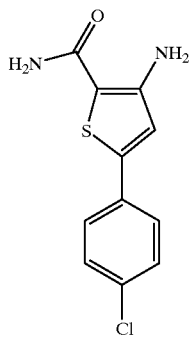
15
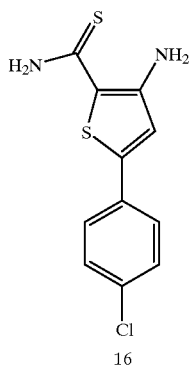
16
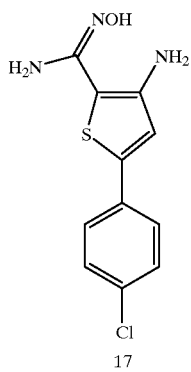
17
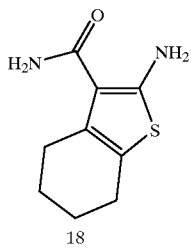
18

TABLE 12-continued
Amines of the type A—NH₂
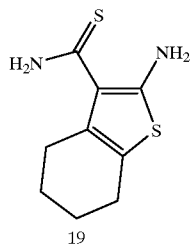
19
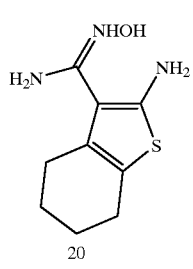
20
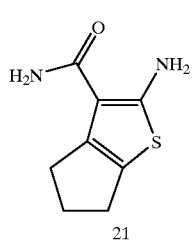
21
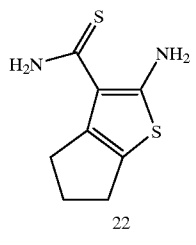
22
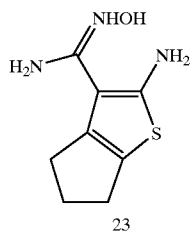
23
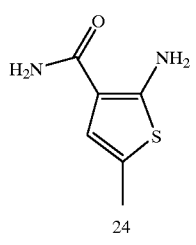
24
TABLE 12-continued
Amines of the type A—NH₂
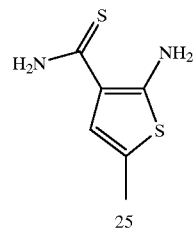
25
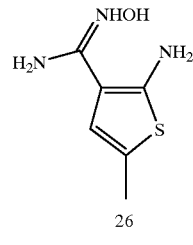
26
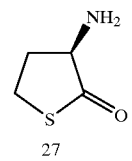
27
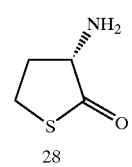
28
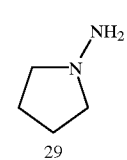
29
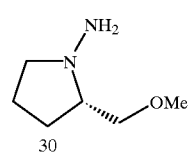
30
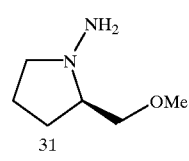
31
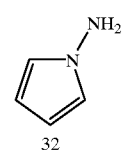
32

TABLE 12-continued
Amines of the type A—NH₂
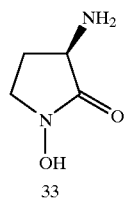
33
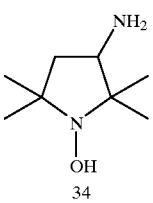
34
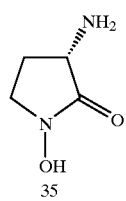
35
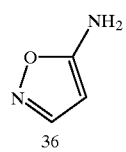
36
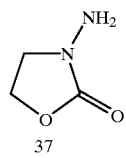
37
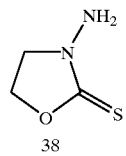
38
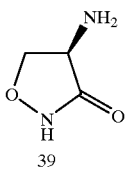
39
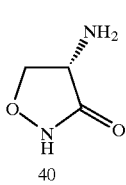
40
TABLE 12-continued
Amines of the type A—NH₂
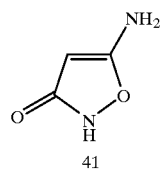
41
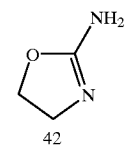
42
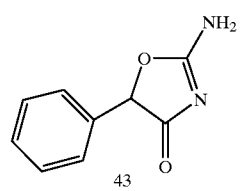
43
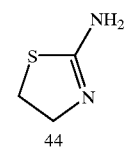
44
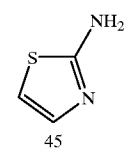
45
46
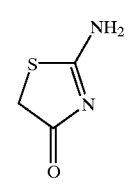
47
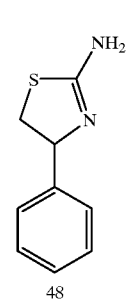
48

TABLE 12-continued
Amines of the type A—NH₂
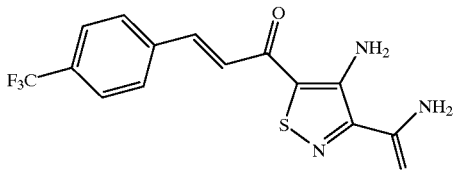
49
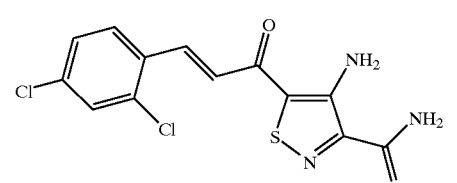
50
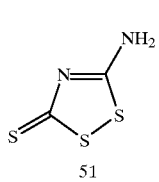
51
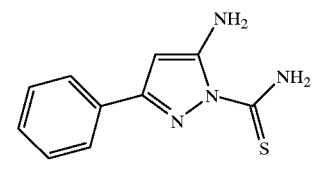
52
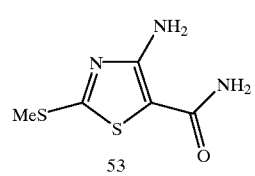
53
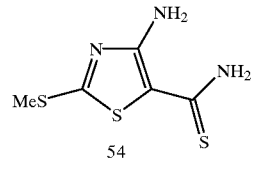
54
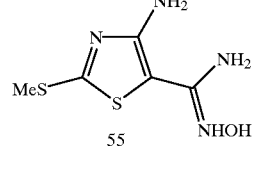
55
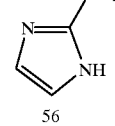
56
TABLE 12-continued
Amines of the type A—NH₂
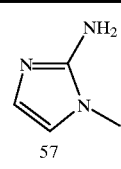
57
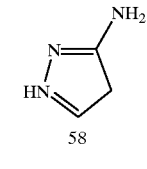
58
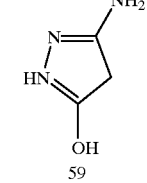
59
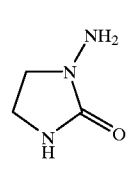
60
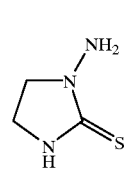
61
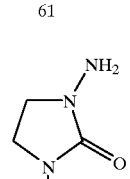
62
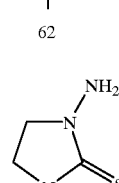
63
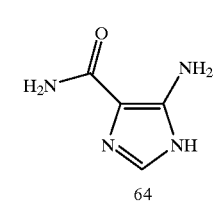
64

TABLE 12-continued
Amines of the type A—NH₂
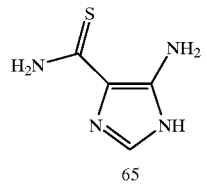
65
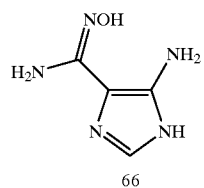
66
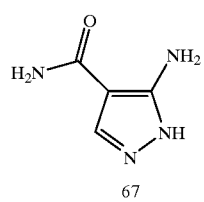
67
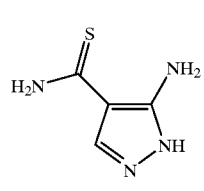
68
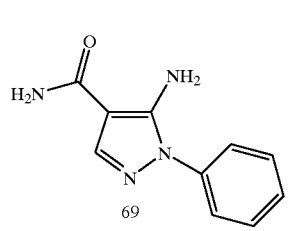
69
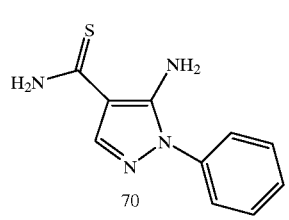
70
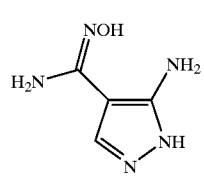
71
TABLE 12-continued
Amines of the type A—NH₂
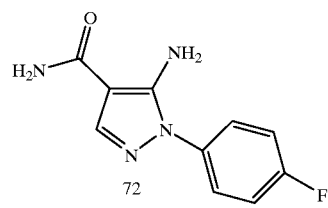
72
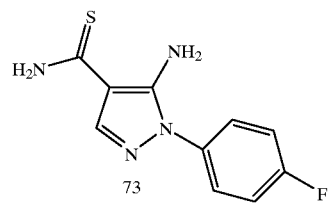
73
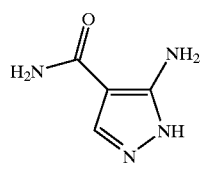
74
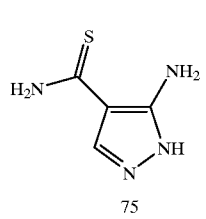
75
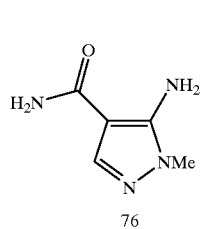
76

77
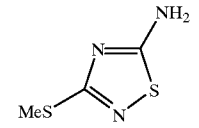
78

TABLE 12-continued
Amines of the type A—NH₂
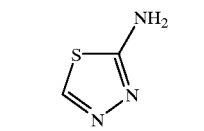
79
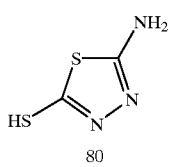
80
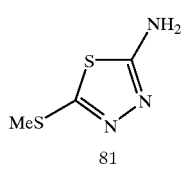
81
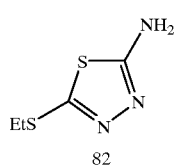
82
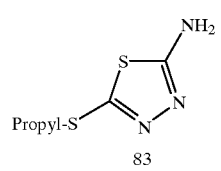
83
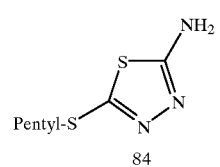
84
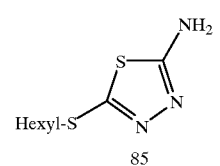
85
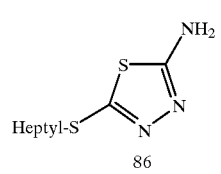
86
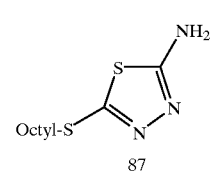
87
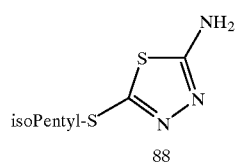
88
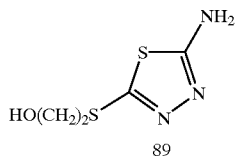
89
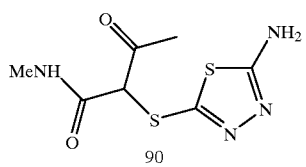
90
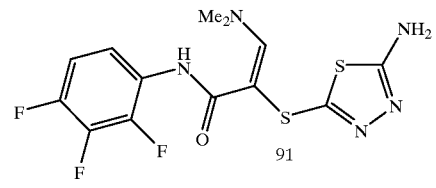
91
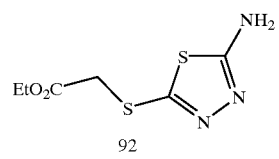
92
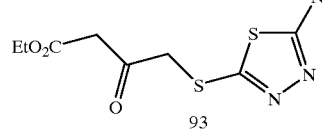
93
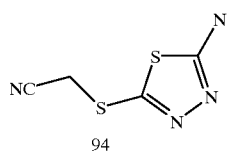
94
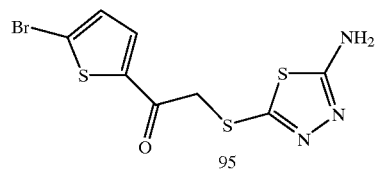
95

TABLE 12-continued
Amines of the type A—NH₂
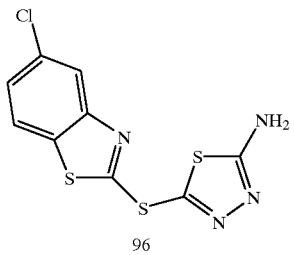
96
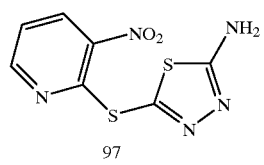
97
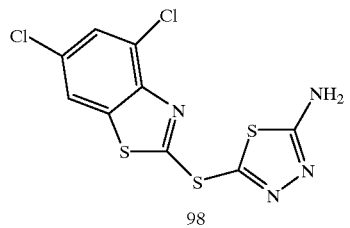
98
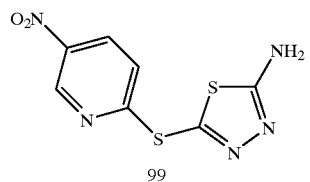
99
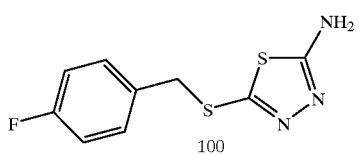
100
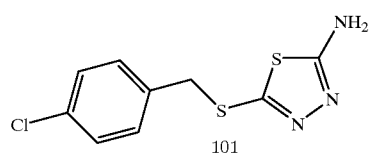
101
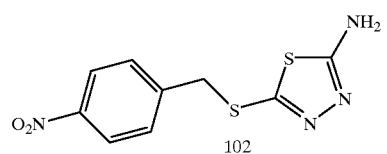
102
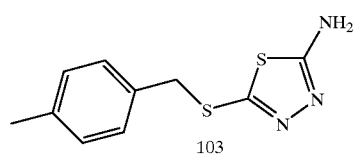
103
TABLE 12-continued
Amines of the type A—NH₂
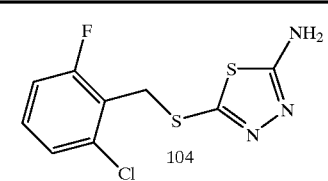
104
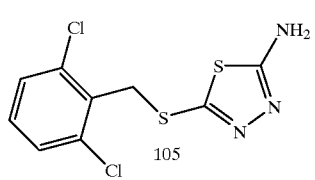
105
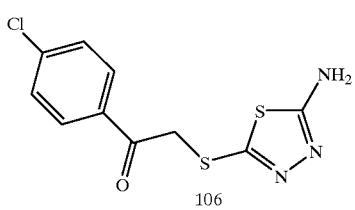
106
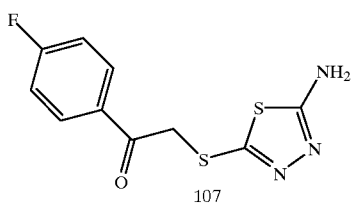
107
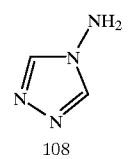
108
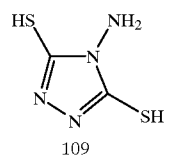
109
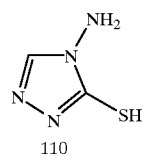
110
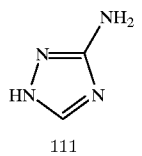
111

TABLE 12-continued
Amines of the type A—NH₂
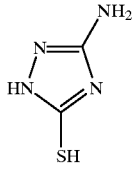
112
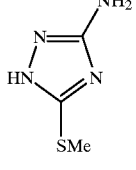
113
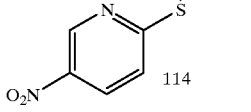
114
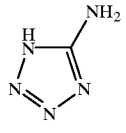
115
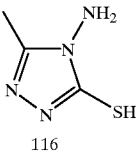
116
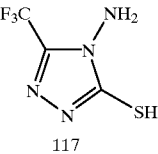
117
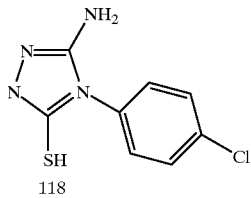
118
TABLE 12-continued
Amines of the type A—NH₂
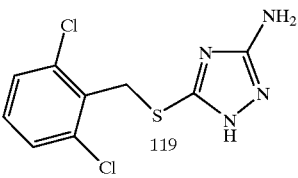
119
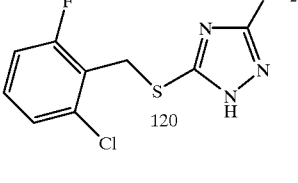
120
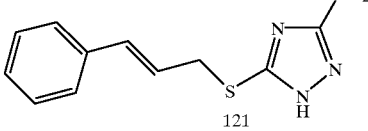
121
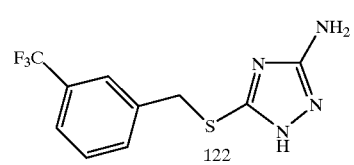
122
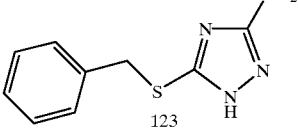
123
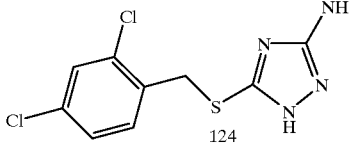
124
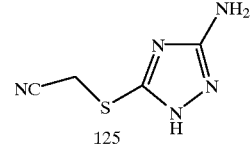
125
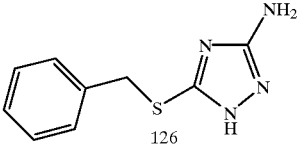
126

TABLE 12-continued
Amines of the type A—NH₂
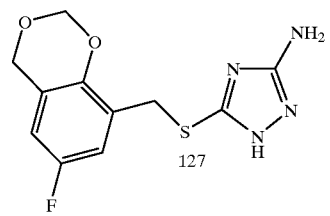
127
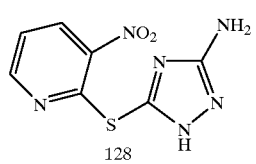
128
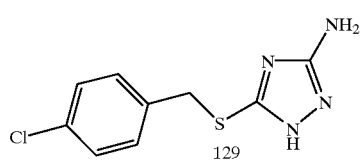
129
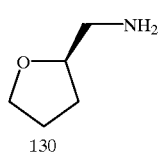
130
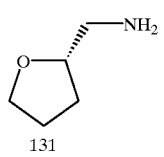
131
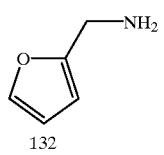
132
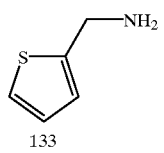
133
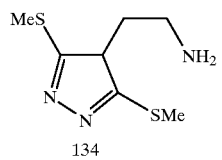
134
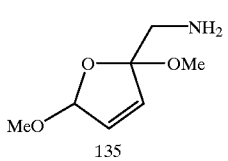
135
TABLE 12-continued
Amines of the type A—NH₂
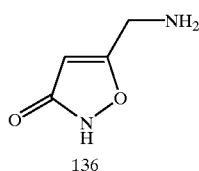
136
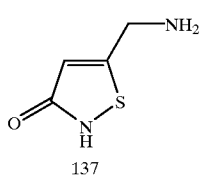
137
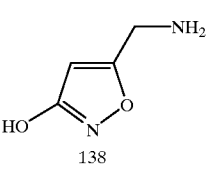
138
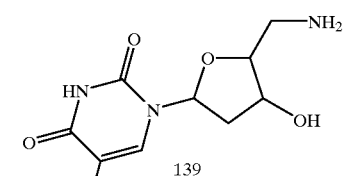
139
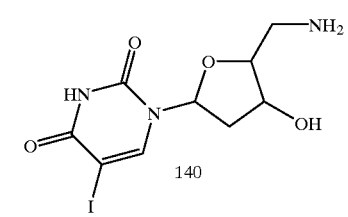
140
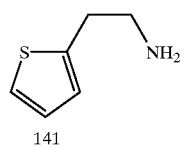
141
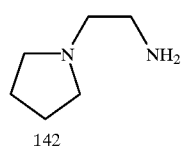
142
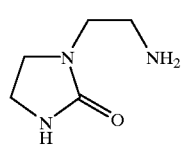
143

TABLE 12-continued
Amines of the type A—NH₂
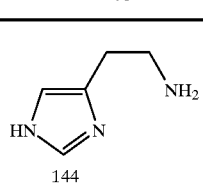
144
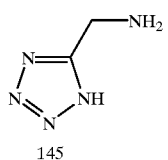
145
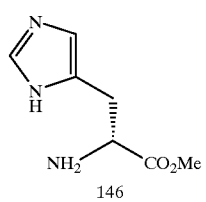
146
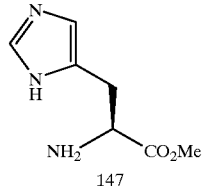
147
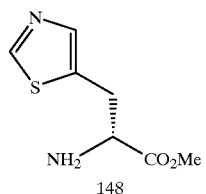
148
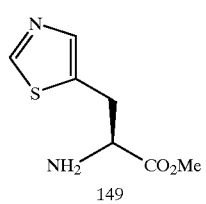
149
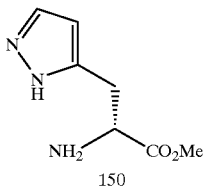
150
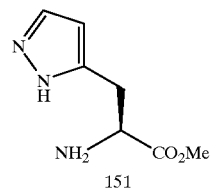
151
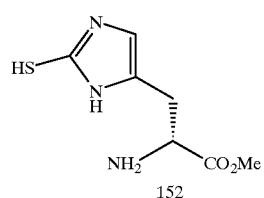
152
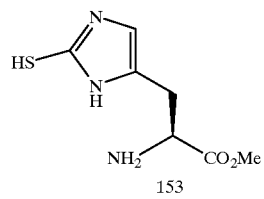
153
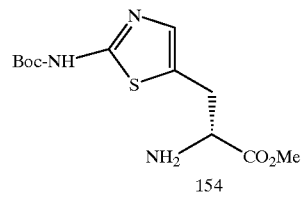
154
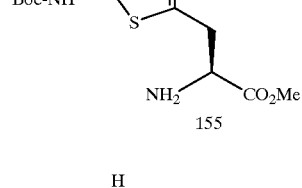
155
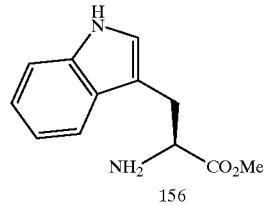
156
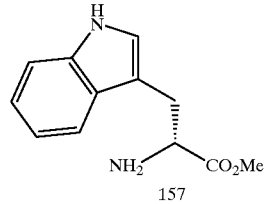
157

TABLE 12-continued
Amines of the type A—NH₂
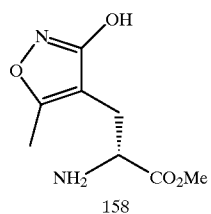
158
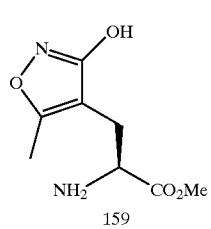
159
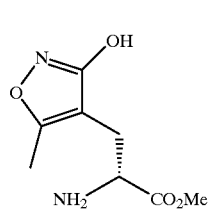
160
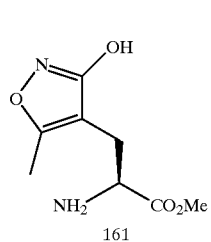
161
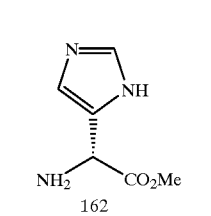
162
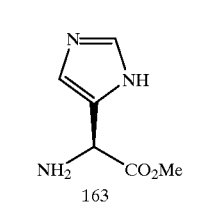
163
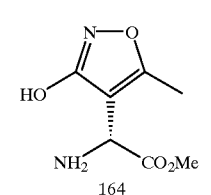
164
TABLE 12-continued
Amines of the type A—NH₂
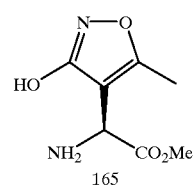
165
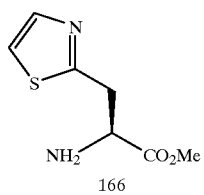
166
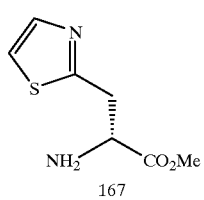
167
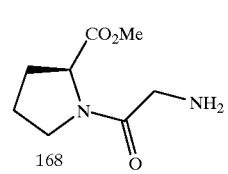
168
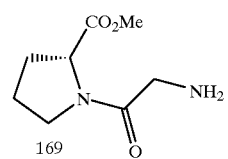
169
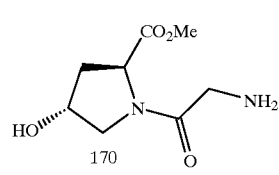
170
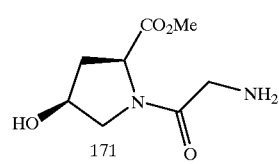
171
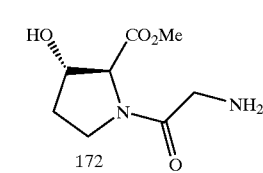
172

TABLE 12-continued
Amines of the type A—NH₂
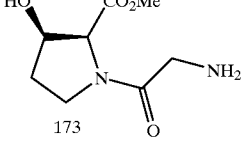
173
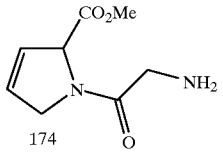
174
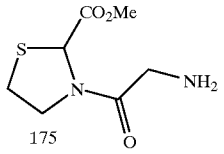
175
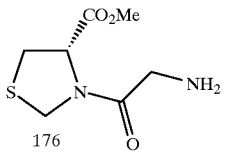
176
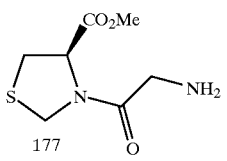
177
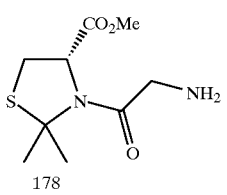
178
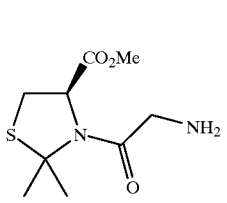
179
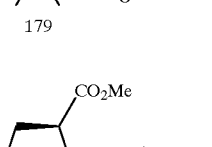
180
TABLE 12-continued
Amines of the type A—NH₂
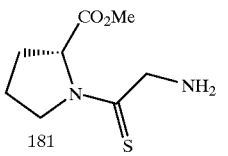
181
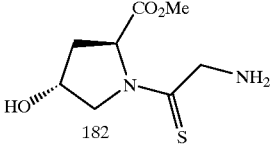
182
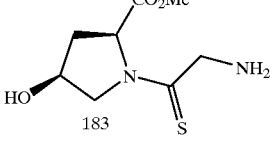
183
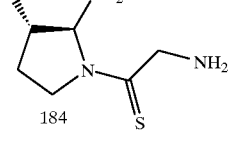
184
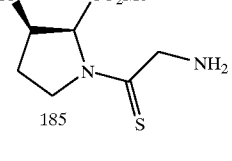
185
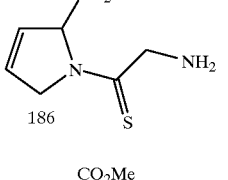
186
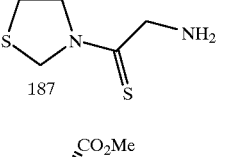
187
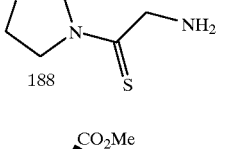
188
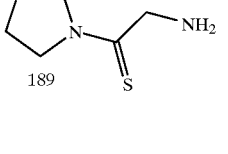
189

TABLE 12-continued
Amines of the type A—NH₂
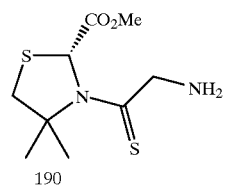
190
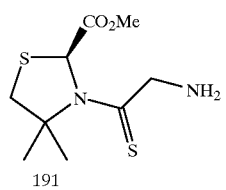
191
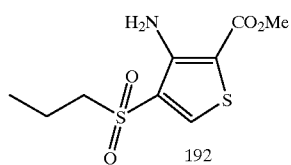
192
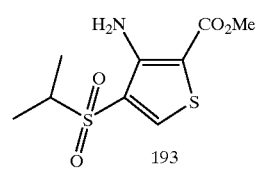
193
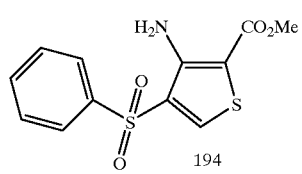
194
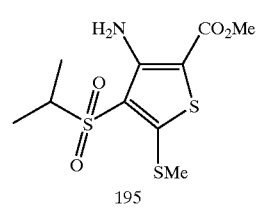
195
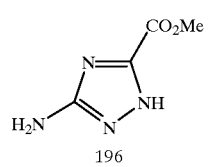
196
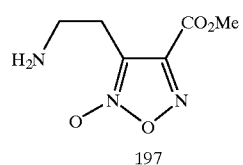
197
TABLE 12-continued
Amines of the type A—NH₂
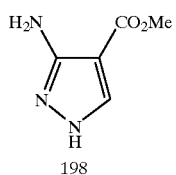
198
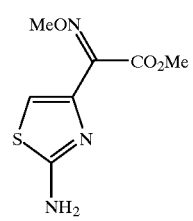
199
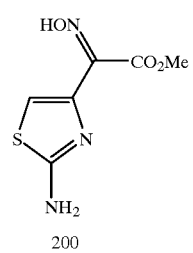
200
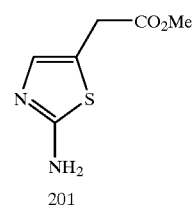
201
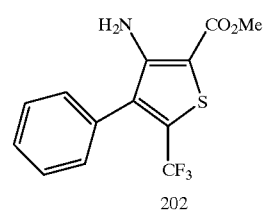
202
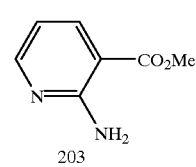
203
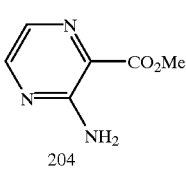
204

TABLE 12-continued
Amines of the type A—NH₂
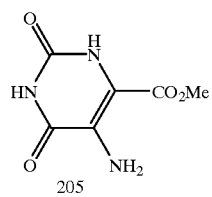
205
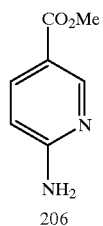
206
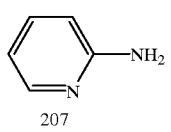
207
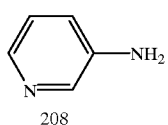
208
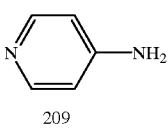
209
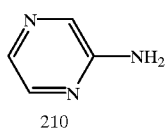
210
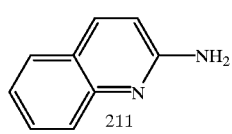
211
212
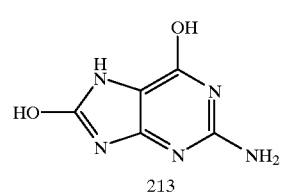
213
TABLE 12-continued
Amines of the type A—NH₂
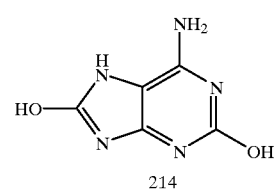
214
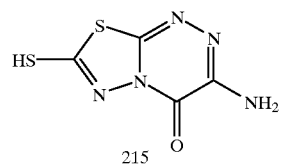
215
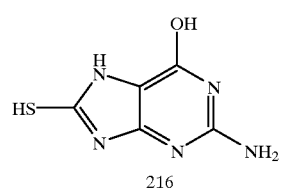
216
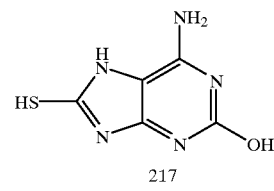
217
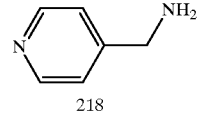
218
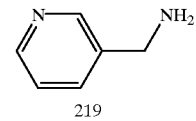
219
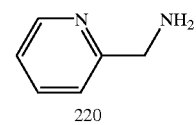
220
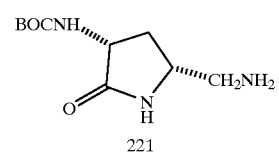
221
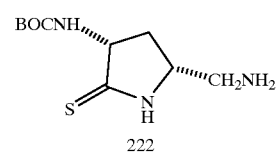
222

TABLE 12-continued
Amines of the type A—NH₂
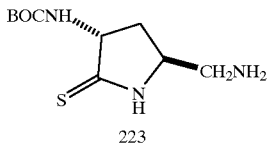
223
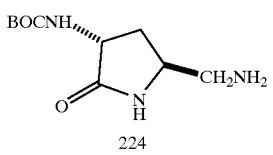
224
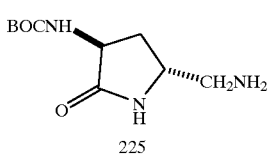
225
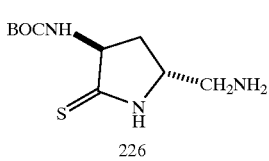
226
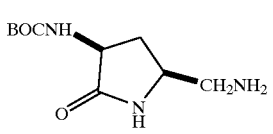
227
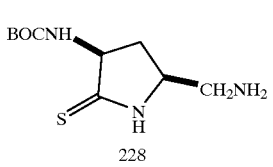
228
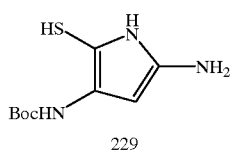
229
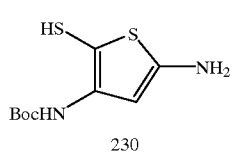
230
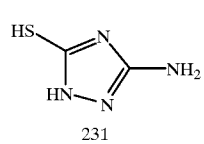
231
TABLE 12-continued
Amines of the type A—NH₂
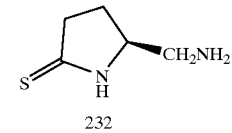
232
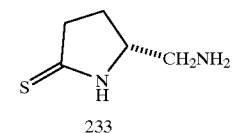
233
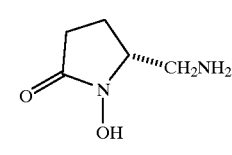
234
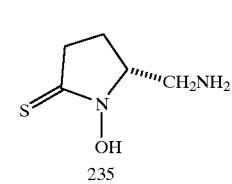
235
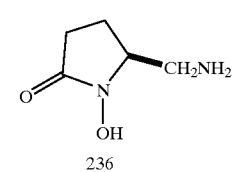
236
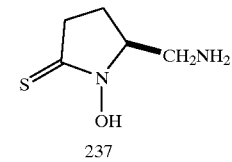
237
TABLE 13
Acids of the type A—CO₂H
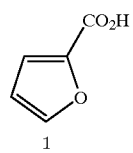
1
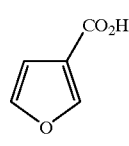
2

TABLE 13-continued
Acids of the type A—CO₂H
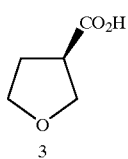
3
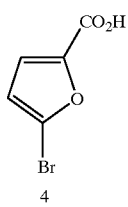
4
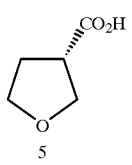
5
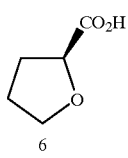
6
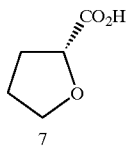
7
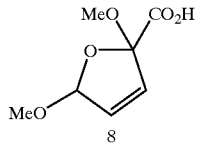
8
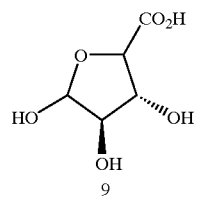
9
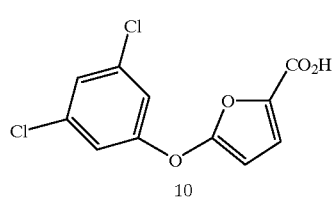
10
TABLE 13-continued
Acids of the type A—CO₂H
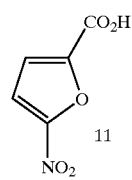
11
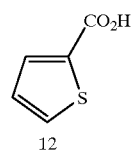
12
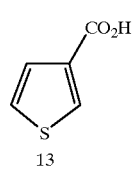
13
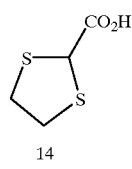
14
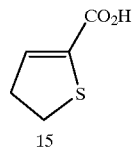
15
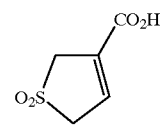
16
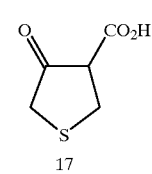
17
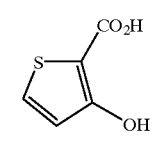
18
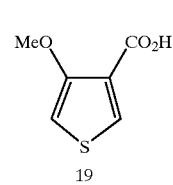
19

TABLE 13-continued
Acids of the type A—CO₂H
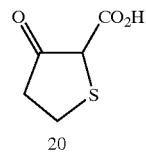
20
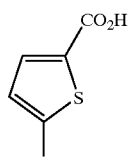
21
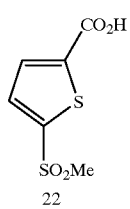
22
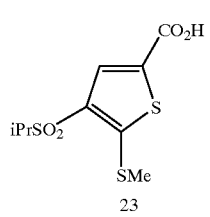
23
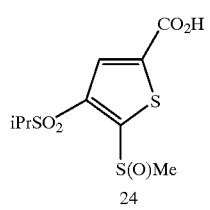
24
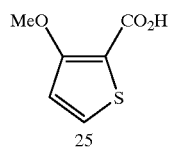
25
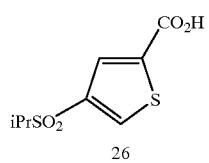
26
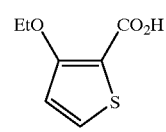
27
TABLE 13-continued
Acids of the type A—CO₂H
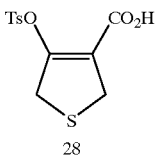
28
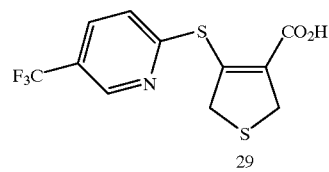
29
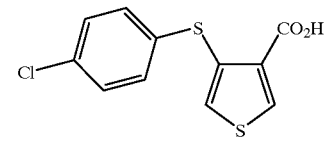
30
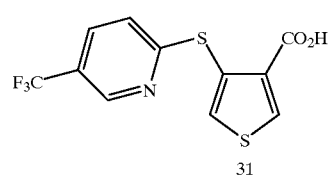
31
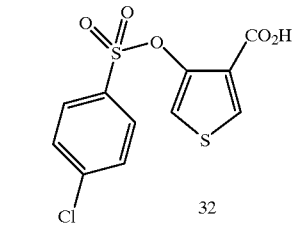
32
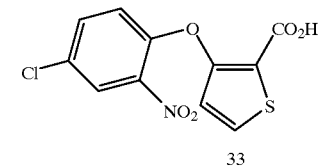
33
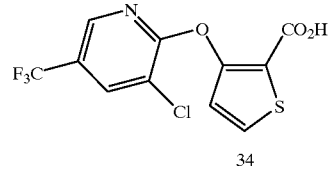
34
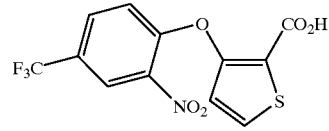
35

TABLE 13-continued
Acids of the type A—CO₂H
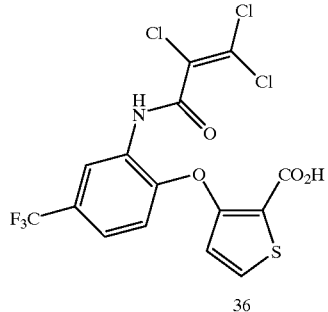
36
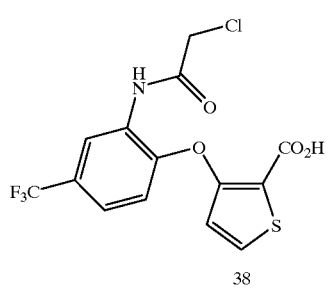
37
38
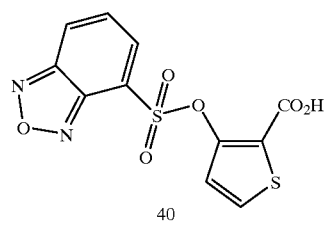
39
40
TABLE 13-continued
Acids of the type A—CO₂H
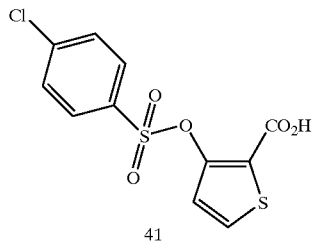
41
42
43
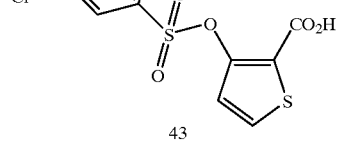
44
45
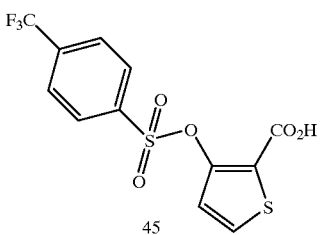
46

TABLE 13-continued
Acids of the type A—CO$_2$H
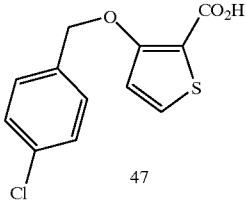
47
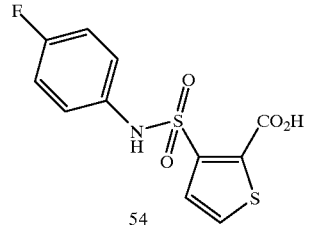
48
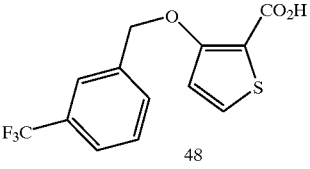
49
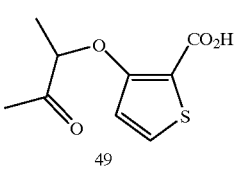
50
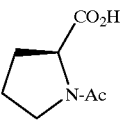
51
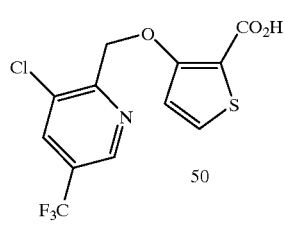
52
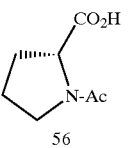
53
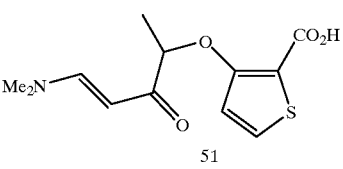
54
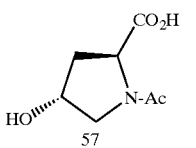
55
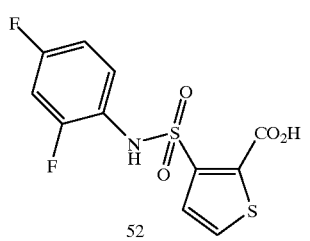
56
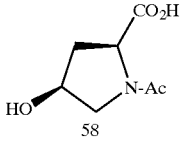
57
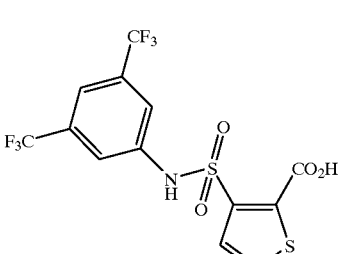
58
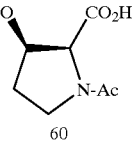
59
60
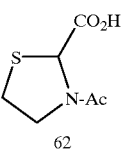
61
62

TABLE 13-continued

Acids of the type A—CO₂H 63, 64, 65, 66, 67, 68, 69, 70, 71, 72, 73, 74, 75, 76, 77, 78

TABLE 13-continued
Acids of the type A—CO$_2$H
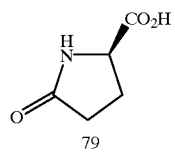
79
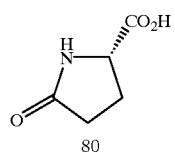
80
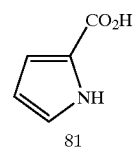
81
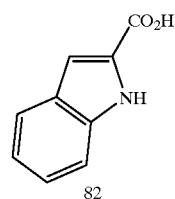
82
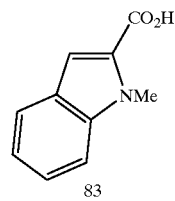
83
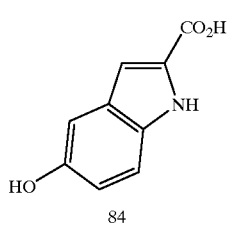
84
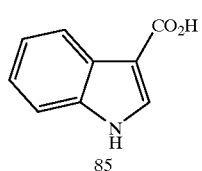
85
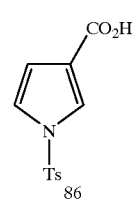
86
TABLE 13-continued
Acids of the type A—CO$_2$H
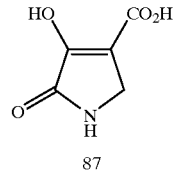
87
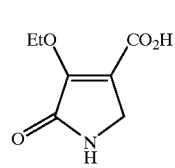
88
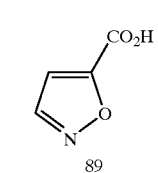
89
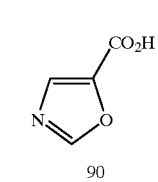
90
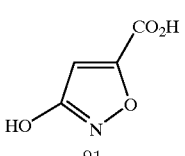
91
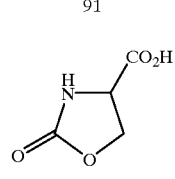
92
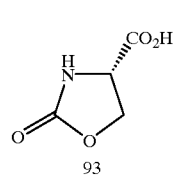
93
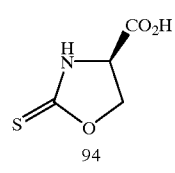
94
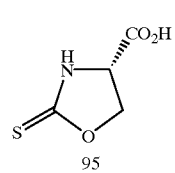
95

TABLE 13-continued
Acids of the type A—CO₂H
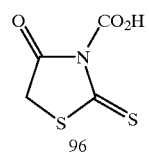
96
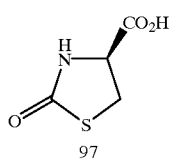
97
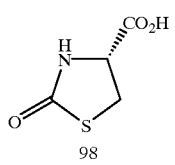
98
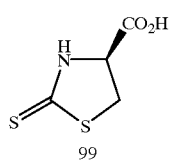
99
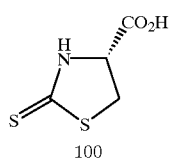
100
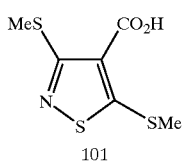
101
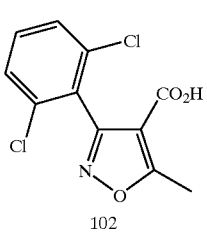
102
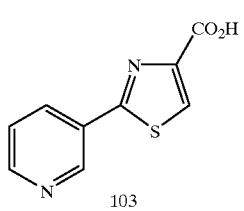
103
TABLE 13-continued
Acids of the type A—CO₂H
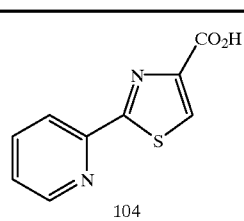
104
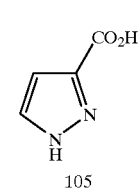
105
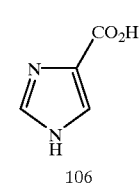
106
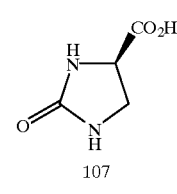
107
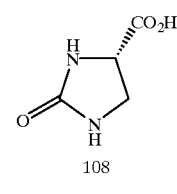
108
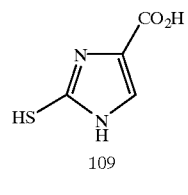
109
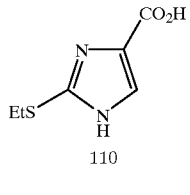
110
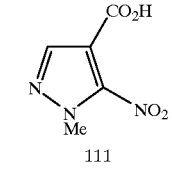
111

TABLE 13-continued
Acids of the type A—CO₂H
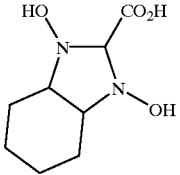
112
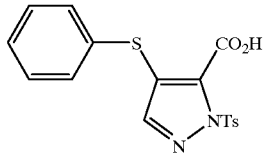
113
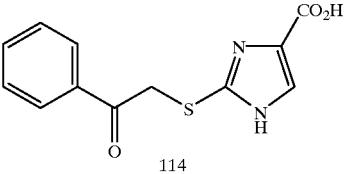
114
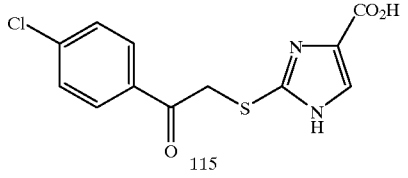
115
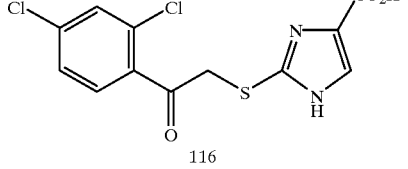
116
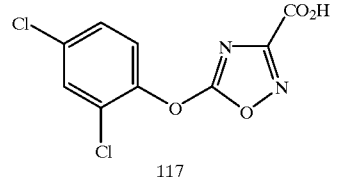
117
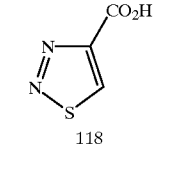
118
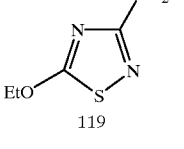
119
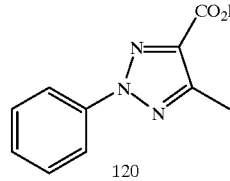
120
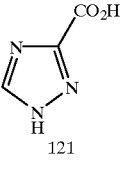
121
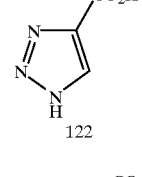
122
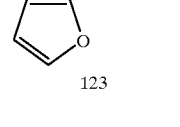
123
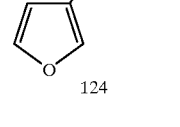
124
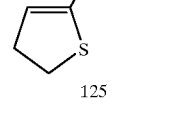
125
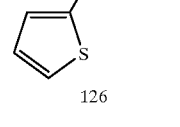
126
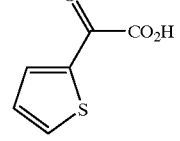
127
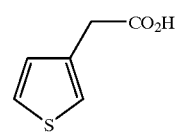
128

TABLE 13-continued
Acids of the type A—CO$_2$H
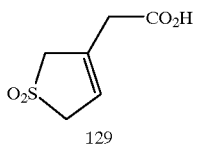
129
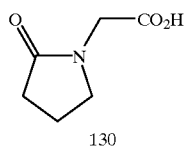
130
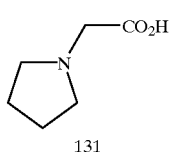
131
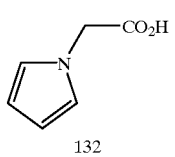
132
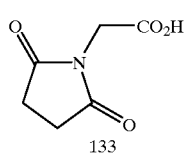
133
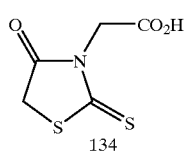
134
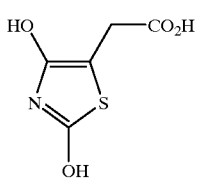
135
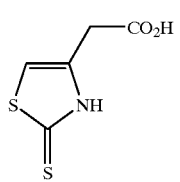
136
TABLE 13-continued
Acids of the type A—CO$_2$H
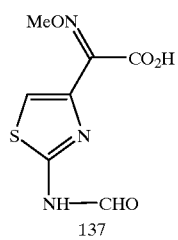
137
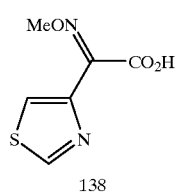
138
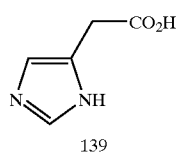
139
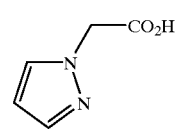
140
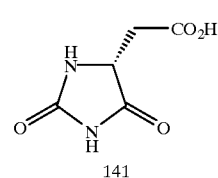
141
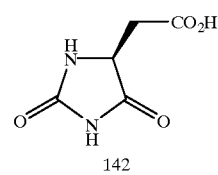
142
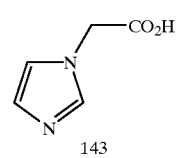
143
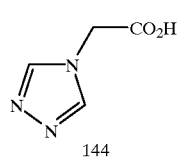
144

TABLE 13-continued
Acids of the type A—CO₂H
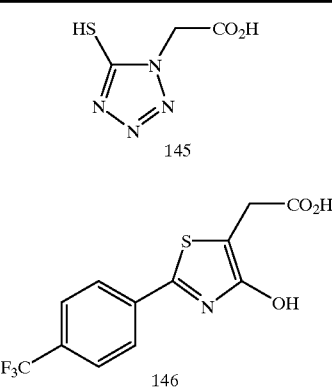
145
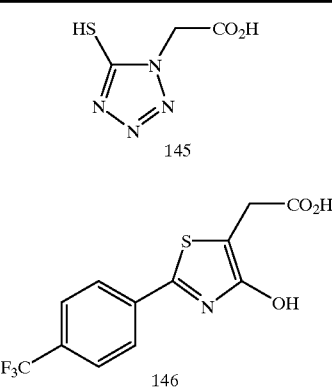
146
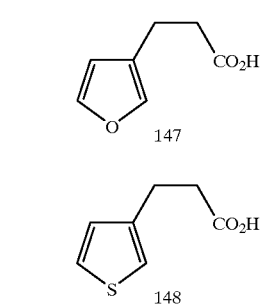
147

148

149
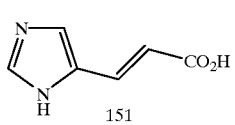
150
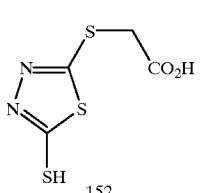
151
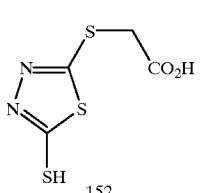
152
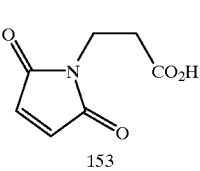
153
TABLE 13-continued
Acids of the type A—CO₂H
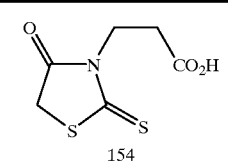
154
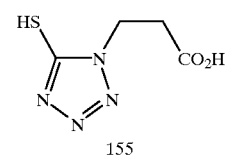
155
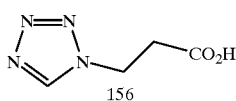
156
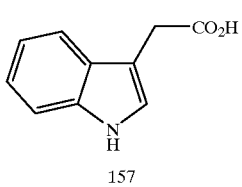
157
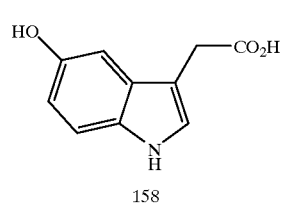
158
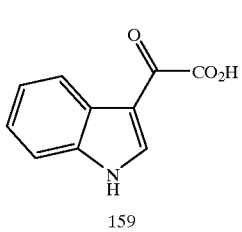
159
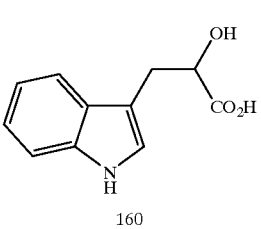
160
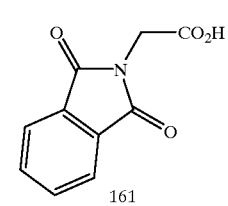
161

TABLE 13-continued
Acids of the type A—CO₂H
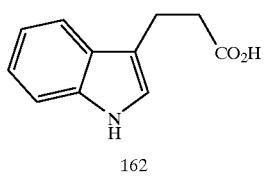
162
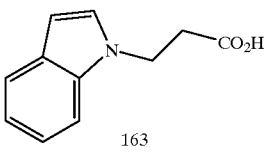
163
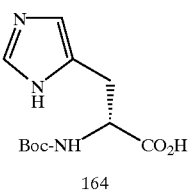
164
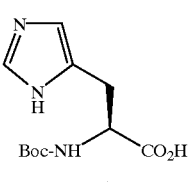
165
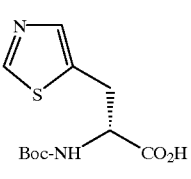
166
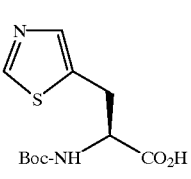
167
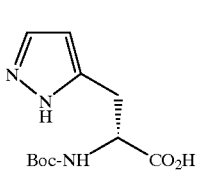
168
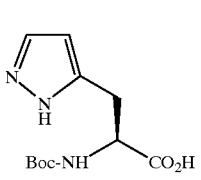
169
TABLE 13-continued
Acids of the type A—CO₂H
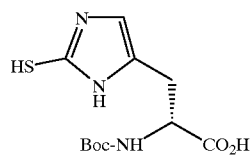
170
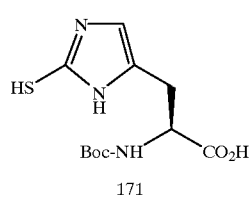
171
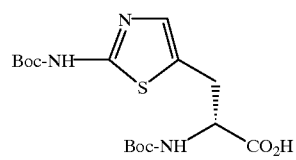
172
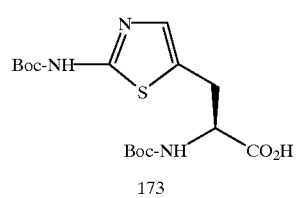
173
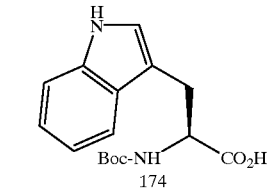
174
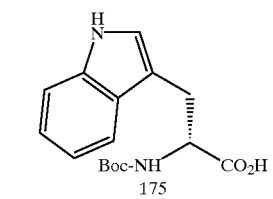
175
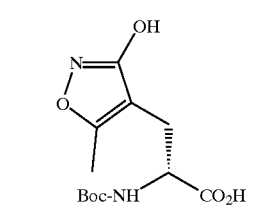
176

TABLE 13-continued
Acids of the type A—CO$_2$H
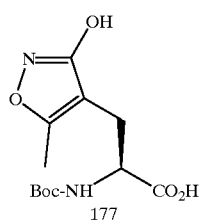
177
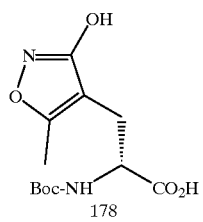
178
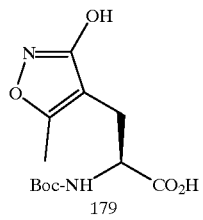
179
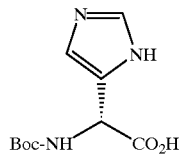
180
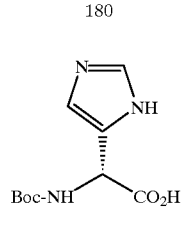
181
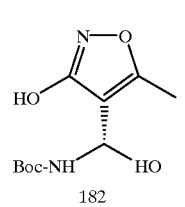
182
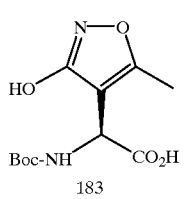
183
TABLE 13-continued
Acids of the type A—CO$_2$H
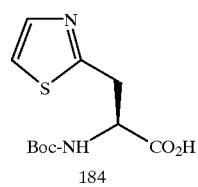
184
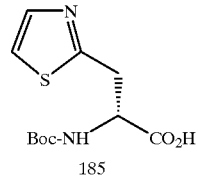
185
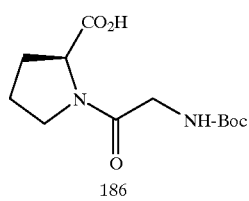
186
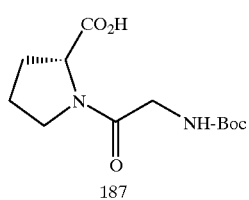
187
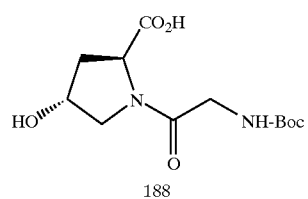
188
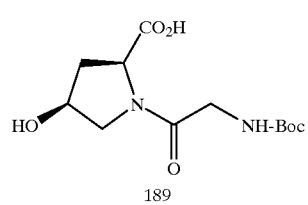
189
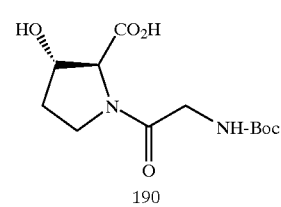
190

TABLE 13-continued
Acids of the type A—CO₂H
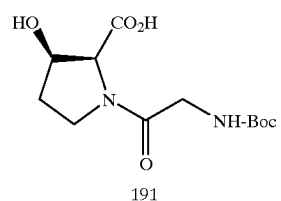
191
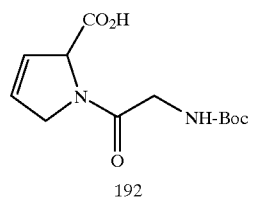
192
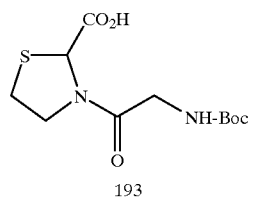
193
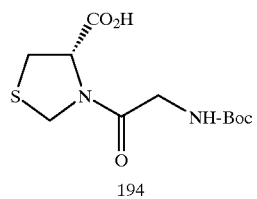
194
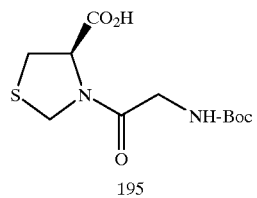
195
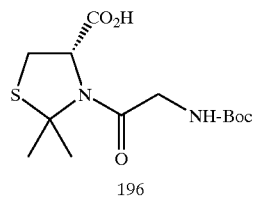
196
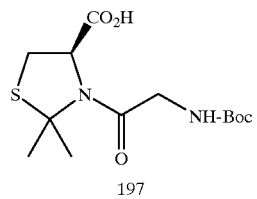
197
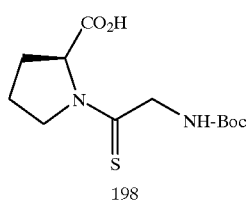
198
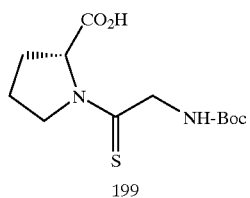
199
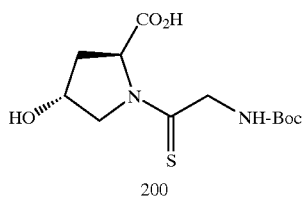
200
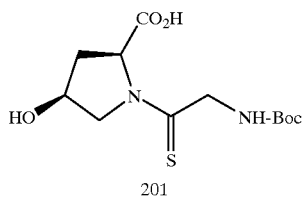
201
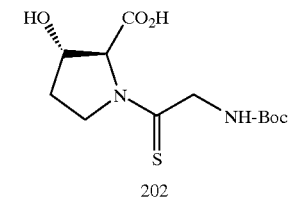
202
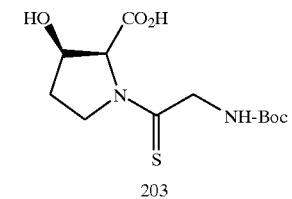
203
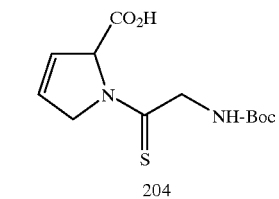
204

TABLE 13-continued
Acids of the type A—CO₂H
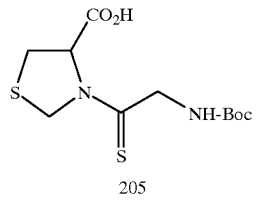
205
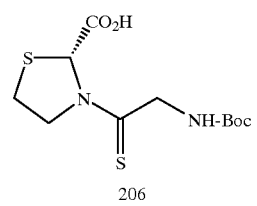
206
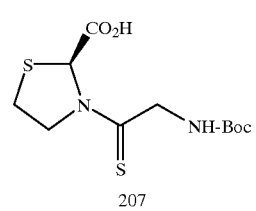
207
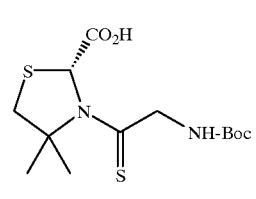
208
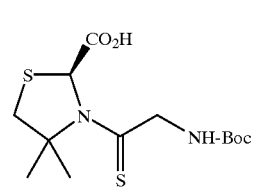
209
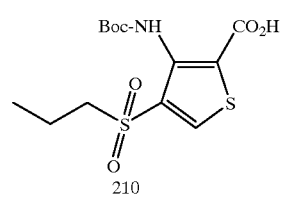
210
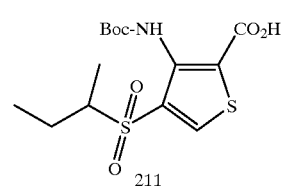
211
TABLE 13-continued
Acids of the type A—CO₂H
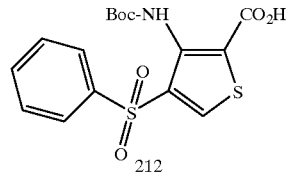
212
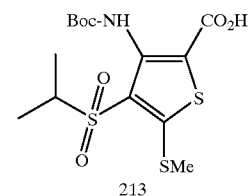
213
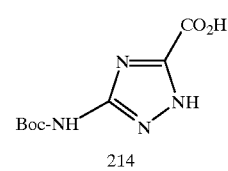
214
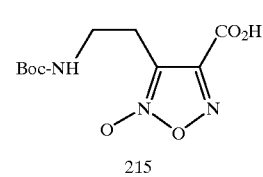
215
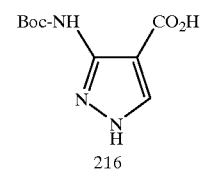
216
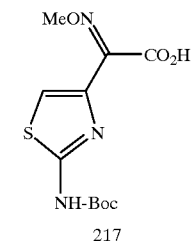
217
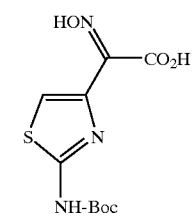
218

TABLE 13-continued
Acids of the type A—CO$_2$H
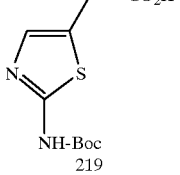
219
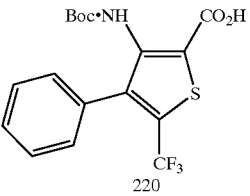
220
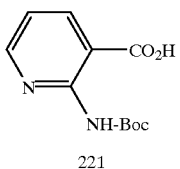
221
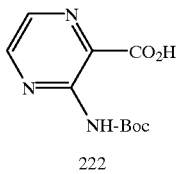
222
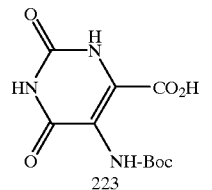
223
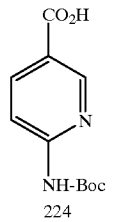
224
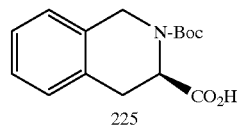
225
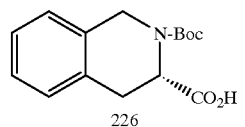
226
TABLE 13-continued
Acids of the type A—CO$_2$H
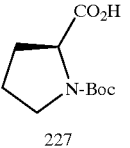
227
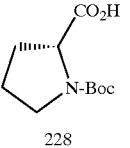
228
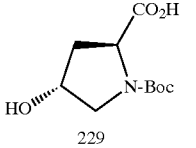
229
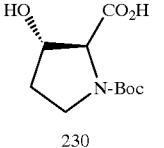
230
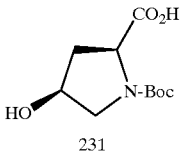
231
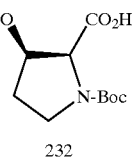
232
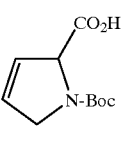
233
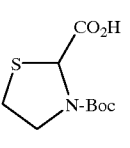
234
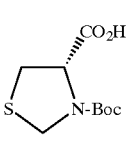
235

TABLE 13-continued
Acids of the type A—CO₂H
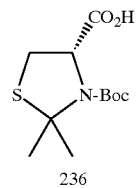
236
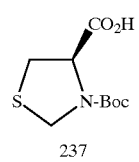
237
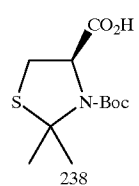
238
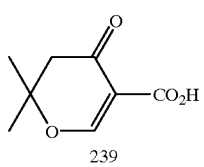
239
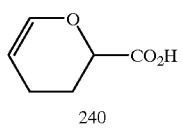
240
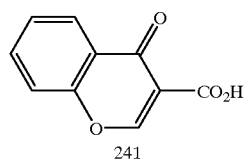
241
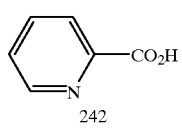
242
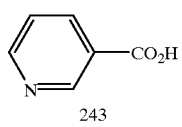
243
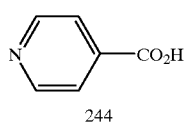
244
TABLE 13-continued
Acids of the type A—CO₂H
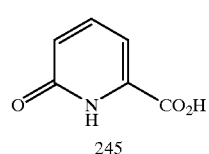
245
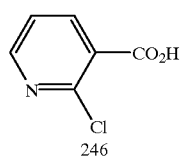
246
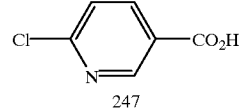
247
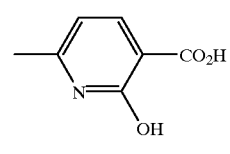
248
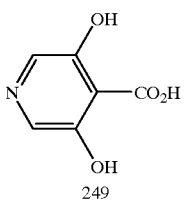
249
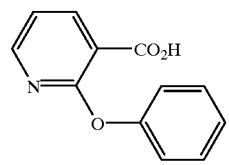
250
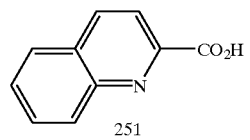
251
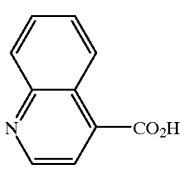
252

TABLE 13-continued
Acids of the type A—CO₂H
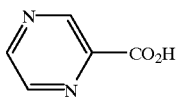
253
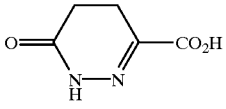
254
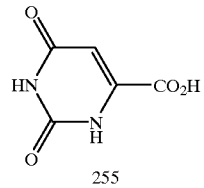
255
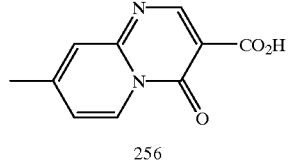
256
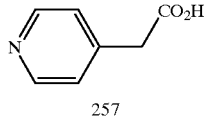
257
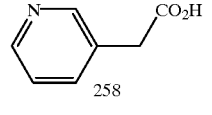
258
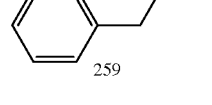
259
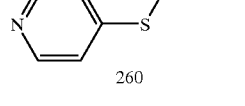
260
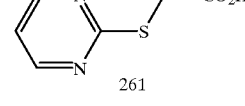
261
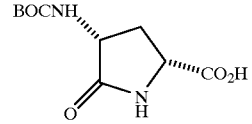
262
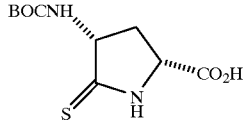
263
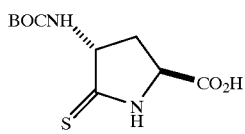
264
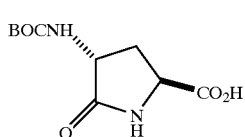
265
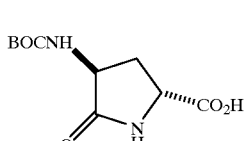
266
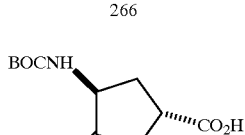
267
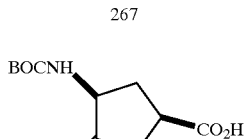
268
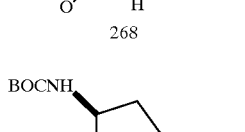
269
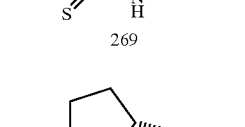
270
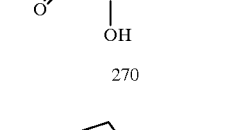
271

TABLE 13-continued
Acids of the type A—CO₂H
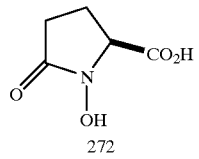
272
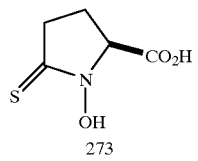
273
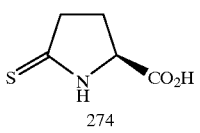
274
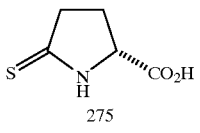
275
TABLE 14
Aldehydes of the type A-CHO
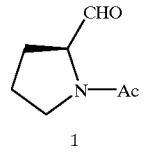
1
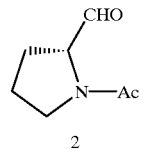
2
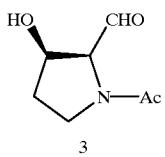
3
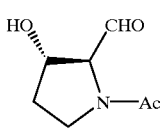
4
TABLE 14-continued
Aldehydes of the type A-CHO
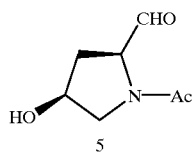
5
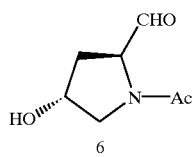
6
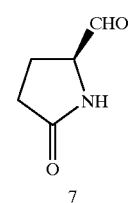
7
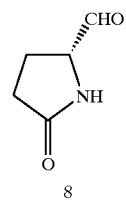
8
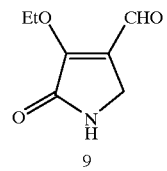
9
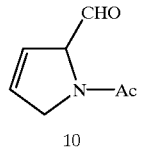
10
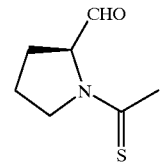
11
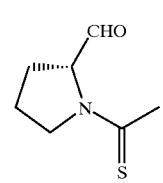
12

TABLE 14-continued
Aldehydes of the type A-CHO
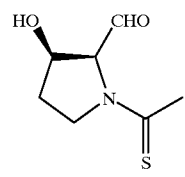
13
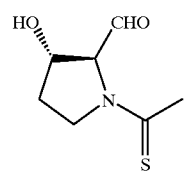
14
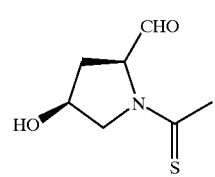
15
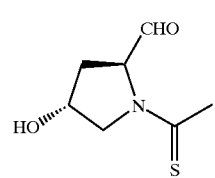
16
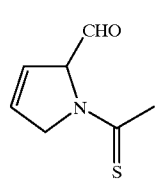
17
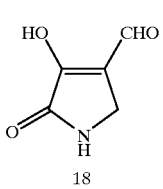
18
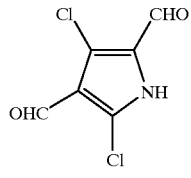
18
TABLE 14-continued
Aldehydes of the type A-CHO
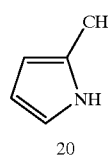
20
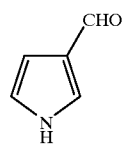
21
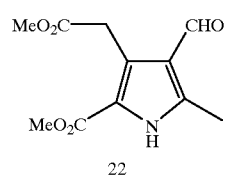
22
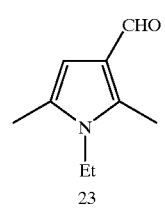
23
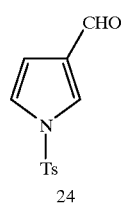
24
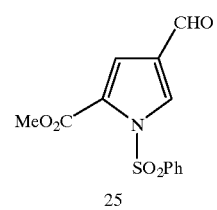
25
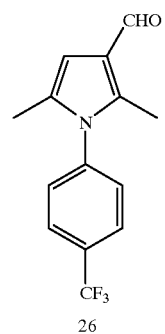
26

TABLE 14-continued
Aldehydes of the type A-CHO
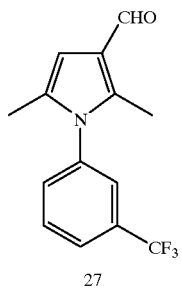
27
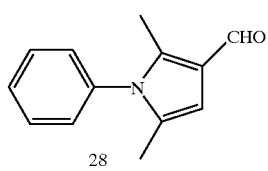
28
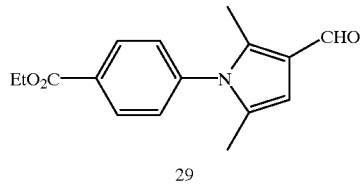
29
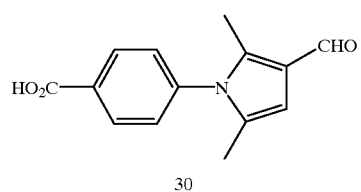
30
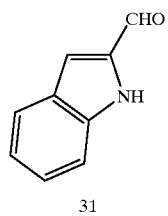
31
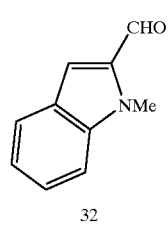
32
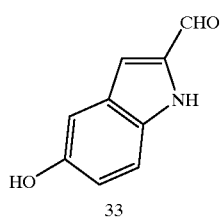
33
TABLE 14-continued
Aldehydes of the type A-CHO
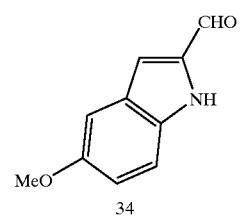
34
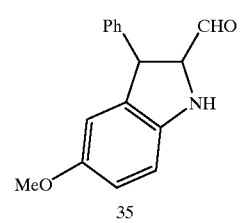
35
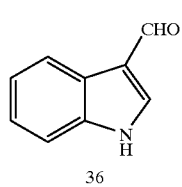
36
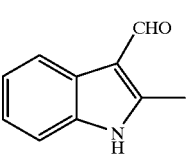
37
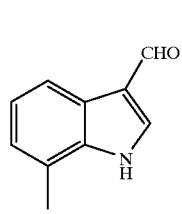
38
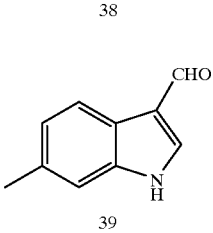
39
40

TABLE 14-continued
Aldehydes of the type A-CHO
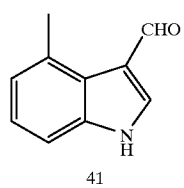
41
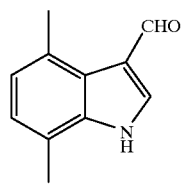
42
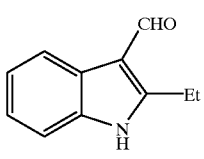
43
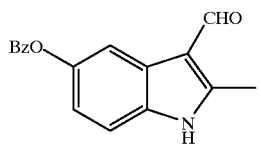
44
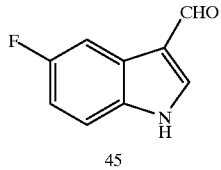
45
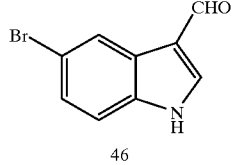
46
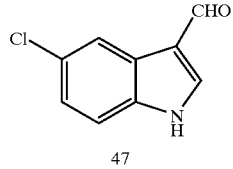
47
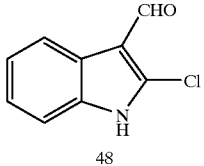
48
TABLE 14-continued
Aldehydes of the type A-CHO
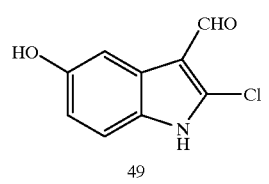
49
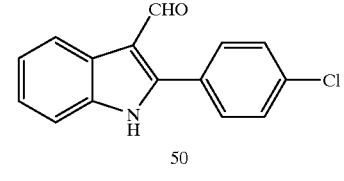
50
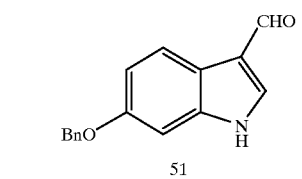
51
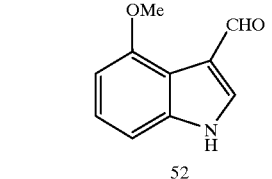
52
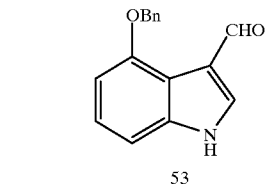
53
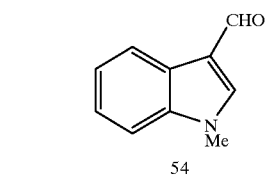
54
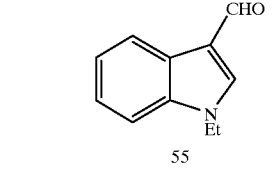
55
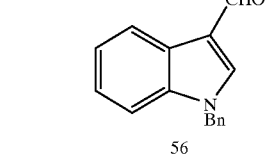
56

TABLE 14-continued
Aldehydes of the type A-CHO
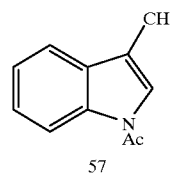
57
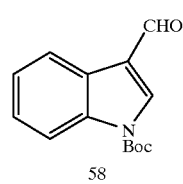
58
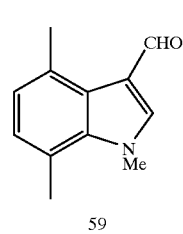
59
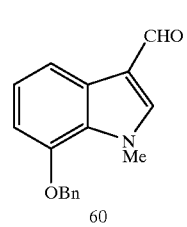
60
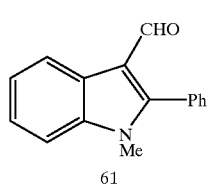
61
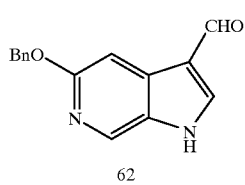
62
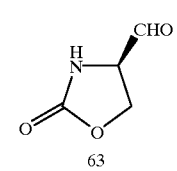
63
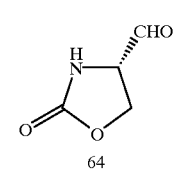
64
TABLE 14-continued
Aldehydes of the type A-CHO
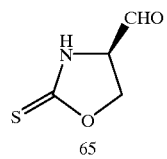
65
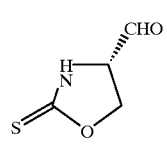
66
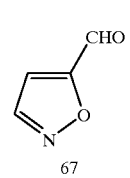
67
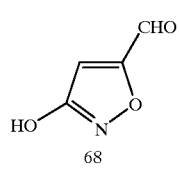
68
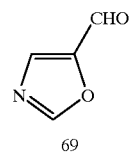
69
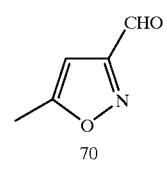
70
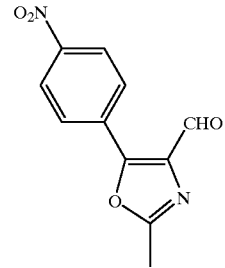
71
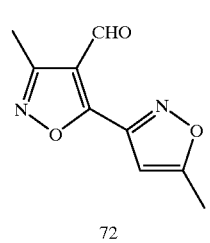
72

TABLE 14-continued
Aldehydes of the type A-CHO
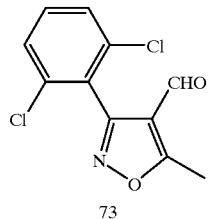
73
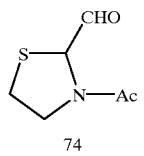
74
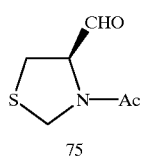
75
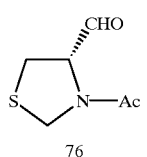
76
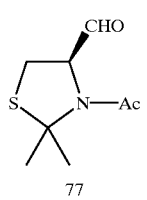
77
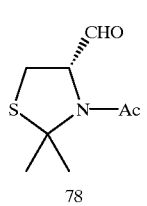
78
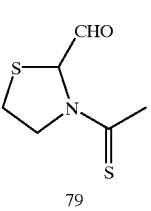
79
TABLE 14-continued
Aldehydes of the type A-CHO
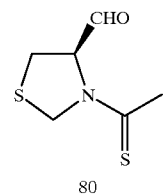
80
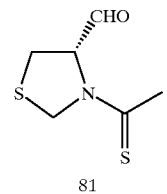
81
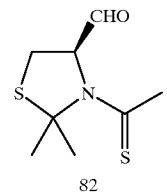
82
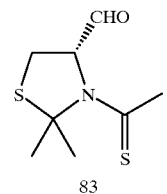
83
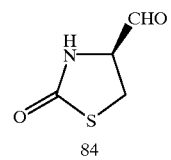
84
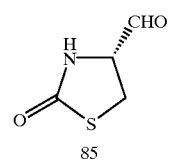
85
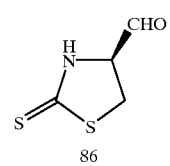
86
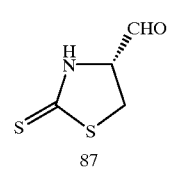
87

TABLE 14-continued

Aldehydes of the type A-CHO 88, 89, 90, 91, 92, 93, 94, 95, 96, 97, 98, 99, 100, 101, 102, 103

TABLE 14-continued
Aldehydes of the type A-CHO
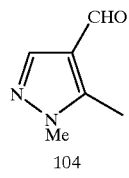
104
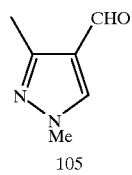
105
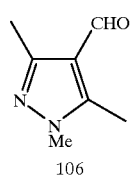
106
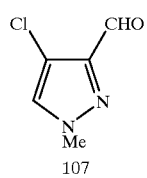
107
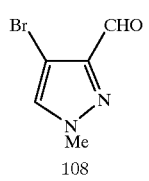
108
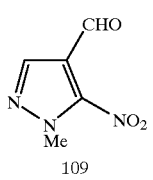
109
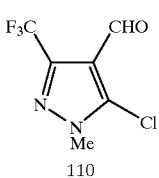
110
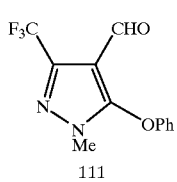
111
TABLE 14-continued
Aldehydes of the type A-CHO
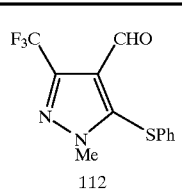
112
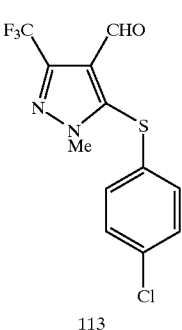
113
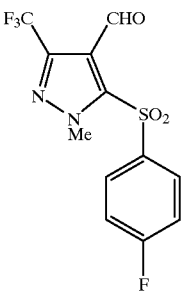
114
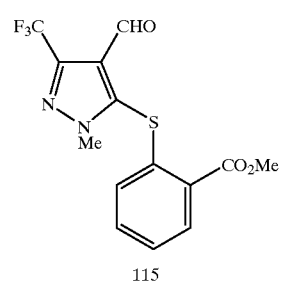
115
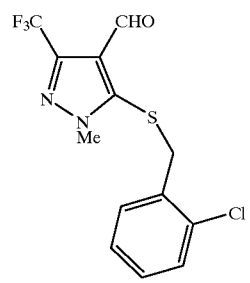
116

TABLE 14-continued
Aldehydes of the type A-CHO
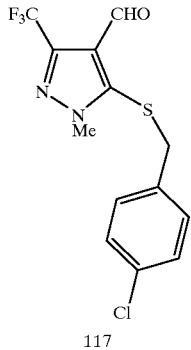
117
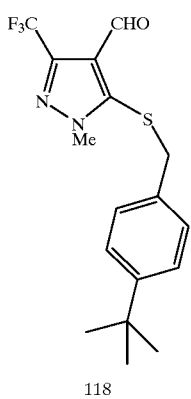
118
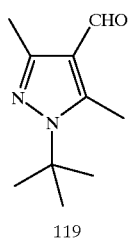
119
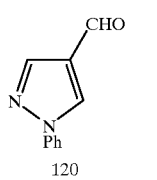
120
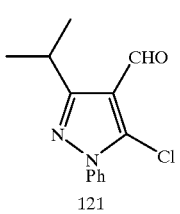
121
TABLE 14-continued
Aldehydes of the type A-CHO
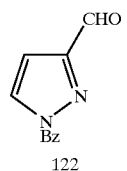
122
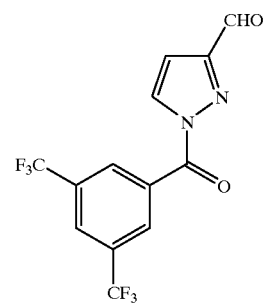
123
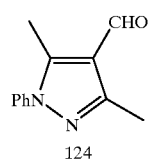
124
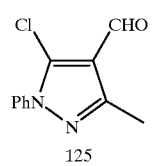
125
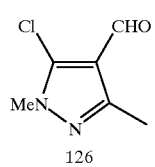
126
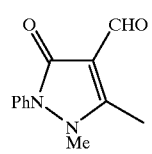
127
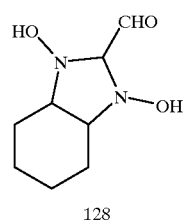
128

TABLE 14-continued
Aldehydes of the type A-CHO
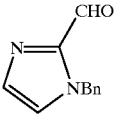
129
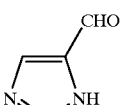
130
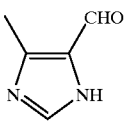
131
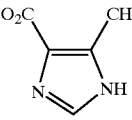
132
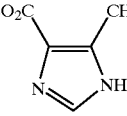
133
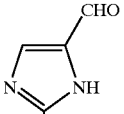
134
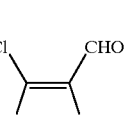
135
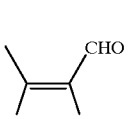
136
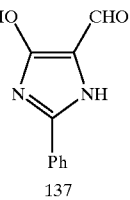
137
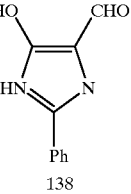
138
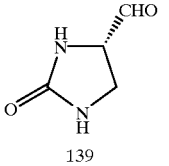
139
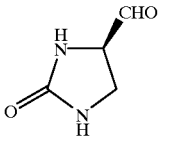
140
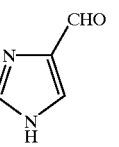
141
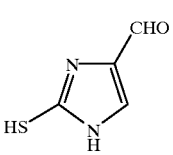
142
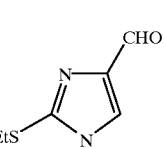
143
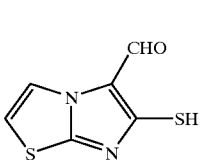
144

TABLE 14-continued
Aldehydes of the type A-CHO
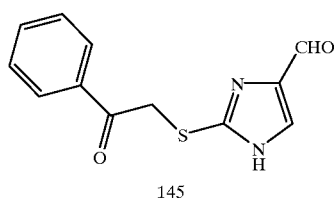
145
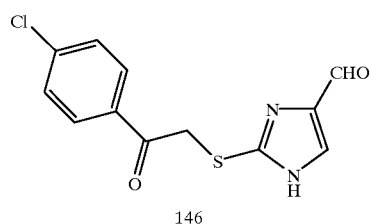
146
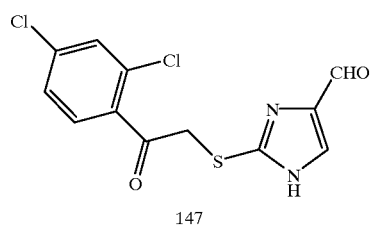
147
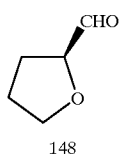
148
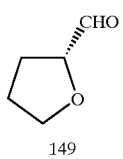
149
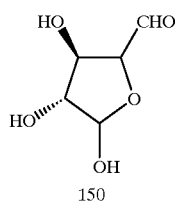
150
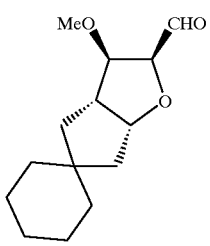
151
TABLE 14-continued
Aldehydes of the type A-CHO
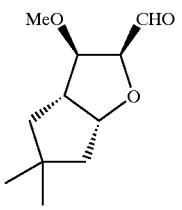
152
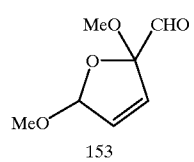
153
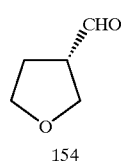
154
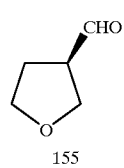
155
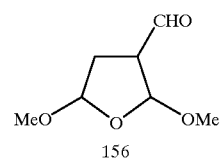
156
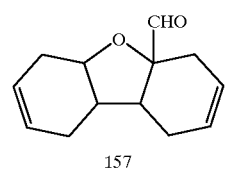
157
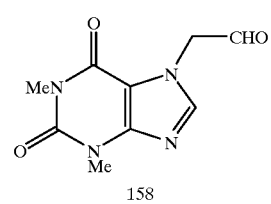
158
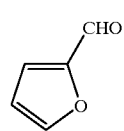
159

TABLE 14-continued
Aldehydes of the type A-CHO
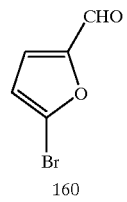
160
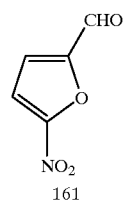
161
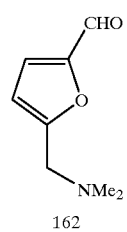
162
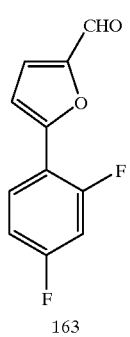
163
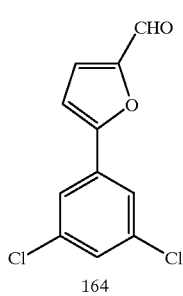
164
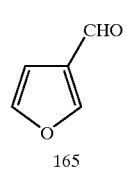
165
TABLE 14-continued
Aldehydes of the type A-CHO
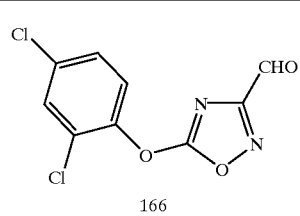
166
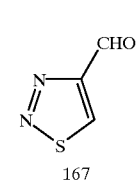
167
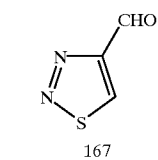
168
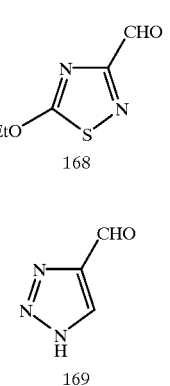
169
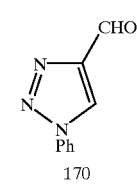
170
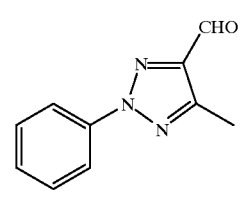
171
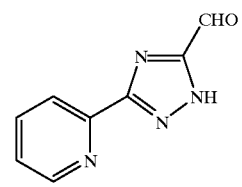
172

TABLE 14-continued
Aldehydes of the type A-CHO
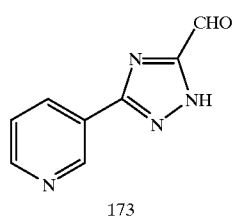
173
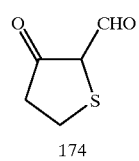
174
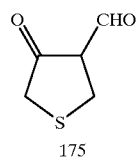
175
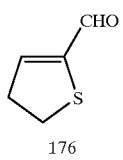
176
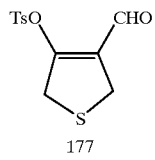
177
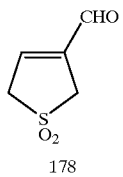
178
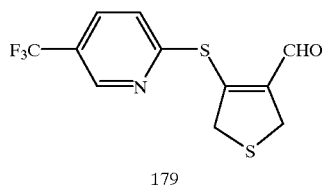
179
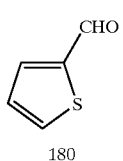
180
TABLE 14-continued
Aldehydes of the type A-CHO
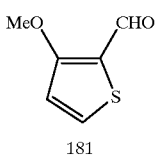
181
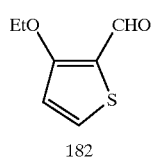
182
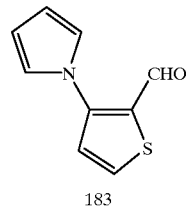
183
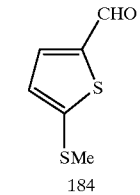
184
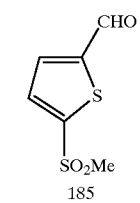
185
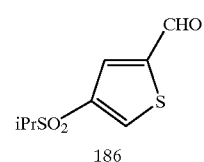
186
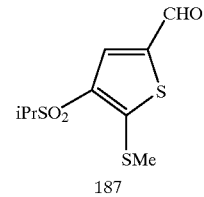
187
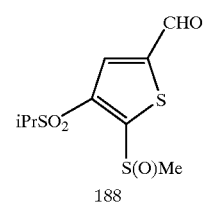
188

TABLE 14-continued
Aldehydes of the type A-CHO
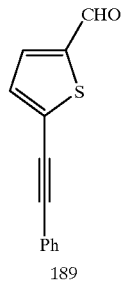
189
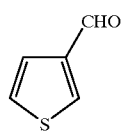
190
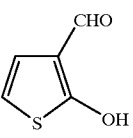
191
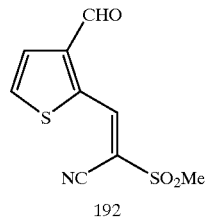
192
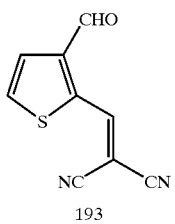
193
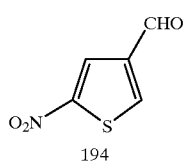
194
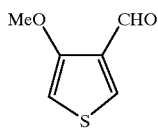
195
TABLE 14-continued
Aldehydes of the type A-CHO
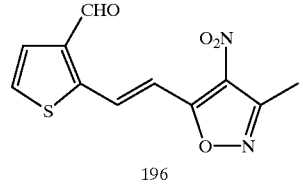
196
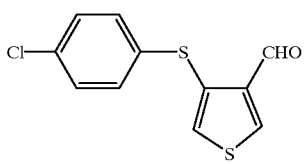
197
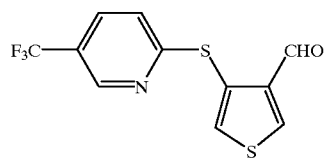
198
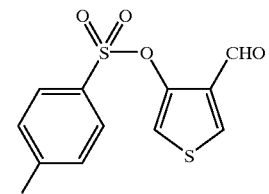
199
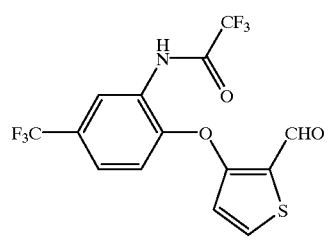
200
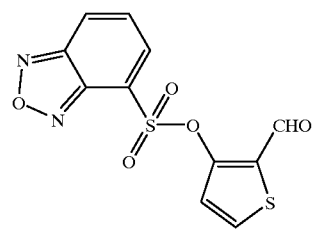
201

TABLE 14-continued
Aldehydes of the type A-CHO
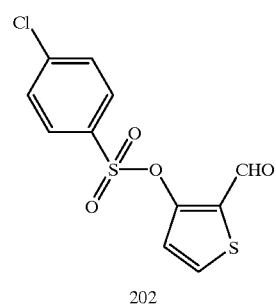
202
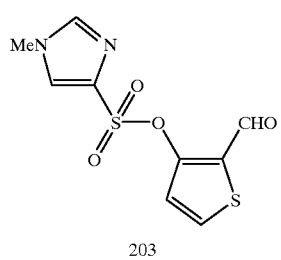
203
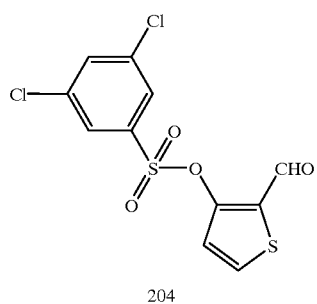
204
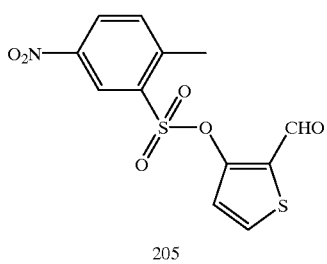
205
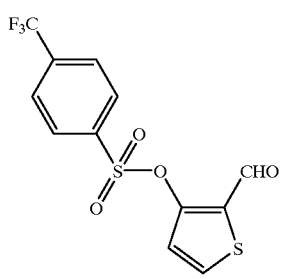
206
TABLE 14-continued
Aldehydes of the type A-CHO
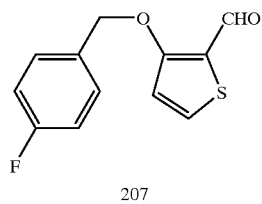
207
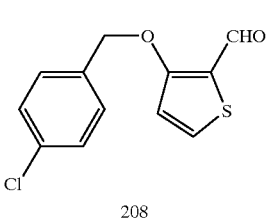
208
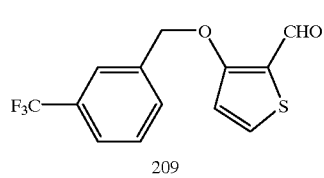
209
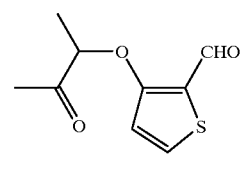
210
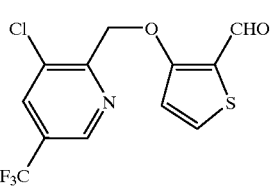
211
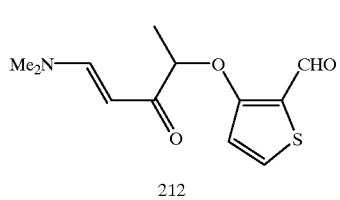
212
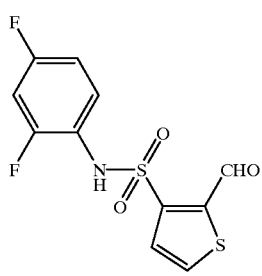
213

TABLE 14-continued
Aldehydes of the type A-CHO
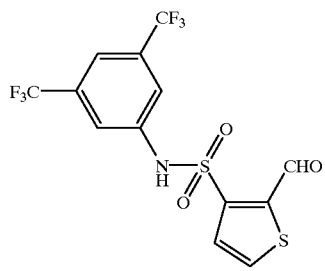
214
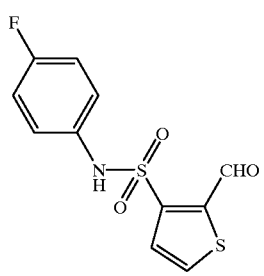
215
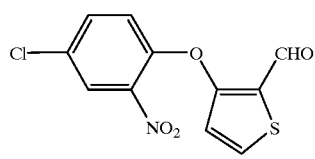
216
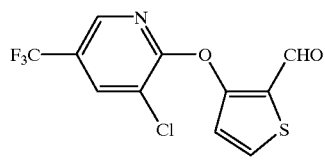
217
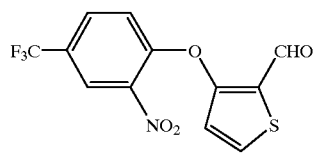
218
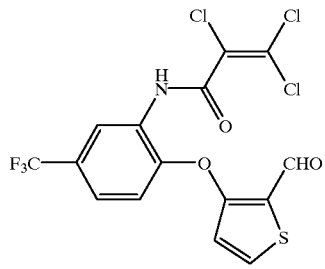
219
TABLE 14-continued
Aldehydes of the type A-CHO
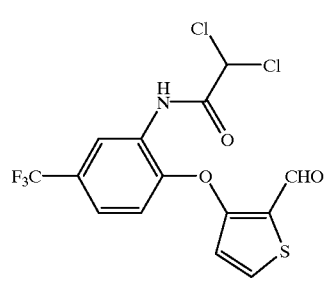
220
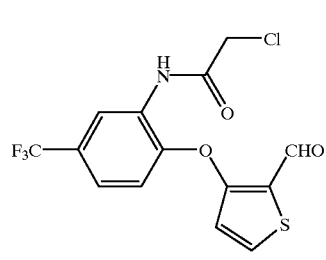
221
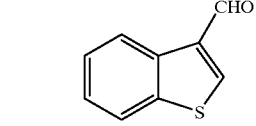
222
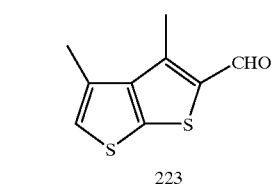
223
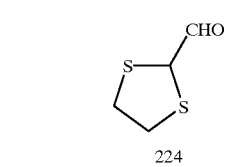
224
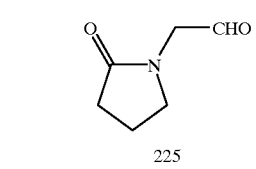
225
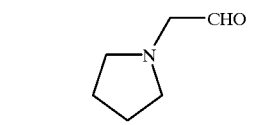
226

TABLE 14-continued
Aldehydes of the type A-CHO
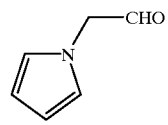
227
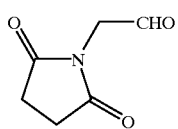
228
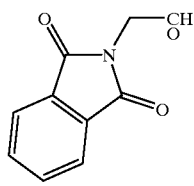
229
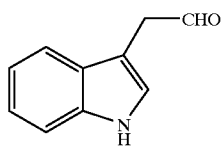
230
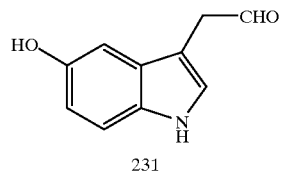
231
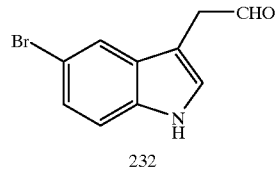
232
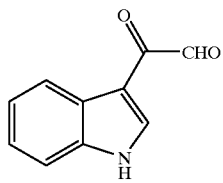
233
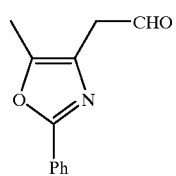
234
TABLE 14-continued
Aldehydes of the type A-CHO
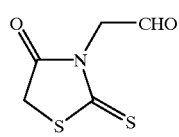
235
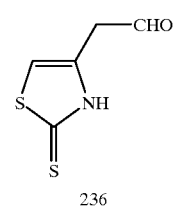
236
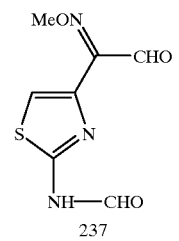
237
238
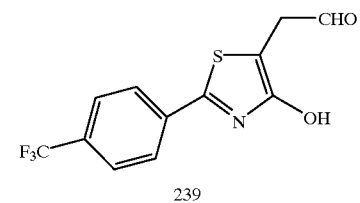
239
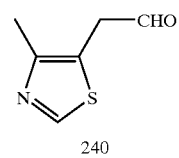
240
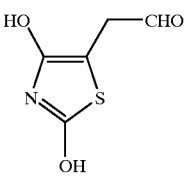
241

TABLE 14-continued
Aldehydes of the type A-CHO
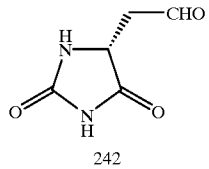
242
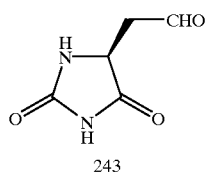
243
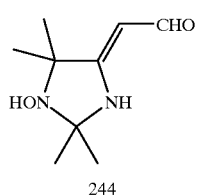
244
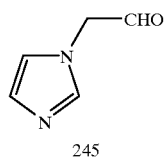
245
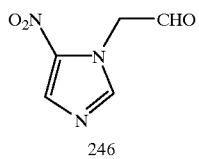
246
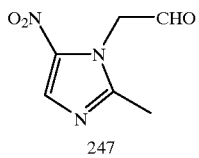
247
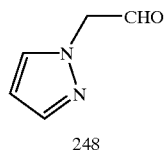
248
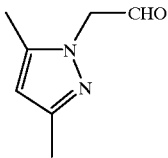
249
TABLE 14-continued
Aldehydes of the type A-CHO
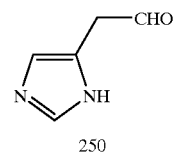
250
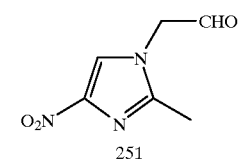
251
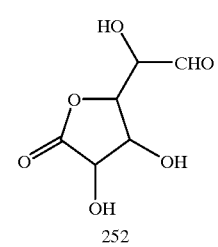
252
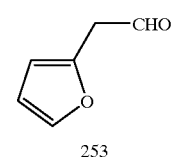
253
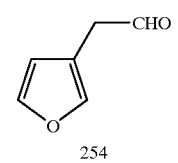
254
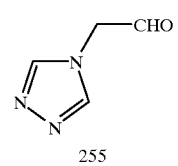
255
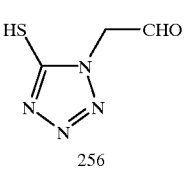
256
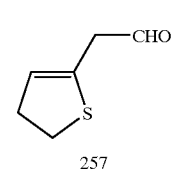
257

TABLE 14-continued
Aldehydes of the type A-CHO
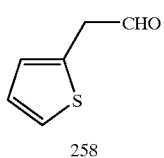
258
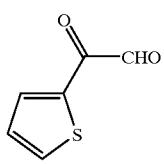
259
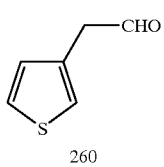
260
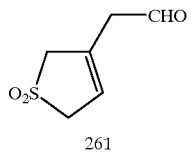
261
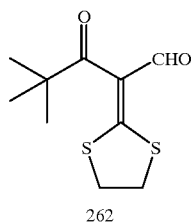
262
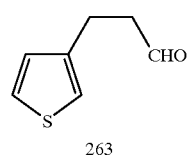
263
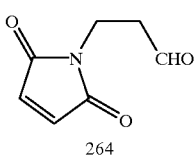
264
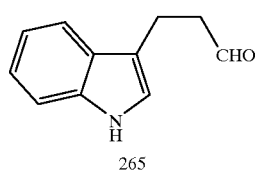
265
TABLE 14-continued
Aldehydes of the type A-CHO
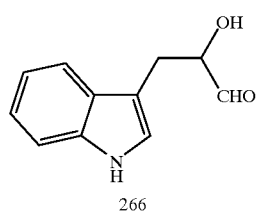
266
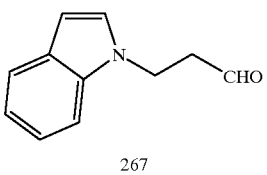
267
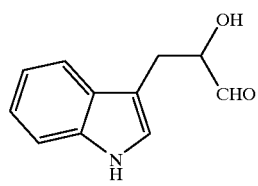
268
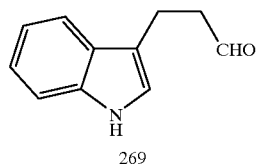
269
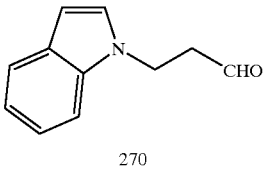
270
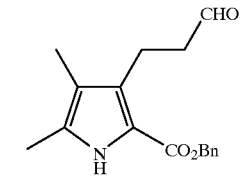
271
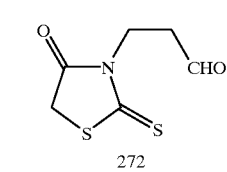
272
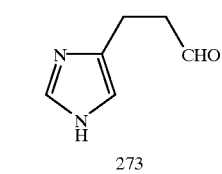
273

TABLE 14-continued
Aldehydes of the type A-CHO
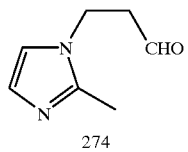
274
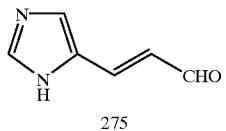
275
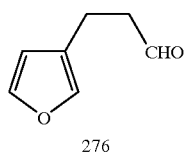
276
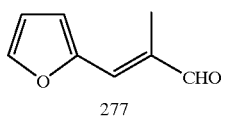
277
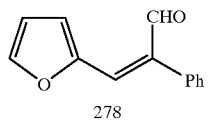
278
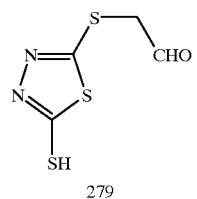
279
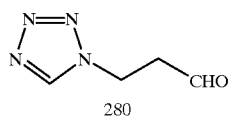
280
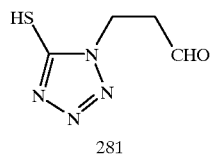
281
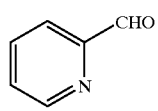
282
TABLE 14-continued
Aldehydes of the type A-CHO
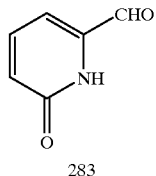
283
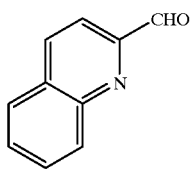
284
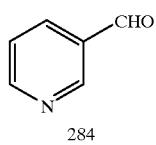
284
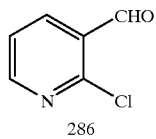
286
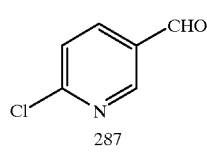
287
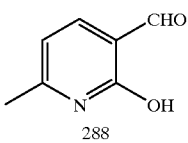
288
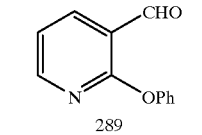
289
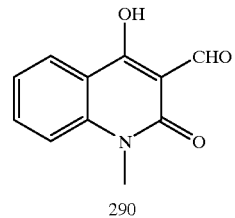
290

TABLE 14-continued
Aldehydes of the type A-CHO
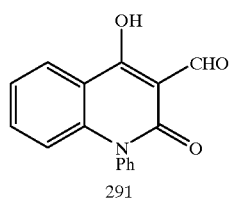
291
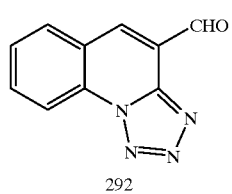
292
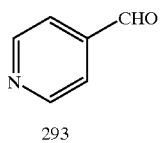
293
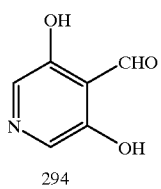
294
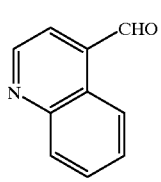
295
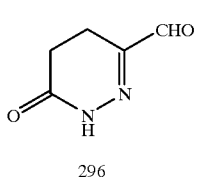
296
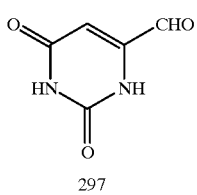
297
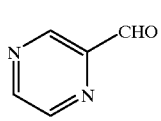
298
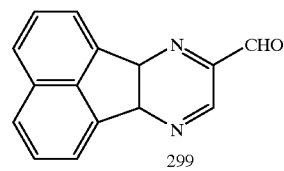
299
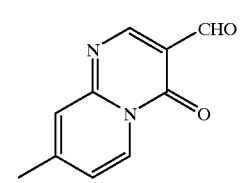
300
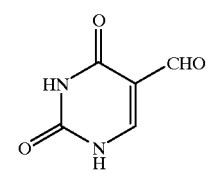
301
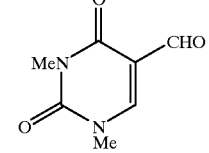
302
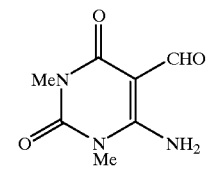
303
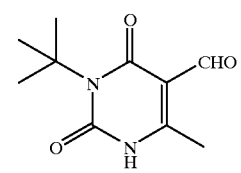
304
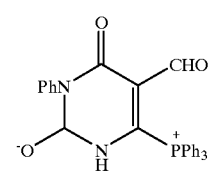
305

TABLE 14-continued
Aldehydes of the type A-CHO
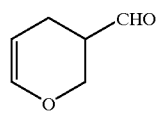
306
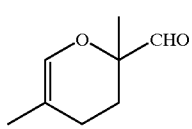
307
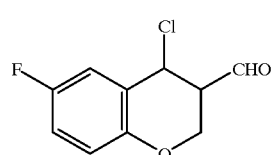
308
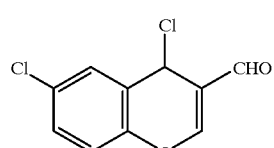
309
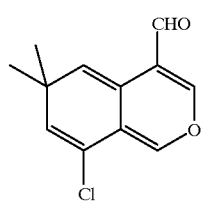
310
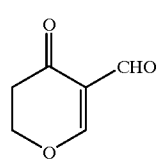
311
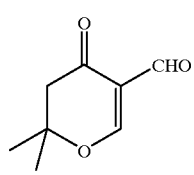
312
TABLE 14-continued
Aldehydes of the type A-CHO
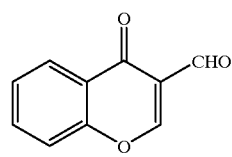
313
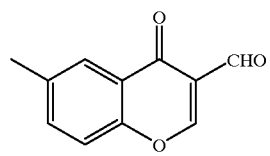
314
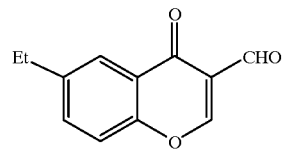
315
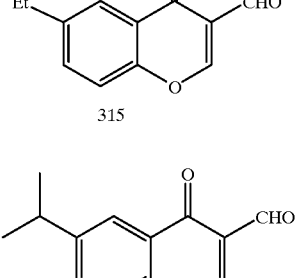
316
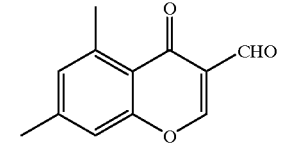
317
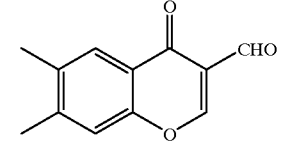
318
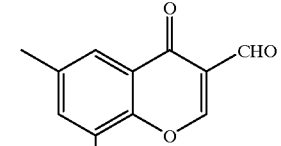
319

TABLE 14-continued
Aldehydes of the type A-CHO
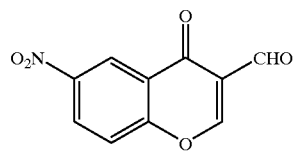
320
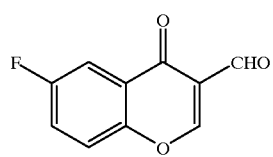
321
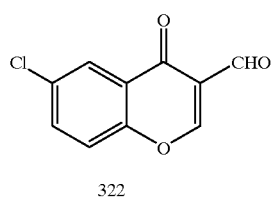
322
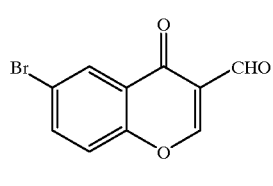
323
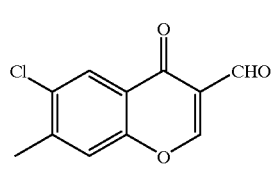
324
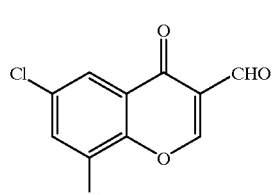
325
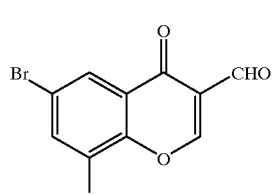
326
TABLE 14-continued
Aldehydes of the type A-CHO
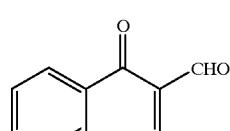
327
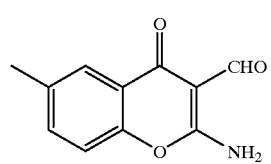
328
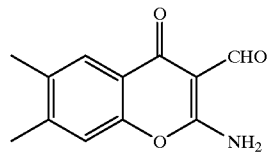
329
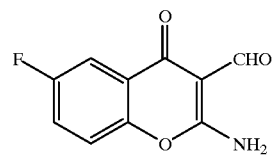
330
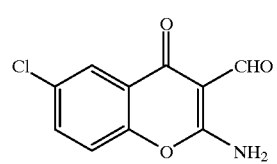
331
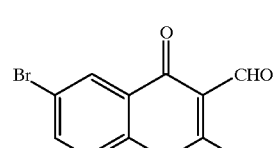
332
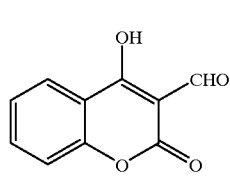
333

TABLE 14-continued
Aldehydes of the type A-CHO
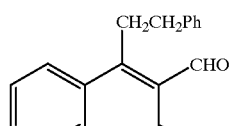
334
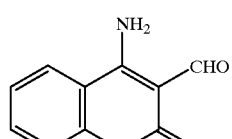
335
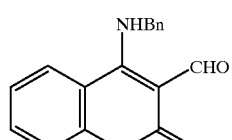
336
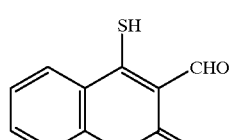
337
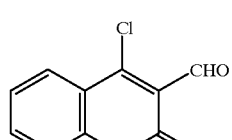
338
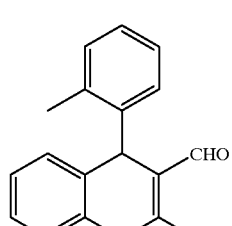
339
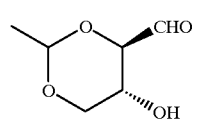
340
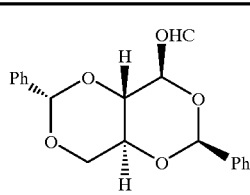
341
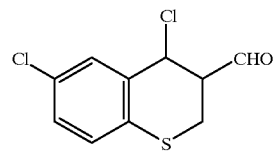
342
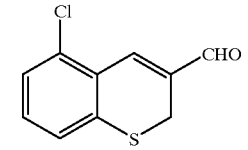
343
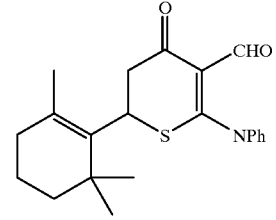
344
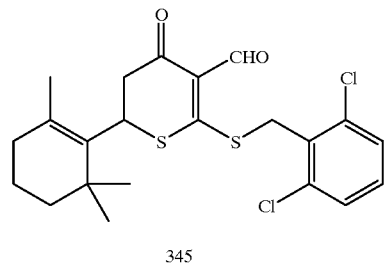
345
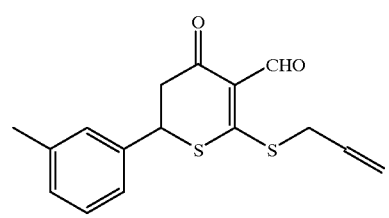
346

TABLE 14-continued

Aldehydes of the type A-CHO

347

348

349

350

351

352

353

354

355

356

357

358

359

TABLE 14-continued
Aldehydes of the type A-CHO
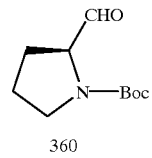
360
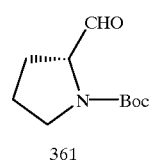
361
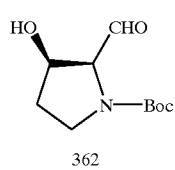
362
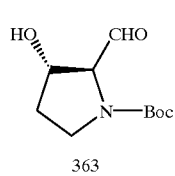
363
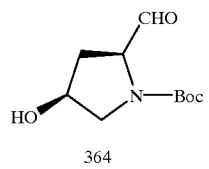
364
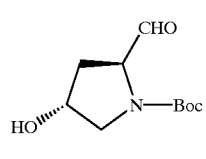
365
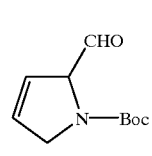
366
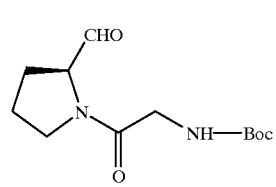
367
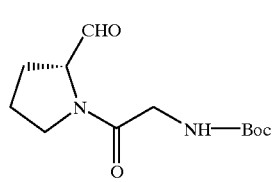
368
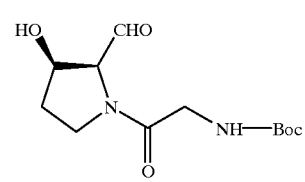
369
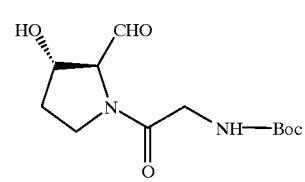
370
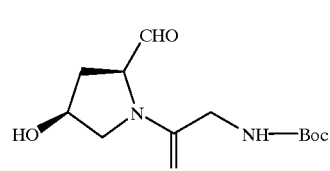
371
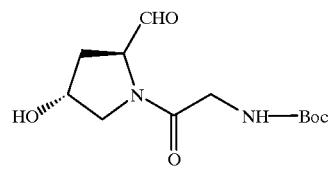
372
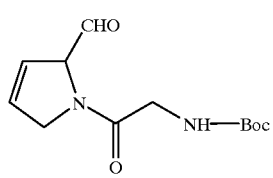
373

TABLE 14-continued
Aldehydes of the type A-CHO
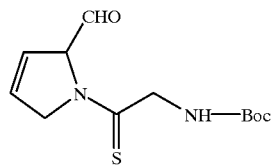
374
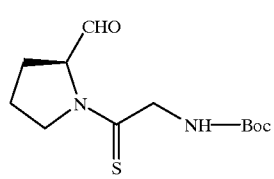
375
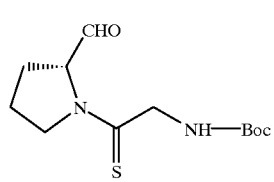
376
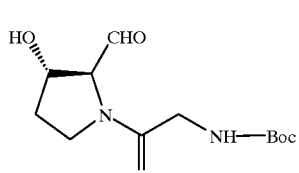
377
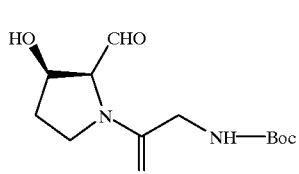
378
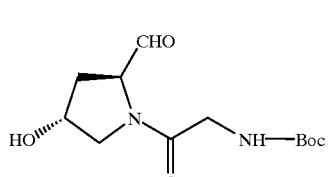
379
TABLE 14-continued
Aldehydes of the type A-CHO
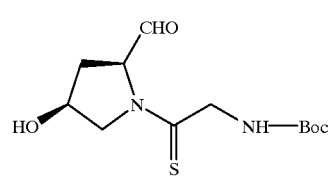
380
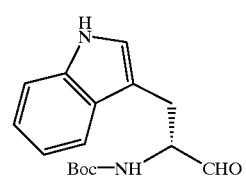
381
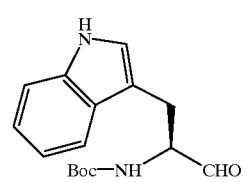
382
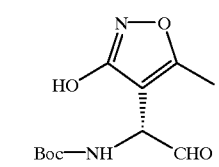
383
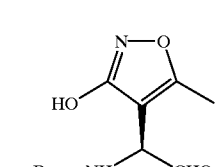
384
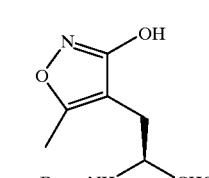
385

TABLE 14-continued
Aldehydes of the type A-CHO
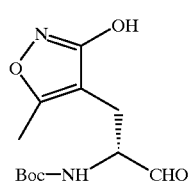
386
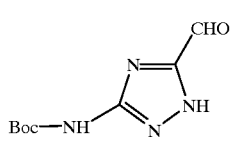
387
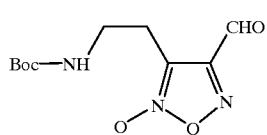
388
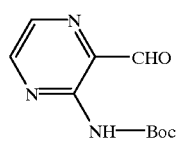
389
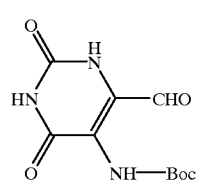
390
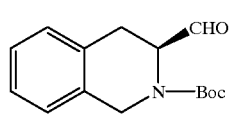
391
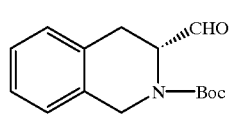
392
TABLE 14-continued
Aldehydes of the type A-CHO
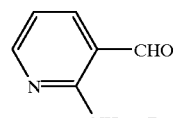
393
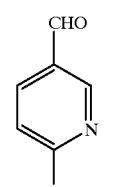
394
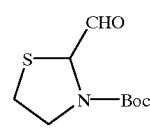
395
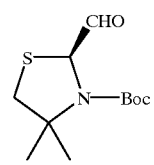
396
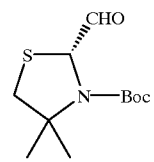
397
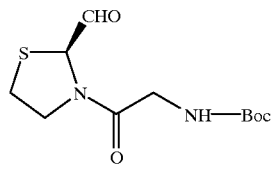
398
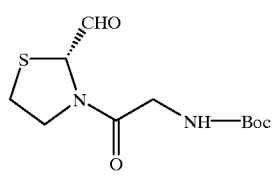
399

TABLE 14-continued
Aldehydes of the type A-CHO
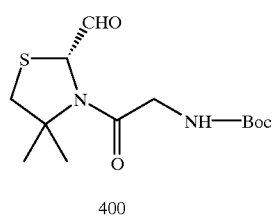
400
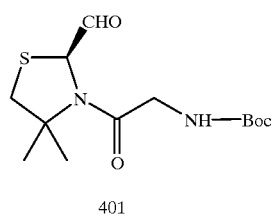
401
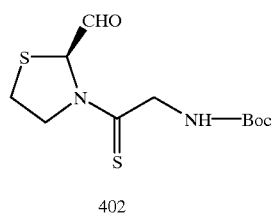
402
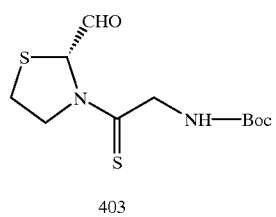
403
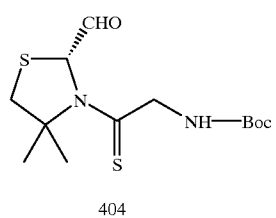
404
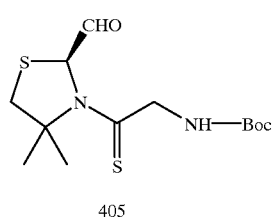
405
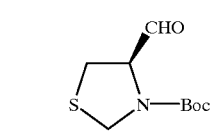
406
TABLE 14-continued
Aldehydes of the type A-CHO
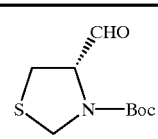
407
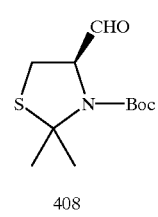
408
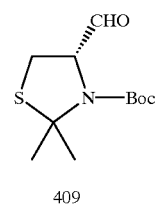
409
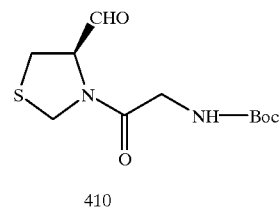
410
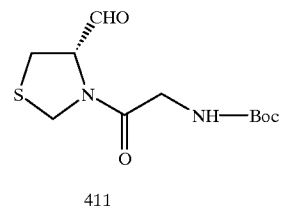
411
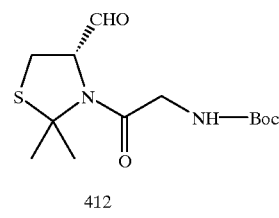
412
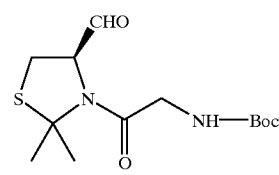
413

TABLE 14-continued
Aldehydes of the type A-CHO
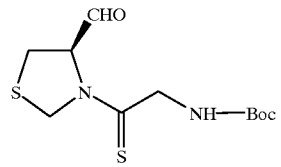
414
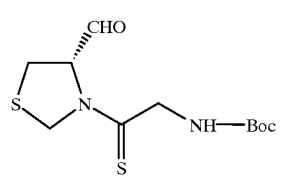
415
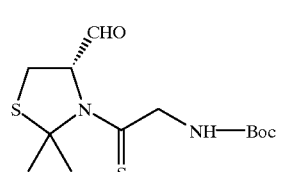
416
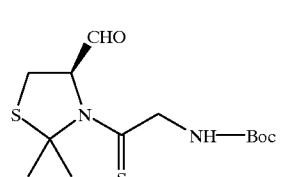
417
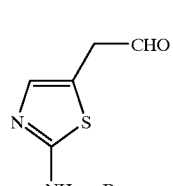
418
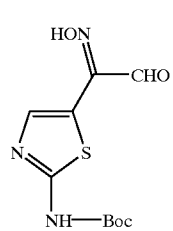
419
TABLE 14-continued
Aldehydes of the type A-CHO
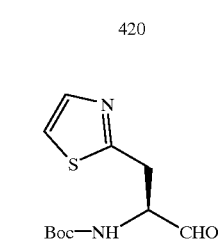
420
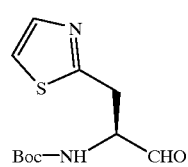
421
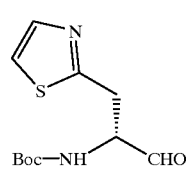
422
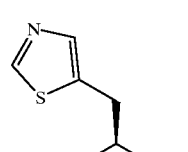
423
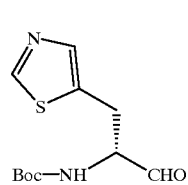
424
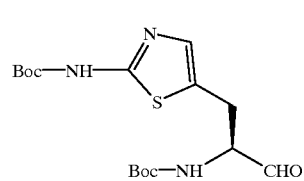
425

TABLE 14-continued
Aldehydes of the type A-CHO
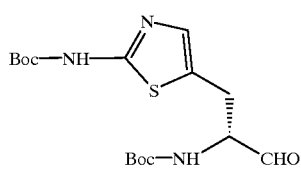
426
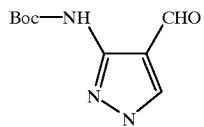
427
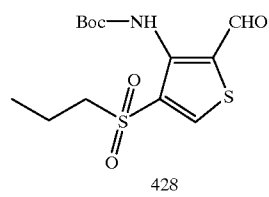
428
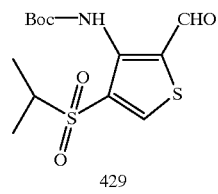
429
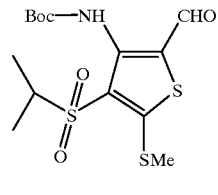
430
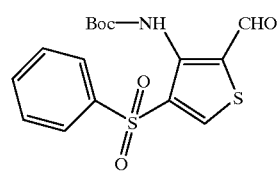
431
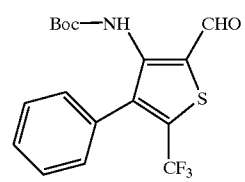
432
TABLE 14-continued
Aldehydes of the type A-CHO
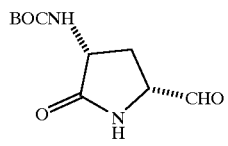
433
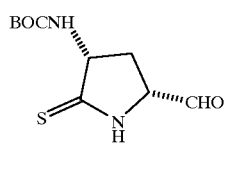
434
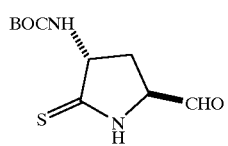
435
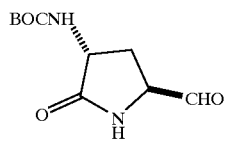
436
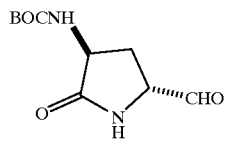
437
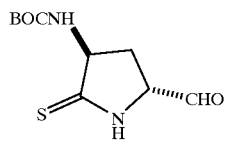
438
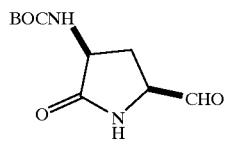
439

TABLE 14-continued
Aldehydes of the type A-CHO
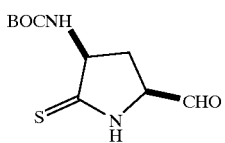
440
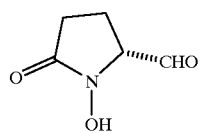
441
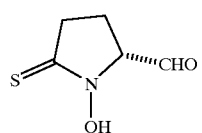
442
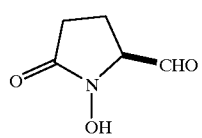
443
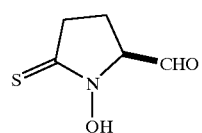
444
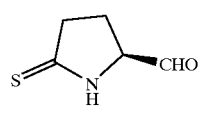
445
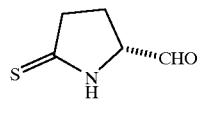
446
TABLE 15
Alcohols of the type A-OH
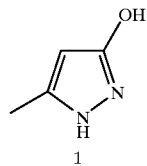
1
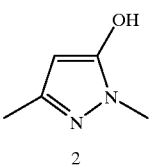
2
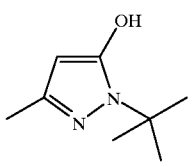
3
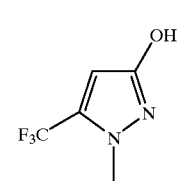
4
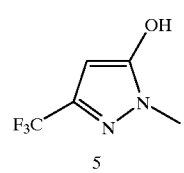
5
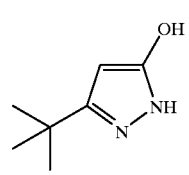
6
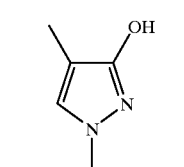
7
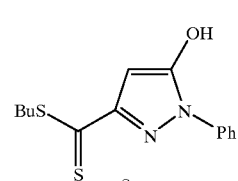
8

TABLE 15-continued
Alcohols of the type A-OH
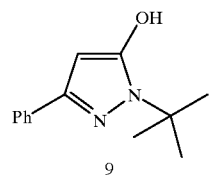
9
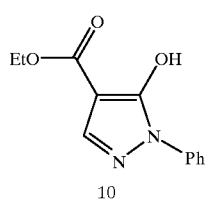
10
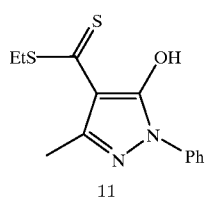
11
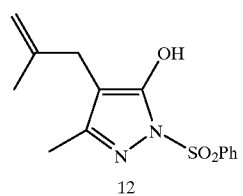
12
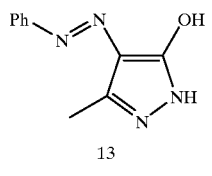
13
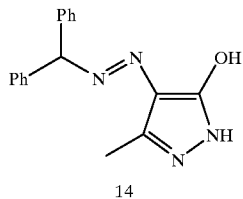
14
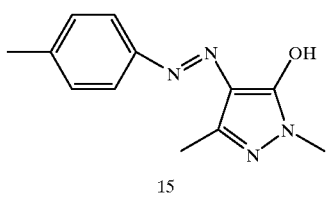
15
TABLE 15-continued
Alcohols of the type A-OH
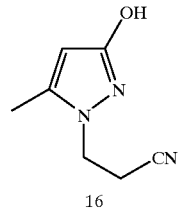
16
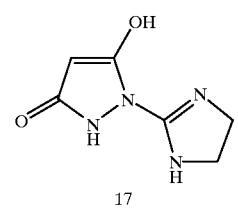
17
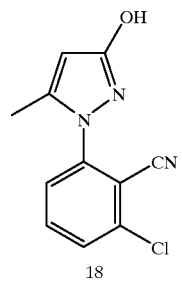
18
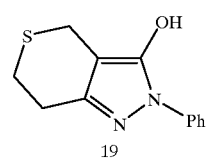
19
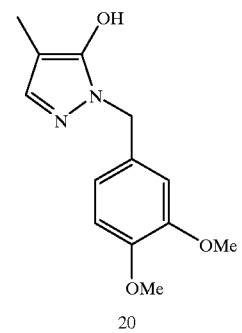
20
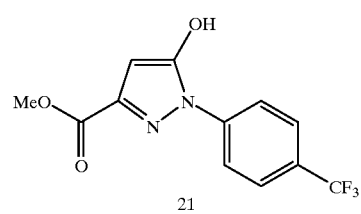
21

TABLE 15-continued
Alcohols of the type A-OH
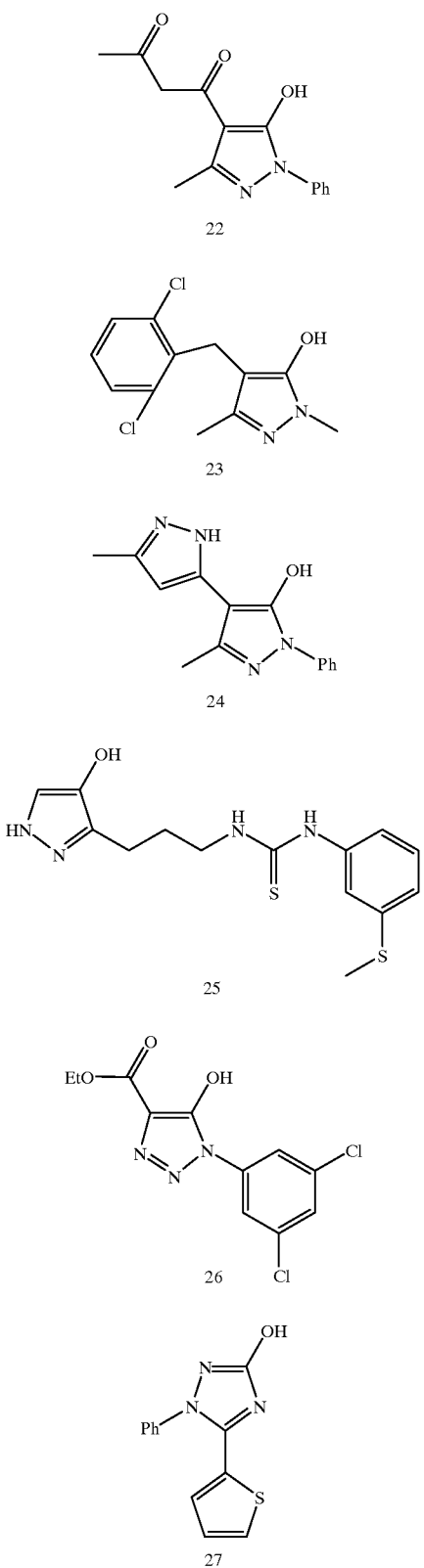
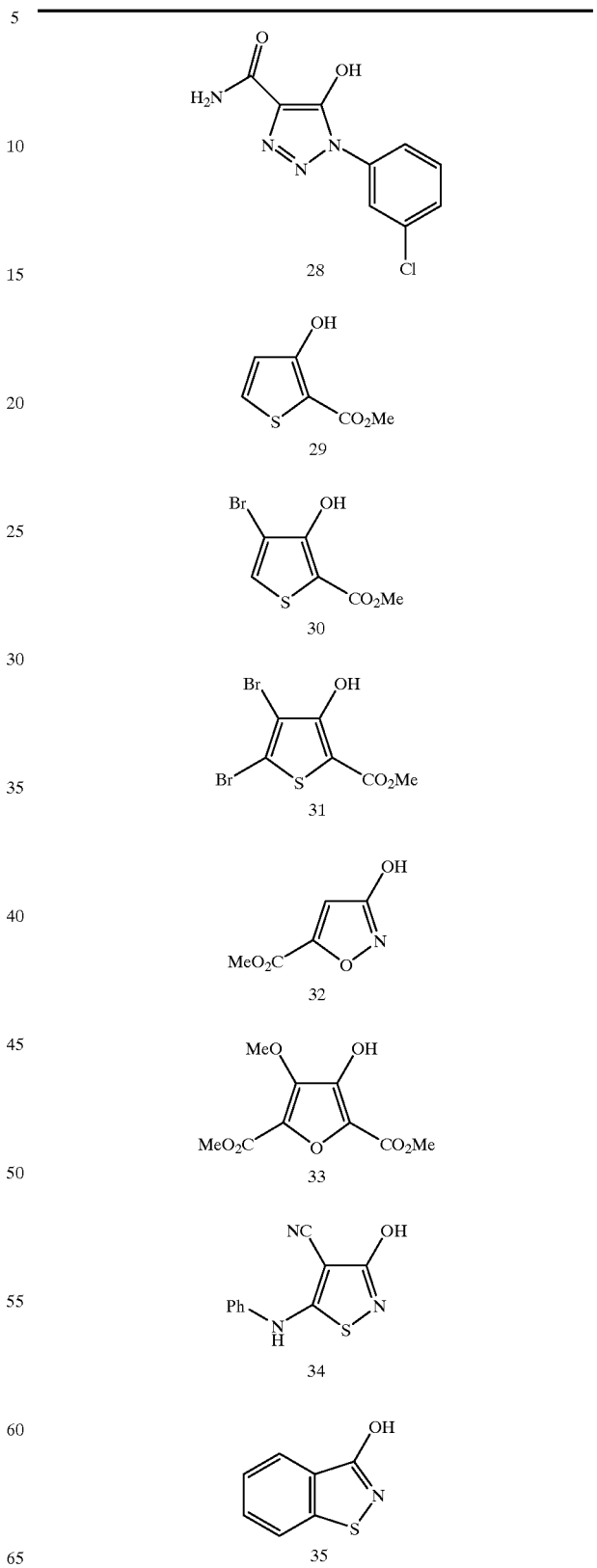

TABLE 15-continued
Alcohols of the type A-OH
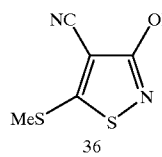
36
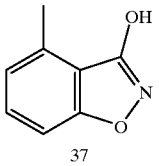
37
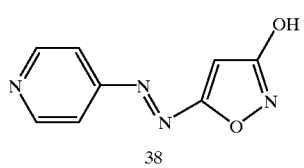
38
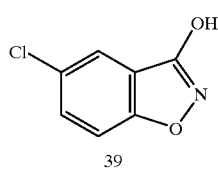
39
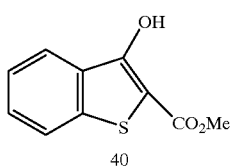
40
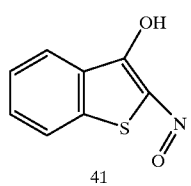
41
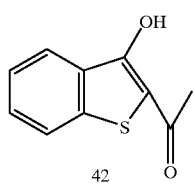
42
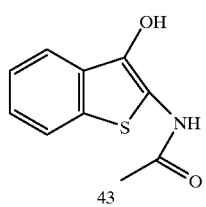
43
TABLE 15-continued
Alcohols of the type A-OH
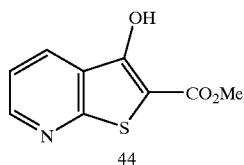
44
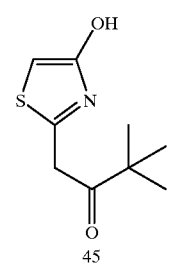
45
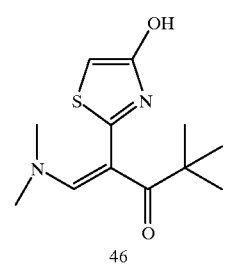
46
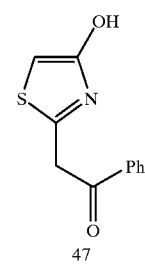
47
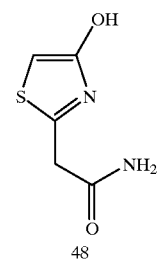
48
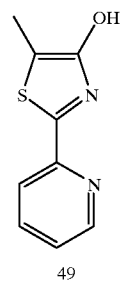
49

TABLE 15-continued
Alcohols of the type A-OH
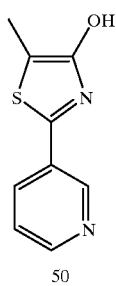
50
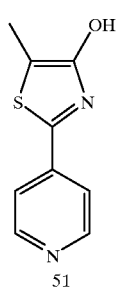
51
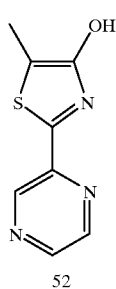
52
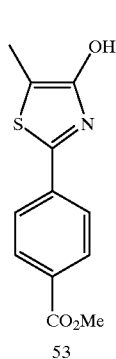
53
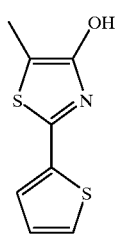
54
TABLE 15-continued
Alcohols of the type A-OH
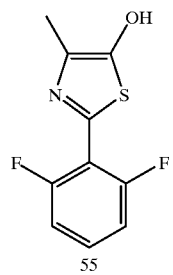
55
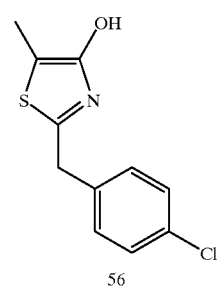
56
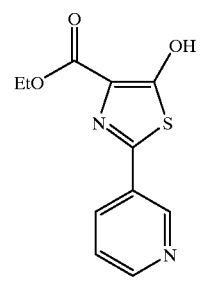
57
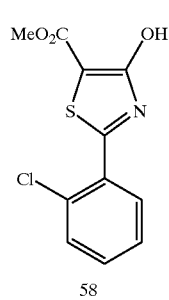
58
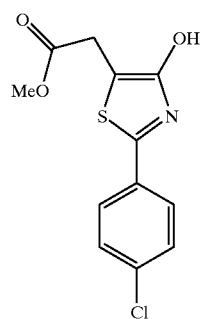
59

TABLE 15-continued
Alcohols of the type A-OH
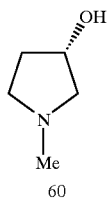
60
61
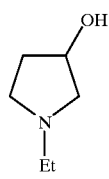
62
63
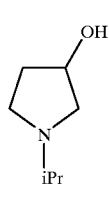
64
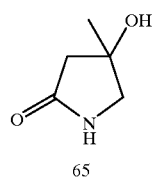
65
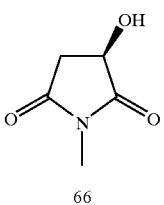
66
TABLE 15-continued
Alcohols of the type A-OH
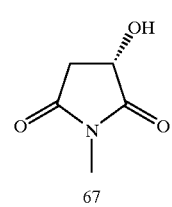
67
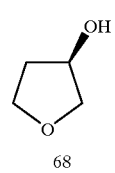
68
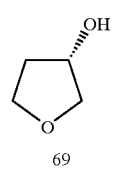
69
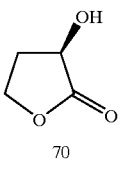
70
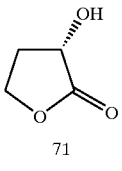
71
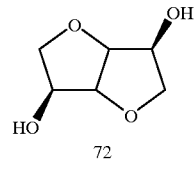
72
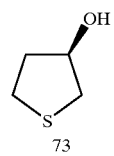
73
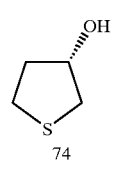
74

TABLE 15-continued
Alcohols of the type A-OH
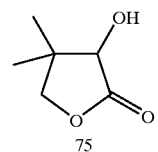
75
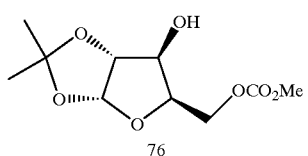
76
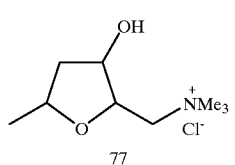
77
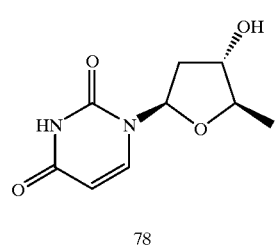
78
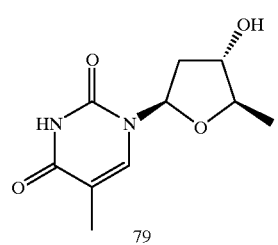
79
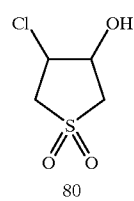
80
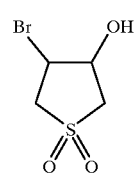
81
TABLE 15-continued
Alcohols of the type A-OH
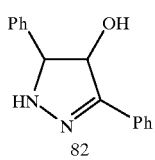
82
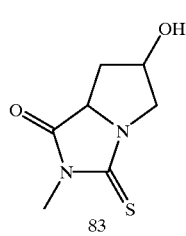
83
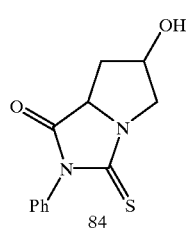
84
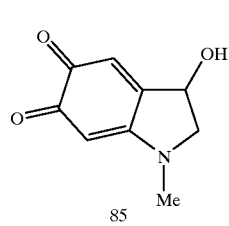
85
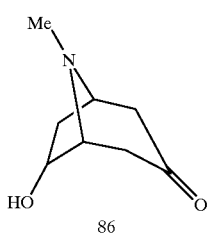
86
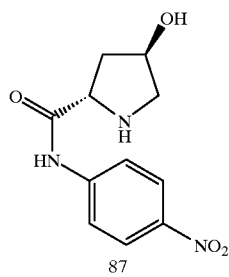
87

TABLE 15-continued
Alcohols of the type A-OH
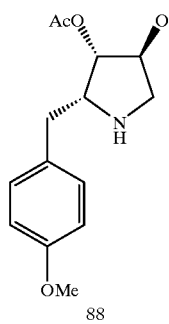
88
89
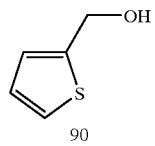
90
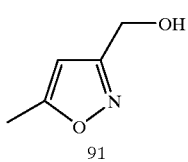
91
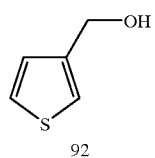
92
93
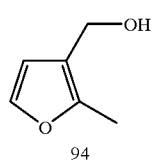
94
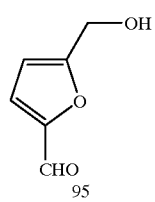
95
TABLE 15-continued
Alcohols of the type A-OH
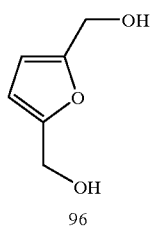
96
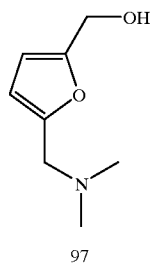
97
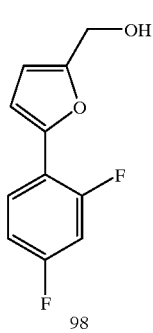
98
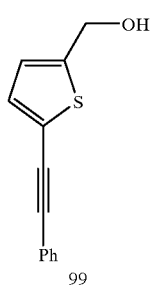
99
100
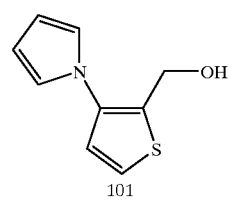
101

TABLE 15-continued
Alcohols of the type A-OH
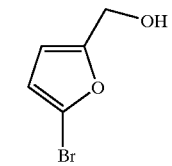
102
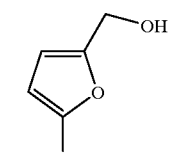
103
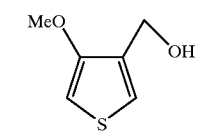
104
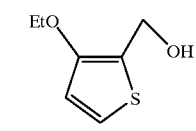
105
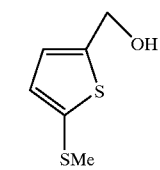
106
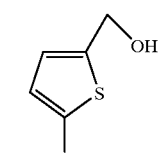
107
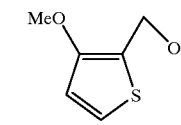
108
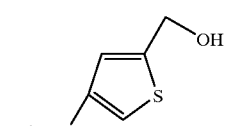
109
TABLE 15-continued
Alcohols of the type A-OH
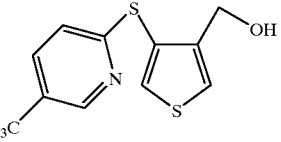
110
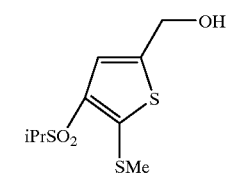
111
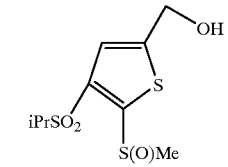
112
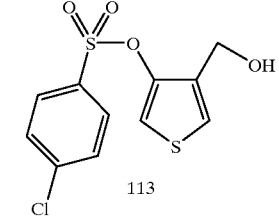
113
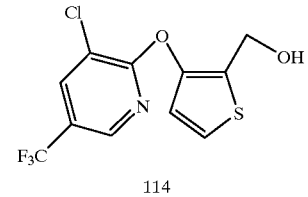
114
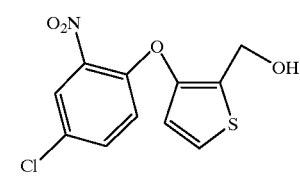
115
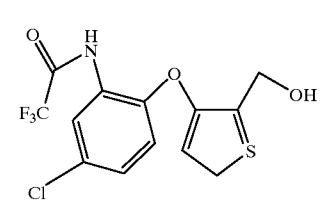
116

TABLE 15-continued
Alcohols of the type A-OH
117
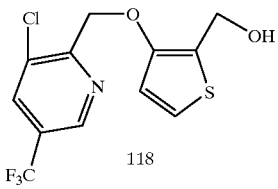
118
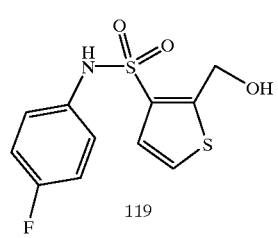
119
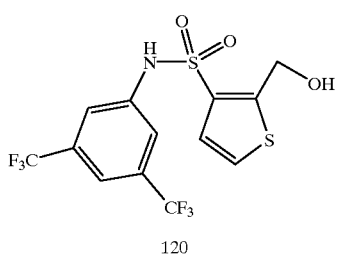
120
121
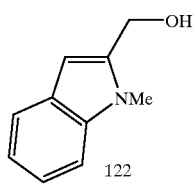
122
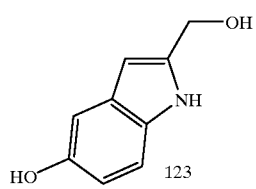
123
TABLE 15-continued
Alcohols of the type A-OH
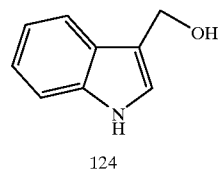
124
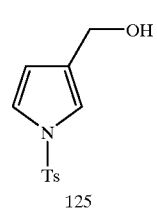
125
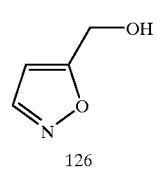
126
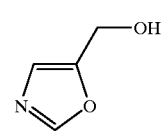
127
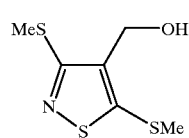
128
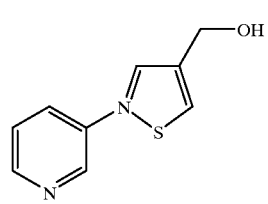
129
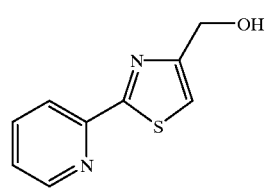
130

TABLE 15-continued
Alcohols of the type A-OH
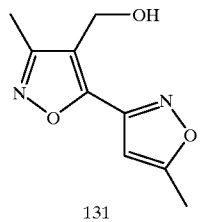
131
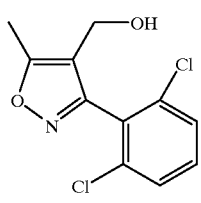
132
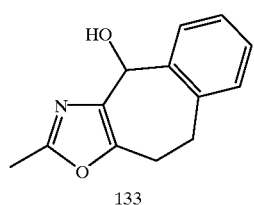
133
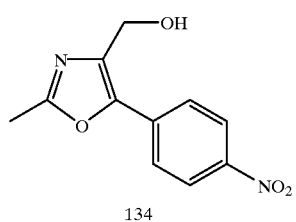
134
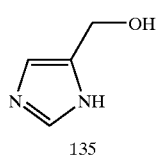
135
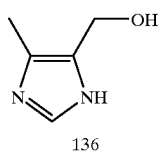
136
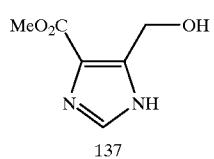
137
TABLE 15-continued
Alcohols of the type A-OH
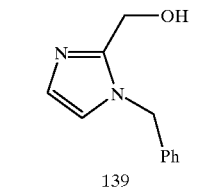
138
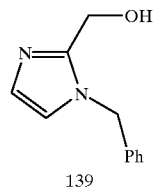
139
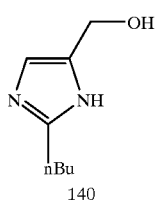
140
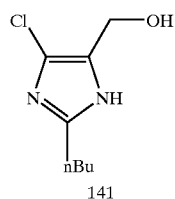
141
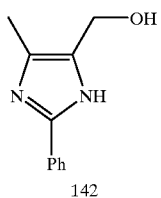
142
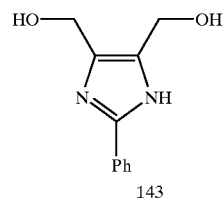
143
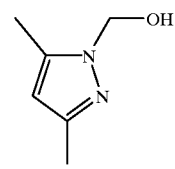
144

TABLE 15-continued
Alcohols of the type A-OH
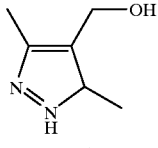
145
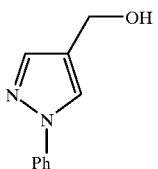
146
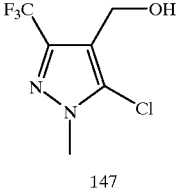
147
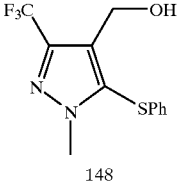
148
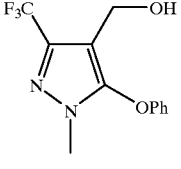
149
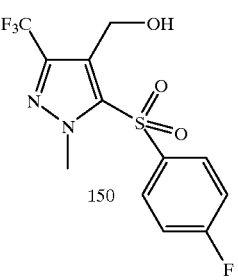
150
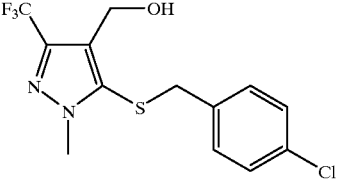
151
TABLE 15-continued
Alcohols of the type A-OH
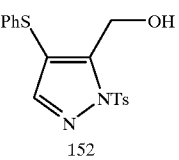
152
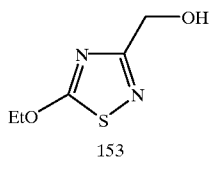
153
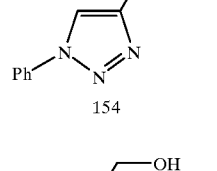
154
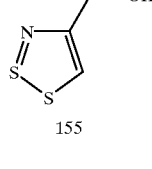
155
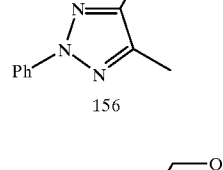
156
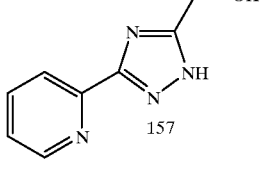
157
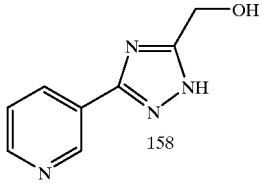
158
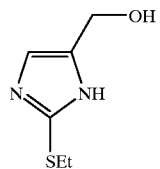
159

TABLE 15-continued
Alcohols of the type A-OH
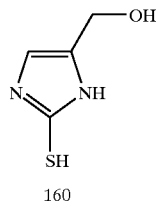
160
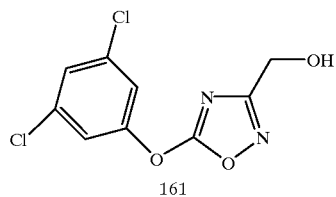
161
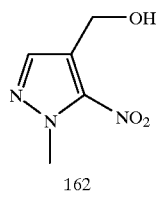
162
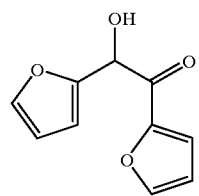
163
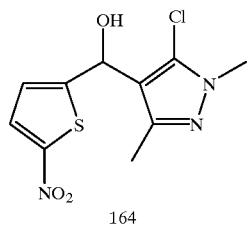
164
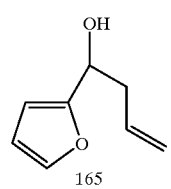
165
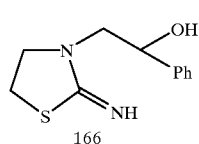
166
TABLE 15-continued
Alcohols of the type A-OH
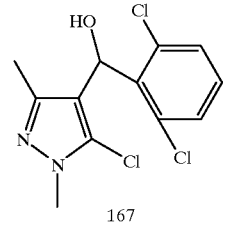
167
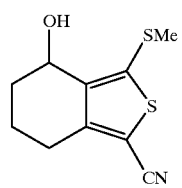
168
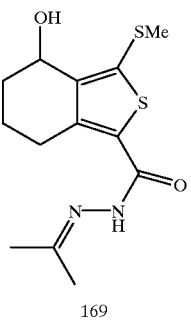
169
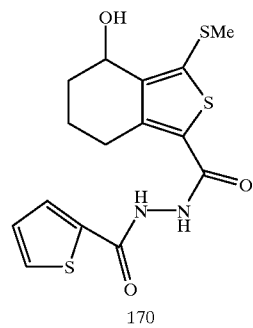
170
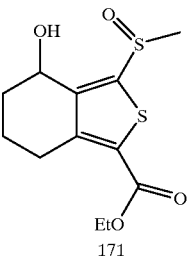
171

TABLE 15-continued
Alcohols of the type A-OH
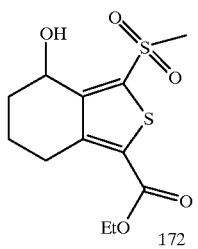
172
173
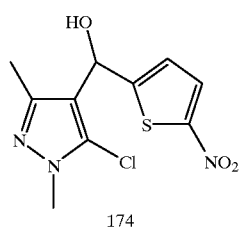
174
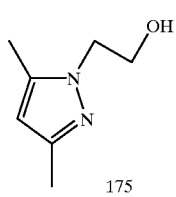
175
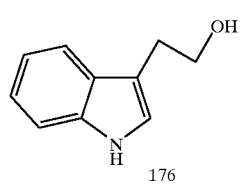
176
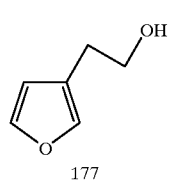
177
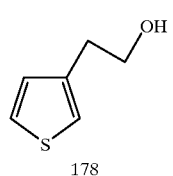
178
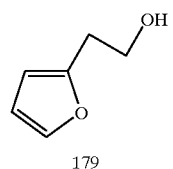
179
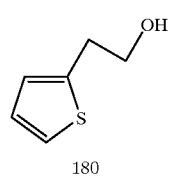
180
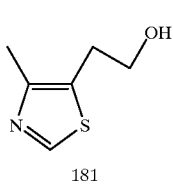
181
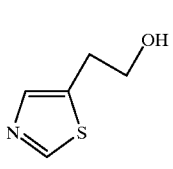
182
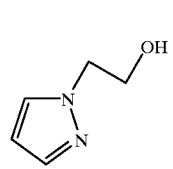
183
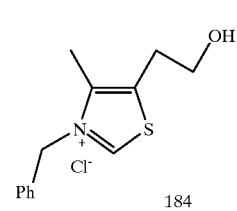
184
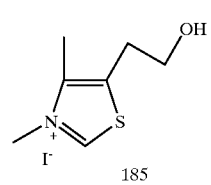
185
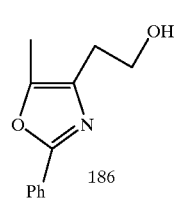
186

TABLE 15-continued
Alcohols of the type A-OH
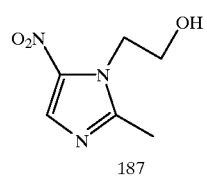
187
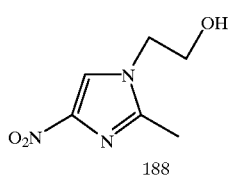
188
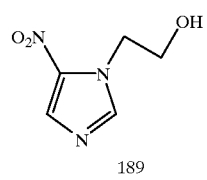
189
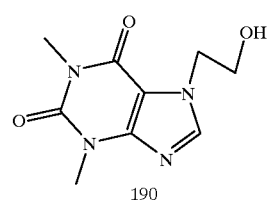
190
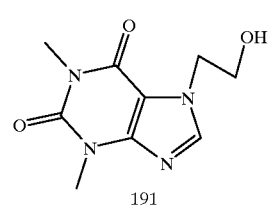
191
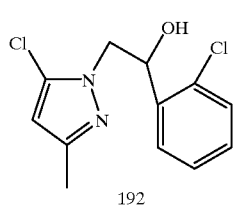
192
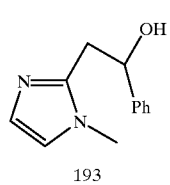
193
TABLE 15-continued
Alcohols of the type A-OH
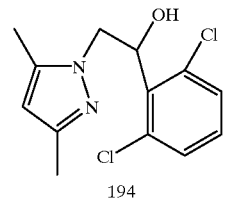
194
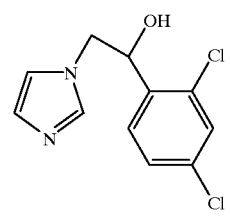
195
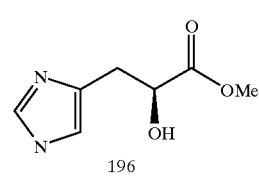
196
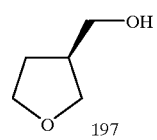
197
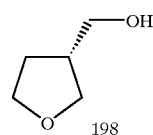
198
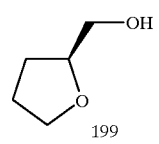
199
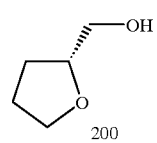
200
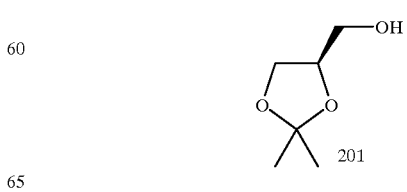
201

TABLE 15-continued

Alcohols of the type A-OH 202, 203, 204, 205, 206, 207, 208, 209, 210, 211, 212, 213, 214

TABLE 15-continued
Alcohols of the type A-OH
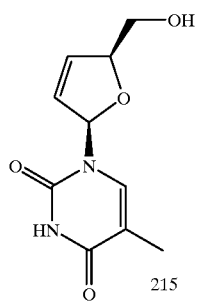
215
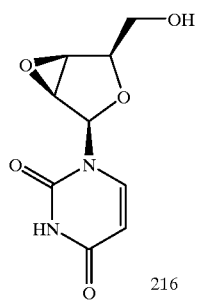
216
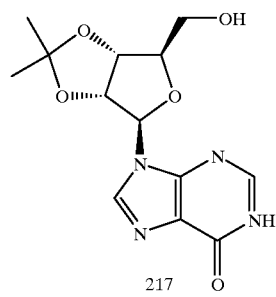
217
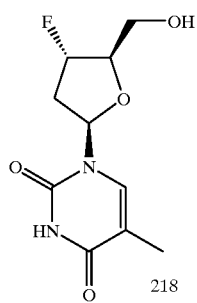
218
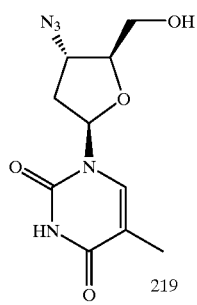
219
TABLE 15-continued
Alcohols of the type A-OH
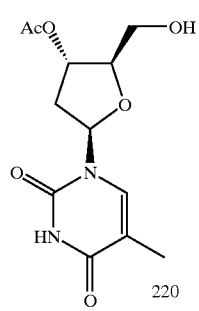
220
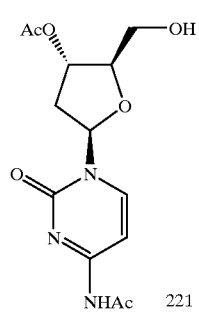
221
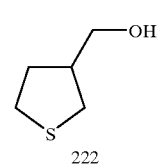
222
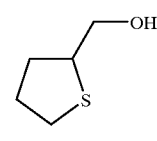
223
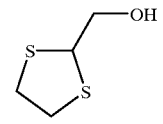
224
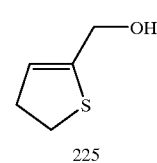
225
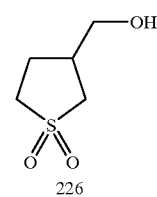
226

TABLE 15-continued
Alcohols of the type A-OH

TABLE 15-continued

Alcohols of the type A-OH (Structures 242–256 depicted)

TABLE 15-continued

Alcohols of the type A-OH 257, 258, 259, 260, 261, 262, 263, 264, 265, 266, 267, 268, 269, 270, 271, 272

TABLE 15-continued
Alcohols of the type A-OH
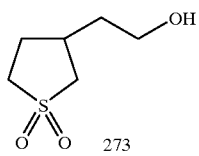
273
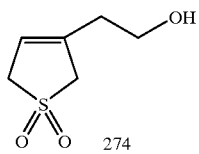
274
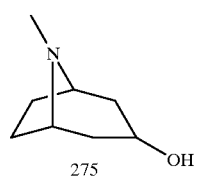
275
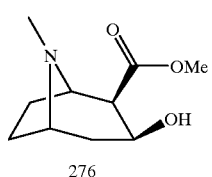
276
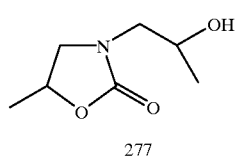
277
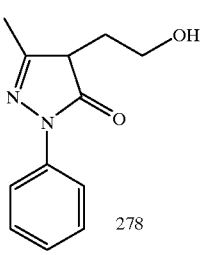
278
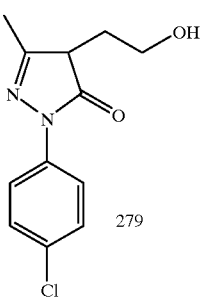
279
TABLE 15-continued
Alcohols of the type A-OH
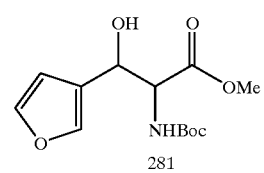
280
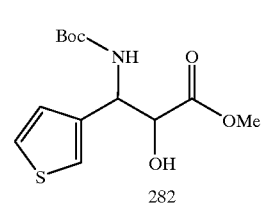
281
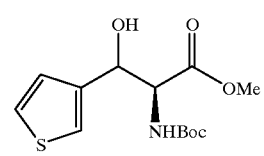
282
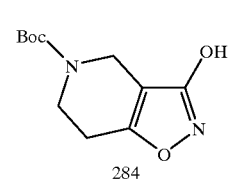
283
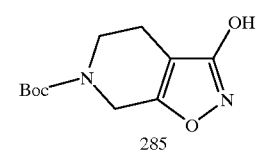
284
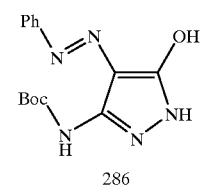
285
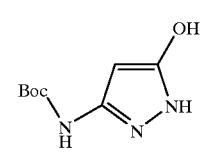
286
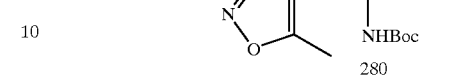
287

TABLE 15-continued
Alcohols of the type A-OH
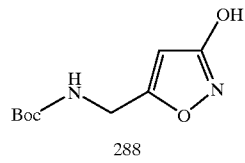
288
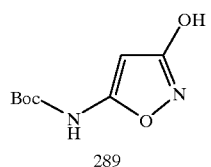
289
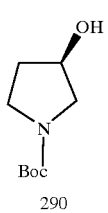
290
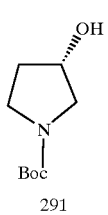
291
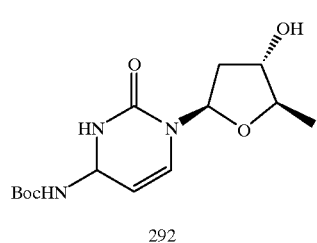
292
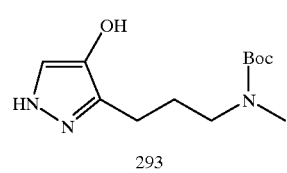
293
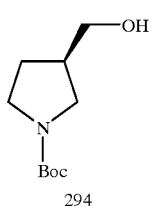
294
TABLE 15-continued
Alcohols of the type A-OH
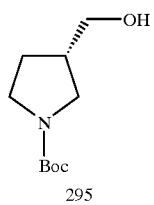
295
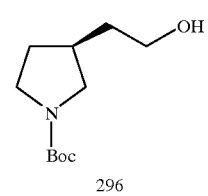
296
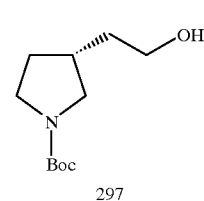
297
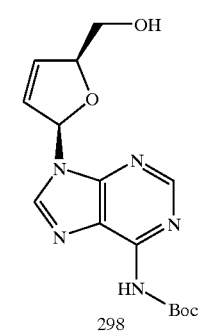
298
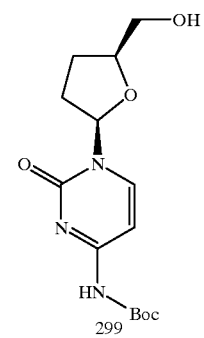
299

TABLE 15-continued
Alcohols of the type A-OH
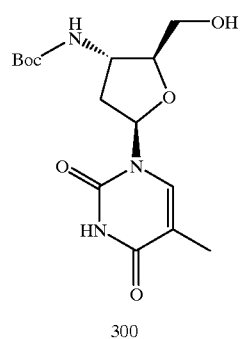
300
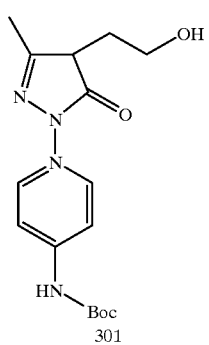
301
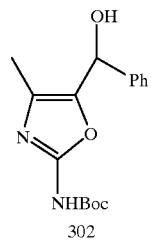
302
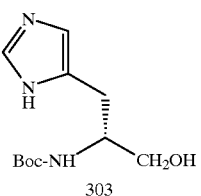
303
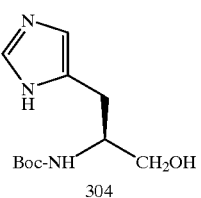
304
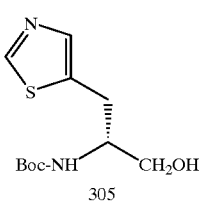
305
TABLE 15-continued
Alcohols of the type A-OH
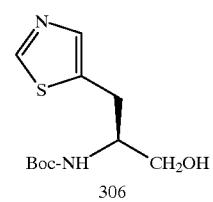
306
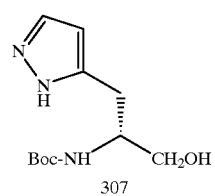
307
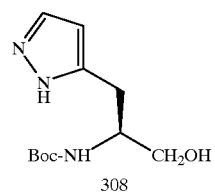
308
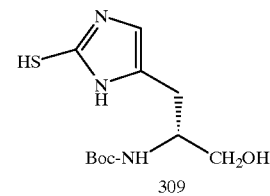
309
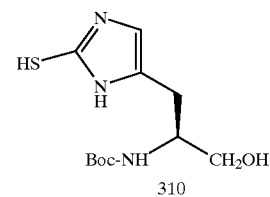
310
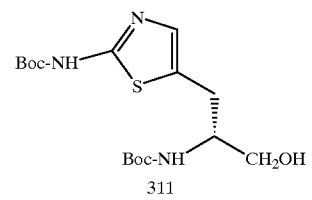
311
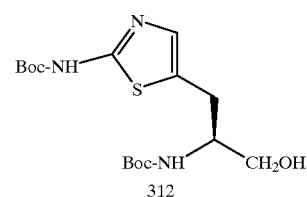
312

TABLE 15-continued
Alcohols of the type A-OH
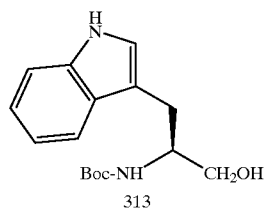
313
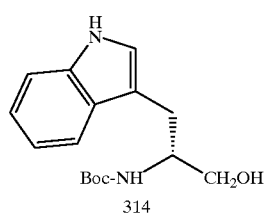
314
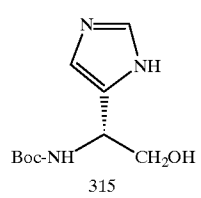
315
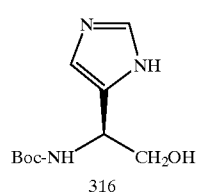
316
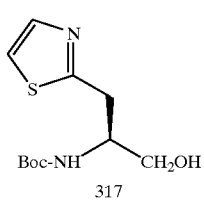
317
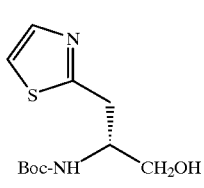
318
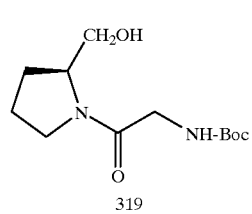
319
TABLE 15-continued
Alcohols of the type A-OH
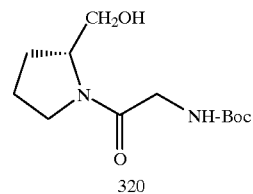
320
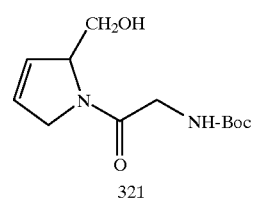
321
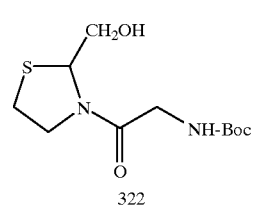
322
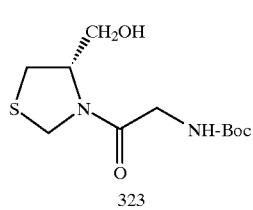
323
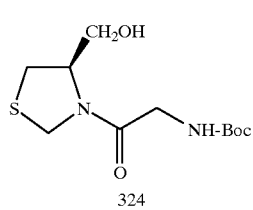
324
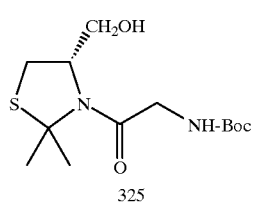
325
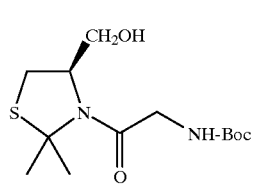
326

TABLE 15-continued

Alcohols of the type A-OH (chemical structures 327–341)

TABLE 15-continued
Alcohols of the type A-OH
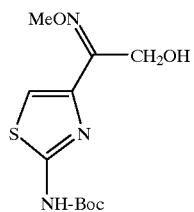
342
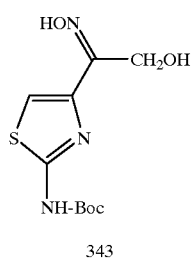
343
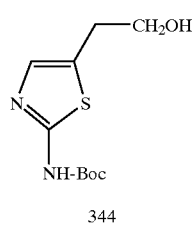
344
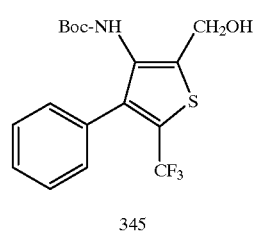
345
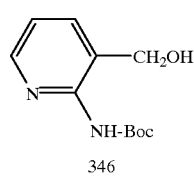
346
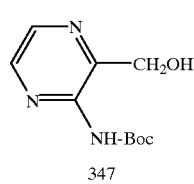
347
TABLE 15-continued
Alcohols of the type A-OH
348
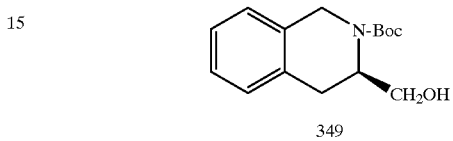
349
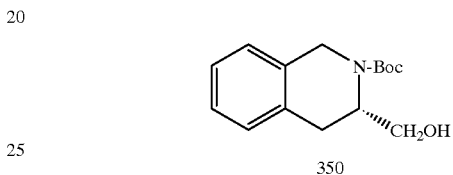
350
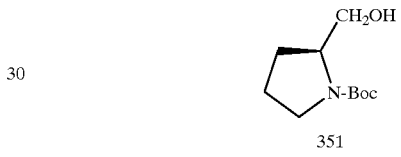
351
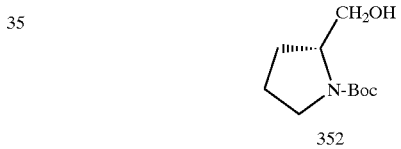
352
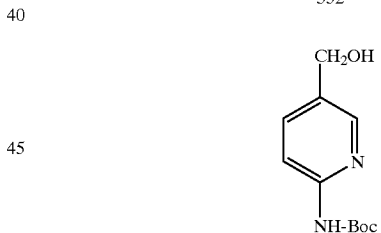
353
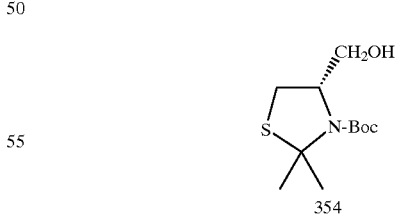
354
355

TABLE 15-continued
Alcohols of the type A-OH
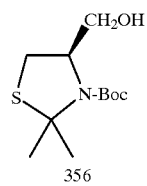
356
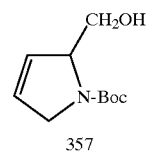
357
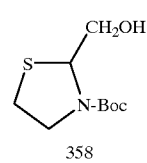
358
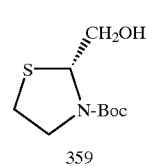
359
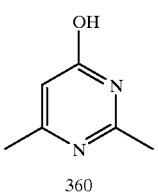
360
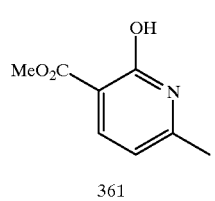
361
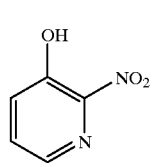
362
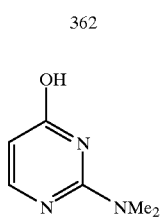
363
TABLE 15-continued
Alcohols of the type A-OH
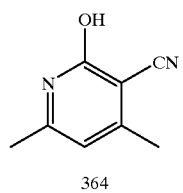
364
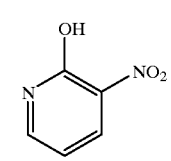
365
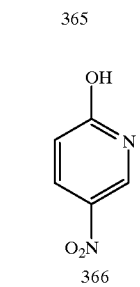
366
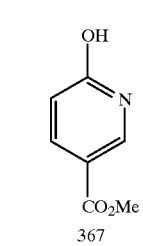
367
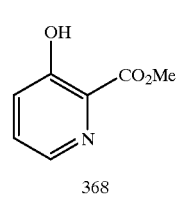
368
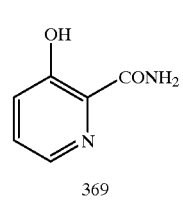
369
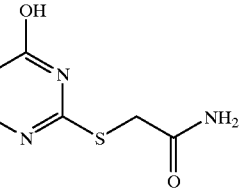
370

TABLE 15-continued
Alcohols of the type A-OH
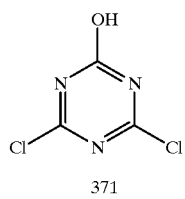
371
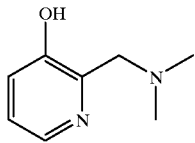
372
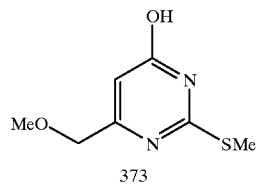
373
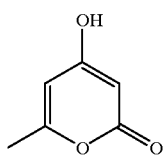
374
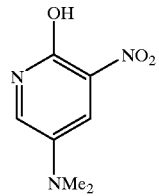
375
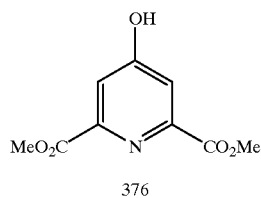
376
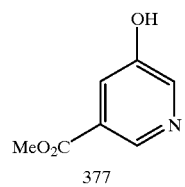
377
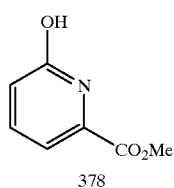
378
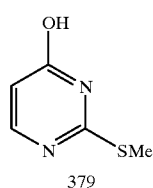
379
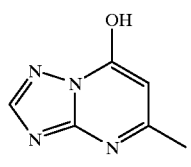
380
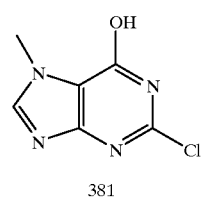
381
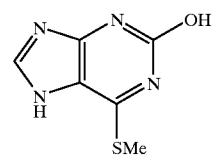
382
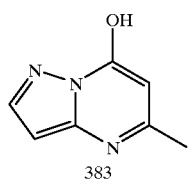
383
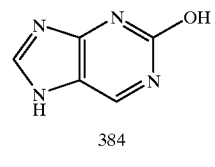
384
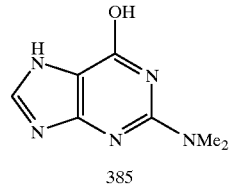
385

TABLE 15-continued
Alcohols of the type A-OH
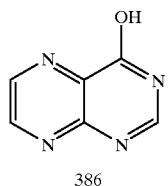
386
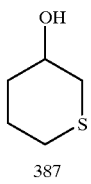
387
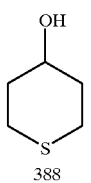
388
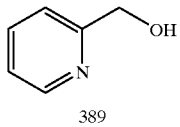
389
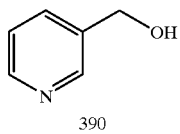
390
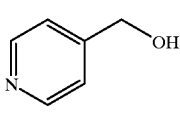
391
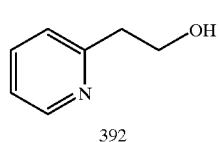
392
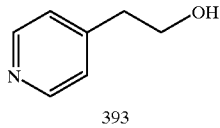
393
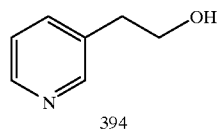
394
TABLE 15-continued
Alcohols of the type A-OH
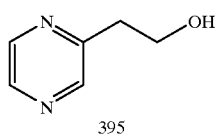
395
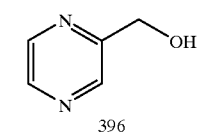
396
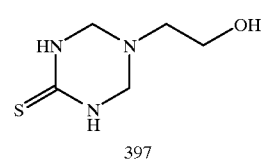
397
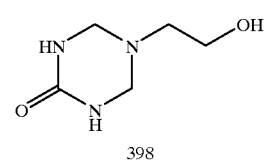
398
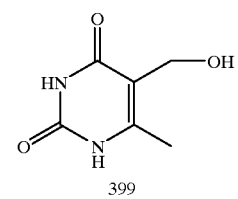
399
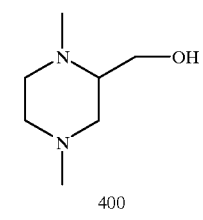
400
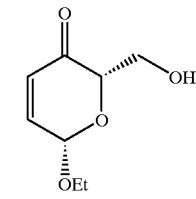
401
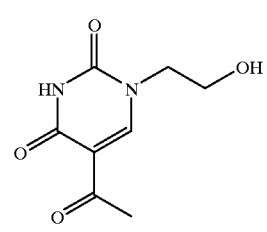
402

TABLE 15-continued
Alcohols of the type A-OH
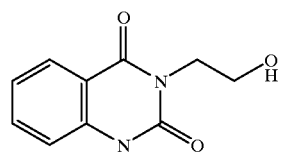
403
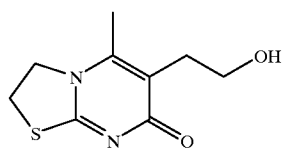
404
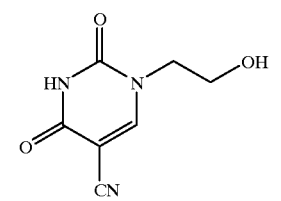
405
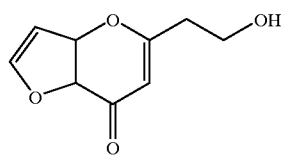
406
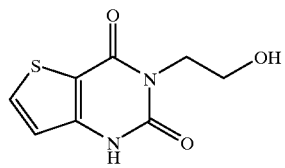
407
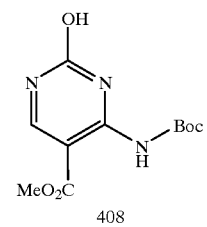
408
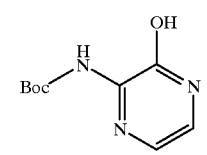
409
TABLE 15-continued
Alcohols of the type A-OH
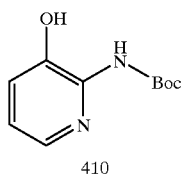
410
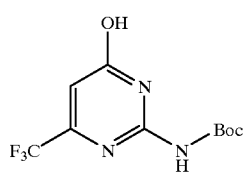
411
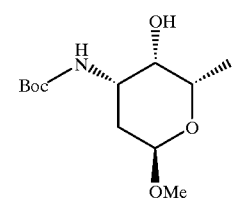
412
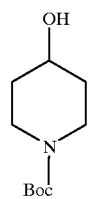
413
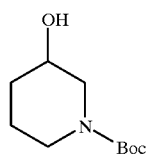
414
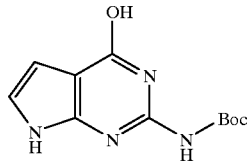
415
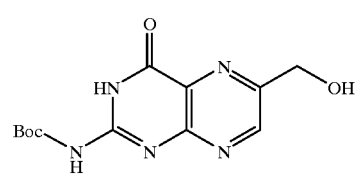
416

TABLE 15-continued
Alcohols of the type A-OH
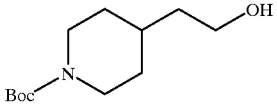
417
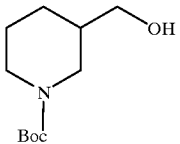
418
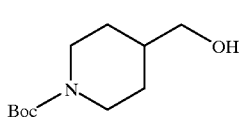
419
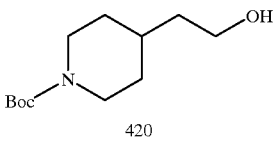
420
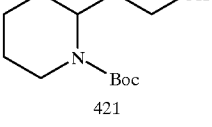
421
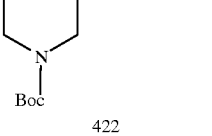
422
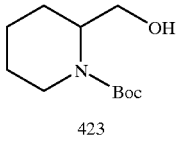
423
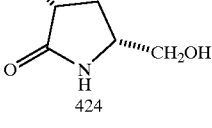
424
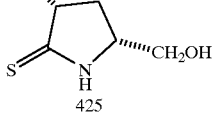
425
TABLE 15-continued
Alcohols of the type A-OH
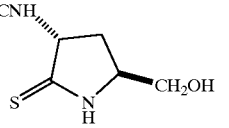
426
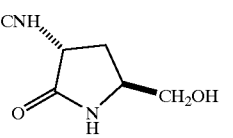
427
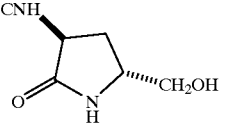
428
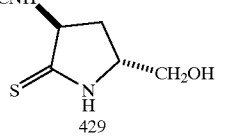
429
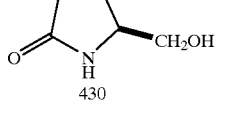
430
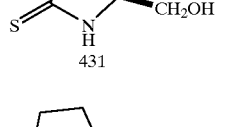
431
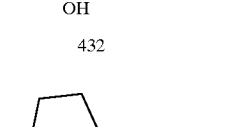
432
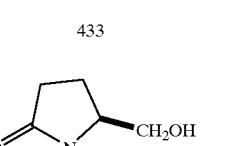
433
434

TABLE 15-continued
Alcohols of the type A-OH
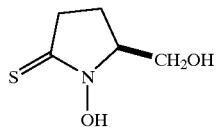
435
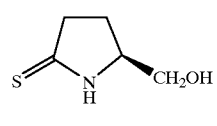
436
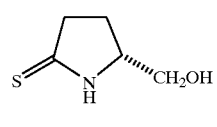
437
TABLE 16
Mercaptans of the type A-SH
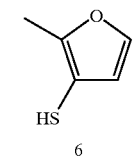
1
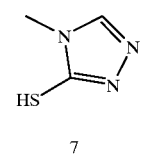
2
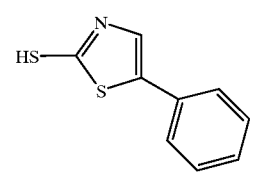
3
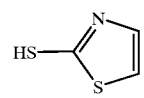
4
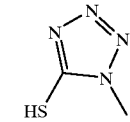
5
TABLE 16-continued
Mercaptans of the type A-SH
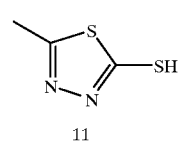
6
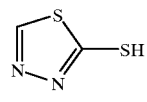
7
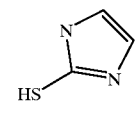
8
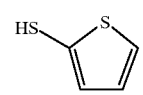
9
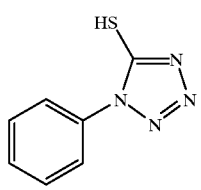
10
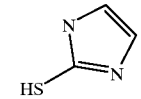
11
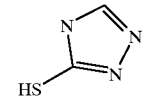
12
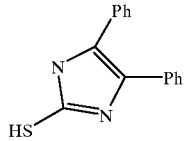
13
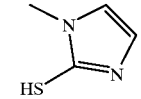
14

TABLE 16-continued

Mercaptans of the type A-SH

15

16

17

18

19

20

21

22

23

24

25

26

27

28

29

TABLE 16-continued
Mercaptans of the type A-SH
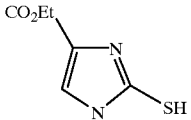
30
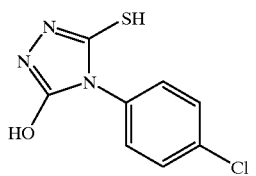
31
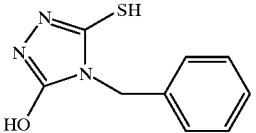
32
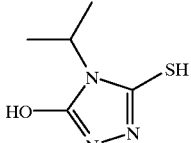
33
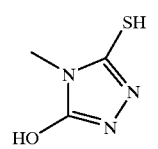
34
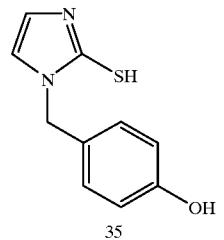
35
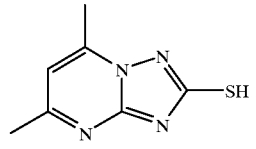
36
TABLE 16-continued
Mercaptans of the type A-SH
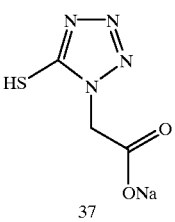
37
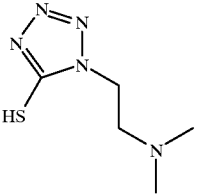
38
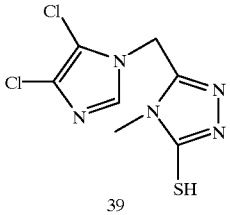
39
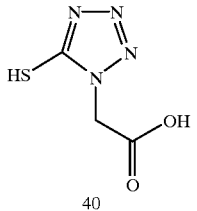
40
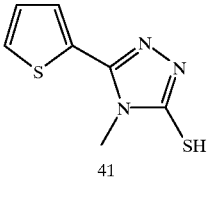
41
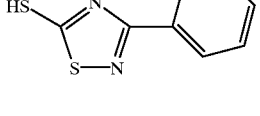
42
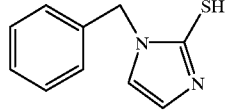
43

TABLE 16-continued
Mercaptans of the type A-SH
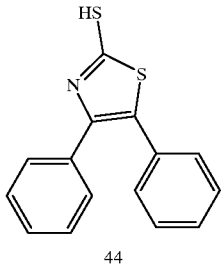
44
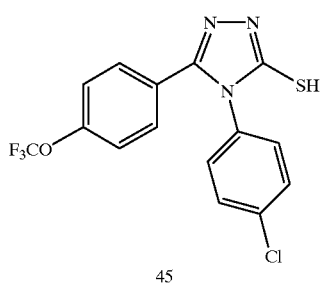
45
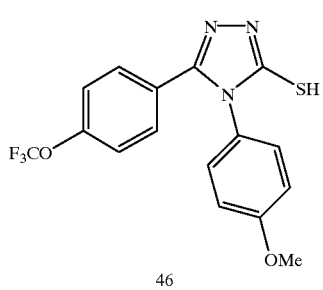
46
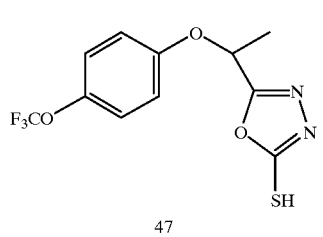
47
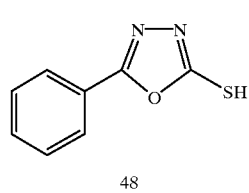
48
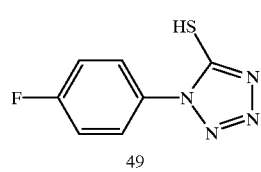
49
TABLE 16-continued
Mercaptans of the type A-SH
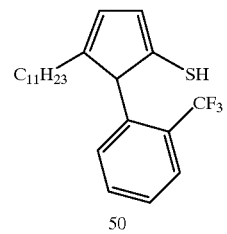
50
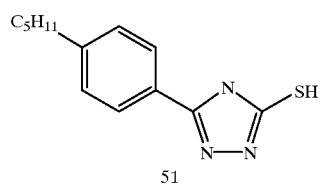
51
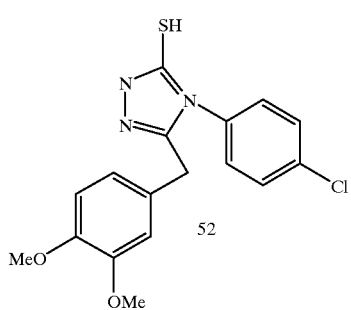
52
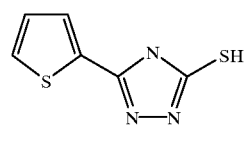
53
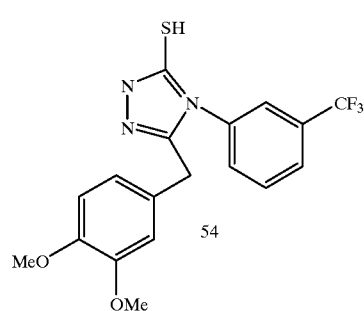
54
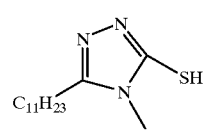
55

TABLE 16-continued
Mercaptans of the type A-SH

TABLE 16-continued
Mercaptans of the type A-SH
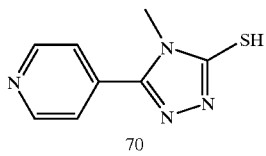
70
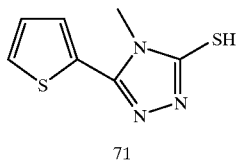
71
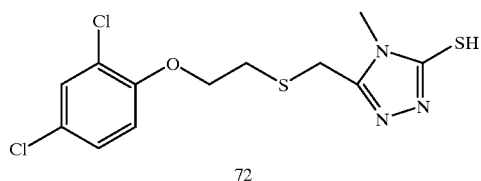
72
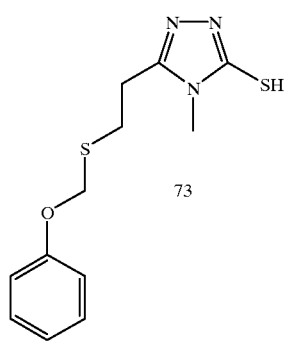
73
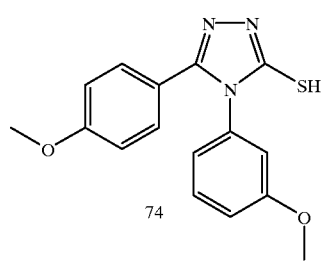
74
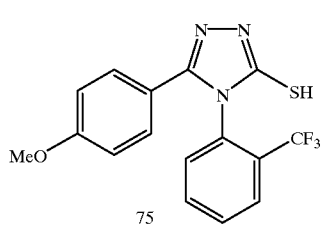
75
TABLE 16-continued
Mercaptans of the type A-SH
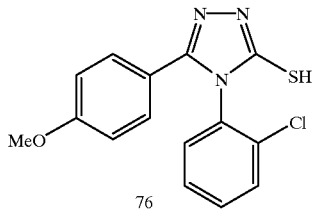
76
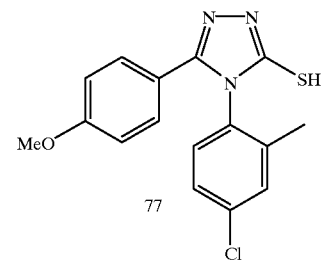
77
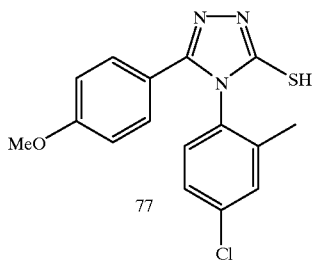
78
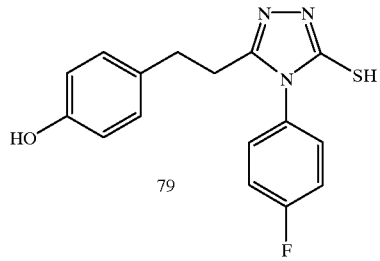
79
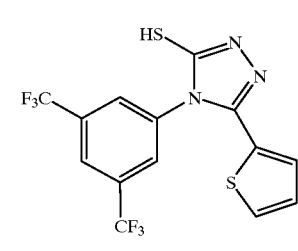
80
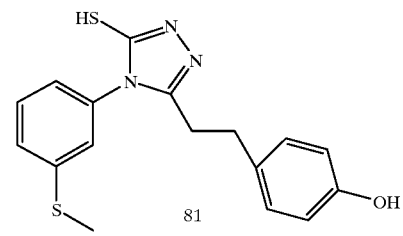
81

TABLE 16-continued
Mercaptans of the type A-SH
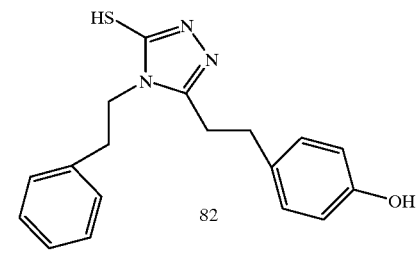
82
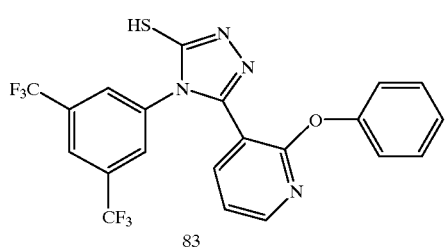
83
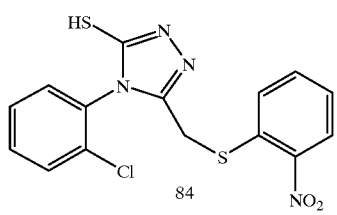
84
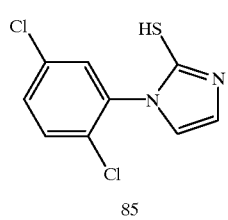
85
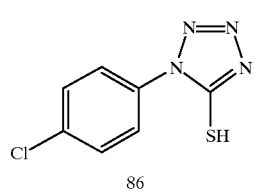
86
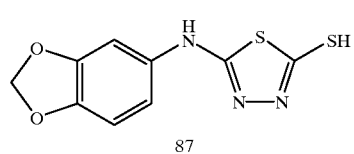
87
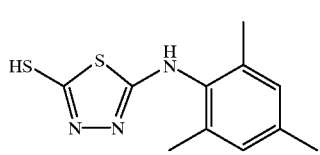
88
TABLE 16-continued
Mercaptans of the type A-SH
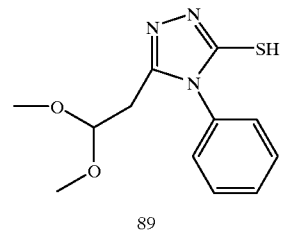
89
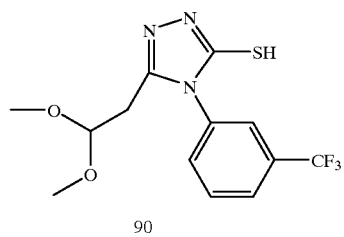
90
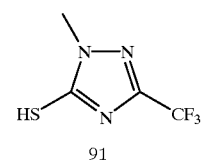
91
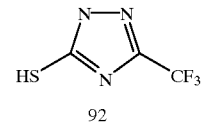
92
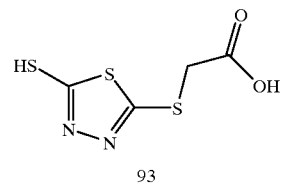
93
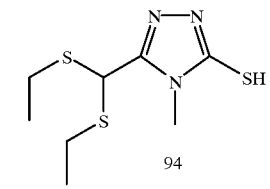
94
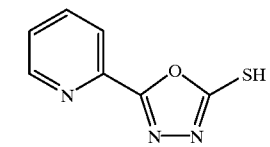
95

TABLE 16-continued
Mercaptans of the type A-SH
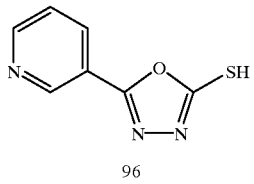
96
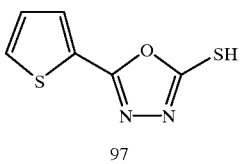
97
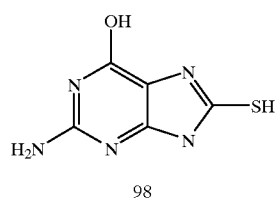
98
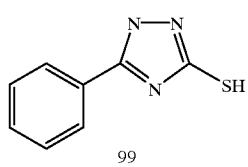
99
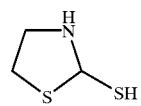
100
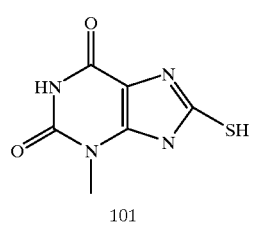
101
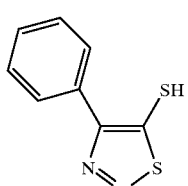
102
TABLE 16-continued
Mercaptans of the type A-SH
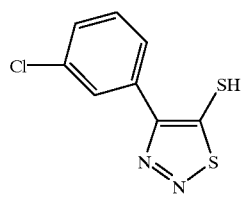
103
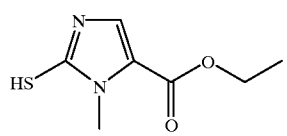
104
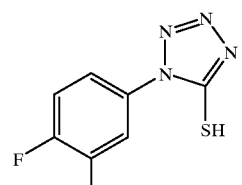
105
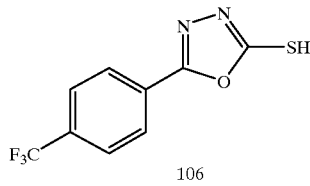
106
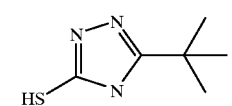
107
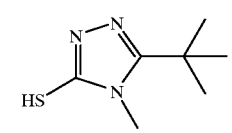
108
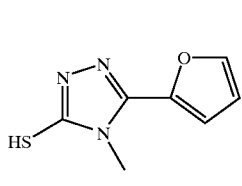
109

TABLE 16-continued
Mercaptans of the type A-SH
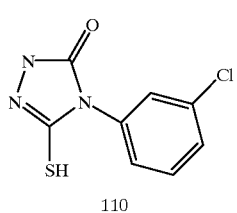
110
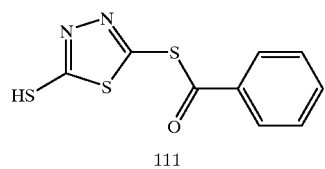
111
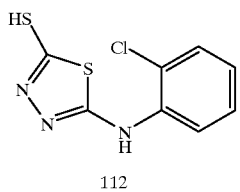
112
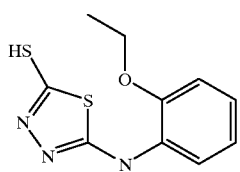
113
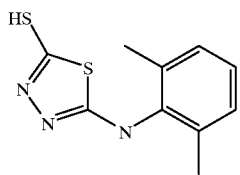
114
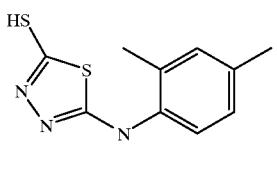
115
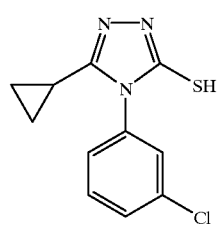
116
TABLE 16-continued
Mercaptans of the type A-SH
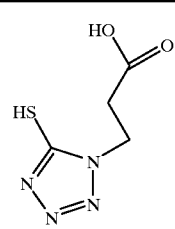
117
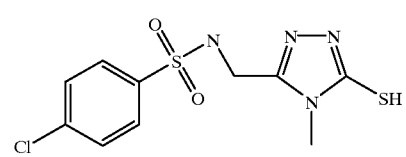
118
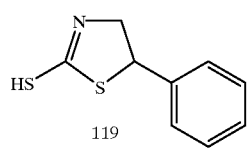
119
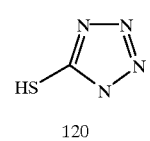
120
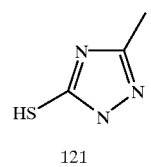
121
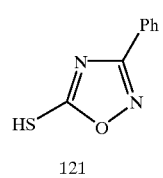
121
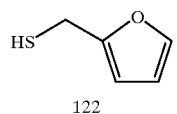
122
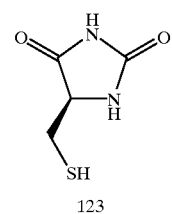
123

TABLE 16-continued
Mercaptans of the type A-SH
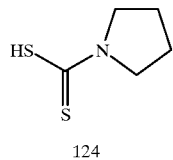
124
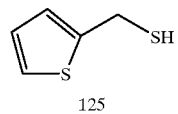
125
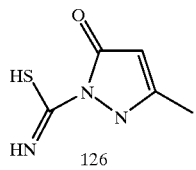
126
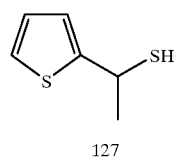
127
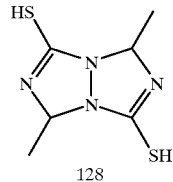
128
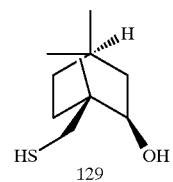
129
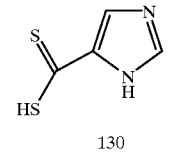
130
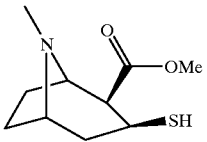
131
TABLE 16-continued
Mercaptans of the type A-SH
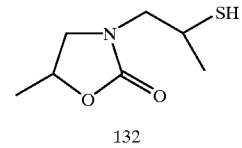
132
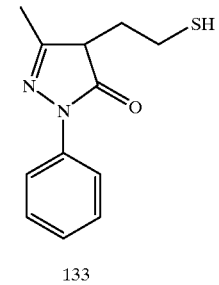
133
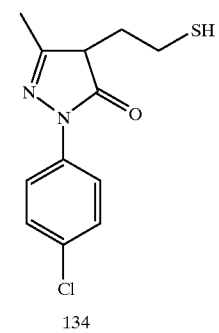
134
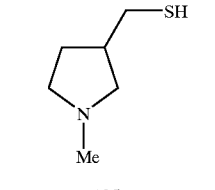
135
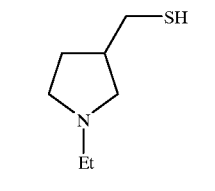
136
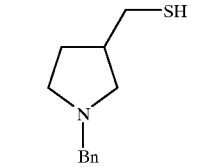
137

TABLE 16-continued
Mercaptans of the type A-SH
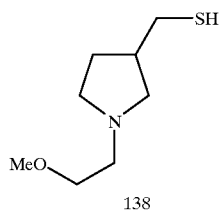
138
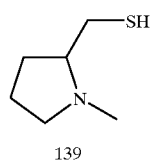
139
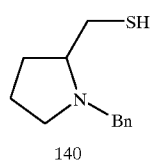
140
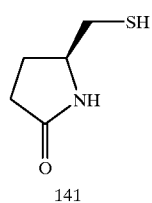
141
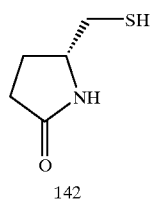
142
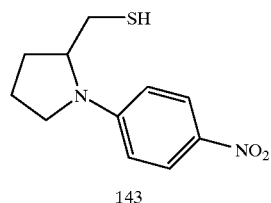
143
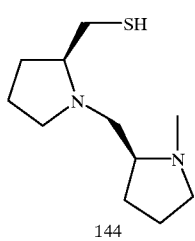
144
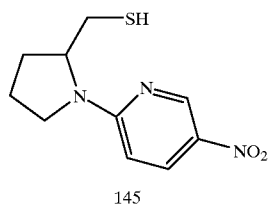
145
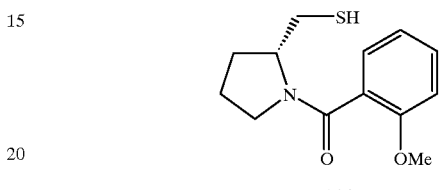
146

147
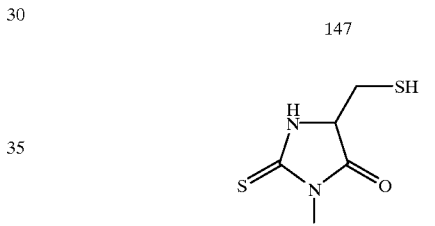
148
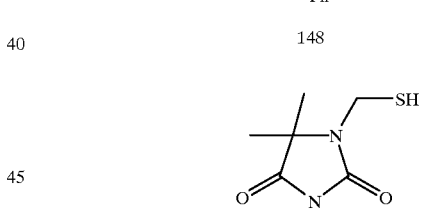
149
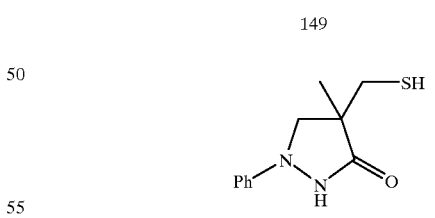
150
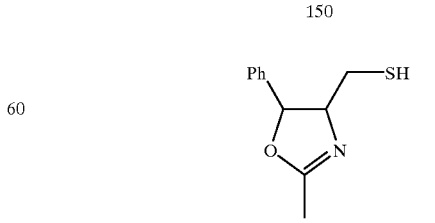
151

TABLE 16-continued
Mercaptans of the type A-SH
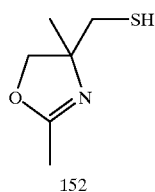
152
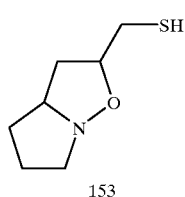
153
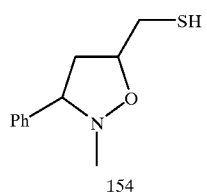
154
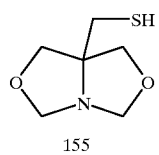
155
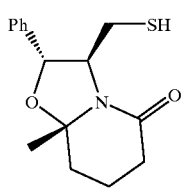
156
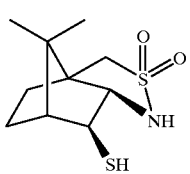
157
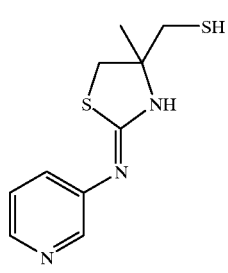
158
TABLE 16-continued
Mercaptans of the type A-SH
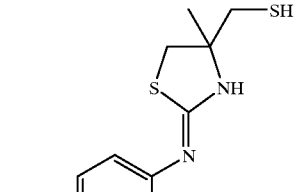
159
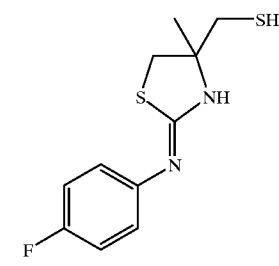
160
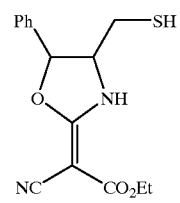
161
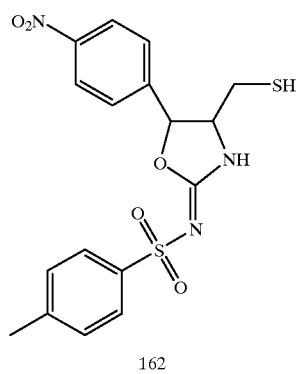
162
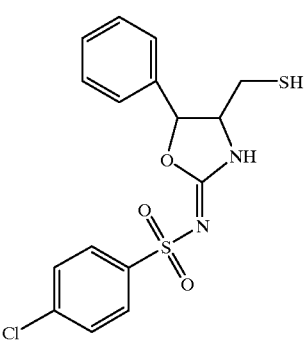
163

TABLE 16-continued

Mercaptans of the type A-SH

164: 5-(4-nitrophenyl)-4-(mercaptomethyl)-2-(cyano(carbamoyl)methylene)oxazolidine 165: furan-2-ylmethanethiol 166: thiophen-2-ylmethanethiol 167: (5-methylisoxazol-3-yl)methanethiol 168: thiophen-3-ylmethanethiol 169: furan-3-ylmethanethiol 170: (2-methylfuran-3-yl)methanethiol 171: 5-(mercaptomethyl)furan-2-carbaldehyde 172: (5-((dimethylamino)methyl)furan-2-yl)methanethiol 173: (5-(2,4-difluorophenyl)furan-2-yl)methanethiol 174: (5-(phenylethynyl)thiophen-2-yl)methanethiol 175: (3,6-dimethylthieno[3,2-b]thiophen-2-yl)methanethiol 176: (3-(1H-pyrrol-1-yl)thiophen-2-yl)methanethiol TABLE 16-continued
Mercaptans of the type A-SH
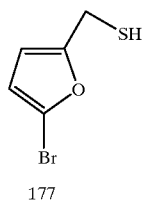
177
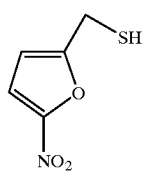
178
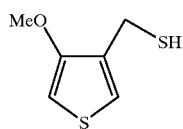
179
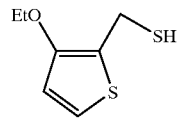
180
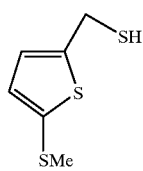
181
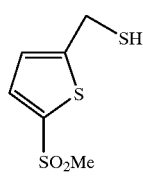
182
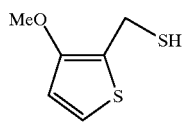
183
TABLE 16-continued
Mercaptans of the type A-SH
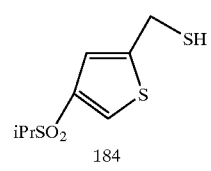
184
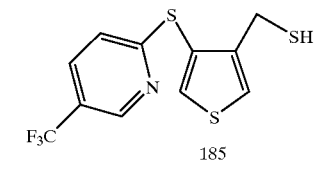
185
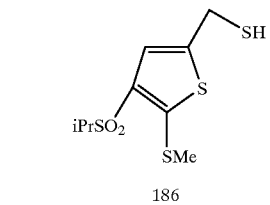
186
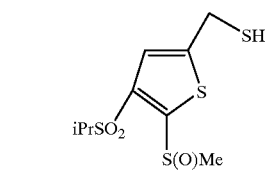
187
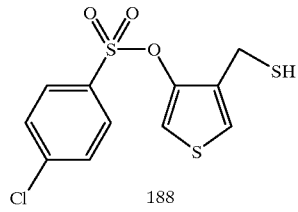
188
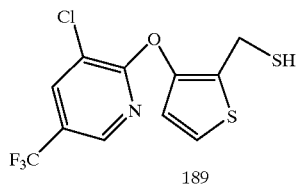
189
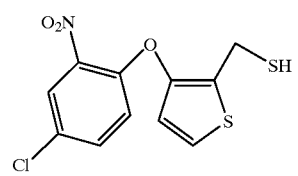
190

TABLE 16-continued
Mercaptans of the type A-SH
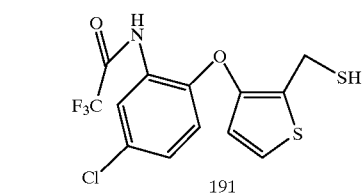
191
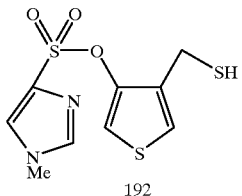
192
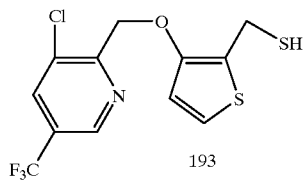
193
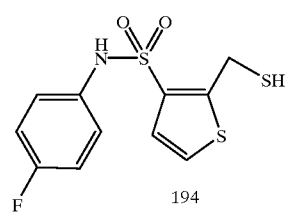
194
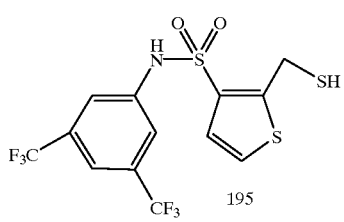
195
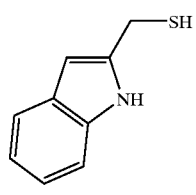
196
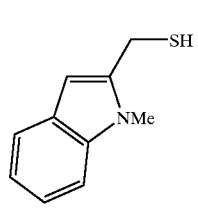
197
TABLE 16-continued
Mercaptans of the type A-SH
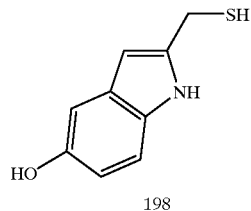
198
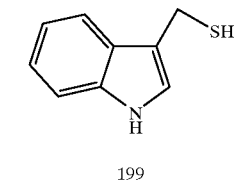
199
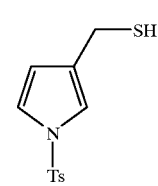
200
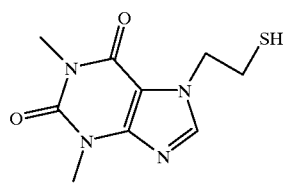
201
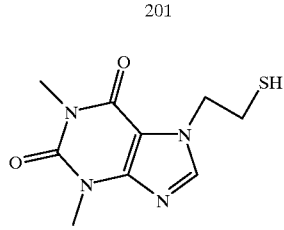
202
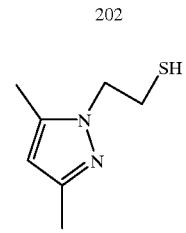
203
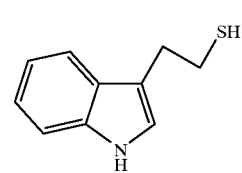
204

TABLE 16-continued
Mercaptans of the type A-SH
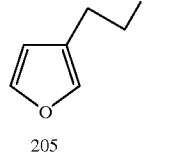
205
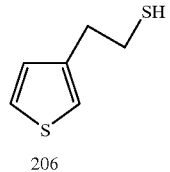
206
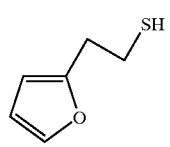
207
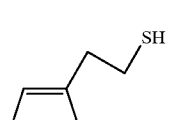
208
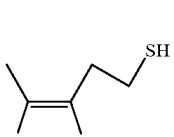
209
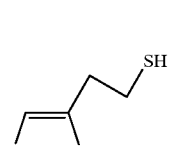
210
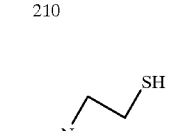
211
TABLE 16-continued
Mercaptans of the type A-SH
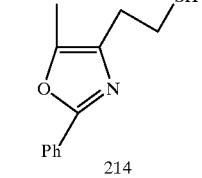
212
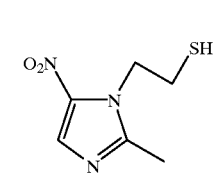
213
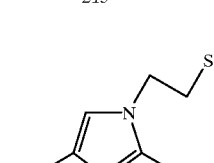
214
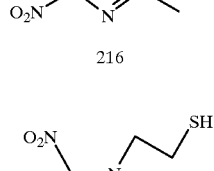
215
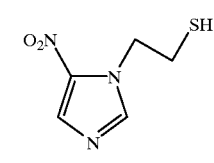
216
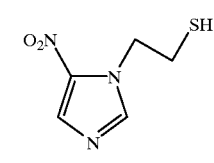
217
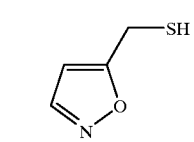
218

TABLE 16-continued
Mercaptans of the type A-SH
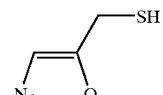
219
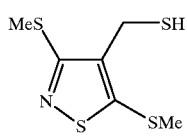
220
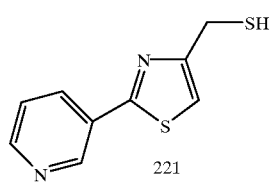
221
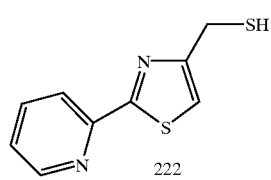
222
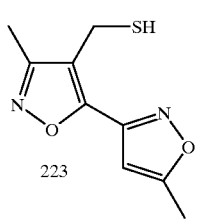
223
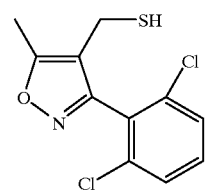
224
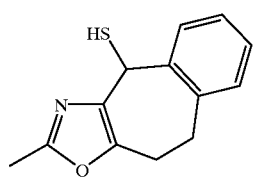
225
TABLE 16-continued
Mercaptans of the type A-SH
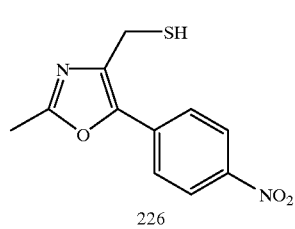
226
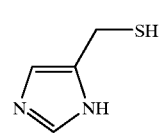
227
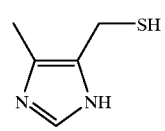
228
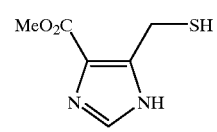
229
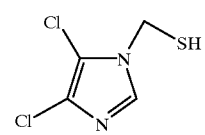
230
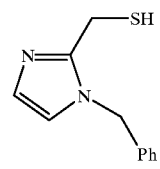
231
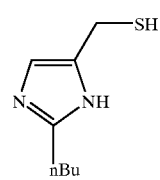
232

TABLE 16-continued
Mercaptans of the type A-SH
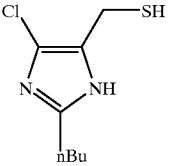
233
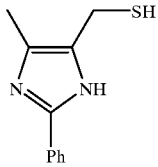
234
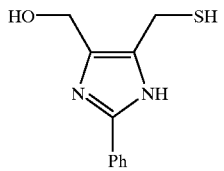
235
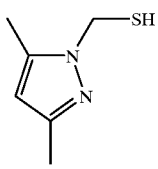
236
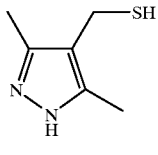
237
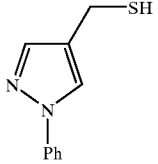
238
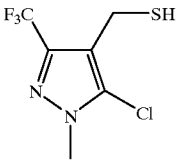
239
TABLE 16-continued
Mercaptans of the type A-SH
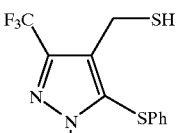
240
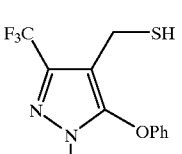
241
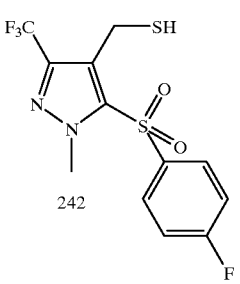
242
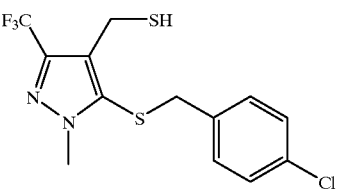
243
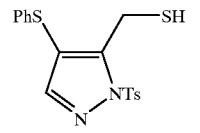
244
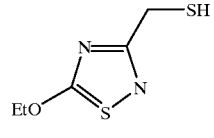
245
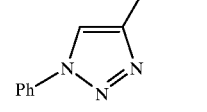
246

TABLE 16-continued
Mercaptans of the type A-SH
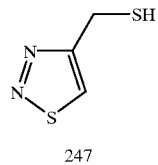
247
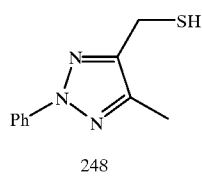
248
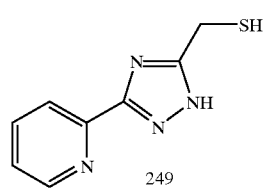
249
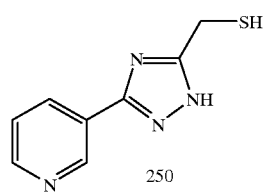
250
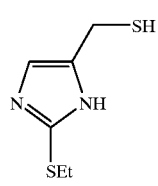
251
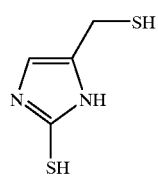
252
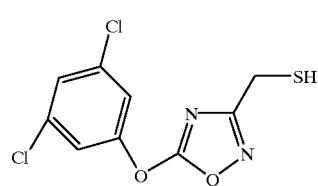
253
TABLE 16-continued
Mercaptans of the type A-SH
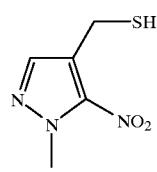
254
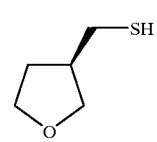
255
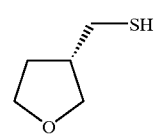
256
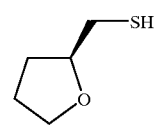
257
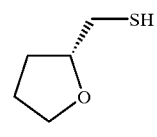
258
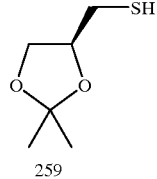
259
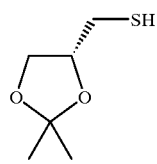
260

TABLE 16-continued
Mercaptans of the type A-SH
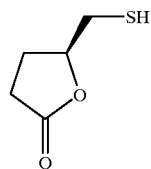
261
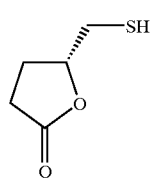
262
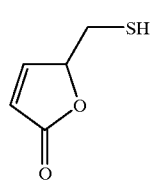
263
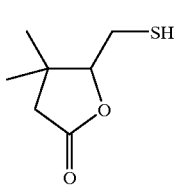
264
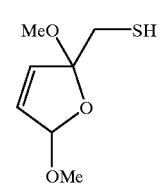
265
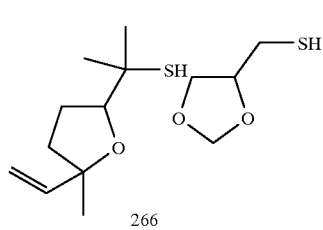
266
TABLE 16-continued
Mercaptans of the type A-SH
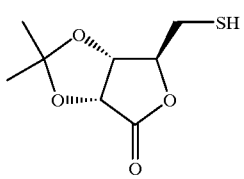
267
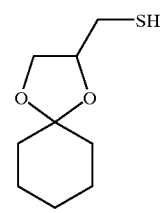
268
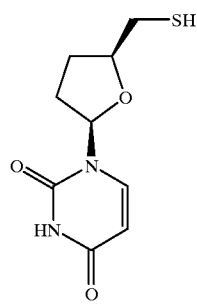
269
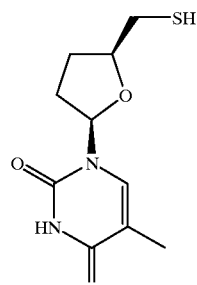
270
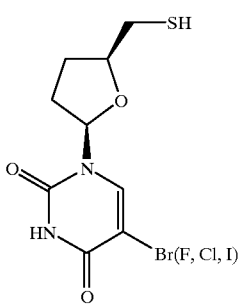
271

TABLE 16-continued
Mercaptans of the type A-SH
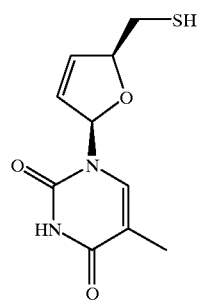
272
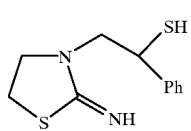
273
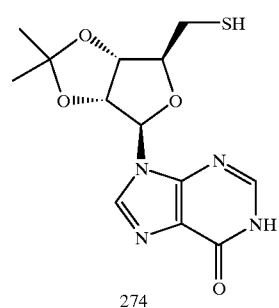
274
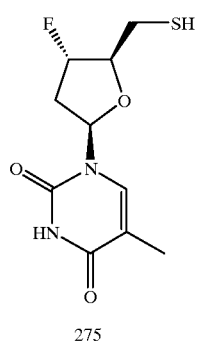
275
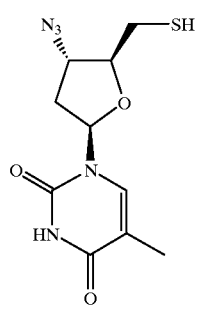
276
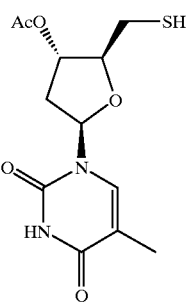
277
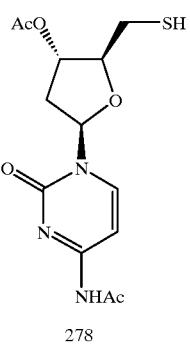
278
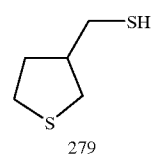
279
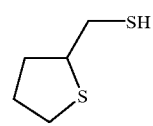
280
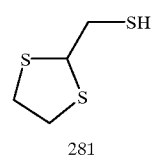
281
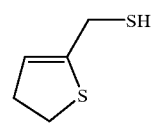
282
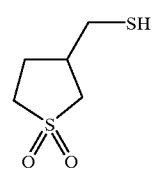
283

TABLE 16-continued
Mercaptans of the type A-SH
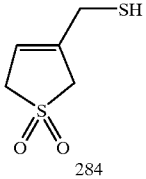
284
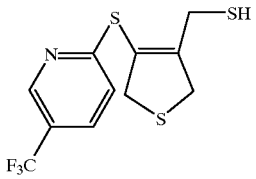
285
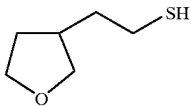
286
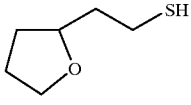
287
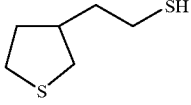
288
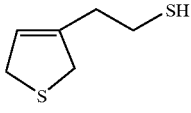
289
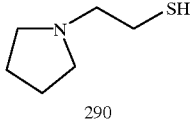
290
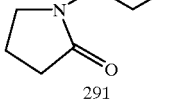
291
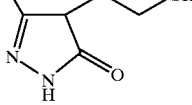
292
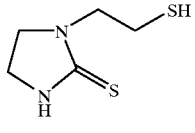
293
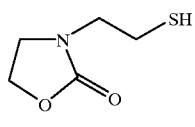
294
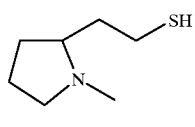
295
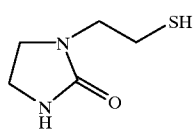
296
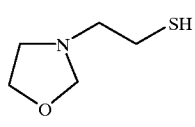
297
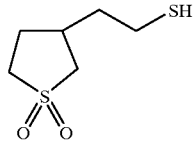
298
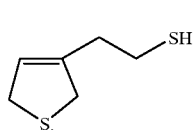
299
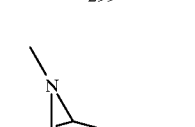
300
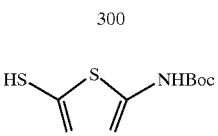
301

TABLE 16-continued
Mercaptans of the type A-SH
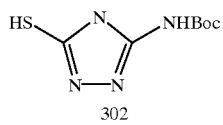
302
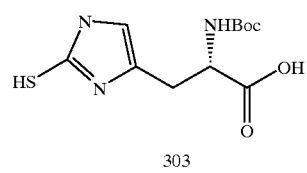
303
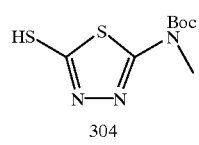
304
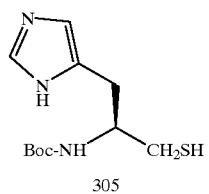
305
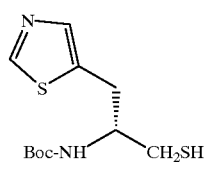
306
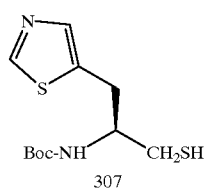
307
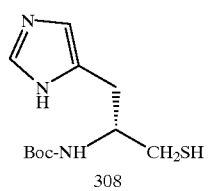
308
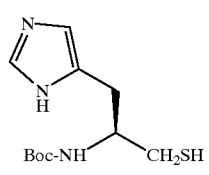
309
TABLE 16-continued
Mercaptans of the type A-SH
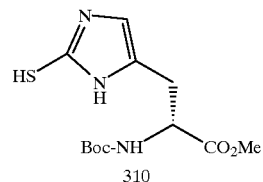
310
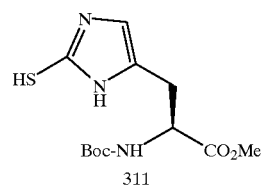
311
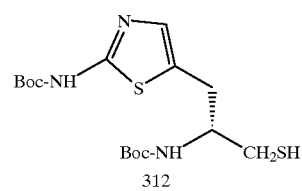
312
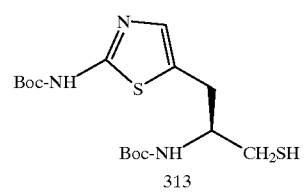
313
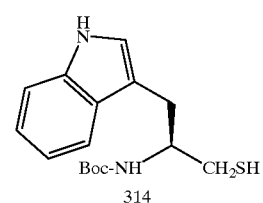
314
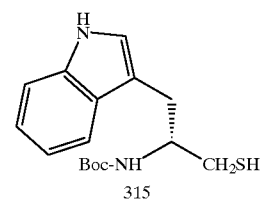
315
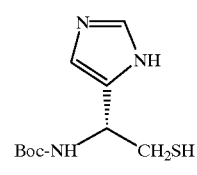
316

TABLE 16-continued
Mercaptans of the type A-SH
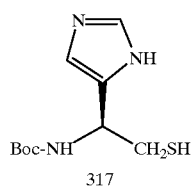
317
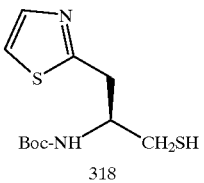
318
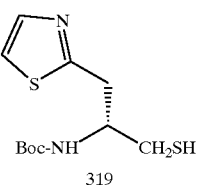
319
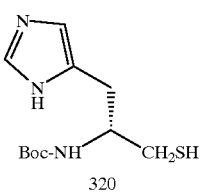
320
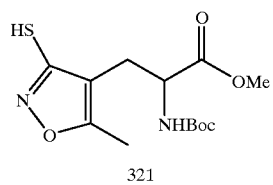
321
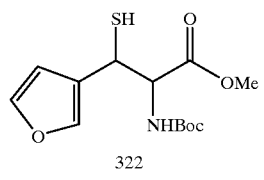
322
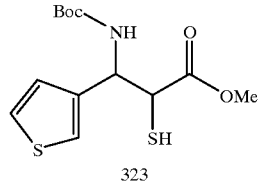
323
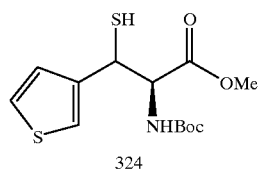
324
TABLE 16-continued
Mercaptans of the type A-SH
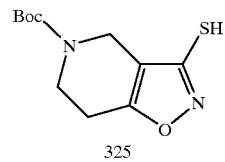
325
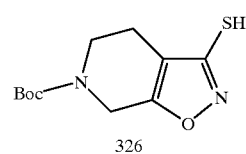
326
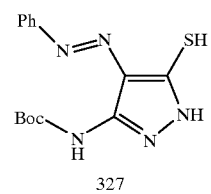
327
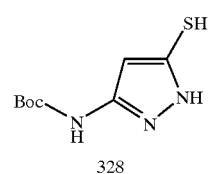
328
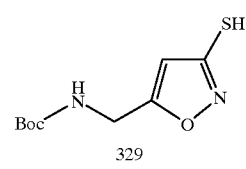
329
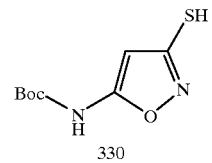
330
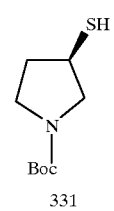
331
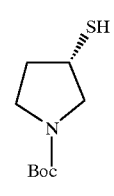
332

TABLE 16-continued
Mercaptans of the type A-SH
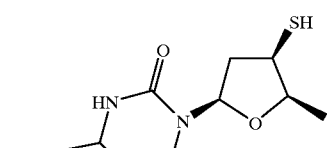
333
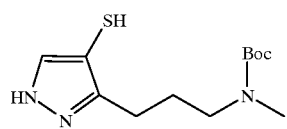
334
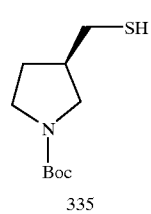
335
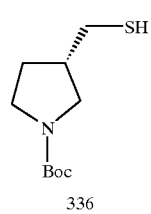
336
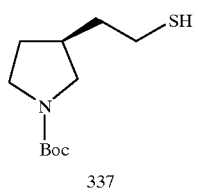
337
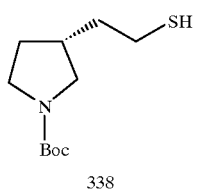
338
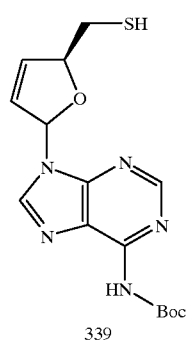
339
TABLE 16-continued
Mercaptans of the type A-SH
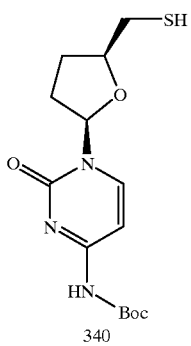
340
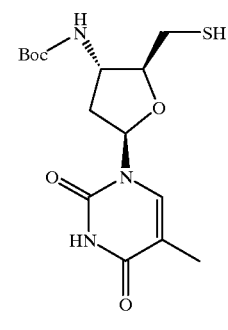
341
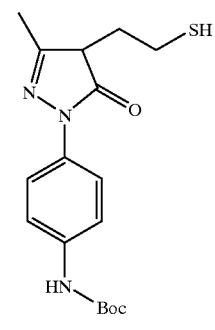
342
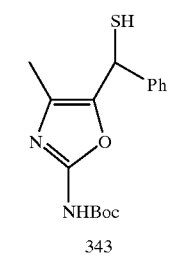
343
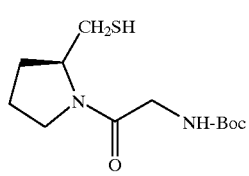
344

TABLE 16-continued
Mercaptans of the type A-SH
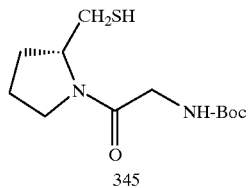
345
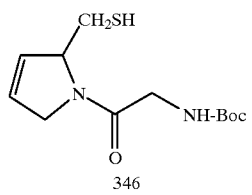
346
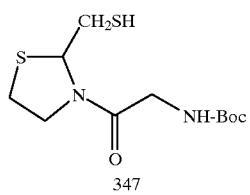
347
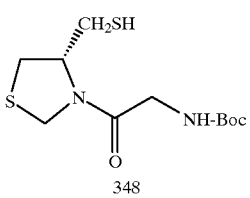
348
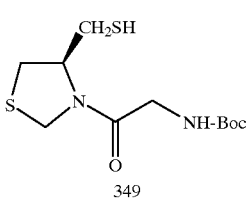
349
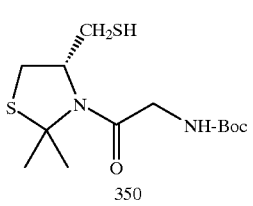
350
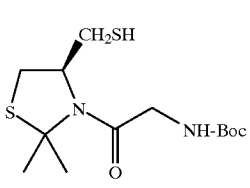
351
TABLE 16-continued
Mercaptans of the type A-SH
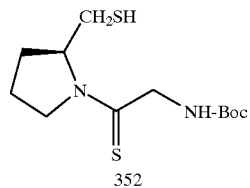
352
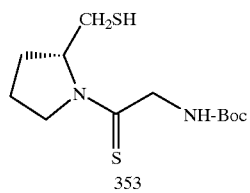
353
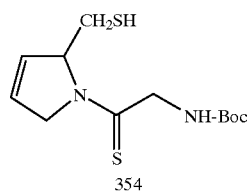
354
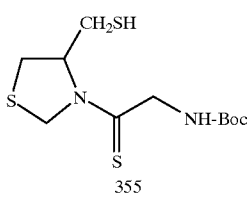
355
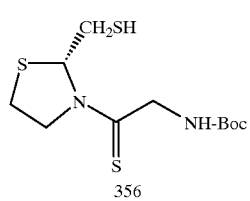
356
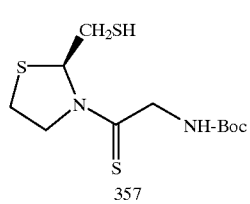
357
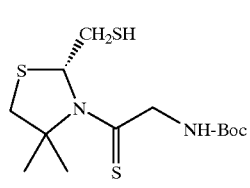
358

TABLE 16-continued
Mercaptans of the type A-SH
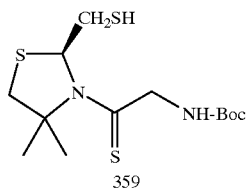
359
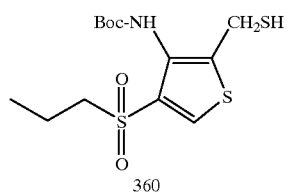
360
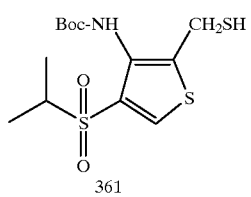
361
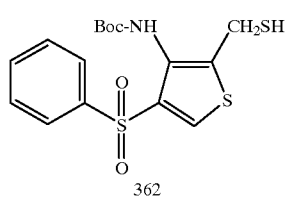
362
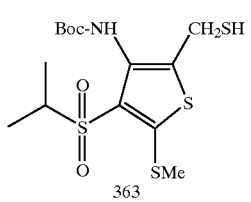
363
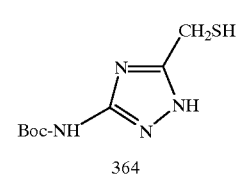
364
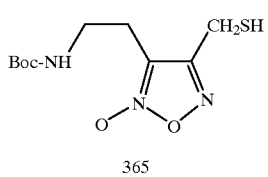
365
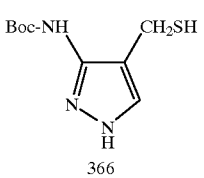
366
TABLE 16-continued
Mercaptans of the type A-SH
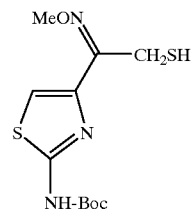
367
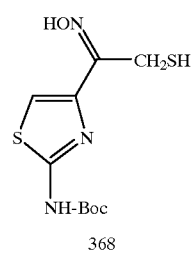
368
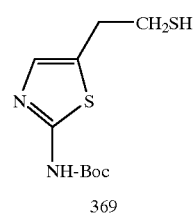
369
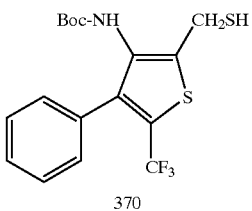
370
371
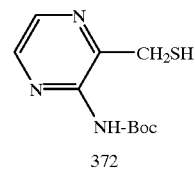
372
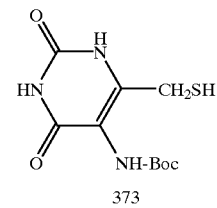
373

TABLE 16-continued
Mercaptans of the type A-SH
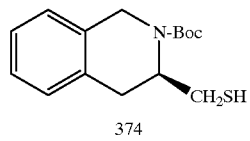
374
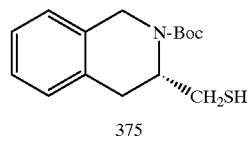
375
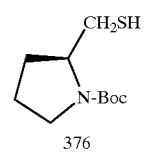
376
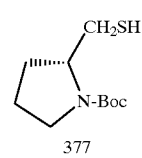
377
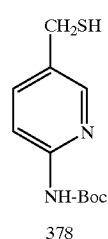
378
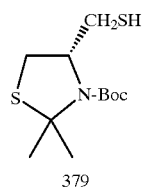
379
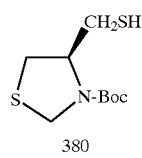
380
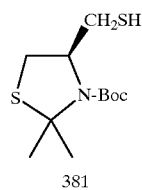
381
TABLE 16-continued
Mercaptans of the type A-SH
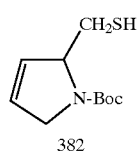
382
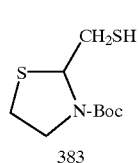
383
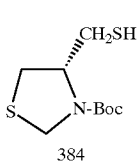
384
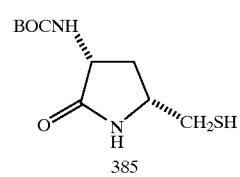
385
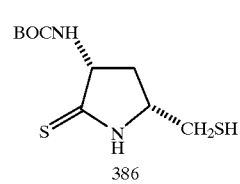
386
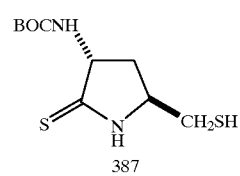
387
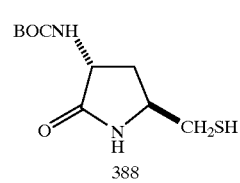
388
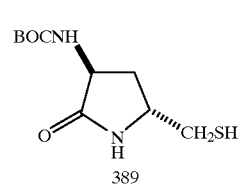
389

TABLE 16-continued
Mercaptans of the type A-SH
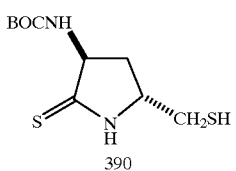
390
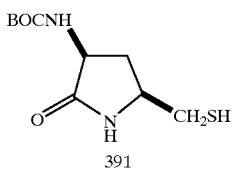
391
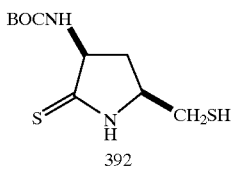
392
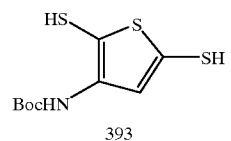
393
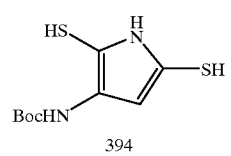
394
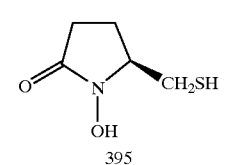
395
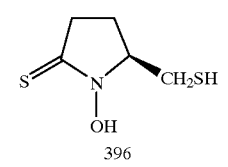
396
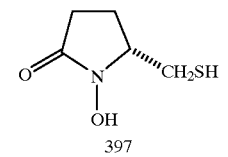
397
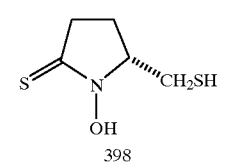
398
TABLE 16-continued
Mercaptans of the type A-SH
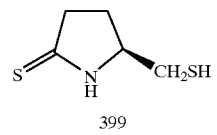
399
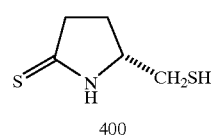
400
TABLE 17
Halides of the type A-Cl, A-Br and A-I
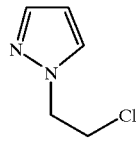
1
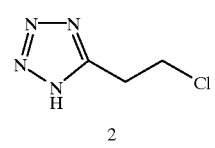
2
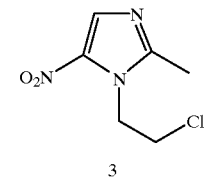
3
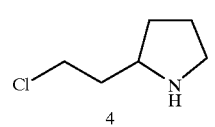
4
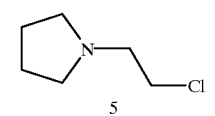
5
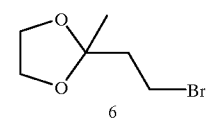
6
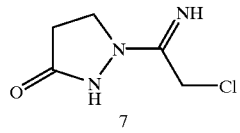
7

TABLE 17-continued
Halides of the type A-Cl, A-Br and A-I
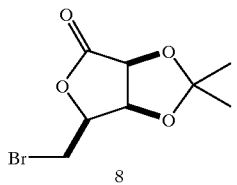
8
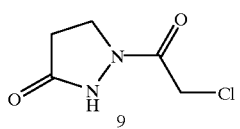
9
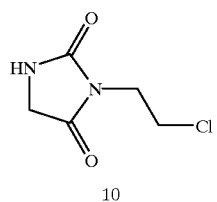
10
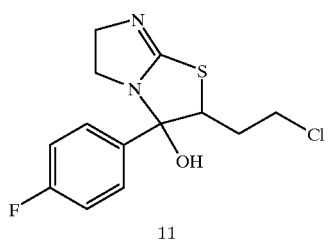
11
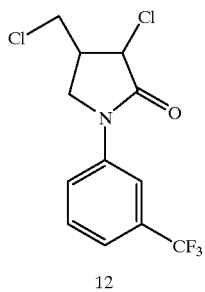
12
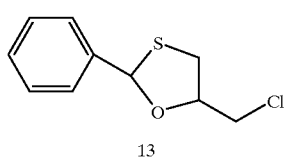
13
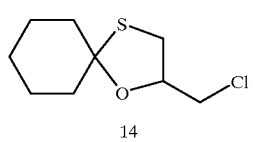
14
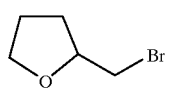
15
TABLE 17-continued
Halides of the type A-Cl, A-Br and A-I
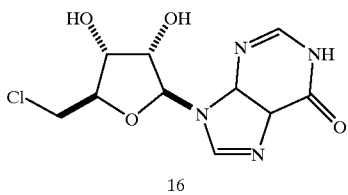
16
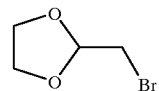
17
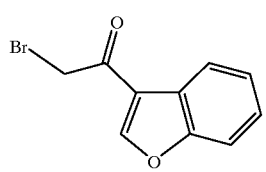
18
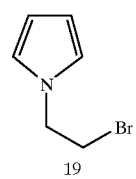
19
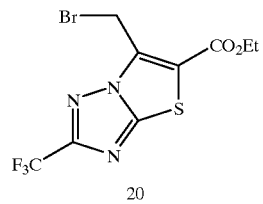
20
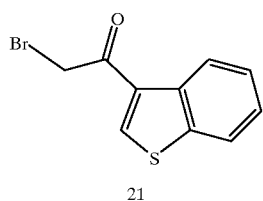
21
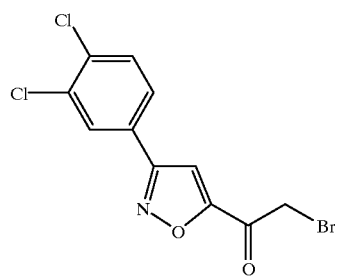
22

TABLE 17-continued
Halides of the type A-Cl, A-Br and A-I
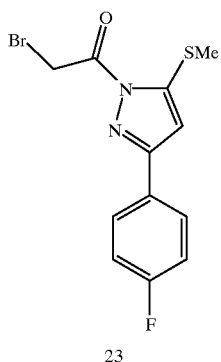
23
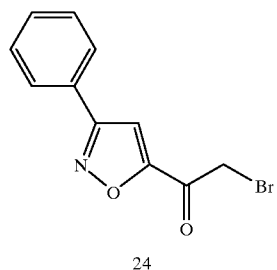
24
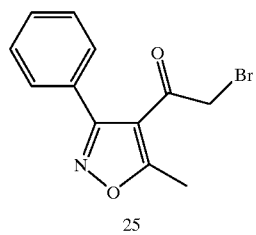
25
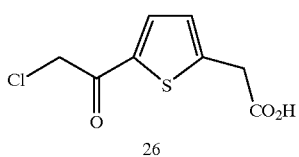
26
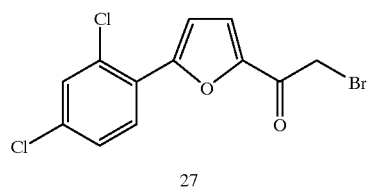
27
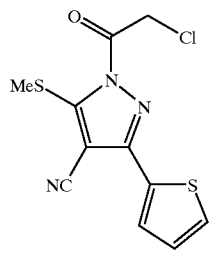
28
TABLE 17-continued
Halides of the type A-Cl, A-Br and A-I
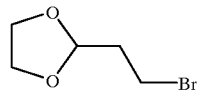
29
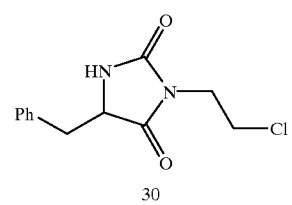
30
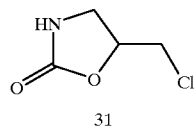
31
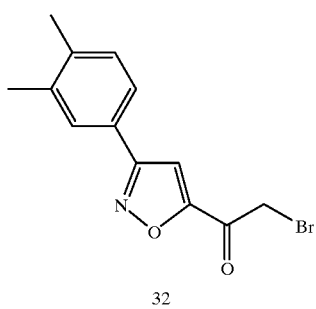
32
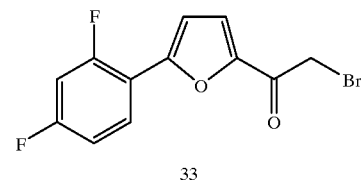
33
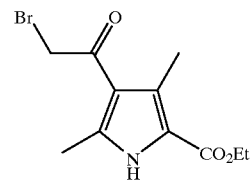
34
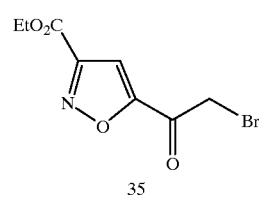
35

TABLE 17-continued
Halides of the type A-Cl, A-Br and A-I
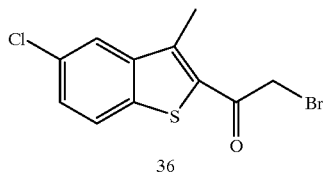
36
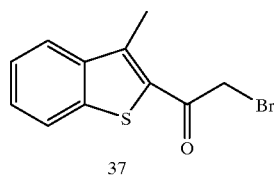
37
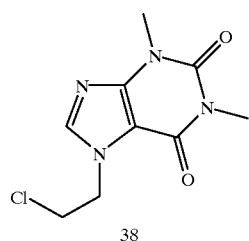
38
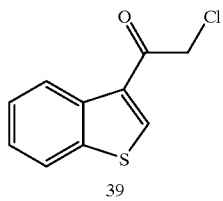
39
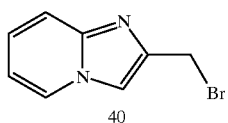
40
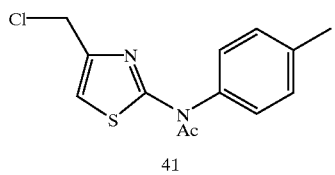
41
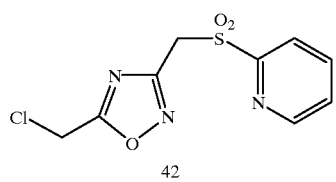
42
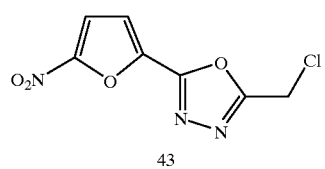
43
TABLE 17-continued
Halides of the type A-Cl, A-Br and A-I
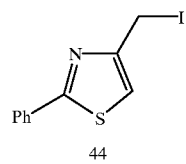
44
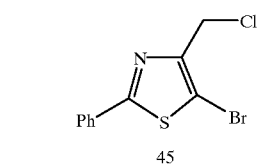
45
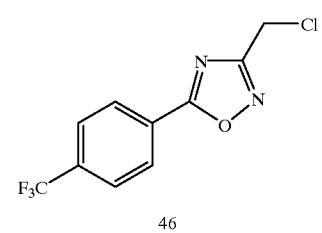
46
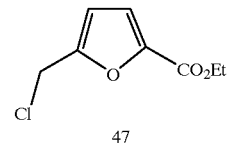
47
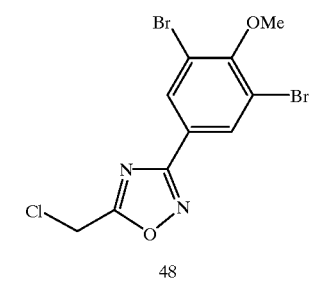
48
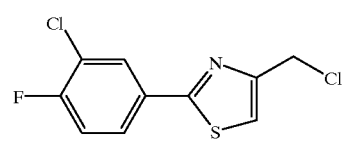
49
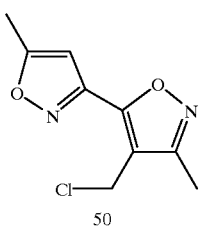
50

TABLE 17-continued
Halides of the type A-Cl, A-Br and A-I
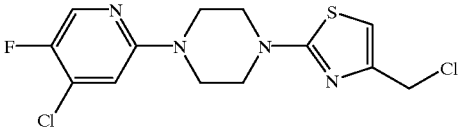
51
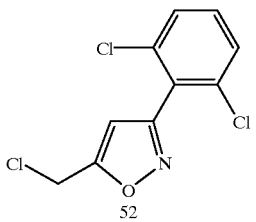
52
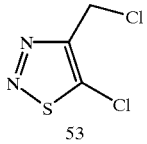
53
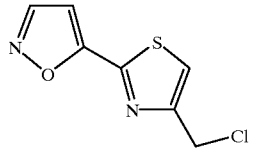
54
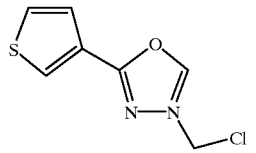
55
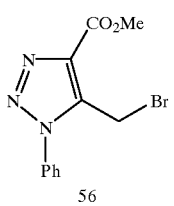
56
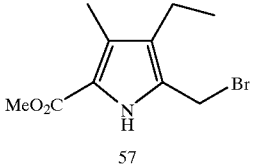
57
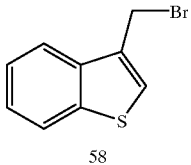
58
TABLE 17-continued
Halides of the type A-Cl, A-Br and A-I
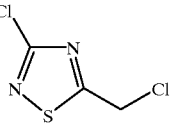
59
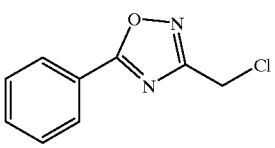
60
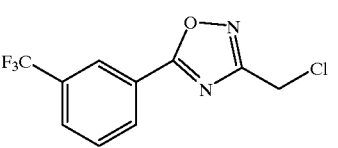
61
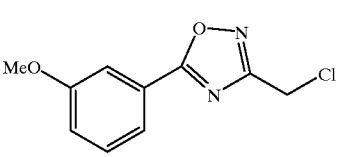
62
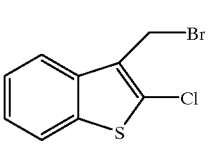
63
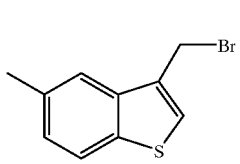
64
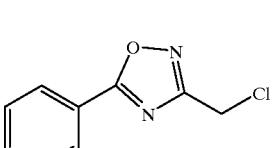
65
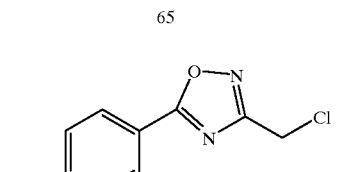
66

TABLE 17-continued
Halides of the type A-Cl, A-Br and A-I
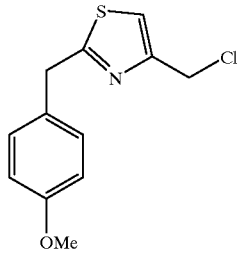
67
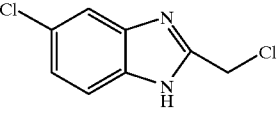
68
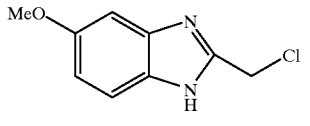
69
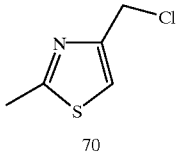
70
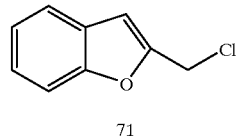
71
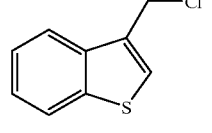
72
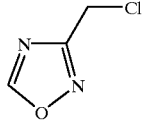
73
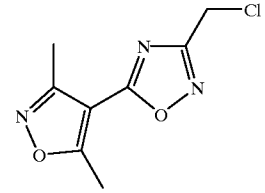
74
TABLE 17-continued
Halides of the type A-Cl, A-Br and A-I
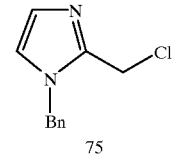
75
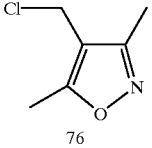
76
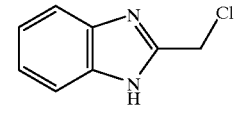
77
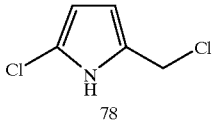
78
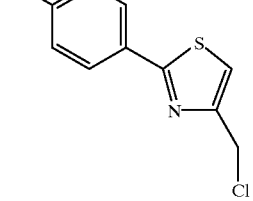
79
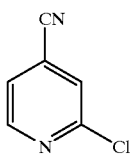
80
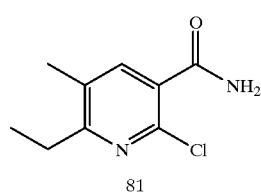
81
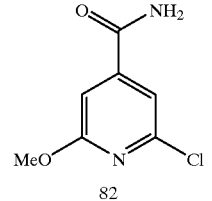
82

TABLE 17-continued
Halides of the type A-Cl, A-Br and A-I
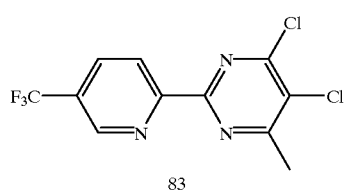
83
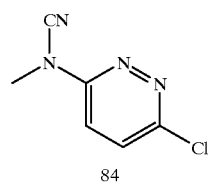
84
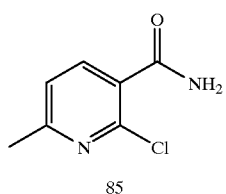
85
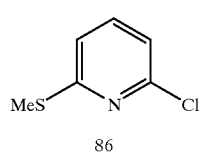
86
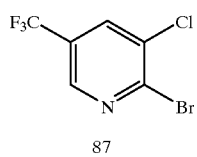
87
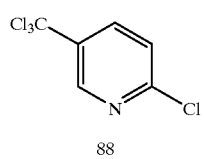
88
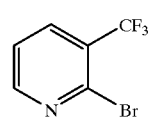
89
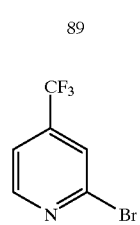
90
TABLE 17-continued
Halides of the type A-Cl, A-Br and A-I
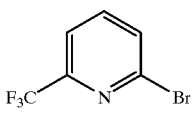
91
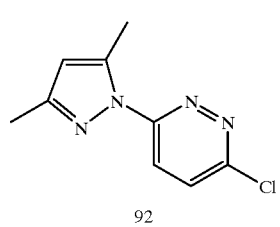
92
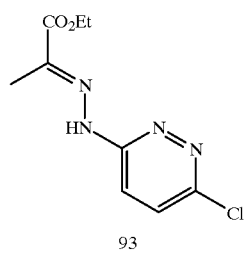
93
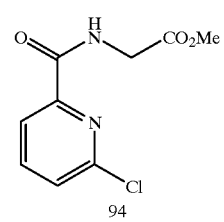
94
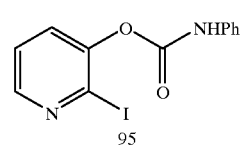
95
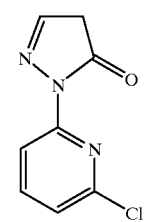
96
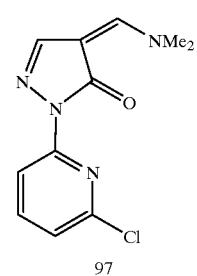
97

TABLE 17-continued
Halides of the type A-Cl, A-Br and A-I
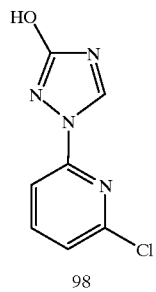
98
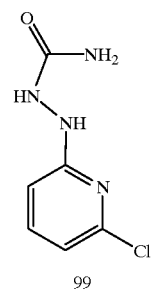
99
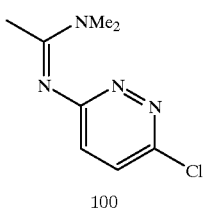
100
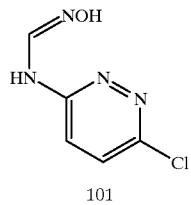
101
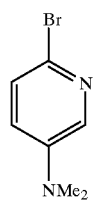
102
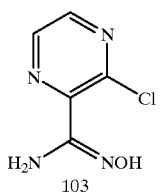
103
TABLE 17-continued
Halides of the type A-Cl, A-Br and A-I
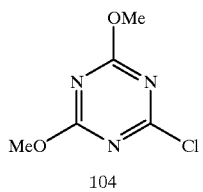
104
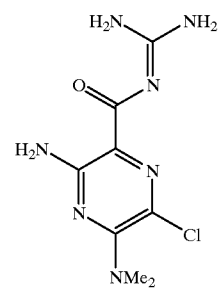
105
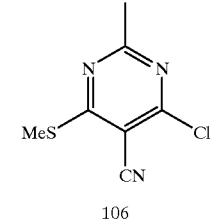
106
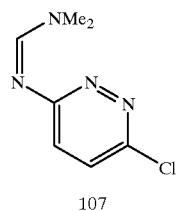
107
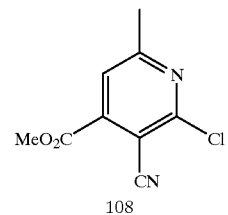
108
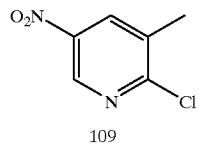
109
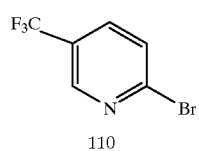
110

TABLE 17-continued
Halides of the type A-Cl, A-Br and A-I
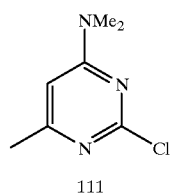
111
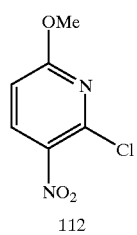
112
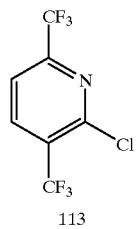
113
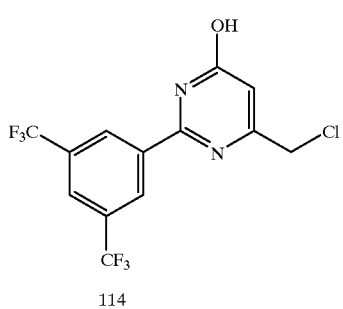
114
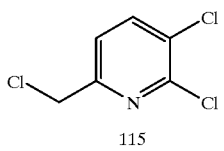
115
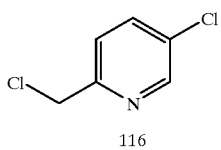
116
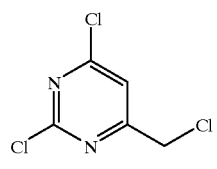
117
TABLE 17-continued
Halides of the type A-Cl, A-Br and A-I
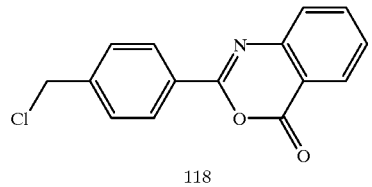
118
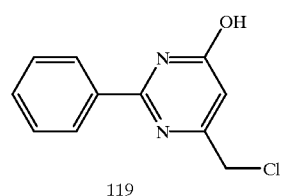
119
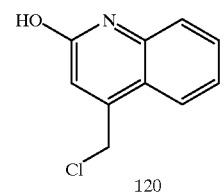
120
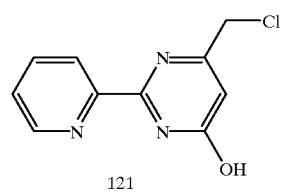
121
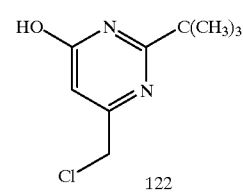
122
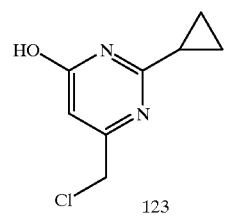
123
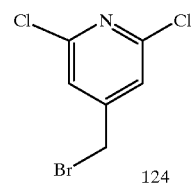
124

TABLE 17-continued
Halides of the type A-Cl, A-Br and A-I
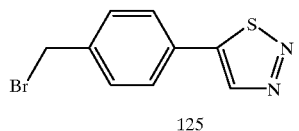
125
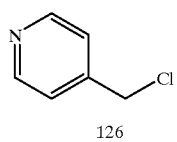
126
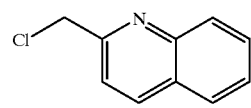
127
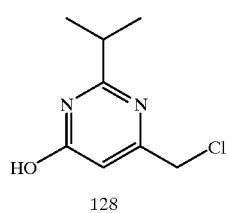
128
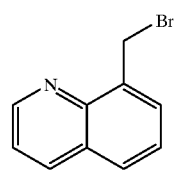
129
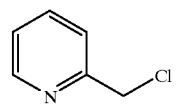
130
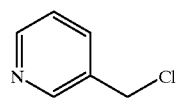
131
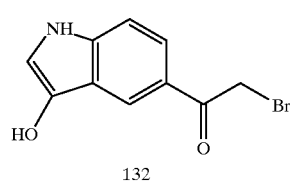
132
TABLE 17-continued
Halides of the type A-Cl, A-Br and A-I
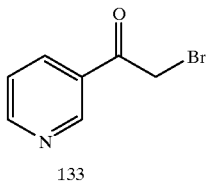
133
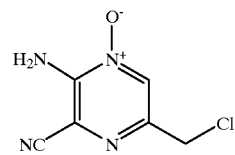
134
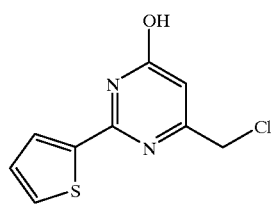
135
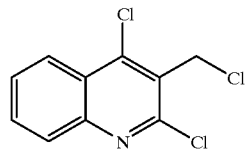
136
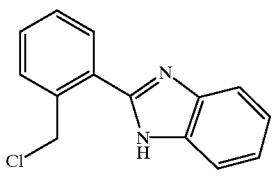
137
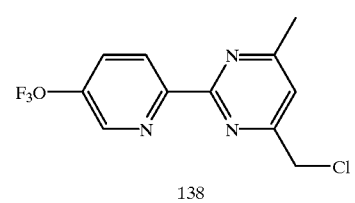
138
139

TABLE 17-continued
Halides of the type A-Cl, A-Br and A-I
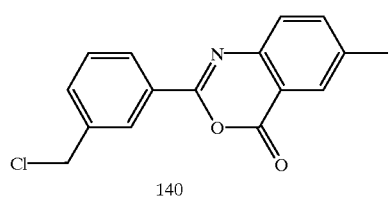
140
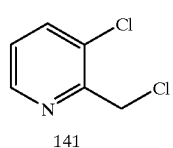
141
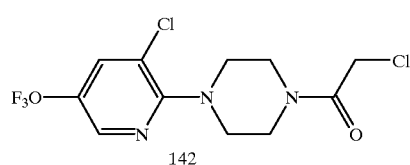
142
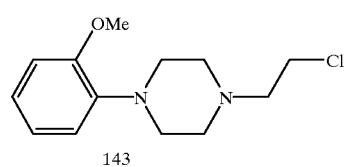
143
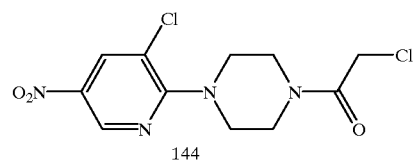
144
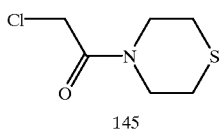
145
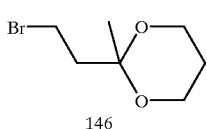
146
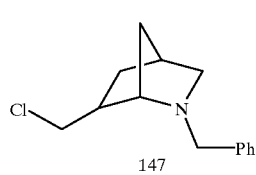
147
TABLE 17-continued
Halides of the type A-Cl, A-Br and A-I
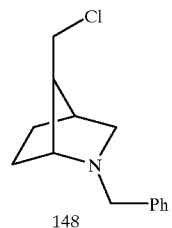
148
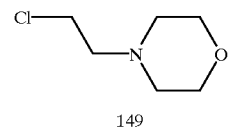
149
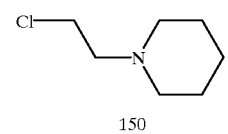
150
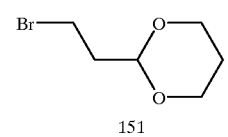
151
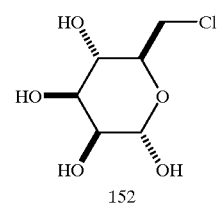
152
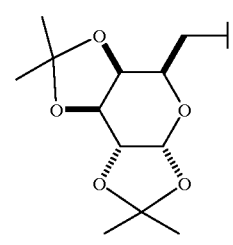
153
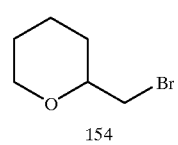
154
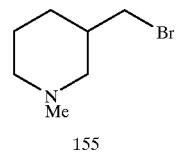
155

TABLE 17-continued
Halides of the type A-Cl, A-Br and A-I
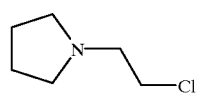
156
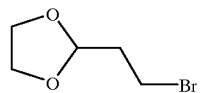
157
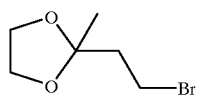
158
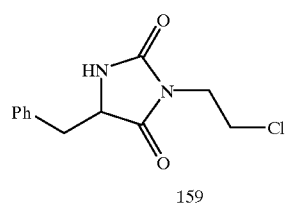
159
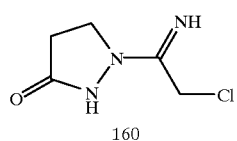
160
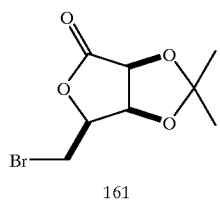
161
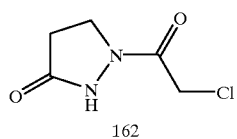
162
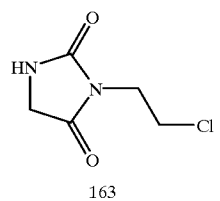
163
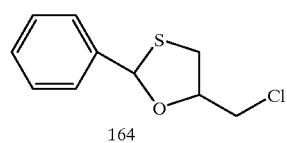
164
TABLE 17-continued
Halides of the type A-Cl, A-Br and A-I
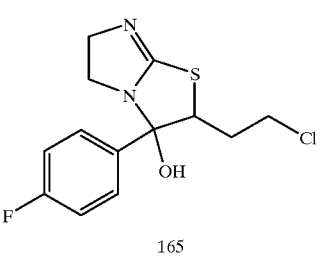
165
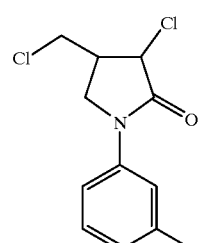
166
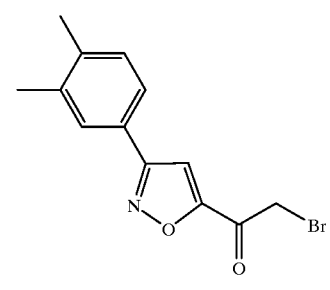
167
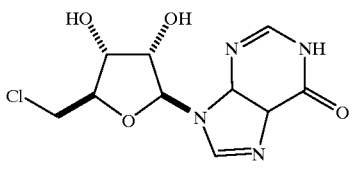
168
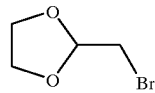
169
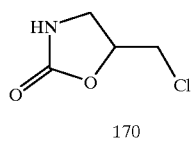
170
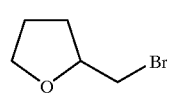
171

TABLE 17-continued
Halides of the type A-Cl, A-Br and A-I
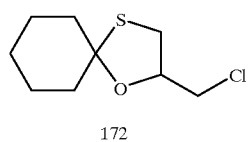
172
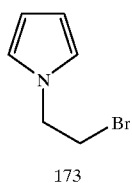
173
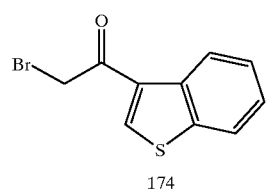
174
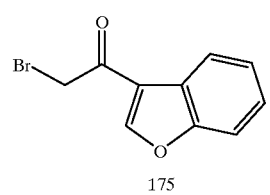
175
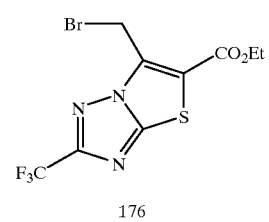
176
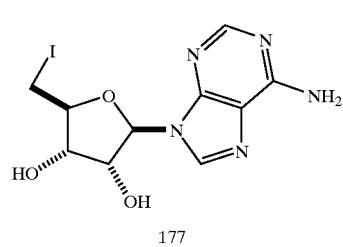
177
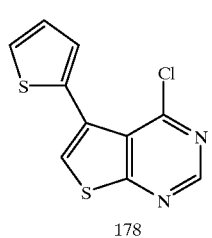
178
TABLE 17-continued
Halides of the type A-Cl, A-Br and A-I
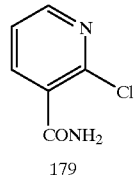
179
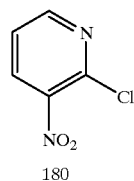
180
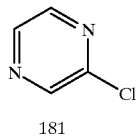
181
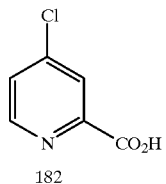
182
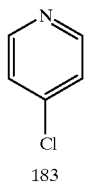
183
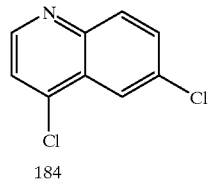
184
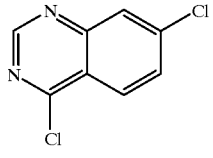
185
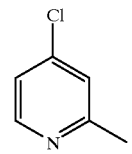
186

TABLE 17-continued
Halides of the type A-Cl, A-Br and A-I
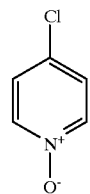
187
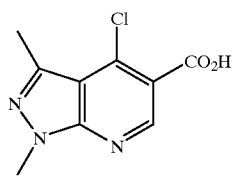
188
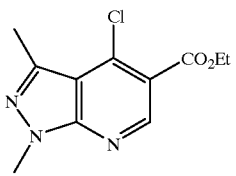
189
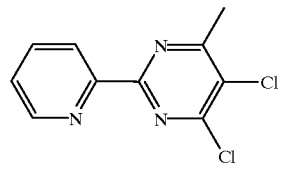
190
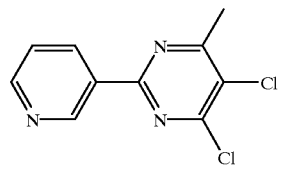
191
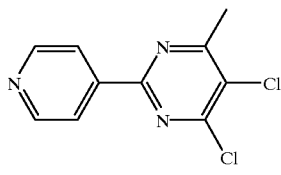
192
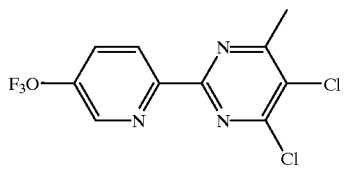
193
TABLE 17-continued
Halides of the type A-Cl, A-Br and A-I
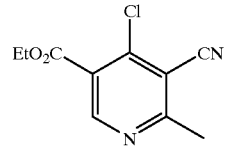
194
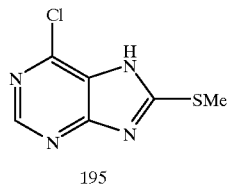
195
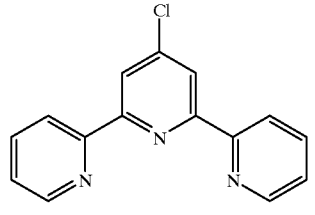
196
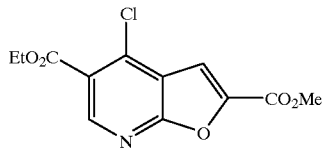
197
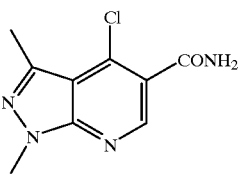
198
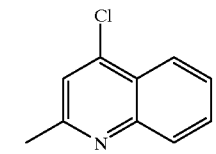
199
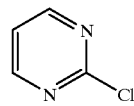
200

TABLE 17-continued
Halides of the type A-Cl, A-Br and A-I
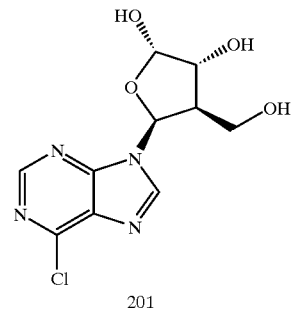
201
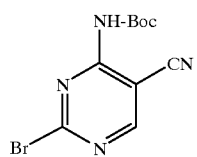
202
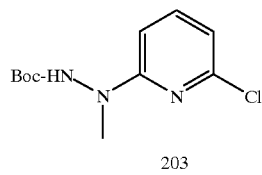
203
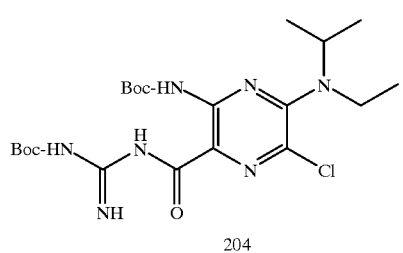
204
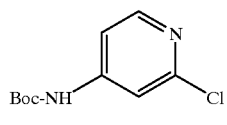
205
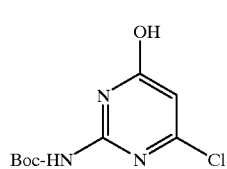
206
TABLE 17-continued
Halides of the type A-Cl, A-Br and A-I
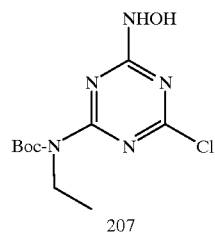
207
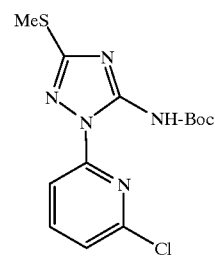
208
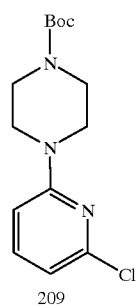
209
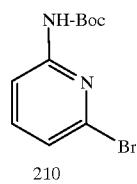
210
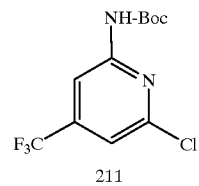
211
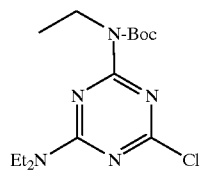
212

TABLE 17-continued
Halides of the type A-Cl, A-Br and A-I
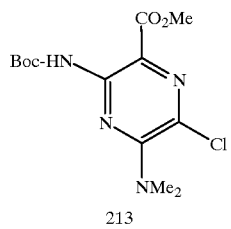
213
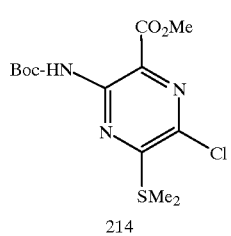
214
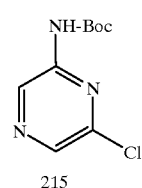
215
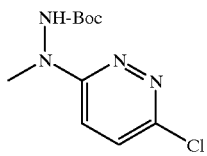
216
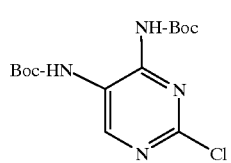
217
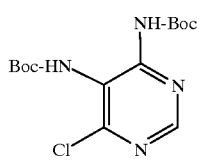
218
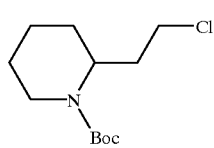
219
TABLE 17-continued
Halides of the type A-Cl, A-Br and A-I
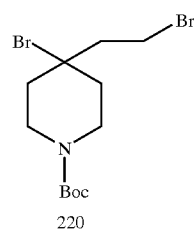
220
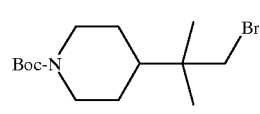
221
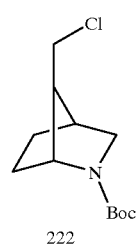
222
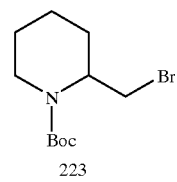
223
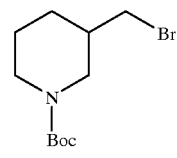
224
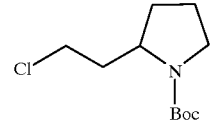
225
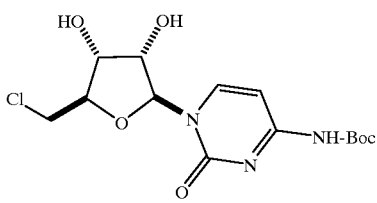
226

TABLE 17-continued
Halides of the type A-Cl, A-Br and A-I
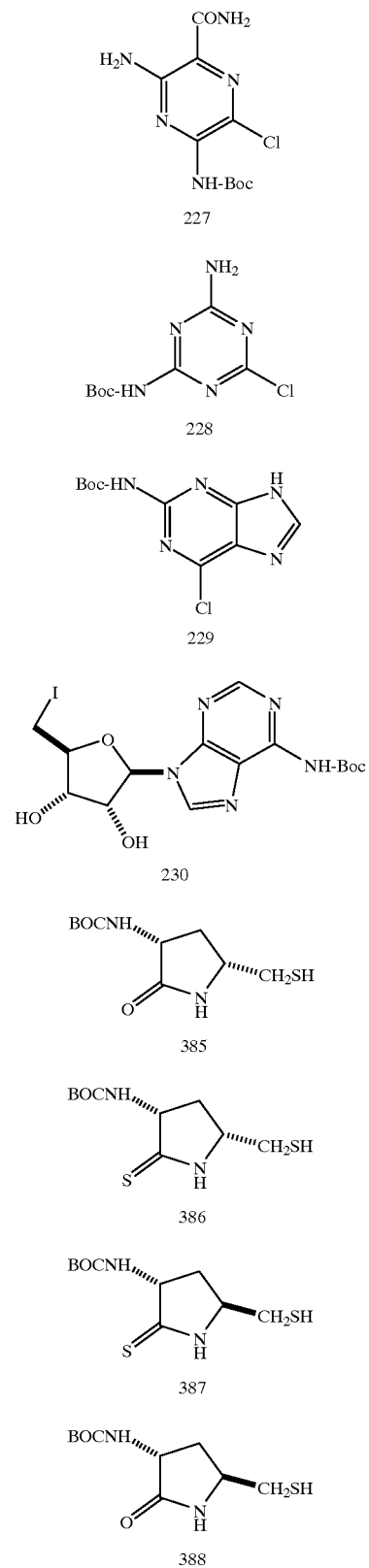
227
228
229
230
385
386
387
388
TABLE 17-continued
Halides of the type A-Cl, A-Br and A-I
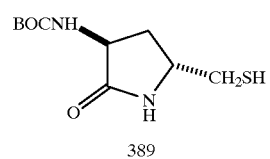
389
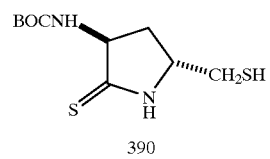
390
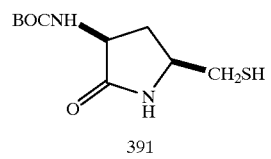
391
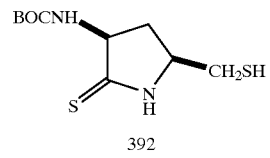
392
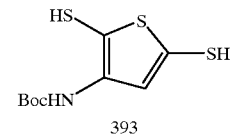
393
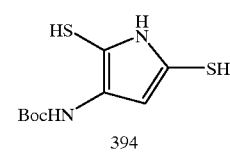
394
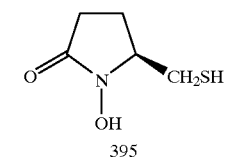
395
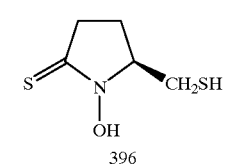
396
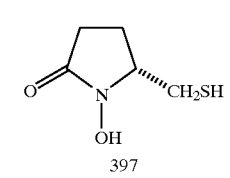
397

TABLE 17-continued
Halides of the type A-Cl, A-Br and A-I
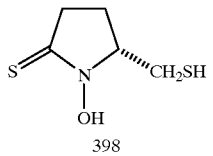
398
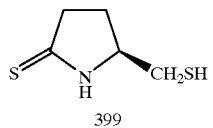
399
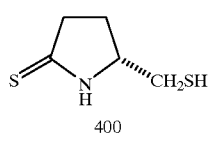
400
TABLE 18
Sulfonyl chlorides of the type A-SO$_2$Cl
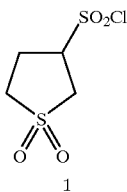
1
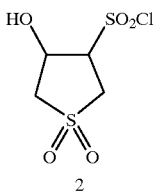
2
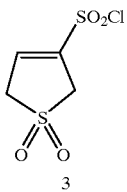
3
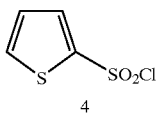
4
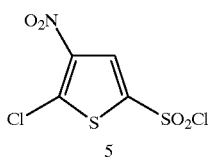
5
TABLE 18-continued
Sulfonyl chlorides of the type A-SO$_2$Cl
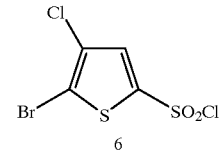
6
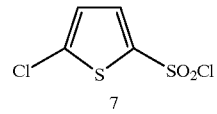
7
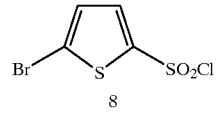
8
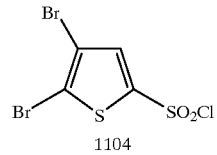
1104
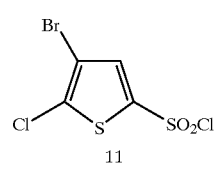
10
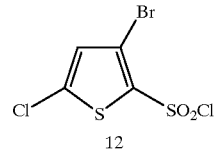
11
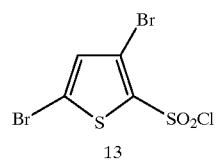
12
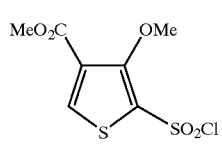
13
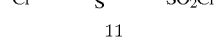
14

TABLE 18-continued
Sulfonyl chlorides of the type A-SO₂Cl
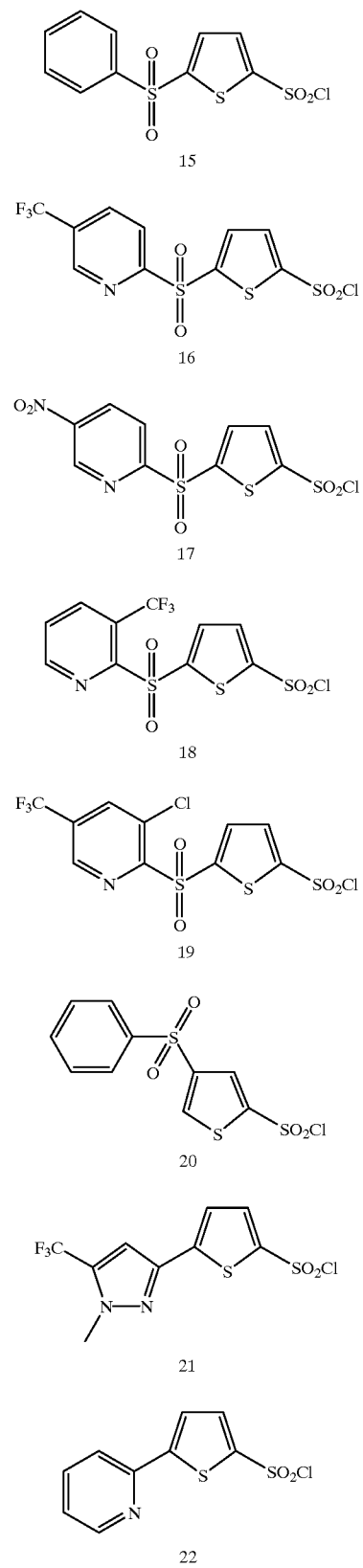
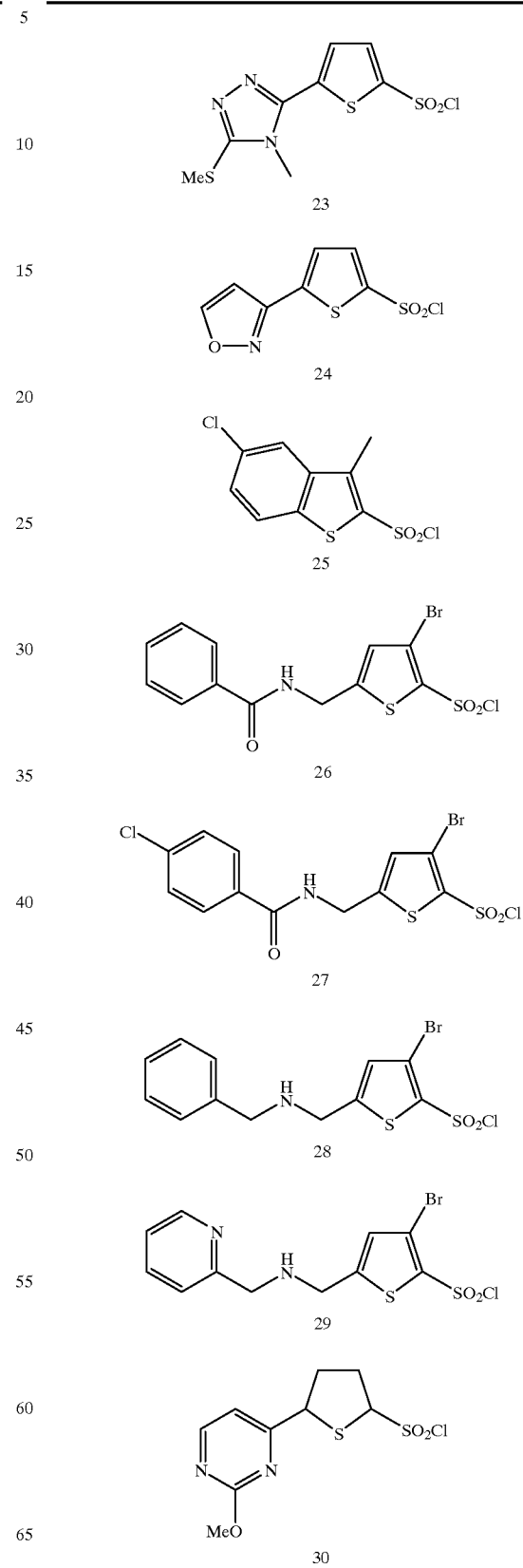

TABLE 18-continued
Sulfonyl chlorides of the type A-SO$_2$Cl
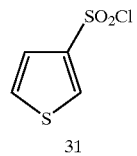
31
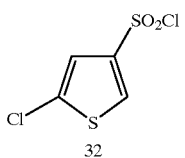
32
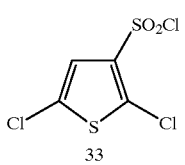
33
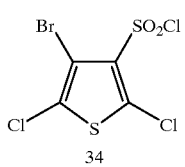
34
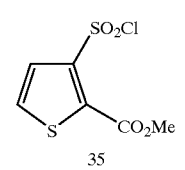
35
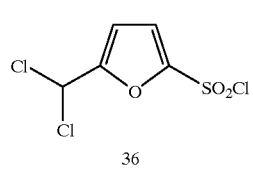
36
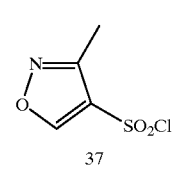
37
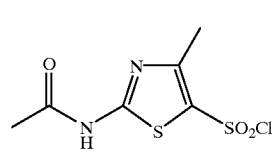
38
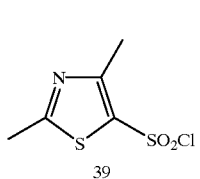
39
TABLE 18-continued
Sulfonyl chlorides of the type A-SO$_2$Cl
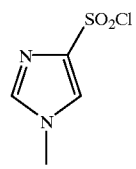
40
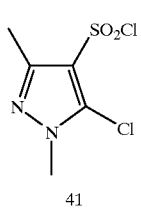
41
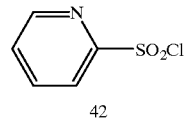
42
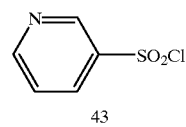
43
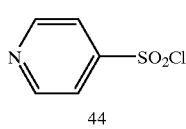
44
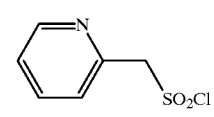
45
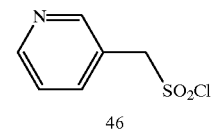
46
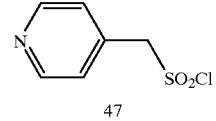
47
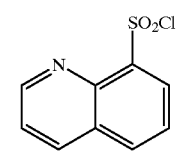
48

TABLE 18-continued

Sulfonyl chlorides of the type A-SO₂Cl

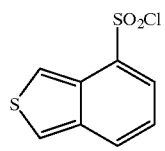

49

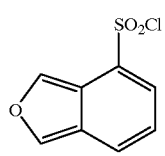

50

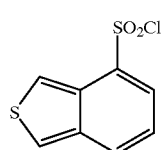

51

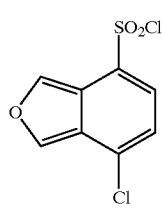

52

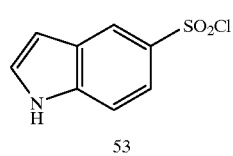

53

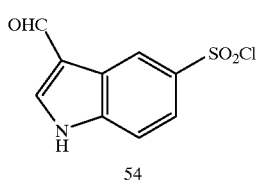

54

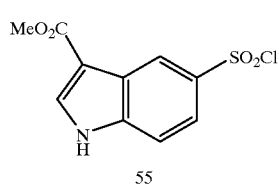

55

The foregoing may be better understood by reference to the following examples which are provided for illustration and not intended to limit the scope of the inventive concept.

In Tables 2–10, the abbreviation bz=benzoyl, bn=benzyl, Ph=phenyl, BOC=t-butyloxycarbonyl and TS=p-toluenesulfonyl.

COMPOUND 1

(3-(Aminomethyl)benzoyl)-Met-OCH₃

Step A (3-(Chloromethyl)benzoyl)-Met-OCH₃

To a solution of methionine methyl ester hydrochloride (2.0 g, 10 mmol) and 3-(chloromethyl)benzoyl chloride (2.08 g, 11.0 mmol) in methylene chloride (50 mL) was slowly added triethylamine (3.07 mL, 22.0 mmol) at ice bath temperature for 2 hours. The mixture was washed with 0.5 N HCl (50 mL×2), brine (50 mL×2) and water (50 mL×2) then dried over anhydrous MgSO₄ and concentrated under reduced pressure. The residue was purified by flash column chromatography (30% ethyl acetate in hexanes) to give the desired product (3.03 g) as a white solid: m.p. 82–83° C.; $^1$H NMR (CDCl₃) d 7.82 (1H, s), 7.74 (1H, d, J=7.7 Hz), 7.53 (1H, d, J=7.7 Hz), 7.42 (1H, t, J=7.7 Hz), 7.06 (1H, br d, J=7.6 Hz), 4.92 (1H, ddd, J=7.6, 7.1, 5.1 Hz), 4.59 (2H, s), 3.78 (3H, s), 2.58 (2H, t, J=7.1 Hz) 2.26 (1H, sm), 2.15 (1H, m), 2.10 (3H, s); $^{13}$C NMR (CDCl₃) d 172.59, 166.54, 138.13, 134.25, 131.95, 129.12, 127.42, 126.97, 52.72, 52.14, 45.55, 31.47, 30.12, 15.55.

Step B (3-(Azidomethyl)benzoyl)-Met-OCH₃

A suspension of (3-(chloromethyl)benzoyl)-Met-OCH₃ (1.58 g, 5.0 mmol) and sodium azide (1.3 g, 20.0 mmol) in DMSO (40 mL) was stirred at 80° C. for 7 hours. The mixture was diluted with methylene chloride (100 mL), washed with brine (70 mL ×2) and water (70 mL×2), and then dried over anhydrous MgSO₄. The solvent was evaporated under reduced pressure to give a yellow residue. Chromatography on silica gel (30% ethyl acetate in hexanes) to provide the desired product (1.45 g) as a colorless solid: m.p. 48–49° C.; $^1$H NMR (CDCl₃; d 7.78 (2H, m), 7.49 (2H, m), 6.99 (1H, br d, J=7.4 Hz), 4.49 (1H, ddd, J=7.4, 7.1, 5.2 Hz), 4.42 (2H, s), 3.80 (3H, s), 2.60 (2H, t, J=7.4 Hz), 2.29 (1H, m), 2.17 (1H, m), 2.12 (3H, s); $^{13}$C NMR (CDCl₃) d 177.50. 166.54, 135.97, 134.06, 131.18, 128.89, 126.84, 126.71, 54.09, 52.47, 51.95, 31.38, 30.00, 15.30.

Step C (3-(Aminomethyl)benzoyl)-Met-OCH₃

A suspension of (3-(azidomethyl)benzoyl)-Met-OCH₃ (1.29 g, 4.0 mmol) and 5% palladium on carbon (0.2 g) in methanol (40 mL) was stirred under a hydrogen atmosphere (1 atm) for two days at room temperature. The catalyst was removed by filtration through celite (1.5 g) and the solvent was evaporated in vacuo. The residue was washed with water (5 mL×2) and dried to give the desired product (1.12 g) as a colorless foam. $^1$H NMR (CDCl₃) d 7.81 (1H, s), 7.68 (1H, d, J=7.4 Hz), 7.45 (1H, d, J=6.5 Hz), 7.36 (1H, t, J=7.4 Hz), 4.91 (1H, ddd, J=7.3, 7.1, 5.1 Hz), 3.90 (2H, s), 3.77 (3H, s), 3.21 (2H, br s), 2.59 (2H, t, J=7.4 Hz), 2.20 (1H, m), 2.12 (1H, m), 2.09 (3H, s).

COMPOUND 2

(4-(Aminomethyl)benzoyl)-Met-OCH₃

The title compound is prepared according to the procedure used to prepare Compound 1 but replacing 3-(chloromethyl)benzoyl chloride with 4-(chloromethyl) benzoyl chloride.

COMPOUND 3

(3-Aniinobenzoyl)-Met-OCH$_3$

The title compound was prepared according to the procedure described in J. Biol. Chem. 269 12410–12413 (1994).

COMPOUND 4

(4-Aminobenzoyl)-Met-OCH$_3$

Step A

N-BOC-4-Aminobenzoic acid

4-Aminobenzoic acid (10 g, 72.9 mmol) was placed into a mixture of dioxane (145.8 mL) and 0.5 M NaOH (145.8 mL). The solution was cooled to 0° C. and di-t-butyl dicarbonate (23.87 g, 109.5 mmol) was added. The reaction mixture was allowed to warm to room temperature and stirred overnight. The next day, the dioxane was removed, the residue was made acidic and extracted into ethyl acetate. The ethyl acetate fractions were combined and washed with 1N HCl to remove any unreacted starting material. The solution was dried over Na$_2$SO$_4$ and the solvent was removed in vacuo. The crude material was recrystallized from ethyl acetate/hexanes to provide the desired product (12.2 g): m.p. 189–190° C.; $^1$H NMR (CD$_3$OD) d 1.52 (9H, s), 7.49 (2H, d, J=8.6 Hz), 7.91 (2H, d, J=8.6 Hz), 9.28 (1H, s); $^{13}$C NMR (CD$_3$OD) d 28.59, 81.29, 118.54, 125.30, 131.81, 145.70, 155.00, 169.80; Anal. Calc. for C$_{12}$H$_{15}$NO$_4$, C: 60.76, H: 6.37, N: 5.90; Found, C: 60.52, H: 6.43, N: 5.83; HRMS Calc. for C$_{12}$H$_{15}$NO$_4$, 237.0961, Found, 237.1001.

Step B

(N-BOC-4-Aminobenzoyl)-Met-OCH$_3$

Into a dried, nitrogen filled flask was placed N-BOC-4-aminobenzoic acid (8.77 g, 36.97 mmol) in dry methylene chloride (148 mL) along with methionine methyl ester hydrochloride (8.12 g, 40.66 mmol). This solution was cooled in an ice bath and triethylamine (6.7 mL), EDCI (7.80 g, 40.66 mmol) and hydroxybenzotriazole (HOBT, 5.50 g, 40.66 mmol) were added. The mixture was stirred overnight, diluted with more methylene chloride and was extracted three times each with 1 M HCl, 1M NaHCO$_3$ and water. The methylene chloride was dried over MgSO$_4$ and the solvent was removed in vacuo. The resulting solid was recrystallized from ethyl acetate/hexanes to yield the desired product (9.72 g): m.p. 184–185° C.; $^1$H NMR (CDCl$_3$) d 1.53 (9H, s), 2.06–2.18 (4H, m), 2.23–2.33 (1H, m), 2.59 (2H, t, J=7.6 Hz), 3.80 (3H, s), 4.92 (1H, m), 7.45 (2H, d, J=8.7 Hz), 7.77 (2H, d, J=8.7 Hz); $^{13}$C NMR (CDCl$_3$) d 15.59, 28.34, 30.15, 31.64, 52.10, 52.73, 81.20, 117.73, 127.8, 128.33, 141.88, 152.33, 166.50, 172.75; Anal. Calc. for C$_{18}$H$_{26}$N$_2$O$_5$S, C: 56.53, H: 6.85, N: 7.29; Found, C: 56.47, H: 6.86, N: 7.29; m/z (EI) 382 (M).

Step C

(4-Aminobenzoyl)-Met-OCH$_3$ hydrochloride

N-BOC4-aminobenzoyl-Met-OCH$_3$ (3.53 g, 9.59 mmol) was placed into methylene chloride (30–35 mL) and to it was added 3M HCl/EtO$_2$ (38.4 mL). After standing, a white precipitate formed. After two hours the solution was decanted and the crystals were collected by centrifugation. The crystals were then washed several times with fresh ether and dried overnight on the vacuum pump. Meanwhile, the filtrate was left to stand overnight to allow additional product to precipitate. The second fraction was washed with ether and dried overnight on the vacuum pump. The total yield of the desired product was 2.87 g: m.p. 158–164° C.; $^1$H NMR (CDCl$_3$) d 2.10 (3H, s), 2.12–2.29 (1H, m), 2.52–2.71 (1H, m), 2.59 (2H, t, J=7.6 Hz), 3.75 (3H, s), 4.79 (1H, m), 7.02 (2H, d, J=8.6 Hz), 7.55 (2H, d, J=8.6 Hz); $^{13}$C NMR (CDCl$_3$) d 15.23, 31.43, 31.53, 52.91, 52.43, 124.35, 130.56, 135.31, 135.76, 168.95, 173.87; HRMS Calc. for C$_{13}$H$_{18}$N$_2$O$_3$S, 282.1038, Found 282.1009.

COMPOUND 5

(4-Amino-3-methylbenzoyl)-Met-OCH$_3$

Step A

N-BOC-4-Amino-3-methylbenzoic acid

4-Amino-3-methylbenzoic acid (5 g, 33.1 mmol) was reacted according to the same procedure as that used in the process for preparing N-BOC-4-aminobenzoic acid. The resulting orange-brown solid was recrystallized from ethyl acetate and hexanes to provide the desired product (4.99 g) as tan prismatic crystals: m.p. 180–182° C.; 1H NMR (CD$_3$OD) d 1.51 (9h, s), 2.27 (3H, s), 7.66 (1H, d, J=8.1 Hz), 7.79–7.82 (2H, m), 8.32 (1H, s); 13C NMR (CD3OD) d 17.98, 28.62, 81.47, 123.12, 127.05, 129.14, 130.65, 132.99, 142.45, 155.33, 168.70; Anal. Calc. for C$_{13}$H$_{17}$NO$_4$, C: 62.15, H: 6.82, N: 5.58; Found C: 62.07, H: 6.86, N: 5.46; m/z (EI) 251; HRMS Calc. for C$_{13}$H$_{17}$NO$_4$, 251.1158; Found, 251.1153.

Step B

(N-BOC-4-Amino-3-methylbenzol)-Met-OCH$_3$

N-BOC-4-amino-3-methylbenzoic acid (2.00 g, 7.96 mmol) was reacted with with methionine methyl ester hydrochloride (1.75 g, 8.76 mmol), triethylamine (1.4 mL), EDCI (1.68 g, 8.76 mmol) and hydroxybenzotriazole (HOBT, 1.18 g, 8.76 mmol) in dry methylene chloride (31.8 mL) according to the procedure described for the preparation of N-BOC-4-aminobenzoyl)-Met-OCH$_3$. The resulting solid was recrystallized from ethyl acetate/hexanes to yield the desired product (2.61 g): m.p. 163–165° C.; IH NMR (CDCl$_3$) d 1.54 (9H, s), 2.06–2.18 (4H, m), 2.23–2.34 (4H, m), 2.59 (2H, t, J=6.8 Hz), 3.80 (3H, s), 4.92 (1H, m), 6.45 (1H, s), 6.88 (1H, d, J=7.5 Hz), 7.63 (1H, d, J=8.6 Hz), 7.66 (1H, s), 8.05 (1H, d, J=8.6 Hz); $^{13}$C NMR (CDCl$_3$) d 15.47, 17.61, 28.22, 30.03, 31.55, 51.93, 52.57, 81.04, 118.73, 125.62, 127.66, 129.54, 139.89, 152.34, 166.58, 172.66.

Step C

(4-Amino-3-methylbenzoyl)-Met-OCH$_3$ hydrochloride

N-BOC-4-Amino-3-methylbenzoyl-Met-OCH$_3$ (0.99 g, 2.59 mmol) was dissolved in methylene chloride (15–20 mL) and precipitated with 3M HCl/Et$_2$O (20.7 mL). A pale orange precipitate was obtained, washed with ether and dried overnight on the vacuum pump. The total yield of the desired product was 0.83 g: m.p. 157–159° C.; $^1$H NMR (CD$_3$OD) d 2.04 (3H, s), 2.11–2.25 (1H, m), 2.47 (3H, s), 2.52–2.68 (3H, m), 3.74 (3H, s), 4.75–4.80 (1H, m), 7.48 (1H, d, J=8.2 Hz), 7.81 (2H, d, J=8.2 Hz), 7.87 (1H, s); $^{13}$C NMR (CD$_3$OD) d 15.23, 17.28, 31.43, 31.51, 52.91, 53.37, 124.41, 127.85, 131.99, 133.63, 134.14, 135.65, 169.05, 173.84; Anal. Calc. for C$_{14}$H$_{21}$N$_2$O$_3$S, C: 50.52, H: 6.36, N: 8.42; Found C: 50.71, H: 6.40, N: 8.34.

COMPOUND 6

(4-Amino-3-methoxybenzoyl)-Met-OCH$_3$

Step A

N-BOC-4-Amino-3-methoxybenzoic acid

4-Amino-3-methoxybenzoic acid (1 g, 5.98 mmol) was reacted according to the same procedure as that used in the process for preparing N-BOC-4-aminobenzoic acid. The resulting solid was recrystallized from ethyl acetate and hexanes to provide the desired product (1.5 g) as tan crystals: m.p. 176–178° C.; $^1$H NMR (CD$_3$OD) d 1.52 (9H, s), 3.92 (3H, s), 7.56 (1H, s), 7.62 (1H, d, J=8.4 Hz), 7.96 (1H, s), 8.03 (1H, d, J=8.4 Hz); $^{13}$C NMR (CD$_3$OD) d 28.53, 56.35, 81.78, 112.01, 118.58, 124.20, 125.76, 133.84, 149.04, 154.20, 169.60; HRMS Calc. for C$_{13}$H$_{17}$NO$_5$, 267.1107; Found, 267.1103.

Step B (N-BOC-4-Amino-3-methoxybenzoyl)-Met-OCH$_3$

N-BOC-4-amino-3-methoxybenzoic acid (0.35 g, 1.31 mmol) was reacted with with methionine methyl ester hydrochloride (0.9 g, 1.43 mmol) using EDCI according to the procedure described for the preparation of (N-BOC4aminobenzoyl)-Met-OCH$_3$.

The resulting solid was recrystallized from ethyl acetate/hexanes to yield the desired product (0.36 g): m.p. 163–165° C.; $^1$H NMR (CDCl$_3$) d 1.53 (9H, s), 2.09–2.18 (4H, m), 2.23–2.35 (1H, m), 2.60 (2H, t, J=6.9 Hz), 3.80 (3H, s), 3.93 (3H, s), 4.92 (1H, br s), 6.93 (1H, d, J=7.6 Hz), 7.25(1H, m), 7.31 (1H, d, J=10.2 Hz), 7.44 (1H, s), 8.15 (1H, d, J=8.5 Hz); $^{13}$C NMR (CDCl$_3$) d 15.47, 28.23, 30.09, 31.48, 52.06, 52.54, 55.81, 80.82, 98.06, 109.38, 116.66, 119.31, 131.52, 147.23, 152.31, 166.57, 172.58; m/z (FAB) 413 (M+1).

Step C (4-Amino-3-methoxybenzoyl)-Met-OCH$_3$ hydrochloride

N-BOC-4-Amino-3-methoxybenzoyl-Met-OCH$_3$ (0.71 g, 1.79 mmol) was dissolved in methylene chloride (4 mL) and precipitated with 3M HCl/Et$_2$O (12 mL). A reddish precipitate was obtained, washed with ether and dried overnight on the vacuum pump. The total yield of the desired product was 0.55 g: m.p. 176–177° C.; $^1$H NMR (CD$_3$OD) d 2.08 (3H, s), 2.21 (2H, m), 2.61 (2H, m), 3.74 (3H, s), 4.02 (3H, s), 4.79 (1H, m), 7.50 (1H, d, J=8.2 Hz), 7.57 (1H, d, J=4.1 Hz), 7.67 (1H, s); $^{13}$C NMR (CD$_3$OD) d 15.26, 31.34, 31.42, 52.95, 53.38, 57.12, 112.29, 121.43, 124.57, 124.77, 136.15, 153.67, 168.79, 173.81.

COMPOUND 7

(4-Amino-1-naphthoyl)-Met-OCH$_3$

Step A

4-Amino-1-naphthoic acid

4-Amino-1-naphthalenecarbonitrile (1.5 g, 8.91 mmol) was suspended in a 50% KOH solution (18 mL). The heterogeneous solution was heated at reflux for 2–3 days. Once the solution became homogeneous and TLC showed no more starting material, the deep red solution was cooled and poured over 200 mL of water. The resulting solution was then filtered and the desired product was precipitated with concentrated HCl. The resulting red crystals were filtered and the filtrate was refiltered to give pink crystals. The first fraction of crystals was treated with activated carbon to remove some of the red color. A total of 1.51 g of the desired product was obtained: m.p. 169–171° C.; $^1$H NMR (CD$_3$OD) d 6.69 (1H, d, J=8.2 Hz), 7.38–7.43 (1H, m), 7.48–7.54 (1H, m), 8.03 (1H, d, J=8.5 Hz), 8.13 (1H, d, J=8.2 Hz), 9.09 (1H, d, J=8.5 Hz); $^{13}$C NMR (CD$_3$OD) d 107.39, 114.61, 122.99, 123.92, 125.21, 127.40, 128.48, 135.04, 151.35, 171.44; HRMS Calc. for C$_{11}$H$_7$NO$_2$, 187.0633; Found, 187.0642.

Step B

N-BOC-4-Amino-1-naphthoic acid

4-Amino-1-naphthoic acid (0.86 g, 4.61 mmol) was dissolved in dioxane (9.2 mL). Di-t-butyl dicarbonate (1.11 g, 5.07 mmol) was added and the mixture was stirred overnight. The reaction mixture was worked up as described above for N-BOC-4-aminobenzoic acid to give 0.76 g of the desired product as a reddish pink solid: m.p. 194–195° C.; $^1$H NMR (CD$_3$OD) d 1.56 (9H, s), 7.53–7.62 (2H, m), 7.79 (1H, d, J=8.1 Hz), 8.12 (1H, d, J=8.0 Hz), 8.22 (1H, d, J=8.18 Hz), 9.02 (1H, d, J=8.9 Hz); $^{13}$C NMR (CD$_3$OD) d 26.68, 81.62, 119.06, 123.40, 124.57, 127.03, 127.37, 128.49, 128.77, 131.89, 133.76, 139.86, 155.95, 170.73; Anal. Calc. for C$_{17}$H$_{17}$NO$_4$, C: 66.90, H: 5.96, N: 4.88; Found C: 66.49, H: 6.08, N: 4.79; m/z (EI), 289; HRMS Calc. for C$_{16}$H$_{17}$NO$_4$, 287.1158; Found, 287.1151.

Step C (N-BOC-4-Amino-1-naphthoyl)-Met-OCH$_3$

N-BOC-4-Amino-naphthoic acid (0.46 g, 1.60 mmol), methionine methyl ester hydrochloride (0.35 g, 1.76 mmol), EDCI (0.43 g, 1.76 mmol), HOBT (0.24 g, 1.76 mmol) and triethylamine (0.27 mL) in methylene chloride (6.4 mL) were reacted as described above for N-BOC-4-aminobenzoyl-Met-OCH3. After workup and recrystallization from ethyl acetate hexanes, the desired product (0.44 g) was obtained as pale pink crystals: m.p. 131–132° C.; $^1$H NMR (CDCl$_3$) d 1.57 (9H, s), 2.11–2.21 (4H, m), 2.29–2.41 (1H, m), 2.65 (2H, t, J=7.1 Hz), 3.83 (3H, s), 4.99–5.06 (1H, m), 6.68 (1H, d, J=8.0 Hz), 7.02 (1H, s), 7.56–7.59 (2H, m) 7.69 (1H, d, J=7.9 Hz), 7.87–7.90 (1H, m), 8.02 (1H, d, J=7.9 Hz), 8.44–8.48 (1H, m); $^{13}$C NMR (CDCl$_3$) d 15.56, 28.31, 30.19, 31.65, 52.06, 52.64, 81.17, 115.82, 120.18, 125.79, 126.37, 126.53, 127.18, 131.02, 135.65, 152.93, 169.04, 172.40; HRMS Calc. for C$_{22}$H$_{28}$N$_2$O$_5$S, 432.1719; Found, 432.1702; m/z (FAB) 433 (M+1).

Step D (4-Amino-1-naphthoyl)-Met-OCH$_3$ hydrochloride (N-BOC-4-Amino-1-naphtholyl)-Met-OCH$_3$ (0.57 g, 1.31 mmol) was deprotected with HCl/ether to yield the desired product (0.31 g) as a white solid: m.p. 178–181° C.; $^1$H NMR (CD$_3$OD) d 2.08–2.16 (4H, m), 2.20–2.30 (1H, m) 2.57–2.75 (2H, m) 3.82 (3H, s), 4.87–4.91 (1H, m), 7.59 (1H, d, J=7.5 Hz), 7.67 (1H, d, J=7.5 Hz) 7.71–7.80 (2H, m), 8.03 (1H, dd, J=7.1, 2.0 Hz), 8.35 (1H, dd, J=6.8, 1.8 Hz);

$^{13}$C NMR (CD$_3$OD) d 15.23, 31.40, 53.01, 53.33, 119.90, 122.20, 126.15, 127.41,127.77, 129.09, 129.31, 131.50, 132.33, 135.64, 171.77, 173.83; m/z (FAB), 369 (M+1).

COMPOUND 8

(4-Amino-2-phenylbenzoyl)-Met-OCH$_3$

Step A

4-Nitro-2-phenyltoluene

2-Bromo4-nitrotoluene (2.16 g, 10.00 mmol) and phenyl-boric acid (1.46 g, 12.00 mmol) were dissolved in anhydrous DMF (25 mL) under nitrogen. To this mixture was added Pd(Ph$_3$P)$_4$ (0.58 g, 5%). The mixture was heated at 100° C. overnight. The solution was poured onto 1N HCl and extracted with Et$_2$O. The crude product was chromatographed on silica gel using hexanes as eluent. After recrystallization from ethanol, the desired product (1.23 g) was obtained as pale orange needles: m.p. 69–71° C.; $^1$H NMR (CDCl$_3$) d 2.36 (3H, s), 7.29–7.40 (2H, m), 7.41–7.49 (5H, m), 8.07–8.10 (2H, m); $^{13}$C NMR (CDCl$_3$) d 20.68, 121.96, 124.51, 127.78, 128.41, 128.83, 131.06, 139.06, 139.44, 142.97, 143.48, 146.05; Anal. Calc. for C$_{13}$H$_{11}$NO$_2$, C: 73.26, H: 5.20, N: 6.57; Found, C: 73.10, H: 5.12, N: 6.50; m/z (EI) 213; HRMS Calc. for C$_{13}$H$_{11}$NO$_2$, 213.0790; Found, 213.0793.

Step B

4-Nitro-2-phenylbenzoic acid

4-Nitro-2-phenyltoluene (0.5 g, 2.34 mmol) was dissolved in water (4.6 mL) and pyridine (2.3 mL). The mixture was heated to reflux and KMnO$_4$ (1.85 g, 11.7 mmol) was added. The reaction mixture was heated overnight and the solution was filtered and washed several times with boiling water. The aqueous solution was made acidic and the product was extracted into ethyl acetate. The ethyl acetate solution was dried over Na$_2$SO$_4$ and the solvent removed in vacuo to provide the desired product (0.37 g): m.p. 174–176° C., $^1$H NMR (CD$_3$OD) d 7.38–7.48 (5H, m), 7.96 (1H, d, J=8.5 Hz), 8.21 (1H, d, J=2.3 Hz), 8.28 (1H, dd, J=8.48, 2.37 Hz); $^{13}$C NMR (CD$_3$OD) d 122.95, 126.09, 129.27, 129.42, 129.49, 131.56, 139.26, 140.42, 144.41, 150.17, 170.52; m/z (EI) 243 (M).

Step C (4-Nitro-2-phenylbenzoyl)-Met-OCH$_3$

4-Nitro-2-phenylbenzoic acid (0.3 g, 1.23 mmol), methionine methyl ester hydrochloride salt (0.27 g, 1.35 mmol), EDCI (0.26 g, 1.35 mmol), HOBT (0.18 g, 1.35 mmol) and triethylamine (0.19 mL) in dry methylene chloride (4.9 mL) were reacted according the procedure described above for (N-BOC-4-aminobenzoyl)-Met-OCH$_3$. After recrystallization of the product from ethyl acetate hexanes, the desired product (0.41 g) was obtained: m.p. 98–101° C.; $^1$H NMR (CDCl$_3$) d 1.62–1.73 (1H, m), 1.79–1.88 (1H, m), 1.91 (3H, s), 1.99 (2H, t, J=7.2 Hz), 3.59 (3H, s), 4.53 (1H, m), 6.45 (1H, d, J=7.8 Hz), 7.33–7.40 (5H, m), 7.67 (1H, d, J=8.3 Hz), 8.07–8.12 (2H, m); $^{13}$C NMR (CDCl$_3$) d 14.92, 29.11, 30.67, 51.51, 52.29, 121.86, 124.74, 128.27, 128.60, 128.69, 129.52, 137.50, 140.56, 141.02, 148.09, 167.23, 171.23; m/z (FAB), 389 (M+1).

Step D (4-Amino-2-phenylbenzoyl)-Met-OCH$_3$ (4-Nitro-2-phenylbenzoyl)-Met-OCH$_3$ (0.35 g, 0.90 mmol) was dissolved in ethyl acetate (9.0 mL). To this mixture was added SnCl$_2$.2H$_2$O (1.02 g, 4.5 mmol) and the reaction mixture was heated under nitrogen at reflux for one hour. The mixture was poured onto ice, the solution was made basic using NaHCO$_3$ and the product was extracted into ethyl acetate several times (7–8). The ethyl acetate solutions were combined, washed with brine and dried over Na$_2$SO$_4$. The solvent was removed in vacuo to the desired product (0.24 g) as a yellow solid: $^1$H NMR (CDCl$_3$) d 1.58–1.70 (1H, m), 1.80–1.92 (1H, m), 1.98 (3H, s) 2.06 (2H, t, J=7.7 Hz), 3.62 (3H, s), 4.00 (2H, br s), 4.56–4.63 (1H, m), 5.84 (1H, d, J=7.7 Hz), 6.50 (1H, s), 6.61 (1H, d, J=8.4 Hz) 7.29–7.42 (5H, m), 7.58 (1H, d, J=8.3 Hz); $^{13}$C NMR (CDCl$_3$) d 15.02, 29.25, 31.25, 51.57, 52.15, 113.27, 115.88, 123.52, 127.56, 128.37, 128.44, 130.92, 140.66, 141.44, 148.53, 168.58, 171.91.

COMPOUND 9

(4-Amino-2-(2-thienyl)benzoyl)-Met-OCH$_3$

The title compound can be prepared according to the method used to prepare Compound 8, only substituting thiophene-2-boronic acid for phenyl boronic acid.

COMPOUND 10

(4-Amino-2-(1-naphthyl)benzoyl)-Met-OCH$_3$

The title compound can be prepared according to the method used to prepare Compound 8, only substituting 1-naphthylboronic acid for phenylboronic acid.

COMPOUND 11

4-Amino-3'-methylbiphenyl

The title compound was prepared by Suzuki coupling of 1-bromo-4-nitrobenzene and 1-bromo-3-methylbenzene.

COMPOUND 12

4-Amino-4'-biphenyl carboxylic acid

Step A

4-Nitro-4'-methylbiphenyl

The title compound was prepared by Suzuki coupling of 1-bromo4-nitrobenzene and 1-bromo-4-methylbenzene.

Step B

4-Nitro-4'-biphenyl carboxylic acid

The title compound was prepared by KMnO$_4$ oxidation of 4-nitro4'-methylbiphenyl.

Step C

4-Amino-4'-biphenyl carboxylic acid

The title compound can be prepared by palladium catalyzed hydrogenation of 4-nitro-4'-biphenyl carboxylic acid.

COMPOUND 13

4-Amino-3'-biphenyl carboxylic acid

Step A

4-Nitro-3'-methylbiphenyl

The title compound was prepared by Suzuki coupling of 1-bromo-4-nitrobenzene and 1-bromo-3-methylbenzene.

Step B

4-Nitro-3'-biphenyl carboxylic acid

The title compound was prepared by KMnO$_4$ oxidation of 4-nitro-3'-methylbiphenyl.

Step C

4-Amino-3'-biphenyl carboxylic acid

The title compound can be prepared by palladium catalyzed hydrogenation of 4-nitro-3'-biphenyl carboxylic acid.

COMPOUND 14

4-Amino-2-methoxy-3'-biphenyl carboxylic acid

Step A

2-Methoxy-4-nitro-3'-methylbiphenyl

The title compound was prepared by reaction of 1-bromo-2-methoxy4-nitrobenzene with 3-methylphenylboronic acid in the presence of palladium acetate.

Step B

2-Methoxy4-nitro-3'-biphenylcarboxylic acid

The title compound was prepared by KMnO$_4$ oxidation of 2-methoxy4-nitro-3'-methylbiphenyl.

Step C

4-Amino-2-methoxy-3'-biphenyl carboxylic acid

The title compound can be prepared by palladium catalyzed hydrogenation of 2-methoxy-4-nitro-3'-biphenyl carboxylic acid.

COMPOUND 15

4-Amino-2-isopropyloxy-3'-biphenyl carboxylic acid

The title compound can be prepared by methods analogous to those used to prepare Compound 14.

COMPOUND 16

4-Amino-2-phenyl-3'-biphenylcarboxylic acid

The title compound can be prepared by methods analogous to those used to prepare Compound 14.

COMPOUND 17

(4-Amino-2-(3,5-dimethylphenyl)benzoyl)-Met-OCH$_3$

Step A

2-Bromo-4-nitrobenzoic acid

2-Bromo-4-nitrotoluene (5.0 g, 23.14 mmol) was dissolved in pyridine (23 mL) and water (46 mL). The heterogeneous mixture was heated to 60° C. and KMnO$_4$ (18.29 g, 115.7 mmol) was added carefully. The mixture was then heated under reflux overnight. The reaction mixture was filtered and washed with boiling water. The solution was then made acidic and extracted into ethyl acetate, dried over Na$_2$SO$_4$ and the solvent was removed in vacuo. The crude product was dissolved in aqueous NaOH and washed with hexanes. The aqueous phase was made acidic and the product was extracted into ethyl acetate. The ethyl acetate solutions were combined and dried over Na$_2$SO$_4$ and the solvent was removed in vacuo to provide the desired product (3.72 g): m.p. 158–160° C.; $^1$H NMR (CD$_3$OD) d 7.81 (1H, d, J=8.5 Hz), 8.08 (1H, d, J=8.5 Hz), 8.30 (1H, s); $^{13}$C NMR (CD$_3$OD) d 121.96, 122.75, 129.36, 132.24, 139.52, 149.54, 167.75; Anal. Calc. for C$_7$H$_4$BrNO$_4$ *0.1 ethyl acetate, C: 34.88, H: 1.90, N: 5.50; Found, C: 34.68, H: 1.86, N: 5.82.

Step B

3.5-Dimethylphenylboronic acid

Magnesium turnings (1.44 g, 59.43 mmol) were covered with dry THF (18.8 mL) in a dried, nitrogen filled flask fitted with an addition funnel and reflux condenser. To this was added 5-bromo-m-xylene (10 g, 54.03 mmol) in THF (15 mnL) after initiation of the Grignard reaction. The addition was carried out over several minutes and the reacton mixture was heated at reflux for 1–2 hours until most of the magnesium had reacted. The reaction mixture was then cooled and transferred to an addition funnel fitted to an nitrogen filled flask containing triisopropyl borate (24.9 mL) at −70° C. The dropwise addition was carried out over several minutes and the mixture warmed to room temperature and stirred overnight. The grey solution was poured onto 2 M HCl and immediately turned yellow. The solution was extracted with Et$_2$O and the Et$_2$O fractions were combined, dried over MgSO$_4$ and the solvent was removed in vacuo to provide the desired product (2.41 g): m.p.249–251° C.; $^1$H NMR (CDCl$_3$) d 2.44 (6H, s), 7.23 (1H, s), 7.84 (2H, s); $^{13}$C NMR (CD$_3$OD) d 21.36, 133.28, 134.39, 137.48.

Step C

4-Nitro-2-(3,5-dimethylphenyl)benzoic acid

2-Bromo4-nitrobenzoic acid (0.43 g, 2.03 mmol) and 3,5-dimethylphenyl boronic acid (0.334 g, 2.23 mmol) were dissolved in anhydrous DMF (25 mL) under nitrogen. To this mixture was added Cs$_2$CO$_3$ (1.66 g, 5.08 mmol) followed by Pd(Ph$_3$P)$_4$ (0.12 g, 5%). The mixture was heated at 100° C. overnight. The solution was poured onto 1N HCl and extracted with Et$_2$O. It was dried over MgSO$_4$ and the solvent was removed in vacuo. The crude product was chromatographed on silica gel using a 9:1 mixture of hexanes and ethyl acetate to provide the desired product (0.34 g): $^1$H NMR (CDCl$_3$) d 2.36 (6H, s), 6.99 (2H, s), 7.07 (1H, s), 8.03 (1H, d, J=9.0 Hz), 8.23–8.25 (2H, m); $^{13}$C NMR (CDCl$_3$) d 21.28, 121.68, 123.68, 125.74, 126.07, 130.22, 131.19, 131.31, 135.04, 138.21, 144.74, 170.75.

Step D

(4-Nitro-2-(3,5-dimethylphenyl)benzoyl)-Met-OCH$_3$

4-Nitro-2-(3,5-dimethylphenyl)benzoic acid (0.15 g, 0.55 mmol), methionine methyl ester hydrochloride (0.11 g, 0.55 mmol), EDCI (0.11 g, 0.55 mmol), HOBT (0.07 g, 0.55 mmol) and triethylamine (0.08 mL) in dry methylene chloride (2.2 mL) were reacted and worked up according to the procedure for (N-BOC4-aminobenzoyl)-Met-OCH$_3$ as described above. After recrystallization from ethyl acetate and hexanes, the desired product was obtained (0.13 g): m.p. 122–124° C.; $^1$H NMR (CDCl$_3$) d 1.2–1.84 (1H, m), 1.85–1.97 (1H, m), 2.01 (3H, s), 2.05 (3H, t, J=7.7 Hz), 2.38 (6H, s), 3.70 (3H, s), 4.67–4.74 (1H, m), 6.03 (1H, d, J=7.9

Hz), 7.05 (2H, s), 7.09 (1H, s), 7.84–7.87 (1H, m), 7.84–7.87 (1H, m) 8.23–8.26 (2H, m); $^{13}$C NMR (CDCl$_3$) d 15.20, 21.26, 29.22, 31.15, 51.79, 52.57, 122.07, 125.11, 126.27, 130.03, 130.53, 137.77, 138.82, 140.29, 141.56, 148.41, 167.14, 171.53.

Step E (4-Amino-2-(3,5-dimethylphenyl)benzoyl)-Met-OCH$_3$ (4-Nitro-2-(3,5-dimethylphenyl)benzoyl)-Met-OCH$_3$ (0.11 g, 0.26 mmol) was dissolved in ethyl acetate (3.0 mL). To this mixture was added SnCl$_2$.2H$_2$O (0.3 g, 1.30 mmol) and the reacton was heated under nitrogen at reflux for 6 hours. The mixture was worked up as described above for (4-amino-2-phenylbenzoyl)-Met-OCH$_3$ to give the desired product (0.15 g): $^1$H NMR (CDCl$_3$) d 1.60–1.70 (1H, m), 1.80–1.90 (1H, m), 1.99 (3H, s), 2.05 (2H, t, J=7.6 Hz), 2.33 (6H, s), 3.64 (3H, s), 3.93 (2H, br s), 4.61–4.64 (1H, m), 5.82 (1H, d, J=7.7 Hz), 6.49 (1H, d, J=2.3 Hz) 6.62 (1H, dd, J=8.4, 2.4 Hz), 6.98 (2H, s), 7.00 (1H, s), 7.65 (1H, d, J=8.3 Hz); $^{13}$C NMR (CDCl$_3$) d 15.08, 21.17, 29.28, 31.49, 51.70, 52.18, 113.30, 115.94, 123.55, 126.36, 129.32, 131.23, 138.15, 140.72, 141.92, 148.40, 168.45, 172.01.

PREPARATION 1

Anilinès of the formula B—NH$_2$

The anilines from Table 1, entries 10–126 (B—NH$_2$) are prepared using the procedures for Compounds 1–18 with the exception that methionine methyl ester is replaced by methioninesulfone methyl ester, (S—Me)cysteine methyl ester, serine methyl ester, (O—Me)serine methyl ester, (O—Me)homoserine methyl ester, homoserine lactone, isoleucine methyl ester, leucine methyl ester, norleucine methyl ester, norvaline methyl ester, cyclohexylalanine methyl ester, phenylalanine methyl ester, or glutamic acid dimethyl ester.

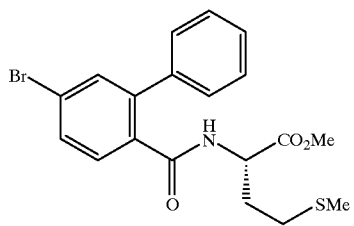

PREPARATION 2

4-Bromo-2-phenylbenzoyl methionine methyl ester

PREPARATION 2A

4-Bromo-2-phenylbenzoic acid methyl ester

A solution of methyl 4-amino-2-phenylbenzoic acid (1.0 equivalent) in dilute aqueous HBr is treated with NaNO$_2$ (1.1 equivalents) to form the diazonium salt. The reaction is treated with CuBr (1.1 equivalents) and heated. When judged complete by TLC analysis, the mixture is extracted into ethyl acetate which is dried and evaporated. The title arylbromide is purified by chromatography on silica gel.

PREPARATION 2B

4-Bromo-2-phenylbenzoic acid

To a solution of the resultant compound from Preparation 2A (1.0 equivalent) in a 3:1 mixture of tetrahydrofuran (THF) and water is added an excess (1.5 equivalents) of LiOH. When hydrolysis is judged complete by TLC analysis, the solvent is evaporated and the remaining aqueous layer is acidified to pH=3 and extracted into ethyl acetate which is dried and evaporated prior to purification by chromatography on silica gel.

PREPARATION 2C

4-Bromo-2-phenylbenzoyl methionine methyl ester

To a solution of the resultant compound from Preparation 2B (1.0 equivalent) in dimethylformamide (DMF) is added 3-hydroxy-1,2,3-benzotriazin-4(3H)-one (1.5 equivalents) followed by methionine methyl ester (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed by 1N HCl and saturated brine, and then is dried and evaporated. The crude reaction mixture is purified by column chromatography to afford the title product.

PREPARATION 2D

4-Bromo-2-phenylbenzoyl methionine methyl ester alternate procedure

A solution of 4-amino-2-phenylbenzoyl methionine methyl ester (1.0 equivalent) in dilute aqueous HBr is treated with NaNO$_2$ (1.1 equivalents) to form the diazonium salt. The reaction is treated with CuBr (1.1 equivalents) and heated. When judged complete by TLC analysis, the mixture is extracted into ethyl acetate which is dried and evaporated. The title arylbromide is purified by chromatography on silica gel.

PREPARATION 3

Arylbromides of the formula B—Br

The anilines from Table 1 (B—NH$_2$) are reacted according to the procedures of Preparation 2 to provide the arylbromides listed in Table 2.

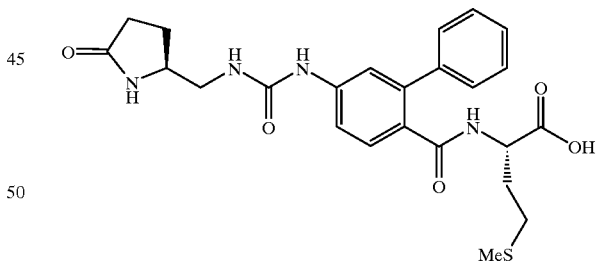

EXAMPLE 1

4-((S)-2-Pyrrolidone-5-aminomethylcarbonyl) amino-2-phenylbenzoyl methionine

EXAMPLE 1A

Methyl 4-((S)-2-Pyrrolidone-5-aminomethylcarbonyl)amino-2-phenylbenzoate

To a solution of methyl 4-amino-2-phenylbenzoate hydrochloride (1.0 equivalent) in toluene is added triphosgene (0.33 equivalent) and the mixture is heated at reflux until judged complete by TLC analysis. The intermediate is reacted without further purification with (S)-5-aminomethyl-2-pyrrolidone (1.0 equivalent) and triethylamine (2.0 equivalents). When judged complete by TLC analysis, the reaction is taken up in ethyl acetate and washed with 1N HCl and brine, evaporated, and purified by chromatography on silica gel.

EXAMPLE 1B 4-((S)-2-Pyrrolidone-5-aminomethylcarbonyl) amino-2-phenylbenzoic acid To a solution of the resultant compound from Example 1A (1.0 equivalent) in a 3:1 mixture of tetrahydrofuran (THF) and water is added an excess (1.5 equivalents) of LiOH. When hydrolysis is judged complete by TLC analysis, the solvent is evaporated and the remaining aqueous layer is acidified to pH=3 and extracted into ethyl acetate which is dried and evaporated prior to purification by chromatography on silica gel.

EXAMPLE 1C 4-((S)-2-Pyrrolidone-5-aminomethylcarbonyl) amino-2-phenylbenzoyl methionine methyl ester To a solution of the resultant compound from Example 1B (1.0 equivalent) in dimethylformamide (DMF) is added 3-hydroxy-1,2,3-benzotriazin-4(3H)-one (1.5 equivalents) followed by methionine methyl ester (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 1D 4-((S)-2-Pyrrolidone-5-aminomethylcarbonyl) amino-2-phenylbenzoyl methionine methyl ester, alternate preparation To a solution of 4-amino-2-phenylbenzoyl methionine methyl ester (1.0 equivalent) in methylene chloride is added a solution of phosgene in toluene (1.0 equivalent) and triethylamine (2.0 equivalents). The intermediate is reacted without further purification with (S)-5-aminomethyl-2-pyrrolidone (1.0 equivalent) and triethylamine (1.0 equivalent). When judged complete by TLC analysis, the reaction is taken up in ethyl acetate and washed with 1N HCl and brine, evaporated, and purified by chromatography on silica gel.

EXAMPLE 1E 4-((S)-2-Pyrrolidone-5-aminomethylcarbonyl) amino-2-phenylbenzoyl methionine To a solution of the resultant compound from Example 1C in a 3:1 mixture of THF and water is added an excess of LiOH (1.5 equivalents). When hydrolysis is judged complete by TLC analysis, the solvent is evaporated and the remaining aqueous layer is acidified to pH=3 and extracted into ethyl acetate which is dried and evaporated prior to purification by chromatography on silica gel.

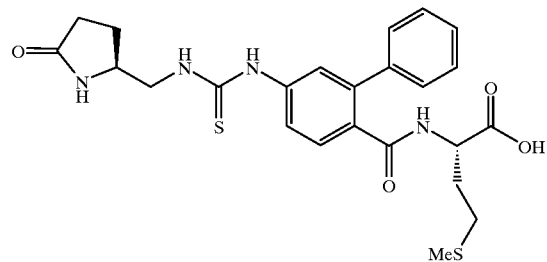

EXAMPLE 2

4-((S)-2-Pyrrolidone-5-aminomethylthiocarbonyl) amino-2-phenylbenzoyl methionine The title compound is prepared as described in Example 1 with the exception that triphosgene (0.33 equivalent) is replaced by thiophosgene (1.0 equivalent).

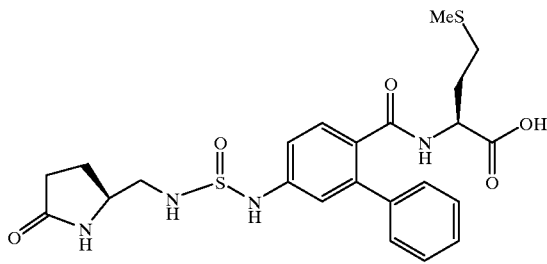

EXAMPLE 3

4-((S)-2-Pyrrolidone-5-aminomethylsulfinyl)amino-2-phenylbenzoyl methionine

EXAMPLE 3A 4-((S)-2-Pyrrolidone-5-aminomethylsulfinyl)amino-2-phenylbenzoyl methionine methyl To a solution of 4-amino-2-phenylbenzoyl methionine methyl ester (1.0 equivalent) in methylene chloride is added thionyl chloride (1.0 equivalent) and triethylarmine (2.0 equivalents). After the amine has fully reacted, (S)-5-aminomethyl-2-pyrrolidone (1.0 equivalent) is added. When the reaction is judged complete by TLC analysis, the product is isolated as described in Example 1A and purified by chromatography on silica gel.

EXAMPLE 3B 4-((S)-2-Pyrrolidone-5-aminomethylsulfinyl)amino-2-phenylbenzoyl methionine To a solution of the resultant compound from Example 3A in a 3:1 mixture of THF and water is added an excess of LiOH (1.5 equivalents). When hydrolysis is judged complete by TLC analysis, the solvent is evaporated and the remaining aqueous layer is acidified to pH=3 and extracted into ethyl acetate which is dried and evaporated prior to purification by chromatography on silica gel.

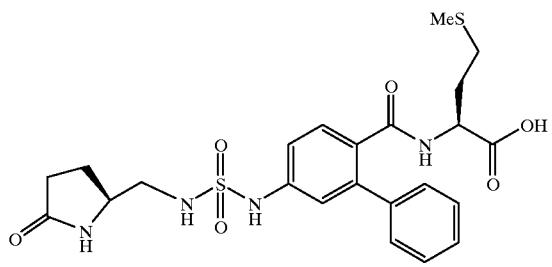
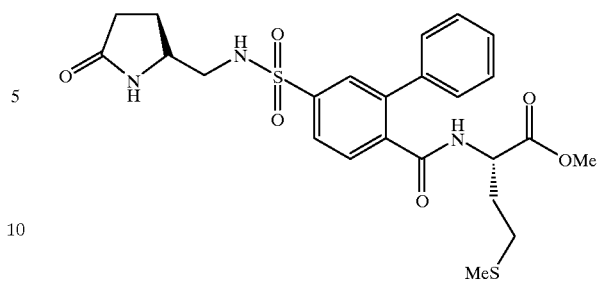

EXAMPLE 4

4-((S)-2-Pyrrolidone-5-aminomethylsulfonyl)amino-2-phenylbenzoyl methionine

EXAMPLE 4A 4-((S)-2-Pyrrolidone-5-aminomethylsulfonyl)amino-2-phenylbenzoyl methionine methyl To a solution of 4-amino-2-phenylbenzoyl methionine methyl ester (1.0 equivalent) in methylene chloride is added sulfuryl chloride (1.0 equivalent) and triethylamine (2.0 equivalents). After the amine has fully reacted, (S)-5-aminomethyl-2-pyrrolidone (1.0 equivalent) is added. When the reaction is judged complete by TLC analysis, the product is isolated as described in Example 1A and purified by chromatography on silica gel.

EXAMPLE 4B 4-((S)-2-Pyrrolidone-5-aminomethylsulfonyl)amino-2-phenylbenzoyl methionine methyl ester, alternate procedure A solution of 1 equivalent of 4amino-2-phenylbenzoyl methionine methyl ester (1.0 equivalent) and sulfuryl chloride (1.0 equivalent) in acetonitrile with a catalytic amount of antimony(V) chloride is heated to reflux until judged complete by TLC analysis. The solution is then cooled, filtered, and all volatiles are removed under reduced pressure. The residue is taken up in dichloromethane and treated with triethylamine (1 equivalent and (S)-5-aminomethyl-2-pyrrolidone (1.0 equivalent). When the reaction is judged complete by TLC analysis, the product is isolated as described in Example 1A and purified by chromatography on silica gel.

EXAMPLE 4C 4-((S)-2-Pyrrolidone-5-aminomethylsulfonyl)amino-2-phenylbenzoyl methionine methyl ester The resultant compound from Example 4A is hydrolyzed according to the procedure of Example 1B to give the title product.

EXAMPLE 5

4-((S)-2-Pyrrolidone-5-methylaminosulfonyl)-2-phenylbenzoyl methionine

EXAMPLE 5A

4-Chlorosulfonyl-2-phenylbenzoic acid methyl ester

To a solution of methyl 4-amino-2-phenylbenzoate (1.0 equivalent) in concentrated HCl is added a solution of sodium nitrite (1.1 equivalents) until an excess of nitrous acid persists. The chlorodiazonium salt is poured into a solution of sulfur dioxide (10 equivalents), coppt (II) chloride (0.5 equivalent) and KCl (1.1 equivalents) in dioxane. When TLC analysis indicated that the reaction is complete, the mixture is diluted with water and extracted into benzene which is dried and evaporated to give the title sulfonyl chloride

EXAMPLE 5B 4-((S)-2-Pyrrolidone-5-aminomethyl)sulfonyl)-2-phenylbenzoic acid methyl ester To a solution of the resultant compound from Example 5A (1.0 equivalent) in methylene chloride is added (S)-5-aminomethyl-2-pyrrolidone (1.0 equivalent) and triethylamine (1.0 equivalent). When the reaction is judged complete by TLC analysis, the solvent is evaporated and the residue is purified by chromatography on silica gel.

EXAMPLE 5C

4((S)-2-Pyrroidone-5-aminomethyl)sulfonyl)-2-phenylbenzoic acid

The resultant compound from Example 5B is hydrolyzed according to the procedure of Example 1B to give the title product.

EXAMPLE 5D 4-((S)-2-Pyrrolidone-5-aminomethyl)sulfonyl)-2-phenylbenzoyl methionine methyl ester To a solution of the resultant compound from Example 5C (1.0 equivalent) in (DMF) is added 3-hydroxy-1,2,3-benzotriazin4(3H)-one (1.5 equivalents) followed by methionine methyl ester (1.0 equivalent) and 1-(3-dimethylaminopropyl)-3-ethylcarbodiimide hydrochloride (1.5 equivalents). When judged complete by TLC analysis, the reaction is taken up in ethyl acetate which is washed by 1N HCl and saturated brine, and then is dried and evaporated. The crude reaction mixture is purified by column chromatography to afford the title product.

EXAMPLE 5E

4-((S)-2-Pyrrolidone-5-aminomethylcarbonyl) amino-2-phenylbenzoyl methionine methyl ester, alternate preparation To a solution of 4-amino-2-phenylbenzoyl methionine methyl ester (1.0 equivalent) in concentrated HCl is added a solution of sodium nitrite (1.1 equivalents) until an excess of nitrous acid persists at which time the chlorodiazonium salt will be treated with gaseous sulfur dioxide and copper (II) chloride to give the sulfonyl chloride (0.1 equivalent). This intermediate is reacted with (S)-5-aminomethyl-2-pyrrolidone (1.0 equivalent) and triethylamine (1.0 equivalent) according to the procedure of Example 5B to give the title compound.

EXAMPLE 5F

4-((S)-2-Pyrrolidone-5-aminomethylcarbonyl) amino-2-phenylbenzoyl methionine To a solution of the resultant compound from Example 5D (1.0 equivalent) in a 3:1 mixture of THF and water is added an excess of LiOH (1.5 equivalents). When hydrolysis is judged complete by TLC analysis, the solvent is evaporated and the remaining aqueous layer is acidified to pH=3 and extracted into ethyl acetate which is dried and evaporated prior to purification by chromatography on silica gel.

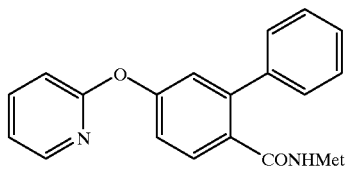

EXAMPLE 6

4-(2-pyridyloxy)-2-phenylbenzoylmethionine

Example 6A

4-Hydroxy-2-phenylbenzoic acid methyl ester

A solution of methyl 4-amino-2-phenylbenzoate (1.0 equivalent) in dilute aqueous $H_2SO_4$ is treated with $NaNO_2$ (1.1 equivalents) until an excess of nitrous acid persists to form the diazonium salt. This salt is then diluted further with water and heated. The mixture is extracted into ethyl acetate which is dried and evaporated. The title ester is purified by chromatography on silica gel.

EXAMPLE 6B

4-(2-Pyridyloxy)-2-phenylbenzoic acid methyl ester

A solution of the resultant phenol from Example 6A (1.0 equivalent) is treated with 2-bromopyridine (1.0 equivalent) in the presence of a NaH (1.0 equivalent), or $K_2CO_3$ (2.0 equivalents) and copper (1.0 equivalent) in DMF or pyridine. The product is isolated by removal of the solvent and chromatography on silica gel.

EXAMPLE 6C

4-(2-Pyridyloxy)-2-phenylbenzoic acid

A solution of the resultant ester from Example 6B (1.0 equivalent) in aqueous methanol is treated with NaOH (2.0 equivalents) and stirred until the reaction is deemed complete by TLC analysis. The mixture is acidified, diluted with water, and extracted into ethyl acetate which is dried and evaporated. Chromatography on silica gel provides the tide product.

EXAMPLE 6D

4-(2-Pyridyloxy)-2-phenylbenzoylmethionine methyl ester

The resultant product from Example 6C is coupled to methionine methyl ester according to the procedure of Example 1C to give the title compound.

EXAMPLE 6E

4-(2-Pyridyloxy)-2-phenylbenzoylmethionine methyl ester, alternate procedure A solution of 4-amino-2-phenylbenzoyl methionine methyl ester (1.0 equivalent) in dilute aqueous $H_2SO_4$ is treated with $NaNO_2$ (1.1 equivalents) until an excess of nitrous acid persists to form the diazonium salt. This salt is then diluted further with water and heated to form the phenol which is purified by chromatography on silica gel. A solution of this phenol (1.0 equivalent) is treated with 3-bromopyridine (1.0 equivalent) in the presence of a NaH (1.0 equivalent), or $K_2CO_3$ (2.0 equivalents) and copper (1.0 equivalent) in DMF or pyridine. The product is isolated by removal of the solvent and chromatography on silica gel.

EXAMPLE 6F

4-(2-pyridyloxy)-2-phenylbenzoylmethionine

The resultant compound from Example 6E is hydrolyzed according to the procedure of Example 1B to give the title compound.

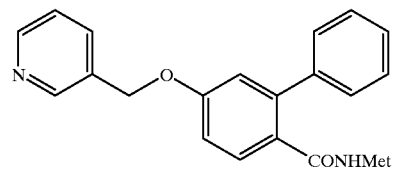

EXAMPLE 7

4-(3-pyridylmethylenoxy)-2-phenylbenzoylmethionine

The title compound is prepared as described in Example 6 with the exception that 2-bromopyridine is replaced by 3-chloromethylpyridine hydrochloride.

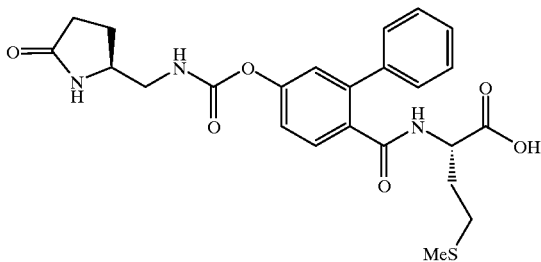

EXAMPLE 8

4-((S)-2-Pyrrolidone-5-aminomethyl)carbonyloxy-2-phenylbenzoyl methionine

EXAMPLE 8A 4-((S)-2-Pyrrolidone-5-aminomethyl)carbonyloxy-2-phenylbenzoyl methionine methyl ester To a solution of 4-hydroxy-2-phenylbenzoyl methionine methyl ester (1.0 equivalent) from Example 6E in methylene chloride is added a solution of phosgene in toluene (1.0 equivalent) and p-dimethylaminopyridine (2.0 equivalents). When the reaction is judged complete by TLC analysis, the solvent is evaporated with toluene chasers. The chloroformate is reacted without further purification with (S)-5-aminomethyl-2-pyrrolidone (1.0 equivalent) and triethylarnine (1.0 equivalent) in dichloromethane. When judged complete by TLC analysis, the reaction is taken up in ethyl acetate and washed with 1N HCl and brine, evaporated, and purified by chromatography on silica gel.

EXAMPLE 8B 4-((S)-2-Pyrrolidone-5-aminomethyl)carbonyloxy-2-phenylbenzoyl methionine The resultant compound from Example 8A is hydrolyzed according to the procedure of Example 1B to give the title product.

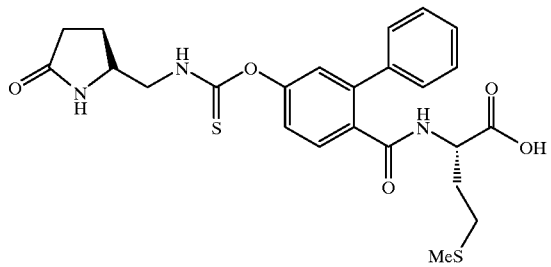

EXAMPLE 9

4-((S)-$^2$-Pyrrolidone-5-aminomethyl)thiocarbonyloxy-2-phenylbenzoyl methionine methyl ester The title compound is prepared as described in Example 8 with the exception that phosgene in toluene is replaced by thiophosgene.

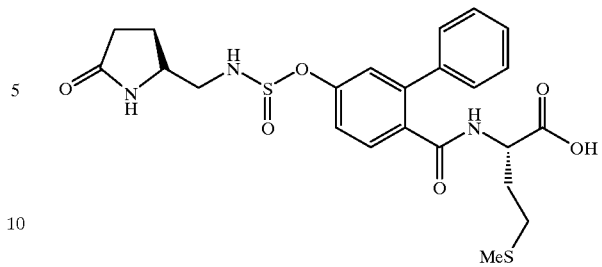

EXAMPLE 10

4-((S)-2-Pyrrolidone-5-aminomethyl)sulfinyloxy)-2-phenylbenzoyl methionine

The title compound is prepared as described in Example 8 with the exception that phosgene in toluene is replaced by thionyl chloride.

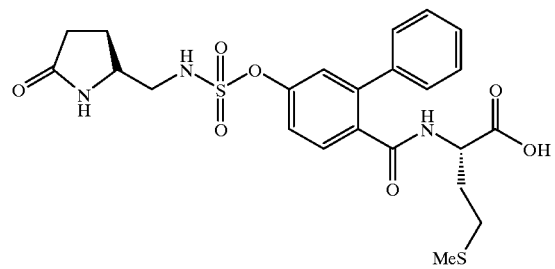

EXAMPLE 11

4-((S)-2-Pyrrolidone-5-aminomethyl)sulfonyloxy)-2-phenylbenzoyl methionine

The title compound is prepared as described in Example 8 with the exception that phosgene in toluene is replaced by sulfuryl chloride.

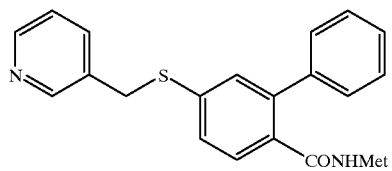

EXAMPLE 12

4-(3-Pyridylmethylenthio)-2-phenylbenzoylmethionine

Example 12A

4-Mercapto-2-phenylbenzoic acid methyl ester

A solution of methyl 4-amino-2-phenylbenzoic acid (1.0 equivalent) in dilute aqueous $H_2SO_4$ is treated with $NaNO_2$ (1.1 equivalents) to form the diazonium salt. The reaction is treated with $S_8$ (10 equivalents) and heated. The mixture is extracted into ethyl acetate which is dried and evaporated. The title thiophenol is purified by chromatography on silica gel.

EXAMPLE 12B 4-(2-Pyridylmethylenthio)-2-phenylbenzoic acid methyl ester

A solution of the resultant thiophenol (1.0 equivalent) from Example 12A is treated with 2-chloromethylpyridine hydrochloride (1.0 equivalent) in the presence of a NaH (2.0 equivalents), or $K_2CO_3$ (3.0 equivalent)s in DMF or pyridine. The product is isolated by removal of the solvent and chromatography on silica gel.

EXAMPLE 12C 4-(2-Pyridylthiomethylen)-2-phenylbenzoic acid

The resultant compound from Example 12B is hydrolyzed according to the procedure of Example 6C to give the title acid.

EXAMPLE 12D 4-(2-Pyridylthiomethylen)-2-phenylbenzoylmethionine methyl ester The resultant product from Example 12C is coupled to methionine methyl ester according to the procedure of Example 1C to give the title compound.

EXAMPLE 12E 4-(2-Pyridylthiomethylen)-2-phenylbenzoylmethionine methyl ester, alternate procedure 1

A solution of 4-amino-2-phenylbenzoyl methionine methyl ester (1.0 equivalent) in dilute aqueous $H_2SO_4$ is treated with $NaNO_2$ (1.1 equivalents) to form the diazonium salt. The reaction is treated with $S_8$ (10 equivalents) and heated. The mixture is extracted into ethyl acetate which is dried and evaporated to afford 2-phenyl-4-mercaptobenzoyl-methionine methyl ester. The thiophenol is purified by chromatography on silica gel. A solution of this thiophenol (1.0 equivalent) is treated with 2-chloromethylpyridine hydrochloride (1.0 equivalent) in the presence of a NaH (2.0 equivalents), or $K_2CO_3$ (3.0 equivalents) in DMF or pyridine. The product is isolated by removal of the solvent and chromatography on silica gel.

EXAMPLE 12F 4-(2-Pyridylthiomethylen)-2-phenylbenzoylmethionine methyl ester, alternate procedure 2

Methyl 4-amino-2-phenylbenzoate (100 mmol) is mixed in 50% sulfuric acid, and is cooled by a ice-water bath. To the above mixture with good stirring is added slowly a cold solution of sodium nitrite (110 mmol) in water, the reaction temperature is kept under 10° C. Powdered anhydrous sodium carbonate (100 mmol) is carefully added to the cold reaction mixture in small portions, until the reaction mixture reaches pH 7 to 8. Then, the reaction mixture is added in small portions to a solution of sodium p-methoxybenzylsulfide (prepared from reaction 110 mmol of p-methoxybenzylthiol with 55 mmol of 2.0 M NaOH aqueous solution). After completion of the addition, the reaction mixture is refluxed until judged complete by TLC analysis. The reaction mixture is then extracted with ether, and the organic extracts are washed sequentially with aqueous sodium carbonate solution, water and brine, dried with anhydrous magnesium sulfate, filtered, and concentrated in vacuo. The residue is then purified by column chromatography on silica gel. The product thus obtained is dissolved in methanol and water, followed by addition of lithium hydroxide (200 mmol), and the mixture is refluxed until hydrolysis is judged complete by TLC analysis. The reaction mixture is then acidified with 6 N HCl, and extracted into ethyl acetate. The organic extracts are washed with brine, dried with anhydrous sodium sulfate, and concentrated in vacuo. The crude product obtained is redissolved in methylene chloride, followed by addition of 1-(3-dimethylaminopropyl)-3-ethylcarbodiimide (1.1 equivalent) and 1-hydroxybenzotriazol (1.2 equivalent). The reaction is stirred until it is judged complete by TLC analysis, and then is diluted with ether. The mixture is washed with water, brine, dried over anhydrous magnesium sulfate, filtered, and concentrated in vacuo. The residue is then purified by column chromatography on silica gel. The resulting product is dissolved in trifluoroacetic acid and anisole (1.5 equivalent), and mercury diacetate (1.2 equivalent) is added. After TLC shows no starting material left, the reaction mixture is diluted with ether, washed with water, brine, dried over anhydrous magnesium sulfate, filtered, and concentrated in vacuo. The resulting crude material is purified by column chromatography to afford 2-phenyl-4-mercaptobenzoyl-methionine methyl ester. A solution of this thiophenol (1.0 equivalent) is treated with 2-chloromethylpyridine hydrochloride (1.0 equivalent) in the presence of a NaH (2.0 equivalents), or $K_2CO_3$ (3.0 equivalents) in DMF or pyridine. The product is isolated by removal of the solvent and chromatography on silica gel.

EXAMPLE 12G 4-(3-Pyridylthiomethylen)-2-phenylbenzoylmethionine

The resultant compound from Example 12D is hydrolyzed according to the procedure of Example 1B to give the title product.

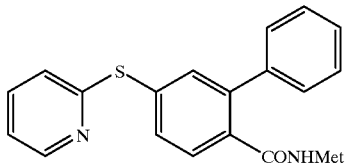

EXAMPLE 13

4-(2-Pyridylthio)-2-phenylbenzoylmethionine

EXAMPLE 13A

4-Fluoro-2-phenyl benzoic acid methyl ester

A solution of methyl 4-amino-2-phenylbenzoate (1.0 equivalent) in dilute aqueous $HBF_4$ is treated with $NaNO_2$ (1.1 equivalents) until an excess of nitrous acid persists. The mixture is extracted into ethyl acetate which is dried and evaporated. The title ester is purified by chromatography on silica gel.

EXAMPLE 13B

4-Fluoro-2-phenyl benzoic acid

The resultant compound from Example 13A is hydrolyzed according to the procedure of Example 6C to give the title acid.

EXAMPLE 13C

4-Fluoro-2-phenyl benzoyl methionine methyl ester

The resultant product from Example 13B is coupled to methionine methyl ester according to the procedure of Example 1C to give the title compound.

EXAMPLE 13D 4-(2-Pyridylthio)-2-phenyl benzoyl methionine methyl ester

A mixture of the resultant fluorobenzoate from Example 13C (1.0 equivalent) and 2-mercaptopyridine (1.0 equivalent) is treated with $K_2CO_3$ (2.0 equivalents) or NaH (1.0 equivalent) in DMF or DMSO and is stirred until the reaction is judged complete by TLC analysis. The mixture is diluted with water and extracted into ethyl acetate which is dried and evaporated. Chromatography of the residue on silica gel affords the title compound.

EXAMPLE 13E 4-(2-Pyridylthio)-2-phenyl benzoyl methionine methyl ester, alternate procedure 1

A solution of 4-amino-2-phenylbenzoyl methionine methyl ester (1.0 equivalent) in dilute aqueous $H_2SO_4$ is treated with $NaNO_2$ (1.1 equivalents) to form the diazonium salt. The reaction is treated with $S_8$ (10 equivalents) and heated. The mixture is extracted into ethyl acetate which is dried and evaporated. The title thiophenol is purified by chromatography on silica gel. A solution of this thiophenol (1.0 equivalent) is treated with 2-bromopyridine hydrobromide (1.0 equivalent) in the presence of a NaH (2.0 equivalent), or $K_2CO_3$ (3.0 equivalent)s in DMF or pyridine. The product is isolated by removal of the solvent and chromatography on silica gel.

EXAMPLE 13F 4-(2-Pyridylthio)-2-phenyl benzoyl methionine methyl ester, alternate procedure 2

A solution of the resultant thiophenol from Example 12A (1.0 equivalent) is treated with 2-bromopyridine hydrobromide (1.0 equivalent) in the presence of a NaH (2.0 equivalents), or $K_2CO_3$ (3.0 equivalents) in DMF or pyridine. The product is isolated by removal of the solvent and chromatography on silica gel. The resultant ester is hydrolyzed according to the procedure of Example 6C and then is coupled to methionine methyl ester according to the procedure of Example 1C to give the title compound.

EXAMPLE 13G 4-(2-Pyridylthio)-2-phenylbenzoylmethionine

The resultant compound from Example 13D is hydrolyzed according to the procedure of Example 1B to give the title product.

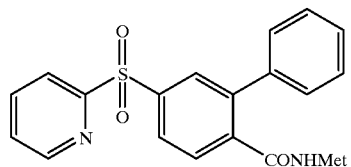

EXAMPLE 14

4-(2-Pyridylsulfonyl)-2-phenylbenzoylmethionine

Example 14A 4-(2-Pyridylsulfonyl)-2-phenylbenzoic acid methyl ester

A solution of 4-(2-pyridylthio)-2-phenylbenzoic acid methyl ester (Example 13F) is carefully treated with two equivalents of meta-chloroperbenzoic acid in methylene chloride at low temperature and the reaction is then quenched with aqueous $Na_2SO_3$ when judged complete by TLC analysis. The layers are separated and the organic phase is extracted with aqueous $NaHCO_3$ to remove the m-chlorobenzoic acid. The product is isolated by removal of the solvent and is purified by chromatography on silica gel.

EXAMPLE 14B 4-(2-Ptridylsulfonyl)-2-phenylbenzoic acid

The resultant compound from Example 14A is hydrolyzed according to the procedure of Example 6C to give the title acid.

EXAMPLE 14C 4-(2-pvridylsulfonyl)-2-phenylbenzoylmethionine methyl ester

The resultant product from Example 14B is coupled to methionine methyl ester according to the procedure of Example 1C to give the title compound.

EXAMPLE 14D 4-(2-Pyridylsulfonyl)-2-phenylbenzoylmethionine

The resultant compound from Example 14C is hydrolyzed according to the procedure of Example 1B to give the title product.

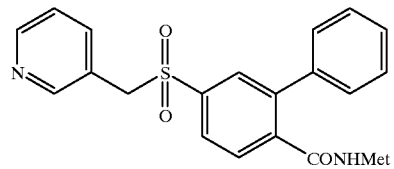

EXAMPLE 15

4-(3-Pyridylthiomethylen)-2-phenylbenzoylmethionine

The title compound is prepared from the resultant product of Example 12B using the procedures from Example 14.

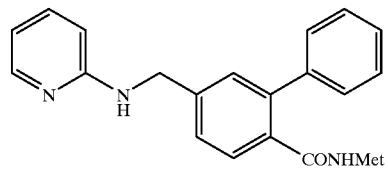

EXAMPLE 16

4-[(2-Aminopyridyl)methylene]-2-phenylbenzoylmethionine

EXAMPLE 16A

2-Phenylterephthalic acid mono methyl ester

A solution of 4-bromo-2-phenylbenzoic acid methyl ester (1.0 equivalent), Pd(OAc)$_2$ (0.05 equivalent) and DPPE (1.0 equivalent) is heated in DMF to 65° C. under 4 atm. of carbon monoxide until TLC analysis indicates that the reaction is complete. The reaction mixture is poured into water and extracted with ethyl acetate which is dried and evaporated. The product is purified by chromatography on silica gel.

EXAMPLE 16B 4-(Hydroxymethyl)-2-phenylbenzoic acid methyl ester

The resultant acid from Example 16A (1.0 equivalent) is treated with a slight excess of N-methylmorpholine (1.1 equivalent) and isobutylchworoformate (1.0 equivalent) in THF at 0° C. The mixture is then treated with NaBH$_4$ (1.0 equivalent) and aqueous NaHCO$_3$ and stirred at 0° C. until the reaction is judged complete by TLC analysis. The mixture is poured into dilute aqueous acid and extracted into ethyl acetate which is dried and evaporated. The product is purified by chromatography on silica gel.

EXAMPLE 16C 4-(Hydroxymethyl)-2-phenylbenzoic acid

The resultant compound from Example 16B is hydrolyzed according to the procedure of Example 6C to give the title acid.

EXAMPLE 16D 4-(Hydroxymethyl)-2-phenylbenzoyl methionine methyl ester

The resultant product from Example 16C is coupled to methionine methyl ester according to the procedure of Example 1C to give the title compound.

EXAMPLE 16E 4-formyl-2-phenylbenzoyl methionine methyl ester

A mixture of the resultant alcohol from Example 16D (1.0 equivalent), N-methylmorpholine-N-oxide (1.5 equivalents), molecular sieves, and a catalytic amount of TPAP is stirred in a CH$_2$Cl$_2$/acetonitrile mixture until the reaction is judged complete by TLC analysis. The mixture is diluted with ethyl ether and filtered through SiO$_2$. The product is purified by chromatography on silica gel.

EXAMPLE 16F 4-(formyl)-2-phenylbenzoyl methionine methyl ester, alternate procedure A mixture of (2-phenyl-4-bromobenzoyl) methionine methyl ester (100 mmol), 4,4,6-trimethyl-2-vinyl-1,3,2-dioxaborinane (100 mmol), tetrakis(triphenylphosphine) palladium (0) (3 mmol) in toluene and 2 M sodium carbonate in water (100 mL) is heated at 80° C. until the starting methyl ester disappears. The resulting mixture is extracted with ether, and washed with water, brine, dried over anhydrous magnesium sulfate, filtered, and concentrated in vacuo. The residue is then purified by column chromatography on silica gel. To a solution of the resulting vinyl compound in dioxane/water (4/1) is added osmium tetraoxide (0.03 equivalent), N-methylmorpholine N-oxide (3 equivalents), and the reaction is stirred at 25° C. until TLC analysis shows the reaction to be complete. The reaction mixture is extracted with ether, which is washed with water and brine, dried over anhydrous magnesium sulfate, filtered, and concentrated in vacuo. The residue is then purified by column chromatography on silica gel to afford the title product.

EXAMPLE 16G 4-(Hydroxymethyl)-2-phenylbenzoyl methionine methyl ester, alternate procedure To a solution of the resultant compound from Example 16E in ethanol at 0° C. is added sodium borohydride (0.5 equivalent), and the reaction is stirred at 0° C. until TLC analysis shows the reaction to be complete. The reaction mixture is extracted with ether, which is washed with water and brine, dried over anhydrous magnesium sulfate, filtered, and concentrated in vacuo. The residue is then purified by column chromatography on silica gel to afford the title product.

EXAMPLE 16H

4-[(2-Aminopyridyl)methylene]-2-phenylbenzoylmethionine methyl ester

A mixture of the resultant aldehyde from Example 16E (1.0 equivalent), 2-aminopyridine (1.0 equivalent) and NaC-NBH$_3$ (1.5 equivalents) in methanol/acetic acid is stirred until the reaction is judged complete by TLC analysis. The mixture is poured into aqueous NaHCO$_3$ and extracted into ethyl acetate which is dried and evaporated. Chromatography of the residue on silica gel affords the title compound.

EXAMPLE 16I

4-[(2-Aminopyridyl)methylene]-2-phenylbenzoylmethionine

The resultant compound from Example 16H is hydrolyzed according to the procedure of Example 1B to give the title product.

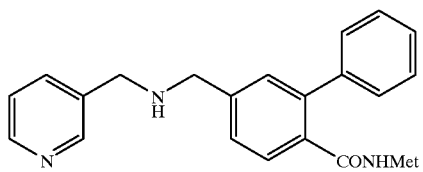

EXAMPLE 17

4-[(3-aminomethylparidyl)methylene]-2-phenylbenzoylmethionine

Using the procedures of Examples 16F–G and replacing 2-aminopyridine with 3-aminomethylpyridine affords the title product.

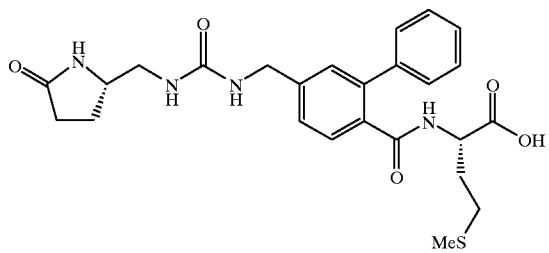

EXAMPLE 18

4-((S)-2-Pyrrolidone-5-aminomethylcarbonyl)aminomethyl-2-phenylbenzoyl methionine

Example 18A 4-(Azidomethyl)-2-phenylbenzoyl methionine methyl ester

To triphenylphosphine (1.0 equivalent) in tetrahydrofuran (THF) at −78° C. is added diethyl azodicarboxylate (1.0 equivalent) in THF. To this mixture is added a solution of hydrazoic acid in benzene (2.0 equivalents) and then the resultant compound from Example 16D (1.0 equivalent). After one hour the mixture was warmed to room temperature, stirred until the reaction is judged complete by TLC analysis, evaporated and chromatographed on silica gel to afford the title product.

EXAMPLE 18B

4(Aminomethyl)-2-phenylbenzoyl methionine methyl ester

To the resultant compound from Example 18A in methanol is added triethylamine (3.0 equivalent) and propane 1,3-dithiol (3.0 equivalents). After the reaction is judged complete by TLC analysis, the mixture is filtered and evaporated. Chromatography of the residue on silica gel provides the title product.

EXAMPLE 18C 4-((S)-2-Pyrrolidone-5-aminomethylcarbonyl)aminomethyl-2-phenylbenzoyl methionine methyl ester To a solution of the resultant compound from Example 18B (1.0 equivalent) in methylene chloride is added triphosgene (0.33 equivalent) and triethyl amine (2.0 equivalents). This intermediate is reacted without further purification with (S)-5-aminomethyl-2-pyrrolidone (1.0 equivalent) and triethylamnine (1.0 equivalent). When judged complete by TLC analysis, the reaction is taken up in ethyl acetate and washed with 1N HCl and brine, evaporated, and purified by chromatography on silica gel.

EXAMPLE 18D 4-((S)-2-Pyrrolidone-5-aminomethylcarbonyl)aminomethyl-2-phenylbenzoyl methionine The resultant compound from Example 18C is hydrolyzed according to the procedure of Example 1B to give the title product.

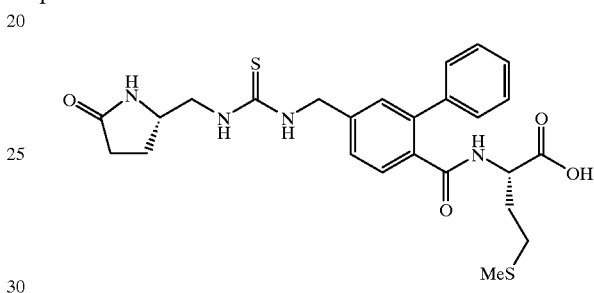

EXAMPLE 19

4-((S)-2-Pyrrolidone-5-aminomethylthiocarbonyl)aminomethyl-2-phenylbenzoyl methionine The title compound is prepared as described in Example 18 with the exception that triphosgene (0.33 equivalent) is replaced by thiophosgene (1.0 equivalent).

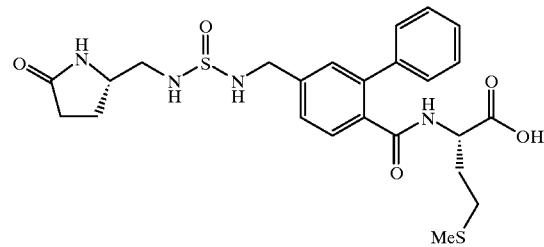

EXAMPLE 20

4-((S)-2-Pyrrolidone-5-aminomethylsulfinyl)aminomethyl-2-phenylbenzoyl methionine The title compound is prepared as described in Example 18 with the exception that triphosgene (0.33 equivalent) is replaced by thionyl chloride (1.0 equivalent).

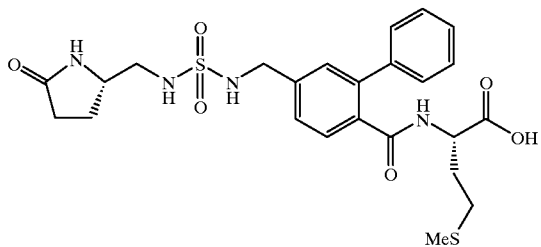

EXAMPLE 21

4-((S)-2-Pyrrolidone-5-aminomethylsulfonyl) aminomethyl-2-phenylbenzoyl methionine Using the Procedure of Example 4 with the resultant compound from Example 18B affords the title product.

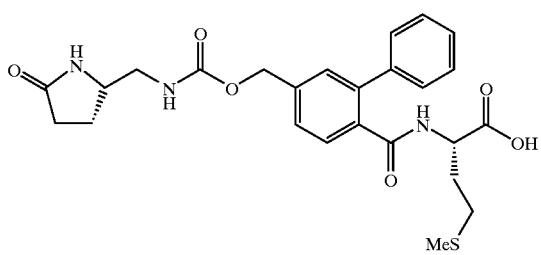

EXAMPLE 22

4-((S)-2-Pyrrolidone-5-aminomethyl) carbonyloxymethylene)-2-phenylbenzoyl methionine Using the procedure of Example 8 with the resultant compound from Example 16D provides the title product.

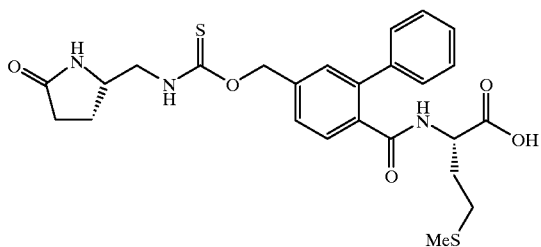

EXAMPLE 23

4-((S)-2-Pyrrolidone-5-aminomethyl) thiocarbonyloxymethylene)-2-phenylbenzoyl methionine Using the procedure of Example 8 with the resultant compound from Example 16D and replacing triphosgene (0.33 equivalent) with thiophosgene (1.0 equivalent) provides the title product.

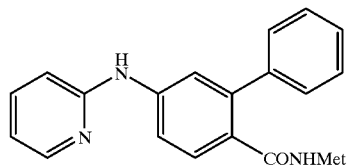

EXAMPLE 24

4-(2-Aminopyridyl)-2-phenylbenzoylmethionine

EXAMPLE 24A 4-(2-Aminopyridyl)-2-phenylbenzoylmethionine methyl ester

4-Amino-2-phenylbenzoyl methionine (1.0 equivalent) methyl ester and 2-bromopyridine hydrobromide (1.0 equivalent) in pyridine are heated until the reaction is judged complete by TLC analysis. The solvent is evaporated and the residue is taken up in ethyl acetate which is washed with water and brine, dried, and evaporated. Chromatography on silica gel affords the title product.

EXAMPLE 24B 4-(2-Aminopyridyl)-2-phenylbenzoylmethionine

The resultant compound from Example 24A is hydrolyzed according to the procedure of Example 1B to give the title product.

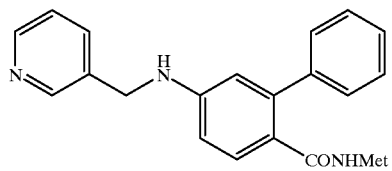

EXAMPLE 25

4-(3-Aminomethylpyridyl)-2-phenylbenzoylmethionine

EXAMPLE 25A 4-(3-Aminomethylpyridyl)-2-phenylbenzoylmethionine methyl ester

A mixture of 3-pyridinecarboxaldehyde (1.0 equivalent), 4-amino-2-phenylbenzoyl methionine methyl ester (1.0 equivalent) and NaCNBH$_3$ (1.0 equivalent) in methanol/acetic acid is stirred until the reaction is judged complete by TLC analysis. The mixture is poured into aqueous NaHCO$_3$ and extracted into ethyl acetate which is dried and evaporated. Chromatography of the residue on silica gel affords the title compound.

EXAMPLE 25B

4-(3-Aminomethylpyridyl)-2-phenylbenzoylmethionine

The resultant compound from Example 25A is hydrolyzed according to the procedure of Example 1B to give the title product.

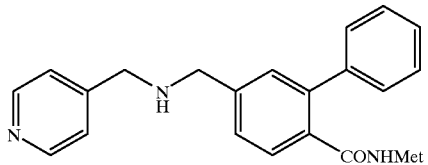

EXAMPLE 26

4-[(4-aminomethylpyridyl)methylene]-2-phenylbenzoylmethionine

Using the procedures of Examples 25 with the resultant amine from Example 18B and 3-pyridinecarboxaldehyde affords the title product.

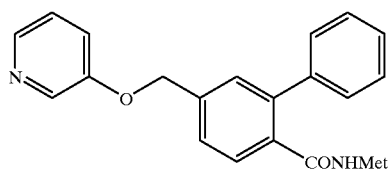

EXAMPLE 27

4-(3-Pyridyloxymethylene)-2-phenylbenzoylmethionine

EXAMPLE 27A

4-(p-Toluenesulfonyloxy)-2-phenylbenzoylmethionine methyl ester

The resultant compound from Example 16D (1.0 equivalent) and p-toluenesulfonyl chloride (1.0 equivalent) in pyridine are stirred until the reaction is judged complete by TLC analysis. The solvent is evaporated and the residue is taken up in ethyl acetate which is washed with water and brine, dried, and evaporated. Chromatography on silica gel affords the title product.

EXAMPLE 27B

4-(3-Pyridyloxymethylene)-2-phenylbenzoylmethionine methyl ester

3-Hydroxypyridine (1.0 equivalent) is treated with sodium hydride (1.0 equivalent) in DMSO, then the resultant compound from Example 27A (1.0 equivalent) is added. When judged complete by TLC analysis, the reaction is diluted with water and ethyl acetate, the organic layer is dried and concentrated, and the crude title compound is purified by chromatography on silica gel.

EXAMPLE 27C

4-(3-Pyridyloxymethylene)-2-phenylbenzoylmethionine

The resultant compound from Example 27B is hydrolyzed according to the procedure of Example 1B to give the title product.

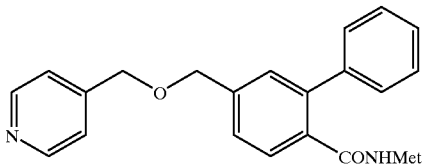

EXAMPLE 28

4-(3-Pyridylmethoxymethylene)-2-phenylbenzoylmethionine

EXAMPLE 28A

4-(3-Pyridylmethoxymethylene)-2-phenylbenzoylmethionine methyl ester

Using the procedure of Example 27B but replacing 3-hydroxypyridine with 3-hydroxymethylpyridine affords the title compound.

EXAMPLE 28B

4-(3-Pyridylmethoxymethylene)-2-phenylbenzoylmethionine methyl ester, alternate procedure The resultant compound from Example 16D (1.0 equivalent) is treated with sodium hydride (2.0 equivalents) in DMSO, then 3-chloromethylpyridine hydrochloride (1.0 equivalent) is added. When judged complete by TLC analysis, the reaction is diluted with water and ethyl acetate, the organic layer is dried and concentrated, and the crude title compound is purified by chromatography on silica gel.

EXAMPLE 28C

4-(3-Pyridylmethoxymethylene)-2-phenylbenzoylmethionine methyl ester

The resultant compound from Example 28A is hydrolyzed according to the procedure of Example 1B to give the title product.

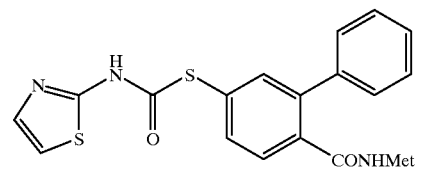

EXAMPLE 29

{2-Phenyl-4-[(thiazol-2-ylamino)carbonylthio]benzoyl}-methionine

EXAMPLE 29A

Thiazol-2-ylisocyanate

A solution of 2-aminothiazol (1.0 mmol), triphosgene (0.34 mmol) and triethylamine (1.0 mmol) in toluene (10 mL) is refluxed until TLC shows no starting amine left. The solvent is then removed in vacuo, and the resulting material is used without further purification.

EXAMPLE 29B

{2-Phenyl-4-[(thiazol-2-ylamino)carbonylthio]benzoyl}-methionine methyl ester

A solution of 2-phenyl-4-mercaptobenzoyl-methionine methyl ester from example 12E or 12F (1.0 mmol) and the isocyanate prepared in example 29A (1.0 mmol) in THF is refluxed until TLC shows no thiol left. The solvent is then evaporated in vacuo, and the residue is purified by column chromatography on silica gel to give the title compound.

EXAMPLE 29C

{2-Phenyl-4-[(thiazol-2-ylamino)carbonylthio]benzoyl}-methionine methyl ester, alternate procedure To a solution of 2-phenyl4-mercaptobenzoyl-methionine methyl ester from example 12E or 12F (1 equivalent) in methylene chloride is added a solution of phosgene in toluene (1.0 equivalent) and p-dimethylaminopyridine (2.0 equivalents). When the reaction is judged complete by TLC analysis, the solvent is evaporated with toluene chasers. The thiochloroformate is reacted without further purification with 2-aminothiazol (1.0 equivalent) and triethylamnine (1.0 equivalent) in dichloromethane. When judged complete by TLC analysis, the reaction is taken up in ethyl acetate and washed with 1N HCl and brine, evaporated, and purified by chromatography on silica gel.

EXAMPLE 29D

{2-Phenyl-4-[(thiazol-2-ylamino)carbonylthio]benzoyl}-methionine

The resultant compound from Example 29B is hydrolyzed according to the procedure of Example 1B to give the title product.

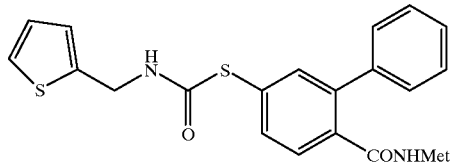

EXAMPLE 30

{2-Phenyl4-[(thien-2-ylmethylamino)carbonylthio]benzoyl}-methionine

Using the procedure of Example 29 but replacing 2-aminothiazol with thien-2-ylmethylamine affords the title product.

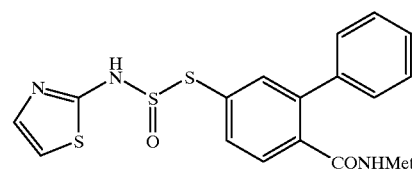

EXAMPLE 31

{2-Phenyl-4-[(thiazol-2-ylamino)thionylthio]benzoyl}-methionine

EXAMPLE 31A (N-Thionyl)thiazol-2-ylamine

A solution of 2-aminothiazol (1.0 mmol), in thionyl chloride is heated at reflux until the reaction is judged to be complete by TLC analysis. Then, the excess thionylchloride is distilled out in vacuo. The resulting material is used without further purification.

EXAMPLE 31B

{2-Phenyl-4-[(thiazol-2-ylamino)thionylthio]benzoyl}-methionine methyl ester

Using the procedure of Example 29B but replacing the resultant product from Example 29A with the resultant product from Example 31A affords the title compound.

EXAMPLE 31C

{2-Phenyl-4-[(thiazol-2-ylamino)thionylthio]benzoyl}-methionine methyl ester, alternate proedure Using the procedure of Example 29C but replacing phosgene in toluene with thionyl chloride affords the title compound.

EXAMPLE 31D

{2-Phenyl-4-[(thiazol-2-ylamino)thionylthio]benzoyl}-methionine

The resultant compound from Example 31B is hydrolyzed according to the procedure of Example 1B to give the title product.

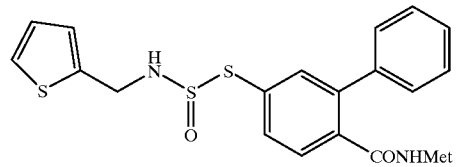

EXAMPLE 32

{12-Phenyl-4-[(thien-2-ylmethylamino)thionylthio]benzoyl}-methionine

Using the procedure of Example 31 but replacing 2-aminothiazol with thien-2-ylmethylamine affords the title product.

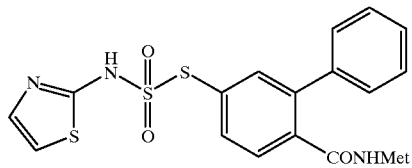

EXAMPLE 33

{2-Phenyl-4-[(thiazol-2-ylamino)sulfonylthio]benzoyl}-methionine methyl ester

Using the procedure of Example 31 but replacing thionyl chloride with sulfuryl chloride affords the title product.

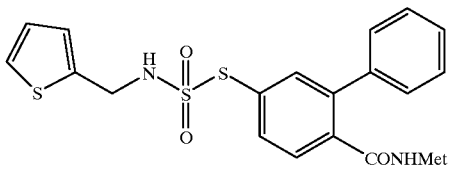

EXAMPLE 34

{2-Phenyl-4-[(thien-2-ylmethylamino)sulfonylthio]
benzoyl}-methionine

Using the procedure of Example 31 but replacing 2-aminothiazol with thien-2-ylmethylamine and replacing thionyl chloride with sulfuryl chloride affords the title product.

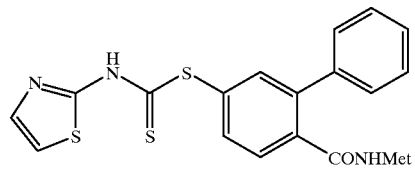

EXAMPLE 35

{2-Phenyl-4-[(thiazol-2-ylamino)thiocarbonylthio]
benzoyl}-methionine

Using the procedure of Example 29 and replacing triphosgene (0.34 mmol) or a solution of phosgene in toluene (1.0 equivalent) with thiophosgene (1.0 mnmol) affords the title product.

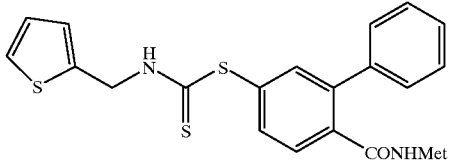

EXAMPLE 36

{2-Phenyl-4-[(thien-2-ylmethylamino)
thiocarbonylthio]benzoyl}-methionine

Using the procedure of Example 29 and replacing triphosgene (0.34 mmol) or a solution of phosgene in toluene (1.0 equivalent) with thiophosgene (1.0 mmol) and replacing 2-aminothiazol with thien-2-ylmethylamine affords the title product.

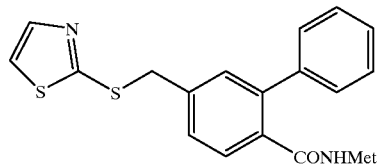

EXAMPLE 37

{2-Phenyl-4-[(thiazol-2-yl)thiomethyl]benzoyl}-
methionine

EXAMPLE 37A

{2-Phenyl-4-[thiomethyl]benzoyl}-methionine
methyl ester

The resultant product from Example 27A is dissolved DMF/water (2/1), and sodium hydrosulfide (5 equivalent) is added to the reaction mixture. The reaction is stirred until TLC analysis shows that the reaction is complete. Then, the reaction mixture is acidified with 3 N HCl to about pH 4, extracted with ether, and washed with water and brine, dried over anhydrous magnesium sulfate, filtered, and concentrated in vacuo. The residue is purified with column chromatography on silica gel to give the title compound.

EXAMPLE 37B

{2-Phenyl-4-[thiomethyl]benzoyl}-methionine
methyl ester, alternate procedure

To triphenylphosphine (1.2 equivalents) in THF at −78° C. is added diethylazodicarboxylate (1.2 equivalents) in THF. After 10 min thiolacetic acid (1.3 equivalents) in THF is added followed by the resultant compound from Example 16D (1. equivalent) in THF. The reaction is stirred at −78° C. for 1 h and then at ambient temperature until it is judged to be complete by TLC analysis. The mixture is evaporated and the residue is taken up in methanol and is treated with $K_2CO_3$ (2 equivalents). When the reaction is judged to be complete by TLC analysis, the solvent is evaporated and the residue is chromatographed on silica gel to afford the title product.

EXAMPLE 37C

{2-Phenyl-4-[(thiazol-2-yl)thiomethyl]benzol}-
methionine methyl ester

A mixture of the resultant thiol from Example 37A (1 mmol), 2-bromothiazole (1.5 mmol), and anhydrous potassium carbonate (5 mmol) in DMF is stirred at 100° C. until TLC analysis shows that the starting thiol disappeared. Then, the reaction mixture is diluted with water, extracted with ether, and washed with water and brine, dried over anhydrous magnesium sulfate, filtered, and concentrated in vacuo. The residue is purified by column chromatography on silica gel to give the title compound.

{2-Phenyl-4-[(thiazol-2-yl)thiomethyl]benzoyl}-
methionine

The resultant compound from Example 37C is hydrolyzed according to the procedure of Example 1B to give the title product.

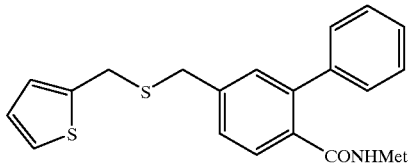

EXAMPLE 38

{2-Phenyl-4-[(thien-2-ylmethyl)thiomethyl]
benzoyl}-methionine

Using the procedure of Example 37 and replacing 2-bromothiazole with 2-bromomethylthiophene affords the title product.

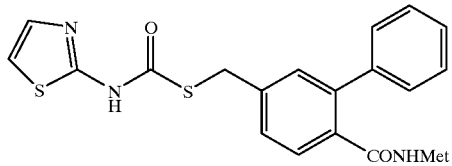

EXAMPLE 39

{2-Phenyl-4-[(thiazol-2-ylamino)
carbonylthiomethyl]benzoyl}-methionine

Using the procedure of Example 29 with the resultant product from Example 37A affords the title product.

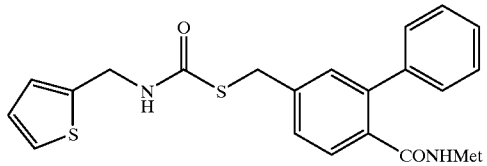

EXAMPLE 40

{2-Phenyl-4-[(thiazol-2-ylamino)
carbonylthiomethyl]benzoyl}-methionine

Using the procedure of Example 29 with the resultant product from Example 37A and replacing 2-aminothiazol with thien-2-ylmethylamine affords the title product.

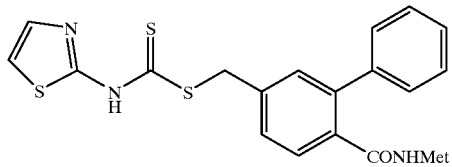

EXAMPLE 41

{2-Phenyl-4-[(thiazol-2-ylamino)
thiocarbonylthiomethyl]benzoyl}-methionine

Using the procedure of Example 29 with the resultant product from Example 37A and replacing triphosgene (0.34 mmol) or a solution of phosgene in toluene (1.0 equivalent) with thiophosgene (1.0 mmol) affords the title product.

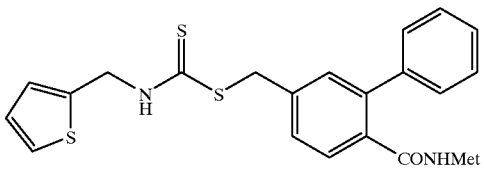

EXAMPLE 42

{2-Phenyl-4-[(thiazol-2-ylamino)
thiocarbonylthiomethyl]benzoyl}-methionine

Using the procedure of Example 29 with the resultant product from Example 37A, replacing triphosgene (0.34 mmol) or a solution of phosgene in toluene (1.0 equivalent) with thiophosgene (1.0 mmol), and replacing 2-aminothiazol with thien-2-ylmethylamiine affords the title product.

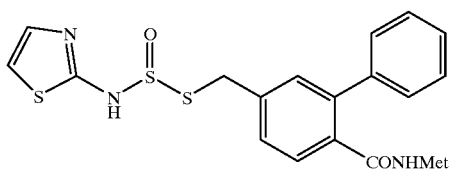

EXAMPLE 43

{2-Phenyl-4-[(thiazol-2-ylamino)thionylthiomethyl]
benzoyl}-methionine

Using the procedure of Example 31 with the resultant product from Example 37A affords the title product.

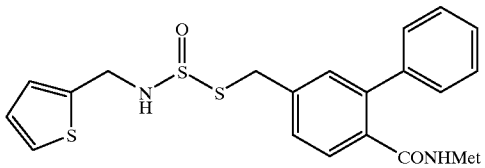

EXAMPLE 44

{2-Phenyl-4-[(thien-2-ylmethylamino)
thionylthiomethl]benzoyl}methionine

Using the procedure of Example 31 with the resultant product from Example 37A and replacing 2-aminothiazol with thien-2-ylmethylamine affords the title product.

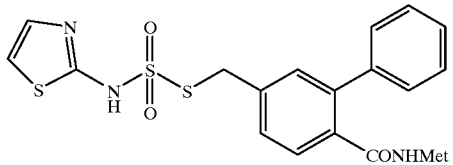

EXAMPLE 45

{2-Phenyl-4-[(thiazol-2-ylamino)
sulfonylthiomethyl]benzoyl}-methionine

Using the procedure of Example 31 with the resultant product from Example 37A and replacing thionyl chloride with sulfuryl chloride affords the title product. affords the title product.

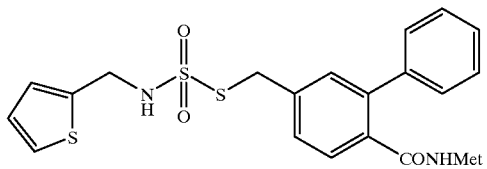

EXAMPLE 46

{2-Phenyl-4-[(thien-2-ylmethylamino)sulfonylthiomethyl]benzoyl}-methionine

Using the procedure of Example 31 with the resultant product from Example 37A, replacing thionyl chloride with sulfuryl chloride, and replacing 2-aminothiazol with thien-2-ylmethylamine affords the title product.

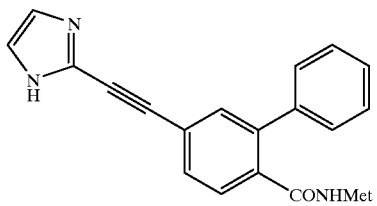

EXAMPLE 47

{4-[2-(Imidazol-2-yl)ethynyl]-2-phenylbenzoyl}methionine

EXAMPLE 47A (4-Ethynyl-2-phenylbenzoyl)methionine methyl ester

A mixture of (2-phenyl-4-bromobenzoyl)-methionine methyl ester (100 mmol), diethylamine (300 mmol), trimethylsilylacetylene (110 mmol), bis(triphenylphosphine) palladium diacetate (5 mmol) and copper(I) iodide (3 mmol) in toluene is heated at 60° C. until TLC analysis indicates the starting methyl ester has disappeared. The reaction mixture is concentrated in vacuo, redissolved in ether, filtered through silica gel, and concentrated. The residue is then dissolved in THF, and is treated with tetrabutylammonium fluoride (120 mmol). After TLC analysis indicates that no starting material is left, the reaction mixture is diluted with ether, washed with water and brine, dried over anhydrous magnesium sulfate, filtered, and concentrated in vacuo. The residue is then purified with column chromatography on silica gel to give the title product.

EXAMPLE 47B

{4-[2-(Imidazol-2-yl)ethynyl]-2-phenylbenzoyl}-methionine methyl ester

The resultant product from Example 47A (5 mmol) is mixed with 4-bromoimidazole (5 mmol), diethylamine (1 mL), bis(triphenylphosphine) palladium diacetate (0.1 mmol) and copper(I) iodide (0.1 mmol) in toluene. The mixture is stied at 25° C. until TLC analysis indicates the reaction is complete. The reaction mixture is concentrated in vacuo, and the residue is purified with column chromatography on silica gel to give the title product.

EXAMPLE 47C

{4-[2-(Imidazol-2-yl)ethynyl]-2-phenylbenzoyl}-methionine

The resultant compound from Example 47B is hydrolyzed according to the procedure of Example 1B to give the title product.

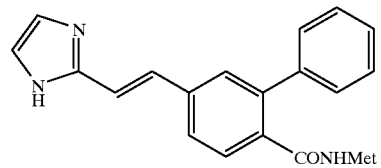

EXAMPLE 48

{4-[2-(Imidazol-4-yl)ethenyl]-2-phenylbenzoyl}-methionine

The resultant acetylene (3 mmol) from Example 47 is mixed with Lindlar catalyst (50 mg), 5 drops of quinoline in ethyl acetate. The reaction mixture is attached to a hydrogenation apparatus, and then is detached from the apparatus after about 95% of the theoretical hydrogen has been absorbed. The reaction mixture is filtered and concentrated in vacuo. The crude product is purified with a column chromatography on silica gel to give the title compound.

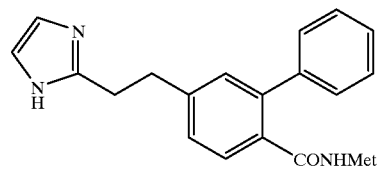

EXAMPLE 49

{4-[2-(Imidazol-4-yl)ethyl]-2-phenylbenzoyl}-methionine

The resultant olefin (1 mmol) from Example 48 is mixed with 5% palladium on carbon (100 mg) in ethyl acetate. The reaction mixture is attached to a hydrogenation apparatus, and then is detached from the apparatus after about 95% of the theoretical hydrogen has been absorbed. The reaction mixture is filtered and concentrated in vacuo. The crude product is purified with a column chromatography on silica gel to give the title compound.

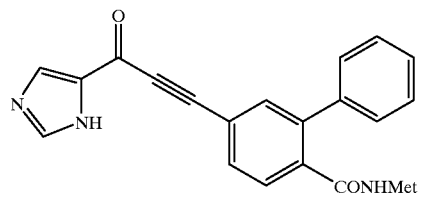

EXAMPLE 50

{4-[2-(Imidazol-4-ylcarbonyl)ethynyl]-2-phenylbenzoyl}-methionine

EXAMPLE 50A

{4-[2-(Imidazol-4-ylcarbonyl)ethynyl]-2-phenylbenzoyl}-methionine methyl ester

A stainless autoclave containing the resultant product from Example 47A (5 mmol), 4-bromoimidazole (5 mmol), 1,1'-bis(diphenylphosphine)-ferrocenepalladium dichloride (0.1 mmol), and triethylamine (10 mL) is flushed with nitrogen, and pressurized to 20 atm with carbon monoxide. The reaction mixture is stirred at 120° C. until judged complete by TLC analysis. After cooling, the triethylamine is evaporated in vacuo, and the residue is purified by column chromatography on silica gel to give the title compound.

EXAMPLE 50B

{4-[2-(Imidazol-4-ylcarbonyl)ethynyl]-2-phenylbenzoyl}-methionine

The resultant compound from Example 50A is hydrolyzed according to the procedure of Example 1B to give the title product.

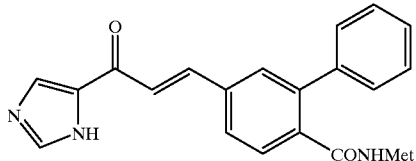

EXAMPLE 51

{4-[2-(Imidazol-4-ylcarbonyl)ethenyl]-2-phenylbenzoyl}-methionine

Using the procedure of Example 48 with the resultant compound from Example 50 affords the title product.

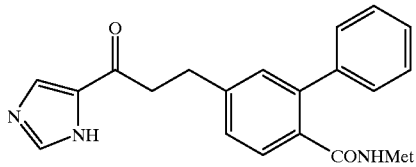

EXAMPLE 52

{4-[2-(Imidazol-4-ylcarbonyl)ethyl]-2-phenylbenzol}-methionine

Using the procedure of Example 49 with the resultant compound from Example 51 affords the title product.

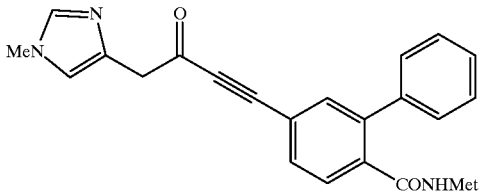

EXAMPLE 53

{4-[4-(1-Methylimidazol-4-yl)-3-keto-1-butynyl]-2-phenylbenzoyl}methionine

EXAMPLE 53A

{4-[4-(1-Methylimidazol-4-yl)-3-keto-1-butynyl]-2-phenylbenzoyl}-methionine methyl ester To a solution of 1-methyl-4imidazoleacetic acid (5 mmol) in methylene chloride at 0° C. is added oxalyl chloride (6 mmol) and DMF (0.05 mmol). After 30 minute, the solvent is evaporated in vacuo. The residue is redissolved in dichloromethane, followed by the addition of the resultant acetylene from Example 47A (5 mmol), triethylamine (10 mmol), and copper(I) iodide (1 mmol). The reaction is stirred at 25° C. until TLC analysis indicates no starting material is left in the reaction mixture. The reaction is diluted with ether, washed with water and brine, dried over anhydrous magnesium sulfate, filtered, and concentrated in vacuo. The residue is then purified by column chromatography on silica gel to give the title compound.

EXAMPLE 53B

{4-[4-(1-Methylimidazol-4-yl)-3-keto-1-butynyl]-2-phenylbenzoyl}-methionine

The resultant compound from Example 53A is hydrolyzed according to the procedure of Example 1B to give the title product.

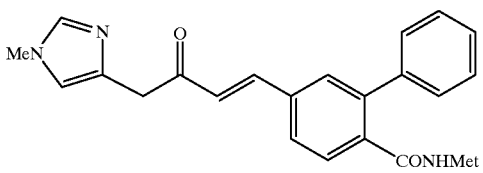

EXAMPLE 54

{4-[4-(1-Methylimidazol-4-yl)-3-keto-1-butenyl]-2-phenylbenzoyl}-methionine

Using the procedure of Example 48 with the resultant compound from Example 53 affords the title product.

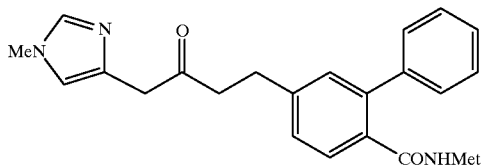

EXAMPLE 55

{4-[4-(1-Methylimidazol-4-yl)-3-keto-1-butyl]-2-phenylbenzoyl}-methionine

Using the procedure of Example 49 with the resultant compound from Example 53 affords the title product.

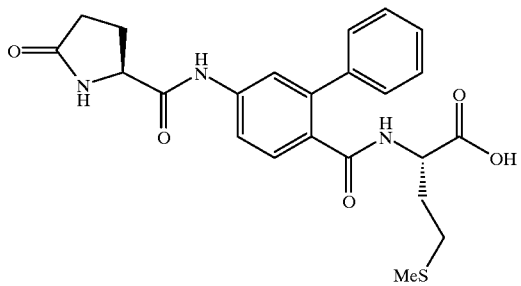

EXAMPLE 56

(S) Pyroglutamyl-(4-amino-2-phenyl)benzoyl methionine

EXAMPLE 56A (S) Pyroglutamyl-(4-amino-2-phenyl)benzoyl methionine methyl ester To a solution of 4-amino-2-phenylbenzoyl methionine methyl ester (1.0 equivalent) in dimethylformamide (DMF) is added 3-hydroxy-1,2,3-benzotriazin-4(3H)-one (1.5 equivalents) followed by pyroglutamnic acid (1.0 equivalent) and 1-(3-dimehtylaminopropyl)-3-ethylcarbodiimnide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 56B (S) Pyroglutaryl-(4-amino-2-phenyl)benzoyl methionine

The resultant compound from Example 56A is hydrolyzed according to the procedure of Example 1B to give the title product.

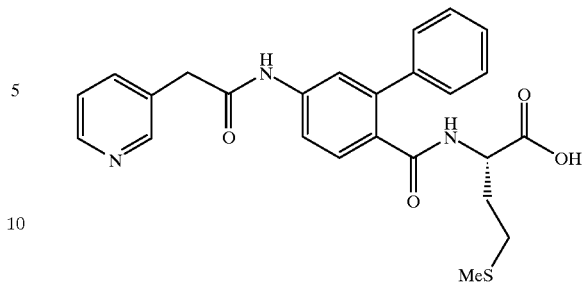

EXAMPLE 57

(S) Pyroglutamyl-(4-amino-2-phenyl)benzoyl methionine

Using the procedure of Example 56 and replacing pyroglutamic acid with 3-pyridylacetic acid affords the title product.

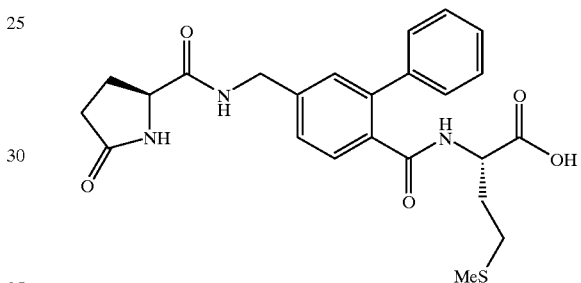

EXAMPLE 58

(S) Pyroglutamyl-(4-aminomethyl-2-phenyl)benzoyl methionine

EXAMPLE 58A (S) Pyroglutamyl-(4-aminomethyl-2-phenyl)benzoyl methionine methyl ester To a solution of the resultant amine from Example 1 8B (1.0 equivalent) in dimethylformamide (DMF) is added 3-hydroxy-1,2,3-benzotriazin-4(3H)-one (1.5 equivalents) followed by pyroglutamic acid (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 58B (S) Pyroglutamyl-(4-aminomethyl-2-phenyl)benzoyl methionine

The resultant compound from Example 58A is hydrolyzed according to the procedure of Example 1B to give the title product.

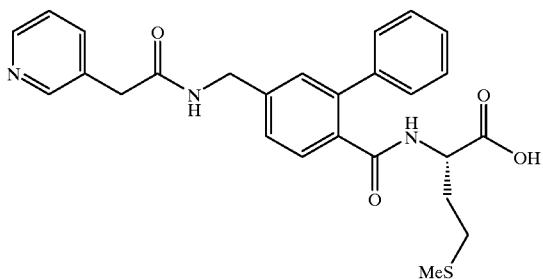

EXAMPLE 59 naming error(S) Proglutamyl-(4-aminomethyl-2-phenyl)benzoyl methionine

Using the procedure of Example 58 and replacing pyroglutamic acid with 3-pyridylacetic acid affords the title product.

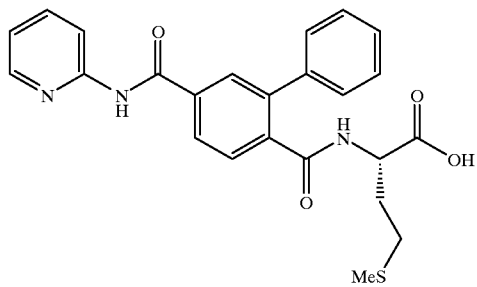

EXAMPLE 60

4-[(Pyridin-2-ylamino)carbonyl]-2-phenylbenzoyl methionine

EXAMPLE 60A

4-Carboxy-2-phenylbenzoyl methionine methyl ester

A solution of 4-bromo-2-phenylbenzoyl methionine methyl ester (1.0 equivalent), Pd(OAc)$_2$ (0.05 equivalent) and DPPE (1.0 equivalent) is heated in DMF to 65° C. under 4 atm. of carbon monoxide until TLC analysis indicates that the reaction is complete. The reaction mixture is poured into water and extracted with ethyl acetate which is dried and evaporated. The product is purified by chromatography on silica gel.

EXAMPLE 60B

4-[(Pyridin-2-ylamino)carbonyl]-2-phenylbenzoyl methionine methyl ester

To a solution of the resultant acid from Example 60A (1.0 equivalent) in DMF is added 3-hydroxy-1,2,3-benzotriazin-4(3H)-one (1.5 equivalents) followed by 2-aminopyridine (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed by 1N HCl and saturated brine, and then is dried and evaporated. The crude reaction mixture is purified by column chromatography to afford the title product.

EXAMPLE 60C

4-[(Pyridin-2-ylamino)carbonyl]-2-phenylbenzoyl methionine

The resultant compound from Example 60B is hydrolyzed according to the procedure of Example 1B to give the title product.

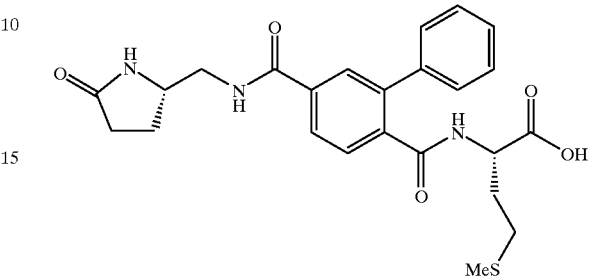

EXAMPLE 61

4-((S)-2-Pyrrolidone-5-aminomethyl)carbonyl)-2-phenylbenzoyl methionine

Using the procedure of Example 60 and replacing 2-aminopyridine with (S)-5-aminomethyl-2-pyrrolidone affords the title product.

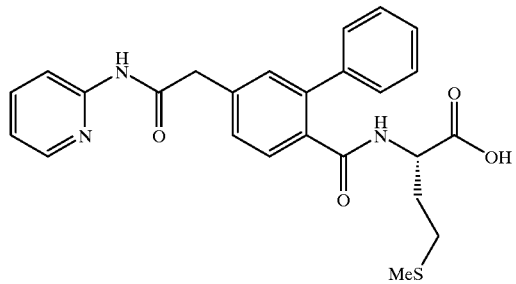

EXAMPLE 62

4-[(Pyridin-2-ylamino)carbonylmethyl]-2-phenylbenzoyl methionine

EXAMPLE 62A

4-Diazocarbonyl-2-phenylbenzoyl methionine methyl ester

The resultant acid from Example 60A (1 equivalent) in dichloromethane is treated with oxalyl chloride (1 equivalent) and DMF (0.05 equivalent). When gas evolution has ceased, the acid chloride solution is added to an ether solution of diazomethane. The reaction is stirred until judged complete by TLC analysis, and then is concentrated to give the crude title compound which is purified by chromatography on silica gel.

EXAMPLE 62B 4-carboxymethyl-2-phenylbenzol methionine methyl ester

The resultant compound from Example 62A (1 equivalent) in dioxane is added to a slurry of sodium thiosulfate (1.1 equivalents) and silver (I) oxide (0.5 equivalent) in water. The reaction is stirred until judged complete by TmC analysis, filtered, acidified, and extracted into ethyl acetate which is dried and evaporated. Chromatography of the residue on silica gel affords the title product.

EXAMPLE 62C

4-[(Pyridin-2-ylaminoicarbonylmethyl]-2-phenylbenzoyl methionine methyl ester

To a solution of the resultant acid from Example 62B (1.0 equivalent) in dimethylformamide (DMF) is added 3-hydroxy-1,2,3-benzotriazin-4(3H)-one (1.5 equivalents) followed by 2-aminopyridine (1.0 equivalent) and 1-(3-dimehtylarninopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 62D

4-[(Pyridin-2-ylamino)carbonylmethyl]-2-phenylbenzoyl methionine

The resultant compound from Example 62C is hydrolyzed according to the procedure of Example 1B to give the title product.

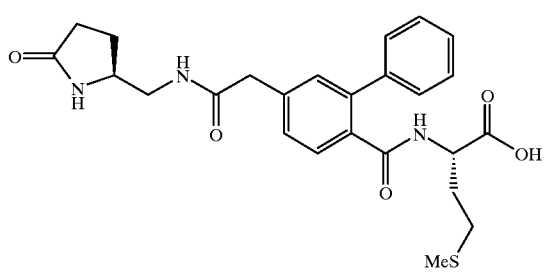

EXAMPLE 63

4-((S)-2-Pyrrolidone-5-aminomethyl)carbonylmethyl)-2-phenylbenzoyl methionine

Using the procedure of Example 62 and replacing 2-aminopyridine with (S)-5-aminomethyl-2-pyrrolidone affords the title product.

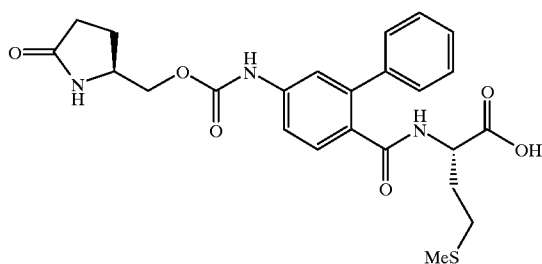

EXAMPLE 64

4-((S)-2-Pyrrolidone-5-methoxycarbonyl)amino-2-phenylbenzoyl methionine

The title compound is prepared as described in Example 1 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

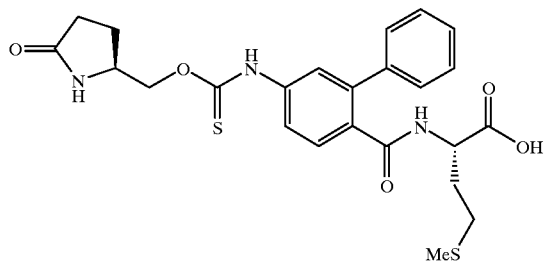

EXAMPLE 65

4-((S)-2-Pyrrolidone-5-methoxythiocarbonyl)amino-2-phenylbenzoyl methionine

The title compound is prepared as described in Example 1 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent), and triphosgene (0.33 equivalent) is replaced by thiophosgene (1.0 equivalent).

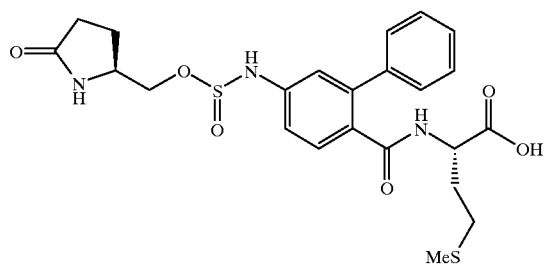

EXAMPLE 66

4-((S)-2-Pyrrolidone-5-methoxysulfinyl)amino-2-phenylbenzoyl methionine

The title compound is prepared as described in Example 3 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

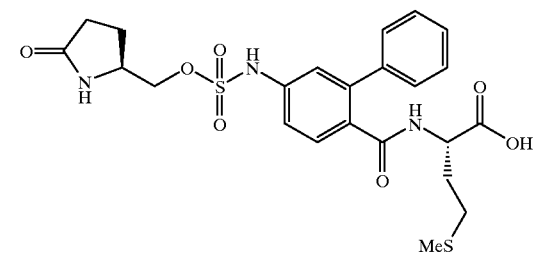

EXAMPLE 67

4-((S)-2-Pyrrolidone-5-methoxysulfonyl)amino-2-phenylbenzoyl methionine

The title compound is prepared as described in Example 4 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

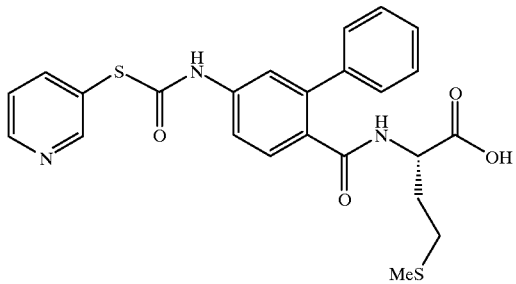

EXAMPLE 68

4-(Pyridin-3-ylmercaptocarbonyl)amino-2-phenylbenzoyl methionine

The title compound is prepared as described in Example 1 with the exception that (S)-5-aminomethyl-2-pyrrolidone (1.0 equivalent) is replaced by 3-mercaptopyridine (1.0 equivalent).

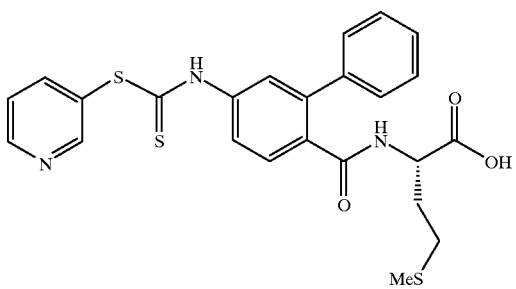

EXAMPLE 69

4-(Pyridin-3-ylmercaptothiocarbonyl)amino-2-phenylbenzoyl methionine

The title compound is prepared as described in Example 1 with the exception that (S)-5-aminomethyl-2-pyrrolidone (1.0 equivalent) is replaced by 3-mercaptopyridine (1.0 equivalent), and triphosgene (0.33 equivalent) is replaced by thiophosgene (1.0 equivalent).

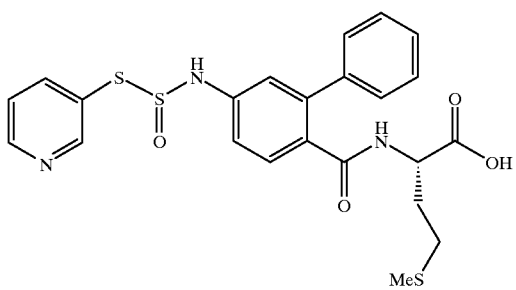

EXAMPLE 70

4-(Pyridin-3-ylmercaptosulfinyl)amino-2-phenylbenzoyl methionine

The title compound is prepared as described in Example 3 with the exception that (S)-5-aminomethyl-2-pyrrolidone (1.0 equivalent) is replaced by 3-mercaptopyridine (1.0 equivalent).

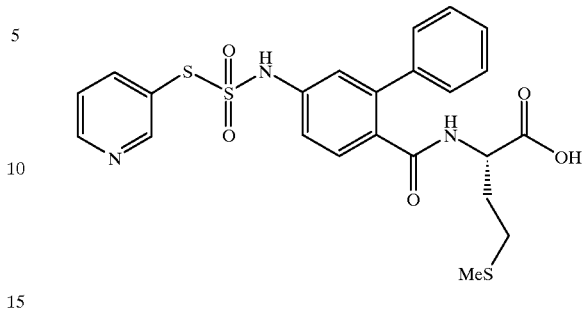

EXAMPLE 71

4-(Pyridin-3-ylmercaptosulfonyl)amino-2-phenylbenzoyl methionine

The title compound is prepared as described in Example 4 with the exception that (S)-5-aminomethyl-2-pyrrolidone (1.0 equivalent) is replaced by 3-mercaptopyridine (1.0 equivalent).

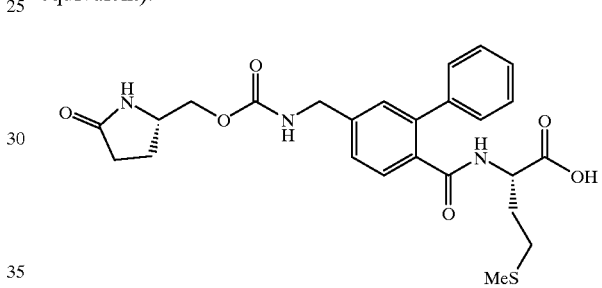

EXAMPLE 72

4-((S)-2-Pyrrolidone-5-methoxycarbonyl)aminomethyl-2-phenylbenzoyl methionine

The title compound is prepared as described in Example 18 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

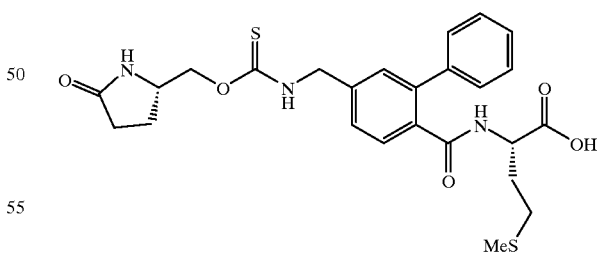

EXAMPLE 73

4-((S)-2-Pyrrolidone-5-methoxythiocarbonyl)aminomethyl-2-phenylbenzoyl methionine The title compound is prepared as described in Example 18 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent), and triphosgene (0.33 equivalent) is replaced by thiophosgene (1.0 equivalent).

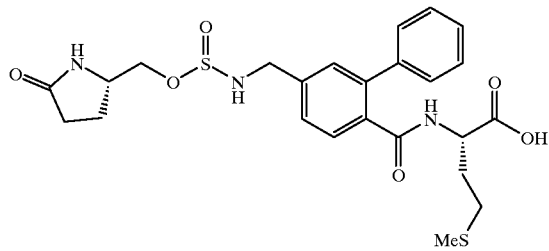

EXAMPLE 74

4-((S)-2-Pyrrolidone-5-methoxysulfinyl) aminomethyl-2-phenylbenzoyl methionine

The title compound is prepared as described in Example 3 using the resultant amine from Example 18B with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

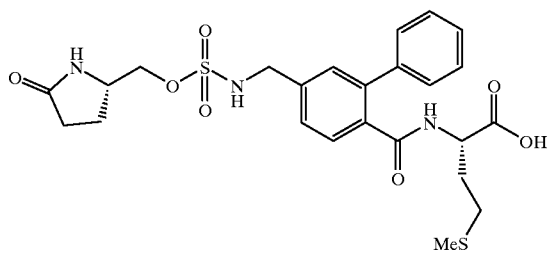

EXAMPLE 75

4-((S)-2-Pyrrolidone-5-methoxysulfonyl) aminomethyl-2-phenylbenzoyl methionine

The title compound is prepared as described in Example 4 using the resultant amine from Example 18B with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

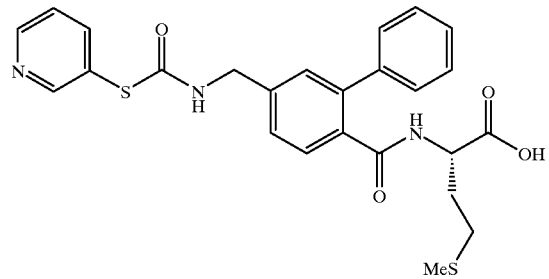

EXAMPLE 76

4-(Pyridin-3-ylmercaptocarbonyl)aminomethyl-2-phenylbenzoyl methionine

The title compound is prepared as described in Example 18 with the exception that (S)-5-aminomethyl-2-pyrrolidone (1.0 equivalent) is replaced by 3-mercaptopyridine (1.0 equivalent).

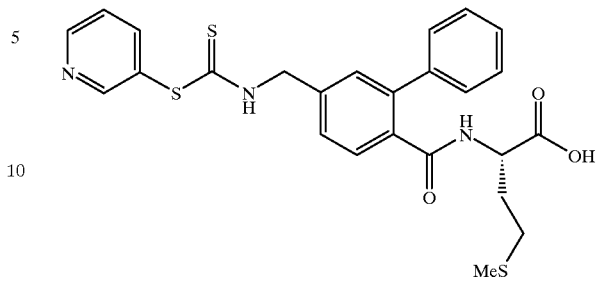

EXAMPLE 77

4-(Pyridin-3-ylmercaptocarbonyl)aminomethyl-2-phenylbenzoyl methionine

The title compound is prepared as described in Example 18 with the exception that (s)-5-aminomethyl-2-pyrrolidone (1.0 equivalent) is replaced by 3-mercaptopyridine (1.0 equivalent), and triphosgene (0.33 equivalent) is replaced by thiophosgene (1.0 equivalent).

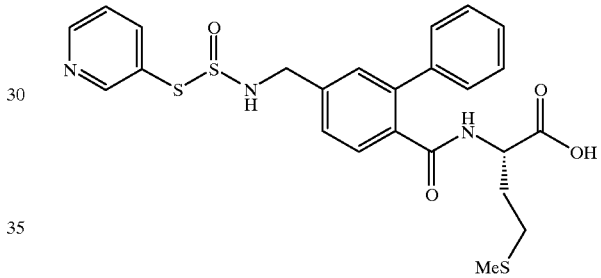

EXAMPLE 78

4-(Pyridin-3-ylmercaptosulfinyl)aminomethyl-2-phenylbenzoyl methionine

The title compound is prepared as described in Example 3 using the resultant amine from Example 18B with the exception that (S)-5-amninomethyl-2-pyrrolidone (1.0 equivalent) is replaced by 3-mercaptopyridine (1.0 equivalent).

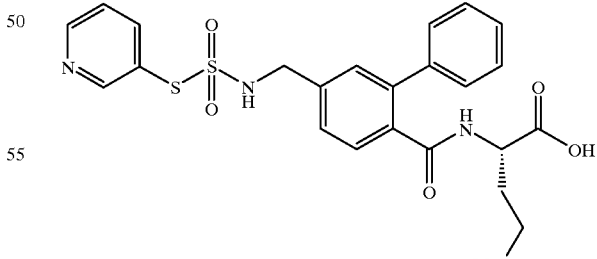

EXAMPLE 79

4-(Pyridin-3-ylmercaptosulfonyl)aminomethyl-2-phenylbenzoyl methionine

The title compound is prepared as described in Example 4 using the resultant amine from Example 18B with the exception that (S)-5-aminomethyl-2-pyrrolidone (1.0 equivalent) is replaced by 3-mercaptopyridine (1.0 equivalent).

EXAMPLE 80

A—NH—CO—NH—B

The procedure of Example 1 is used with the exception that 4-amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amnines 146–206. This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 81

A—NH—CS—NH—B

The procedure of Example 1 is used with the exception that triphosgene (0.33 equivalent) is replaced by thiophosgene (1.0 equivalent), 4-amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 82

A—NH—SO—NH—B

The procedure of Example 3 is used with the exception that 4amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206. This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 83

A—NH—SO$_2$—NH—B

The procedure of Example 4 is used with the exception that 4-amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 84

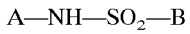
A—NH—SO$_2$—B

The procedure of Example 5 is used with the exception that 4-amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206. This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 85

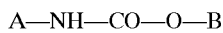
A—NH—CO—O—B

The anilines from Table 1 (B—NH$_2$) are reacted according to the procedure of Example 6E. The resultant phenols are reacted according to the procedure of Example 8 with the exception that (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 86

A—NH—CS—O—B

The anilines from Table 1 (B—NH$_2$) are reacted according to the procedure of Example 6E. The resultant phenols are reacted according to the procedure of Example 8 with the exception that phosgene in toluene is replaced by thiophosgene and (S)-5-aninomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206. This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 87

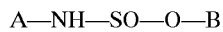
A—NH—SO—O—B

The anilines from Table 1 (B—NH$_2$) are reacted according to the procedure of Example 6E. The resultant phenols are reacted according to the procedure of Example 8 with the exception that phosgene in toluene is replaced by thionyl chloride and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206. This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 88

A—NH—SO$_2$—O—B

The anilines from Table 1 (B—NH$_2$) are reacted according to the procedure of Example 6E. The resultant phenols are reacted according to the procedure of Example 8 with the exception that phosgene in toluene is replaced by sulfuryl chloride and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from am-ines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 89

A—NH—CH$_2$—B

The procedure of Example 16 is used with the exception that (2-phenyl-4-bromobenzoyl)-methionine methyl ester is replaced by a bromide from Table 2 (B—Br) and 2-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 90

A—NH—CO—NH—CH$_2$—B

The bromides from Table 2 (B—Br) are reacted according to the procedures of Example 16F–G. The resultant alcohols are reacted according to the procedure of Example 18 with the exception that (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 91

A—NH—CS—NH—CH$_2$—B

The bromides from Table 2 (B—Br) are reacted according to the procedures of Example 16F–G. The resultant alcohols are reacted according to the procedure of Example 18 with the exception that triphosgene (0.33 equivalent) is replaced by thiophosgene (1.0 equivalent) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 92

A—NH—SO—NH—CH$_2$—B

The bromides from Table 2 (B—Br) are reacted according to the procedures of Example 16F–G. The resultant alcohols are reacted according to the procedure of Example 18 with the exception that triphosgene (0.33 equivalent) is replaced by thionyl chloride (1.0 equivalent) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 93

A—NH—SO$_2$—NH—CH$_2$—B

The bromides from Table 2 (B—Br) are reacted according to the procedures of Example 16F–G. The resultant alcohols are reacted according to the procedure of Example 18 with the exception that triphosgene (0.33 equivalent) is replaced by sulfuryl chloride (1.0 equivalent) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 94

A—NH—CO—O—CH$_2$—B

The bromides from Table 2 (B—Br) are reacted according to the procedures of Example 16F–G. The resultant alcohols

EXAMPLE 95

A—NH—CS—O—CH$_2$—B

The bromides from Table 2 (B—Br) are reacted according to the procedures of Example 16F–G. The resultant alcohols are reacted according to the procedure of Example 8 with the exception that phosgene in toluene is replaced by thiophosgene and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 96

A—NH—CO—S—B

The anilines Table 1 (B—NH$_2$) are converted into the corresponding mercaptans according to the procedure of Example 12E. These mercaptans are reacted according to the procedure of Example 29 with the exception that 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 97

A—NH—CS—S—B

The anilines Table 1 (B—NH$_2$) are converted into the corresponding mercaptans according to the procedure of Example 12E. These mercaptans are reacted according to the procedure of Example 29 with the exception that phosgene in toluene is replaced by thiophosgene and 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 98

A—NH—SO—S—B

The anilines Table 1 (B—NH$_2$) are converted into the corresponding mercaptans according to the procedure of Example 12E. These mercaptans are reacted according to the procedure of Example 29 with the exception that phosgene in toluene is replaced by thionyl chloride and 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 99

A—NH—SO$_2$—S—B

The anilines Table 1 (B—NH$_2$) are converted into the corresponding mercaptans according to the procedure of Example 12E. These mercaptans are reacted according to the procedure of Example 29 with the exception that phosgene in toluene is replaced by sulfuryl chloride and 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 100

A—NH—CO—S—CH$_2$—B

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 101

A—NH—CS—S—CH$_2$—B

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that phosgene in toluene is replaced by thiophosgene and 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 102

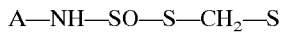
A—NH—SO—S—CH$_2$—S

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that phosgene in toluene is replaced by thionyl chloride and 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 103

A—NH—SO$_2$—S—CH$_2$—B

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that phosgene in toluene is replaced by sulfuryl chloride and 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 104

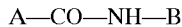
A—CO—NH—B

The procedure of Example 56 is used with the exception that 4-amino-2-phenylbenzoyl methionine methyl ester is replaced by an aniline from Table 1 (B—NH$_2$) and pyroglutamic acid is replaced by an acid from Table 4 (A—CO$_2$H). For products derived from acids 164–238 and 262–269 from Table 4, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 105

A—CO—NH—CH$_2$—B

The bromides from Table 2 (B—Br) are reacted according to the procedures of Example 16F–G. The resultant alcohols are converted to the corresponding amines according to the procedures of Examples 18A–B. These amines are reacted according to the procedure of Example 58 with the exception that pyroglutamic acid is replaced by an acid from Table 4 (A—CO$_2$H). For products derived from acids 164–238 and 262–269 from Table 4, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 106

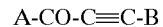
A-CO-C≡C-B

The bromides from Table 2 (B—Br) are reacted according to the procedure of Example 47A. The resultant acetylenes are reacted according to the procedure of Example 53 with the exception that 1-methyl4-imidazoleacetic acid is replaced by an acid from Table 4 (A—CO$_2$H). For products derived from acids 164–238 and 262–269 from Table 4, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 107

A—CO—CH=CH—B

The products from Example 106 are reacted according to the procedure of Example 54.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 108

A—CO—CH$_2$—CH$_2$—B

The products from Example 107 are reacted according to the procedure of Example 55.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 109

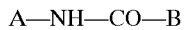
A—NH—CO—B

The procedure of Example 60 is used with the exception that 4-bromo-2-phenylbenzoyl methionine methyl ester is replaced by a bromide from Table 2 (B—Br) and 2-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 110

A—NH—CO—CH$_2$—B

The bromides from Table 2 (B—Br) are reacted according to the procedure of Example 60A. The resultant carbocyclic acids are reacted according to the procedure of Example 62 with the exception that 2-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 111

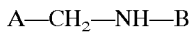
A—CH$_2$—NH—B

The procedure of Example 25 is used with the exception that 4-amino-2-phenylbenzoyl methionine methyl ester is replaced by an amine from Table 1 (B—NH$_2$) and 3-pyridinecarboxaldehyde is replaced by an aldehyde from Table 5 (A—CHO). For products derived from aldehydes 360–432 and 433–440 from Table 5, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 112

A—CH$_2$—NH—CH$_2$—B

The bromides from Table 2 (B—Br) are reacted according to the procedures of Example 16F–G. The resultant alcohols are converted to the corresponding amines according to the procedures of Examples 18A–B. These amines are reacted according to the procedure of Example 25 with the exception that 3-pyridinecarboxaldehyde is replaced by an aldehyde from Table 5 (A—CHO). For products derived from aldehydes 360–432 and 433–440 from Table 5, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoanyl, hexyl, octyl, cyclohexyl or phenethyl esters.

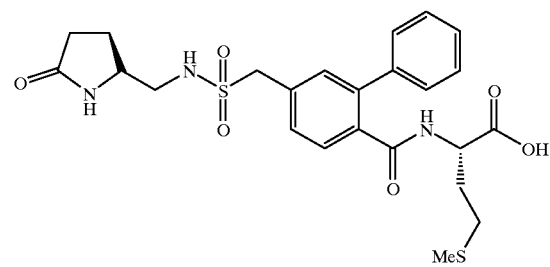

EXAMPLE 113

4-((S)-2-Pyrrolidone-5-aminomethyl) sulfonylmethyl)-2-phenylbenzoyl methionine

EXAMPLE 113A

4-Thioacetoxymethyl-2-phenylbenzoic acid methyl ester

To triphenylphosphine (1.2 equivalents) in THF at −78° C. is added diethylazodicarboxylate (1.2 equivalents) in THF. After 10 min thiolacetic acid (1.3 equivalents) in THF is added followed by the resultant compound from Example 16B (1. equivalent) in THF. The reaction is stirred at −78° C. for 1 h and then at ambient temperature until it is judged to be complete by TLC analysis. The mixture is evaporated and the residue is taken up in methanol and is treated with K$_2$CO$_3$ (2 equivalents). When the reaction is judged to be complete by TLC analysis, the solvent is evaporated and the residue is chromatographed on silica gel to afford the title product.

EXAMPLE 113B

4-Chlorosulfonylmethylene-2-phenylbenzoic acid methyl ester

The resultant compound from Example 113A in water is stirred vigorously while gaseous chlorine is bubbled through the mixture. When the reaction is judged to be done by TLC analysis, the reaction is extracted with dichloromethane which is dried and evaporated to afford the title product.

EXAMPLE 113C 4-((S)-2-Pyrrolidone-5-aminomethyl) sulfonylmethylene-2-phenylbenzoic acid methyl ester To a solution of the resultant compound from Example 113B (1.0 equivalent) in methylene chloride is added (S)-5-aminomethyl-2-pyrrolidone (1.0 equivalent) and triethylamine (1.0 equivalent). When the reaction is judged complete by TLC analysis, the solvent is evaporated and the residue is purified by chromatography on silica gel.

EXAMPLE 113D 4-((S)-2-Pyrrolidone-5-aminomethyl) sulfonylmethylene-2-phenylbenzoic acid The resultant compound from Example 113C is hydrolyzed according to the procedure of Example 1B to give the title product.

EXAMPLE 113E 4-((S)-2-Pyrrolidone-5-aminomethyl) sulfonylmethylene-2-phenylbenzoyl methionine methyl ester To a solution of the resultant compound from Example 113D (1.0 equivalent) in dimethylformamide (DMF) is added 3-hydroxy-1,2,3-benzotriazin4(3H)-one (1.5 equivalents) followed by methionine methyl ester (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 113F 4-((S)-2-Pyrrolidone-5-aminomethyl) sulfonylmethylene-2-phenylbenzoyl methionine The resultant compound from Example 113E is hydrolyzed according to the procedure of Example 1B to give the title product.

EXAMPLE 114

A—NH—SO$_2$—CH$_2$—B

The procedure of Example 113 is used with the exception that (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

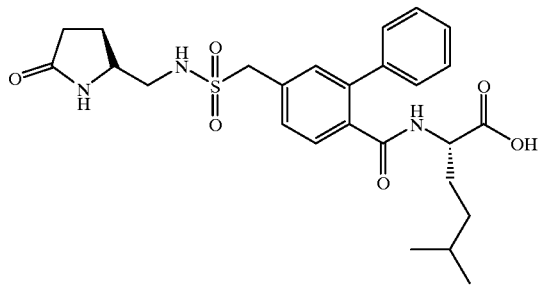

EXAMPLE 115

4-((S)-2-Pyrrolidone-5-amninomethyl) sulfonylmethyl)-2-phenylbenzoyl leucine

EXAMPLE 115A 4-(Hydroxymethyl)-2-phenylbenzoyl leucine methyl ester (2-phenyl-4-bromobenzoyl)-leucine methyl ester is reacted according to the procedures of Example 16F–G.

EXAMPLE 115B

4-Thioacetoxymethyl-2-phenylbenzoyl leucine methyl ester

To triphenylphosphine (1.2 equivalents) in THF at −78° C. is added diethylazodicarboxylate (1.2 equivalents) in THF. After 10 min thiolacetic acid (1.3 equivalents) in THF is added followed by the resultant compound from Example 115A (1. equivalent) in THF. The reaction is stirred at −78° C. for 1 h and then at ambient temperature until it is judged to be complete by TLC analysis. The mixture is evaporated and the residue is taken up in methanol and is treated with K$_2$CO$_3$ (2 equivalents). When the reaction is judged to be complete by TLC analysis, the solvent is evaporated and the residue is chromatographed on silica gel to afford the title product.

EXAMPLE 115C

4-Chlorosulfonylmethylene-2-phenylbenzoyl leucine methyl ester

The resultant compound from Example 115B in water is stirred vigorously while gaseous chlorine is bubbled through the mixture. When the reaction is judged to be done by TLC analysis, the reaction is extracted with dichloromethane which is dried and evaporated to afford the title product.

EXAMPLE 115D 4-((S)-2-Pyrrolidone-5-aminomethyl) sulfonylmethylene-2-phenylbenzoyl leucine methyl ester To a solution of the resultant compound from Example 115C (1.0 equivalent) in methylene chloride is added (S)-5-aminomethyl-2-pyrrolidone (1.0 equivalent) and triethylamine (1.0 equivalent). When the reaction is judged complete by TLC analysis, the solvent is evaporated and the residue is purified by chromatography on silica gel.

EXAMPLE 115E 4-((S)-2-Pyrrolidone-5-aminomethyl)sulfonylmethylene-2-phenylbenzoyl leucine The resultant compound from Example 115D is hydrolyzed according to the procedure of Example 1B to give the title product.

EXAMPLE 116

A—NH—SO$_2$—CH$_2$—B

The procedure of Example 115 is used with the exception that (2-phenyl-4-bromobenzoyl)-leucine methyl ester is replaced by a bromide from Table 2, entries 28–132 (B—Br) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

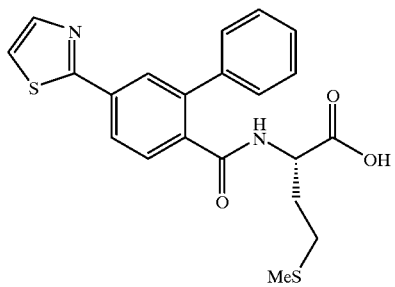

EXAMPLE 117

4-(2-Thiazolyl)-2-phenylbenzoyl methionine

EXAMPLE 117A

2-Thiazole boronic acid

A solution of thiazole (1.0 equivalent) is lithiated with a slight excess of n-butyl lithium in THF (1.05 equivalents) and then treated with trimethyl borate (1.05 equivalents). The reaction mixture is quenched by the addition of aqueous HCl and the resulting boronate ester is cleaved by the addition of excess aqueous NaOH. After acidification and extraction into ethyl acetate the crude boronic acid is used without further purification.

EXAMPLE 117B 4-(2-Thiazolyl)-2-phenylbenzoyl methionine methyl ester

A mixture of 4-bromo-2-phenylbenzoic acid methyl ester (1.0 equivalent), 2-thiazole boronic acid (1.0 equivalent) and catalytic Pd(PPh$_3$)$_4$ is heated in a two phase system of toluene and aqueous Na$_2$CO$_3$. After cooling, the resulting biaryl compound is isolated by evaporation of the organic phase and is purified by chromatography on silica gel.

EXAMPLE 117C 4-(2-Thiazolyl)-2-phenylbenzoyl methionine

The resultant compound from Example 117C is hydrolyzed according to the procedure of Example 1B to give the title product.

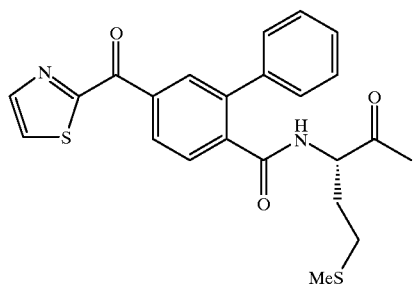

EXAMPLE 118

4-(2-Thiazolylcarbonyl)-2-phenylbenzoyl methionine

EXAMPLE 118A 4-(2-Thiazolylcarbonyl)-2-phenylbenzoyl methionine methyl ester A mixture of 4-bromo-2-phenylbenzoic acid methyl ester (1.0 equivalent), 2-thiazole boronic acid from Example 117A (1.0 equivalent) and catalytic Pd(PPh$_3$)$_4$ is heated in a two phase system of toluene and aqueous Na$_2$CO$_3$ previously purged with a large excess of carbon monoxide. The resulting diaryl ketone is isolated by evaporation of the organic phase and is purified by chromatography on silica gel.

EXAMPLE 118B 4-(2-Thiazolylcarbonyl)-2-phenylbenzoyl methionine

The resultant compound from Example 118A is hydrolyzed according to the procedure of Example 1B to give the title product.

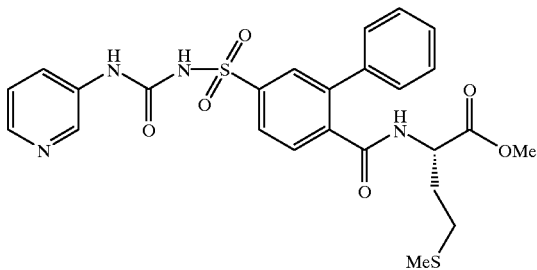

EXAMPLE 119

4-[(3-Aminopyridyl)carbonylaminosulfonyl]-2-phenylbenzoylmethionine

EXAMPLE 119A

4-Aminosulfonyl-2-phenylbenzoylmethiomine methyl ester

To a solution of 4-chlorosulfonyl-2-phenylbenzoyl methionine methyl ester from Example 5E in dichloromethane is added aqueous ammonia and the mixture is stirred until the reaction is judged complete by TLC analysis. The organic phase is separated, dried and evaporated and the product is purified by chromatography on silica gel.

EXAMPLE 119B

4-Isocyanatosulfonyl-2-phenylbenzoylmethionine methyl ester

A mixture of the resultant sulfonamide from Example 119A in chlorobenzene is treated with with oxalyl chloride according to the procedure of Franz et al. (*J. Org. Chem*, 1964, 29, 2592) to give the title compound.

EXAMPLE 119C

4-[(A-aminopyridyl)carbonylaminosulfonyl]-2-phenylbenzoylmethionine methyl ester A mixture of the resultant isocyanate from Example 119B (1 equivalent) in dichloromethane is treated with 3-aminopyridine (1 equivalent) and stirred until the reaction is judged complete by tlc analysis. The solvent is evaporated and the product is purified by chromatography on silica gel.

EXAMPLE 119D

4-[(A-aminopyridyl)carbonylaminosulfonyl]-2-phenylbenzoylmethionine

The resultant compound from Example 119C is hydrolyzed according to the procedure of Example 1B to give the title product.

EXAMPLE 120

A—NH—CO—NH—SO$_2$—B

The anilines from Table 1 (B—NH$_2$) are reacted according to the procedures of Example 5E to afford the corresponding sulfonyl chlorides. These are reacted according to the procedure of Example 119 with the exception that 3-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 121

A—NH—CO—NH—SO$_2$—CH$_2$—B

The bromides from Table 2, entries 28–132 (B—Br) are reacted according to the procedures of Example 115A–C to afford the corresponding sulfonyl chlorides. These are reacted according to the procedure of Example 119 with the exception that 3-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 122

A—O—CH$_2$—B

The bromides from Table 2 (B—Br) are reacted according to the procedures of Example 16F–G. The resultant alcohols are reacted according to the procedure of Example 27 with the exception that 3-hydroxypyridine is replaced by an alcohol from Table 6 (A—OH). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 123

A—O—CO—NH—B

The procedure of Example 1 is used with the exception that 4-amino-2-phenylbenzoyl methionine methyl ester is replaced by an aniline from Table 1 (B—NH$_2$) and (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 124

A—O—CS—NH—B

The procedure of Example 1 is used with the exception that 4-amino-2-phenylbenzoyl methionine methyl ester is replaced by an aniline from Table 1 (B—NH$_2$), (S)-5-aminomethyl-2-pyrrolidone (1.0 equivalent) is replaced by an alcohol from Table 6 (A—OH, 1.0 equivalent) and CuCl (0.1 equivalent), and triphosgene (0.33 equivalent) is replaced by thiophosgene (1.0 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 125

A—O—SO—NH—B

The procedure of Example 3 is used with the exception that 4-amino-2-phenylbenzoyl methionine methyl ester is replaced by an aniline from Table 1 (B—NH$_2$) and (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichioromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 126

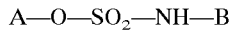
A—O—SO$_2$—NH—B

The procedure of Example 4 is used with the exception that 4-amino-2-phenylbenzoyl methionine methyl ester is replaced by an aniline from Table 1 (B—NH$_2$) and (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichioromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 127

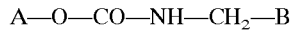
A—O—CO—NH—CH$_2$—B

The bromides from Table 2 (B—Br) are reacted according to the procedures of Example 16F–G. The resultant alcohols are reacted according to the procedure of Example 18 with the exception that (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 128

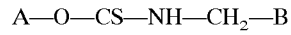
A—O—CS—NH—CH$_2$—B

The bromides from Table 2 (B—Br) are reacted according to the procedures of Example 16F–G. The resultant alcohols are reacted according to the procedure of Example 18 with the exception that (S)-5-aminomethyl-27-pyrrolidone (1.0 equivalent) is replaced by an alcohol from Table 6 (A—OH, 1.0 equivalent) and CuCl (0.1 equivalent), and triphosgene (0.33 equivalent) is replaced by thiophosgene (1.0 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichioromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 129

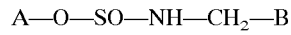
A—O—SO—NH—CH$_2$—B

The bromides from Table 2 (B—Br) are reacted according to the procedures of Example 16F–G and 18A–B. The resultant amines are reacted according to the procedure of Example 3 with the exception that (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichioromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 130

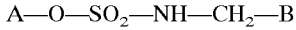
A—O—SO$_2$—NH—CH$_2$—B

The bromides from Table 2 (B—Br) are reacted according to the procedures of Example 16F–G and 18A–B. The resultant amines are reacted according to the procedure of Example 4 with the exception that (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 131

A—S—B

The anilines from Table 1 (B—NH$_2$) are reacted according to the procedures of Example 13A. The resultant fluorides are reacted according to the procedure of Example 13 with the exception that 2-mercaptopyridine is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 132

A—S—CO—NH—B

The procedure of Example 1 is used with the exception that 4-amino-2-phenylbenzoyl methionine methyl ester is replaced by an aniline from Table 1 (B—NH$_2$) and (S)-5-aminomethyl-2-pyrrolidone (1.0 equivalent) is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 133

A—S—CS—NH—B

The procedure of Example 1 is used with the exception that 4-amino-2-phenylbenzoyl methionine methyl ester is replaced by an aniline from Table 1 (B—NH$_2$), (S)-5-aminomethyl-2-pyrrolidone (1.0 equivalent) is replaced by a mercaptan from Table 7 (A—SH), and triphosgene (0.33 equivalent) is replaced by thiophosgene (1.0 equivalent). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 134

A—S—SO—NH—B

The procedure of Example 3 is used with the exception that 4-amino-2-phenylbenzoyl methionine methyl ester is replaced by an aniline from Table 1 (B—NH$_2$) and (S)-5-aminomethyl-2-pyrrolidone (1.0 equivalent) is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 135

A—S—SO$_2$—NH—B

The procedure of Example 4 is used with the exception that 4-amino-2-phenylbenzoyl methionine methyl ester is replaced by an aniline from Table 1 (B—NH$_2$) and (S)-5-aminomethyl-2-pyrrolidone (1.0 equivalent) is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 136

A—S—CO—NH—CH$_2$—B

The bromides from Table 2 (B—Br) are reacted according to the procedures of Example 16F–G. The resultant alcohols are reacted according to the procedure of Example 18 with the exception that (S)-5-aminomethyl-2-pyrrolidone is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 137

A—S—CS—NH—CH$_2$—B

The bromides from Table 2 (B—Br) are reacted according to the procedures of Example 16F–G. The resultant alcohols are reacted according to the procedure of Example 18 with the exception that (S)-5-aminomethyl-2-pyrrolidone is replaced by a mercaptan from Table 7 (A—SH) and triphosgene (0.33 equivalent) is replaced by thiophosgene (1.0 equivalent). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 138

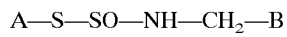

A—S—SO—NH—CH$_2$—B

The bromides from Table 2 (B—Br) are reacted according to the procedures of Example 16F–G and 18A–B. The resultant amines are reacted according to the procedure of Example 3 with the exception that (S)-5-aminomethyl-2-pyrrolidone is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 139

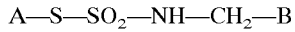

A—S—SO$_2$—NH—CH$_2$—B

The bromides from Table 2 (B—Br) are reacted according to the procedures of Example 16F–G and 18A–B. The resultant amines are reacted according to the procedure of Example 4 with the exception that (S)-5-aminomethyl-2-pyrrolidone is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 140

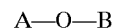

A—O—B

The procedure of Example 6 is used with the exception that 4amino-2-phenylbenzoyl methionine methyl ester is replaced by an aniline from Table 1 (B—NH$_2$) and 3-bromopyridine is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 141

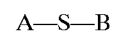

A—S—B

The procedure of Example 12 is used with the exception that 4-amino-2-phenylbenzoyl methionine methyl ester is replaced by an aniline from Table 1 (B—NH$_2$) and 2-chloromethylpyridine hydrochloride is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 142

A—NH—B

The procedure of Example 24 is used with the exception that 4-amino-2-phenylbenzoyl methionine methyl ester is replaced by an aniline from Table 1 (B—NH$_2$) and 2-bromopyridine hydrobromide is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 143

A—O—CH$_2$—B

The bromides from Table 2 (B—Br) are reacted according to the procedures of Example 16F–G. The resultant alcohols are reacted according to the procedure of Example 28 with the exception that 3-chloromethylpyridine hydrochloride is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 144

A—S—CH$_2$—B

The bromides from Table 2 (B—Br) are reacted according to the procedures of Example 16F–G. The resultant alcohols are reacted according to the procedure of Example 37 with the exception that 2-bromothiazole is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichioromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 145

A—C≡C—B

The procedure of Example 47 is used with the exception that (2-phenyl-4-bromobenzoyl)-methionine methyl ester is replaced by a bromide from Table 2 (B—Br) and 4-bromoimidazole is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 146

A—CH=CH—B

The products from Example 145 are reacted according to the procedure of Example 48. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 147

A—CH$_2$—CH$_2$—B

The products from Example 146 are reacted according to the procedure of Example 49. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 148

A—CO—C≡C—B

The bromides from Table 2 (B—Br) are reacted according to the procedure of Example 47A. The resultant acetylenes are reacted according to the procedure of Example 50 with the exception that 4-bromoimidazole is replaced by a halide from Table 8 (A—Cl, A—Br, or A—I). For products derived from halides 202–230 from Table 8, the LiOH hydrolysis step is followed by removal of the tert-butyloxycarbonyl (Boc) amine protecting group by stirring the resultant compound from the LiOH hydrolysis step in a 1:1 mixture of dichioromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 149

A—CO—CH=CH—B

The products from Example 148 are reacted according to the procedure of Example 48.

645

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 150

A—CO—CH₂—CH₂—B

The products from Example 149 are reacted according to the procedure of Example 49.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 151

A—SO₂—B

The anilines from Table 1, entries 28–132 (B—NH₂) are reacted according to the procedures of Example 13A. The resultant fluorides are reacted according to the procedure of Example 13 with the exception that 2-mercaptopyridine is replaced by a mercaptan from Table 7 (A—SH). The resultant sulfides are oxidized according to the procedure of Example 14A. For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 152

A—CH₂SO₂—B

The procedure of Example 12 is used with the exception that 4-amino-2-phenylbenzoyl methionine methyl ester is replaced by an aniline from Table 1, entries 28-(B—NH₂) and 2-chloromethylpyridine hydrochloride is replaced by a halide from Table 8 (A—Cl, A—Br, or A—I). The resultant sulfides are oxidized according to the procedure of Example 14A. For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

646

EXAMPLE 153

A—SO₂—CH₂—B

The bromides from Table 2, entries 28–132 (B—Br) are reacted according to the procedures of Example 16F–G. The resultant alcohols are reacted according to the procedure of Example 37 with the exception that 2-bromothiazole is replaced by a halide from Table 8 (A—Cl, A—Br, or A—I). The resultant sulfides are oxidized according to the procedure of Example 14A. For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

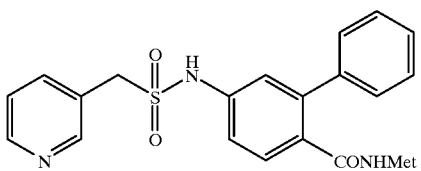

EXAMPLE 154

{4-[(3-sulfonylmethylpyridyl)amino]-2-phenylbenzoyl}methionine

EXAMPLE 154A

{4-[(3-sulfonylmethylpyridyl)amino]-2-phenylbenzoyl}methionine methyl ester

A mixture of 3-chlorosulfonylmethylpyridine hydrochloride (1.0 equivalent) and (4-amino-2-phenylbenzoyl) methionine methyl ester (1.0 equivalent) in dichloromethane is treated with triethylamine (2.2 equivalents). When judged complete by TLC analysis, the reaction is diluted with ethyl acetate, and then is washed with pH 4 water, saturated NaHCO₃, and brine. The mixture is dried and concentrated to give the crude title compound which is purified by chromatography on silica gel.

EXAMPLE 154B

{4-[(3-sulfonylmethylpyridyl)amino]-2-phenylbenzoyl}methionine

The resultant compound from Example 154A is hydrolyzed according to the procedure of Example 1B to give the title product.

EXAMPLE 155

A—CH₂SO₂—NH—B

The procedure of Example 154 is used with the exception that 4-amino-2-phenylbenzoyl methionine methyl ester is replaced by an aniline from Table 1 (B—NH₂) and 3-chlorosulfonylmethylpyridine hydrochloride is replaced by a sulfonyl chloride from Table 9 (A—SO₂Cl).

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 156

The bromides from Table 2 (B—Br) are reacted according to the procedures of Example 16F–G. The resultant alcohols are converted to the corresponding aniines according to the procedures of Examples 18A–B. These amines are reacted according to the procedure of Example 154 with the exception that -chlorosulfonylmethylpyridine hydrochloride is replaced by a sulfonyl chloride from Table 9 (A—SO₂Cl).

This example also encompasses compounds comprising a C-teriunal ester moiety, in which case the fmal LiOH step is elirninated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

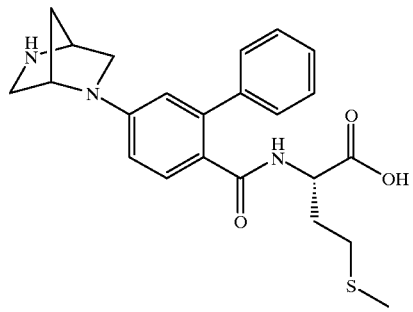

EXAMPLE 173

[4-((2S,5S)-1,4-diazabicyclo(2,2,1)octan-1-yl)-2-phenylbenzoyl]methionine hydrochloride To a solution of 74 mg (0.13 mmol) of 2-phenyl-4-[(2S,5S)-4-Boc-1,4-diazabicyclo(2,2,1)octan-1-yl]benzoylmethionine methyl ester, prepared as in Example 172A, in 5 ml of THF was added 0.4 ml (0.4 mmol) of 1 N LiOH in an ice bath. The reaction mixture was stirred for 2 hours. The reaction mixture was adjusted to pH 2–3 with 1 N HCl at the same temperature and the solvent was evaporated. The residue was partitioned with dichloromethane and water, and extracted 3 times with dichioromethane. The combined organic solution was washed with 1 N HCl and water, dried over anhydrous magnesium sulfate, and concentrated in vacuo to give 60 mg of the resulting free acid as a oily residue. To a 2 ml of a 1:1 solution of TFA and dichloromethane was added 60 mg of the acid. After 30 min, The reaction mixture was thoroughly evaporated in high vacuum to give an oily residue. The residue was triturated with 0.3 ml of 3 M anhydrous HCl-ether in 5 ml of ether and the white solid was collected by filtration to give 43 mg (66%) of [4-((2S,5S)-1,4-diazabicyclo(2,2,1)octan-1-yl)-2-phenylbenzoyl]methionine hydrochloride: HPLC 95% (purity); ¹H NMR (300 MHz, CD₃OD) δ 7.49–7.36 (m, 6H), 6.73 (dd, 1H, J=2.2, 8.4 Hz), 6.60 (d, 1H, J=2.1 Hz), 4.77 (s, 1H), 4.50 (m, 12H), 3.73 (m, 2H), 3.32 (m, 2H), 2.31–1.85 (m, 6H); ¹³C NMR (CD₃OD) δ 175.0, 173.1, 148.5, 143.7, 142.4, 131.4, 129.9, 129.6, 128.8, 126.6, 115.5, 112.4, 59.7, 56.8, 53.6, 53.2, 51.8, 37.1, 31.9, 31.1, 15.8.

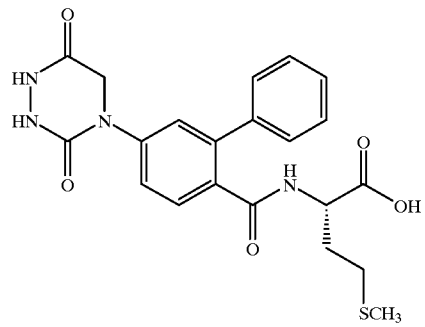

EXAMPLE 224

[4-(2,4-dioxohexahydro-1,3,5-triazin-2-yl)-2-phenylbenzoyl]methionine

EXAMPLE 224A (4-carboxymethylamino-2-phenylbenzoyl)methionine methyl ester

A mixture of (4-amino-2-phenylbenzoyl)methionine methyl ester (compound 8, 1.51 g, 4.21 mmol), glyoxylic acid monohydrate (466 mg, 5.06 mmol), sodium cyanoborohydride (1.0 M in THF, 4.2 mL), sodium acetate (0.5 g) and acetic acid (0.5 mL) in methanol (10 mL) was stirred for 14 hours. The reaction mixture was diluted with ethyl acetate (100 mL), washed with saturated aqueous potassium dihydrogenphosphate, water and brine, dried over anhydrous sodium sulfate, filtered, and concentrated in vacuo. The residue was purified by column chromatography (ethyl acetate, then 3% methanol-ethyl acetate) to give (4-carboxymethylamino-2-phenylbenzoyl)methionine methyl ester (1.46 g, 83%). ¹H NMR (300 MHz, CDCl₃) δ 7.67 (d, 1H), 7.39 (m, 5H), 6.54 (dd, 1H), 6.45 9d, 1H), 5.96 (br d, 1H), 4.63 (m, 1H), 3.88 (d, 2H), 3.67 (s, 3H), 2.04 (m, 2H), 2.00 (s, 3H), 1.86 (m, 1H), 1.67 (m, 1H). MS (APCI⁺) m/e 417 (M+H)⁺.

EXAMPLE 224B

[4-(N-tert-butoxycarbonylamino)carboxamidomethylamino-2-phenylbenzoyl]methionine methyl ester A mixture of the (4-carboxymethylamino-2-phenylbenzoyl)methionine methyl ester prepared in Example 224A (1.04 g, 2.50 mmol), tert-butylcarbazate (661 mg, 5.0 mmol), 3-hydroxy1,2,3-benzotriazin-4(3H)-one (489 mg, 3.0 mmol) and 1-(3-dimethylaminopropyl)-3-ethylcarbodiimide (576 mg, 3.0 mmol) in dichloromethane (10 mL) was stirred at room temperature for 15 hours. The reaction mixture was diluted with ethyl acetate (100 mL), washed with water and brine, dried over anhydrous magnesium sulfate, filtered, and concentrated in vacuo. The residue was purified by column chromatography (ethyl acetate) to give [4-(N-tertbutoxycarbonylamino)carboxamidomethylamino-2-phenylbenzoyl]methionine methyl ester (671 mg, 51%). ¹H NMR (300 MHz, CDCl₃) δ 8.16 (d, 1H), 7.69 (d, 1H), 7.40 (m, 5H), 6.64 (dd, 1H), 6.53 (d, 1H), 6.45 (m, 1H), 5.96 (br d, 1H), 4.63 (m, 1H), 3.97 (d, 2H), 3.67 (s, 3H), 2.99 (m, 4H), 2.06 (m, 2H), 2.00 (s, 3H), 1.88 (m, 1H), 1.68 (m, 1H), 1.46 (s, 9H). MS (APCI$^+$) m/e 531 (M+H)$^+$.

EXAMPLE 224C

[4-(N-tertbutoxycarbonylamino)carboxamidomethyl-(N-chloroformyl)amino-2-phenylbenzoyl] methionine methyl ester To a −78° C. solution of the [4-(N-tert-butoxycarbonylamino)carboxamidomethylamino-2-phenylbenzoyl]methionine methyl ester prepared in Example 224B (258 mg, 0.481 mmol) in dichloromethane (3 mL) was added phosgene (1.93 M in toluene, 0.38 mL, 0.74 mmol), followed by triethylamine (0.20 mL, 1.5 mmol). The reaction was then left to warm to ambient temperature over 14 hours. The reaction mixture was then filtered through silica gel (10 g), rinsed with ethyl acetate, and concentrated in vacuo. The residue was purified by column chromatography (40% ethyl acetate-hexane) to give [4-(N-tertbutoxycarbonylamino)carboxamidomethyl-(N-chloroformyl)amino-2-phenylbenzoyl]methionine methyl ester (171 mg, 60%). $^1$H NMR (300 MHz, DMSO-d$_6$) δ 8.24 (d, 1H), 7.33 (m, 5H), 7.28 (d, 1H), 6.68 (m, 3H), 4.39 (m, 2H), 4.30 (m, 1H), 3.62 (s, 3H), 2.25 (m, 2H), 2.00 (s, 3H), 1.83 (m, 2H), 1.51 (s, 9H).

EXAMPLE 224D

[4-(2,4-dioxohexahydro-1,3,5-triazin-2-yl)-2-phenylbenzoyl]methionine methyl ester To a solution of the [4-(N-tertbutoxycarbonylamino)carboxamidomethyl-(N-chloroformyl)amino-2-phenylbenzoyl]methionine methyl ester prepared in Example 224C (70 mg, 0.118 mmol) in dichloromethane (2 mL) was added 2-mercaptoethanol (5 drops) and trifuoro-acetic acid (1 mL). After 1.5 hour, the solvent was evaporated in vacuo and the residue was purified by column chromatography (30% ethyl acetate-hexane) to give [4-(2,4-dioxohexahydro-1,3,5-triazin-2-yl)-2-phenylbenzoyl] methionine methyl ester (43 mg, 80%). $^1$H NMR (300 MHz, CDCl$_3$) δ 8.86 (br s, 1H), 8.69 (d, 1H), 7.40 (m, 5H), 6.69 (dd, 1H), 6.56 (d, 1H), 5.76 (br d, 1H), 4.63 (m, 1H), 4.32 (s, 2H), 3.65 (s, 3H), 2.99 (m, 4H), 2.09 (t, 2H), 2.01 (s, 3H), 1.89 (m, 1H), 1.68 (m, 1H). MS (CI$^+$) m/e 457 (M+H)$^+$.

EXAMPLE 224E

[4-(2,4-dioxohexahydro-1,3,5-triazin-2-yl)-2-phenylbenzoyl]methionine

The desired compound was prepared by saponification of the product of Example 224D using the procedure of Example 211. $^1$H NMR (300 MHz, DMSO-d$_6$) δ 7.32 (m, 5H), 7.23 (d, 1H), 6.79 (d, 1H), 6.63 (dd, 1H), 6.56 (d, 1H), 6.38 (m, 1H), 4.00 (m, 1H), 3.50 (s, 2 H), 2.07 (m, 2H), 1.97 (s, 3H), 1.79 (m, 2H). MS (APCI$^+$) m/e 465 (M+Na)$^+$.

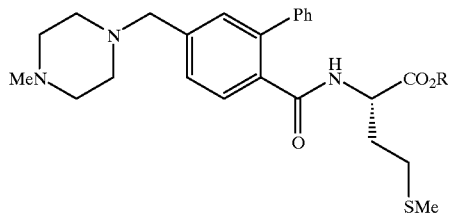

EXAMPLE 289

[4-(4-methylpiperazinylmethyl)-2-phenylbenzoyl] methionine

EXAMPLE 289A

[4-(4-methylpiperazinylmethyl)-2-phenylbenzoyl] methionine methyl ester

A solution of 4-chloromethyl-2-phenylbenzoic acid methyl ester (0.521 g, 2.00 mmol), prepared as in Example 286A, 1-methylpiperazine (0.607 g, 6.00 mmol), K$_2$CO$_3$ (0.663 g, 4.80 mmol), KI (0.332 g, 2.00 mmol), and Bu$_4$NBr (0.032 g, 0.10 mmol) in DMF (5 mL) was stirred for 2 hours at ambient temperature and then concentrated under reduced pressure. The residue was treated with a saturated LiOH-methanol (10 mL) and then heated at reflux for 5 hours. The mixture was concentrated and the residue was dissolved in H$_2$O. This solution was extracted with ethyl acetate (5×), and the aqueous phase was then acidified by the addition of 3 M HCl and lyopholized. The resulting white foam was dissolved in DMF (20 mL) and the solution was treated with L-methionine, methyl ester hydrochloride (0.807 g, 4.00 mmol), 3-hydroxy-1,2,3-benzotriazin-4(3H)-one (1.33 g, 8.00 mmol), 1-(3-dimethylaminopropyl)-3-ethylcarbodiimide (1.56 g, 8.00 mmol), and N-methylmorpholine (1.23 g, 12.0 mmol). The reaction mixture was stirred at ambient temperature for 20 hours, diluted with ethyl acetate, and extracted with a 2:1 mixture of H$_2$O and saturated aqueous NaHCO$_3$ (2×), 1:1 mixture of the same (2×) and brine (2×). The organic phase was dried (MgSO$_4$) and concentrated to provide a gold oil. Radial chromatography (30% methanol-ethyl acetate) afforded the desired compound (0.321 g, 35%).

EXAMPLE 289

[4-(4-methylpiperazinylmethyl)-2-phenylbenzoyl] methionine

Saponification of the product of Example 289A using the procedure of Example 287D gave the desired compound as a white foam as the bis-hydrochloride, mono-sodium chloride. $^1$H NMR (d$_6$-DMSO) δ 1.76–1.95 (comp, 2H), 2.00 (s, 3H), 2.17–2.36 (comp, 2H), 2.52 (br, 3H), 3.18–3.80 (br, 8H), 4.28–4.60 (br, 3H), 7.30–7.42 (comp, 3H), 7.47–7.55 (comp, 3H), 7.67–7.73 (m, 1H), 7.74–7.80 (br, 1H), 8.63 (d, J=7.8 Hz, 1H). LRMS (CI): 442 (M+H)$^+$.

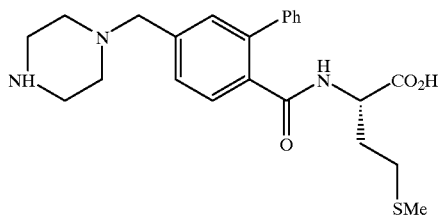

EXAMPLE 290

(4-piperazinylmethyl-2-phenylbenzoyl)methionine

EXAMPLE 290A

4-N-tert-butoxycarbonylpiperazinylmethyl-2-phenylbenzoic acid

A solution of 4-chloromethyl-2-phenylbenzoic acid methyl ester (0.521 g, 2.00 mmol), prepared as in Example 286A, piperazine (1.39 g, 16.0 mmol), $K_2CO_3$ (0.663 g, 4.80 mmol), KI (0.332 g, 2.00 mmol), and $Bu_4NBr$ (0.032 g, 0.10 mmol) in DMF (7 mL) was stirred for 2 hours at ambient temperature and then concentrated under reduced pressure. The residue was treated with saturated LiOH-methanol (10 mL) and then heated at reflux for 5 hours. The mixture was concentrated and the residue was dissolved in $H_2O$. This solution was extracted with ethyl acetate (5×), and the aqueous phase was then acidified by the addition of 3 M HCl and lyopholized. The resulting white foam was dissolved in a 1:1 mixture of $H_2O$ and 0.979 M NaOH (86 mL), and the solution was treated with di-tert-butyldicarbonate (6.68 g, 30.0 mmol). The reaction mixture was stirred at ambient temperature for 15 hours and then concentrated to remove THF. The mixture was treated with $H_2O$ and saturated aqueous $NaHCO_3$ and then extracted with a ether (4×). The aqueous phase was acidified to pH 3 by the addition of 3 M HCl and then extracted with 4:1 $CHCl_3$-methanol (10×). The combined organic extracts were dried twice with saturated aqueous $Na_2SO_4$ and concentrated to provide the desired compound (0.544 g, 69%) as an amber wax.

EXAMPLE 290B (4-N-tert-butoxycarbonylpiperazinylmethyl-2-phenylbenzoyl)methionine methyl ester A solution of the product of Example 290A (0.544 g, 1.37 mmol), L-methionine, methyl ester hydrochloride (0.553 g, 2.74 mmol), 3-hydroxy-1,2,3-benzotriazin-4(3H)-one (1.14 g, 6.85 mmol), 1-(3-dimethylaminopropyl)-3-ethylcarbodiimide (1.34 g, 6.85 mmol), and N-methylmorpholine (0.980 g, 9.59 mmol) in DMF (14 nlL) was stirred at ambient temperature for 16 hours. The mixture was diluted with ethyl acetate and then extracted with a 2:1 mixture of $H_2O$ and saturated aqueous $NaHCO_3$ (2×), a 1:1 mixture of the same (2×) and brine (2×). The organic phase was dried ($MgSO_4$) and concentrated to provide an amber oil. Radial chromatography (1:1 hexane-ethyl acetate) afforded the desired compound (0.356 g, 48%) as an amber oil.

EXAMPLE 290C (4-piperazinylmethyl-2-phenylbenzoyl)methionine

The desired compound was prepared frbm the product of Example 290B according to the method of Example 286E.

$^1$H NMR (300 MHz, DMSO-d6) δ 1.75–1.96 (comp, 2H), 2.00 (s, 3H), 2.17–2.35 (comp, 2H), 3.3–3.7 (br, 8H), 4.28–4.38 (m, 1H), 4.28–4.38 (m, 1H), 4.38–4.54 (br, 2H), 7.30–7.44 (comp, 3H), 7.46–7.56 (comp, 3H), 7.70 (d, J=7.3 Hz, 1H), 7.76–7.82 (br, 1H), 8.66 (d, J=7.7 Hz, 1H), 9.86–10.06 (br, 12.30–12.70 (br, 1H). LRMS (CI) m/e 248 (M+H)$^+$.

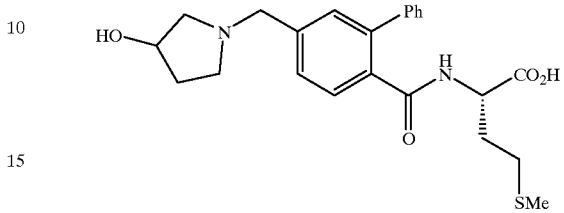

EXAMPLE 291

[4-(3-hydroxypyrrolidinyl)-2-phenylbenzoyl]methionine

EXAMPLE 291A

[4-(3-hydroxypyrrolidinyl)-2-phenylbenzoyl]methionine methyl ester

A solution of 4-chloromethyl-2-phenylbenzoic acid methyl ester (0.521 g, 2.00 mmol), prepared as in Example 286A, 3-pyrrolidinol (0.178 g, 2.00 mmol), $K_2CO_3$ (0.553 g, 4.00 mmol), and $Bu_4NI$ (0.0754 g, 0.20 mmol) in $CH_3CN$ (5 mL) was stirred for 15 hours, treated with $LiOH.H_2O$ (0.506 g, 12.0 mmol), and then heated at reflux for 5 hours. The solution was cooled to ambient temperature and added to a mixture of L-methionine methyl ester hydrochloride (0.807 g, 4.00 mmol), 3-hydroxy-1,2,3-benzotriazin-4(3H)-one (1.66 g, 10.00 mmol), 1-(3-dimethylaminopropyl)-3-ethylcarbodiimide (1.96 g, 10.00 mmol), and triethylamine hydrochloride (2.81 g, 20 mmol) in $CH_3CN$ (15 mL). After 12 days the mixture was concentrated under reduced pressure and the residue was dissolved in ethyl acetate. The solution was extracted with a 1:1 mixture of $H_2O$ and saturated aqueous $NaHCO_3$ (4×) and brine. The organic phase was dried ($MgSO_4$) and concentrated to provide a gold oil. Radial chromatography (12% methanol-ethyl acetate) afforded the desired compound (0.494 g, 56%).

EXAMPLE 291B

[4-(3-hydroxypyrrolidinyl)-2-phenylbenzoyl]methionine

Saponification of the product of Example 289A using the procedure of Example 287D gave the desired compound as a white foam as the bis-hydrochloride, mono-sodium chloride. $^1$H NMR (300 MHz, DMSO-d6) δ 1.77–2.06 (comp, 5H), 2.16–2.36 (comp, 2H), 2.94–3.04 (m, 1H), 3.12–3.34 (comp, 2H), 3.34–3.56 (comp, 2H), 4.28–4.37 (m, 1H), 4.37–4.60 (comp, 2H), 4.60–5.50 (br, 2H), 7.32–7.43 (comp, 3H), 7.45–7.56 (comp, 3H), 7.65–7.80 (comp, 2H), 8.68 (d, J=7.8 Hz, 1H), 11.2–11.9 (m, 1H). LRMS (CI) m/e 429 (M+H)$^+$.

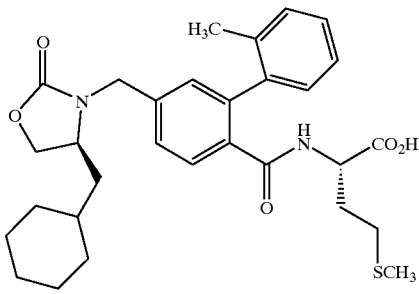

EXAMPLE 349

[4-(5-cyclohexylmethyloxazolid-2-on-1-ylmethyl)-2-(2-methylphenyl)benzoyl]methionine

EXAMPLE 349A

[4-(1-hydroxy-3-cyclohexylprop-2-ylaminomethyl)-2-(2-methylphenyl)benzoyl]methionine A mixture of [4-formyl-2-(2-methylphenyl)benzoyl]methionine ethyl ester (614 mg, 1.54 mmol), prepared according to Example 158F except substituting [4-hydroxmethyl-2-(2-methylphenyl)benzoic acid for 4-hydroxymethyl-2-phenylbenzoic acid in Example 158E, (S)-(+)-2-amino-3-cyclohexyl-1-propanol hydrochloride (357 mg, 1.84 mmol) and diisopropylethylamine (0.135 mL, 0.77 mmol) in toluene was refluxed for 5 hours using a Dean-Stark apparatus. The reaction mixture was cooled to ambient temperature and diluted with ethanol. Sodium cyanoborohydride (145 mg) and o-bromocresol green was added. The reaction mixture was stirred while acidity was maintained using HCl-ethanol. The reaction was quenched with saturated aqueous potassium carbonate and the mixture was extracted with dichloromethane (2x). The combined organic layers were dried over magnesium sulfate, filtered, and concentrated in vacuo. Chromatography on silica gel (5% methanol-chloroform) gave the desired compound (840 mg).

EXAMPLE 349B

[4-(1-hydroxy-3-cyclohexylprop-2-yl-N-ethoxycarbonylaminomethyl)-2-(2-methylphenyl)benzoyl]methionine To a solution in THF of the product of Example 348A (173 mg, 0.32 mmol) and diisopropylethylamine (66 μL, 0.38 mmol) was added ethyl chloroformate (40 μL, 0.38 mmol) and the reaction mixture was stirred for 1.5 hours at ambient temperature. The reaction mixture was poured into ethyl acetate and the organic phase was washed with aqueous 2N HCl, dried over magnesium sulfate, filtered, and concentrated in vacuo to give the desired compound as a clear oil which was used without further purification.

EXAMPLE 349C

[4-(5-cyclohexylmethyl-2-oxazolidon-1-ylmethyl)-2-(2-methylphenyl)benzoyl]methionine To a 100° C. solution of the product of Example 348B in toluene was added sodium ethoxide (21% in ethanol, 30 μL) and the reaction mixture was stirred for 10 minutes. The reaction mixture was cooled to ambient temperature and diluted with saturated aqueous ammonium chloride. The mixture was extracted with ethyl acetate. The organic phase was dried over magnesium sulfate, filtered, and concentrated in vacuo. Chromatography on silica gel (33% ethyl acetate-hexane) gave the title compound as the ethyl ester. Saponification of the ethyl ester using lithium hydroxide gave the title compound. $^1$H NMR (DMSO-d$_6$, 300 MHz) δ 8.13 (m, 1H), 7.41 (d, J=7 Hz, 1H), 7.25 (d, J=7 Hz, 1H), 7.11–7.02 (m, 4H), 4.45 (d, J=15 Hz, 1H), 4.34 (dd, J=9, 8 Hz, 1H), 4.19 (d, J=15 Hz, 1H), 4.10 (m, 1H), 3.84 (dd, J=8, 8 Hz, 1H), 3.58 (m, 1H), 2.10–1.83 (m, 5H), 1.85 (s, 3H), 1.47–1.37 (m, 8H), 1.10–0.92 (m, 5H), 0.85–0.57 (m, 2H). MS (DCI—NH3) m/e 539 (M+H)$^+$, 556 (M+NH$_4$)$^+$.

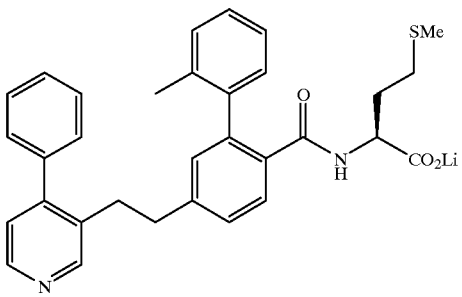

EXAMPLE 452

N-[4-(2-(2-phenylphenyl)ethyl)-2-(2-methylphenyl)benzoyl]methionine lithium salt The desired compound was prepared according to the method of Examples 210–212 $^1$H nmr (300 MHz, DMSO-d$_6$): δ 7.2–7.04 (m, 15 H), 6.89 (dd, 1 H), 6.54 (br d, 1 H), 4.12 (m, 1 H), 2.81 (t, 2 H), 2.63 (t, 2 H), 2.00 (m, 1 H), 1.88–1.87 (br s, 6 H), 1.73 (m, 2 H), 1.56 (m, 1 H). MS (ESI-): m/e 522 (M-H)$^-$.

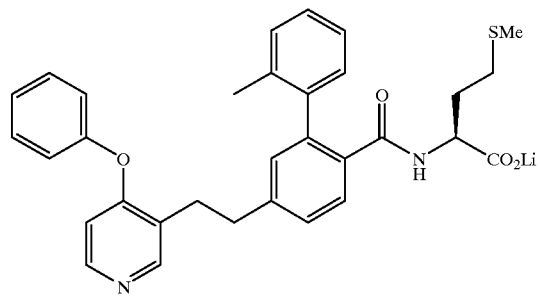

EXAMPLE 453

N-[4-(2-(2-phenoxyphenyl)ethen-1-yl)-2-(2-methylphenyl)benzoyl]methionine lithium salt The desired compound was prepared according to the method of Examples 210 and 211. $^1$H nmr (300 MHz, DMSO-d$_6$): δ 7.88 (br d, 1 H), 7.55 (m, 2 H), 7.40–7.17 (m, 11 H), 7.10 (t, 1 H), 6.96 (m, 4 H), 3.65 (m, 1 H), 2.15 (m, 1 H), 2.00 (m, 1 H), 1.91 (br s, 6 H), 1.75–1.55 (m, 2 H). MS (APCI-): m/e 536 (M-H)$^-$.

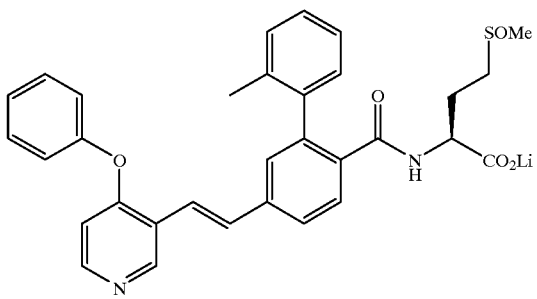

EXAMPLE 454

N-[4-(2-(2-phenoxyphenyl)ethenyl)-2-(2-methylphenyl)benzoyl]-2-amino-4-methylsulfinylbutanoic acid lithium salt The desired compound was prepared according to the method of Examples 210 and 211. $^1$H nmr (300 MHz, DMSO-$d_6$): δ 7.88 (br d, 1 H), 7.62–7.50 (m, 2 H), 7.40–7.17 (m, 11 H), 7.10 (t, 1 H), 6.98 (m, 4 H), 3.90 (m, 1 H), 2.45 (s, 3 H), 2.39,2.36 (2 s's, 3 H), 2.10–1.64 (m, 4 H). MS (ESI–): m/e 552 (M–H)$^-$.

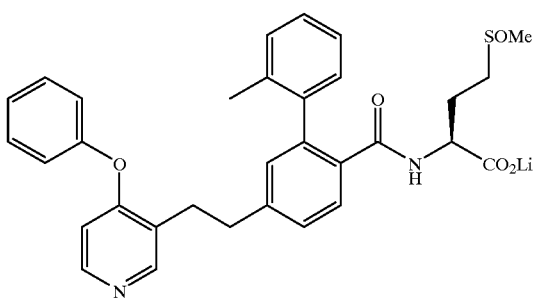

EXAMPLE 455

N-[4-(2-(2-phenoxyphenyl)ethyl)-2-(2-methylphenyl)benzoyl]methionine lithium salt The desired compound was prepared according to the method of Examples 210–212. $^1$H nmr (300 MHz, DMSO-$d_6$): δ 7.45–6.90 (m, 17 H), 3.65 (m, 1 H), 2.88 (br s, 4 H), 2.18–2.00 (m, 2 H), 1.91 (br s, 6 H), 1.70–1.50 (m, 2 H). MS (APCI–): m/e 538 (M–H)$^-$.

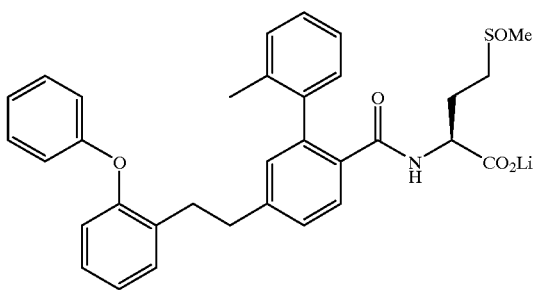

EXAMPLE 456

N-[4-(2-(2-phenoxyphenyl)ethyl)-2-(2-methylphenyl)benzoyl]-2-amino-4-methylsulfinylbutanoic acid lithium salt The desired compound was prepared according to the method of Examples 210–212. $^1$H nmr (300 MHz, DMSO-$d_6$): δ 7.43 (m, 1 H), 7.34 (m, 3 H), 7.25–7.00 (m, 9 H), 6.95 (m, 1 H), 6.85 (m, 3 H),. 3.90 (m, 1 H), 2.88 (br s, 4 H), 2.41–2.37 (4 s's, 6 H), 2.10–1.64 (m, 4 H). MS (ESI–): m/e 554 (M–H)$^-$.

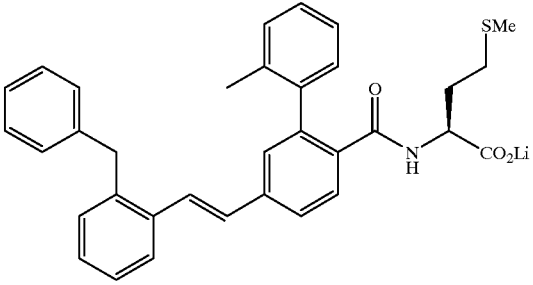

EXAMPLE 457

N-[4-(2-(2-benzylphenyl)ethenyl)-2-(2-methylphenyl)benzoyl]methionine lithium salt The desired compound was prepared according to the method of Examples 210 and 211. $^1$H nmr (300 MHz, DMSO-$d_6$): δ 7.70 (m, 1 H), 7.59 (m, 1 H), 7.51 (m, 2 H), 7.34–7.10 (m, 14 H), 6.96 (br s, 1 H).4.17 (br s, 2 H), 3.63 (m, 1 H), 2.19 (m, 1 H), 2.02 (m, 1 H), 1.92 (br 5, 6 H), 1.73–1.52 (m, 2 H). MS (APCI–): m/e 534 (M–H)$^-$.

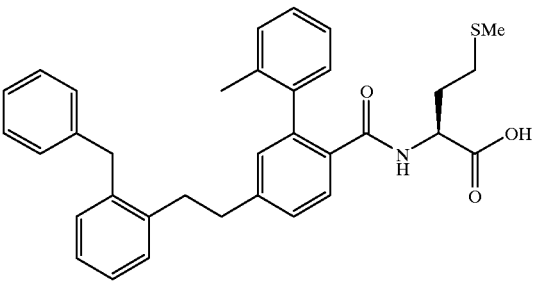

EXAMPLE 458

N-[4-(2-(2-benzylphenyl)ethenyl)-2-(2-methylphenyl)benzoyl]methionine lithium salt The desired compound was prepared according to the method of Examples 210–212. $^1$H nmr (300 MHz, DMSO-$d_6$): δ 7.60–7.40 (m, 3 H), 7.25–7.07 (m, 12 H), 7.00–6.80 (m, 2 H), 3.97 (s, 2 H), 3.61 (m, 1 H), 2.83 (m, 2 H), 2.72 (m, 2 H), 2.08 (m, 1 H), 1.97 (m, 1 H), 1.96,1.91(2 br s's, 6 H), 1.80–1.52 (m, 2 H). MS (APCI–): m/e 536 (M–H)$^-$.

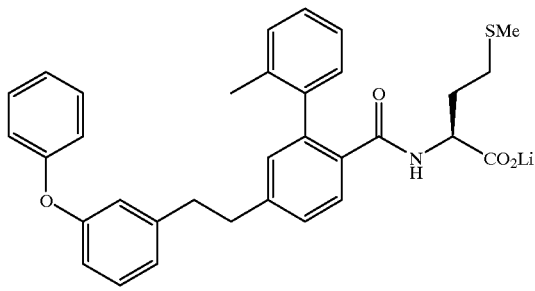

EXAMPLE 459

N-[4-(2-(3-phenoxyphenyl)ethyl)-2-(2-methylphenyl)benzoyl]methionine lithium salt The desired compound was prepared according to the method of Examples 210–212. $^1$H nmr (300 MHz, DMSO-$d_6$): δ 7.44 (d, 1 H), 7.35 (tt, 2 H), 7.25 (dt, 1H), 7.19 (m, 4 H), 7.10 (tt, 2 H), 6.98 (dt, 1 H), 6.96–6.83 (m, 5 H), 6.79 (ddd, 1 H), 3.64 (m, 1 H), 2.91 (br s, 4 H), 2.08 (m, 1 H), 1.95 (m, 1 H), 1.91 (br s, 6 H), 1.73–1.52 (m, 2 H). MS (APCI–): m/e 538 (M–H)$^-$.

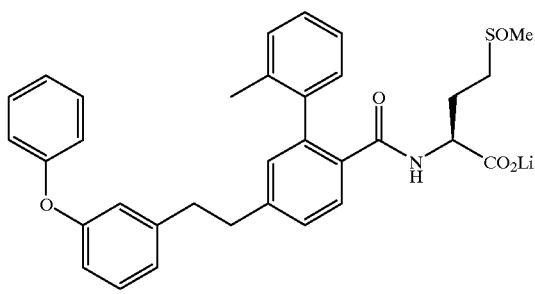

EXAMPLE 460

N-[4-(2-(3-phenoxyphenyl)ethyl)-2-(2-methylphenyl)benzoyl]-2-amino-4-methylsulfinylbutanoic acid lithium salt The desired compound was prepared according to the method of Examples 210–212. $^1$H nmr (300 MHz, DMSO-$d_6$): 7.44 (dd, 1 H), 7.35 (tt, 2 H), 7.25 (dt, 1H), 7.19 (m, 4 H), 7.10 (tt, 2 H), 6.98 (dt, 1 H), 6.96–6.83 (m, 5 H), 6.79 (ddd, 1 H), 3.90 (m, 1 H), 2.91 (br s, 4 H), 2.45 (s, 3 H), 2.39, 2.36 (2 s's, 3 H), 2.20–1.54 (m, 4 H). MS (ESI–): m/e 554 (M–H)$^-$.

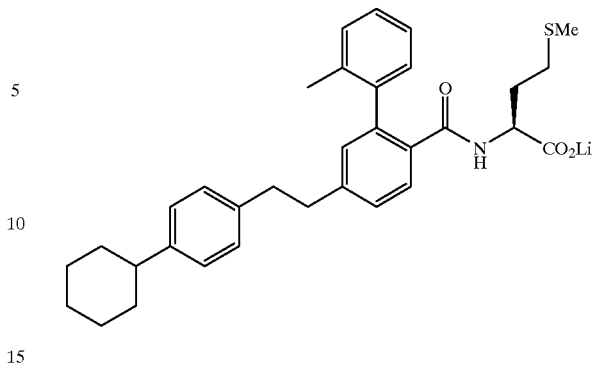

EXAMPLE 461

N-[4-(2-(4-cyclohexylphenyl)ethyl)-2-(2-methylphenyl)benzoyl]methionine lithium salt The desired compound was prepared according to the method of Examples 210–212. $^1$H nmr (300 MHz, DMSO-$d_6$): δ 7.45 (d, 1 H), 7.29 (dd, 1 H), 7.25–7.05 (m, 8 H), 6.88 (m, 2 H), 3.64 (m, 1 H), 2.88 (m, 4 H), 2.44 (m, 1 H), 2.10–1.30 (m, 14 H), (br s, 6 H). MS (APCI–): m/e 528 (M–H)$^-$.

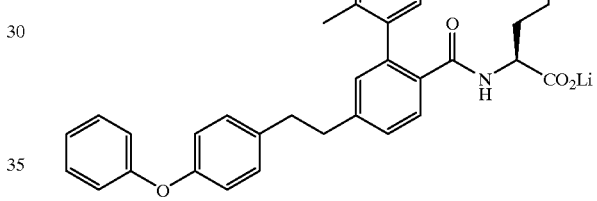

EXAMPLE 462

N-[4-(2-(4-phenoxyphenyl)ethyl)-2-(2-methylphenyl)benzoyl]methionine lithium salt The desired compound was prepared according to the method of Examples 210–212. $^1$H nmr (300 MHz, DMSO-$d_6$): 7.45 (d, 1 H), 7.40–7.27 (m, 3 H), 7.25–7.12 (m, 7 H), 7.10 (tt, 1 H), 6.98–6.87 (m, 5 H), δ 3.67 (m, 1 H), 2.91 (br s, 4 H), 2.16–1.95 (m, 2 H), 1.91 (br s, 6 H), 1.73–1.52 (m, 2 H). MS (APCI–): m/e 538 (M–H)$^-$.

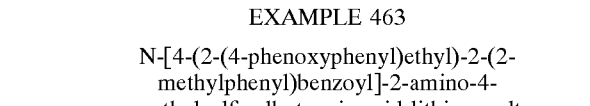

EXAMPLE 463

N-[4-(2-(4-phenoxyphenyl)ethyl)-2-(2-methylphenyl)benzoyl]-2-amino-4-methylsulfinylbutanoic acid lithium salt The desired compound was prepared according to the method of Examples 210–212. $^1$H nmr (300 MHz, DMSO-d$_6$): 7.66–6.87 (m, 17 H), 3.70 (m, 1 H), 2.92 (br s, 4 H), 2.40–2.37 (4 s's, 6 H), 2.20–1.54 (m, 4 H). MS (ESI–): m/e 554 (M–H)$^-$.

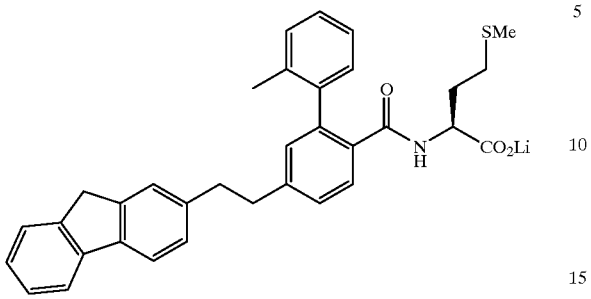

EXAMPLE 464

N-[4-(2-fluoren-4-ylethyl)-2-(2-methylphenyl)benzoyl]methionine lithium salt

The desired compound was prepared according to the method of Examples 210–212. $^1$H nmr (300 MHz, DMSO-d$_6$): δ 7.84 (d, 1 H), 7.77 9d, 1 H), 7.56 (d, 1 H), 7.45 (d, 1 H), 7.44 (s, 1 H), 7.40–6.86 (m, 10 H), 3.86 (s, 2 H), 3.64 (m, 1 H), 2.98 (br s, 4 H), 2.08 (m, 1 H), 1.95 (m, 1 H), 1.91 (br s, 6 H), 1.73–1.52 (m, 2 H). MS (APCI–): m/e 538 (M–H)$^-$.

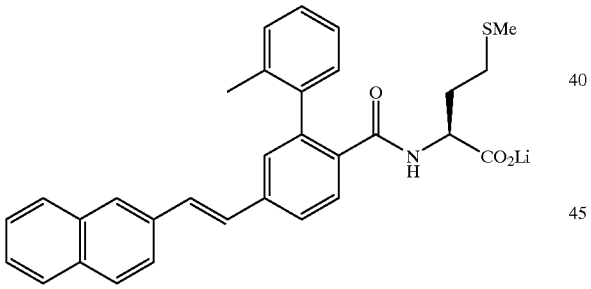

EXAMPLE 465

N-[4-(2-naphth-2-ylethenyl)-2-(2-methylphenyl)benzoyl]methionine

The desired compound was prepared according to the method of Examples 210 and 211. $^1$H nmr (300 MHz, CDCl$_3$): δ: δ 8.07 (dd, 1 H), 7.90–7.80 (m, 4 H), 7.74 (dd, 1 H), 7.66 (dd, 1 H), 7.51 (m, 2 H), 7.42–7.31 (m, 6 H), 7.25 (m, 1 H), 5.94 (t, 1 H), 4.60 (m, 1 H), 2.20–2.00 (4 s s, 6 H), 2.12 (m, 1 H), 2.03 (m, 1 H), 1.94 (m, 1 H), 1.58 (m, 1 H). MS (CI+): m/e 496 (M+H)$^+$.

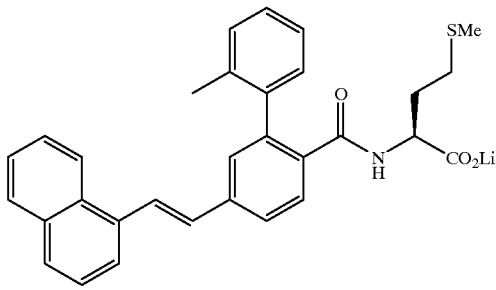

EXAMPLE 466

N-[4-(2-naphth-1-ylethenyl)-2-(2-methylphenyl)benzoyl]methionine lithium salt

The desired compound was prepared according to the method of Examples 210 and 211. $^1$H nmr (300 MHz, MeOD-d$_4$): δ 8.28 (d, 1 H), 8.12 (dd, 1 H), 7.90–7.72 (m, 5 H), 7.63–7.42 (m, 5 H), 7.35–7.10 (m, 5 H), 4.25 (m, 1 H), 2.98 (br s, 4 H), 2.30 (m, 1 H), 2.10 (m, 1 H), 2.02–1.97 (4 s's, 6 H), 1.84 (m, 1 H), 1.68 (m, 1 H). MS (ESI–): m/e 494 (M–H)$^-$.

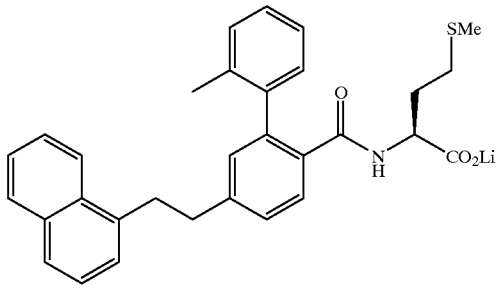

EXAMPLE 467

N-[4-(2-naphth-1-ylethyl)-2-(2-methylphenyl)benzoyl]methionine lithium salt

The desired compound was prepared according to the method of Examples 210–212. $^1$H nmr (300 MHz, MeOD-d$_4$): δ 8.08 (d, 1 H), 7.85 (dd, 1 H), 7.70 (d, 1 H), 7.63–7.38 (m, 4 H), 7.37–7.15 (m, 6 H), 7.05–6.83 (m, 2 H), 4.24 (m, 1 H), 3.42 (t, 2 H), 3.12 (t, 2 H), 2.27–2.05 (m, 2 H), 2.00 (br s, 6 H), 1.90–1.60 (m, 2 H). MS (ESI–): m/e 496 (M–H)$^-$.

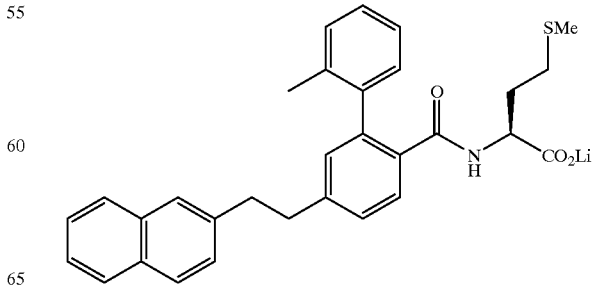

EXAMPLE 468

N-[4-(2-naphth-1-ylethyl)-2-(2-methylphenyl)benzoyl]methionine lithium salt

The desired compound was prepared according to the method of Examples 210–212. ¹H nmr (300 MHz, MeOD-$d_4$): δ 7.66 (m, 3 H), 7.45 (m, 2 H), 7.31 (m, 2 H), 7.24 (dd, 1 H), 7.20 (dd, 1 H), 7.13–7.00 (m, 4 H), 6.80 (br d, 1 H), 4.13 (m, 1 H), 3.01 (t, 4 H), 1.91,1.88,1.81 (3 br s's, 6 H), 1.95–1.48 (m, 4 H). MS (ESI-): m/e 496 (M-H)⁻.

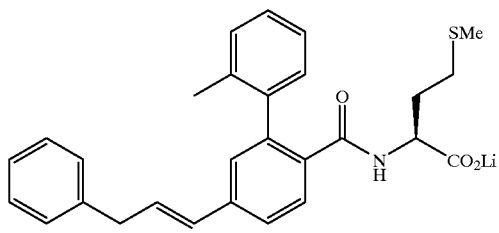

EXAMPLE 469

N-[4-(3-phenylprop-1-enyl)-2-(2-methylphenyl)benzoyl]methionine (1:1 mixture of olefin isomers)

The desired compound was prepared according to the method of Examples 210 and 211. ¹H nmr (300 MHz, CDCl₃): δ 8.00,7.96 (2 d's, from each of the isomers, 1 H), 7.48–7.08 (11 H), 6.52–6.30 (m, 2 H), 5.88 (m, 1 H), 4.56 (m, 1 H), 3.60 (2 d's, from each of the isomers, 2 H), 2.20–2.00 (m, 8 H), 1.90 (M, 1 H), 1.52 (m, 1 H). MS (CI+) m/e 460 (M+H)⁺.

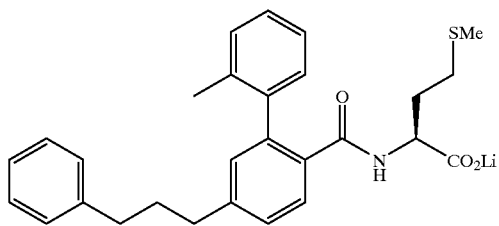

EXAMPLE 470

N-[4-(3-naphth-2-ylpropyl)-2-(2-methylphenyl)benzoyl]methionine lithium salt

The desired compound was prepared according to the method of Examples 210–212. ¹H nmr (300 MHz, MeOD-$d_4$): δ 7.68 (t, 1 H), 7.65 (t, 1 H), 7.51 (m, 2 H), 7.34–7.06 (m, 9 H), 6.93 (m, 1 H), 4.17 (m, 1 H), 2.73 (t, 2 H), 2.66 (t, 2 H), 1.96 (m, 1 H), 1.99 (m, 3 H), 1.97,1.89 (2 br s's, 6 H), 1.72 (m, 1 H), 1.53 (m, 1 H). MS (ESI-): m/e 510 (M-H)⁻.

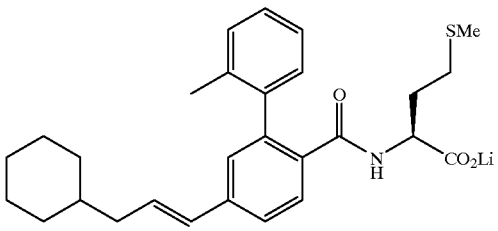

EXAMPLE 471

N-[4-(3-cyclohexylprop-1-enyl)-2-(2-methylphenyl)benzoyl]methionine lithium salt The desired compound was prepared according to the method of Examples 210 and 211. ¹H nmr (300 MHz, DMSO-$d_6$): δ 7.46 (m, 2 H), 7.25–7.09 (m, 6 H), 6.96 (m, 1 H), 6.40 (m, 1 H), 3.64 (m, 1 H), 3.18 (m, 2 H), 2.2–2.05 (m, 2 H), 2.03–1.92 (3 br s's, 6 H), 1.75–0.90 (m, 13 H). MS (ESI-): m/e 464 (M-H)⁻.

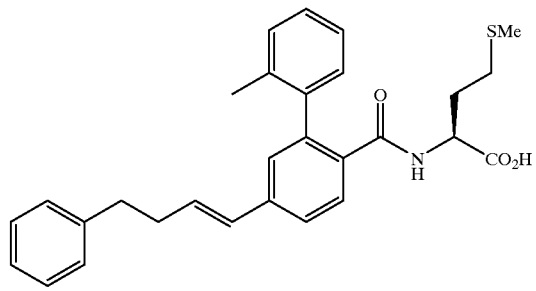

EXAMPLE 472

N-[4-(4-phenylbut-1-enyl)-2-(2-methylphenyl)benzoyl]methionine

The desired compound was prepared according to the method of Examples 210 and 211. ¹H nmr (300 MHz, CDCl₃): δ 7.98 (m, 1 H), 7.50–7.10 (m, 12 H), 6.41 (m, 1 H), 5.88 (m, 1 H), 4.57 (m, 1 H), 2.82 (m, 2 H), 2.57 (m, 2 H), 2.20–2.00 (m, 8 H), 1.92 (m, 1 H), 1.52 (m, 1 H). MS (CI+) m/e 474 (M+H)⁺.

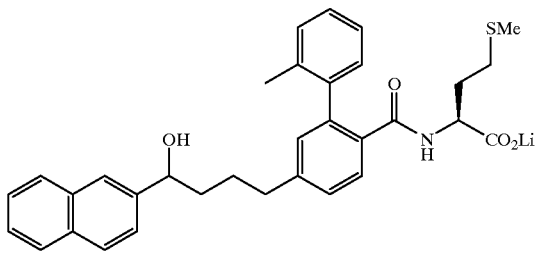

EXAMPLE 473

N-[4-(4-naphth-2-ylbut-4-on-1-yl)-2-(2-methylphenyl)benzoyl]methionine lithium salt The desired compound was prepared according to the method of Examples 210–212. ¹H nmr (300 MHz, DMSO-d$_6$): δ 8.61 (s, 1 H), 8.10 (br d, 1 H), 7.98 (m, 2 H), 7.63 (m, 2 H), 7.46 (m, 2 H), 7.31 (m, 1 H), 7.23–6.87 (m, 6 H), 3.44 (m, 1 H), 3.20 (m, 2 H), 2.75 (m, 2 H), 2.30–1.97 (m, 4 H), 1.95 (br s, 3 H), 1.91 (br s, 3 H), 1.90–1.56 (m, 2 H). MS (ESI–): m/e 538 (M–H)$^-$.

CDCl$_3$): δ 8.00 (tt, 1 H), 7.43 (dt, 1 H), 6.38–7.15 (m, 11 H), 6.39 (m, 1 H), 5.85 (m, 1 H), 4.52 (m, 1 H), 2.70 (m, 2 H), 2.19 (m, 1 H), 2.20–2.00 (4 s's, 6 H), 2.10 (m, 3 H), 1.90–1.50 (m, 4 H). MS (CI+): m/e 488 (M+H)$^+$.

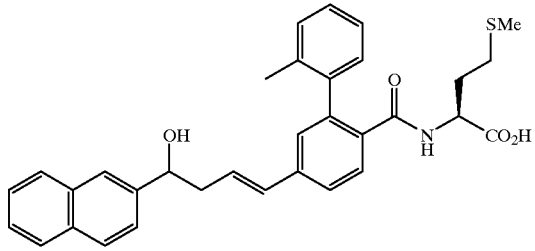

EXAMPLE 474

N-[4-(4-naphth-2-ylbut-4-ol-1-enyl)-2-(2-methylphenyl)benzoyl]methionine

The desired compound was prepared according to the method of Examples 210 and 211. $^1$H nmr (300 MHz, DMSO-d$_6$): δ 7.95–7.83 (m, 4 H), 7.56 (dd, 1 H), 7.48 (m, 3 H), 7.43 (m, 1 H), 7.25–7.08 (m, 5 H), 7.00–6.85 (m, 1 H), 6.45 (m, 1 H), 4.86 (t, 1 H), 3.64 (m, 1 H), 2.63 (br t, 2 H), 2.17 (m, 1 H), 1.98,1.91 (2 br s's, 6 H), 1.95 (m, 1 H), 1.90–1.56 (m, 2 H). MS (ESI–) m/e 538 (M–H)$^-$.

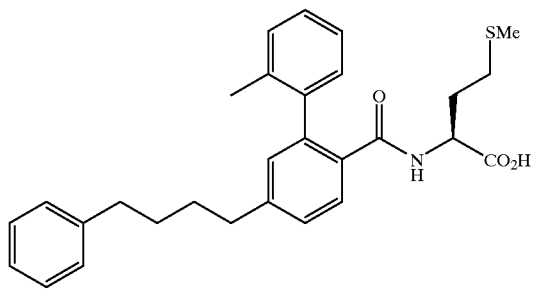

EXAMPLE 478

N-[4-(4-cyclohexylbutyl)-2-(2-methyphenyl)benzoyl]methionine sodium salt

The desired compound was prepared according to the method of Examples 210–212. $^1$H nmr (300 MHz, DMSO-d$_6$): δ 7.45 (d, 1 H), 7.27–7.10 (m, 5 H), 6.96 (m, 1 H), 6.89 (br s, 1 H), 3.67 (m, 1 H), 2.62 (t, 2 H), 2.15 (m, 1 H), 1.98,1.91 (2 br s's, 6 H), 1.97 (m, 1 H), 1.70–0.75 (m, 19 H). MS (ESI–): m/e 480 (M–H)$^-$.

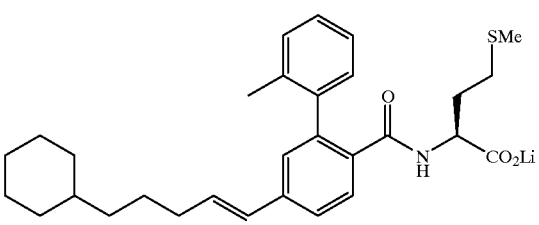

EXAMPLE 480

N-[4-(5-phenylpent-1-enyl)-2-(2-methylphenyl)benzoyl]methionine

The desired compound was prepared according to the method of Examples 210 and 211. $^1$H nmr (300 MHz,

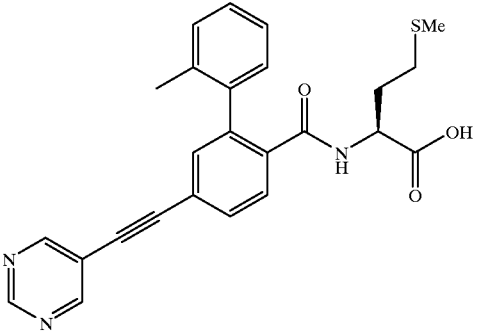

EXAMPLE 493

N-[4-(2-pyrimidin-5-ylethynyl)-2-(2-methylphenyl)benzoyl]methionine lithium salt The desired compound was prepared according to the method of Examples 210–211 $^1$H nmr (300 MHz, DMSO-d$_6$): δ 9.20 (s, 1 H), 9.04 (s, 2 H), 7.63 (m, 3 H), 7.42 (m, 1 H), 7.30–7.18 (m, 4 H), 7.16–7.00 (m, 2 H), 3.48 (m, 1 H), 2.18 (m, 1 H), 2.02 (m, 1 H), 1.92 (br s, 6 H), 1.70 (m, 1 H), 1.58 (m, 1 H).

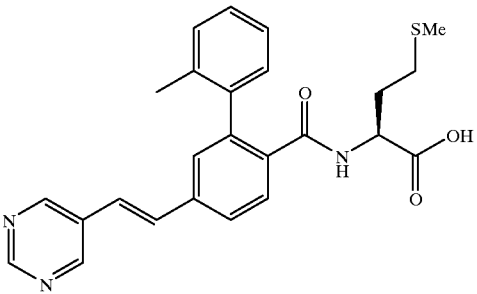

EXAMPLE 494

N-[4-(2-pyrimidin-5-ylethen-1-yl)-2-(2-methylphenyl)benzoyl]methionine lithium salt The desired compound was prepared according to the method of Examples 210–211 $^1$H nmr (300 MHz, DMSO-d$_6$): δ 9.06 (s, 1 H), 9.04 (s, 2 H), 7.67 (br d, 1 H), 7.00 (m, 2 H), 7.47 (m, 1 H), 7.38 (d, 1 H), 7.30–7.15 (m, 3 H), 7.10–6.97 (m, 2 H), 3.66 (m, 1 H), 2.20 (m, 1 H), 2.03 (m, 1 H), 1.92 (br s, 6 H), 1.70 (m, 1 H), 1.58 (m, 1 H). MS (ESI–): m/e 446 (M–H)$^-$.

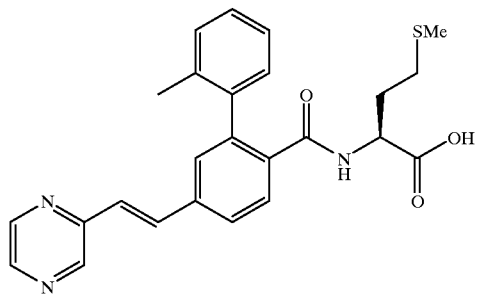

EXAMPLE 495

N-[4-(2-pyrazin-2-ylethen-1-yl)-2-(2-methylphenyl)benzoyl]methionine lithium salt The desired compound was prepared according to the method of Examples 210–211 $^1$H nmr (300 MHz, DMSO-$d_6$): δ 8.78 (s, 1 H), 8.63 (dd, 1 H), 8.51 (d, 1 H), 7.82 (d, 1 H), 7.76 (dd, 1 H), 7.59 (d, 1 H), 7.52 (m, 2 H), 7.30–7.10 (m, 4 H), 7.02 (m, 1 H), 3.68 (m, 1 H), 2.20 (m, 1 H), 2.03 (m, 1 H), 1.93 (br s, 16 H), 1.70 (m, 1 H), 1.58 (m, 1 H). MS (ESI-): m/e 446 (M–H)$^-$.

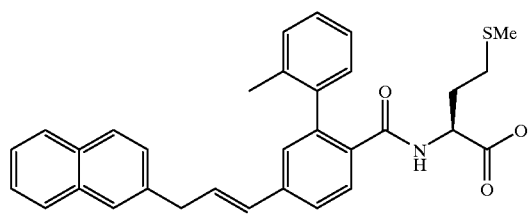

EXAMPLE 496

N-[4-(3-naphth-2-ylprop-1-enyl)-2-(2-methylphenyl)benzoyl]methionine lithium salt (1:1 mixture of olefin isomers)

The desired compound was prepared according to the method of Examples 210–211 $^1$H nmr (300 MHz, MeOD-$d_4$): δ 7.85–7.58 (m, 5 H), 7.51–7.36 (m, 4 H), 7.32–7.10 (m, 5 H), 6.61 (m, 1 H), 4.24 (m, 1 H), 3.72,3.67 (2 d's, 2 H, 1:1 ratio), 2.24 (m, 1 H), 2.08–1.95 (4 s's, 6 H), 1.99 (m, 1 H), 1.90–1.60 (m, 2 H). MS (ESI-) m/e 508 (M–H)$^-$.

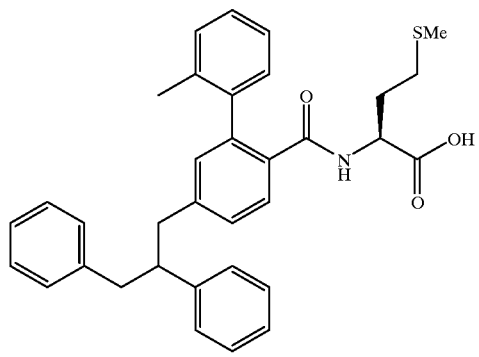

EXAMPLE 572

N-[4-(2,3-diphenylpropan-1-yl)-2-(2-methylphenyl)benzoyl]methionine lithium salt The desired compound was prepared according to the method of Examples 210–212 (DMSO-$d_6$) δ 7.38 (d,1H), 7.10, 6.90, 6.73 (all m, total 17H), 3.75 (m, 1H), 2.98 (m, 5H), 2.10–1.50 (envelope, 10H). MS (ESI) 536 (M–H)$^-$. Anal calcd for $C_{34}H_{34}LiNO_3S \cdot 0.25\ H_2O$: C, 74.50; H, 6.34; N, 2.56. Found: C, 7.10; H, 5.95; N, 2.53.

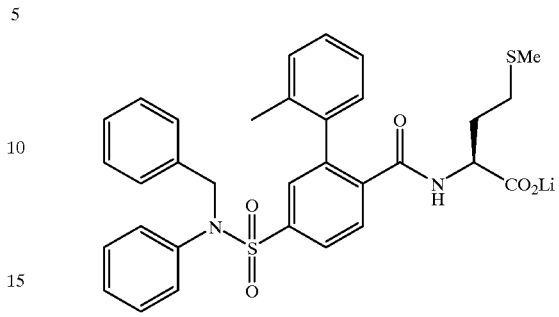

EXAMPLE 768

N-[4-(N-Benzyl-N-phenylaminosulfonyl)-2-(2-methylphenyl)benzoyl]methionine lithium salt The desired compound was prepared according to the method of Example 5E. $^1$H ($d_6$-DMSO): δ 7.7–7.9 (4H, m); 7.3–7.1 (13H, m); 4.84 (2H, s); 4.1 (1H, m) 3.2 (3H, s); 1.9 (3H, s); 2.1–1.6 (4H, m). ESI(-)/MS: 587 (M—Li)

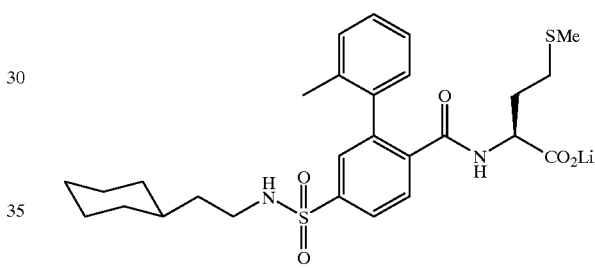

EXAMPLE 772

N-[4-(N-2-cyclohexylethylaminosulfonyl)-2-phenylbenzoyl]methionine lithium salt

The desired compound was prepared according to the method of Example 5E. $^1$H (CD$_3$OD): 7.85–7.9 (1H, d); 7.7–7.8 (1H, d); 7.6–7.7 (1H, s); 7.2–7.3 (4H, m); 4.2–4.3 (1H, m); 2.8–2.9 (2H, t); 2.05–2.1 (2H, m); 2.0 (3H, s); 1.9 (3H, s); 1.6–1.7 (6H, m) 1.1–1.4 (7H, m); 1.7–1.86 (2H, m). ESI(-)/MS: 521(M—Li); 487, 459.

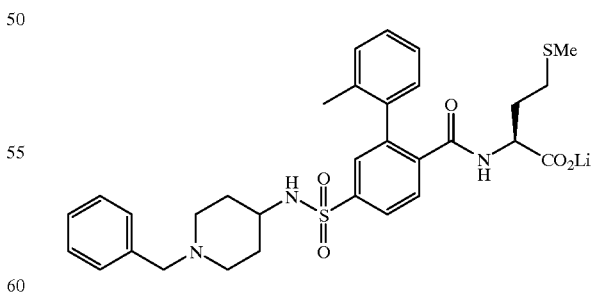

EXAMPLE 773

N-[4-(1-Benzylpiperidin-4-ylaminosulfonyl)-2-phenylbenzoyl]methionine lithium salt The desired compound was prepared according to the method of Example 5E. $^1$H (CD$_3$OD): 7.82–7.94 (1H, d);

7.75–7.81 (1H, d); 7.62–7.72 (1H, s); 7.1–7.38 (9H, m); 4.2–4.3 (1H, m); 3.1(2H, s); 3.0–3.1 (1H, m); 2.7–2.8 (2H, d); 2.42–2.54 (2H, t); 1.78–2.3 (11H, m); 1.6–1.78 (3H, m); 1.4–1.6 (2H, m). ESI(-)/MS: 594(M—Li).

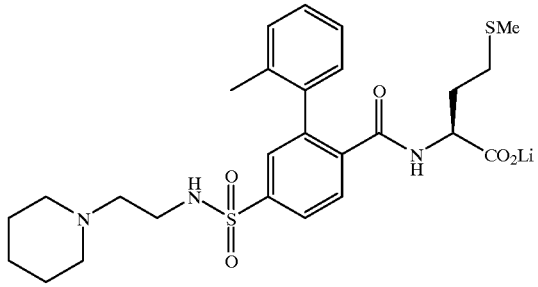

EXAMPLE 774

N-[4-N-(2-piperidin-1ylethyl-2aminosulfonyl)-2-phenylbenzoyl]methionine lithium salt The desired compound was prepared according to the method of Example 5E. $^1$H CD$_3$OD): 7.82–7.94 (1H, d); 7.75–7.81 (1H, d); 7.62–7.72 (1H, s); 7.1–7.38 (4H, m); 4.18–4.3 (1H, m); 3.1(2H, m); 2.34–2.5 (5H, m); 2.2–2.35 (2H, m); 2.05–2.2 (2H; m); 1.93–2.05 (3H, s); 1.8–1.95 (4H, m); 1.6–1.7 (2H, m); 1.55–1.6 (3H, m); 1.4–1.5 (2H, m). ESI(-)/MS: 532 (M—Li); 488; 357.

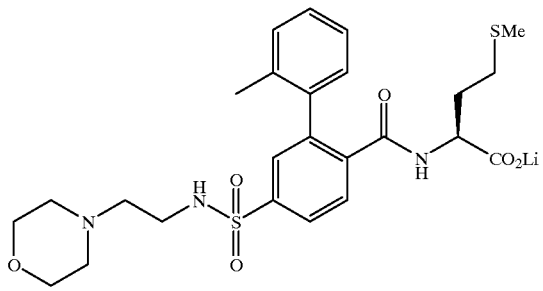

EXAMPLE 775

N-[4-N-(2-moipholin-1ylethyl)aminosulfonyl)-2-phenylbenzoyl]methionine lithium salt The desired compound was prepared according to the method of Example 5E. $^1$H (CD$_3$OD): 7.9–8.1 (1H, d); 7.8–7.9 (1H, d); 7.67–7.8 (1H, s); 7.1–7.4 (4H, m); 4.2–4.3 (1H, m); 3.4–3.7 (4H, m); 3.4–3.2 (4H, m); 2.9–3.2 (2H, t); 1.6–2.6 (12H, m) ESI(-)/MS: 534(M—Li); 490; 462.

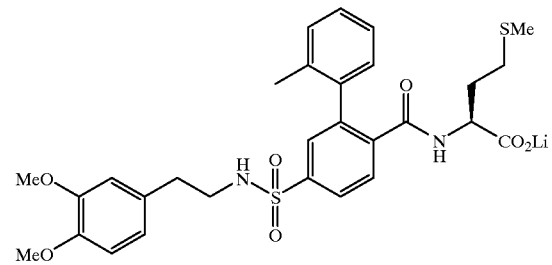

EXAMPLE 776

N-[4-(2-(3,4-dimethoxyphenyl)ethylaminosulfonyl)-2-phenylbenzoyl]methionine lithium salt The desired compound was prepared according to the method of Example 5E. $^1$H(MeOH-d$_4$): δ 7.78–7.9 (2H, m); 7.62–7.7 (1H, s); 7.1–7.3 (4H, m); 6.78–6.82 (1H, d); 6.72–6.78 (1H, d); 6.65–6.72 (1H, q); 4.2–4.3 (1H, m); 3.75–3.8 (6H, s); 3.08–3.18 (2H, m); 2.58–2.7 (2H, t); 1.6–2.26 (10H, m). ESI(-)/MS: 585(M—Li); 541; 410.

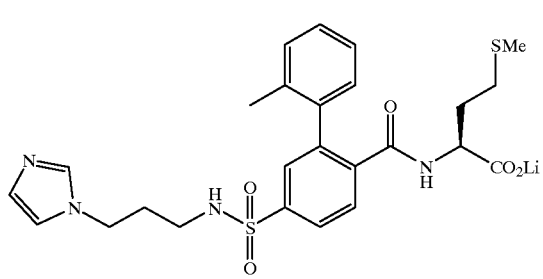

EXAMPLE 777

N-[4-(3-imidazol-1-ylpropylaminosulfonyl)-2-phenylbenzoyl]methionine lithium salt The desired compound was prepared according to the method of Example 5E. $^1$H(MeOH-d$_4$): δ 7.78–7.9 (2H, dd); 7.5–7.6 (2H, m); 7.1–7.3 (4H, m); 7.1 (1H, s); 6.92 (1H, s); 4.2–4.3 (1H, m); 4.05–4.18 (2H, t); 2.8–2.9 (2H, t); 1.6–2.3 (12H, m). ESI(-)/MS: 529(M—Li); 281; 255.

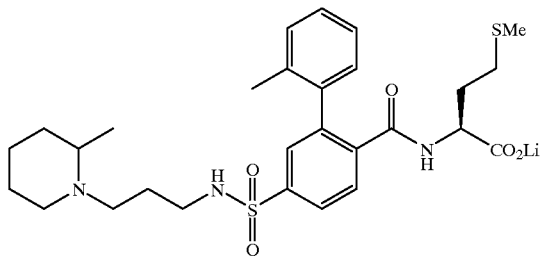

EXAMPLE 778

N-[4-(3-(2-methylpiperidin-1-yl)propylaminosulfonyl)-2-phenylbenzoyl]methionine lithium salt The desired compound was prepared according to the method of Example 5E. $^1$H(MeOH-d$_4$): δ 7.8–7.94(2H, dd);

7.6–7.7 (1H, s); 7.1–7.4 (4H, m); 4.2–4.3 (1H, m); 2.84–2.94 (2H, t); 2.7–2.87 (2H, m); 1.8–2.5 (13H, m); 1.4–1.8 (6H, m); 1.24–1.349 (2H, m); 1.0–1.1 (3H, m). ESI(−)/MS: 560(M—Li); 385; 281.

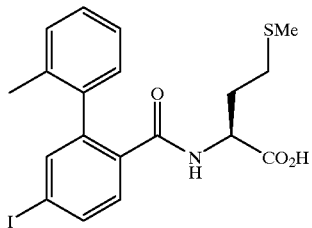

EXAMPLE 783

N-[4-iodo-2-(2-methylphenyl)benzoyl]methionine

The desired compound was prepared according to the method of Example 210C. $^1$H nmr (300 MHz, CDCl$_3$): δ 7.83 (dd, 1 H), 7.72 (dd, 1 H), 7.60 (s, 1 H), 7.39–7.16 (m, 4 H), 5.89 (m, 1 H), 4.58 (m, 1 H), 2.20–2.00 (m, 8 H), 1.96 (m, 1 H), 1.58 (m, 1 H). MS (CI+) m/e 452 (M+H)$^+$.

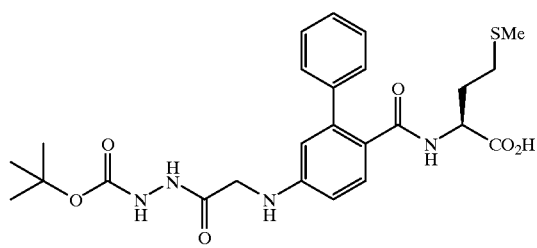

EXAMPLE 784

N-[4-N(t-Butylcarbazatocarbonylmethyl)amino-2-phenylbenzoyl]methionine

The desired compound was prepared according to the method of Example 57, except t-Butylcarbazatocarbonylmethyl bromide was used as the alkylating agent. $^1$H nmr (300 MHz, DMSO-d$_6$): δ 9.79 (s, 1 H), 8.85 (s, 1 H), 8.12 (d, 1 H), 7.47–7.29 (m, 6 H), 6.65 (br d, 1 H), 6.56 (d, 1 H), 6.43 (t, 1 H), 4.30 (m, 1 H), 3.81 (d, 2 H), 2.32 (m, 2 H), 2.05 (br s, 6 H), 1.90 (m, 2 H), 1.47 (s, 9 H). MS (APCI+) m/e 517 (M+H)$^+$.

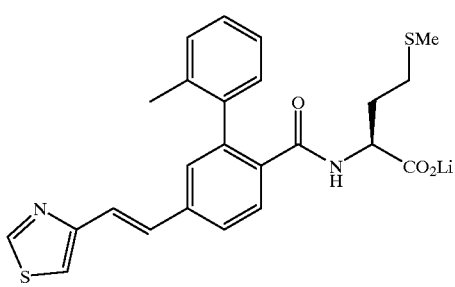

EXAMPLE 785

N-[4-(2-(thiazol-5-yl)ethen-1-yl)-2-(2-methylphenyl)benzoyl]methionine lithium salt The desired compound was prepared according to the method of Examples 210–211. $^1$H nmr (300 MHz, DMSO-d$_6$): δ 9.01 (s, 1 H), 7.98 (s, 1 H), 7.67 (d, 1 H), 7.63 (m, 1 H), 7.55 (d,1 H), 7.42 (m, 1 H), 7.30–7.15 (m, 4 H), 3.65 (m, 1 H), 2.18 (m, 2 H), 2.02 (br s, 3 H), 1.92 (br s, 3 H), 1.70 (m, 1 H), 1.58 (m, 1 H). MS (ESI−): m/e 451 (M−H)$^−$.

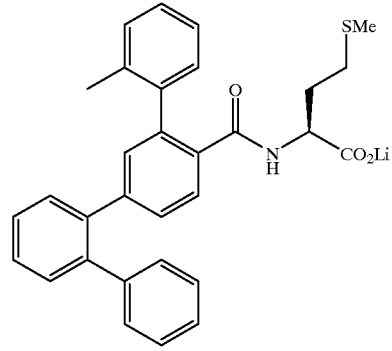

EXAMPLE 786

N-[4-(2-phenylphenyl)-2-(2-methylphenyl)benzoyl]methionine lithium salt

The desired compound was prepared according to the method of Examples 210–211. $^1$H nmr (300 MHz, DMSO-d$_6$): δ 7.96 (s, 1 H), 7.83 (d, 1 H), 7.77 (d, 2 H), 7.74 (d, 1 H), 7.66 (t, 2 H), 7.56 (t, 2 H), 7.48 (t, 2 H), 7.38 (t, 1 H), 7.24 (m, 3 H), 7.02 (m, 1 H), 3.66 (m, 1 H), 2.22 (m, 2 H), 2.05 (br s, 3 H), 1.93 (br s, 3 H), 1.77 (m, 1 H), 1.58 (m, 1 H). MS (ESI−): m/e 494 (M−H)$^−$.

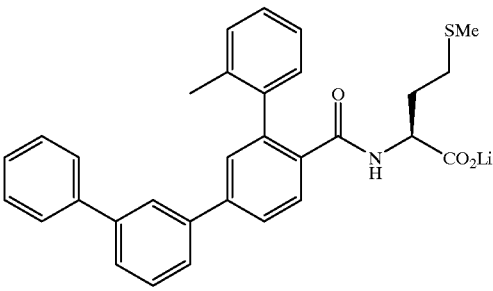

EXAMPLE 787

N-[4-(3-phenylphenyl)-2-(2-methylphenyl)benzoyl]methionine lithium salt

The desired compound was prepared according to the method of Examples 210–211. $^1$H nmr (300 MHz, DMSO-d$_6$): δ 7.7.54–7.44 (m, 4 H), 7.51 (m, 1 H), 7.38 (m, 1 H), 7.34–7.22 (m, 3 H), 7.19–7.00 (m, 5 H), 6.90–6.85 (m, 2 H), 6.66 (m, 1 H), 3:62 (m, 1 H), 2.22 (m, 2 H), 2.05 (br s, 3 H), 1.93 (br s, 3 H), 1.77 (m, 1 H), 1.58 (m, 1 H). MS (ESI−): m/e 494 (M−H)$^−$.

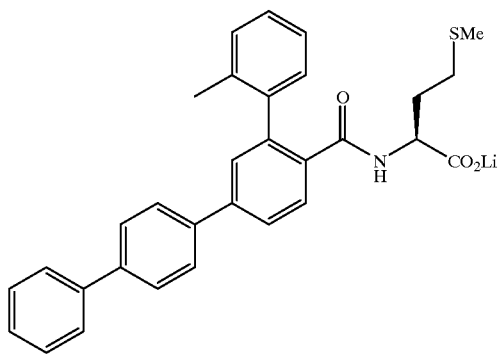

EXAMPLE 788

N-[4-(4-phenylphenyl)-2-(2-methylphenyl)benzoyl]methionine lithium salt

The desired compound was prepared according to the method of Examples 210–211. $^1$H nmr (300 MHz, DMSO-$d_6$): δ 7.87–7.80 (m, 3 H), 7.78 (t, 2 H), 7.73 (d, 2 H), 7.65 (d, 1 H), 7.49 (m, 3 H), 7.39 (m, 1 H), 7.33–7.15 (m, 4 H), 7.02 (m, 1 H), 3.66 (m, 1 H), 2.22 (m, 2 H), 2.05 (br s, 3 H), 1.93 (br s, 3 H), 1.77 (m, 1 H), 1.58 (m, 1 H). MS (ESI–): m/e 494 (M–H)$^-$.

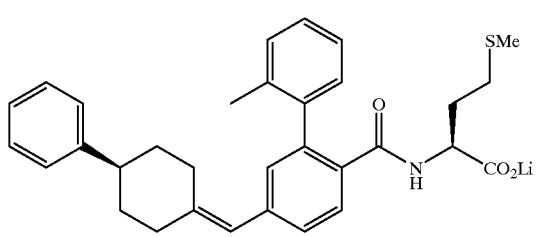

EXAMPLE 789

N-[4-(4-phenylcyclohexylidenyl)-2-(2-methylphenyl)benzoyl]methionine lithium salt The desired compound was prepared according to the method of Examples 210–211. $^1$H nmr (300 MHz, CD$_3$OD): δ 7.56 (m, 1 H), 7.25–6.94 (m, 10 H), 6.27 (s, 1 H), 4.16 (m, 1 H), 2.60 (m, 1 H), 2.40 (m, 2 H), 2.17 (m, 2 H), 2.00–1.70 (m, 13 H), 1.58 (m, 1 H). MS (ESI–): m/e 522 (M–H)$^-$.

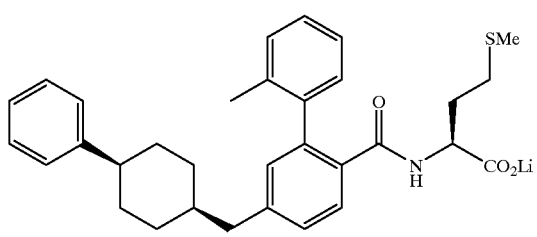

EXAMPLE 790

N-[4-syn-(4-phenylcyclohexylmethyl)-2-(2-methylphenyl)benzoyl]methionine lithium salt The desired compound was prepared according to the method of Examples 210–212. $^1$H nmr (300 MHz, CD$_3$OD):

δ 7.53 (m, 2 H), 7.22–6.92 (m, 10 H), 4.15 (m, 1 H), 2.73 (br d, 2 H), 2.52 (m, 1 H), 2.15 (m, 2 H), 2.02–1.90 (m, 6 H), 1.75 (m, 5 H), 1.57 (m, 5 H). MS (ESI–): m/e 514 (M–H)$^-$.

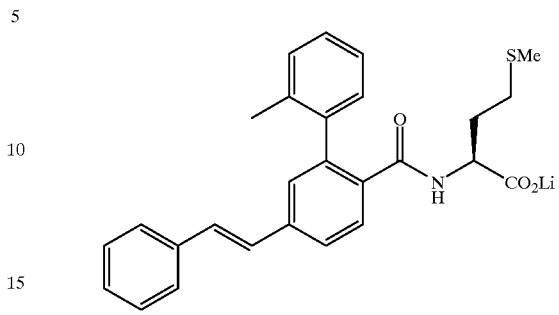

EXAMPLE 791

N-[4-(2-phenylethen-1-yl)-2-(2-methylphenyl)benzoyl]methionine

The desired compound was prepared according to the method of Examples 210–211. $^1$H nmr (300 MHz, CDCl$_3$): δ 8.03 (dd, 1 H), 7.61 (dd, 1 H), 7.52 (m, 2 H), 7.40–7.22 (m, 8 H), 7.20 (d, 1 H), 7.10 (d, 1 H), 5.93 (m, 1 H), 4.59 (m, 1 H), 2.20–2.00 (m, 8 H), 1.96 (m, 1 H), 1.56 (m, 1 H). MS (CI+) m/e 446 (M+H)$^+$.

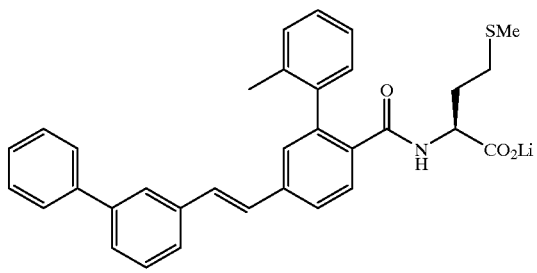

EXAMPLE 792

N-[4-(2-(3-phenylphenyl)ethen-1-yl)-2-(2-methylphenyl)benzoyl]methionine lithium salt The desired compound was prepared according to the method of Examples 210–211. $^1$H nmr (300 MHz, CD$_3$OD): δ 7.83–7.10 (m, 18 H), 4.27 (m, 1 H), 2.30 (m, 1 H), 2.15–1.95 (m, 8 H), 1,88 (m, 1 H), 1.69 (m, 1 H). MS (ESI–): m/e 520 (M–H)$^-$.

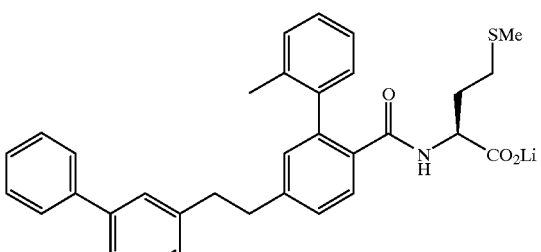

EXAMPLE 793

N-[4-(2-(3-phenylphenyl)ethyl)-2-(2-methylphenyl)benzoyl]methionine lithium salt The desired compound was prepared according to the method of Examples 210–212. $^1$H nmr (300 MHz, CD$_3$OD):

δ 7.60 (br d, 1 H), 7.51 (br d, 2 H), 7.45–7.20 (m, 12 H), 6.98 (m, 1 H), 4.23 (m, 1 H), 3.04 (br s, 4 H), 2.12 (m, 2 H), 2.03–1.91 (m, 6 H), 1.83 (m, 1 H), 1.65 (m, 1 H). MS (ESI–): m/e 522 (M–H)⁻.

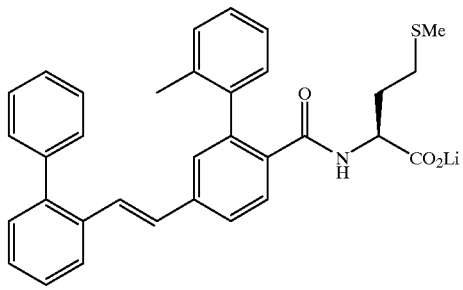

EXAMPLE 794

N-[4-(2-(3-phenylphenyl)ethen-1-yl)-2-(2-methylphenyl)benzoyl]methionine lithium salt The desired compound was prepared according to the method of Examples 210–211. ¹H nmr (300 MHz, DMSO-$d_6$): δ 7.85 (dd, 1 H), 7.54–7.30 (m, 9 H), 7.30–7.10 (m, 6 H), 7.10 (d, 1 H), 6.95 (m, 1 H), 3.67 (m, 1 H), 2.16 (m, 2 H), 2.02 (br s, 3 H), 1.91 (br s, 3 H), 1.70 (m, 1 H), 1.57 (m, 1 H). MS (ESI–): m/e 521 (M–H)⁻.

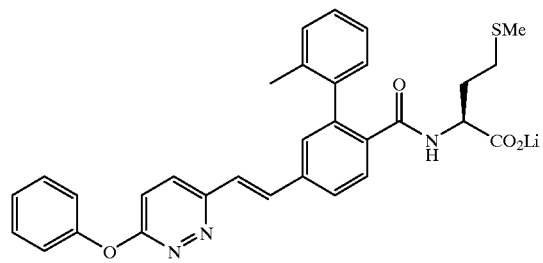

EXAMPLE 810

N-[4-(2-(3-phenoxypyridazin-6-yl)ethen-1-yl)-2-(2-methylphenyl)benzoyl]methionine lithium salt The desired compound was prepared according to the method of Examples 210–211. ¹H nmr (300 MHz, DMSO-$d_6$): δ 8.08 (d, 1 H), 7.76 (dd, 1 H), 7.59 (d, 1 H), 7.52 (d, 1 H), 7.52–7.43 (m, 4 H), 7.31–7.10 (m, 7 H), 7.00 (m, 1 H), 2.18 (m, 1 H), 2.02 (m, 1 H), 1.92 (br s, 6 H), 1.70 (m, 1 H), 1.58 (m, 1 H). MS (ESI–): m/e 538 (M–H)⁻.

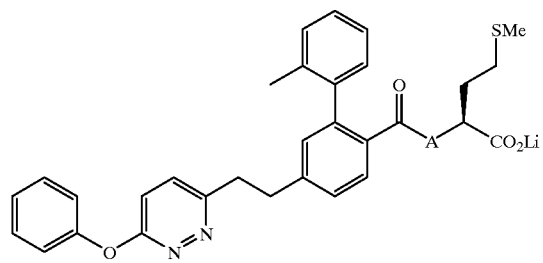

EXAMPLE 811

N-[4-(2-(3-phenoxylyridazin-6-yl)ethyl)-2-(2-methylphenyl)benzoyl]methionine lithium salt The desired compound was prepared according to the method of Examples 210–211. ¹H nmr (300 MHz, DMSO-$d_6$): δ 7.65 (d, 1 H), 7.46 (d, 1 H), 7.44 (d, 1 H), 7.38–7.10 (m, 9 H), 6.94 (m, 1 H), 6.88 (m, 1 H), 6.75 (m, 1 H), 3.65 (m, 1 H), 3.19 (t, 2 H), 3.07 (t, 2 H), 2.18 (m, 1 H), 2.02 (m, 1 H), 1.92 (br s, 6 H), 1.70 (m, 1 H), 1.58 (m, 1 H). MS (ESI–): m/e 540 (M–H)⁻.

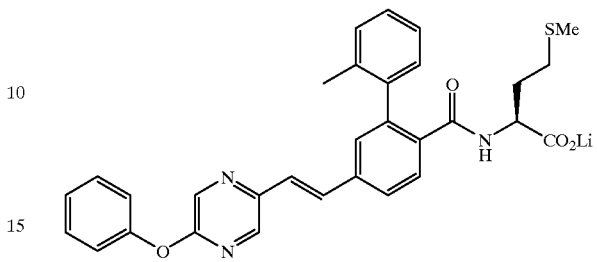

EXAMPLE 812

N-[4-(2-(2-phenoxypyridazin-5-yl)ethen-1-yl)-2-(2-methylphenyl)benzoyl]methionine lithium salt The desired compound was prepared according to the method of Examples 210–211. ¹H nmr (300 MHz, DMSO-$d_6$): δ 8.51 (s, 1 H), 8.33 (s, 1 H), 7.64 (m, 1 H), 7.53–7.38 (m, 6 H), 7.30–7.15 (m, 7 H), 7.00 (m, 1 H), 3.65 (m, 1 H), 2.18 (m, 1 H), 2.02 (m, 1 H), 1.92 (br s, 6 H), 1.70 (m, 1 H), 1.58 (m, 1 H). MS (ESI–): m/e 538 (M–H)⁻.

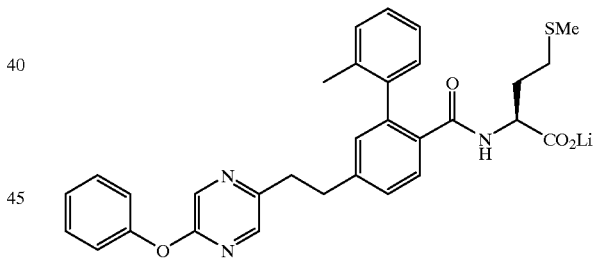

EXAMPLE 813

N-[4-(2-(2-phenoxypyridazin-5-yl)ethyl)-2-(2-methylphenyl)benzoyl]methionine lithium salt The desired compound was prepared according to the method of Examples 210–212. ¹H nmr (300 MHz, DMSO-$d_6$): δ 8.26 (s, 1 H), 8.21 (s, 1 H), 7.50–7.30 (m, 6 H), 7.30–7.10 (m, 5 H), 7.00 (m, 1 H), 3.65 (m, 1 H), 2.97 (m, 4 H), 2.18 (m, 1 H), 2.02 (m, 1 H), 1.92 (br s, 6 H), 1.70 (m, 1 H), 1.58 (m, 1 H). MS (ESI–): m/e 540 (M–H)⁻.

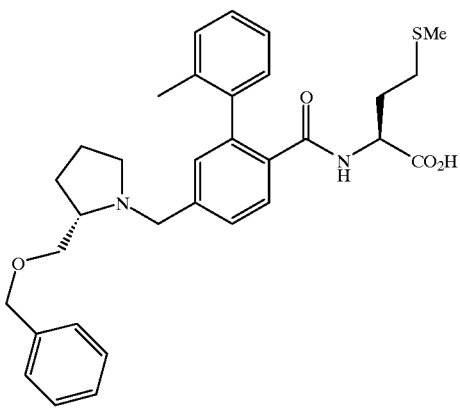

EXAMPLE 824

N-[4-(2-benzyloxymethylpyrrolidin-1-ylmethyl)-2-(2-methylphenyl)benzoyl]methionine The desired compound was prepared according to the method of Example 157. $^1$H nmr (300 MHz, DMSO d$_6$): δ 8.13, d, 1H; 7.47, d, 1H; 7.37, d, 1H; 7.13–7.32, m, 10H; 4.48, s, 2H; 4.21, m 2H; 3.51, m, 2H; 3.38, m, 2H; 2.89, m, 2H; 1.99–2.40 m, 7H; 1.98, s, 3H; 1.50–1.96, m, 4H. MS (ESI(-)): 545 (M−H); (ESI(+)): 547. Calc'd for C$_{32}$H$_{38}$N$_2$O$_4$S+0.70 H$_2$O: C, 68.72, H, 7.10, N, 5.01: Found: C, 68.71, H, 6.6,88, N, 4.92.

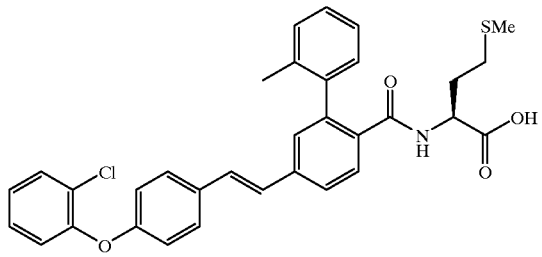

EXAMPLE 854

N-[4-(2-(4-(2-chlorophenoxy)phenyl)ethen-1-yl)-2-(2-methylphenyl)benzovyl]methionine The desired compound was prepared according to the method of Examples 210–211. MS m/e 570 (M−H)$^-$. $^1$H NMR (CDCl$_3$, 300 MHz) δ 1.58 (m, 1H), 1.95 (m, 1H), 2.1 (m, 8H), 4.59 (m, 1H), 5.91 (m, 1H), 6.91–7.62 (m, 16H), 8.03 (m, 1H).

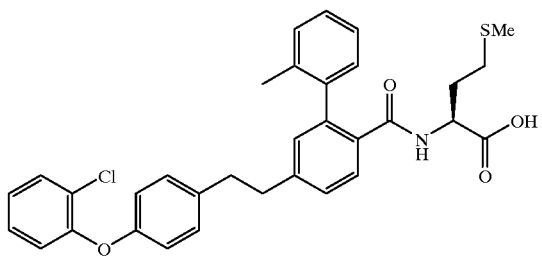

EXAMPLE 855

N-[4-(2-(4-(2-chlorophenoxy)phenyl)ethyl)-2-(2-methylphenyl)benzoyl]methionine

The desired compound was prepared according to the method of Examples 210–211. MS m/e 574 (M+H)$^+$. $^1$H NMR (CDCl$_3$, 300 MHz) δ 1.53 (m, 1H), 1.93 (m, 1H), 2.1 (m, 8H), 2.95 (m, 4H), 4.59 (m, 1H), 5.83 (m, 1H), 6.83–7.50 (m, 14H), 7.97 (m, 1H).

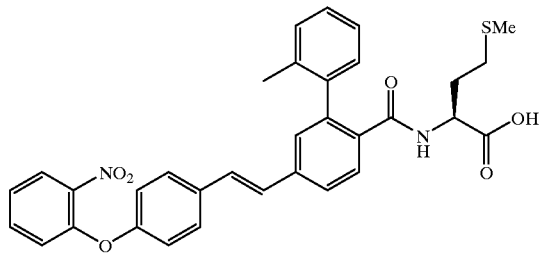

EXAMPLE 856

N-[4-(2-(4-(2-nitrophenoxy)phenyl)ethen-1-yl)-2-(2-methylphenyl)benzoyl]methionine The desired compound was prepared according to the method of Examples 210–211. MS m/e 583 (M+H)$^+$. $^1$H NMR (CDCl$_3$, 300 MHz) δ 1.57 (m, 1H), 1.93 (m, 1H), 2.1 (m, 8H), 4.58 (m, 1H), 5.90 (m, 1H), 6.65 (m, 2H), 6.90–7.50 (m, 14H), 7.96 (m, 1H).

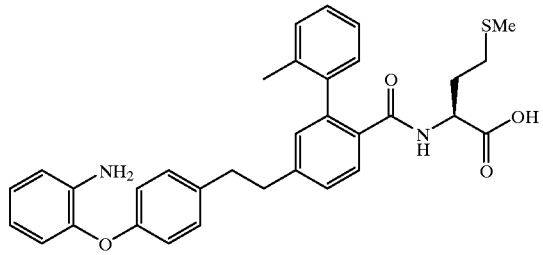

EXAMPLE 857

N-[4-(2-(4-(2-aminophenoxy)phenyl)ethyl)-2-(2-methylphenyl)benzoyl]methionine

The title compound was prepared in an analogous manner Example 212 except that the final compound was extracted out of pH 7 buffer after the final hydrolysis. MS m/e 555 (M+H)$^+$. $^1$H NMR (CDCl$_3$, 300 MHz) δ 1.49 (m, 1H), 1.91 (m, 1H), 2.1 (m, 8H), 2.95 (m, 4H), 4.56 (m, 1H), 5.84 (m, 1H), 6.68–7.38 (m, 14H), 7.97 (m, 1H).

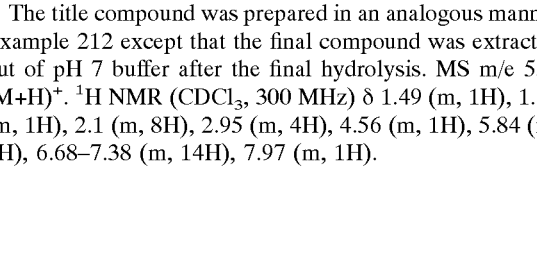

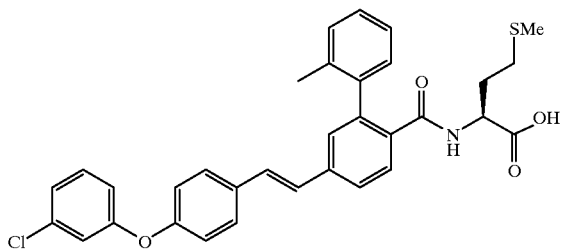

EXAMPLE 858

N-[4-(2-(4-(3-chlorophenoxy)phenyl)ethen-1-yl)-2-(2-methylphenyl)benzoyl]methionine The desired compound was prepared according to the method of Examples 210–211. MS m/e 570 (M–H)⁻. $^1$H NMR (CDCl$_3$, 300 MHz) δ 1.57 (m, 1H), 1.95 (m, 1H), 2.1 (m, 8H), 4.59 (m, 1H), 5.91 (m, 1H), 6.91–7.62 (m, 16H), 8.04 (m, 1H).

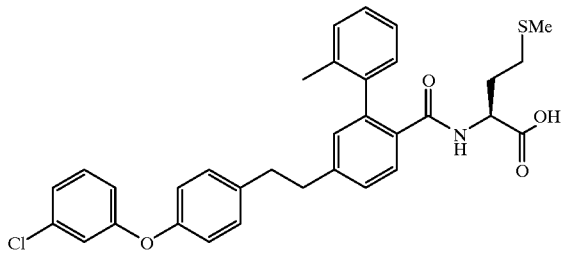

EXAMPLE 859

N-[4-(2-(4-(3-chlorophenoxy)phenyl)ethyl)-2-(2-methylphenyl)benzoyl]methionine

The desired compound was prepared according to the method of Examples 210–212. MS m/e 572 (M–H)⁻. $^1$H NMR (CDCl$_3$, 300 MHz) δ 1.49 (m, 1H), 1.93 (m, 1H), 2.1 (m, 8H), 2.97 (m, 4H), 4.55 (m, 1H), 5.84 (m, 1H), 6.81–7.37 (m, 14H), 7.98 (m, 1H).

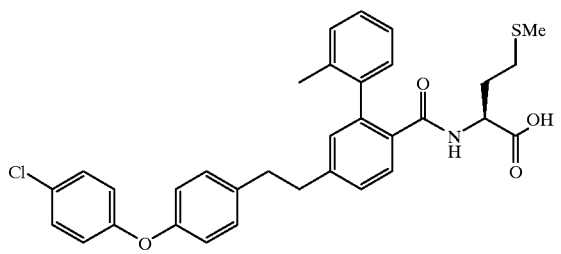

EXAMPLE 860

N-[4-(2-(4-(4-chlorophenoxy)phenyl)ethyl)-2-(2-methylphenyl)benzoyl]methionine

The desired compound was prepared according to the method of Examples 210–212. MS m/e 574 (M+H)⁺. $^1$H NMR (d$_6$-DMSO, 300 MHz) δ 1.75 (m, 2H), 1.94 (m, 6H), 2.06 (m, 2H), 2.94 (m, 4H), 4.13 (m, 1H), 6.92–7.48 (m, 12H), 7.66 (m, 2H), 7.97 (m, 1H).

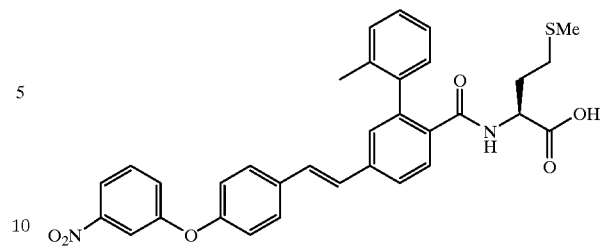

EXAMPLE 861

N-[4-(2-(4-(3-nitrophenoxy)phenyl)ethen-1-yl)-2-(2-methylphenyl)benzoyl]methioziine The desired compound was prepared according to the method of Examples 210–211. MS m/e 583 (M+H)⁺. $^1$H NMR (CDCl$_3$, 300 MHz) δ 1.54 (m, 1H), 1.92 (m, 1H), 2.1 (m, 8H), 4.58 (m, 1H), 5.91 (m, 1H), 6.7–7.6 (m, 16H), 8.02 (m, 1H).

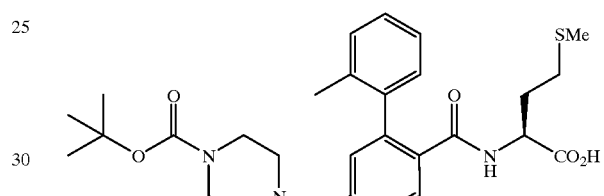

EXAMPLE 866

N-[4-(4-t-butoxycarbonylpiperazin-1-ylmethyl)-2-(2-methylphenyl)benzoyl]methionine The desired compound was prepared according to the method of Example 158. $^1$H NMR (CDCl$_3$, 300 MHz) δ 1.45 (s, 9H), 1.60 (m, 1H), 1.82 (m, 1H), 2.05 (m, 8H), 2.53 (m, 4H), 3.46 (m, 4H), 3.62 (m, 2H), 4.38 (m, 1H), 6.00 (m, 1H), 7.10–7.50 (m, 6H), 7.86 (m, 1H). MS m/e 540 (M–H)⁻.

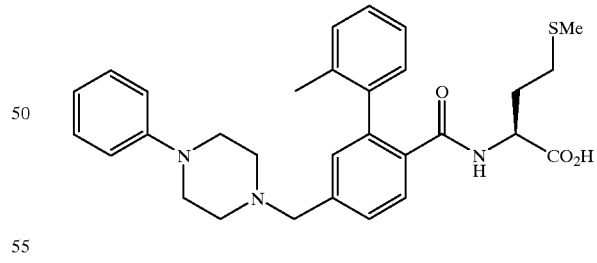

EXAMPLE 867

N-[4-(4-phenylpiperazin-1-ylmethyl)-2-(2-methylphenyl)benzoyl]methionine

The desired compound was prepared according to the method of Example 158. $^1$H NMR (CDCl$_3$, 300 MHz) δ 1.47 (m, 1H), 1.82 (m, 1H), 2.0 (m, 8H), 2.75 (m, 4H), 3.21 (m, 4H), 3.65 (m, 2H), 4.30 (m, 1H), 6.11 (m, 1H), 6.89 (m, 2H), 7.22 (m, 8H), 7.40 (m, 1H), 7.82 (m, 1H). MS m/e 516 (M–H)⁻.

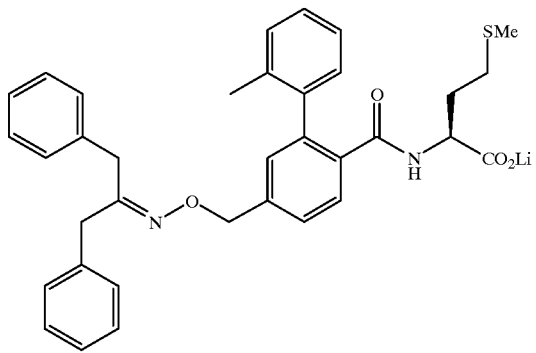

EXAMPLE 888

N-[4-N-(1,3-Diphenylpropan-2-yl)iminooxymethyl-2-(2-methylphenyl)benzoyl]-methionine lithium salt The desired compound was prepared according to the method of Example 157. $^1$H NMR (300 MHz, DMSO) δ 1.50–1.62 (m, 1H), 1.63–1.76 (m, 1H), 1.92 (s, 3H), 1.95–2.15 (m, 5H), 3.38 (s, 2H), 3.53 (s, 2H), 3.69 (brs, 1H), 5.18 (s, 2H), 6.98 (d, J=6.4 Hz, 1H), 7.04–7.28 (m, 15H), 7.36 (dd, J=7.8, 1.7 Hz, 1H), 7.52 (d, J=7.8 Hz, 1H). MS (ESI) m/z 587 (M+H); Analysis calc'd for $C_{35}H_{35}LiN_2O_4S \cdot 1.0H_2O$: C, 69.52; H, 6.17; N, 4.63; found: C, 69.47; H, 6.09; N, 4.58.

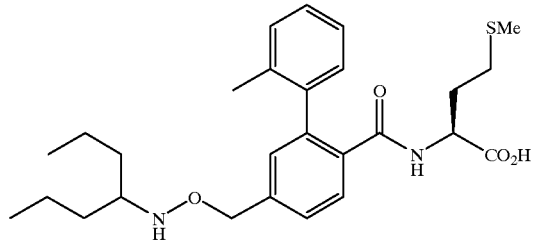

EXAMPLE 929

N-[4-(N-Hept-4-ylaminooxymethyl)-2-(2-methylphenyl)benzoyl]methionine

The desired compound was prepared according to the method of Example 157 $^1$H (300 MHz, DMSO-d6, δ) 7.52 (1H, d, J=8 Hz), 7.37 (1H, dd, J=9&2 Hz), 7.30–7.10 (4H, m), 7.10 (1H, bs), 6.97 (1H, m), 6.33 (1H, bd, J=10 Hz), 4.63 (2H, s), 3.68 (1H, m), 2.74 (1H, m), 2.20–1.95 (3H, m), 1.92 (3H, s), 1.90–1.40 (4H, m), 1.40–1.20 (8H, m), 0.83 (6H, t, J=8 Hz). m/z (ESI) 485 (MH$^-$) Anal.calc. for $C_{27}H_{37}LiN_2O_4S \cdot 0.25 H_2O$ C, 65.24, H, 7.60, N, 5.64 Found C, 65.14, H, 7.81, N, 5.33

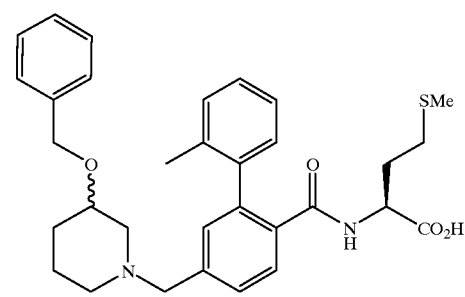

EXAMPLE 988

N-[4-(3-benzyloxypyrrolidin-1-ylmethyl)-2-(2-methylphenyl)benzoyl]methionine

The desired compound was prepared according to the method of Example 158 $^1$H nmr (300 MHz, DMSO d$_6$): δ 8.08, d, 1H; 7.47, d, 1H; 7.37, dd, 1H; 7.29, m, 5H; 7.20, m, 2H; 7.14, m, 3H; 4.40, q (AA'), 2H; 4.21, m, 1H; 4.11, m, 1H; 3.68, q (AA'), 2H; 2.41–2.76, m, 4H; 1.98–2.23, m, 6H; 1.97, s, 3H; 1.64–1.93, m, 3H. MS (ESI(–)): 531 (M–H); (ESI(+)): 533. Calc'd for $C_{31}H_{36}N_2O_4S$: C, 69.90, H, 6.81, N, 5.26: Found: C, 69.21, H, 6.86, N, 5.06

EXAMPLE 989

N-[4-(3-benzyloxypiperidin-1-ylmethyl)-2-(2-methylphenyl)benzoyl]methionine

The desired compound was prepared according to the method of Example 158 $^1$H nmr (300 MHz, DMSO d$_6$): δ 8.09, d, 1H; 7.49, d, 1H; 7.37, dd, 1H; 7.23–7.34, m, 5H; 7.22, m, 2H; 7.12, m, 3H; 4.48, s, 2H; 4.23, ddd, 1H; 3.60, m, 2H; 3.46, m, 1H; 3.30, m, 2H; 2.95, m, 1H; 2.64, m, 1H; 2.00–2.24, m, 6H; 1.98, s, 3H; 1.63–1.96, m, 3H; 1.42, m, 1H; 1.22, m, 1H. MS (ESI(–)): 545 (M–H); (ESI(+)): 547. Calc'd for $C_{32}H_{38}N_2O_4S + 0.37 H_2O$: C, 69.46, H, 7.06, N, 5.06: Found: C, 69.45, H, 7.14, N, 4.76.

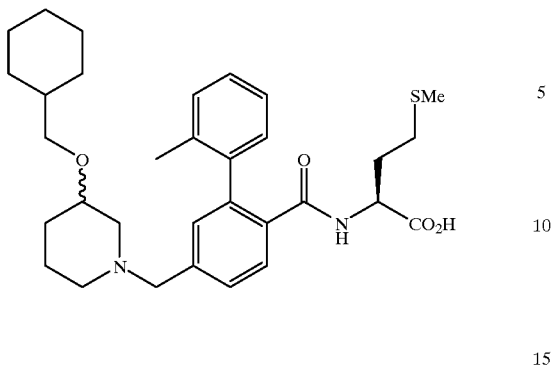

EXAMPLE 990

N-[4-(3-cyclohexylmethoxypiperidin-1-ylmethyl)-2-(2-methylphenyl)benzoyl]methionine The desired compound was prepared according to the method of Example 158 $^1$H nmr (300 MHz, DMSO d$_6$): δ 7.98, d, 0.5H; 7.97, d, 0.5H; 7.37, d, 1H; 7.25, d, 1H; 7.09, m, 2H; 7.02, m, 3H; 4.10, m, 1H; 3.44, s, 2H; 3.15, m, 2H; 3.05, m, 2.77, m, 1H; 2.52, m, 1H; 1.88–2.13, m, 5H; 1.60–1.82, m, 3H; 1.51, m, 5H; H; 1.85, s, 3H; 1.30, m, 2H; 0.90–1.16, m, 4H; 0.75, m, 2H. MS (ESI(−)): 551 (M−H); (ESI(+)): 553. Calc'd for C$_{32}$H$_{44}$N$_2$O$_4$S+1.13 H$_2$O: C, 67.06, H, 8.14, N, 4.89: Found: C, 67.06, H, 7.88, N, 4.80.

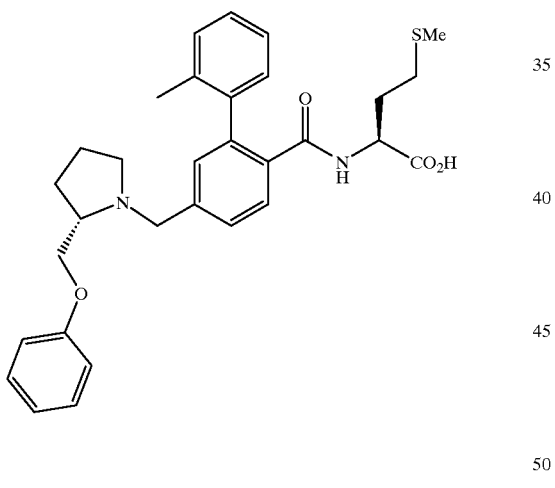

EXAMPLE 991

N-[4-(2-phenoxymethylpyrrolidin-1-ylmethyl)-2-(2-methylphenyl)benzoyl]methionine The desired compound was prepared according to the method of Example 158 $^1$H nmr (300 MHz, DMSO d$_6$): δ 8.10, d, 1H; 7.48, d, 1H; 7.40, d, 1H; 7.01–7.30, m, 6H; 6.90, m, 3H; 4.22, m, 2H; 4.01, m, 1H; 3.85, m, 1H; 3.59, m, 1H; 3.34, m, 1H; 3.03, m, 1H; 2.91, m, 1H; 2.36, m, 1H; 1.98–2.24, m, 6H; 1.96, s, 3H; 1.60–1.90, m, 4H. MS (ESI(−)): 531 (M−H); (ESI(+)): 533. Calc'd for C$_{31}$H$_{36}$N$_2$O$_4$S+0.87 H$_2$O: C, 67.90, H, 6.94, N, 5.11: Found: C, 67.90, H, 6.95, N, 4.87.

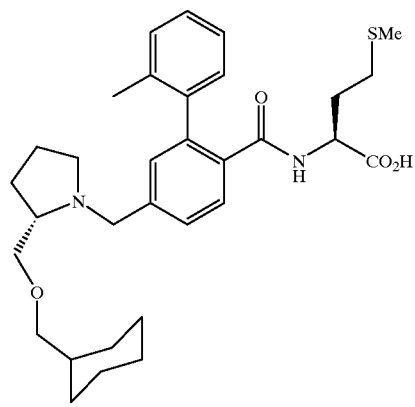

EXAMPLE 992

N-[4-(2-cyclohexylmethoxymethylpyrrolidin-1-ylmethyl)-2-(2-methylphenyl)benzoyl]methionine The desired compound was prepared according to the method of Example 158 $^1$H nmr (300 MHz, DMSO d$_6$): δ 8.11, d, 1H; 7.47, d, 1H; 7.38, d, 1H; 7.21, m, 2H; 7.16, m, 3H; 4.21, m, 2H; 3.53, m, 1H; 3.25–3.46, m, 3H; 3.18, dq (AA'), 2H; 2.87, m, 2H; 2.30, m, 1H; 1.99–2.24, m, 6H; 1.97, s, 3H; 1.77–1.95, m, 2H; 1.56–1.76, m, 6H; 1.40–1.55, m, 2H; 1.51, m, 3H; 0.88, m, 2H. MS (ESI(−)): 551 (M−H); (ESI(+)): 553. Calc'd for C$_{32}$H$_{44}$N$_2$O$_4$S+0.74 H$_2$O: C, 67.90, H, 8.10, N, 4.95: Found: C, 67.89, H, 7.83, N, 4.79.

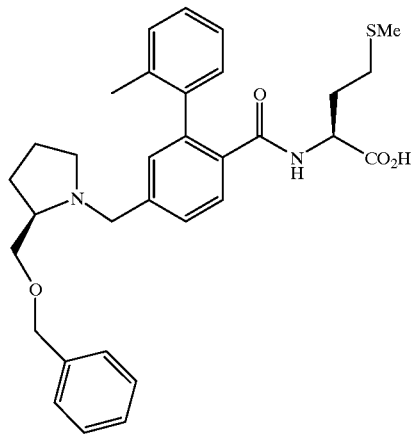

EXAMPLE 993

N-[4-(2-benzyloxymethylpyrrolidin-1-ylmethyl)-2-(2-methylphenyl)benzoyl]methionine The desired compound was prepared according to the method of Example 158 $^1$H nmr (300 MHz, DMSO d$_6$): δ 8.12, d, 1H; 7.49, d, 1H; 7.39, d, 1H; 7.30, m, 5H; 7.21, m, 2H; 7.15, m, 3H; 4.48, s, 2H; 4.22, m, 2H; 3.53, m, 2H; 3.40, m, 2H; 2.89, m, 2H; 2.23–2.40, m, 1H; 2.00–2.22, m, 5H; 1.98, s, 3H; 1.50–1.94, m, 6H. MS (ESI(−)): 545 (M−H); (ESI(+)): 547. Calc'd for C$_{32}$H$_{38}$N$_2$O$_4$S+1.60 H$_2$O: C, 66.78, H, 7.22; N, 4.87: Found: C, 66.79, H, 6.88, N, 4.70.

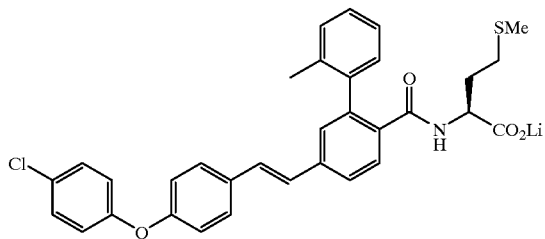

EXAMPLE 1016

N-[4-(2-(4-(4-chlorophenoxy)phenyl)ethen-1-yl)-2-(2-methylphenyl)benzoyl]methionine lithium salt Prepared as in Example 210. MS m/e 570 (M–H)⁻. $^1$H NMR (d$_6$-DMSO, 300 MHz) δ 1.5–2.2 (m, 10H), 3.65 (m, 1H), 6.95 (m, 1H), 7.02–7.69 (m, 17H).

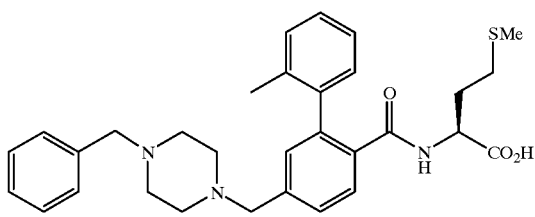

EXAMPLE 1035

N-[4-(4-benzylpiperazin-1-ylmethyl)-2-(2-methylphenyl)benzoyl]methionine

Prepared similarly. MS m/e 530 (M–H)⁻. $^1$H NMR (CDCl$_3$, 300 MHz) δ 1.65 (m, 1H), 1.95 (m, 1H), 2.08 (m, 8H), 2.75 (m, 8H), 3.71 (m, 4H), 4.42 (m, 1H), 6.21 (m, 1H), 7.3 (m, 11H), 7.79 (m, 1H).

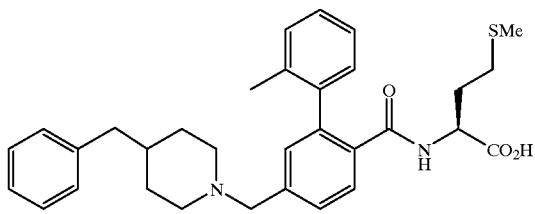

EXAMPLE 1036

N-[4-(4-benzylpiperidin-1-ylmethyl)-2-(2-methylphenyl)benzoyl]methionine

Prepared similarly. MS m/e 529 (M–H)⁻. $^1$H NMR (CDCl$_3$, 300 MHz) δ 1.65 (m, 5H), 1.95 (m, 1H), 2.06 (m, 8H), 2.41 (m, 1H), 2.56 (m, 2H), 3.30 (m, 2H), 3.55 (m, 1H), 3.71 (m, 2H), 4.13 (m, 1H), 4.42 (m, 1H), 6.30 (m, 1H), 7.18 (m, 10H), 7.47 (m, 1H), 7.77 (m, 1H).

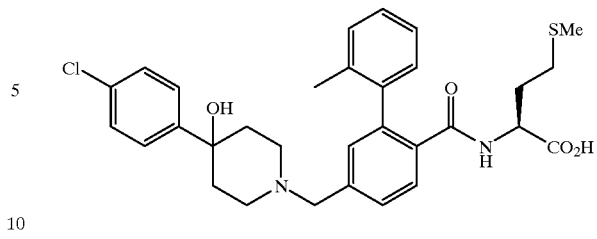

EXAMPLE 1037

N-[4-(4-(4-chlorophenyl)-4-hydroxypiperidin-1-ylmethyl)-2-(2-methylphenyl)benzoyl]methionine Prepared similarly. MS m/e 565 (M–H)⁻. $^1$H NMR (d$_6$-DMSO, 300 MHz) δ 1.61 (m, 4H), 1.80 (m, 1H), 1.93 (m, 1H), 1.99 (s, 3H), 2.15 (m, 5H), 2.48 (m, 2H), 2.69 (m, 2H), 3.63 (s, 2H), 4.18 (m, 1H), 4.92 (s, 1H), 6.95 (m, 2H), 7.45 (m, 8H), 7.95 (m, 1H).

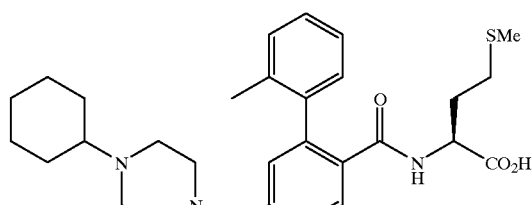

EXAMPLE 1038

N-[4-(4-cyclohexylpiperazin-1-ylmethyl)-2-(2-methylphenyl)benzoyl]methionine

Prepared similarly. MS m/e 522 (M–H)⁻. $^1$H NMR (CDCl$_3$, 300 MHz) δ 1.29 (m, 6H), 1.68 (m, 1H), 1.88 (m, 5H), 2.05 (m, 8H), 2.71 (m, 4H), 2.89 (m, 1H), 3.58 (m, 6H), 4.38 (m, 1H), 6.42 (m, 1H), 7.2–7.5 (m, 6H), 7.74 (m, 1H).

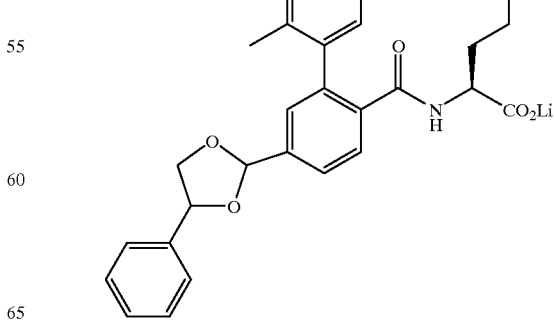

EXAMPLE 1083

(2S) 2-[4-(4-phenyl-1,3-dioxolan-2-yl)-2-(2-methylphenyl)benzoyl]methionine, Lithium Salt

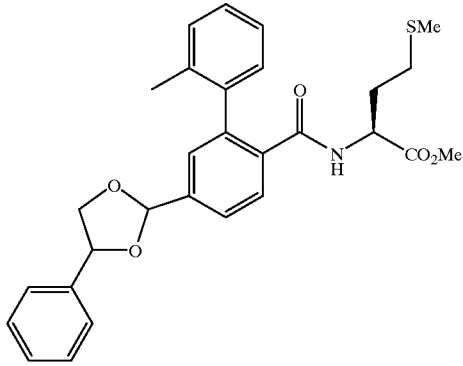

EXAMPLE 1083A (2S) 2-[4-(4-phenyl-1,3-dioxolan-2-yl)-2-(2-methylphenyl)benzoyl]methionine, Methyl Ester To a solution of N-[4-formyl-2-(2-methylphenyl)benzoyl] methionine methyl ester (example 403G, 340 mg) and 1,2-dihydroxyethylbenzene (134 mg) in-toluene (3 mL) was added p-toluenesulfonic acid hydrate (17 mg), and magnesium sulfate (212 mg). After 7 h at ambient temperature, the reaction was filtered through infusorial earth and concentrated. The residue was purified by silica gel chromatography eluting with 30% EtOAc/hexane to give the title compound as a colorless oil (330mg, 74%). MS (APCI(+)) m/e 506 (M+H)$^+$. MS (APCI(−)) m/e 540 (M+Cl)$^-$.

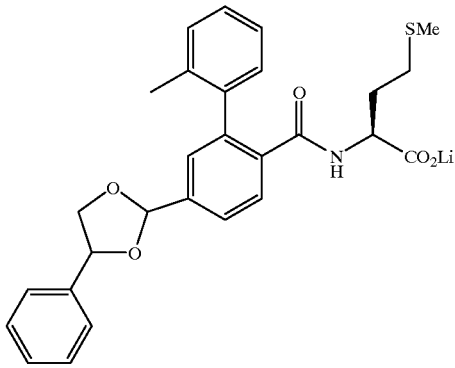

EXAMPLE 1083B (2S) 2-[4-(4-phenyl-1,3-dioxolan-2-yl)-2-(2-methylphenyl)benzoyl]methionine, Lithium Salt The title compound was prepared from (2S) 2-[4-(4-phenyl-1,3-dioxolan-2-yl)-2-(2-methylphenyl)benzoyl] methionine methyl ester according to the procedure in example 608E, and was isolated as a white powder. $^1$H NMR (300 MHz, DMSO) δ 1.51–1.88 (m, 4H), 1.92 (s, 3H), 1.98–2.20 (m, 3H), 3.62–3.73 (m, 1H), 3.76 (t, J=7.8 Hz, 0.5H), 3.85 (t, J=7.2 Hz, 0.5H), 4.38 (t, J=7.2 Hz, 0.5H), 4.56 (ddd, J=8.4, 6.6, 1.8 Hz, 0.5H), 5.25 (t, J=6.9 Hz, 1H), 6.20 (s, 0.5H), 6.22 (s, 0.5H), 7.00–7.12 (m, 1H), 7.25–7.47 (m, 10H), 7.59 (d, J=6 Hz, 2H). MS (APCI(+)) m/e 492 (M+H); Analysis calc'd for $C_{28}H_{28}LiNO5S \cdot 1.30H_2O$: C, 64.56; H, 5.92; N, 2.69; found: C, 64.56; H, 5.69; N, 2.54

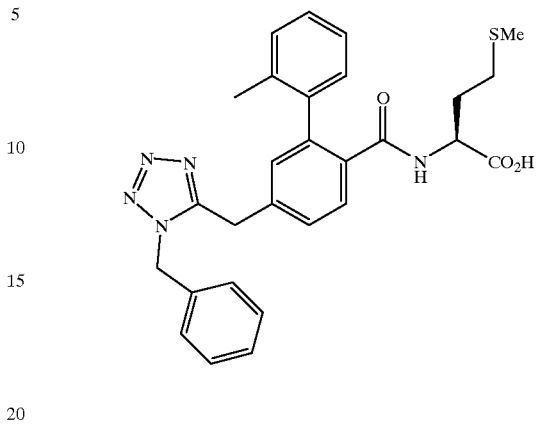

EXAMPLE 1099

N-[4-(1-benzyltetrazol-5-ylmethyl)-2-(2-methylphenyl)benzoyl]methionine

Step 1: 4-nitrilemethyl-2-(2-methylphenyl)phenylacetate

A 100 mL round-bottom flask was charged with 4-bromomethyl-2-(2-methylphenyl)phenylacetate (798.0 mg, 2.5 mmol and MeOH (23 mL)/$H_2O$ (2 mL). Potassium cyanide (489.4 mg, 7.5 mmol) was added and allowed to stir at room temperature for 12 h, then heated to reflux for 1 h, monitoring by TLC (1:1 EtOAc/hexane). The reaction was cooled and solvent was removed under vacuum. It was then diluted with water and extracted with EtOAc (3×10 mL). The combined organic layers were washed with brine, dried over $MgSO_4$, filtered and concentrated under vacuum. The product was purified by silica gel column (1:1 EtOAc/Hexane). Yield: 597.3 mg (90%), off-white solid.

$^1$H NMR (δ, $CDCl_3$): 8.0 (2H), 7.0–7.5 (5H), 2.83 (2H), 3.6 (3H), 2.05 (3H), 1.55 (1H). Mass spec(ESI): 266 (M+1), 264 (M−1).

Step 2: 4-tetrazol-5-ylmethyl-2-(2-methylphenyl)phenylacetate

A 100 mL 3-neck round-bottom flask was charged with 4-nitrilemethyl-2-(2-methylphenyl)phenylacetate (533.3 mg, 2 mmol) and dmf (25 mL) under $N_2$ purge. Sodium azide (910.1 mg, 12 mmol) and triethylamine hydrochloride (1.3780 g, 10 mmol) were added. The reaction was heated at 100° C. for 48 h. After cooling, 1 M $NaHCO_3$ (50 mL) was added. The reaction was extracted with $Et_2O$ (3×25 mL). The aqueous layer was acidified with 1 M $H_3PO_4$ to pH=3. Then extracted with EtOAc (3×50 mL). The combined organic layers were washed with water (50 mL) and brine (50 mL), dried over $MgSO_4$, filtered and concentrated under vacuum. The product was purified by silica gel column ($CHCl_3$/MeOH/HOAc (95:5:1)). Yield: 691.2 mg, yellow oil. Mass spec(ESI): 309 (M+1), 307 (M−1).

Step 3: 4-(1-benzyltetrazol-5-ylmethyl)-2-(2-methylphenyl)benzoate (A) and 4-(2-benzyltetrazol-5-ylmethyl)-2-(2-methylphenyl)benzoate (B)

A 25 mL round-bottom flask was charged with 4-tetrazol-5-ylmethyl-2-(2-methylphenyl)phenylacetate (618.1 mg, 2 mmol) in $CH_3CN$ (9.5 mL)/water (0.5 mL). Benzyl bromide (0.36 mL, 3 mmol) and potassium hydrogen carbonate (1 g) were added. The reaction was stirred for 4 h and then diluted with water. The mixture was extracted with $Et_2O$ (3×10 mL). The organic layer was washed with water (10 mL) and brine (10 mL), dried over $MgSO_4$, filtered and concentrated under vacuum. The two regioisomers were separated by silica gel column (40% EtOAc/Hexane). Yield: 255.7 mg (product A) and 277.6 mg (product B). Product A: $^1$H NMR ($\delta$, CDCl$_3$): 7.9 (2H), 7.0–7.4 (10H), 5.7 (2H), 4.27 (2H), 3.6 (3H), 2.0 (3H). Mass spec(ESI): 399 (M+1), 397 (M−1). Product B: $^1$H NMR ($\delta$, CDCl$_3$): 7.9 (2H), 6.9–7.4 (10H), 5.4 (2H), 4.2 (2H), 3.6 (3H), 2.0 (3H). Mass spec(ESI): 399 (M+1), 397 (M−1).

Step 4: 4-(1-benzyltetrazol-5-ylmethyl)-2-(2-methylphenyl) benzoic acid

A 50 mL round-bottom flask was charged with 4-(1-benzyltetrazol-5-ylmethyi)-2-(2-methylphenyl)benzoate (A) (205.8 mg, 0.52 mmol) and ethanol (10 mL). 4 N sodium hydroxide (1.1 mL, 4.16 mmol) was added. The reaction was refluxed for 2 h and then cooled. The solvent was removed under vacuum and then diluted with water. The reaction was extracted with Et$_2$O (3×10 mL). The pH of the aqueous layer was adjusted to 2 with 1 M H$_3$PO$_4$. The aqueous layer was extracted with EtOAc (3×10 mL). The combined organic layers were washed with brine (10 mL), dried over MgSO$_4$, filtered and concentrated under vacuum. Yield: 205.1 mg, white solid. $^1$H NMR ($\delta$, CDCl$_3$): 8.0 (2H), 7.0–7.4 (10H), 5.7 (2H), 4.3 (2H), 2.0 (3H).

Step 5: N-[4-(1-benzyltetrazol-5-ylmethyl)-2-(2-methylphenyl)benzoyl]methionine

A 50 mL round-bottom flasks was charged with 4-(1-benzyltetrazol-5-ylmethyl)-2-(2-methylphenyl)benzoic acid (205.1 mg, 0.52 mmol), 1-(3-dimethylaminopropyl-3-ethylcarbodiimide hydrochloride (EDAC) (110.1 mg, 0.0.572 mmol), L-methionine methyl ester hydrochloride (135.0 mg, 0.676 mmol), 1-hydroxybenzotriazole (78.6 mg, 0.572 mmol) and dmf (3 mL). The reagents were stirred until completely dissolved and then triethylamine (0.14 mL, 0.936mmol) was added. The reaction was stirred about 48 h until no starting material was present. Water (2 mL) and EtOAc (2 mL) were added to dissolve the precipitate. The mixture was extracted with EtOAc (3×10 mL). The combined organic layers were washed with 2 M Na$_2$CO$_3$ (10 mL), water (10 mL) and brine (10 mL), dried over MgSO$_4$, filtered and concentrated under vacuum. Yield: 273.0 mg, yellow solid. $^1$H NMR ($\delta$, CDCl$_3$): 8.0 (2H), 7.0–7.4 (10H), 5.85 (1H), 5.7 (2H), 4.6 (1H), 4.3 (2H), 3.65 (3H), 1.95–2.2 (6H), 1.5–1.9 (4H).

Step 6: N-[4-(1-benzyltetrazol-5-ylmethyl)-2-(2-methylphenyl)benzoyl]methionine-carboxylic acid A 25 mL round-bottom flask was charged with N-[4-(1-benzyltetrazol-5-ylmethyl)-2-(2-methylphenyl)benzoyl] methionine (273.0 mg, 0.53 mmol) and 3 mL of MeOH/THF (1:1). The flask was cooled to 0° C. and 1 M lithium hydroxide (1.1 mL, 1.07 mmol) was added. The bath was removed and the reaction stirred for about 3 h, monitoring by TLC (1:1 EtOAc/Hexane). The solvent was removed under vacuum and the reaction diluted with water. The mixture was extracted with EtOAc (3×10 mL), washed with brine (10 mL), dried over MgSO$_4$, filtered and concentrated under vacuum. Yield: 176.2 mg yellow solid.

$^1$H NMR ($\delta$, CDCl$_3$): 7.9 (2H), 7.0–7.4 (10H), 5.9 (1H), 5.7 (2H), 4.57 (1H), 4.3 (2H), 2.0–2.2 (6H), 1.9 (2H), 1.5 (2H); Mass spec (ESI): 516 (M+1), 514 (M−1) C$_{29}$H$_{29}$N$_5$O$_3$S.1.30 H$_2$O Anal. Calc'd.: C, 62.39 H, 5.91 N, 12.99. Found: C, 62.43 H, 5.64 N, 12.83.

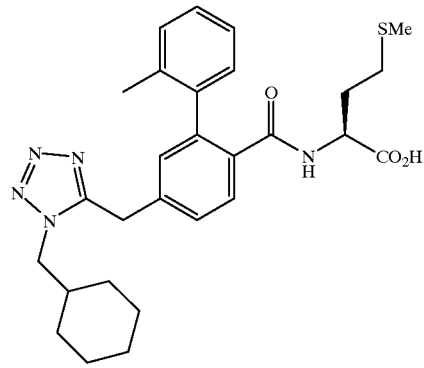

EXAMPLE 1100

N-[4-(1-cyclohexylmethyltetrazol-5-ylmethyl)-2-(2-methylphenyl)benzoyl]methionine Procedure: Follow example 1102 (product B). Yield: 105.7 mg, pale yellow solid. N-[4-(1-cyclohexylmethyltetrazol-5-ylmethyl)-2-(2-methylphenyl)benzoyl]methionine.

$^1$H NMR ($\delta$, CDCl$_3$): 7.95 (1H), 7.0–7.4 (5H), 5.9 (1H), 4.55 (1H), 4.3 (2H), 4.0 (2H), 2.9 (3H), 0.8–2.2 (20H); Mass spec (ESI): 522 (M+1), 520 (M−1) C$_{28}$H$_{35}$N$_5$O$_3$S.0.90 H$_2$O0.05 CH$_3$CN Anal Calc'd.: C, 62.51 H, 6.90 N 13.10 Found: C, 62.51 H, 6.43 N, 12.92.

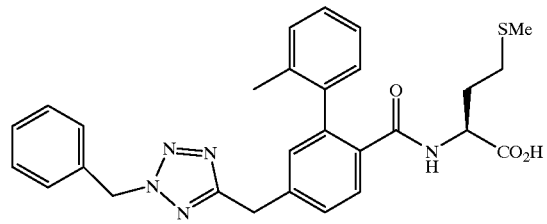

EXAMPLE 1101

N-[4-(2-benzyltetrazol-5-ylmethyl)-2-(2-methylphenyl)benzoyl]methionine

Procedure: Follow example 1099 (product B). Yield: 176.2 mg. N-[4-(2-benzyltetrazol-5-ylmethyl)-2-(2-methylphenyl)benzoyl]methionine.

$^1$H NMR ($\delta$, CDCl$_3$): 7.92 (2H), 6.8–7.4 (10H), 5.9 (1H), 5.4 (2H), 4.55 (1H), 4.2 (2H), 2.0–2.2 (6H), 1.9 (2H), 1.55 (2H); Mass spec (ESI): 516 (M+1), 514 (M−1) C$_{28}$H$_{29}$N$_5$O$_3$S.1.30H$_2$O; Anal. calc'd.: C, 62.39 H, 5.91 N, 12.99 Found: C, 62.43 H, 5.65 N, 12.53.

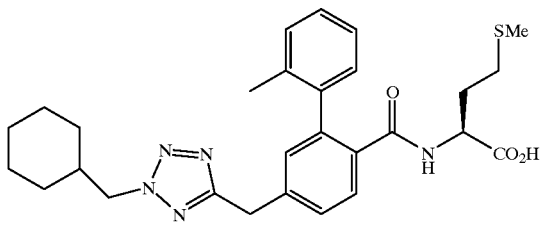

EXAMPLE 1102

N-[4-(2cyclohexylmethyltetrazol-5-ylmethyl)-2-(2-methylphenyl)benzoyl]methionine Procedure: Follow example 1099, except use bromomethylcyclohexane instead of benzylbromide (product A). Yield: 220.2 mg, pale yellow solid. N-[4-(2cyclohexylmethyltetrazol-5-ylmethyl)-2-(2-methylphenyl)benzoyl]methionine $^1$H NMR (δ, CDCl$_3$): 7.95 (1H), 7.0–7.5 (5H), 5.9 (1H), 4.55 (1H), 4.4 (2H), 4.3 (2H), 2.9 (3H), 0.9–2.2 (20H); Mass spec (ESI): 522 (M+1), 520 (M−1) C$_{28}$H$_{35}$N$_5$O$_3$S.0.50H$_2$O; Anal. Calc'd.: C 63.37 H, 6.84 N, 13.20 Found: C 63.58 H, 6.54 N, 12.80.

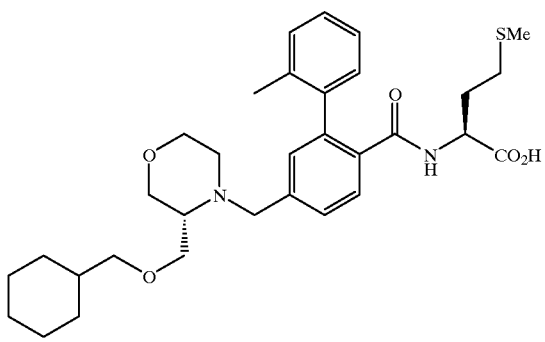

EXAMPLE 1109

N-[4-(3(S)-cyclohexylmethoxymethylmorpholin-4-ylmethyl)-2-(2-methylphenyl)benzoyl]methionine

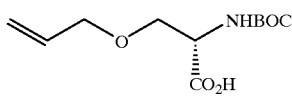

EXAMPLE 1109A

O-Allyl-N-t-butoxycarbonyl-L-serine

Serine (5.13 g, 25.0 mmol) in 60 mnL of DMF was cooled in an ice bath and treated with sodium hydride (60%, 3.30 g, 82.5 mmol) in 3 portions over ~15 minutes and the mixture stirred until the ceasation of bubbling (~20 minutes). The mixture was treated with allyl bromide (2.4 mL, 27.5 mmol) and after 5 minutes, the ice bath was removed. The mixture was stirred for 1.5 hours at ambient temperature and then quenched by the careful addition of water. The pH of the solution was adjusted to 2 with 1M aqueous phosphoric acid and extracted with 3 portions of ethyl acetate. The combined organic fractions were extrated with 3–30 mL portions of IN aqueous sodium hydroxide and the combined aqueous phases washed with ether. The pH of the aqueous phase was adjusted to 2 with 1M aqueous phosphoric acid and extracted with 3 portions of ethyl acetate. The combined organic fractions were washed with water and brine, dried, filtered and concentrated to provide 6.10 g (99%) of the title compound. MS (DCI, NH$_3$): 246 (MH$^+$); 263 (M+NH$_4$)$^+$.

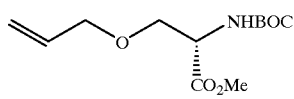

EXAMPLE 1109B

O-Allyl-N-t-butoxycarbonyl-L-serine, methyl ester

A solution of example 1109A (6.09 g, 24.8 mmol) in 30 mL of 50% aqueous DMF was treated with cesium carbonate (8.09, 24.8 mmol) and the mixture stirred 30 minutes. Methyl iodide (3.1 mL, 49.7 mmol) was added and the mixture stirred for 60 hours at ambient temperature. The mixture was diluted with water and extracted with 3 portions of ethyl ether. The combined organic extracts were washed with water, 1N aqueous sodium hydroxide and brine, dried filtered and concentrated to provide 1.51 g (23%) of the title compound. MS (DCI, NH$_3$): 260 (MH$^+$); 277 (M+NH$_4$)$^+$.

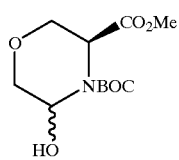

EXAMPLE 1109C

3(S)-Methoxycarbonyl-4-t-butoxycarbonyl-5-hydroxymorpholine

Ozone was passed through a solution of example 1109B (1.50 g, 5.8 mmol) in 20 mL of 1:1 methanol/methylene chloride cooled in a dry ice/acetone bath until the solution turned blue. Nitrogen was passed through the cold solution until the blue color was discharged and then dimethyl sulfide (3 mL) was added and the cooling bath removed and the mixture stirred overnight and concentrated. The residue was dissolved in ether and washed with water, brine, dried, filtered and concentrated to provide 1.5 g of the title compound that was used directly.

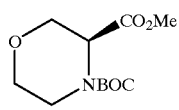

EXAMPLE 1109D

3(S)-Methoxycarbonyl-4-t-butoxycarbonylmorpholine

A solution of example 1109C (522 mg, 2.0 mmol) in 4 mL of methylene chloride was cooled in an ice/acetone bath and triethylsilane (1.6 mL, 10.0 mmol) was added. The solution was then treated with a solution of boron trifluoride etherate (0.27 mL, 2.2 mmol) in 1 mL of methylene chloride. After stirring 30 minutes, the bath was removed and stirring continued for 30 minutes and the mixture was quenched by the addition of 2M aqueous sodium carbonate. The mixture was diluted with water and methylene choride and the layers separated. The aqueous layer was extracted with 2 portions of methylene chloride and the combined organic layers were dried, filtered and concentrated. The residue was purified by column chromatography on silica gel (40 g, 20% ethyl acetate/hexanes) to provide 200 mg (41%) of the title compound. MS (DCI, $NH_3$): 246 ($MH^+$); 263 $(M+NH_4)^+$.

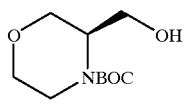

EXAMPLE 1109E

3(S)-Hydroxymethyl-4-t-butoxycarbonylmorpholine

A solution of example 1109D (376 mg, 1.53 mmol) in 4 mL of ethanol was treated with calcium chloride (310 mg, 3.06 mmol) nad the mixture stirred until a clear solution resulted. The solution was diluted with 2 mL of THF and then treated with sodium borohydride (232 mg, 6.13 mmol) and the mixture stirred for 4 hours. The reaction was quenched by the addition of water, diluted with 2M aqueous sodium carbonate and extracted with 3 portions of methylene chloride. The combined organic fraactions were dried, filtered and concentrated to provide 268 mg (83%) of the title compound. MS (DCI, $NH_3$): 218 ($MH^+$); 235 $(M+NH_4)^+$.

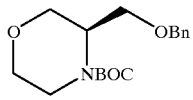

EXAMPLE 1109F

3(S)-Benzyloxymethyl-4-t-butoxycarbonylmorpholine

A solution of example 1109E (261 mg, 1.2 mmol) and benzyl bromide (0.18 mL, 1.44 mmol) in 1 mL of DMF was cooled in an ice bath and treated with sodium hydride (60%, 72 mg, 1.80 mmol) and the mixture stirred for 15 minutes. The cooling bath was removed and stirring continued for 6 hours and then the mixture was quenched by the addition of water. The mixture was partitioned between water and 3 portions of ethyl acetate. The combined organic extracts were washed with water, brine, dried, filtered and concentrated. The residue was purified by column chromatography on silica gel (20 g, 25% ethyl acetate/hexanes) to provide 275 mg (74%) of the title compound. MS (DCI, $NH_3$): 308 ($MH^+$); 325 $(M+NH_4)^+$.

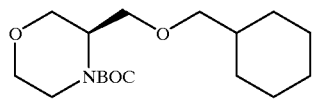

EXAMPLE 1109G

3(S)-Cyclohexylmethyloxymethyl-4-t-butoxycarbonylmorpholine

A solution of example 1109F (270 mg, 0.88 mmol) in 15 mL of methanol was treated with 135 mg of 5% rhodium on alumina and stirred under 4 atmospheres of hydrogen gas for 24 hours. The mixture was filtered and concentrated to provide 274 mg (99%) of the title compound. MS (DCI, $NH_3$): 314 ($MH^+$).

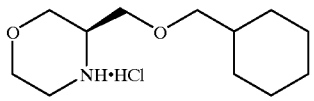

EXAMPLE 1109H

3(S)-Cyclohexylmethyloxymethylmorpholine

Using the procedure of example 1106C, example 1109G (265 mg, 0.84 mmol) was converted to the title compound. MS (DCI, $NH_3$): 214 ($MH^+$).

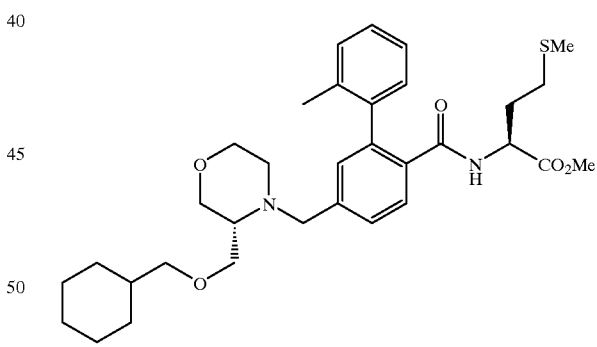

EXAMPLE 1109I

N-[4-(3(S)-cyclohexylmethoxyymethylmorpholin-4-ylmethyl)-2-(2-methylphenyl)benzoyl]methionine, methyl ester Using the procedure described in example 1106C, part 1, example 1109H (204 mg, 0.82 mmol) provided 29 mg (10%) of the title compound. MS (ESI+): 583 (MH+): (ESI−): 581 (M−H).

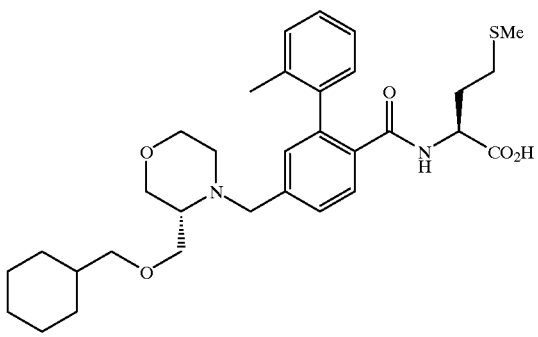

EXAMPLE 1109J

N-[4-(3(S)-cyclohexylmethoxymethylmorpholin-4-ylmethyl)-2-(2-methylphenyl)benzoyl]methionine Prepared according to the procedure of example 1104D. ¹H nmr (300 MHz., CD₃OD): δ 7.64, d, 1H; 7.48, d, 1H; 7.14–7.34, m, 5H; 4.41, m, 1H; 4.28, bd, 1H; 3.85, dd, 1H; 3.76, m, 1H; 3.49, 3.70, m, 6H; 3.23, d, 2H; 2.82, m, 2H; 2.51, m, 1H; 2.06–2.24, m, 5H; 1.99, s, 3H; 1.93, m, 2H; 1.70, m, 6H; 1.55, m, 1H; 1.09–1.32, m, 4H; 0.92, m, 2H. MS (ESI+): 569 (MH+): (ESI–): 567 (M–H). Calc'd for $C_{32}H_{44}N_2O_5S \cdot 0.40\ H_2O$; C, 66.73; H, 7.84; N, 4.86; Found: C, 66.72; H, 7.82; N, 4.71.

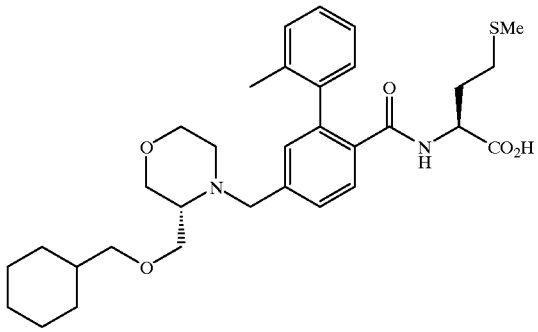

EXAMPLE 1111F

N-[4-(3(R)-cyclohexylmethoxymethylthiomorpholin-4-ylmethyl)-2-(2-methylphenyl)benzoyl]methionine

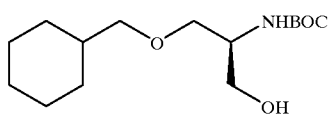

EXAMPLE 1111A

3(S)-cyclohexylmethoxy-2-t-butoxycarbonylaminopropan-1-ol

Following the procedure of example 1109G, example 1108A (1.00 g, 3.55 mmol) was converted to 0.85 g (83%) of the title compound. MS (DCI, NH₃): 288 (MH⁺).

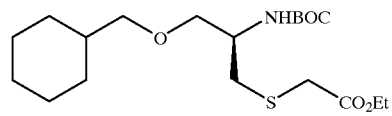

EXAMPLE 1111B

R-[2-t-butoxycarbonylamino-3-cyclohexylmethyloxy]propylmercaptoacetic acid, ethyl ester Following the procedure described in example 1106B (and substituting the potassium salt of ethyl mercaptoacetate for sodium thiomethoxide), example 1111A (0.84 g, 2.91 mmol) was converted to 0.89 g (78% overall) the title compound. MS (DCI, NH₃): 390 (MH⁺).

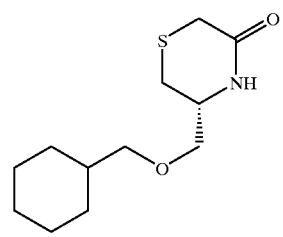

EXAMPLE 1111C

3-Oxo-5(R)-cyclohexylmethyloxymethyl-thiomorpholine

Example 1111B (0.88 g, 2.24 mmol) was dissolved in 4 mL of 4N HCl/dioxane and the mixture stirred overnight and concentrated. The residue was dissolved in 5 mL of acetonitrile and diisopropylethylamine (0.80 ml, 4.48 mmol) was added. The mixture was stirred for 1 hour at room temperature and 4 days at 65° C. The mixture was cooled to room temperature, diluted with water and exatracted with 3 portions of ethyl ether. The combined organic extracts were washed with 1M aqueous phosphoric acid, water, brine, dried, filtered and concentrated. The residue was purified by cloumn chromatography on silica gel (30 g, 40%–100% ethyl acetateihexanes) to provide 0.35 g (65%) of the title compound. MS (DCI, NH₃): 244 (MH⁺); 261 (M+NH₄)⁺.

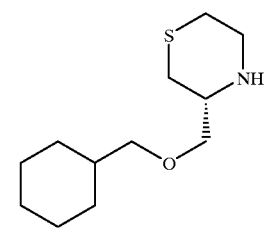

EXAMPLE 1111D

5(R)-cyclohexylmethyloxymethyl-thiomorpholine

Following the procedure of example 1178F, example 1111C (0.34 g, 1.40 mmol) provided 0.34 g (100%) of the title compound. MS (DCI, NH₃): 230 (MH⁺).

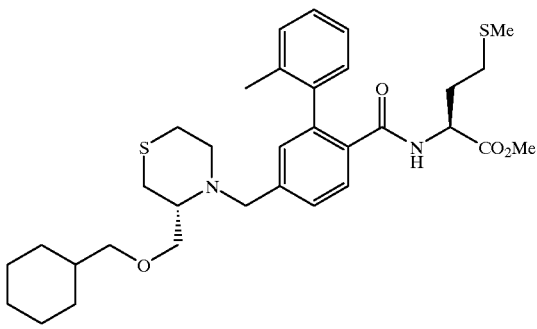

EXAMPLE 1111E

N-[4-(3-(R) cyclohexylmethoxymnethylthiomorpholin-4-ylmethyl)-2-(2-methylphenyl)benzoyl]methionine, methyl ester Following the procedure of example 1103C, example 1111D (172 mg, 0.75 mmol) was converted to 67 mg (11%) of the title compound. MS (ESI+): 599 (MH+): (ESI−): 597 (M−H).

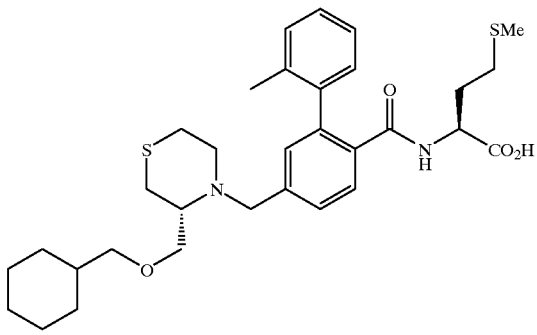

EXAMPLE 1111F

N-[4-(3(R)-cyclohexylmethoxymethylthiomorpholin-4-ylmethyl)-2-(2-methylphenyl)benzoyl]methionine Following the procedure of example 1104D, the title compound was prepared. $^1$H nmr (300 MHz., CD$_3$OD): δ 7.65, d, 1H; 7.48, d, 1H; 7.14–7.32, m, 5H; 4.40, m, 1H; 4.10, d, 1H; 3.91, d, 1H; 3.80, dt, 1H; 3.24, dd, 2H; 3.16, m, 2H; 2.84, m, 2H; 2.56–2.77, m, 3H; 2.05–2.13, m, 5H; 2.00, s, 3H; 1.93, m, 2H; 1.69, m, 6H; 1.55, m, 1H; 1.09–1.32, m, 4H; 0.94, m, 2H. MS (ESI+): 585 (MH+): (ESI−): 583 (M−H). Calc'd for C$_{32}$H$_{40}$N$_2$O$_4$S$_2$.0.30 H$_2$O; C, 65.12; H, 7.62; N, 4.75; Found: C, 65.14; H, 7.72; N, 4.60.

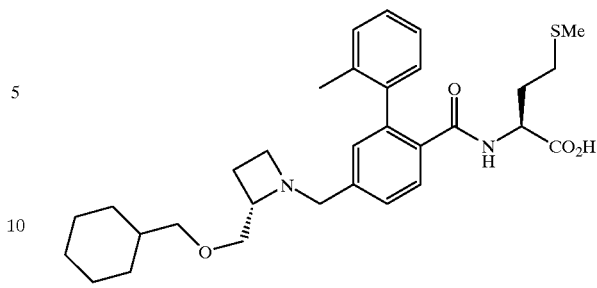

EXAMPLE 1114

N-[4-(2(S)-cyclohexylmethoxymethylazetidin-1-ylmethyl)-2-(2-methylphenylhbenzoyl]methionine

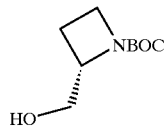

EXAMPLE 1114A

N-t-Butoxycarbonyl-2(S)-hydroxymethylazetidine

Azetidine-2-carboxylic acid (1.25 g, 12.4 mmol) was dissolved in 10 mL of 2M aqueous sodium carbonate and a solution of di-tert-butyldicarbonate in 10 mL of THF was added and the mixture was stirred overnight. The mixture was diluted with water and ether and the layers were separated. The ether layer was washed with water and pH of the combined aqueous phases adjusted to ~2 with phosphoric acid. The mixture was extracted with 4 portions of 20% isopropanot/chloroform and the combined organic phases were dried, filtered and concentrated. The residue was dissolved in 15 mL of THF and cooled in an ice bath. The solution was treated with 25 mL of borane in THF (1M, 25 mmol) and stirring was continued for 1 hour. The ice bath was removed and the solution stirred for 2 hours and then quenched by the careful addition of 25 mL of 4:1 THF/water. The mixture was stirred for 15 minutes, carefully treated with 25 mL of 1N aqueous HCl, and diluted with ethyl acetate. The layers wre separated and the aqueous layer extracted with 2 additional portions of ethyl acetate. The combined organic fractions were washed with 2M aqueous sodium carbonate, water, brine, and dried, filtered and concentrated to provide 2.18 g (94%) of the title compound. MS (DCI, NH$_3$): 188 (MH$^+$).

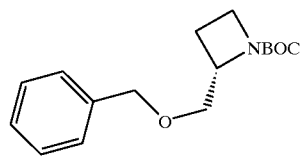

EXAMPLE 1114B

N-t-Butoxycarbonyl-2(S)-benzyloxymethylazetidine

Following the procedure of example 1109F, example 1114A (0.94 g, 5 mmol) was converted to the crude product.

The crude residue was purified by chromatography on silica gel (50 g, 20% ethyl acetate/hexanes) to provide 0.44 g, (32%) of the title compound. MS 7895 (DCI, NH₃): 278 (MH⁺).

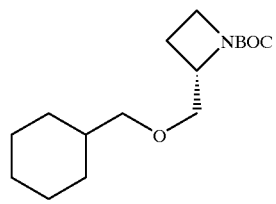

EXAMPLE 1114C

N-t-Butoxycarbonyl-2(S)-cyclhexylmethyloxymethylazetidine

Following the procedure described in example 1109G, example 1114B (0.43 g, 1.56 mmol) provided 0.42 g, (95%) of the title compound. MS (DCI, NH₃): 284 (MH⁺).

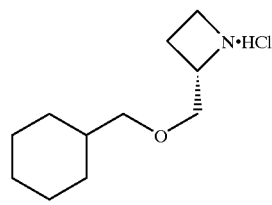

EXAMPLE 1114D

2(S)-cyclhexylmethyloxymethylazetidine, hydrochloride salt

Following the procedure described in example 1106C, example 1114C (0.42 g, 1.48 mmol) was converted to 0.32 g (100%) of the title compound. MS (DCI, NH₃): 184 (MH⁺).

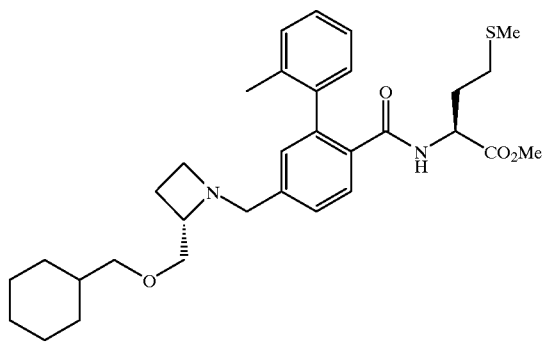

EXAMPLE 1114E

N-[4-(2(S)-cyclohexylmethoxymethylazetidin-1-ylmethyl)-2-(2-methylphenyl)benzoyl]methionine, methyl ester Following the procedure described in example 1106D, part 1, example 1114D (220 mg, 1.0 mmol) provided 145 mg (53%) of the title compound. MS (ESI+): 553 (MH+): (ESI−): 551 (M−H).

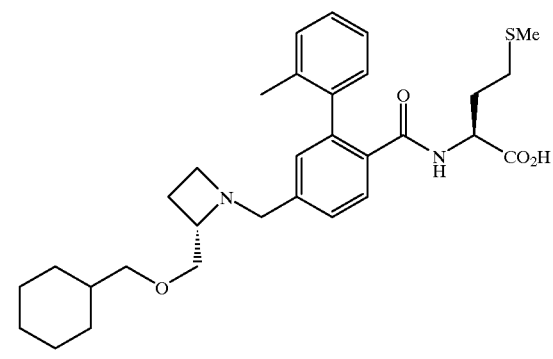

EXAMPLE 1114F

N-[4-(2(S)-cyclohexylmethoxymethylazetidin-1-ylmethyl)-2-(2-methylphenyl)benzoyl]methionine Following the procedure of example 1104D, example 114E (100 mg, 0.18 mmol) provided 92 mg (95%) of the title compound. ¹H nmr (300 MHz., dmso d6): δ 8.10, bd, 1H; 7.47, d, 1H; 7.33, d, 1H; 7.20, m, 2H; 7.11, m, 3H; 4.21, m, 1H; 3.83, d, 1H; 3.54, d, 1H; envelope 3.07–3.48, m, 4H; 2.84, m, 1H; 1.98–2.22, m, 5H; 1.97, s, 3H; envelope, 0.77–1.95, 17H. MS (ESI+): 539 (MH+): (ESI−): 537 (M−H). Calc'd for $C_{31}H_{42}N_2O_4S \cdot 0.90\ H_2O$; C, 67.09; H, 7.96; N, 5.05; Found: C, 67.09; H, 7.84; N, 5.00.

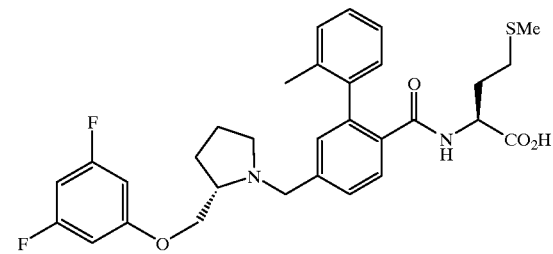

EXAMPLE 1115

N-[4-(2(S)-(3,5-difluorolphenoxy)methylpyrrolidin-1-ylmethyl)-2-(2-methylphenyl)benzoyl]methionine

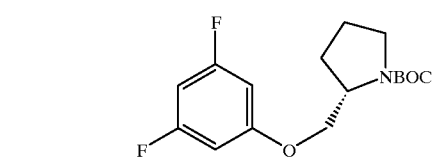

EXAMPLE 1115A

N-t-Butoxycarbonyl-2(S)-(3,5-difluorophenoxy) pyrrolidine

A solution of N-t-butoxycarbonyl-2-hydroxymethylpyrrolidine (0.40 g, 2.00 mmol), triphenylphosphine (1.05 g, 4.00 mmol), and 3,5-diflurorophenol (0.52 g, 4.00 mmol) in 5 mL of 1,2-dichloroethane was cooled in an ice bath and treated with a solution of diethylazodicarboxylate (0.63 mL, 4.00 mmol) in 3 mL of toluene. The cooling bath was removed and the solution was stirred for 70 hours at ambient temperature. The mixture was diluted with ether and extracted with 4N aqueous sodium hydroxide, dried, filtered and concentrated. The residue was purified by column chromatography on silica gel (30 g, 10% ethyl acetatelhexanes) provided 0.49 g, (80%) of the title compound. MS (DCI, NH$_3$): 314 (MH$^+$).

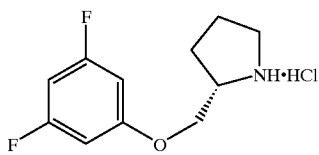

EXAMPLE 1115B

2(S)-(3,5-difluorophenoxy)pyrrolidine, hydrochloride salt

Following the procedure of example 1106C, example 1115A (0.48 g, 1.53 mmol) was provided 0.35 g (91 %) of the title compound. MS (DCI, NH$_3$): 214 (MH$^+$); 231 (M+NH$_4$)$^+$.

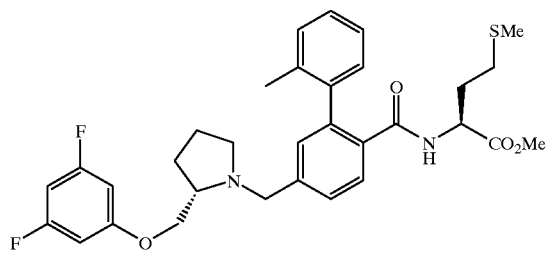

EXAMPLE 1115C

N-[4-(2(S)-(3,5-difluorophenoxy)methylpyrrolidin-1-ylmethyl)-2-(2-methylphenyl)benzoyl]methionine, methyl ester Following the procedure of example 1106C, part 1, example 1115B (0.19 g, 0.75 mmol) provided 0.22 g (76%) of the title compound. MS (ESI+): 583 (MH+): (ESI−): 581 (M−H).

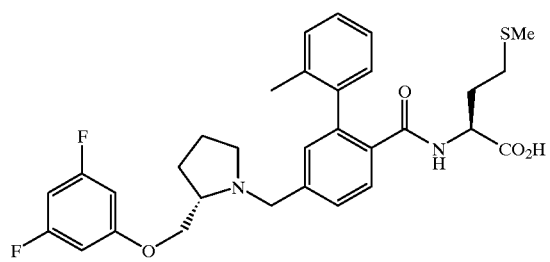

EXAMPLE 1115D

N-[4-(2(S)-(3,5-difluorophenoxy)methylparrolidin-1-ylmethyl)-2-(2-methylphenyl)benzoyl]methionine Following the procedure of example 1104D, example 1115C (0.21 g, 0.36 mmol) provided the title compound. $^1$H nmr (300 MHz., CD$_3$OD): δ 7.69, d, 1H; 7.53, dd, 1H; 7.33, m, 1H; 7.05–7.29, m, 4H; 6,48–6,62, m, 3H; 4.48, m, 1H; 4.34, m, 1H; 4.12, m, 3H; 3.65, m, 1H; 3.31, m, 1H; 2.96, m, 1H; envelope 1.82–2.41, 13H; 1.68, m, 1H. MS (ESI+): 569 (MH+): (ESI−): 567 (M−H). Calc'd for C$_{31}$H$_{34}$F$_2$N$_2$O$_4$S.0.35 H$_2$O; C, 64.76; H, 6.08; N, 4.87; Found: C, 64.72; H, 5.97; N, 4.75.

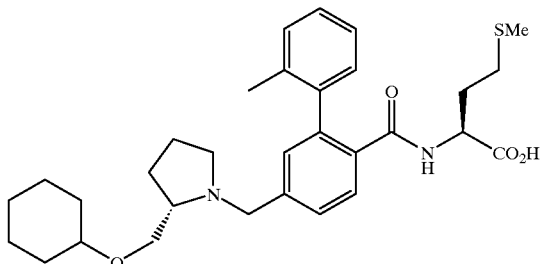

EXAMPLE 1116

N-[4-(2(S)-cyclohexyloxymethylpyrrolidin-1-ylmethyl)-2-(2-methylphenyl)benzoyl]methionine

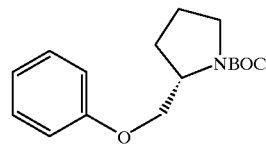

EXAMPLE 1116A

N-t-Butoxycarbonyl-2(S)-phenoxymethylpyrrolidine

Following the procedure of example 1115 A, N-t-butoxycarbonyl-2-hydroxymethylpyrrolidine (0.80 g, 4.00 mmol) and phenol (1.13 g, 12.00 mmol) provided 0.99 g (89%) of the title compound. MS (DCI, NH$_3$): 278 (MH$^+$).

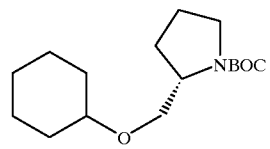

EXAMPLE 1116B

N-t-Butoxycarbonyl-2(S)-cyclohexyloxymethylpyrrolidine

Following the procedure of example 1109G, example 1116A (0.56 g, 2.00 mmol) rovided 0.55 g (96%) of the title compound. MS (DCI, NH$_3$): 284 (MH$^+$).

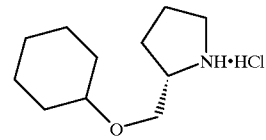

EXAMPLE 1116C

2(S)-cyclohexyloxymethylpyrrolidine, hydrochloride salt

Following the procedure of example 1106C, example 1116B (0.54 g, 1.90 mmol) provided 0.41 g (99%) of the title compound. MS (DCI, NH$_3$): 184 (MH$^+$); 201 (M+NH$_4$)$^+$.

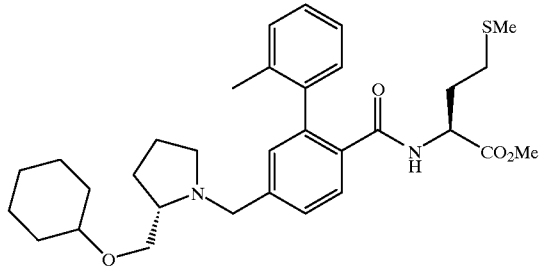

EXAMPLE 1116D

N-[4-(2(S)-cyclohexyloxymethylpyrrolidin-1-ylmethyl)-2-(2-methylphenyl)benzoyl]methionine, methyl ester Following the procedure of example 1106D, part 1, example 1116C (0.22 g, 1.00 mmol) provided 0.22 g (83%) of the title compound. MS (ESI+): 553 (MH+): (ESI−): 551 (M−H).

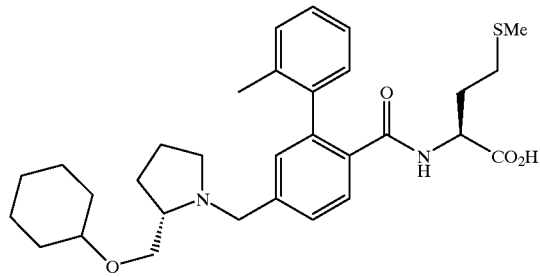

EXAMPLE 1116E

N-[4-(2(S)-cyclohexyloxymethylpyrrolidin-1-ylmethyl)-2-(2-methylphenyl)benzoyl]methionine Following the procedure of example 1104D, example 1116D (0.22 g, 0.40 mmol) provided 0.18 g (81%). $^1$H nmr (300 MHz., dmso d6): δ 8.09, bd, 1H; 7.48, d, 1H; 7.36, d, 1H; 7.21, m, 2H; 7.13, m, 3H; 4.21, m, 2H; 3.49, d, 1H; envelope 3.15–3.45, 3H; 2.84, m, 1H; 2.70, m, 1H; 2.00–2.29, m, 7H; 1.96, s, 3H; 1.34–1.94, m, 8H; 1.18, m, 6H. MS (ESI+): 539 (MH+): (ESI−): 537 (M−H). Calc'd for C$_{31}$H$_{42}$N$_2$O$_4$S.0.50 H$_2$O; C 67.98; H7.91; N 5.11; Found: C, 67.95; H, 7.81; N, 5.05.

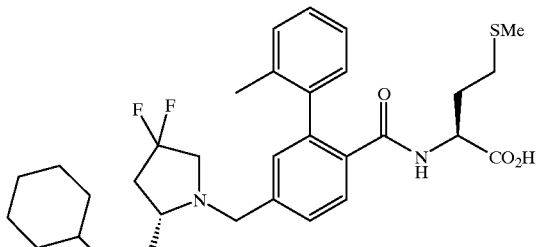

EXAMPLE 1117

N-[4-(2(S)-cyclohexylmethyloxymethyl-4,4-difluoropyrrolidin-1-ylmethyl)-2-(2-methylphenyl)benzoyl]methionine

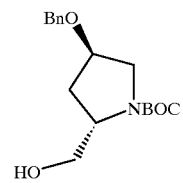

EXAMPLE 1117A

N-t-butoxycarbonyl-2(S)-hydroxymethyl-4(R)-benzyloxypyrrolidine

A solution of trans-N-t-butoxycarbonyl-4-benzyloxy-L-proline (3.32 g, 10.3 mmol) in 20 mL of THF was cooled in an ice/acetone bath and a solution of borane in THF (1M, 20.6 mL, 20.6 mrnmol) was added dropwise. The solution was stirred for 2 hours then the cooling bath was removed and the mixture stirred overnight. The reaction was quenched by the careful addition of water followed by the addition of 20 mL of 1N aqueous HCl and then poured into ethyl acetate. The layers were separated and the aqueous layer extracted with 2 portions of ethyl acetate. The combined organic extracts were 2M aqueous sodium carbonate, water and brine, dried, filtered and concentrated to provide 3.19 g (100%) of the title compound. MS (DCI, NH$_3$): 308 (MH$^+$).

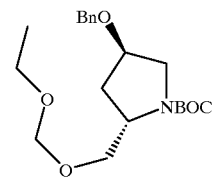

EXAMPLE 1117B

N-t-butoxycarbonyl-2(S)-ethoxymethyloxmethyl-4(R)-benzyioxypyrrolidine

A solution of example 1117A (2.14 g, 7.00 mmol) in 15 mL of methylene chloride was cooled in an ice bath and treated with diisopropylethylamine (1.87 mL, 10.50 mmol) 8045 followed by the addition of chloromethylethyl ether (0.97 mL, 10.50 mmol). The cooling bath was removed, the mixture stirred for 24 hours and then poured into 100 mL of ethyl ether. The organic phase washed with water, aqueous HCl, brine, dried, filtered and concentrated to provide 2.32 g (94%) of the title compound. MS (DCI, NH$_3$): 366 (M+NH$_4$)$^+$.

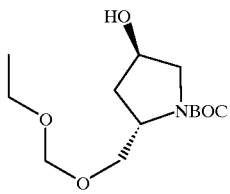

EXAMPLE 1117C

N-t-butoxycarbonyl-2(S)-ethoxymethyloxymethyl-4(R)-hydroxypyrrolidine

A solution of exaomple 1117B (2.29 g, 6.50 mmol) in 20 mL of degassed methanol was treated with Perleman's catalyst (0.40 g) and then the mixture was stirred under a balloon of hydrogen gas overnight. The mixture was diluted with ethyl acetate and filtered through a plug of silica gel. The silica gel plug was washed well with ethyl acetate and the filtrated concentrated to provide 1.77 g (99%) of the title compound. MS (DCI, NH$_3$): 276 (MH$^+$).

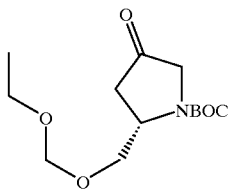

EXAMPLE 1117D

N-t-butoxycarbonyl-2(S)-ethoxymethyloxymethyl-4-oxopyrrolidine

A solution of example 1117C (0.99 g, 3.59 mmol) in 20 mL of 10% acetonitrile/methylene chloride was treated with powdered, activated 4 Å molecular sieves (1 g), 4-methylmorpholine-4-oxide (0.63 g, 5.38 mmol) and the mixture stirred for 30 minutes. The suspension was treated with tetrapropylammonium perruthenate (0.04 g, 0.11 mmol) and the resulting black mixture stirred for 30 minutes. The mixture was treated with ~3 g of celite and diluted with 30 mL of ether and stirred for 20 minutes. The suspension was then filtered through a pad of silica gel (which was washed well with ether) and the filtrate conecentrated to provide 0.91 g (93%) of the title compound. MS (DCI, NH$_3$): 274 (MH$^+$); 291 (M+NH$_4$)$^+$.

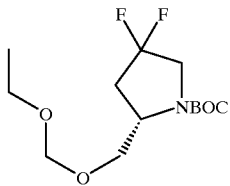

EXAMPLE 1117E

N-t-butoxycarbonyl-2(S)-ethoxymethyloxymethyl-4,4-difluoropyrrolidine

A solution of example 1117D (0.90 g, 3.30 mmol) in 20 mL of methylene chloride was cooled in an dry ice/acetone bath and treated with DAST (1.80 mL, 13.20 mmol). The bath was removed and the mixture stirred for 48 hours, cooled in an ice bath and carefully quenched by the addition of 2M aqueous sodium carbonate. The layers were separated and the aqueous layer was extracted with 2 additional portions of methylene chloride and the combined organic fractions were dried, filtered and concentrate. The residue was purified by column chromatography on silica gel (40 g, 15% ethyl acetate/hexanes) provided 0.70 g (72%) of the title compound. MS (DCI, NH$_3$): 296 (MH$^+$); 313 (M+NH$_4$)$^+$.

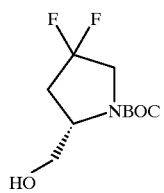

EXAMPLE 1117F

N-t-butoxycarbonyl-2(S)-hydroxymethyl-4,4-difluoropyrrolidine

A solution of example 1117E (0.69 g, 2.30 mmol) in 10 mL of methanol was treated with 0.5 mL of concentrated aqueous HCl and the mixture stirred overnight. The yellow solution was poured into 2M aqueous sodium carbonate and concentrated to remove the methanol. The mixture was diluted with THF and ~1 g of di-t-butyldicarbonate was added and the mixture stirred for 3 hours and diluted with ethyl ether. The phasees were separated and the aqueous phase was extracted with 3 portions of methylene chloride. The combined organic phases were dried, filtered and concentrated to provide 0.48 g (88%) of the title compound. MS (DCI, NH$_3$): 238 (MH$^+$); 255 (M+NH$_4$)$^+$.

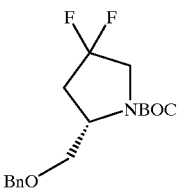

EXAMPLE 1117G

N-t-butoxycarbonyl-2(S)-benzyloxymethyl-4,4-difluoropyrrolidine

Following the procedure of example 1109F, example 1117G (0.24 g, 1.00 mmol) rovided 0.26 g (78%) of the title compound. MS (DCI, NH$_3$): 328 (MH$^+$).

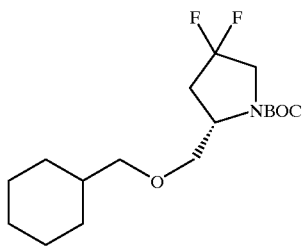

EXAMPLE 1117H

N-t-butoxycarbonyl-2(S)-cyclohexylmethyloxymethyl-4,4-difluoropvrrolidine

Following the procedure of example 1109G, example 1117G (0.25 g, 1.10 mmol) rovided 0.22 g (87%) of the title compound. MS (DCI, NH$_3$): 334 (MH$^+$).

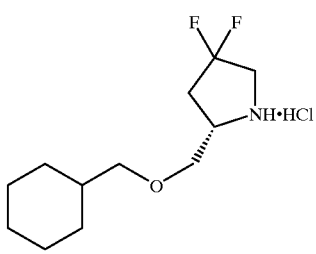

EXAMPLE 1117I

2(S)-cyclohexylmethyloxymethyl-4,4-difluoropyrrolidine, hydrochloride salt

Following the procedure of example 1106C, example 1117H (0.22 g, 0.92 mmol) provided 0.17 g (98%) of the title compound. MS (DCI, NH$_3$): 234 (MH$^+$).

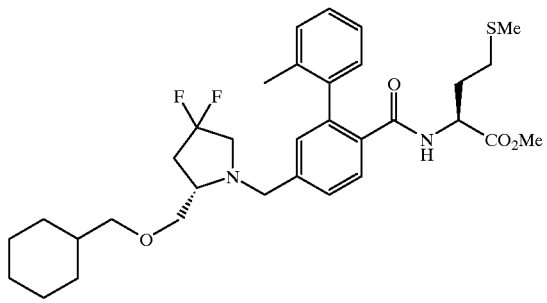

EXAMPLE 1117J

N-[4-(2(S)-cyclohexylmethyloxymethyl-4,4-difluoropyrrolidin-1-ylmethyl)-2-(2-methylphenyl)benzoyl]methionine, methyl ester Following the procedure of example 1106D, part 1, example 1117I (0.16 g, 0.60 mmol) provided 0.13 g (43%) of the title compound. MS (ESI+): 603 (MH+): (ESI−): 601 (M−H).

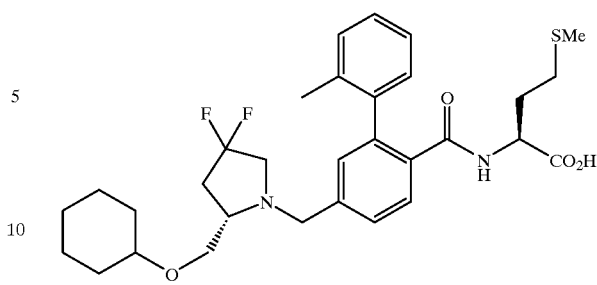

EXAMPLE 1117K

N-[4-(2(S)-cyclohexylmethyloxymethyl-4,4-difluoropyrrolidin-1-ylmethyl)-2-(2-methylphenyl)benzoyl]methionine Following the procedure of example 1104D, example 1117J (123 mg, 0.20 mmol) provided 116 mg (98%) of the title compound. $^1$H nmr (300 MHz., CD$_3$OD): δ 7.62, d, 1H; 7.43, d, 1H; 7.13–7.32, m, 5H; 4.44, m, 1H; 4.26, d, 1H; 3.56, d, 1H; 3.54, dd, 1H; 3.48, dd, 1H; 3.24, m, 2H; 3.10, m, 1H; 2.71, m, 1H; 2.37, m, 1H; 2.03–2.25, m, 6H; 2.00, s, 3H; 1.87–2.00, m, 1H; 1.68, m, 5H; 1.53, m, 1H; 1.18, m, 3H; 0.90, m, 2H. MS (ESI+): 589 (MH+): (ESI−): 587 (M−H). Calc'd for C$_{32}$H$_{42}$F$_2$N$_2$O$_4$S; C, 65.28; H, 7.19; N, 4.76; Found: C, 64.99; H, 7.16; N, 4.54.

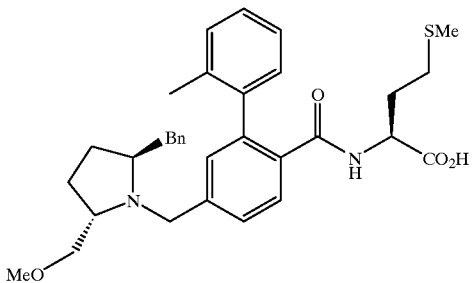

EXAMPLE 1118

N-[4-(2-methoxymethyl-5-benzylpyrrolidin-1-ylmethyl)-2-(2-methylphenyl)benzoyl]methionine

EXAMPLE 1118A

5(S)-t-butyldimethylsiloxymethyl-2-pyrrolidinone

A stirred solution of 5(S)-hydroxymethyl-2-pyrrolidinone (5.00 g, 0.043 mol) in 20 mL of DMF was treated with imidazole (6.81 g, 10 mol) and then t-8145 butyldimethylchlorosilane (7.20 g, 0.047 mol) and the mixture stirred for 2 hours. The thick mixture was diluted with water and extracted with 3 portions of ethyl acetate. The combined ethyl acetate layer were washed with water, brine, dried filtered and concentrated to provide 7.50 g (75%) of the title compound. MS (DCI, NH$_3$): 230 (MH$^+$); 247 (M+NH$_4$)$^+$.

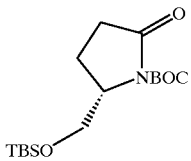

EXAMPLE 1118B

N-t-butoxycarbonyl-5(S)-t-butyldimethylsiloxymethyl-2-pyrrolidinone

A stirred solution of example 1118A (1.65 g, 7.20 mmol) in 5 mL of acetonitrile at rt was treated with DMAP (0.15 g, 1.25 mmol) and ditertbutyldicarbonate (1.09 g, 7.20 mmol) and the mixture stirred at ambient temperature for 48 hours at which time an additional 0.80 g of ditertbutyldicarbonate was added. The mixture was stirred an additional 6 hours and then diluted with 80 mL of ether and washed with 1M aqueous phosphoric acid, water, brine, dried filtered and concentrated. The residue was purified by column chromatography on silica gel (100 g, 15% ethyl acetate/hexanes) to provide 1.50 g (63%) of the title compound. MS (DCI, NH$_3$): 347 (M+NH$_4$)$^+$.

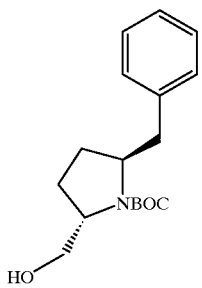

EXAMPLE 1118C

N-t-butoxycarbonyl-2(S)-hydroxymethyl-5(S)-benzylpyrrolidine

A solution of example 1118C (1.05 g, 3.17 mmol) in 10 mL of toluene was cooled in a dry ice/acetone bath and treated with diisobutylaluminum hydride (3.2 mL of a 1.5M solution in toluene, 4.75 mmol) and the mixture stirred for 1 hour. The dry ice bath was replaced with an ice/acetone bath and the mixture stirred for an additional hour and then quenched with the careful addition of methanol (0.25 mL) and stirring continued until the evolution of gas ceased. The solution was then treated with 1N aqueous HCl and ethyl acetate and the mixture stirred until 2 clear phases resulted. The aqueous layer was extracted with ethyl acetate and the combined organic fractions were washed with 1N HCl, saturated sodium bicarbonate, brine, dried, filtered and concentrated. The residue was dissolved in 10 mL of methylene chloride and cooled in a dry ice/acetone bath and then treated with boron trifluoride etherate (0.41 mL, 3.34 mmol) followed by benzylmagnesium chloride (4 mL of a 2.0M solution in THF, 8.00 mmol) and the mixture stirred for 1.5 hours and quenched by the addition of saturated sodium bicarbonate. The cooling bath was removed and the mixture allowed to reach room temperature. The mixture was diluted with ether and extracted with water and then 3N aqueous HCl. The combined organic layers were back extracted with ether and the combined organic extracts dried, filtered and concentrated. The residue was diluted with THF (10 mL) and treated with TBAF (10 mL of a 1.0M THF solution, 10.0 mmol) and the mixture stirred overnight. The mixture was diluted with water and extracted with 3 portions of ethyl acetate. The combined organic fractions were washed with water, brine, dried, filtered and concentrated. The rsidue was purified by column chromatography on silica gel (50 g, 30% ethyl acetate/hexanes) to provide 0.15 g (16%) of the title compound. MS (DCI, NH$_3$): 292 (MH)$^+$.

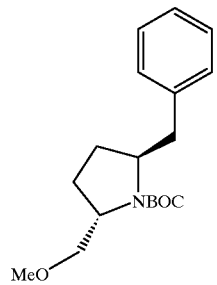

EXAMPLE 1118D

N-t-butoxycarbonyl-2(S)-methoxymethyl-5-benzylpyrrolidine

A solution of example 1118C (224 mg, 0.77 mmol) in 1 mL of DMF wa treated with methyl iodide (96 µL, 1.54 mnmol) and cooled in an ice bath. The mixture was treated with sodium hydride (60%, 62 mg, 1.54 mmol) and after 10 minutes the cooling bath removed and stirring continued for 2 hours. The reaction was quenched by the addition of water and the the mixture diluted with water and extracted with 3 portions of ethyl ether. The combined organic fractions were washed with water, brine, dried filtered and concentrated. The residue was purified by column chromatography on silica gel (20 g, 20% ethyl acetate/hexane) to provide 158 mg (67%) of the title compound. MS (DCI, NH$_3$): 306 (MH)$^+$.

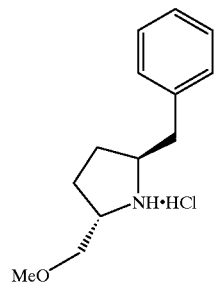

EXAMPLE 1118E

2(S)-methoxymethyl-5-benzylplyrrolidine, hydrochloride salt

Following the procedure of example 1106C, example 1118D (152 mg, 0.5 mmol) provided 110 mg, (91%) of the title compound. MS (DCI, NH$_3$): 306 (MH)$^+$.

EXAMPLE 1118F

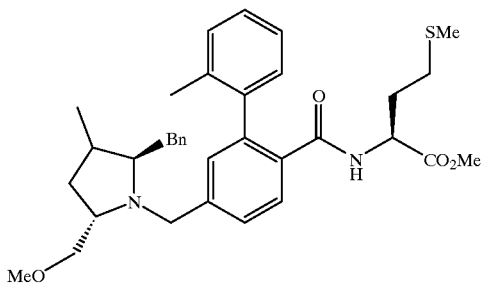

N-[4-(2-methoxymethyl-5-benzylpyrrolidin-1-ylmethyl)-2-(2-methylphenyl)benzoyl]methionine, methyl ester Following the procedure of example 1106D, part 1, example 1118E (106 mg, 0.44 mmol) provided 95 mg (41%) of the title compound. MS (ESI+): 575 (MH+): (ESI−): 573 (M−H).

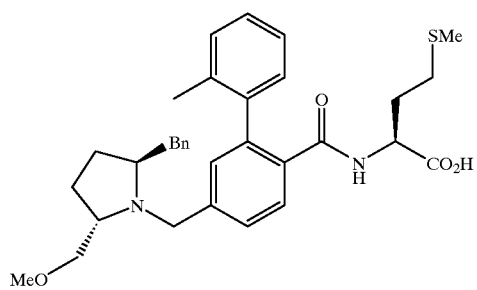

EXAMPLE 1118G

N-[4-(2-methoxymethyl-5-benzylpyrrolidin-1-ylmethyl)-2-(2-methylphenyl)benzoyl]methionine Following the procedure of example 1105D, example 1118F (88 mg, 0.15 mmol) provided 50 mg (60%) of the title compound. $^1$H nmr (300 MHz., dmso d6): δ 8.11, d, 1H; 7.48, m, 2H; 7.19, m, 8H; 7.03, d, 2H; 4.22, m, 1H; 4.08, d, 1H; 3.93, d, 1H; 3.22, s, 3H; 3.09, m, 2H; 2.94, dd, 1H; 2.37, dd, 1H; 1.99–0.22, m, 4H; 1.97, s, 3H; 1.78, bm, 2H; 1.56, m, 2H; 1.42, m, 2H. MS (ESI+): 561 (MH+): (ESI−): 559 (M−H). Calc'd for $C_{33}H_{40}N_2O_4S \cdot 0.43\ H_2O$; C, 69.72; H, 7.24; N, 4.93; Found: C, 69.72; H, 7.11; N, 4.78.

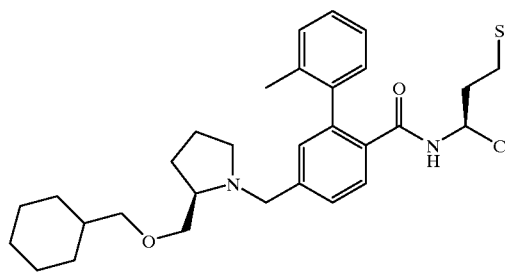

EXAMPLE 1119

N-[4-(2-cyclohexylmethoxymethylpyrrolidin-1-ylmethyl)-2-(2-methylphenyl)benzoyl]methionine

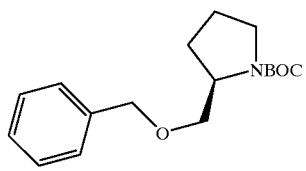

EXAMPLE 1119A

N-t-Butoxycarbonyl-2(R)-benzyloxymethylpyrrolidine

Following the procedure of example 1109F, N-t-butoxycarbonyl-2(R)-hydroxymethylpyrrolidine (1.06 g, 5.00 mmol) provided 1.20 g (82%) of the title compound. MS (DCI, $NH_3$): 292 (MH)+.

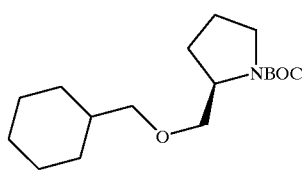

EXAMPLE 1119B

N-t-Butoxycarbonyl-2(R)-cyclohexylmethoxymethylpyrrolidine

Following the procedure of example 1109G, example 1119A (0.60 g, 2.06 mmol) provided 0.59 g (97%) of the title compound. MS (DCI, $NH_3$): 298 (MH)+.

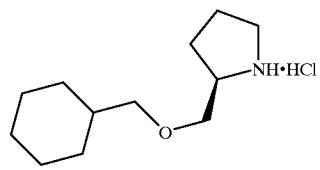

EXAMPLE 1119C

2(R)-cyclohexylmethoxymethylpyrrolidine, hydrochloride salt

Following the procedure of example 1106C, example 1119B (573 mg, 1.93 mmol) provided 467 mg (100%) of the title compound. MS (DCI, $NH_3$): 198 (MH)+.

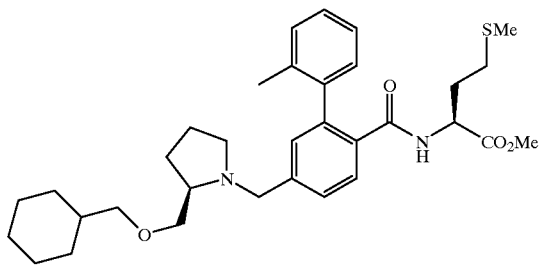

EXAMPLE 1119D

N-[4-(2-cyclohexylmethoxymethylpvrrolidin-1-ylmethyl)-2-(2-methylphenyl)benzoyl]methionine, methyl ester Following the procedure of example 1106C, example 1119C (175 mg, 0.75 mmol) provided 181 mg (64%) of the title compound. MS (ESI+): 567 (MH+): (ESI–): 565 (M–H).

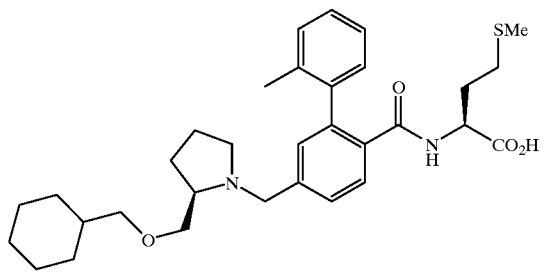

EXAMPLE 1119E

N-[4-(2-cyclohexylmethoxymethylpyrrolidin-1-ylmethyl)-2-(2-methylphenyl)benzoyl]methionine Following the procedure of example 1104D, example 1119D (174 mg, 0.31 mmol) provided 163 mg (95%) of the title compound. $^1$H nmr (300 MHz., dmso d6): δ 8.10, d, 1H; 7.47, d, 1H; 7.36, d, 1H; 7.20, m, 2H; 7.11, m, 3H; 4.21, m, 1H; 4.17, d, 1H; 3.48, d, 1H; 3.18, m, 2H; 2.85, m, 1H; 2.76,m, 1H; 1.98–2.30, m, 7H; 1.97, s, 3H; 1.70–1.90, m, 3H; 1.62, m, 7H; 1.49, m, 2H; 1.10, m, 4H; 0.88, m, 2H. MS (ESI+): 553 (MH+): (ESI–): 551 (M–H). Calc'd for $C_{32}H_{44}N_2O_4S \cdot 0.50\ H_2O$; C, 68.42; H, 8.07; N, 4.99; Found: C, 68.47; H, 7.82; N, 4.77.

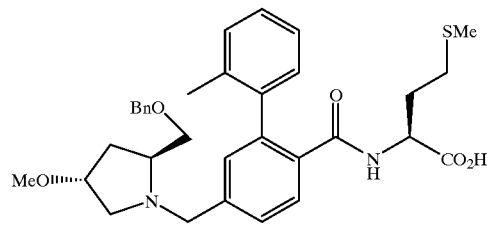

EXAMPLE 1120

N-[4-(2-benzyloxymethyl-4-methoxypyrrolidin-1-ylmethyl)-2-(2-methylphenyl)benzoyl]methionine

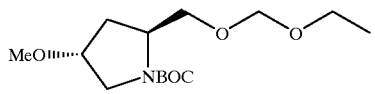

EXAMPLE 1120A

N-t-Butoxycarbonyl-2(S)-ethoxymethyloxymethyl-4(R)-methoxypyrrolidine

Following the procedure of example 1118D, example 1117C (0.76g, 2.76 mmol) provided 0.64 g (80%) of the title compound. MS (DCI, NH$_3$): 290 (MH)$^+$.

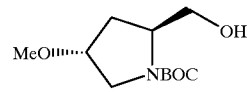

EXAMPLE 1120B

N-t-Butoxycarbonyl-2(S)-hydroxymethyl-4(R)-methoxypyrrolidine

Following the procedure of example 1117F, example 1120A (0.64g, 2.21 mmol) provided 0.39 g (77%) of the title compound. MS (DCI, NH$_3$): 232 (MH)$^+$.

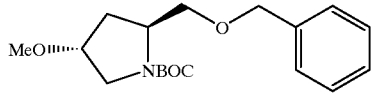

EXAMPLE 1120C

N-t-Butoxycarbonyl-2(S)-Benzyloxymethyl-4(R)-methoxypyrrolidine

Following the procedure of example 1109F, example 1120B (0.39 g, 1.68 mmol) provided 0.42 g (78%) of the title compound. MS (DCI, NH$_3$): 332 (MH)$^+$.

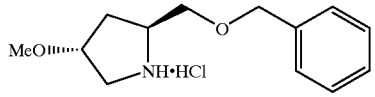

EXAMPLE 1120D

2(S)-Benzyloxymethyl-4(R)-methoxypyrrolidine, hydrochloride salt

Following the procedure of example 1106C, example 1120C (0.41 g, 1.28 mmol) provided 0.32 g (97%) of the title compound. MS (DCI, NH$_3$): 232 (MH)$^+$.

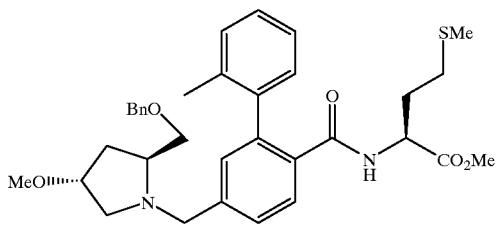

EXAMPLE 1120E

N-[4-(2-benzyloxymethyl-4-methoxypyrrolidin-1-ylmethyl)-2-(2-methylphenyl)benzoyl]methionine, methyl ester Following the procedure of example 1106D, part 1, example 1120D (0.26 g, 1.00 mmol) provided 0.21 g (70%) of the title compound. MS (ESI+): 591 (MH+): (ESI−): 589 (M−H).

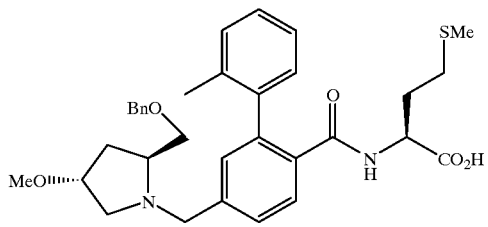

EXAMPLE 1120F

N-[4-(2-benzyloxymethyl-4-methoxypyrrolidin-1-ylmethyl)-2-(2-methylphenyl)benzoyl]methionine Following the procedure of example 1104D, example 1120E (197 mg, 0.33 mmol) provided 163 mg (86%) of the title compound. $^1$H nmr (300 MHz., dmso d6): δ 8.12, d, 1H; 7.48, d, 1H; 7.36, dd, 1H; 7.27, m, 5H; 7.20, m, 2H; 7.13, m, 3H; 4.48, s, 2H; 4.21, m, 2H; 3.82, m, 1H; 3.53, m, 2H; 3.42, m, 2H; 3.14, s, 3H; 1.99–2.30, m, 6H; 1.96, s, 3H; 1.64–1.90, m, 4H. MS (ESI+): 577 (MH+): (ESI−): 575 (M−H). Calc'd for $C_{33}H_{40}N_2O_5S.0.55\ H_2O$; C, 67.56; H, 7.06; N, 4.77; Found: C, 67.56; H, 7.02; N, 4.80.

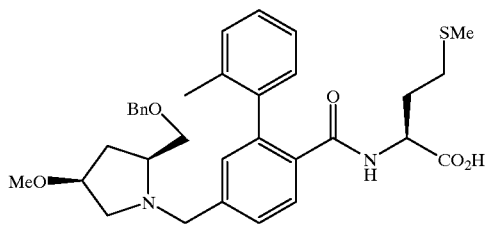

EXAMPLE 1121

N-[4-(2-benzyloxymethyl-4-methoxypyrrolidin-1-ylmethyl)-2-(2-methylphenyl)benzoyl]methionine

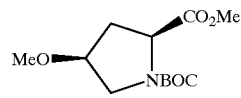

EXAMPLE 1121A

N-t-Butoxycarbonyl-4(S)-methyoxy-L-proline, methyl ester

Following the procedure of example 1118D, N-t-butoxycarbonyl-4(S)-hydroxy-L-proline, methyl ester (1.22 g, 5.00 mmol) provided 1.04 g (80%) of the title compound. MS (DCI, NH$_3$): 260 (MH$^+$); 277 (M+NH$_4$)$^+$.

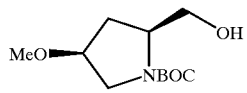

EXAMPLE 1121B

N-t-Butoxycarbonyl-2(S)-hydroxymethyl-4(S)-methyoxypyrrolidine

Following the procedure of example 1109E, example 1121A (1.03 g, 3.97 mmol) provided 0.83 g (90%) of the title compound. MS (DCI, NH$_3$): 232 (MH$^+$).

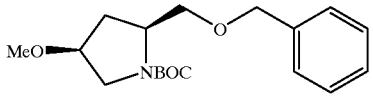

EXAMPLE 1121C

N-t-Butoxycarbonyl-2(S)-benzyloxymethyl-4(S)-methyoxypyrrolidine

Following the procedure of example 1109F, example 1121B (0.41 g, 1.78 mmol) provided 0.46 g (80%) of the title compound. MS (DCI, NH$_3$): 322 (MH$^+$).

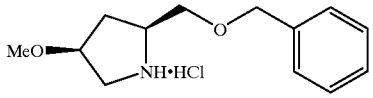

EXAMPLE 1121D

2(S)-benzyloxymethyl-4(S)-methyoxypyrrolidine, hydrochloride salt

Following the procedure of example 1106C, example 1121C (228 mg, 0.71 mmol) provided 183 mg (100%) of the title compound. MS (DCI, NH$_3$): 222 (MH$^+$).

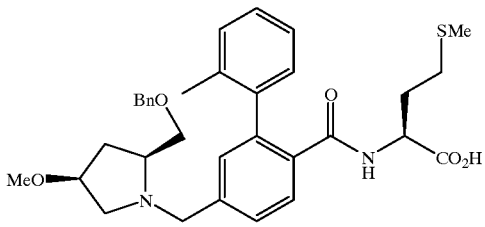

EXAMPLE 1121E

N-[4-(2-benzyloxymethyl-4-methoxypyrrolidin-1-ylmethyl)-2-(2-methylphenyl)benzoyl]methionine, methyl ester Following the procedure of example 1106D, part 1, example 1121D (178 mg, 0.69 mmol) provided 210 mg (71%) of the title compound. MS (ESI+): 591 (MH+): (ESI−): 589 (M−H).

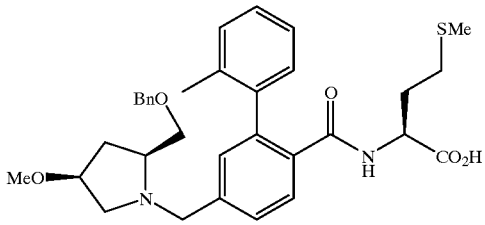

EXAMPLE 1121F

N-[4-(2-benzyloxymethyl-4-methoxypyrrolidin-1-ylmethyl)-2-(2-methylphenyl)benzoyl]methionine Following the procedure used in example 1104D, example 1121E (204 mg, 0.34 mmol) provided 195 mg (99%) of thetitle comppound. $^1$H nmr (300 MHz., dmso d6): δ 8.08, d, 1H; 7.45, d, 1H; 7.33, d, 1H; 7.28, m, 5H; 7.21, m, 2H; 7.14, m, 3H; 4.49, s, 2H; 4.22, m, 1H; 4.18, m, 1H; 3.79, m, 1H; 3.56, dd, 1H; 3.43, dd, 1H; 3.0 9, s, 3H; 2.90, d, 1H; 2.75, m, 1H; envelope 1.99–2.35, 11H; 1.97, s, 3H; 1.78, bm, 2H; 1.51, ddd, 1H. MS (ESI+): 577 (MH+): (ESI−): 575 (M−H). Calc'd for $C_{33}H_{40}N_2O_5S \cdot 0.45 H_2O$; C, 67.77; H, 7.05; N, 4.79; Found: C, 67.80; H, 6.93; N, 4.62.

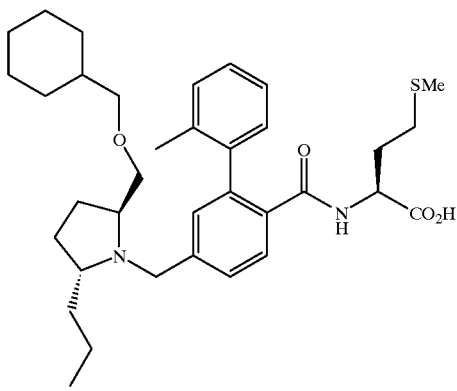

EXAMPLE 1122

N-[4-(2-cyclohexyloxymethyl-5-propylpyrrolidin-1-ylmethyl)-2-(2-methylphenyl)benzoyl]methionine

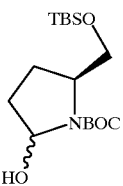

EXAMPLE 1122A

N-t-Butoxycarbonyl-2(R,S)-hydroxy-5(S)-t-buiyldimethylsiloxmethylpyrrolidine

Example 1118B (3.10 g, 9.36 mmol) was dissolved in 20 mL of toluene and cooled in a dry ice/acetone bath. The cold solution was treated with diisobutylaluminum hydride (9.4 mL of a 1.5M toluene solution, 14.0 mmol), the dry ice bath was removed and the mixture stirred for 2 hours. The mixture was cooled in an ice/acetone bath and quenched by the careful addition of 10 mL of a 10% methanol/toluene solution. After the ceasation of bubbling, the mixture was treated with 75 mL of 1N aqueous HCl and 100 mL of ether and vigorously stirred for 30 minutes and poured into a separatory funnel. The layers were separated and the aqueous layer was extracted with 2 portions of ether and the combined organic fractions were washed with 1N HCl, water and brine, dried, filtered and concentrated to provide 2.93 g (94%) of the title compound. MS (DCI, NH$_3$): 332 (MH$^+$); 314 (M+NH$_4$)$^+$—H$_2$O.

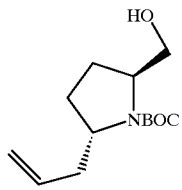

EXAMPLE 1122B

N-t-Butoxycarbonyl-5(S)-allyl-2(S)-hydroxymethylpyrrolidine

A solution of example 1122A (663 mg, 2 mmol) and allyltrimethylsilane (1.2 mL, 8 mmol) in 12 mL methylene chloride was cooled in a dry ice/acetone bath and treated with boron trifluoride etherate (0.49 mL, 4.00 mmol) dropwise. The solution was stirred for 30 minutes and then the dry ice bath was replaced with an ice/acetone bath and the mixture stirred an additional 30 minutes and quenched by the addtion of 2M sodium carbonate. The mixture was diluted with water and methylene chloride and the layers separated. The aqueous phase was extracted with 2 additional portions of methylene chloride and the combined organic fractions were dried, filtered and concentrated. The residue was dissolved in 4 mL of THF and treated with TBAF (4 mL of a 1.0M THF solution, 4 mmol) and the mixture stirred overnight. The reaction was partitioned between water and 3 portions of ethyl acetate. The combined organic extracts were washed with water, brine, dried, filtered and concentrated. The residue was purified by column chromatography on silica gel (25 g, 30% ethyl acetate/hexanes) to provide 227 mg (47%) of the title compound. MS (DCI, NH₃): 242 (MH⁺).

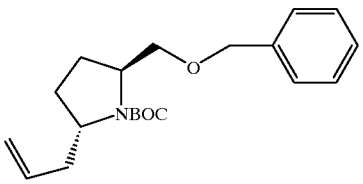

EXAMPLE 1122C

N-t-Butoxycarbonyl-5(S)-allyl-2(S)-benzyloxymethylpyrrolidine

Following the procedure of example 1109F, example 1122B (223 mg, 0.92 mmol) provided 250 mg (82%) of the title compound. (DCI, NH₃): 332 (MH⁺).

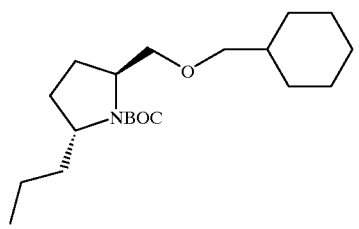

EXAMPLE 1122D

N-t-Butoxcarbonyl-5(R)-propyl-2(S)-cyloenzylomethyloxymethylpyrrolidine

Following the procedure of example 1109G, example 1122C (245 mg, 0.74 mmol) provided 246 mg (100%) of the title compound. (DCI, NH₃): 340 (MH⁺).

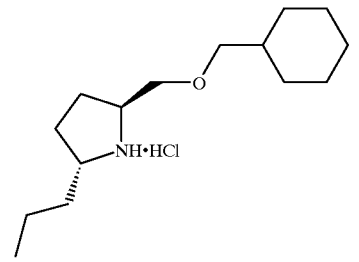

EXAMPLE 1122E

5(R)-propyl-2(S)-cyclohexylmethyloxymethylpyrrolidine, hydrochloride salt

Following the procedure of example 1106C, example 1122D (245 mg, 0.74 mmol) provided 204 mg (100%) of the title compound. (DCI, NH₃): 240 (MH⁺).

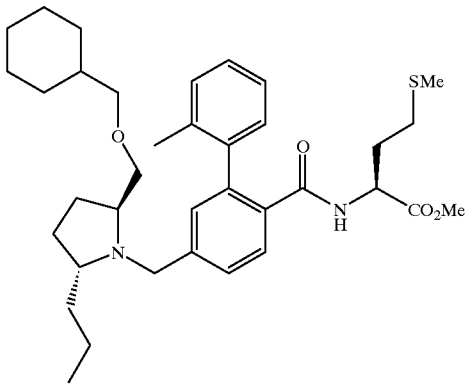

EXAMPLE 1122F

N-[4-(2(S)-cyclohexylmethyloxymethyl-5(R)-propylpyrrolidin-1-ylmethyl)-2-(2-methylphenyl)benzoyl]methionine, methyl ester Following the procedure of example 1106D, part 1, example 1122E (204 mg, 0.74 mmol) provided 110 mg (36%) of the title compound, MS (ESI+): 609 (MH+): (ESI–): 607 (M–H).

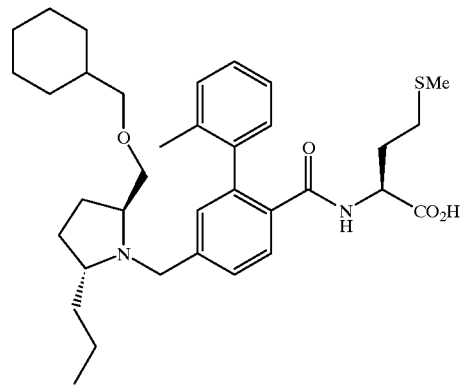

EXAMPLE 1122G

N-[4-(2-cyclohexyloxymethyl-5-propylpyrrolidin-1-ylmethyl)-2-(2-methylphlenyl)benzoyl]methionine Following the procedure of example 1104D, example 1122F (104 mg, 0.17 mmol) provided 87 mg (86%) of the title compound. ¹H nmr (300 MHz., dmso d6): δ 8.04, d. 1H; 7.46, d, 1H; 7.35, d, 1H; 7.20, m, 2H; 7.13, m, 3H; 4.22, m, 1H; 3.83, dd, 2H; 3.08, m, 2H; 3.04, d, 2H; 2.88, pentet, 1H; 2.63, m, 1H; 1.99–2.24, m, 6H; 1.96, s, 3H; 1.77, bm, 4H; 1.59, m, 6H; envelope 1.00–1.55, 11H; 0.81, m, 5H. MS (ESI+): 595 (MH+): (ESI–): 593 (M–H). Calc'd for $C_{35}H_{50}N_2O_4S \cdot 0.55 H_2O$; C, 69.51; H, 8.52; N, 4.63; Found: C, 69.54; H, 8.32; N, 4.58.

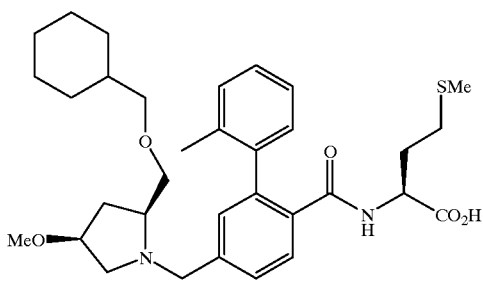

EXAMPLE 1123

N-[4-(2(S)-cyclohexylmethoxymethyl-4(R)-methoxypyrrolidin-1-ylmethyl)-2-(2-methylphenyl)benzoyl]methionine

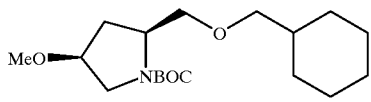

EXAMPLE 1123A

N-t-Butoxycarbonyl-2(S)-cyclohexymethyloxymethyl-4(S)-methyoxypyrrolidine

Following the procedure of example 1109G, example 1112C (227 mg, 0.71 mmol) provided 232 (100%) of the title compound. (DCI, NH$_3$): 328 (MH$^+$).

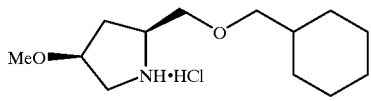

EXAMPLE 1123B

2(S)-cyclohexymethyloxymethyl-4(S)-methyoxypyrrolidine, hydrochloride salt

Following the procedure of example 1106C, example 1123A (232 mg, 0.71 mmol) provided 187 mg (100%) of the title compound. (DCI, NH$_3$): 228 (MH$^+$).

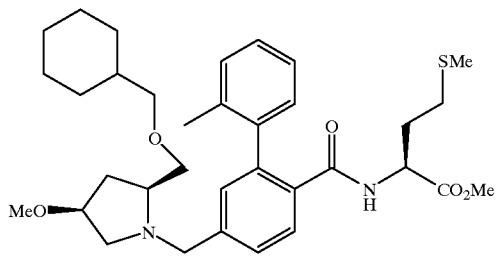

EXAMPLE 1123C

N-[4-(2(S)-cyclohexylmethoxymethyl-4(R)-methoxypyrrolidin-1-ylmethyl)-2-(2-methylphenyl)benzoyl]methionine, methyl ester Following the procedure of example 1106D, part 1, example 1123B (181 mg, 0.69 runol) provided 196 mg (66%) of the title compound. MS (ESI+): 597 (MH+): (ESI–): 595 (M–H).

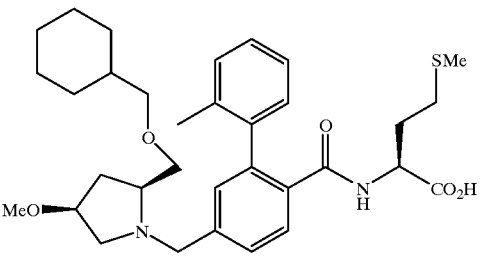

EXAMPLE 1123D

N-[4-(2(S)-cyclohexylmethoxymethyl-4(R)-methoxypyrrolidin-1-ylmethyl)-2-(2-methylphenyl)benzoyl]methionine Following the procedure of example 1104D, example 1123C (190 mg, 0.32 mmol) provided 174 mg (93%) of the title compound. $^1$H nmr (300 MHz., dmso d6): δ 8.12, d, 1H; 7.46, d, 1H; 7.35, dd, 1H; 7.19, m, 2H; 7.13, m, 3H; 4,18, m, 2H; 3.78, m, 1H; 3.45, dd, 1H; 3.29, d, 1H; 3.17, dd, 1H; 3.15, dd, 1H; 3.08, s, 3H; 2.89, bd, 1H; 2.72, m, 1H; 2.29, m, 1H; envelope 1.97–2.25, 6H; 1.96. s, 3H; 1.77, bm, 2H; 1.62, m, 5H; 1.47, m, 2H; 1.12, m, 3H; 0.86, bq, 2H. MS (ESI+): 583 (MH+): (ESI–): 581 (M–H). Calc'd for C$_{33}$H$_{46}$N$_2$O$_5$SH$_2$O; C, 68.01; H, 7.96; N, 4.81; Found: C, 67.96; H, 7.96; N, 4.81.

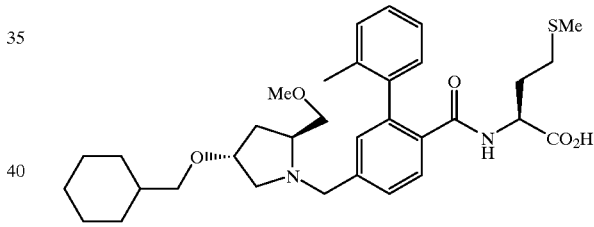

EXAMPLE 1124

N-[4-(3-cyclohexylmethoxy-2-methoxymethylpyrrolidin-1-ylmethyl)-2-(2-methylphenyl)benzoyl]methionine

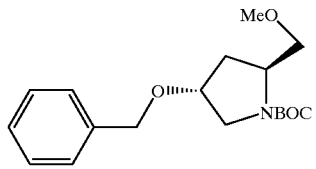

EXAMPLE 1124A

N-t-Butoxycarbonyl-2(S)-methoxymethyl-4(S)-benzyloxypyrrolidine

Following the prodedure of example 1118D, example 1117A (922 mg, 3.00 mmol) provided 0.64 g (67%) of the title compound. (DCI, NH$_3$): 322 (MH$^+$).

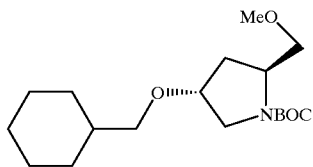

EXAMPLE 1124B

N-t-Butoxycarbonyl-2(S)-methoxymethyl-4(S)-cyclohexylmethyloxypyrrolidine

Following the procedure of example 1109G, example 1124A (0.63 g, 1.96 mmol) provided 0.63 g (99%) of the title compound. (DCI, NH$_3$): 328 (MH$^+$).

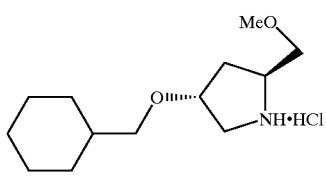

EXAMPLE 1124C

2(S)-methoxymethyl-4(S)-cyclohexylmethyloxypyrrolidine, hydrochloride salt

Following the procedure of example 1106C, example 1124B (627 mg, 1.91 mmol) provided 511 mg (101%) of the title compound. (DCI, NH$_3$): 228 (MH$^+$).

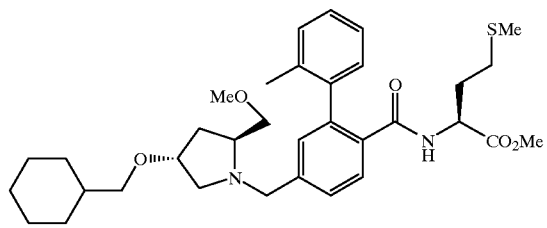

EXAMPLE 1124D

N-[4-(3-cyclohexylmethoxy-2-methoxymethylpyrrolidin-1-ylmethyl)-2-(2-methylphenyl)benzoyl]methionine, methyl ester Following the procedure of example 1106D, part 1, example 1124C (264 mg, 1.50 mmol) provided 209 mg (70%) of the title compound. MS (ESI+): 597 (MH+): (ESI–): 595 (M–H).

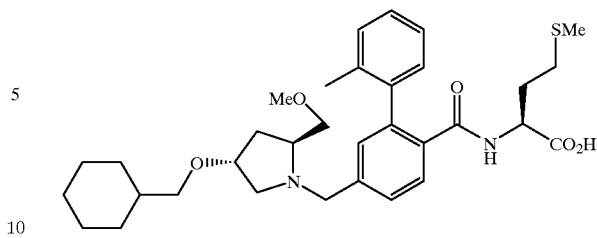

EXAMPLE 1124E

N-[4-(3-cyclohexylmethoxy-2-methoxymethylpyrrolidin-1-ylmethyl)-2-(2-methylphenyl)benzoyl]methionine Following the procedure of example 1104D, example 1124D (197 mg, 0.33 mmol) provided 176 mg (92%) of the title compound. $^1$H nmr (300 MHz., dmso d6): δ 8.14, d, 1H; 7.47, d, 1H; 7.38, d, 1H; 7.22, m, 2H; 7.13, m, 3H; 4.23, m, 1H; 4.13, bd, 1H; 3.87, m, 1H; 3.55, bm, 1H; 3.42, dd, 2H; 3.27, dd, 1H; 3.23, s, 3H; 3.11, dd, 1H; envelope 1.98–2.24, 6H; 1.96, s, 3H; envelope 1.55–1.93, 8H; 1.43, bm, 1H; 1.12–1.30, m, 4H; 0.86. bq, 2H. MS (ESI+): 583 (MH+): (ESI–): 581 (M–H). Calc'd for C$_{33}$H$_{46}$N$_2$O$_5$S.0.50 H$_2$O; C, 66.97; H, 8.00; N, 4.73; Found: C, 67.04; H, 7.97; N, 4.51.

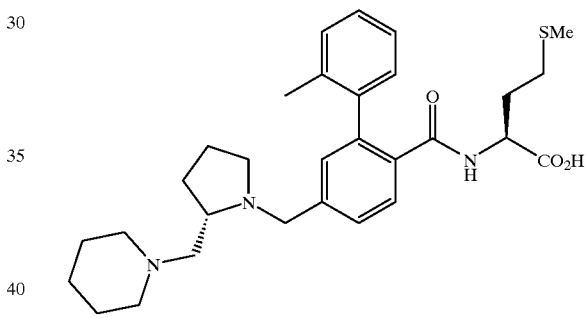

EXAMPLE 1125

N-[4-(2-piperidin-1-ylmethylpyrrolidin-1-ylmethyl)-2-(2-methylphenyl)benzoyl]methionine

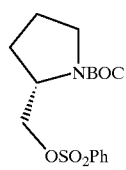

EXAMPLE 1125A

N-t-Butoxycarbonyl-2(S)-phenylsulfonyloxymethylpyrrolidine

A solution of N-t-Butoxycarbonyl-2(S)-hydroxymethylpyrrolidine (2.01 g, 10.00 mmol) and triethyl amine (1.70 mL, 12.00 mmol) in 10 mL of methylene chloride was cooled in an ice bath and treated with benzenesulfonylchloride (1.96 g, 11.00 mmol) and the mixture placed in a refrigerator overnight. The mixture was allowed to reach room temperaure and partioned between ethyl ether and water. The aqueous phase was extracted with ether and the combined organic layers washed with water 1N HCl, saturated sodium bicarbonate, brine, dried, filtered and concentrated. The residue was purified by column chromatography on silica gel (120 g, 25% ethyl acetate/hexanes) to provide 2.82 g (83%) of the title compound. MS (DCI, NH₃): 359 (M+NH₄)⁺.

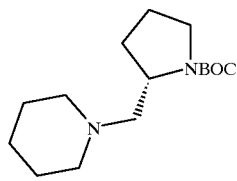

EXAMPLE 1125B

N-t-Butoxycarbonyl-2(S)-piperidinylmethylpyrrolidine

Example 1125B (341 mg, 1.00 mmol) was dissolved in 1 mL of piperidine and the mixture heated in a screw-cap vial to 100° C. for 16 hours. The mixture was cooled to room temperature and concentrated. The residue was partitioned between water and 3 portions of ethyl acetate. The combined organic layers were washed with water, brine, dried filtered and concentrated to provide 234 mg (87%) of the title compound. (DCI, NH₃): 269 MH⁺).

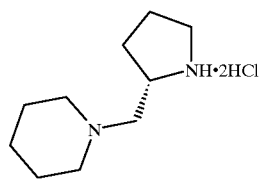

EXAMPLE 1125C

2(S)-piperidinylmethylpyrrolidine, methyl ester

Using the procedure of example 1106C, example 1125C (230 mg, 0.85 mmol) rovided 195 mg (100%) of the title compound. (DCI, NH₃): 159 (MH⁺).

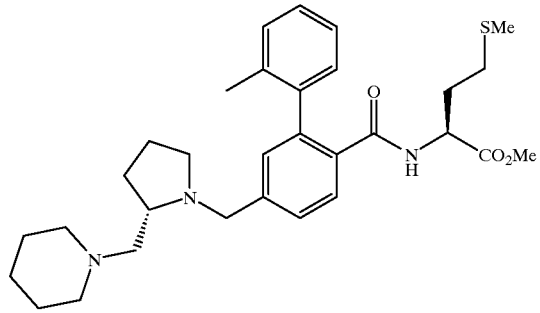

EXAMPLE 1125D

N-[4-(2-piperidin-1-ylmethylpyrrolidin-1-ylmethyl)-2-(2-methylphenyl)benzoyl]methionine, methyl ester Using the procedure described in example 1106D, part 1, example 1125C (195 mg, 0.86 mmol) provided 206 mg (77%) of the title compound. MS (ESI+): 538 (MH+); (ESI−): 536 (M−H).

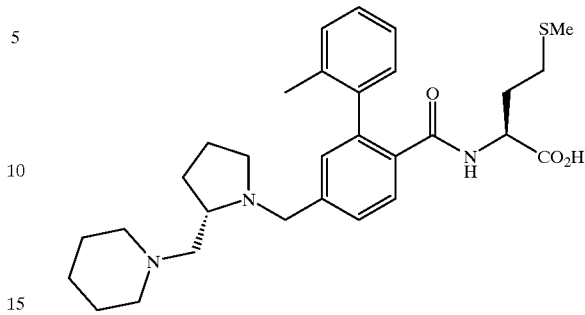

EXAMPLE 1125E

N-[4-(2-piperidin-1-ylmethylpyrrolidin-1-ylmethyl)-2-(2-methylphenyl)benzoyl]methionine Following the procedure of example 1104D, example 1125D (195 mg, 0.36 mmol) provided 117 mg of the title compound. ¹H nmr (300 MHz., dmso d6): δ 8.12, d, 1H; 7.51, d, 1H; 7.43, d, 1H; 7.21, m, 2H; 7.14, m, 3H; 4.22, m, 2H; 3.55, d, 1H; 3.06, m, 1H; 2.90, m, 6H; 2.75, m, 1H; 2.41, m, 1H; 1.97–2.24, m, 6H; 1.96, s, 3H; 1.74, bm, 4H; 1.62, m, 4H; 1.45, m, 2H. MS (ESI+): 524 (MH+): (ESI−): 522 (M−H). Calc'd for $C_{30}H_{41}N_3O_3S.0.65\ H_2O.1.00$ TFA; C, 59.50; H, 6.77; N, 6.71; Found: C, 60.10; H, 6.89; N, 6.46.

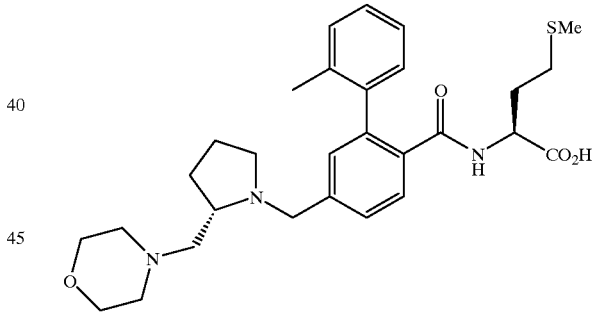

EXAMPLE 1126

N-[4-(2-morpholin-4-ylmethylpyrrolidin-1-ylmethyl)-2-(2-methylphenyl)benzoyl]methionine Prepared according to the procedure of example 1125 by substituting morpholine for piperidine in example 1125B. ¹H nmr (300 MHz., dmso d6): δ 8.17, d, 1H; 7.53, d, 1H; 7.48, d, 1H; 7.28, m, 1H; 7.23, m, 2H; 7.15, m, 2H; 4.39, d, 1H; 4.23, m, 1H; envelope 3.00–3.90, 5H; 2.58, m, 1H; 2.51, m, 3H; 2.42, m, 4H; 1.97–2.24, m, 6H; 1.96, s, 3H; 1.79, bm, 3H; 1.62, m, 1H. MS (ESI+): 524 (MH+): (ESI−): 526 (M−H). Calc'd for $C_{29}H_{39}N_3O_4S.0.65\ H_2O.0.55$ TFA; C, 60.24; H, 6.86; N, 7.00; Found: C, 60.26; H, 6.94; N, 6.87.

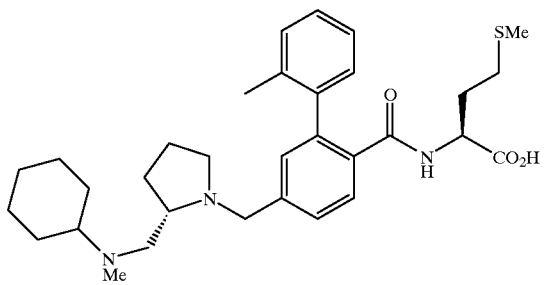

EXAMPLE 1127

N-[4-(2-(N-cyclohexyl-N-methylaminoernethylpyrrolidin-1-ylmethyl)-2-(2-methylphenyl)benzoyl]methionine Prepared according to the procedure of example 1125 by substituting N-methylcyclohexyarine for piperidine in example 1125B. $^1$H nmr (300 MHz., dmso d6): δ 8.00, d, 1H; 7.49, d, 1H; 7.40, d, 1H; 7.20, m, 3H; 7.13, m, 2H; 4.22, m, 1H; 4.18, d, 1H; 3.47, d, 1H; envelope 2.60–2.95. 3H; 2.50, s, 3H; 2.42, s, 2H; 2.33, m, 1H; envelope 1.90–2.22, 6H; 1.96, s, 3H; 1.75, bm, 6H; 1.56, m, 2H; envelope 0.95–1.35, 6H. MS (ESI+): 552 (MH+): (ESI−): 550 (M−H). Calc'd for $C_{32}H_{45}N_3O_3S \cdot 0.75\ H_2O \cdot 0.50\ TFA$; C, 63.69; H, 7.61; N, 6.75; Found: C, 63.69; H, 7.66; N, 6.67.

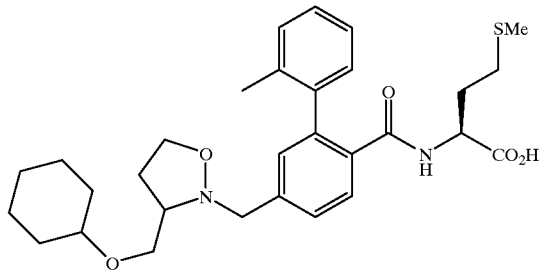

EXAMPLE 1130

N-[4-(3-cyclohexyloxymethylisoxazolidin-2-ylmethyl)-2-(2-methylphenyl)benzoyl]methionine

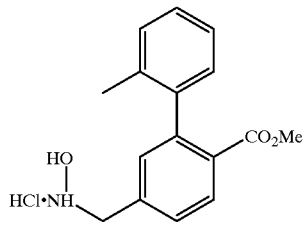

EXAMPLE 1130A

4-N-Hydroxyaminomethyl-2-(2-methylphenyl)benzoic acid, methyl ester

A solution of example 1178D (1.76 g (5.50 mmol) and N,O-bis-t-butoxoycarbonylhydroxylamine (1.09 g, 5.00 mmol) in 10 mL of DMF were cooled in an ice bath and treated with sodium hydride (60%, 0.24 g, 6.00 mmol). After stirring for 4 hours, the mixture was quenched by the addition of pH 6 phosphate buffer and partitioned between water and 3 portion of ethyl ether. The combined organic fractions were washed with water and brine, dried, filtered and concentrated. The residue was dissolved in 10 mL of 4N HCl/dioxane and stirred overnight. The mixture was diluted with ethyl ether and placed in a freezer for 3 days. The precipitate was collected, wshed with ether and dried under vacuum to provide 1.17 g (74%) of the title compound. MS (DCI, NH$_3$): 272 (MH)$^+$; 289 (M+NH$_4$)$^+$.

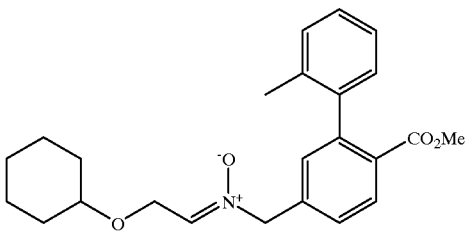

EXAMPLE 1130B 4-(N-Oxy-2-cyclohexyoxyacetaldoximinomethyl)-2-(2-methylphenyl)benzoic acid, methyl ester A solution of example 1130A (1.15 g, 4.29 mmol) and 2-cyclohexyloxyacetaldehyde (0.55 g, 3.90 mmol) in 10 mL of acetonitrile was treated with powdered, activated 4 Å molecular sieves (0.50 g) and potassium hydrogen carbonate (0.47 g. 4.70 mmol) and stirred overnight. The mixture was filtered throught a plug of silica gel (prewetted with ether) and the pad washed well with ether. The filtrate was concentrated to provide 0.82 g (55%) of the title compound. MS (DCI, NH$_3$): 272 (MH)$^+$.

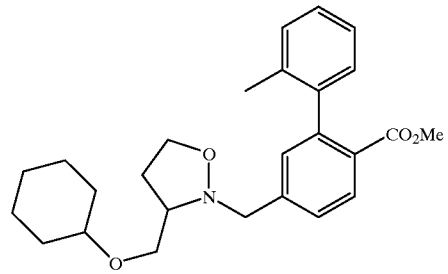

EXAMPLE 1130C

N-[4-(3-cyclohexyloxymethylisoxazolidin-2-ylmethyl)-2-(2-methylphenyl)benzoic acid methyl ester A solution of example 1130B (0.81 g, 2.05 mmol) in 30 mL of chloroform was heated to 75° C. under 640 psi of ethylene for 72 hours. The mixture was cooled to room temperature and vented. The chloroform was evaporated and the residue purified by column chromatograhy on silica gel (40 g, 15% ethyl acetate/hexanes) to provide 363 mg (40%) of the title compound. MS (ESI+): 424 (MH+).

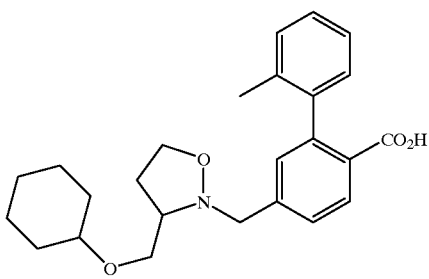

EXAMPLE 1130D

N-[4-(3-cyclohexyloxymethylisoxazolidin-2-ylmethyl)-2-(2-methylphenyl)benzoic acid A mixture of example 1130C (355 mg, 0.84 mmol) and sodium hydroxide (1 mL of a 4N aqueous solution, 4 mmol) in 4 mnL of ethanol was heated to reflux for 6 hours and then cooled to room temperature. The mixture was diluted with water and the pH adjusted to 5 with aqueuos phosphoric acid. The mixture was extracted with 3 portions of ethyl acetate and the combined organic fractions were washed with water and brine, dried, filtered and concentrated to provide 270 mg (78%) of the title compound. MS (ESI+): 410 (MH+).

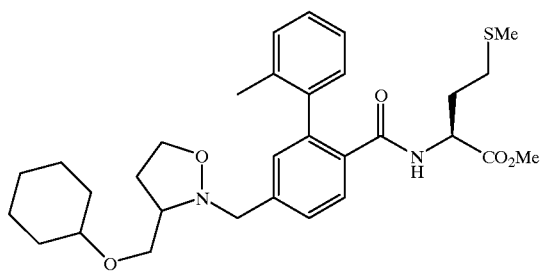

EXAMPLE 1130E

N-[4-(3-cyclohexyloxymethylisoxazolidin-2-ylmethyl)-2-(2-methylphenyl)benzoyl]methionine, methyl ester Following the procedure of example 1178I, example 1130D (265 mg, 0.65 mmol) provided 147 mg (41%) of the title compound. MS (ESI+): 555 (MH+): (ESI-): 553 (M-H).

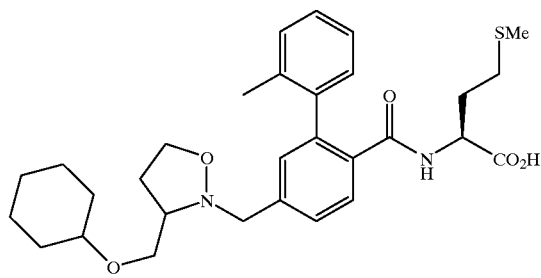

EXAMPLE 1130F

N-[4-(3-cyclohexyloxymethylisoxazolidin-2-ylmethyl)-2-(2-methylphenyl)benzoyl]methionine Following the procedure of example 1104, example 1130E (140 mg, 0.25 mmol) provided 78 mg (70%) after preparative HPLC purification. $^1$H nmr (300 MHz., CDCl$_3$): δ 7.91, m, 1H; 7.56, m, 1H; 7.13–7.35, m, 5H; 5.99, d, 1H; 4.62, m, 2H; 4.41, m, 1H; 4.24, m, 1H; 4.05, m, 1H; 3.91, m, 1H; 3.52, m, 1H; 3.33, m, 1H; 2.40, m, 1H; 2.29, m, 1H; 2.00–2.28, m, 7H; 2.02, s, 3H; 1.89, bm, 3H; envelope, 1.43–1.75, 5H; 1.26, bm, 5H. MS (ESI+): 541 (MH+): (ESI-): 539 (M-H). Calc'd for C$_{30}$H$_{40}$N$_2$O$_5$S.1.10 TFA; C, 58.06; H, 6.22; N, 4.21; Found: C, 57.97; H, 6.28; N, 4.17.

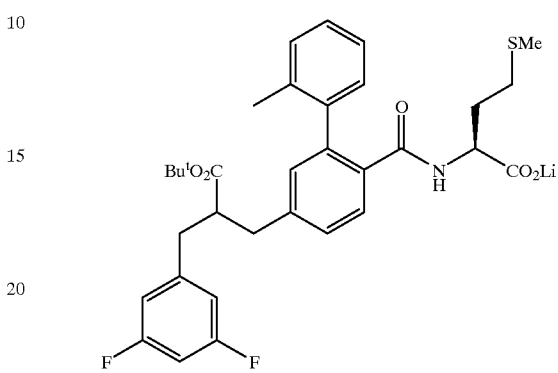

EXAMPLE 1135

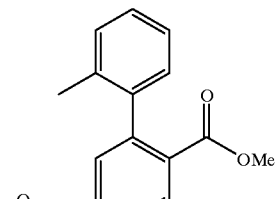

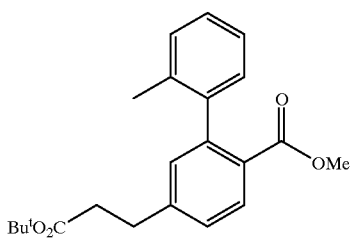

EXAMPLE 1135A

Methyl 4-(tert-Butoxycarbonylethyl)-2-(2-methylphenyl)benzoate

To a solution of (t-butoxycarbonylmethyl)triphenylphosphonium bromide (10.98 g, 24.0 mmol) in THF (150 mL) at 0° C. was added potassium t-butoxide (1.0 M in THF, 24 mL) over 5 min. After 2 h, the aldehyde in THF (10 mL) was added slowly over 5 min., and the reaction was further stirred for 30 min. The reaction mixture was diluted with hexane (200 mL), and the resulting muddy mixture was filtered through silica gel (200 g), rinsed with ether, and concentrated to give an intermediate olefin. $^1$H NMR (300 MHz, CDCl$_3$) δ 7.97 (d, 1 H), 7.59 (d, 1 H), 7.54 (dd, 1 H), 7.37 (d, 1 H), 7.30–7.27 (m, 3 H), 7.06 (d, 1 H), 6.44 (d, 1 H), 3.61 (s, 3 H), 2.06 (s, 3 H), 1.52 (s, 9 H). MS(CI/NH$_3$) m/z: 353 (M+H)$^+$, 370 (M+NH$_4$)$^+$.

That intermediate was mixed with palladium on carbon (10%, 2.0 g) in ethanol (30 mL), and was stirred under a hydrogen balloon overnight. The mixture was then filtered through Celite™ (5 g), and the filtrate was concentrated. The residue was then redesolved in ether (100 mL) and the solution was filtered through silica gel (30 g). Concentration of the filtrate afforded the title compound (7.27 g, 99% for 2 steps). $^1$H NMR (300 MHz, CDCl$_3$) δ 7.91 (d, 1H), 7.28–7.15 (m, 4 H), 7.07–7.03 (m, 2 H), 3.60 (s, 3 H), 2.97 (t, 2 H), 2.57 (t, 2 H), 2.05 (s, 3 H), 1.40 (s, 9 H). MS(CI/NH$_3$) m/z: 355 (M+H)$^+$, 372 (M+NH$_4$)$^+$.

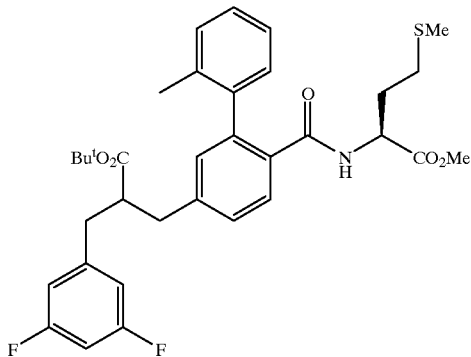

EXAMPLE 1135B

N-[4-(2-t-butoxycarbonyl-3-(3,5-difluorophenyl)propyl)-2-(2-methylphenyl)benzoyl]methionine Methyl Ester To a −78° C. solution of intermediate 1135A (487 mg, 1.32 mmol) in THF (5 mL) was added sodium hexamethyldisilylazide (NaHMDS, 1.0 M in THF, 1.6 ML). After 30 min., 3,5-difluorobenzyl bromide (329 mg, 1.59 mmol) was added to the reaction, and the reaction mixture was then gradually warmed to room temperature over 2 h. The reaction mixture was then partitioned between ethyl acetate (80 mL) and water (20 mL). The organic layer was washed with water (20 mL), brine (20 mL), dried over anhydrous magnesium sulfate, filtered and concentrated. The residue was purified by column chromatography with 8% ethyl acetate in hexane (the product and starting material had identical Rf on TLC) in to give the methyl ester intermediate.

The product obtained from the previous step was stirred with saturated aquous LiOH (2 mL) in MeOH (3 mL) at 50° C. overnight. Then, the reaction mixture was carefully adjusted to pH 3 to 4, and extracted with ethyl acetate (100 mL). The organic layer was rinsed once with brine (15 mL), an dried with anhydrous magnesium sulfate, filtered, and concentrated. The crude monoacid obtained this way was stirred with L-methionine methyl ester hydrochloride (383 mg, 2 mmol), 1-hydroxybenzotriazole (266 mg, 2.0 mmol), triethylamine (303 mg, 3.0 mmol) and 1-ethyl-3-(3-dimethylaminopropyl)carbodiimide (400 mg, 2.0 mmol) in DMF for 5 h. The reaction mixture was then partitioned between ethyl acetate (80 mL) and water (20 mL). The organic layer was washed with water (2×20 mL), brine (20 mL), dried over anhydrous magnesium sulfate, filtered and concentrated. The residue was purified by column chromatography with 20% ethyl acetate in hexane to give the title compound (277 mg, 34% for 3 steps). $^1$H NMR (300 MHz, CDCl$_3$) δ 7.92 (2 d's, 1 H), 7.37–7.12 (m, 5 H), 7.02 (d, 1 H), 6.75–6.60 (m, 3 H), 5.90 (br d, 1 H), 4.62 (m, 1 H), 3.66 (s, 3H), 3.05–2.72 (m, 5 H), 2.17,2.06,2.02,2.00 (4 s's, 6 H), 2.03 (m, 2 H), 1.95 (m, 1 H), 1.60 (m, 1 H), 1.22 (3 s's, 9 H). MS(CI/NH$_3$) m/z: 612 (M+H)$^+$.

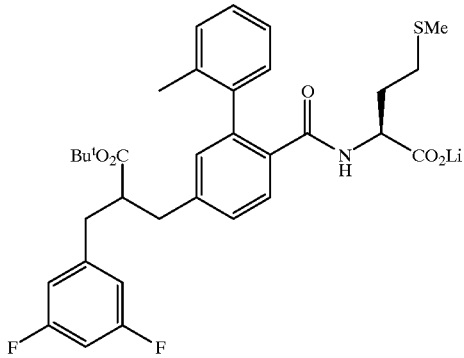

EXAMPLE 1135C

N-[4-(2-t-butoxycarbonyl-3-(3,5-difluorophenyl)propyl)-2-(2-methylphenyl)benzoyl]methionine Lithium Salt The procedure descriped in the Example 403I was used here to convert the intermediate 1135B (66 mg) to the title lithium salt (65 mg, 100%). $^1$H NMR (300 MHz, MeOD-d$_4$) δ 7.52 (br s, 1 H), 7.35–7.21 (m, 5 H), 7.06 (m, 1 H), 6.87–6.72 (m, 3 H), 4.24 (m, 1 H), 3.00–2.85 (m, 5 H), 2.08–1.93 (m, 8 H), 1.84 (m, 1 H), 1.65 (m, 1 H), 1.18–1.12 (3 s's, 9 H). MS(ESI−) m/z: 596 (M−H)$^-$.

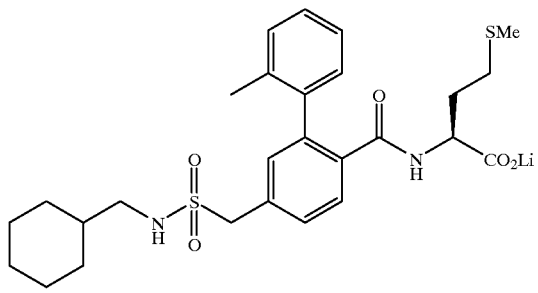

EXAMPLE 1138

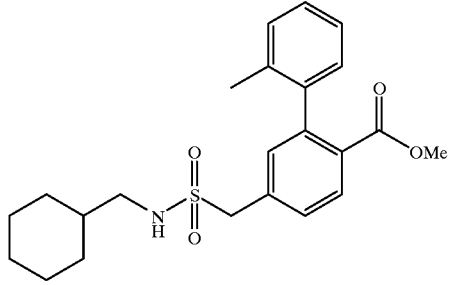

EXAMPLE 1138A

Methyl 4-(N-Cyclohexylmethylaminosulfonylmethyl)-2-(2-methylphenyl)benzoate

To a room temperature solution of 1178D (1.21 g, 3.79 mmol) in THF (10 mL) was added potassium thioacetate (0.48 g, 4.2 mmol). After 5 hours, NaOH (3.5 M in water, 3 mL) was added, and the reaction mixture was stirred another 30 min. Reaction mixture was then acidified with HCl (1.0 M, 15 mL), and partitioned between ethyl acetate (100 mL) and water (10 mL). The organic layer was washed with water (20 mL), brine (20 mL), dried over anhydrous magnesium sulfate, filtered and concentrated.

The residue desolved acetic acid (5 mL) and hydrogen peroxide (30%, 5 mL), and heated at 80° C. for 16 hours. The reaction mixture was diluted with brine (10 mL), and extrated with ethyl acetate (3×30 mL). The combined extrats were washed with brine (20 mL), dried over anhydrous magnesium sulfate, filtered and concentrated to give the crude sulfonic acid. MS(ESI−) m/z: 319 (M−H)−.

The crude sulfonic acid was then refluxed with thionyl chloride (5 mL) and DMF (0.5 mL) for 8 hours. Solvent was then evaporated, and the residue was dried under high vacuum (5 mmHg) for 3 hours. The sulfonyl chloride obtained this way was then desolved in DCM (10 mL), and to it was added cyclohexylmethylamine (0.5 g) and triethylamine (2 mL). Afte 20 min., the reaction was diluted with ether (20 mL), filtered through silica gel (20 g), rinsed with ether (50 mL), and concentrated. The residue was purified by column chromatography with hexane:chloroform:ethyl acetate (50:50: 10) to give the title compound (61 mg, 3.9%, 3 steps). 7.97 (d, 1 H), 7.46 (dd, 1 H), 7.30–7.15 (m, 5 H), 7.05 (br d, 1 H), 4.30 (s, 2 H), 3.61 (s, 3 H), 2.83 (t, 2 H), 2.07 (s, 3 H), 1.80–0.90 (m, 11 H).MS(CI/NH₃) m/z: 433 (M+NH₄)+.

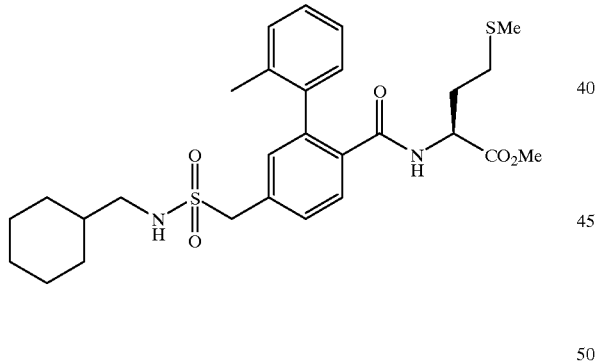

EXAMPLE 1138B

N-[4-N-Cyclohexlmethylaminosulfonylmethyl)-2-(2-methylphenyl)benzoyl]methionine Methyl Ester The procedures descriped in the Example 403E and 403F were used here to convert the above intermediate 1138A (45 mg) to the title methyl ester (37 mg, 63%). ¹HNMR (300 MHz, CDCl₃) δ 7.97 (2 d'd, 1 H), 7.48 (d, 1 H), 7.37–7.22 (m, 5 H), 5.93 (d, 1 H), 4.63 (m, 1 H), 4.29 (s, 2 H), 3.67 (s, 3 H), 2.87 (t, 2 H), 2.20–2.00 (m, 8 H), 2.86 (m, 1 H), 2.80–0.80 (m, 12 H). MS(ESI−) m/z: 545 (M−H)−.

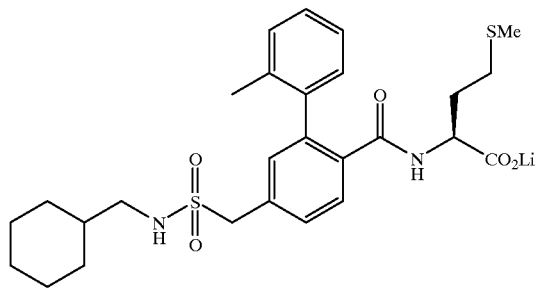

EXAMPLE 1138C

N-[4-(N-Cyclohexylmethylaminosulfonylmethyl)-2-(2-methylphenyl)benzoyl]methionine Lithium Salt The procedure descriped in the Example 403I was used here to convert the intermediate 1135B (32 mg) to the title lithium salt (32 mg, 100%). ¹H NMR (300 MHz, dmso-d₆) δ 7.46 (d, 1 H), 7.36 (m, 1 H), 7.20–6.92 (m, 6 H), 7.08 (m, 1 H), 4.30 (s, 2 H), 3.58 (m, 1 H), 2.64 (br d, 2 H), 2.00–1.80 (m, 8 H), 1.80–0.68 (m, 13 H). MS(ESI−) m/z: 531 (M−H)−.

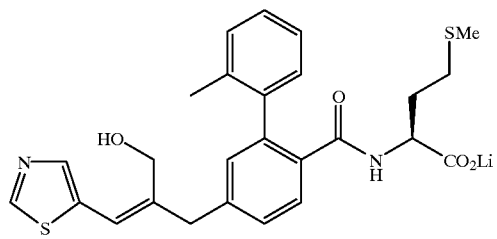

EXAMPLE 1162

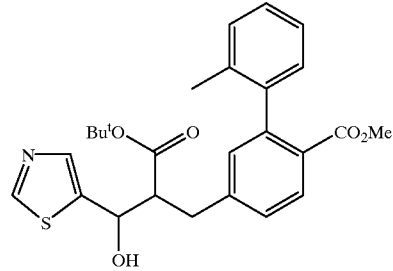

EXAMPLE 1162A

Methyl 4-[2-t-Butoxycarbonyl-3-hydroxy-3-(thiazol-5-yl)propyl]-2-(2-methylphenyl)benzoate To a −78° C. solution of intermediate 1135A (1.75 g, 4.94 mmol) in THF (20 mL) was added sodium hexamethyldisilylazide (1.0 M in THF, 5.9 mL). After 10 min, 5-thiazolcarboxaldehyde (838 mg, 7.41 mmol) in THF (10 mL) was added to the reaction, and the reaction mixture was then gradually warmed to room temperature over 2 h. The reaction mixture was then partitioned between ethyl acetate (80 mL) and water (20 mL). The organic layer was washed with water (20 mL), brine (20 mL), dried over anhydrous magnesium sulfate, filtered and concentrated. The residue was purified by column chromatography with 50% ethyl acetate in hexane to give the title intermediate as a rnnixture of diastereomers (1.41 g, 61%, ratio of diastereomers, 2.5:1). ¹H NMR (300 MHz, CDCl₃) δ 8.90 (2 br s's, 1 H), 7.91 (2 d's, 1 H), 7.80 (2 br s's, 1 H), 7.31–7.25 (m, 5 H), 7.05 (m, 2 H), 5.30,5.05 (2 m'm, 1 H), 3.60 (s, 3 H), 3.14–3.00 (m, 3 H), 2.05 (4 s's, 3 H), 1.26,1.19,1.18 (3 s's, 9 H). MS(CI/NH₃) m/z: 468 (M+H)⁺.

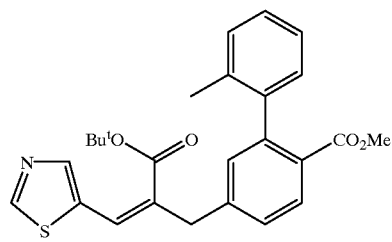

EXAMPLE 1162B

Methyl 4-[E-2-t-Butoxycarbonyl-3-(thiazol-5-yl)prop-2-enyl]-2-(2-methylphenyl)benzoate To a solution of intermediate 1162A (267 mg, 0.57 mmol) in 1,2-dichloroethane (10 mL) was added pyridine (0.5 mL), POCl₃ (0.2 mL) and DBU (5 drops) in that order. After 4 hours at room temperature, the reaction mixture was diluted with ether (10 mL), filtered through silica gel (30 g), rinsed with ether (2×20 mL), and concentrated. The residue was purified by column chromatography with 30% ethyl acetate in hexane to give the title compound as a single isomer (230 mg, 90%). ¹H NMR (300 MHz, CDCl₃) δ 8.81 (s, 1 H), 8.02 (s, 1 H), 7.96 (s, 1 H), 7.89 (d, 1 H), 7.26–7.15 (m, 5 H), 7.02 (m, 2 H), 4.06 (br s, 2 H), 3.59 (s, 3 H), 2.00 (s, 3 H), 1.43 (s, 9 H). MS(CI/NH₃) m/z: 450 (M+H)⁺.

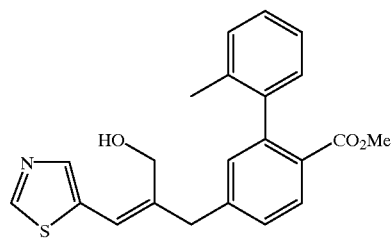

EXAMPLE 1162C

Methyl 4-E-2-Hydroxymethyl-3-thiazol-5-yl)prop-2-enyl]-2-(2-methylphenyl)benzoate A mixture of intermediate 1162B (205 mg, 0.456 mmol) and HCl (anhydrous, 4.0 M in 1,4-dioxane, 2 mL) was stirred for 16 h at room temperature. The reaction mixture was then concentrated to dryness, and the residue was desolved in THF (3 mL) and cooled to 0° C. To it was added isobutyl chloroformate (0.089 mL, 0.685 mmol) and N-methylmorpholine (0.15 mL, 1.4 mmol). After 15 min. at 0° C., sodium borohydride (53 mg, 1.4 mmol) was added to the reaction, followed by addition of methanol (1 mL). The reaction was then stirred at room temperature for 2 hours. The reaction mixture was then partitioned between ethyl acetate (50 mL) and water (5 mL). The organic layer was washed with water (10 mL), brine (10 mL), dried over anhydrous magnesium sulfate, filtered and concentrated. The residue was purified by column chromatography with 50% ethyl acetate in hexane to give the title compound (69.7 mg, 40%). ¹H NMR (300 MHz, CDCl₃) δ 8.70 (s, 1 H), 7.90 (d, 1 H), 7.81 (s, 1 H), 7.27–7.15 (m, 4 H), 7.05 (m, 2 H), 6.93 (s, 1 H), 4.21 (d, 2 H), 3.85 (s, 2 H), 3.59 (s, 3 H), 2.02 (s, 3 H). MS(CI/NH₃) m/z: 380 (M+H)⁺.

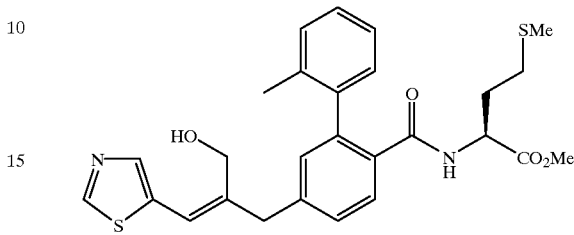

EXAMPLE 1162D

N-{4-[E-2-Hydroxymethyl-3-(thiazol-5-yl)prop-2-enyl]-2-(2-methylphenyl)benzoyl}methionine Methyl Ester The procedures described in the Example 403E and 403F were used here to convert the intermediate 1162D (69 mg) to the title methyl ester (74 mg, 80%). ¹H NMR (300 MHz, CDCl₃) δ 8.78 (s, 1 H), 7.95–7.81 (m, 2 H), 7.35–7.15 (m, 5 H), 7.01 (s, 1 H), 6.94 (s, 1 H), 5.86 (m, 1 H), 4.62 (m, 1 H), 4.22 (s, 2 H), 3.84 (s, 2 H), 3.77 (s, 3 H), 2.14–2.00 (m, 8 H), 1.87 (m, 1 H), 1.60 (m, 1 H). MS(CI/NH₃) m/z: 511 (M+H)⁺.

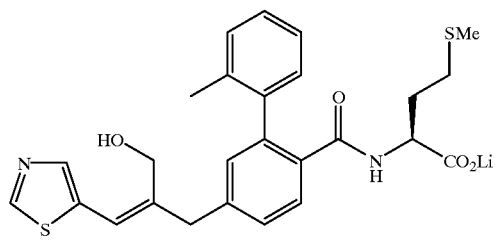

EXAMPLE 1162E

N-{4-[E-2-Hydroxymethyl-3-(thiazol-5-yl)prop-2-enyl]-2-(2-methylphenyl)benzoyl}methionine Lithium Salt The procedure described in the Example 403I was used here to convert the intermediate 1162D (20.2 mg) to the title lithium salt (20 mg, 100%). ¹H NMR (300 MHz, dmso-d₆) δ 8.97 (s, 1 H), 7.90 (s, 1 H), 7.47 (d, 1 H), 7.25 (dd, 1 H), 7.22–7.07 (m, 4 H), 6.92 (m, 2 H), 6.89 (m, 1 H), 5.42 (t, 1 H), 3.99 (d, 2 H), 3.75 (s, 2 H), 3.60 (m, 1 H), 2.08 (m, 1 H), 1.95 (m, 1 H), 1.90 (br s, 6 H), 1.68 (m, 1 H), 1.55 (m, 1 H). MS(ESI-) m/z: 495 (M-H)⁻.

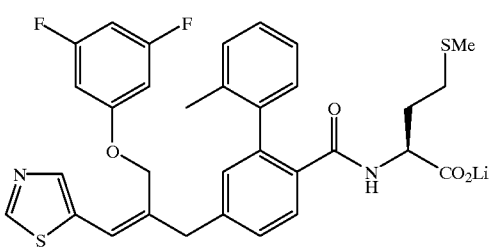

EXAMPLE 1163

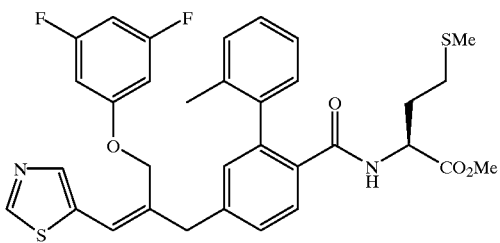

EXAMPLE 1163A

N-{4-[E-2-(3,5-diflourophenoxy)methyl-3-(thiazol-5-yl)prop-2-enyl]-2-(2-methylphenyl)benzoyl}methionine Lithium Salt To a 0° C. solution of triphenylphosphine (55 mg, 0.21 mmol) in DCM (1 mL) was added diethyl azodicarboxylate (36 mg, 0.21 mmol). After 10 min., the solution thus prepared was transfered to a 0° C. solution of intermediate 1162D (35.1 mg, 0.069 mmol) and 3,5-difluorophenol (27.3 mg, 0.21 mmol) in DCM (1 mL). After the reaction mixture was stirred at room temperature for 15 hours, it eas diluted with ether (5 mL), filtered through silica gel (5 g), rinsed with ether (10 mL), and concentrated. The residue was purified twice by column chromatography with 30% ethyl acetate in hexane to give the title methyl ester (13.2 mg, 31%). $^1$H NMR (300 MHz, CDCl$_3$) δ 8.78 (s, 1 H), 7.95–7.85 (m, 2 H), 7.35–7.05 (m, 9 H), 7.02 (s, 1 H), 6.97 (s, 1 H), 5.88 (m, 1 H), 4.62 (m, 1 H 4.49 (s, 2 H), 3.92 (s, 2 H), 3.66 (s, 3 H), 2.17–1.98 (m, 8 H), 1.87 (m, 1 H), 1.60 (m, 1 H). MS(CI/NH$_3$) m/z: 623 (M+H)$^+$.

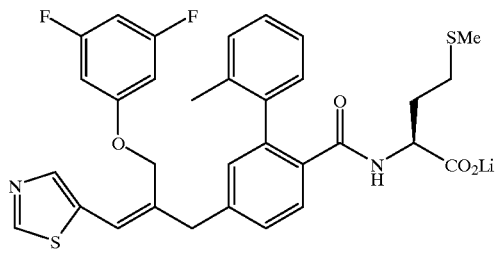

EXAMPLE 1163B

N-{4-[E-2-(3,5-diflourophenoxy)methyl-3-(thiazol-5-yl)prop-2-enyl]-2-(2-methylphenyl)benzoyl}methionine Lithium Salt The procedure descriped in the Example 4031 was used here to convert the intermediate 1163A (13.2 mg) to the title lithium salt (13.0 mg, 100%). $^1$H NMR (300 MHz, dmso-d$_6$) δ 9.05 (s, 1 H), 7.98 (s, 1 H), 7.47 (d, 1 H), 7.25 (dd, 1 H), 7.22–7.07 (m, 5 H), 6.95 (m, 1 H), 6.87 (m, 1 H), 6.80–6.70 (m, 4 H), 4.62 (s, 2 H), 3.87 (s, 2 H), 3.60 (m, 1 H), 2.10–1.92 (m, 2 H), 1.90 (br s, 6 H), 1.68 (m, 1 H), 1.55 (m, 1 H). MS(ESI–) m/z: 607 (M–H)$^-$.

EXAMPLE 1176

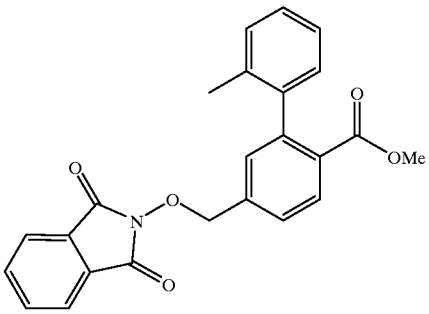

EXAMPLE 1176A

4-Phthalimidoyloxymethyl-2-(2-methylphenyl)benzoic acid methyl ester

To a stirred solution at 0° C. under N$_2$ of 4-hydroxymethyl-2-(2-methylphenyl)benzoic acid methyl ester (5.00 g, 19.5 mmol), prepared as in Example 1178A–C, N-hydroxyphthalimide (3.19 g, 19.5 mmol), and triphenylphosphine (5.12 g, 19.5 mmol) in anhydrous THF (150 ML) was added diethyl azodicarboxylate (3.38 mL, 21.5 mmol). Cooling bath removed and reaction warmed to 50° C. overnight. Solvents concentrated in vacuo, and residue taken up in ether and washed with 2M Na$_2$CO$_3$ (3×), water, and brine. Organic layer dried with Na$_2$SO$_4$, filtered, and concentrated in vacuo. Residue was purified by flash chromatography on silica gel eluting with 20% EtOAc/Hexanes to afford the desired product as a white solid (3.32 g, 41%). $^1$H (300 MHz, CDCl$_3$, δ) 7.99 (1H, d, J=8 Hz), 7.79 (4H, m), 7.63 (1H, dd, J=7&2 Hz), 7.38 (1H, d, J=2 Hz), 7.30–7.10 (3H, m), 7.02 (1H, dd, J=8&2 Hz), 5.26 (2H, s), 3.62 (3H, s), 1.99 (3H, s).

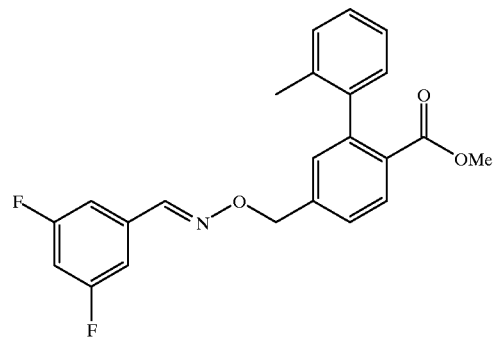

EXAMPLE 1176B 4-(N-(3,5-difluorobenzylidenoyl)aminooxymethyl)-2-(2-methylphenyl)benzoic acid methyl ester To a solutuon under N$_2$ of 4-phthalimidoyloxymethyl-2-(2-methylphenyl)benzoic acid methyl ester (575 mg, 1.43 mmol), prepared as in Example 1176A, in boiling EtOH (10 mL) was added while hot 55% hydrazine hydrate (0.089 mL, 1.58 mmol). Reaction allowed to cool to ambient temperature, and to this mixture was added 3,5-difluorobenzaldehyde (0.172 mL, 1.58 mmol). Reaction stirred overnight at ambient temperature. Solvents concentrated in vacuo, and residue stirred with $CCl_4$ (30 mL) and $MgSO4$ for 15 minutes at ambient temperature. Mixture filtered through celite, and filtrate concentrated in vacuo. Residue was purified by flash chromatography on silica gel eluting with 10% EtOAc/Hexanes to afford the desired product as a pale yellow solid (551 mg, 97%). m/e (ESI) 396 (MH$^+$).

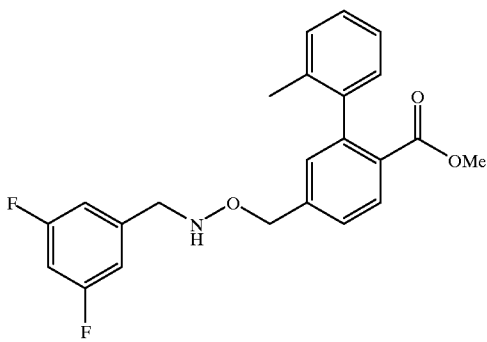

EXAMPLE 1176C 4-(N-(3,5-difluorobenzyl)aminooxymethyl)-2-(2-methylphenyl)benzoic acid methyl ester To a stirred solution at room temperature under $N_2$ of 4-(N-(3,5-difluorobenzylidenoyl)aminooxymethyl)-2-(2-methylphenyl)benzoic acid methyl ester (551 mg, 1.40 mmol), prepared as in Example 1176B, in MeOH (5 mL) was added sodium cyanoborohydride (263 mg, 4.18 mmol) and bromocresol green indicator. To this was added a 1:1 solution of conc. HCl/MeOH dropwise to maintain a yellow-orange color (pH less than 3). After reaction mixture remained yellow, it was allowed to stir 30 minutes at room temperature. Reaction quenched with 1.0M $NaHCO_3$, and product extracted out with EtOAc (2x). Extracts washed with 1.0M $NaHCO_3$ (2x) and brine, dried with $Na_2SO_4$, filtered, and concentrated in vacuo. Residue was purified by flash chromatography on silica gel eluting with 25% EtOAc/Hexanes to afford the desired product. (254 mg, 46%). m/e (ESI) 398 (MH$^+$)

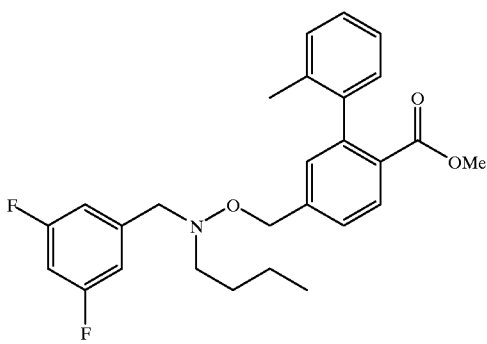

EXAMPLE 1176D 4-(N-Butyl—N-(3,5-difluorobenzyl)aminooxymethyl)-2-(2-methylphenyl)benzoic acid methyl ester To a stirred solution at ambient temperature under $N_2$ of 4-(N-(3,5-difluorobenzyl)aminooxymethyl)-2-(2-methylphenyl)benzoic acid methyl ester (254 mg, 0.640 mmol), prepared as in Example 1176 C, in DMF (2 mL) was added potassium carbonate (265 mg, 1.92 mmol) and 1-iodobutane (0.146 mL, 1.28 mmol). Reaction stirred vigorously at 80° C. overnight. Reaction diluted with EtOAc and washed with water and brine. Organic layer dried with $Na_2SO_4$, filtered, and concentrated in vacuo. Residue was purified by flash chromatography on silica gel eluting with 7% EtOAc/Hexanes to 30% EtOAc/Hexanes to afford the desired product. (44 mg, 15%). m/e (ESI) 454 (MH$^+$)

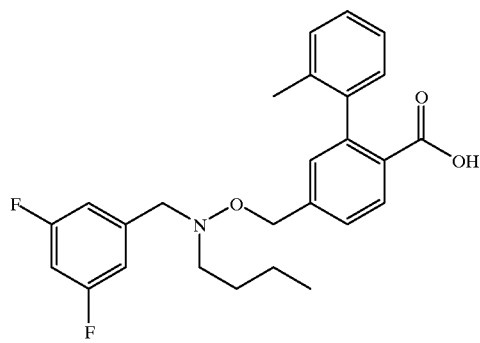

EXAMPLE 1176E 4-(N-Butyl—N-(3,5-difluorobenzyl)aminooxymethyl)-2-(2-methylphenyl)benzoic acid The desired acid was prepared using the method described in Example 403E starting with the compound prepared in Example 1176D.

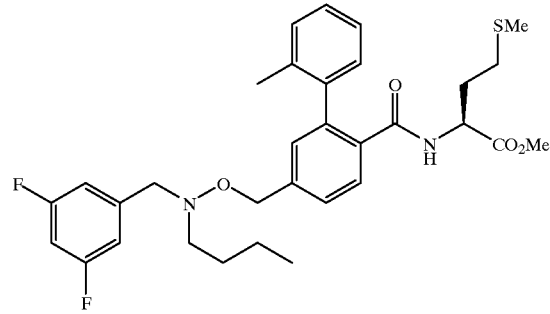

EXAMPLE 1176F

N-[4-N-Butyl-N-(3,5-difluorobenzyl)aminooxymethyl-2-(2-methylphenyl)benzoyl]methionine methyl ester The desired product was prepared using the method described in Example 403F starting with the compound prepared in Example 1176E.

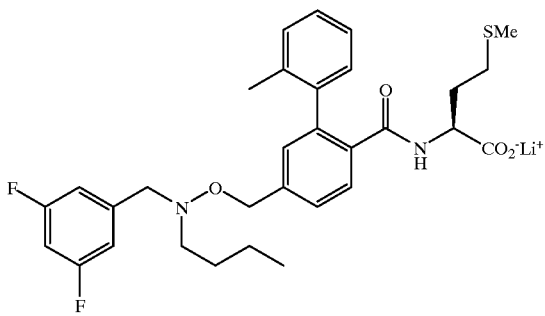

EXAMPLE 1176G

N-[4-N-Butyl-N-(3,5-difluorobenzyl)
aminooxymethyl-2-(2-methylphenyl)benzoyl]
methionine lithium salt The desired compound was prepared according to the method of Example 403I starting with the compound from Example 1176F. $^1$H (300 MHz, CDCl$_3$, δ) 7.70 (1H, m), 7.30–7.00 (6H, m), 6.94 (1H, m), 6.85 (1H, dd, J=7&2 Hz), 6.65 (1H, m), 4.53 (2H, bs), 4.03 (1H, m), 3.80 (2H, bs), 2.72 (2H, t, J=8 Hz), 2.30–1.90 (5H, m), 1.80 (3H, s), 1.58 (2H, m), 1.50–1.20 (4H, m), 0.87 (3H, t, J=8 Hz). m/e (ESI) 569 (MH$^-$)

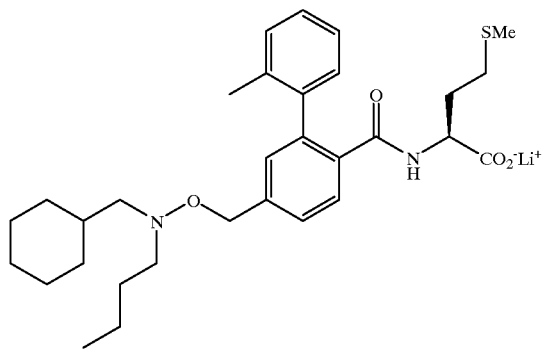

EXAMPLE 1186

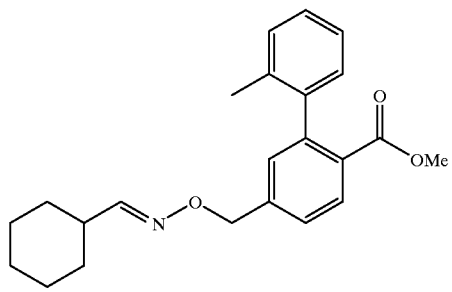

EXAMPLE 1186A

4-N-(Cyclohexylmethylidene)aminooxymethyl-2-(2-methylphenyl)benzoic acid methyl ester The desired product was prepared using the method described in Example 1176B ting with 4-phthalimidoyloxymethyl-2-(2-methylphenyl)benzoic acid methyl ester, ared as in Example 1176A and cyclohexanecarboxaldehyde. m/e (ESI) 366 (MH$^+$)

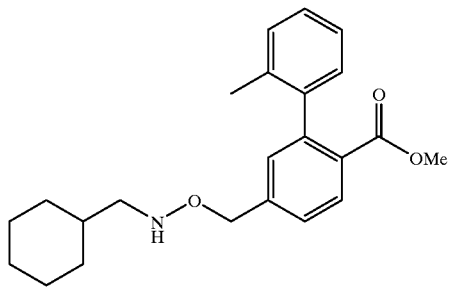

EXAMPLE 1186B

4-N-(Cyclohexylmethyl)arrunooxymethyl-2-(2-methylphenyl)benzoic acid methyl ester The desired product was prepared using the method described in Example 1176C starting with the compound in Example 1186A. m/e (ESI) 368 (MH$^+$)

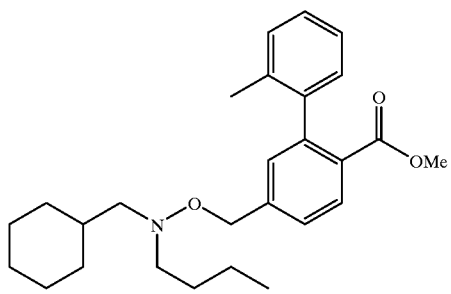

EXAMPLE 1186C

N-[4-N-Butyl-N-(cyclohexylmethyl)
aminooxymethyl-2-(2-methylphenyl)benzoic acid
methyl ester The desired product was prepared using the method described in Example 1176D starting with the compound in Example 1186B. ni/e (ESI) 424 (MH$^+$)

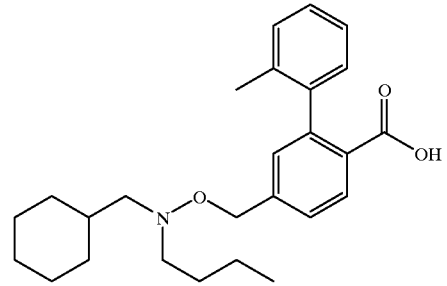

EXAMPLE 1186D

N-[4-N-Butyl-N-(cyclohexylmethyl)
aminooxymethyl-2-(2-methylphenyl)benzoic acid

The desired product was prepared using the method described in Example 403E starting with the compound in Example 1186C.

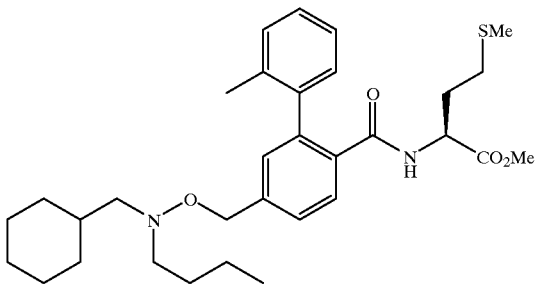

EXAMPLE 1186E

N-[4-N-Butyl-N-(cyclohexylmethyl)
aminooxymethyl-2-(2-methylphenyl)benzoyl]
methionine methyl ester The desired product was prepared using the method described in Example 403F starting with the compound in Example 1186D. m/e (ESI) 555 (MH$^+$)

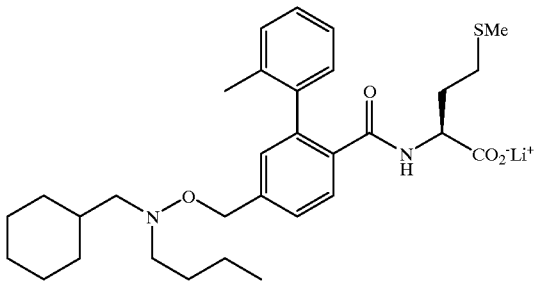

EXAMPLE 1186F

N-[4-N-Butyl-N-(cyclohexylmethyl)
aminooxymethyl-2-(2-methylphenyl)benzoyl]
methionine methyl ester The desired compound was prepared according to the method of Example 403I starting with th compound in Example 1186E. $^1$H (300 MHz, DMSO-d6, δ) 7.53 (1H, d, J=9 Hz), 7.37 (1H, dd, J=7&2 Hz), 7.30–7.05 (5H, m), 6.96 (1H, m), 4.63 (2H, s), 3.68 (1H, m), 2.62 (2H, t, J=8 Hz), 2.42 (2H, d, J=8 Hz), 2.25–1.95 (5H, m), 1.92 (3H, s), 1.80–1.50 (7H, m), 1.42 (3H, m), 1.26 (2H, m), 1.13 (3H, m), 0.85 (5H, t, J=8 Hz). m/e (ESI) 539 (MH$^-$) Anal.calc. for C$_{31}$H$_{43}$LiN$_2$O$_4$S.0.75 H$_2$O C, 66.46, H 8.01, N, 5.00 Found C, 66.43, H, 8.02, N, 4.88.

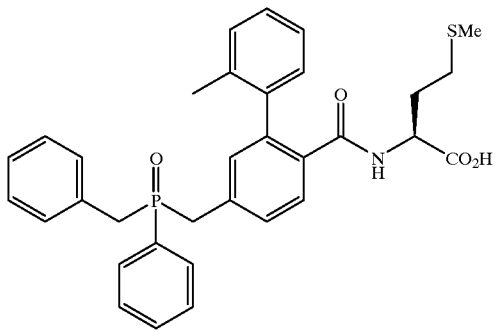

EXAMPLE 1211

N-[4-(Benzylphenyl(oxophosphinyl)methyl)-2-(2-methylphenyl)benzoyl]methionine

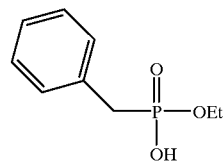

EXAMPLE 1211A

Benzylphosphonic acid monoethyl ester

Diethyl benzylphosphonate (5.0 mL, 5.5 g, 24 mmol) was dissolved in absolute EtOH (25 mL), then 50% NaOH (3 mL) was added. The reaction was heated under reflux overnight, allowed to cool to RT, then partitioned between 2N HCl and EtOAc. Washed organic layer with brine, extracted combined aqueous layers with EtOAc, dried combined organic layers over Na$_2$SO$_4$. After filtration and concentration recovered 4.5 g (93%). MS (DCI/NH$_3$) 201/218 (M+H)$^+$/(M+H+NH$_3$)$^+$.

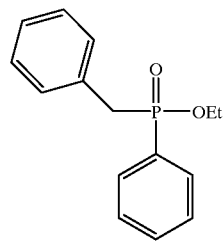

EXAMPLE 1211B

Benzylphenylphosphinic acid ethyl ester

The compound described in Example 1211A (2.5 g, 12.5 mmol) was dissolved in CH$_2$Cl$_2$ (100 mL), cooled to 0–5° C., then added DMF (50 μL) and oxalyl chloride (1.25 mL, 1.82 g, 14.3 mmol). After 15 min. removed the bath, and let the reaction warm to RT over 1 h. The reaction was then concentrated, dissolved in toluene, reconcentrated, dissolved in Et$_2$O (8 mL), and cooled to −10° C. Under N$_2$, 3.0M phenylmagnesium chloride (3.3 mL) was added dropwise (removed bath after ca. 7 mL had been added because the reaction was too thick to stir). Stirred the reaction at RT for 3 h, then partitioned between 2N HCl and Et$_2$O. Washed organic layer with water and brine, then dried over Na$_2$SO$_4$. After filtration and concentration the compound was purified by hromatography using 1/4 hex/EtOAc. Recovered 1.38 g (42%). MS (DCI/NH$_3$) 261/278 (M+H)$^+$/(M+H+NH$_3$)$^+$.

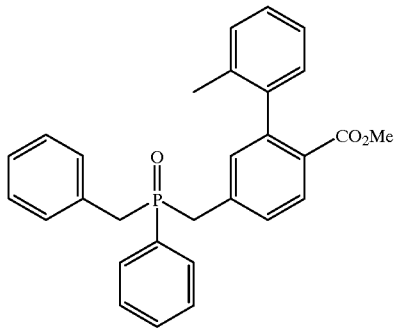

EXAMPLE 1211C 4-(Benzylphenyl(oxophosphinyl)methyl)-2-(2-methylphenyl)benzoic acid methyl ester The title compound was prepared from the compound described in Example 1211B and the bromide described in Example 1178D using the method found in JACS, 94, 1774 (1972).

After chromatography using 1/2 hex/EtOAc the product still contained 35–40% (wt.) starting ethyl phosphinate. MS (APCI) 455 (M+H)$^+$ & 261 (M+H)$^+$ (for starting material).

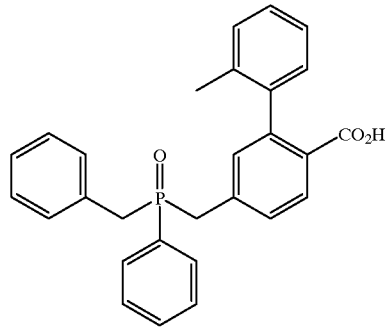

EXAMPLE 1211D 4-(Benzylphenyl(oxophosphinyl)methyl)-2-(2-methylphenyl)benzoic acid The title compound was prepared from the compound described in Example 1211C by the method of Example 1178H. The title compound was seperated from the phosphinic acid by chromatography using 98/2/0.5 CHCl$_3$/MeOH/CH$_3$CO$_2$H. MS (ESI) 439 (M–H)$^-$.

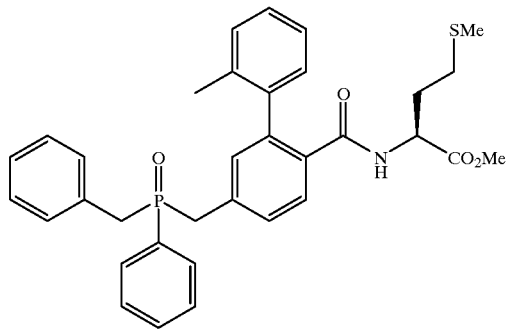

EXAMPLE 1211E

N-[4-(Benzylphenyl(oxophosphinyl)methyl)-2-(2-methylphenyl)benzoyl]methionine methyl ester The title compound was prepared from the compound described in Example 1211D using the method of Example 1205D, except the chromatography used 1.5% EtOH in EtOAc. MS (APCI) 586 (M+H)$^+$.

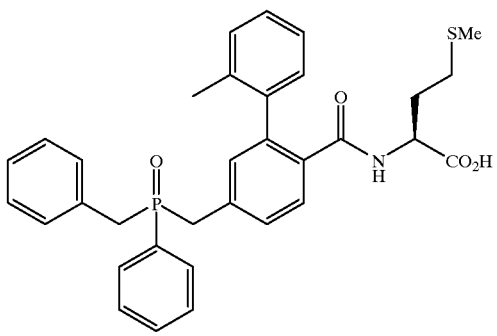

EXAMPLE 1211F

N-[4-(Benzylphenyl(oxophosphinyl)methyl)-2-(2-methylphenyl)benzoyl]methionine

The above compound was prepared from the compound described in Example 1211E according to the method of Example 1178J, except the lithium salt was not made. $^1$H NMR (DMSO-d$_6$) δ 8.08 (m, 1H), 7.68 (m, 2H), 7.45 (m, 4H), 7.36 (d, 1H), 7.17, 7.10, 6.92, 6.82 (all m, total 10H), 4.19 (m, 1H), 3.50 (m, 4H), 2.10, 1.95, 1.80 (all m, total 10H). MS (ESI) 570 (M–H)$^-$. Anal calcd for C$_{33}$H$_{34}$NO$_4$PS.0.15 CHCl$_3$: C, 67.53; H, 5.84; N, 2.38. Found: C, 67.55; H, 5.90; N, 2.24.

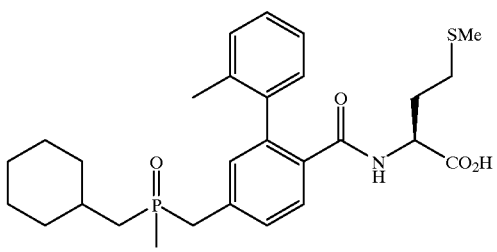

EXAMPLE 1212

N-[4-((Cylohexylmethyl)methyl(oxophosphinyl)methyl)-2-(2-methylphenyl)benzoyl]methionine

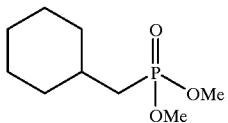

EXAMPLE 1212A

Cyclohexylmethylphosphonic acid dimethyl ester

Using the Grignard reagent made from bromomethyl cyclohexane and dimethyl phosphochloridate, the title compound was prepared by the method found in Engel, Robert, ed. *Synthesis of Carbon—Phosphorous Bonds*, p. 179. Boca Raton, Fla.: CRC Press, 1988. The compound was purified by chromatography using EtOAc. MS (DCI/NH$_3$) 207/224 (M+H)$^+$/(M+H+NH$_3$)$^+$.

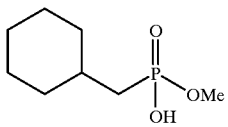

EXAMPLE 1212B

Cyclohexylmethylphosphonic acid monomethyl ester

The title compound was prepared from the compound described in Example 1212A by the method of Example 1211A. MS (DCI/NH$_3$) 193/210 (M+H)$^+$/(M+H+NH$_3$)$^+$.

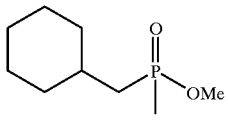

EXAMPLE 1212C (Cyclohexylmethyl)methylphosphinic acid methyl ester

The title compound was prepared from the compound described in Example 1212B and methylmagnesium bromide by the method of Example 1211B. MS (DCI/NH$_3$) 191/208 (M+H)$^+$/(M+H+NH$_3$)$^+$.

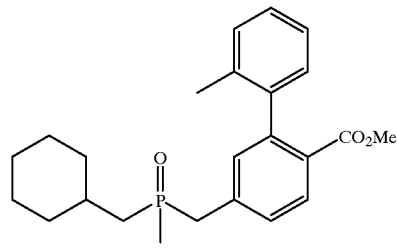

EXAMPLE 1212D 4-((Cylohexylmethyl)methyl(oxophosphinyl)methyl)-2-(2-methylphenyl)benzoic acid methyl ester The title compound was prepared from the compound described in Example 1212C and the bromide described in Example 1178D using the method found in JACS, 94, 1774 (1972), followed by purification with chromatography using EtOAc/EtOH 93/7. MS (DCI/NH$_3$) 399/416 (M+H)$^+$/(M+H+NH$_3$)$^+$.

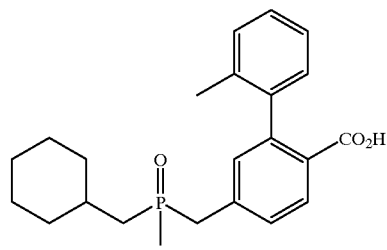

EXAMPLE 1212E 4-((Cylohexlmethyl)methyl(oxophosphinyl)methyl)-2-(2-methlphenyl)benzoic acid The title compound was prepared from the compound described in Example 1212D using the method of Example 1178H. MS (DCI/NH$_3$) 385/402 (M+H)$^+$/(M+H+NH$_3$)$^+$.

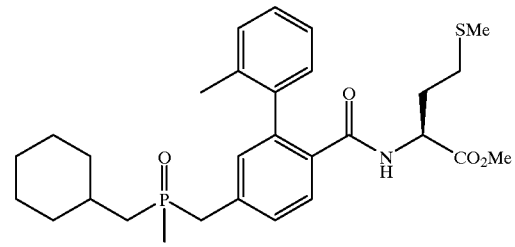

EXAMPLE 1212F

N-[4-((Cylohexylmethyl)methyl(oxophosphinyl)methyl)-2-(2-methylphenyl)benzoyl]methionine methyl ester The above compound was prepared from the compound described in Example 1212E according to the method of Example 1205D. MS (APCI) 530 (M+H)$^+$.

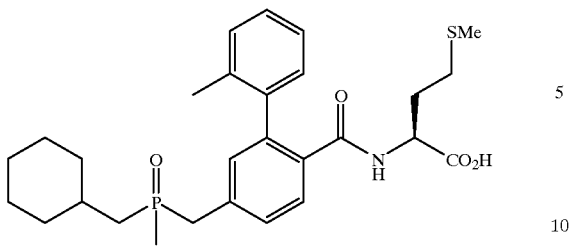

EXAMPLE 1212G

N-[4-(((Cylohexylmethyl)methyl(oxophosphinyl)methyl)-2-(2-methylphenyl)benzoyl]methionine The above compound was prepared from the compound described in Example 1212F according to the method of Example 1178J, except the lithium salt was not made. $^1$H NMR (DMSO-d$_6$) δ 8.08 (d, 1H), 7.46 (d, 1H), 7.30 (d, 1H), 7.20, 7.10 (both m, total 5H), 4.21 (m, 1H), 3.20 (dd, 2H), 2.10 (m, 5H), 1.95 (s, 3H), 1.80, 1.60 (both m, total 10H), 1.30 (d, 3H), 1.20, 1.00 (both m, total 5H). MS (ESI) 514 (M−H)⁻. Anal calcd for C$_{28}$H$_{38}$NO$_4$PS: C, 65.22; H, 7.43; N, 2.72. Found: C, 64.86; H, 7.44; N, 2.60.

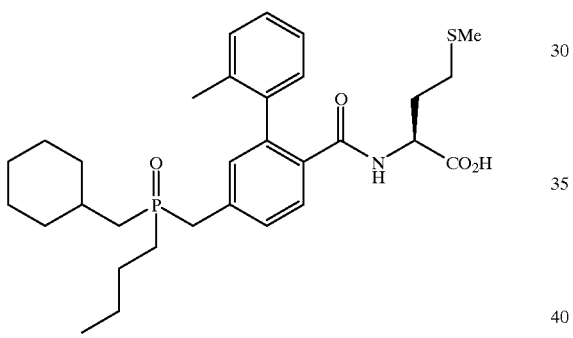

EXAMPLE 1213

N-[4-(((Cylohexylmethyl)butyl(oxophosphinyl)methyl)-2-(2-methylphenyl)benzoyl]methionine

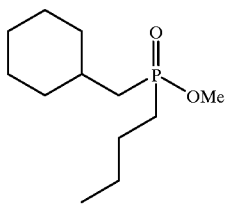

EXAMPLE 1213A (Cyclohexylmethyl)butylphosphinic acid methyl ester

The title compound was prepared from the compound described in Example 1212B and butylmagnesium chloride by the method of Example 1211B. MS (DCI/NH$_3$) 233/250 (M+H)⁺/(M+H+NH$_3$)⁺.

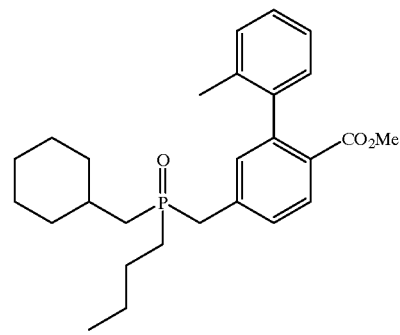

EXAMPLE 1213B 4-((Cylohexylmethyl)butyl(oxophosphinyl)methyl)-2-(2-methylphenyl)benzoic acid methyl ester The title compound was prepared from the compound described in Example 1213A and the bromide described in Example 1178D using the method of Example 1212D. MS (DCI/NH$_3$) 441/458 (M+H)⁺/(M+H+NH$_3$)⁺.

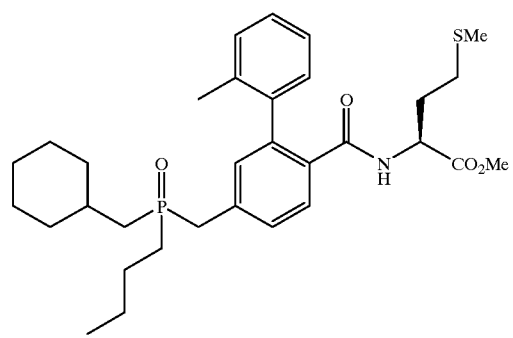

EXAMPLE 1213C 4-((Cylohexylmethyl)butyl(oxophosphinyl)methyl)-2-(2-methylphenyl)benzoic acid The title compound was prepared from the compound described in Example 1213B using the method of Example 1178H. MS (DCI/NH$_3$) 427/444 (M+H)⁺/(M+H+NH$_3$)⁺.

EXAMPLE 1213D

N-[4-((Cylohexylmethyl)butyl(oxophosphinyl)methyl)-2-(2-methlphenyl)benzoyl]methionine methyl ester The above compound was prepared from the compound described in Example 1213C according to the method of Example 1205D. MS (APCI) 572 (M+H)+.

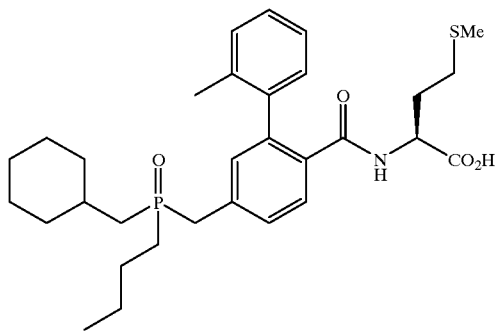

EXAMPLE 1213E

N-[4-((Cylohexylmethyl)butyl(oxophosphinyl)methyl)-2-(2-methylphenyl)benzoyl]methionine The above compound was prepared from the compound described in Example 1213D according to the method of Example 1178J, except the lithium salt was not made. $^1$H NMR (DMSO-d$_6$) δ 8.08 (d, 1H), 7.46 (d, 1H), 7.30 (d, 1H), 7.20, 7.10 (both m, total 5H), 4.21 (m, 1H), 3.20 (d, 2H), 2.10 (m, 5H), 1.97 (s, 3H), 1.85–0.90 (envelope 21H), 0.85 (t, 3H). MS (ESI) 556 (M−H)−. Anal calcd for C$_{31}$H$_{44}$NO$_4$PS: C, 66.76; H, 7.95; N, 2.51. Found: C, 66.73; H, 8.00; N, 2.42.

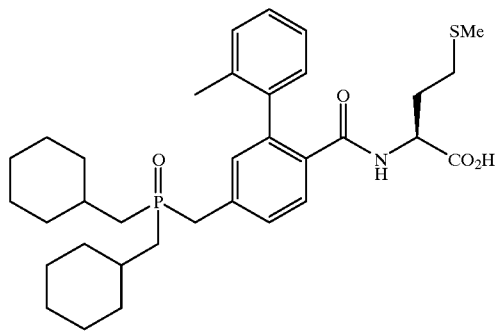

EXAMPLE 1214

N-[4-(Di(cylohexylmethyl)(oxophoslphinyl)methyl)-2-(2-methylphenyl)benzoyl]methionine

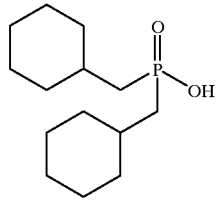

EXAMPLE 1214A

Di(cyclohexylmethylphosphinic acid

Using the Grignard reagent made from bromomethyl cyclohexane, the title compound was prepared by the method found in JACS, 72, 5508 (1950). MS (DCI/NH$_3$) 259/276 (M+H)+/(M+H+NH$_3$)+.

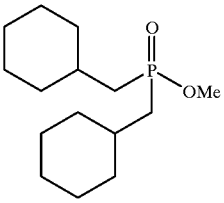

EXAMPLE 1214B

Di(cyclohexylmethyl)phosphinic acid methyl ester

Using the compound described in Example 1214A, the title compound was prepared by the method found in JOC, 59, 7616 (1994)-specifically Method B on p. 7623. MS (DCI/NH$_3$) 273/290 (M+H)+/(M+H+NH$_3$)+.

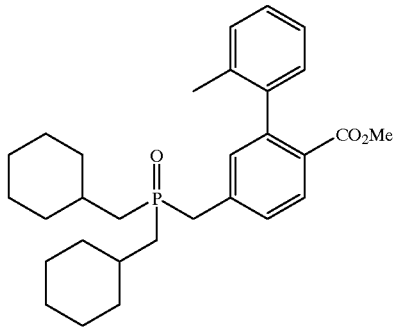

EXAMPLE 1214C 4-(Di(cylohexylmethyl)(oxophosphinyl)methyl)-2-(2-methylphenylibenzoic acid methyl ester The title compound was prepared from the compound described in Example 1214B and the bromide described in Example 1178D using the method of Example 1212D. MS (APCI) 481 (M+H)+.

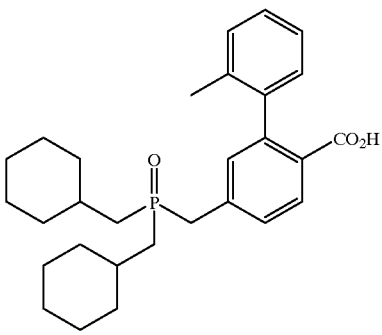

EXAMPLE 1214D 4-(Di(cylohexylmethyl)(oxophosphinyl)methyl)-2-(2-methlphenyl)benzoic acid The title compound was prepared from the compound described in Example 1214C using the method of Example 1178H. MS (APCI) 467 (M+H)$^+$.

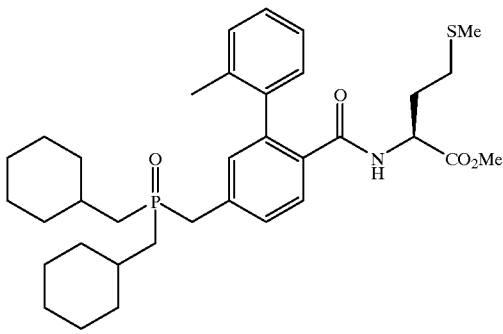

EXAMPLE 1214E

N-[4-(Di(cylohexylmethyl)(oxohosphinyl)methyl)-2-(2-methylphenyl)benzoyl]methionine methyl ester The above compound was prepared from the compound described in Example 1214D according to the method of Example 1205D. MS (APCI) 612 (M+H)$^+$.

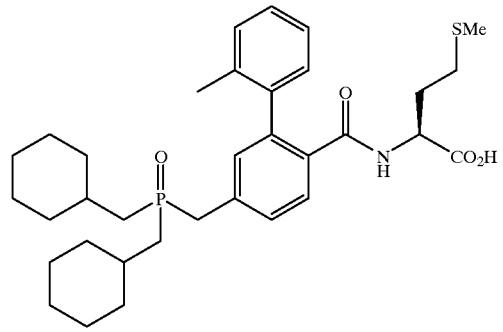

EXAMPLE 1214F

N-[4-(Di(cylohexylmethyl)(oxophosphinyl)methyl)-2-(2-methylphenyl)benzoyl]methionine The above compound was prepared from the compound described in Example 1214E according to the method of Example 1178J, except the lithium salt was not made. $^1$H NMR (DMSO-d$_6$) δ 8.04 (d, 1H), 7.46 (d, 1H), 7.30 (d, 1H), 7.20, 7.10 (both m, total 5H), 4.21 (m, 1H), 3.20 (d, 2H), 2.10 (m, 5H), 1.97 (s, 3H), 1.80, 1.60 (both m, total 18H), 1.20 (m, 6H), 0.95 (m, 4H). MS (ESI) 596 (M–H)$^-$. Anal calcd for C$_{34}$H$_{48}$NO$_4$PS: C, 68.31; H, 8.09; N, 2.34. Found: C, 68.20; H, 8.19; N, 2.36.

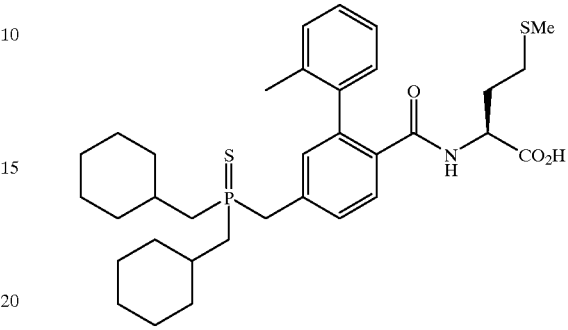

EXAMPLE 1215

N-[4-(Di(cylohexylmethyl)(thiaphosphinyl)methyl)-2-(2-methylphenyl)benzoyl]methionine

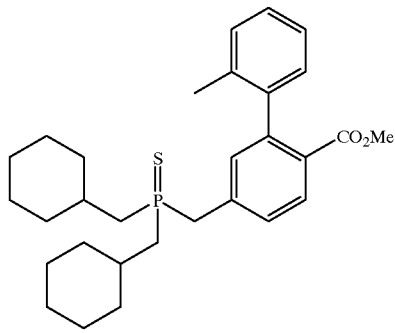

EXAMPLE 1215A 4-(Di(cylohexylmethyl)(thiaphosphinyl)methyl)-2-(2-methylphenyl)benzoic acid methyl ester The compound described in Example 1214C (390 mg, 0.81 mmol) was dissolved in CH$_3$CN (15 mL), then Lawesson's reagent (1.57 g, 3.88 mmol) was added. The reaction was heated under reflux for 3 h, then stirred at RT overnight. After filtration through celite and concentration of the filtrate, purification by chromatography using hex/EtOAc 85/15 gave 335 mg (83%) of the title compound. MS (APCI) 497 (M+H)$^+$.

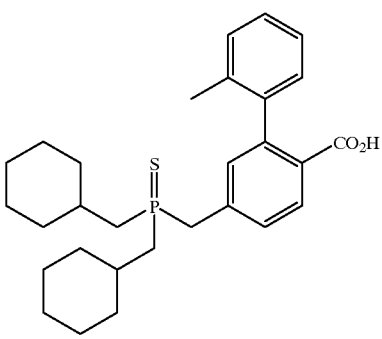

EXAMPLE 1215B 4-(Di(cylohexylmethyl)(thiaphosphinyl)methyl)-2-(2-methylphenyl)benzoic acid The title compound was prepared from the compound described in Example 1215A using the method of Example 1178H. MS (ESI) 483 (M+H)+.

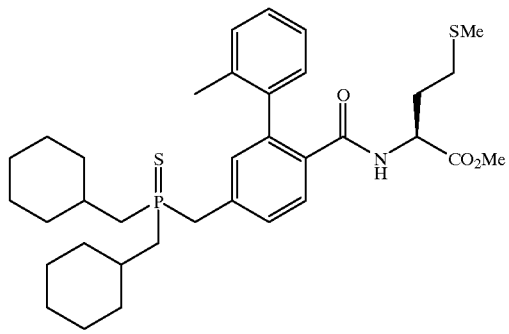

EXAMPLE 1215C 4-(Di(cylohexylmethyl)(thiaphosphinyl)methyl)-2-(2-methylphenyl)benzoyl]methionine methyl ester The above compound was prepared from the compound described in Example 1215B according to the method of Example 1205D. MS (APCI) 628 (M+H)+.

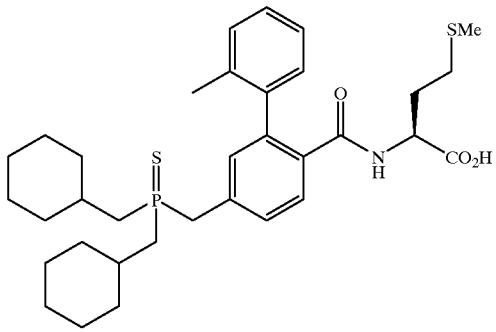

EXAMPLE 1215D

N-[4-(Di(cylohexylmethyl)(thiaphosphinyl)methyl)-2-(2-methylphenyl)benzoyl]methionine The above compound was prepared from the compound described in Example 1215C according to the method of Example 1178J, except the lithium salt was not made. $^1$H NMR (DMSO-$d_6$) δ 8.14 (d, 1H), 7.46 (d, 1H), 7.38 (d, 1H), 7.20, 7.14 (both m, total 5H), 4.21 (m, 1H), 3.40 (d, 2H), 2.10 (m, 5H), 1.97 (s, 3H), 1.80, 1.60 (both m, total 18H), 1.20, 1.00 (both m, total 10H). MS (ESI) 612 (M−H)−. Anal calcd for $C_{34}H_{48}NO_3PS_2$: C, 66.53; H, 7.88; N, 2.28. Found: C, 66.26; H, 7.86; N, 2.19.

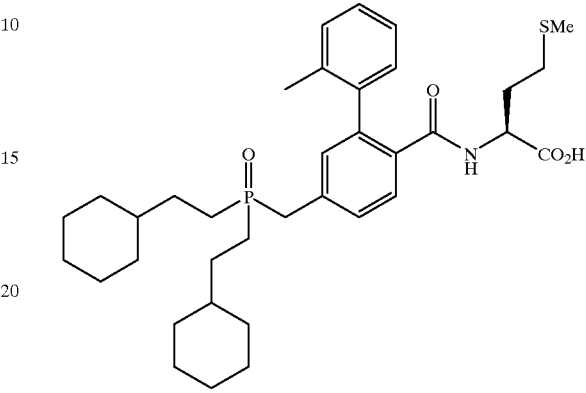

EXAMPLE 1219

N-[4-(Di(2-cylohexylethyl)(oxophosphinyl)methyl)-2-(2-methylphenyl)benzoyl]methionine

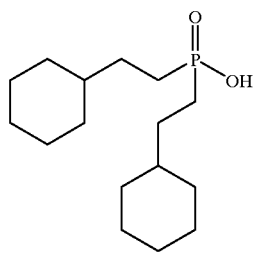

EXAMPLE 1219A

Di(2-cylohexylethyl)phosphinic acid

The bromide described in Example 1207A was converted to the Grignard reagent, then used to prepare the title compound by the method of Example 1214A. MS (DCI/NH$_3$) 287/304 (M+H)+/(M+H+NH$_3$)+.

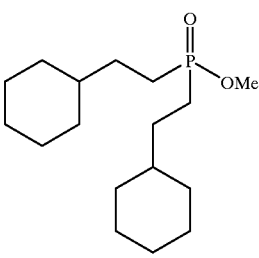

EXAMPLE 1219B

Di(2-cylohexylethyl)phosphinic acid methyl ester

Using the compound described in Example 1219A, the title compound was prepared by the method of Example 1214B. MS (DCI/NH$_3$) 301/318 (M+H)$^+$/(M+H+NH$_3$)$^+$.

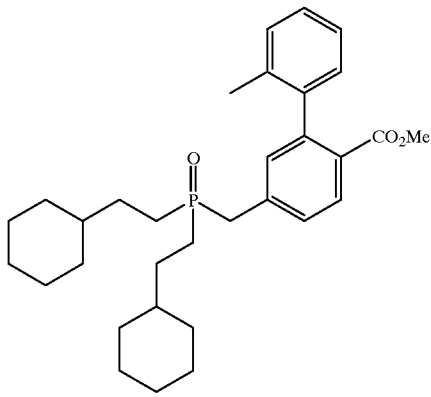

EXAMPLE 1219C 4-(Di(2-cylohexylethyl)(oxophosphinyl)methyl)-2-(2-methylphenyl)benzoic acid methyl ester The title compound was prepared from the compound described in Example 1219B and the bromide described in Example 1178D using the method of Example 1212D. MS (APCI) 509 (M+H)$^+$.

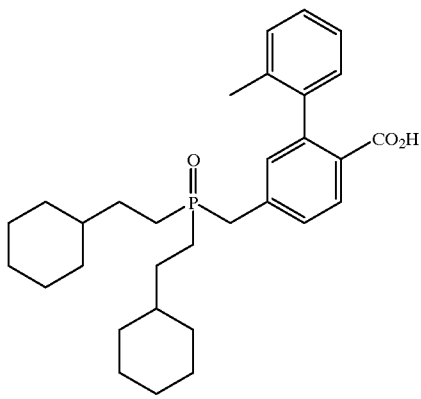

EXAMPLE 1219D 4-(Di(2-cylohexylethyl)(oxophosphinyl)methyl)-2-(2-methylphenyl)benzoic acid The title compound was prepared from the compound described in Example 1219C using the method of Example 1178H. MS (APCI) 495 (M+H)$^+$.

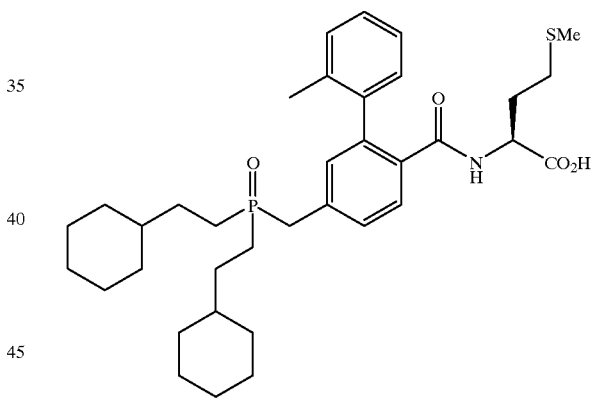

EXAMPLE 1219E

N-[4-(Di(2-cyloheiylethyl)(oxolphosphinyl)methyl)-2-(2-methylphenyl)benzoyl]methionine methyl ester The above compound was prepared from the compound described in Example 1219D according to the method of Example 1205D. MS (APCI) 640 (M+H)$^+$.

EXAMPLE 1219F

N-[4-(Di(2-cylohexylethyl)(oxophosphinyl)methyl)-2-(2-methylphenyl)benzoyl]methionine The above compound was prepared from the compound described in Example 1219E according to the method of Example 1178J, except the lithium salt was not made. $^1$H NMR (DMSO-d$_6$) δ 8.07 (d, 1H), 7.46 (d, 1H), 7.30 (d, 1H), 7.20, 7.10 (both m, total 5H), 4.21 (m, 1H), 3.20 (d, 2H), 2.10 (m, 5H), 1.97 (s, 3H), 1.80, 1.60 (both m, total 16H), 1.32 (m, 4H), 1.15 (m, 8H), 0.83 (m, 4H). MS (ESI) 624 (M−H)$^-$. Anal calcd for C$_{36}$H$_{52}$NO$_4$PS: C, 69.09; H, 8.37; N, 2.24. Found: C, 68.98; H, 8.33; N, 2.20.

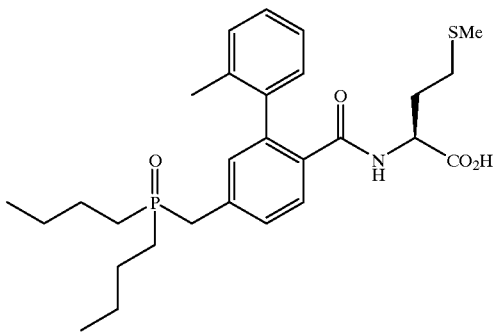

EXAMPLE 1222

N-[4-(Dibutyl(oxophosphinyl)methyl)-2-(2-methylphenyl)benzoyl]methionine

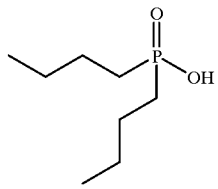

EXAMPLE 1222A

Dibutylphosphinic acid

Using butylmagnesium chloride, the title compound was prepared by the method of Example 1214A. MS (DCI/NH$_3$) 179/196 (M+H)$^+$/(M+H+NH$_3$)$^+$.

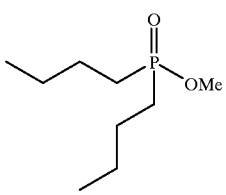

EXAMPLE 1222B

Dibutylphosphinic acid methyl ester

Using the compound described in Example 1222A, the title compound was prepared by the method of Example 1214B. MS (DCI/NH$_3$) 193/210 (M+H)$^+$/(M+H+NH$_3$)$^+$.

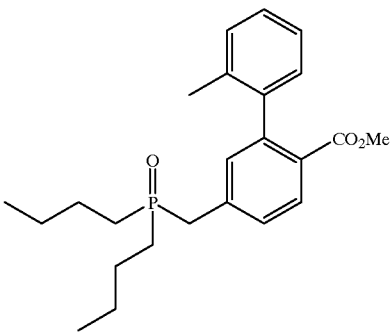

EXAMPLE 1222C 4-(Dibutyl(oxophosphinyl)methyl)-2-(2-methylphenyl)benzoic acid methyl ester The title compound was prepared from the compound described in Example 1222B and the bromide described in Example 1178D using the method of Example 1212D. MS (DCI/NH$_3$) 401/418 (M+H)$^+$/(M+H+NH$_3$)$^+$.

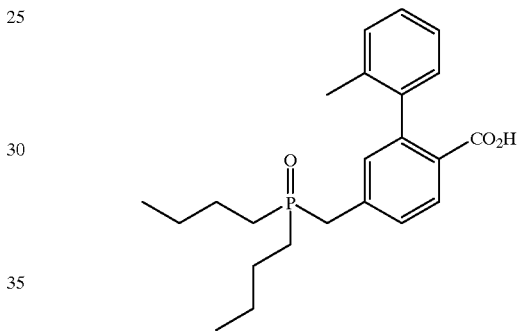

EXAMPLE 1222D 4-(Dibutyl(oxophosphinyl)methyl)-2-(2-methylphenyl)benzoic acid The title compound was prepared from the compound described in Example 1222C using the method of Example 1178H. MS (DCI/NH$_3$) 387/404 (M+H)$^+$/(M+H+NH$_3$)$^+$.

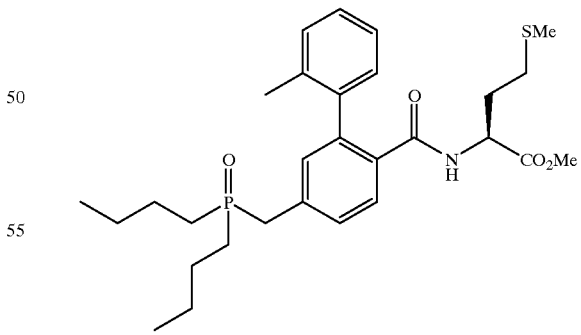

EXAMPLE 1222E

N-[4-(Dibutyl(oxophosphinyl)methyl)-2-(2-methylphenyl)benzoyl]methionine methyl ester The above compound was prepared from the compound described in Example 1222D according to the method of Example 1205D. MS (APCI) 532 (M+H)$^+$.

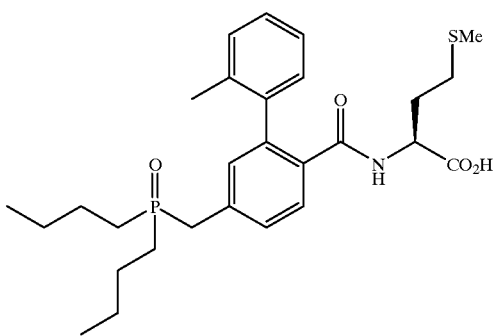

EXAMPLE 1222F

N-[4-(Dibutyl(oxophosphinyl)methyl)-2-(2-methylphenyl)benzoyl]methionine

The above compound was prepared from the compound described in Example 1222E according to the method of Example 1178J, except the lithium salt was not made. $^1$H NMR (DMSO-$d_6$) δ 8.15 (d, 1H), 7.46 (d, 1H), 7.31 (d, 1H), 7.20, 7.10 (both m, total 5H), 4.21 (m, 1H), 3.20 (d, 2H), 2.10 (m, 5H), 1.97 (s, 3H), 1.80 (m, 2H), 1.60 (m, 4H), 1.40 (m, 8H), 0.85 (t, 6H). MS (ESI) 516 (M−H)$^-$. Anal calcd for $C_{28}H_{40}NO_4PS$: C, 64.97; H, 7.79; N, 2.71. Found: C, 64.87; H, 7.83; N, 2.72.

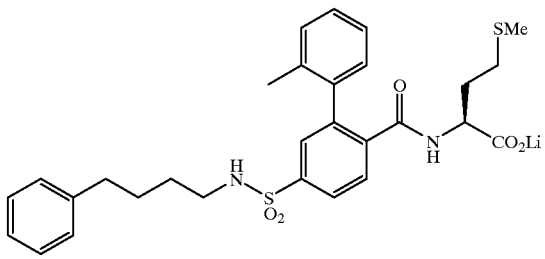

EXAMPLE 1278

N-[4-phenyl-butylaminosulfonyl)-2-phenylbenzoyl]methionine lithium salt

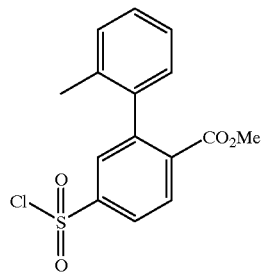

EXAMPLE 1278A 4-amino-2-(2-methylphenyl)benzoic acid methyl ester (4.5 g, 0.018 mol) in an excess of concentrated (38%) hydrochloric acid (25 ml), was diazotized at 0° C. with sodium nitrite (1.45 g, 0.0216 mol). The solution of diazonium chloride was added with stirring to a mixture of sulfur dioxide(40 g), 1,2-dichlorobenzene(10 ml), copper(II) chloride(1.4 g), and potassium chloride(1.4 g) in dioxane(20 ml), and heated to 40–50° C. After the evolution of nitrogen was complete(about 30 min.), water (200 ml) was added and the sulfonyl chloride was extracted with methylene chloride. The organic layer was washed quickly with 10% sodium hydroxide (3*50 ml), followed by washing with water. After drying over anhydrous magnesium sulfate, the organic solvents were removed under reduced pressure. A brown liquid of the title compound(4.8 g, 82%) was obtained. $^1$H NMR: 2.09(3H, s), 3.65(3H, s), 7.0–7.1(1H, d), 7.2–7.4(3H, m), 7.9–8.0(1H, d), 8.1–8.2(2H, m). $^{13}$C NMR: 20.0 ($CH_3$), 52.6($OCH_3$), 125.5, 125.6, 128.4, 129.2, 130.0, 131.0, 135.0, 135.0, 138.6, 144.2, 146.0, 166.0. (DSI/$NH_3$)MS: 324 (M+$NH_4$)$^+$.

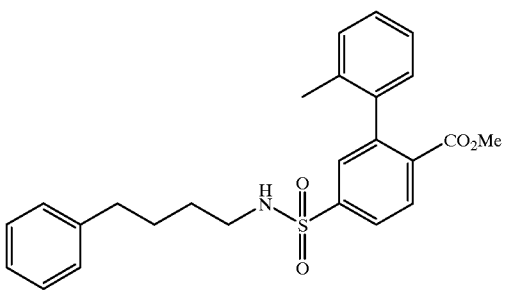

EXAMPLE 1278B

A mixture of 1278B (0.32 g, 1.0 mmol), 4-phenylbutylamine (0.223 g, 1.5 mmol), and 0.2 ml of pyridine in 5 ml of anhydrous methylene chloride was stirred for 12 hours. The reaction mixture was washed by 10% HCl, brine, and dried over anhydrous $MgSO_4$. Flash chromatography of the residue eluting with 4:6EtOAc/Hexane afforded 0.205 g of the title compound. NMR (CDCl$_3$) 8.00–8.05 (m, 1H); 7.85–7.92 (m, 1H); 7.73 (s, 1H); 7.00–7.30 (m, 8H); 4.35–4.45 (m, 1H); 3.65 (s, 3H); 2.95–3.08 (t, 2H); 2.55–2.6 (t, 2); 2.08 (s, 3H); 1.4–1.67 (m, 4H). (DSI/$NH_3$)MS: 455 (M+$NH_4$)$^+$.

EXAMPLE 1278C

Prepared according to the procedure of example 1258C from 1278B NMR(CDCl$_3$) 8.00–8.10 (m, 1H); 7.88–7.94 (m, 1H); 7.73 (s, 1H); 7.10–7.40 (m, 8H); 5.93–6.00 (m, 1H); 4.52–4.60 (m, 1H); 4.32–4.40 (m, 1H); 3.70 (s, 3H); 2.95–3.08 (t, 2H); 2.55–2.62 (t, 2); 2.0–2.2 (m, 10H); 1.70–2.00 (m, 1H); 1.50–1.70 (m, 4H). (DSI/$NH_3$)MS: 569(M+H)$^+$; 586 (M+$NH_4$)$^+$.

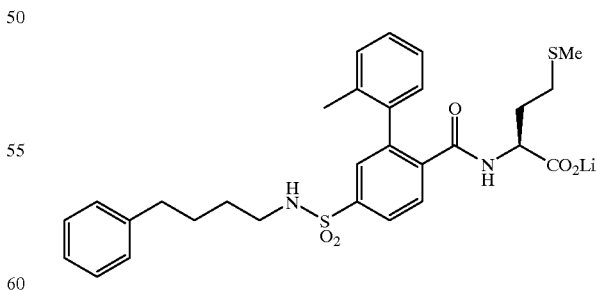

EXAMPLE 1278

N-[4-phenyl-butylaminosulfonyl)-2-phenylbenzoyl]methionine lithium salt

Prepared according to the procedure of example 1178J from 1296C. NMR $^1$H(MeOH-$d_4$): 7.8–7.9 (2H, m); 7.7

(1H, s); 7.1–7.3 (13H, m); 4.2–4.3 (1H, m); 2.85–2.95 (2H, m); 2.5–2.6 (2H, m); 1.6–2.3 (14H, m). ESI(-)/MS: 553 (M—Li).

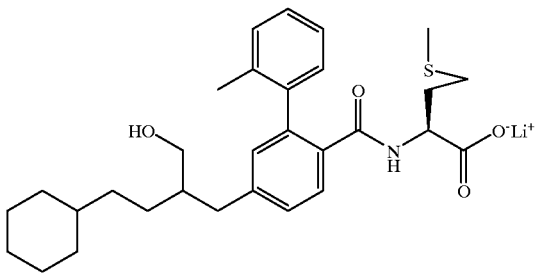

EXAMPLE 1299

N-[4-(2-(2-Cyclohexylethyl)-1-hydroxyprop-3-yl)-2-(2-methylphenyl)benzoyl]methionine Lithium Salt

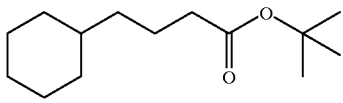

EXAMPLE 1299A tert-Butyl 4-cyclohexylbutyrate

4-Cyclohexylbutyric acid (1.8 g, 10.6 mmol), isobutylene (25 mL) and concentrated sulfuric acid (0.3 mL) were combined in $CH_2Cl_2$ (25 mL) in a pressure bottle. After shaking for 8 days, the pressure bottle was placed in a −78° C. bath and a saturated solution of $NaHCO_3$ was added and the phases separated. The organic phase was dried ($MgSO_4$) and concentrated to afford crude ester as a clear oil (2.3 g). $^1H$ NMR ($CDCl_3$, 300 MHz) δ 0.81–0.94 (m, 2H), 1.14–1.25 (m, 6H), 1.44 (s, 9H) 1.55–1.74 (m, 7H), 2.18 (t, J=7.5 Hz, 2H); MS ($CI/NH_3$) m/z: $(M+H)^+$ 227.

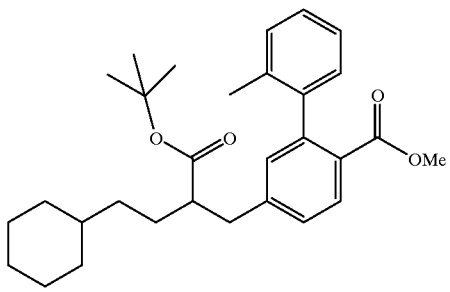

EXAMPLE 1299B

4-[2-(2-Cyclohexylethyl)t-butylpropion-3-yl]-2-(2-methylphenyl)benzoic acid, methyl ester A 1.6M solution of n-BuLi in hexanes (1.7 mL, 2.7 mmol) was added to a solution of diisopropylamine (385 μL, 2.7 mmol) at ambient temperature. After 10 minutes of stirring, the solution was cooled to −78° C. and the product from Example 1299A (600 mg, 2.6 mmol) in THF (2.5 mL) was added to the reaction mixture. After stirring for 15 min, the cold bath was removed. After 30 min of stirring, the mixture was recooled to −78° C. and the product from Example 1308E (1.0 g, 2.7 mmol) in THF (2.0 mL) was added to the reaction mixture. The mixture was allowed to gradually warm to ambient temperature and stir over night. A solution of 2N HCl was added and the mixture extracted with EtOAc (2x). The organic phases were combined, dried ($MgSO_4$) and concentrated. The residue was chromatographed (silica gel; EtOAc/hexanes, 1:40) to afford a clear oil (572 mg, 47%). MS (CI/NH3) m/z: $(M+H)^+$ 465.

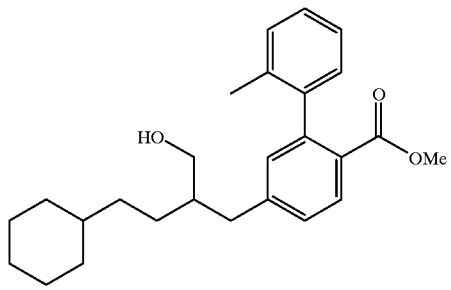

EXAMPLE 1299C

4-[2-(2-Cyclohexylethyl)-1-hydroxyprop-3-yl]-2-(2-methylphenyl)benzoic acid, methyl ester Trifluoroacetic acid (3 mL) was added to a solution of the product from Example 1299B (448 mg, 1.0 mmol) in $CH_2Cl_2$ (3 mL) at ambient temperature. After stirring for 90 min, solvent was evaporated to dryness. MS (CI/NH3) m/z: $(M+H)^+$ 409.

A 1.0M solution of borane THF complex (2.1 mL, 2.1 mmol) was added to a solution of the crude product described above in THF (3 mL) at ambient temperature. After stirring for 6 hours, a 2N solution of HCl was added to the reaction mixture. After 90 min of stirring, the mixture was extracted with EtOAc (2x). The organic phases were combined, dried ($MgSO_4$) and concentrated. The residue was chromatographed (silica gel; EtOAc/hexanes, 1:8) to afford a clear oil (256 mg, 68%). MS ($CI/NH_3$) mlz: $(M+H)^+$ 395.

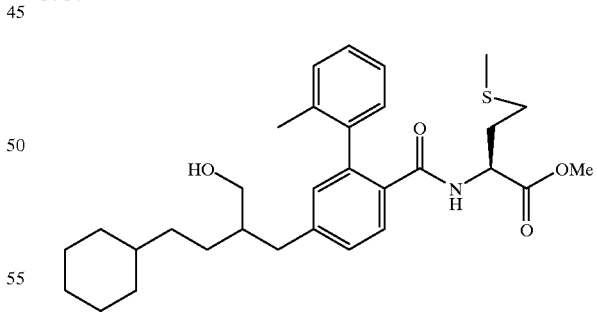

EXAMPLE 1299D

N-[4-[2-(2-Cyclohexylethyl)-1-hydroxyprop-3-yl]-2-(2-methylphenyl)benzoyl]methionine methyl ester The product from Example 1299C (97 mg, 0.25 mmol) was saponified in a similar manner as that described in Example 608C. The crude acid was then allowed to react with EDCI (55 mg, 0.28 mmol), Hobt (30 mg, 0.22 mmol), (L)-methionine methyl ester hydrochloride (48 mg, 0.24 mmol) and NMM (40 μL, 0.36 mmol) in DMF (1 mL) in a manner similar to that described in Example 608 D. The crude residue was chromatographed (silica gel; EtOAc/hexanes, 1:2) to afford the title compound as a clear oil (66 mg, 63%). MS (CI/NH$_3$) m/z: (M+H)$^+$ 526.

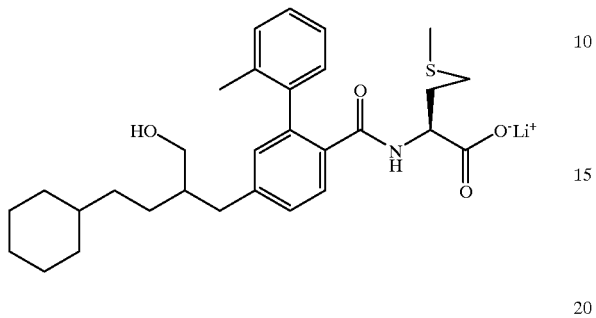

EXAMPLE 1299E

N-[4-(2-(2-Cyclohexylethyl)-1-hydroxyprop-3-yl)-2-(2-methylphenyl)benzoyl]methionine Lithium Salt The product from Example 1299D (60 mg, 0.11 mmol) was allowed to react with lithium hydroxide monohydrate (5 mg, 0.12 mmol) in a manner similar to that described in Example 608E to afford the title compound. $^1$H NMR (DMSO-d$_6$, 300 MHz) δ 0.72–0.88 (m, 2H), 1.03–1.30 (m, 8H), 1.52–1.70 (m, 9H), 1.88–2.03 (m, 6H), 2.15 (m, 1H), 2.47 (m, partially buried under DMSO peak 1H), 2.70 (m, 1H), 3.32 (d, partially buried under water peak 2H), 4.42 (m, 1H), 6.90 (d, J=6 Hz, 1H), 6.94 (s, 1H), 7.10–7.25 (m, 4H), 7.46 (d, J=8 Hz, 1H); MS (APCI(-)) m/z: (M–H)$^-$ 510; Anal. Calcd for C$_{30}$H$_{40}$LiNO$_4$S.2.1 H$_2$O: C, 64.87; H, 8.02; N, 2.52. Found: C, 64.89; H, 7.37; N, 2.37.

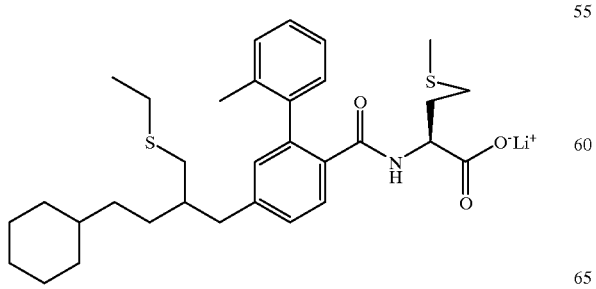

EXAMPLE 1300

N-[4-(2-(2-Cyclohexylethyl)-1-ethylthioprop-3-yl)-2-(2-methylphenyl)benzoyl]methionine Lithium Salt

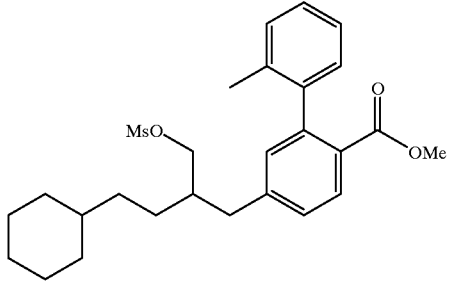

EXAMPLE 1300A

4-[2-(2-Cyclohexylethyl-1-methylsulfonyloxyprop-3-yl]-2-(2-methylphenyl)benzoic acid, methyl ester Methanesulfonyl chloride (33 μL) was added to a solution of the product from Example 1299C (149 mg, 0.38 mmol) and triethylamine (60 μL, 0.42 mmol) in THF (1 mL) at 0° C. The reaction mixture was allowed to warm to ambient temperature and stir for 3 hours. A solution of 2N HCl was added to the mixture which was then extracted with EtOAc. The organic phase was separated, dried (MgSO$_4$) and concentrated. The residue was chromatographed (silica gel; EtOAc/hexanes, 1:8) to afford a clear oil (111 mg, 62%). $^1$H NMR (CDCl$_3$, 300 MHz) δ 0.75–0.90 (m, 2H), 1.07–1.27 (m, 6H), 1.35–1.43 (m, 2H), 1.60–1.66 (m, 5H), 2.04 (m, 1H), 2.05 (s, 3H), 2.66–2.81 (m, 2H), 2.96 (s, 3H), 3.61 (s, 3H), 4.10 (d, J=5 Hz, 2H), 7.04–7.07 (m, 2H), 7.18–7.29 (m, 4H), 7.92 (d, J=8 Hz, 1H); MS (CI/NH$_3$) m/z: (M+H)$^+$ 473.

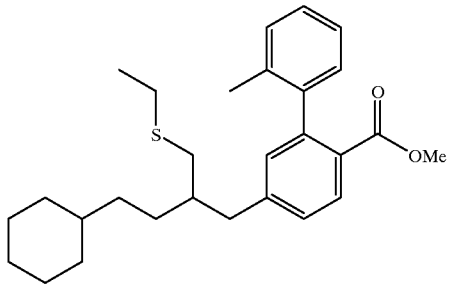

EXAMPLE 1300B

4-[2-(2-Cyclohexylethyl)-1-ethylthioprop-3-yl]-2-(2-methylphenyl)benzoic acid, methyl ester Ethanethiol (50 μL, 0.66 mmol) was added to a 60% dispersion in mineral oil NaH (27 mg, 0.68 mmol) slurry in THF (0.7 mL) at ambient temperature. After stirring for 40 min, the product from Example 1300A (105 mg, 0.22 mmol)

in THF (0.7 mL) was added to the reaction mixture followed by heating at reflux for 90 min. The mixture was allowed to cool to ambient temperature and a solution of 2N HCl was added to the reaction vessel. The mixture was extracted with EtOAc (2x). The organic phases were combined, dried (MgSO$_4$) and concentrated. The residue was chromatographed (silica gel; EtOAc/hexanes, 1:10) to afford a clear oil (83 mg, 86%). MS (CI/NH$_3$) m/z: 439 (M+H)$^+$.

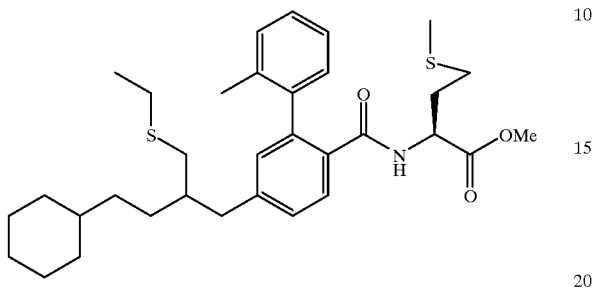

EXAMPLE 1300C

N-[4-[2-(2-Cyclohexylethyl)-1-ethylthioprop-3-yl]-2-(2-methylphenyl)benzoyl]methionine methyl ester The product from Example 1300B (78 mg, 0.18 mmol) was saponified in a similar manner as that described in Example 608C. The crude acid was then allowed to react with EDCI (48 mg, 0.25 mmol), Hobt (27 mg, 0.20 mmol), (L)-methionine methyl ester hydrochloride (43 mg, 0.22 mmol) and NMM (35 µL, 0.32 mmol) in DMF (1.0 mL) in a manner similar to that described in Example 608 D. The crude residue was chromatographed (silica gel; EtOAclhexanes, 1:8) to afford the title compound as a clear oil (46.5 mg, 45%).

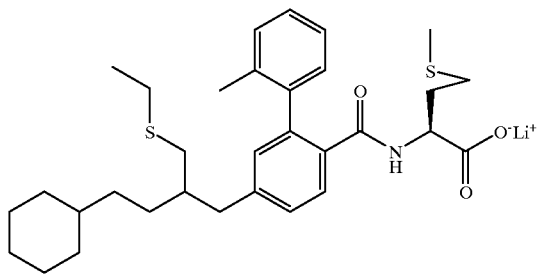

EXAMPLE 1300D

N-[4-(2-(2-Cyclohexylethyl)-1-ethylthioprop-3-yl)-2-(2-methylphenyl)benzoyl]methionine Lithium Salt The product from Example 1300C (46.5 mg, 0.08 mmol) was allowed to react with lithium hydroxide monohydrate (4 mg, 0.08 mmol) in a manner similar to that described in Example 608E to afford the title compound. $^1$H NMR (DMSO-d$_6$, 300 MHz) δ 0.75–0.88 (m, 2H), 1.08–1.38 (m, 10H), 1.53–2.01 (m, 14H), 2.15 (m, 1H), 2.39–2.49 (m, 4H), 2.57–2.75 (m, 2H), 3.32 (d, partially buried under water peak 2H), 3.66 (m, 1H), 6.86 (d, J=6 Hz, 1H), 6.95 (m, 1H), 7.12–7.26 (m, 4H), 7.47 (d, J=8 Hz, 1H); MS (APCI(-)) m/z: (M–H)$^-$ 554; Anal. Calcd for C$_{32}$H$_{44}$LiNO$_3$S$_2$.1.75 H$_2$O: C, 64.78; H, 8.07; N, 2.36. Found: C, 64.75; H, 7.40; N, 2.20.

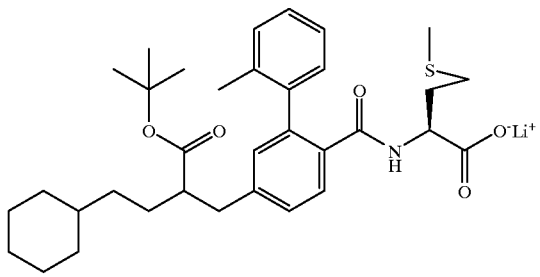

EXAMPLE 1301

N-[4-(2-(2-cyclohexylethyl)t-butylpropion-3-yl)-2-(2-methylphenyl)benzoyl]methionine Lithium Salt

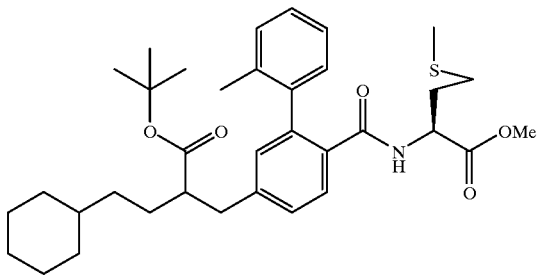

EXAMPLE 1301A

N-[4-(2-(2-Cyclohexylethyl)t-butylpropion-3-yl)-2-(2-methylphenyl)benzoyl]methionine methyl ester The product from Example 1299B (99 mg, 0.21 mmol) was saponified in a similar manner as that described in Example 608C. The crude acid was then allowed to react with EDCI (56 mg, 0.29 mmol), Hobt (31 mg, 0.23 mmol), (L)-methionine methyl ester hydrochloride (50 mg, 0.25 mmol) and NMM (42 µL, 0.38 mmol) in DMF (1.0 mL) in a manner similar to that described in Example 608 D. The crude residue was chromatographed (silica gel; EtOAc/hexanes) to afford the title compound as a clear oil (62 mg, 49.5%).

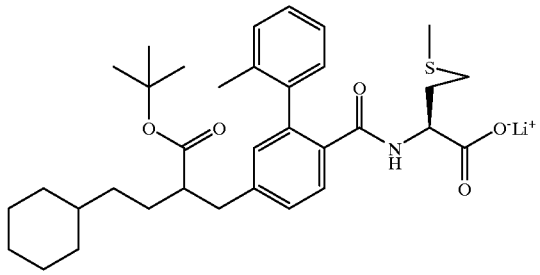

EXAMPLE 1301B

N-[4-(2-(2-Cyclohexylethyl)t-buiylpropion-3-yl)-2-(2-methylphenyl)benzoyl]methionine Lithium Salt The product from Example 1301A (61 mg, 0.10 mmol) was allowed to react with lithium hydroxide monohydrate (4.5 mg, 0.08 mmol) in a manner similar to that described in Example 608E to afford the title compound. $^1$H NMR (DMSO-d$_6$, 300 MHz) δ 0.75–0.90 (m, 2H), 1.05–1.35 (m, 15H), 1.45–2.03 (m, 17H), 2.15 (m, 1H), 2.75–2.80 (m, 2H), 3.65 (m, 1H), 6.86–7.00 (m, 2H), 7.07–7.25 (m, 4H), 7.46 (d, J=8 Hz, 1H); MS (APCI(–)) m/z: (M–H)$^-$ 580; Anal. Calcd for C$_{34}$H$_{46}$LiNO$_5$S.1.70 H$_2$O: C, 66.04; H, 8.05; N, 2.26. Found: C, 66.01; H, 7.54; N, 2.27.

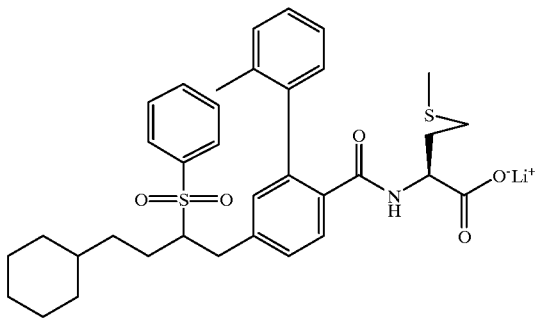

EXAMPLE 1302

N-[4-(4-Cyclohexyl-2-phenylsulfonylbut-1-yl)-2-(2-methylphenyl)benzoyl]methionine Lithium Salt

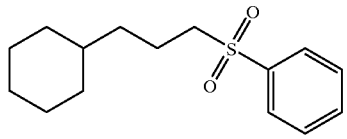

EXAMPLE 1302A

3-Cyclohexylpropyl phenyl sulfone

A solution of 2.5M nBuLi in hexanes (1.9 mL, 4.7 mmol) was added to a solution of diisopropylamine (660 μL, 4.7 mmol) in THF (9.0 mL) at ambient temperature. After 10 min, the mixture was cooled to –78° C. and methyl phenyl sulfone (700 mg, 4.5 mmol) was added to the reaction vessel. The cold bath was removed and after stirring for 30 min, 1-bromo-2-cyclohexylethane (1.3 g, 6.7 mmol) was added to the reaction mixture. The mixture was allowed to warm to ambient temperature and stir for 18 hours. A solution of 2N HCl was added to the reaction mixture followed by extraction with EtOAc (2×). The organic phases were combined, dried (MgSO$_4$) and concentrated. The residue was chromatographed (silica gel; EtOAc/hexanes, 1:8) to afford a clear oil (620 mg, 52%). $^1$H NMR (CDCl$_3$, MHz) δ 0.75–0.91 (m, 2H), 1.07–1.26 (m, 6H), 1.58–1.76 (m, 7H), 3.06 (t, J=8 Hz, 2H), 7.55–7.70 (m, 3H), 7.92 (m, 2H); MS (CI/NH$_3$) m/z: (M+NH$_4$)$^+$ 284.

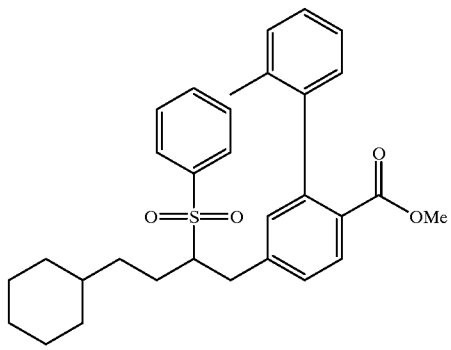

EXAMPLE 1302B

N-[4-(4-Cyclohexyl-2-phenylsulfonylbut-1-yl)-2-(2-methylphenyl)benzoyl]methionine methyl ester The product from Example 1302A (200 mg, 0.75 mmol) was allowed to react with diisopropylamine (110 μL, 0.79 mmol), 1.6M nBuLi in hexanes (495 μL, 0.79 mmol) and the product from Example 1308E (302 mg, 0.82 mmol) in a manner similar to that described under Example 1302A. The crude residue was chromatographed (silica gel; EtOAc/hexanes, 1:8) to afford a clear oil (179 mg, 47%). $^1$H NMR (CDCl$_3$, MHz) δ 0.60–0.75 (m, 2H), 0.90–1.15 (m, 6H), 1.43 (m, 1H), 1.50–1.64 (m, 5H), 1.84 (m, 1H), 2.02 (s, 3H), 2.78 (m, 1H), 3.22 (m, 1H), 3.38 (m, 1H), 3.60 (s, 3H), 6.95–7.02 (m, 2H), 7.14–7.29 (m, 4H), 7.53–7.88 (m, 3H), 7.86–7.93 (m, 3H); MS (CI/NH$_3$) m/z: (M+NH$_4$)$^+$ 522.

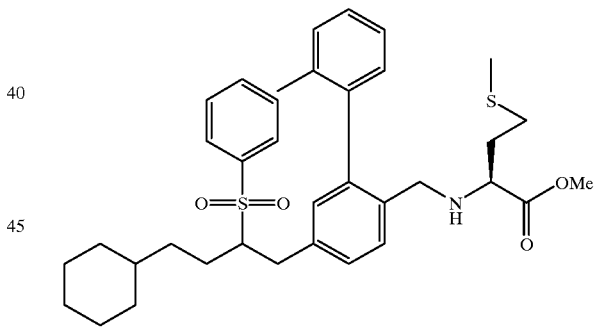

EXAMPLE 1302C

N-[4-(4-Cyclohexyl-2-phenylsulfonylbut-1-yl)-2-(2-methylphenyl)benzoyl]methionine methyl ester The product from Example 1302B (168 mg, 0.33 mmol) was saponified in a similar manner as that described in Example 608C. The crude acid was then allowed to react with EDCI (90 mg, 0.46 mmol), Hobt (50 mg, 0.36 mmol), (L)-methionine methyl ester hydrochloride (80 mg, 0.39 mmol) and NMM (65 μL, 0.39 mmol) in DMF (1.3 mL) in a manner similar to that described in Example 608 D. The crude residue was chromatographed (silica gel; EtOAc/hexanes, 1:4) to afford the title compound as a clear oil (117 mg, 56%).

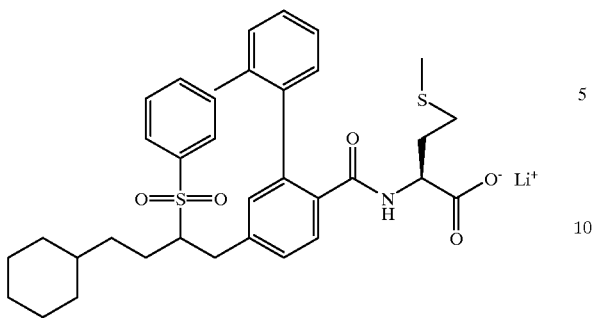

EXAMPLE 1302D

N-[4-(4-Cyclohexyl-2-phenylsulfonylbut-1-yl)-2-(2-methylphenyl)benzoyl]methionine Lithium Salt The product from Example 1302C (107 mg, 0.17 mmol) was allowed to react with lithium hydroxide monohydrate (8 mg, 0.18 mmol) in a manner similar to that described in Example 608E to afford the title compound. $^1$H NMR (DMSO-$d_6$, 300 MHz) δ 0.54–0.70 (m, 2H), 0.85–1.10 (m, 6H), 1.30–2.04 (m, 16H), 2.14 (m, 1H), 2.80 (m, 1H), 3.16 (m, 1H), 3.60–3.73 (m, 2H), 6.85–7.26 (m, 6H), 7.43 (d, J=8 Hz, 1H), 7.62–7.68 (m, 2H), 7.75 (m, 1H), 7.93 (d, J=7 Hz, 2H); MS (APCI(−)) m/z: (M−H)$^-$ 620; Anal. Calcd for $C_{35}H_{42}LiNO_5S_2 \cdot 3.20\ H_2O$: C, 61.33; H, 7.12; N, 2.04. Found: C, 61.31; H, 6.63; N, 1.70.

What is claimed is:

1. A compound having Formula I

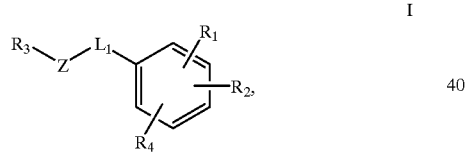

or a pharmaceutically acceptable salt thereof, wherein $R_1$ is phenyl, unsubstituted or substituted with loweralkyl;
$R_2$ is —C(W)N(R)—C($R_{14}$)($R_v$)—C(O)O$R_{15}$, wherein
  W is O or S,
  R is hydrogen or loweralkyl,
  $R_{14}$ is unsubstituted thioalkoxyalkyl,
  $R_v$ is hydrogen, and
  $R_{15}$ is hydrogen or loweralkyl; or
—$L_{11}$—C($R_{14}$)($R_v$)—C(O)O$R_{15}$, wherein $L_{11}$ is a covalent bond,
  $R_v$ is hydrogen,
  $R_{14}$ is unsubstituted thioalkoxyalkyl,
  $R_{15}$ is hydrogen or loweralkyl;
$L_1$ is methylene;
Z is a covalent bond;
$R_3$ is pyrrolidin-1-yl wherein the pyrrolidinyl is unsubstituted or substituted with 1, 2, 3, 4, or 5 substituents independently selected from the group consisting of
  (a) alkanoyl,
  (b) alkoxy wherein the alkoxy is unsubstituted or substituted with 1, 2, 3, 4, or 5 substituents indepen dently selected from the group consisting of
  halogen,
  aryl, and
  cycloalkyl,
  (c) alkoxyalkyl wherein the alkoxyalkyl is unsubstituted or substituted with 1 or 2, 3, 4 or 5 substituents independently selected from the group consisting of
  aryl and
  cycloalkyl,
  (d) alkoxycarbonyl wherein the alkoxycarbonyl is unsubstituted or substituted with 1, 2, 3, 4, or 5 substituents independently selected from the group consisting of
  aryl and cycloalkyl,
  (e) alkylsilyloxyalkyl,
  (f) arylalkyl,
  (g) aryl wherein the aryl is unsubstituted or substituted with 1, 2, 3, 4, or 5 substituents independently selected from the group consisting of
  alkanoyl,
  alkoxy wherein the alkoxy is unsubstituted or substituted with 1 or 2 substituents selected from the group consisting of cycloalkyl,
  carboxaldehyde,
  haloalkyl,
  halogen,
  loweralkyl,
  nitro,
  —NRR', and
  thioalkoxy,
  (h) arylalkyl,
  (i) aryloxy wherein the aryloxy is unsubstituted or substituted with 1, 2, 3, 4, or 5 substituents independently selected from the group consisting of,
  halogen,
  nitro, and
  —NRR',
  (j) (aryl)oyl,
  (k) carboxaldehyde,
  (l) carboxy,
  (m) carboxyalkyl,
  (n) —C(O)NRR" wherein R is defined previously and R" is selected from the group consisting of
  hydrogen,
  loweralkyl, and
  carboxyalkyl,
  (o) cyano,
  (p) cyanoalkyl,
  (q) cycloalkyl,
  (r) cycloalkylalkyl,
  (s) cycloalkoxyalkyl,
  (t) halogen,
  (u) haloalkyl wherein the haloalkyl is unsubstituted or substituted with 1, 2, 3, 4, or 5 hydroxyl substituents, with the proviso that no two hydroxyls are attached to the same carbon,
  (v) heterocycle,
  (w) hydroxyl,
  (x) hydroxyalkyl wherein the hydroxyalkyl is unsubstituted or substituted with substitutients selected from the group consisting of aryl,
  (y) loweralkyl wherein the loweralkyl is unsubstituted or substituted with substituents selected from the group consisting of
heterocycle,
hydroxyl,
with the proviso that no two hydroxyls are attached to the same carbon, and
—$NR^{R3}R^{R3'}$,
(z) nitro,
(aa) —NRR',
(bb) oxo,
(cc) —$SO_2NR_{A'}R_{B'}$ wherein $R_{A'}$ and $R_{B'}$ are independently selected from the group consisting of
hydrogen,
(aryl)oyl,
loweralkyl, and
heterocycle wherein the heterocycle is unsubstituted or substituted with 1, 2, or 3 substituents independently selected from the group consisting of loweralkyl, and $R_4$ is hydrogen.

2. A compound according to claim 1 wherein the pyrrolidin-1-yl is monosubstituted.

3. A compound according to claim 2 selected from the group consisting of

[4-(3-hydroxypyrrolidinyl)-2-phenylbenzoyl]methionine,

N-[4-(2-benzyloxymethylpyrrolidin-1-ylmethyl)-2-(2-methylphenyl)benzoyl]methionine, N-[4-(3-benzyloxypyrrolidin-1-ylmethyl)-2-(2-methylphenyl)benzoyl]methionine, N-[4-(2-phenoxymethylpyrrolidin-1-ylmethyl)-2-(2-methylphenyl)benzoyl]methionine, N-[4-(2-cyclohexylmethoxymethylpyrrolidin-1-ylmethyl)-2-(2-methylphenyl)benzoyl]methionine, N-[4-(2-benzyloxymethylpyrrolidin-1-ylmethyl)-2-(2-methylphenyl)benzoyl]methionine, N-[4-(2(S)-cyclohexyloxymethylpyrrolidin-1-ylmethyl)-2-(2-methylphenyl)benzoyl]methionine, N-[4-(2-cyclohexylmethoxymethylpyrrolidin-1-ylmethyl)-2-(2-methylphenyl)benzoyl]methionine, N-[4-(2-piperidin-1-ylmethylpyrrolidin-1-ylmethyl)-2-(2-methylphenyl)benzoyl]methionine, N-[4-(2-morpholin-4-ylmethylpyrrolidin-1-ylmethyl)-2-(2-methylphenyl)benzoyl]methionine, and N-[4-(2-(N-cyclohexyl-N-methylamino)methylpyrrolidin-1-ylmethyl)-2-(2-methylphenyl)benzoyl]methionine.

4. A compound according to claim 1 wherein the pyrrolidin-1-yl is disubstituted.

5. A compound according to claim 4 selected from the group consisting of

N-[4-(2-methoxymethyl-5-benzylpyrrolidin-1-ylmethyl)-2-(2-methylphenyl)benzoyl]methionine, N-[4-(R)-(2-benzyloxymethyl-4-(R)-methoxypyrrolidin-1-ylmethyl)-2-(2-methylphenyl)benzoyl]methionine, N-[4-(R)-(2-benzyloxymethyl-4-(S)-methoxypyrrolidin-1-ylmethyl)-2-(2-methylphenyl)benzoyl]methionine, N-[4-(2-cyclohexyloxymethyl-5-propylpyrrolidin-1-ylmethyl)-2-(2-methylphenyl)benzoyl]methionine, N-[4-(2(S)-cyclohexylmethoxymethyl-4(R)-methoxypyrrolidin-1-ylmethyl)-2-(2-methylphenyl)benzoyl]methionine, and N-[4-(3-cyclohexylmethoxy-2-methoxymethylpyrrolidin-1-ylmethyl)-2-(2-methylphenyl)benzoyl]methionine.

6. A compound according to claim 1 wherein the pyrrolidin-1-yl is trisubstituted.

7. A compound according to claim 6 which is

N-[4-(2(S)-cyclohexylmethyloxymethyl-4,4-difluoropyrrolidin-1-ylmethyl)-2-(2-methylphenyl)benzoyl]methionine.

8. A method of inhibiting protein isoprenyl transferases in a mammal in need of such treatment comprising administering to the mammal a therapeutically effective amount of a compound of claim 1.

9. A composition for inhibiting protein isoprenyl transferases comprising a pharmaceutical carrier and a therapeutically effective amount of a compound of claim 1.

10. A method for inhibiting or treating cancer in a mammal, comprising administering to the mammal a therapeutically effective amount of a compound of claim 1 alone or in combination with another chemotherapeutic agent.

11. A composition for the treatment of cancer comprising a compound of claim 1 in combination with another chemotherapeutic agent and a pharmaceutically acceptable carrier.

12. A method for inhibiting post-translational modification of the oncogenic Ras protein by protein farnesyltransferase, protein geranylgeranyltransferase, or both in a mammal comprising administering to the mammal a therapeutically effective amount of a compound of claim 1.

13. A composition for inhibiting post-translational modification of the oncogenic Ras protein by protein farnesyltransferase, protein geranylgeranyltransferase, or both comprising a compound of claim 1 in combination with a pharmaceutical carrier.

14. A method for treating or preventing intimal hyperpiasia associated with restenosis and atherosclerosis in a mammal comprising administering to the mammal a therapeutically effective amount of a compound of claim 1.

15. A composition for treating or preventing restenosis in a mammal comprising a compound of claim 1 in combination with a pharmaceutically acceptable carrier.

* * * * *